US012202845B2

(12) United States Patent
Knox et al.

(10) Patent No.: US 12,202,845 B2
(45) Date of Patent: Jan. 21, 2025

(54) RAS INHIBITORS

(71) Applicant: Revolution Medicines, Inc., Redwood City, CA (US)

(72) Inventors: John E. Knox, Emerald Hills, CA (US); Elena S. Koltun, Foster City, CA (US); Yang Liu, Foster City, CA (US); G. Leslie Burnett, Redwood City, CA (US); James Cregg, Belmont, CA (US); Anne V. Edwards, San Mateo, CA (US); Adrian L. Gill, Atherton, CA (US); Andreas Buckl, San Francisco, CA (US); Christopher Semko, Fremont, CA (US)

(73) Assignee: Revolution Medicines, Inc., Redwood City, CA (US)

( * ) Notice: Subject to any disclaimer, the term of this patent is extended or adjusted under 35 U.S.C. 154(b) by 0 days.

(21) Appl. No.: 17/938,890

(22) Filed: Oct. 7, 2022

(65) Prior Publication Data

US 2023/0303591 A1 Sep. 28, 2023

Related U.S. Application Data

(60) Provisional application No. 63/254,013, filed on Oct. 8, 2021.

(51) Int. Cl.
*C07D 519/00* (2006.01)
*A61P 35/00* (2006.01)

(52) U.S. Cl.
CPC ............ *C07D 519/00* (2013.01); *A61P 35/00* (2018.01); *C07B 2200/05* (2013.01)

(58) Field of Classification Search
CPC .................................................. C07D 519/00
See application file for complete search history.

(56) References Cited

U.S. PATENT DOCUMENTS

| 6,183,965 | B1 | 2/2001 | Verdine et al. |
|---|---|---|---|
| 6,372,712 | B1 | 4/2002 | Briesewitz et al. |
| 6,686,454 | B1 | 2/2004 | Yatscoff et al. |
| 6,713,607 | B2 | 3/2004 | Caggiano et al. |
| 7,220,552 | B1 | 5/2007 | Crabtree et al. |
| 7,396,660 | B2 | 7/2008 | Huang et al. |
| 7,851,183 | B2 | 12/2010 | Zotchev et al. |
| 8,664,186 | B2 | 3/2014 | Aigle et al. |
| 9,119,853 | B2 | 9/2015 | Moss et al. |
| 9,211,291 | B2 | 12/2015 | Berkenblit et al. |
| 9,250,237 | B2 | 2/2016 | Liu et al. |
| 9,260,484 | B2 | 2/2016 | Briesewitz et al. |
| 9,428,845 | B1 | 8/2016 | Verdine et al. |
| 9,989,535 | B2 | 6/2018 | Verdine et al. |
| 10,039,839 | B2 | 8/2018 | Verdine et al. |
| 10,203,323 | B2 | 2/2019 | Verdine et al. |
| 10,466,249 | B2 | 11/2019 | Verdine et al. |
| 10,533,016 | B2 | 1/2020 | Verdine et al. |
| 10,800,787 | B2 | 10/2020 | Bodhuri et al. |
| 10,948,495 | B2 | 3/2021 | Verdine et al. |
| 10,989,710 | B2 | 4/2021 | Verdine et al. |
| 11,059,830 | B2 | 7/2021 | Verdine et al. |
| 11,566,007 | B2 | 1/2023 | Koltun et al. |
| 11,608,346 | B2 | 3/2023 | Koltun et al. |
| 11,644,460 | B2 | 5/2023 | Verdine et al. |
| 11,690,915 | B2 | 7/2023 | Aay et al. |
| 11,739,074 | B2 | 8/2023 | Aggen et al. |
| 2002/0110874 | A1 | 8/2002 | Khosla et al. |
| 2002/0147133 | A1 | 10/2002 | Briesewitz et al. |
| 2003/0153053 | A1 | 8/2003 | Reid |
| 2003/0175901 | A1 | 9/2003 | Reeves et al. |
| 2004/0087496 | A1 | 5/2004 | Kim et al. |
| 2004/0157768 | A1 | 8/2004 | Or et al. |
| 2005/0233431 | A1 | 10/2005 | Ashley et al. |
| 2007/0203168 | A1 | 8/2007 | Zhao |
| 2007/0218502 | A1 | 9/2007 | Hahn et al. |
| 2007/0265333 | A1 | 11/2007 | Fu et al. |
| 2011/0117606 | A1 | 5/2011 | Jorgensen et al. |
| 2012/0208720 | A1 | 8/2012 | Kashiwagi et al. |
| 2012/0270800 | A1 | 10/2012 | Verdine et al. |
| 2013/0072439 | A1 | 3/2013 | Nash et al. |
| 2013/0344030 | A1 | 12/2013 | Steadman et al. |
| 2014/0073581 | A1 | 3/2014 | Liu et al. |
| 2014/0256717 | A1 | 9/2014 | Fernandez et al. |
| 2014/0316104 | A1 | 10/2014 | Fischer et al. |
| 2015/0250896 | A1 | 9/2015 | Zhao |
| 2015/0307855 | A1 | 10/2015 | Yuzawa et al. |
| 2016/0083373 | A1 | 3/2016 | Xu |
| 2016/0199506 | A1 | 7/2016 | Verdine et al. |
| 2016/0296528 | A1 | 10/2016 | Pastor Fernandez et al. |

(Continued)

FOREIGN PATENT DOCUMENTS

| CN | 107001387 A | 8/2017 |
|---|---|---|
| EP | 0194972 A2 | 9/1986 |

(Continued)

OTHER PUBLICATIONS

Banteli et al., "A synthesis of the C1-N12 tripeptide fragment of sanglifehrin A," Tetrahedron Letters. 40(11):2109-2112 (Mar. 12, 1999).
Doak et al., "Cyclophilin Succumbs to a Macrocyclic Chameleon," J Med Chem. 61(21):9469-9472 (Nov. 2018).
Pei et al., "Targeting Ras with Macromolecules," Cold Spring Harb Perspect Med. 8(3):a031476 (Mar. 2018) (13 pages).
"On Target to Outsmart Cancer™," Revolution Medicines (Jan. 11, 2022) (33 pages).
"Registration No. 333-235968: Amendment No. 2 to Form S-1 Registration Statement Under The Securities Act of 1933 for Revolution Medicines, Inc.," United States Securities and Exchange Commission, Washington, D.C., 20549, dated Feb. 11, 2020 (354 pages).

(Continued)

*Primary Examiner* — Laura L Stockton
(74) *Attorney, Agent, or Firm* — Clark & Elbing LLP

(57) ABSTRACT

The invention features macrocyclic compounds, and pharmaceutical compositions and protein complexes thereof, capable of inhibiting Ras proteins, and their uses in the treatment of cancers.

6 Claims, 5 Drawing Sheets

(56) References Cited

U.S. PATENT DOCUMENTS

| | | |
|---|---|---|
| 2016/0341719 A1 | 11/2016 | Verdine et al. |
| 2017/0190734 A1 | 7/2017 | Aciro et al. |
| 2018/0318434 A1 | 11/2018 | Verdine et al. |
| 2020/0197391 A1 | 6/2020 | Jin et al. |
| 2020/0199102 A1 | 6/2020 | Mulvihill et al. |
| 2021/0130303 A1 | 5/2021 | Koltun et al. |
| 2021/0130326 A1 | 5/2021 | Aggen et al. |
| 2021/0130369 A1 | 5/2021 | Koltun et al. |
| 2021/0285955 A1 | 9/2021 | Mulvihill et al. |
| 2021/0405060 A1 | 12/2021 | Verdine et al. |
| 2022/0082556 A1 | 3/2022 | Verdine et al. |
| 2022/0105185 A1 | 4/2022 | Aay et al. |
| 2022/0143202 A1 | 5/2022 | Verdine et al. |
| 2022/0144849 A1 | 5/2022 | Verdine et al. |
| 2022/0396589 A1* | 12/2022 | Buckl .................. C07D 498/18 |
| 2023/0100838 A1 | 3/2023 | Pitzen et al. |
| 2023/0106174 A1 | 4/2023 | Koltun et al. |
| 2023/0303591 A1 | 9/2023 | Buckl et al. |

FOREIGN PATENT DOCUMENTS

| | | |
|---|---|---|
| EP | 0393934 A1 | 10/1990 |
| EP | 0562853 A1 | 9/1993 |
| EP | 1079859 B1 | 7/2010 |
| KR | 10-2009-0041971 A | 4/2009 |
| WO | WO-86/02080 A1 | 4/1986 |
| WO | WO-95/32294 A1 | 11/1995 |
| WO | WO-96/20216 A1 | 7/1996 |
| WO | WO-98/01546 A2 | 1/1998 |
| WO | WO-98/07743 A1 | 2/1998 |
| WO | WO-98/12217 A1 | 3/1998 |
| WO | WO-99/61055 A1 | 12/1999 |
| WO | WO-00/47724 A2 | 8/2000 |
| WO | WO-01/36460 A2 | 5/2001 |
| WO | WO-01/36612 A1 | 5/2001 |
| WO | WO-01/90070 A2 | 11/2001 |
| WO | WO-03/033010 A1 | 4/2003 |
| WO | WO-2008/069824 A2 | 6/2008 |
| WO | WO-2010/031185 A1 | 3/2010 |
| WO | WO-2010/034243 A1 | 4/2010 |
| WO | WO-2010/088573 A1 | 8/2010 |
| WO | WO-2012/075048 A2 | 6/2012 |
| WO | WO-2012/078915 A1 | 6/2012 |
| WO | WO-2012/131371 A1 | 10/2012 |
| WO | WO-2012/131377 A1 | 10/2012 |
| WO | WO-2012/174489 A2 | 12/2012 |
| WO | WO-2013/001310 A1 | 1/2013 |
| WO | WO-2013/022818 A1 | 2/2013 |
| WO | WO-2013/185090 A1 | 12/2013 |
| WO | WO-2013/185093 A1 | 12/2013 |
| WO | WO-2013/185103 A1 | 12/2013 |
| WO | WO-2014/009774 A1 | 1/2014 |
| WO | WO-2014/121942 A1 | 8/2014 |
| WO | WO-2014/169167 A1 | 10/2014 |
| WO | WO-2014/187959 A2 | 11/2014 |
| WO | WO-2015/132784 A1 | 9/2015 |
| WO | WO-2016/112279 A1 | 7/2016 |
| WO | WO-2016/112295 A1 | 7/2016 |
| WO | WO-2016/160362 A1 | 10/2016 |
| WO | WO-2017/059207 A1 | 4/2017 |
| WO | WO-2018/081592 A2 | 5/2018 |
| WO | WO-2018/091634 A1 | 5/2018 |
| WO | WO-2018/187401 A1 | 10/2018 |
| WO | WO-2018/187423 A1 | 10/2018 |
| WO | WO-2018/217651 A1 | 11/2018 |
| WO | WO-2020/101736 A1 | 5/2020 |
| WO | WO-2020/132597 A1 | 6/2020 |
| WO | WO-2021/086833 A1 | 5/2021 |
| WO | WO-2021/091956 A1 | 5/2021 |
| WO | WO-2021/091967 A1 | 5/2021 |
| WO | WO-2021/091982 A1 | 5/2021 |
| WO | WO-2021/108683 A1 | 6/2021 |
| WO | WO-2022/060583 A1 | 3/2022 |
| WO | WO-2022/060836 A1 | 3/2022 |
| WO | WO-2022/212894 A1 | 10/2022 |
| WO | WO-2022/217053 A1 | 10/2022 |
| WO | WO-2022/235864 A1 | 11/2022 |
| WO | WO-2022/235866 A1 | 11/2022 |
| WO | WO-2022/235870 A1 | 11/2022 |
| WO | WO-2022/251292 A1 | 12/2022 |
| WO | WO-2022/271658 A1 | 12/2022 |
| WO | WO-2023/015559 A1 | 2/2023 |
| WO | WO-2023/025832 A1 | 3/2023 |
| WO | WO-2023/086341 A1 | 5/2023 |
| WO | WO-2023/208005 A1 | 11/2023 |
| WO | WO-2023/232776 A1 | 12/2023 |
| WO | WO-2024/008610 A1 | 1/2024 |
| WO | WO-2024/008834 A1 | 1/2024 |
| WO | WO-2024/017859 A1 | 1/2024 |

OTHER PUBLICATIONS

"Smart™ Drugs: Engineering Nature's Solution to the Undruggable Target Challenge," WarpDrive Bio, 2016, available <http://www.warpdrivebio.com/docs/Warp%20Drive%20Bio_SMART%20Drugs%20Platform_2016.pdf> (31 pages).

"Streptomyces iranensis regulatory protein LuxR," EBI Database Accession No. CDR13506 (2014) (2 pages).

"Streptomyces rapamycinicus NRRL 5491 hypothetical protein," EBI Database Accession No. AGP59507 (2014) (2 pages).

"Substructure Search Report on Specifically Substituted Macrocycles - Substances Only," prepared by Science IP, dated Dec. 17, 2014 (6177 pages).

"Translating Frontier Oncology Targets to Outsmart Cancer™," Corporate Overview Q3-2020, Revolution Medicines, Aug. 20, 2020 (35 pages).

Aebi et al., "Synthesis, Conformation, and Immunosuppressive Activities of Three Analogues of Cyclosporin A Modified in the 1-Position," J Med Chem. 33(3):999-1009 (1990).

Allain et al., "Cyclophilin B mediates cyclosporin A incorporation in human blood T-lymphocytes through the specific binding of complexed drug to the cell surface," Biochem J. 317 (Pt 2):565-70 (1996).

Andrei et al., "Stabilization of protein-protein interactions in drug discovery," Expert Opin Drug Discov. 12(9):925-40 (2017) (17 pages).

Antunes et al., "A mutational analysis defines Vibrio fischeri LuxR binding sites," J Bacteriol. 190(13): 4392-7 (2008).

Archibald et al., "Discovery and Evaluation of Potent, Cysteine-based alpha4beta1 Integrin Antagonists," Bioorg Med Chem Lett. 10(9):993-995 (2000).

Baillie, "Targeted Covalent Inhibitors for Drug Design," Covalent Inhibitor Drug Discovery & Development Symposium PBSS, February 7, Foster City, California. (2019) (16 pages).

Banaszynski et al., "Characterization of the FKBP.rapamycin.FRB ternary complex," J Am Chem Soc. 127(13):4715-21 (2005).

Baranasic et al., "Draft Genome Sequence of Streptomyces rapamycinicus Strain NRRL 5491, the Producer of the Immunosuppressant Rapamycin," Genome Announc. 1(4):e00581-13 (2013) (2 pages).

Bayle et al., "Rapamycin analogs with differential binding specificity permit orthogonal control of protein activity," Chem Biol. 13(1):99-107 (2006).

Bender et al., "Periodate Oxidation of alpha-Keto gamma-Lactams. Enol Oxidation and beta-Lactam Formation. Mechanism of Periodate Hydroxylation Reactions," J Org Chem. 43(17):3354-3362 (1978).

Benjamin et al., "Rapamycin passes the torch: a new generation of mTOR inhibitors," Nat Rev Drug Discov. 10(11):868-80 (2011).

Bhuyan et al., "Antioxidant activity of peptide-based angiotensin converting enzyme inhibitors," Org Biomol Chem. 10(11):2237-47 (2012).

Blodgett et al., "Unusual transformations in the biosynthesis of the antibiotic phosphinothricin tripeptide," Nat Chem Biol. 3(8):480-5 (2007).

Briesewitz et al., "Affinity modulation of small-molecule ligands by borrowing endogenous protein surfaces," Proc Natl Acad Sci U.S.A. 96(5):1953-8 (1999).

(56) References Cited

OTHER PUBLICATIONS

Bruce, "In vivo protein complex topologies: sights through a cross-linking lens," Proteomics. 12(10):1565-75 (2012).
Burgess et al., "Controlled translocation of palladium(II) within a 22 ring atom macrocyclic ligand," Dalton Trans. 43(45):17006-16 (2014) (12 pages).
Chaurasia et al., "Molecular insights into the stabilization of protein-protein interactions with small molecule: The FKBP12-rapamycin-FRB case study," Chem Phys Lett. 587:68-74 (2013).
Che et al., "Inducing protein-protein interactions with molecular glues," Bioorg Med Chem Lett. 28(15):2585-92 (2018) (18 pages).
Chen et al., "Emerging strategies to target RAS signaling in human cancer therapy," J Hematol Oncol. 14(1):116 (Jul. 23, 2021) (23 pages).
Chevalier et al., "Straightforward synthesis of bioconjugatable azo dyes. Part 1: Black Hole Quencher-1 (BHQ-1) scaffold," Tetrahedron Lett. 55(50):6759-63 (2014).
Ding et al., "Insights into Bacterial 6-Methylsalicylic Acid Synthase and Its Engineering to Orsellinic Acid Synthase for Spirotetronate Generation," Chem Biol. 17(5):495-503 (2010).
Eberle et al., "Preparation of Functionalized Ethers of Cyclosporin A," Tetrahedron Lett. 35(35):6477-6480 (1994).
Findlay et al., "The structure of demethoxyrapamycin," Can J Chem. 60:2046-7 (1982).
Garg et al., "Elucidation of the Cryptic Epimerase Activity of Redox-Inactive Ketoreductase Domains from Modular Polyketide Synthases by Tandem Equilibrium Isotope Exchange," J Am Chem Soc. 136(29):10190-10193 (2014).
Gill et al., "Discovery of Small Molecule Inhibitors of the Oncogenic, GTP-Bound (ON) Form of $KRAS^{G12C}$ and $KRAS_{G13C}$," Revolution Medicines (Sep. 2019) (1 page).
Gill, "Discovery of Small Molecule Inhibitors of Oncogenic Mutants of RAS," Revolution Medicines, ACS, April 2, Orlando (2019) (23 pages).
Gordon et al., "A SARS-CoV-2 Protein Interaction Map Reveals Targets for Drug Repurposing," Nature. 583(7816):459-68 (Apr. 2020).
Guerra et al., "LAL regulators SCO0877 and SCO7173 as pleiotropic modulators of phosphate starvation response and actinorhodin biosynthesis in Streptomyces coelicolor," PLoS One. 7(2):e31475 (2012) (11 pages).
Guo et al., "Rapamycin-inspired macrocycles with new target specificity," Nat Chem. 11(3):254-263 (Mar. 2019) (13 pages).
Halford, "Covalent drugs go from fringe field to fashionable endeavor: Designing molecules that make bonds with their biological targets is in vogue," Chemical and Engineering News, 98(43) (Nov. 2020) (6 pages).
Hansson et al., "Bioengineering and Semisynthesis of an Optimized Cyclophilin Inhibitor for Treatment of Chronic Viral Infection," Chem Biol. 22(2):285-92 (2015) (24 pages).
He et al., "The LuxR family members GdmRI and GdmRII are positive regulators of geldanamycin biosynthesis in Streptomyces hygroscopicus 17997," Arch Microbiol. 189(5):501-10 (2008).
Hong et al., "Evidence for an iterative module in chain elongation on the azalomycin polyketide synthase," Beilstein J Org Chem. 12:2164-2172 (2016).
Horn et al., "Draft Genome Sequence of Streptomyces iranensis," Genome Announc. 2(4):e00616-14 (2014) (2 Pages).
Horton et al., "Engineering hybrid genes without the use of restriction enzymes: gene splicing by overlap extension," Gene. 77(1):61-8 (1989).
Hosted et al., "Use of rpsL for dominance selection and gene replacement in *Streptomyces roseosporus*," J Bacteriol. 179(1):180-6 (1997).
Huang et al., "Conjugation to Albumin-Binding Molecule Tags as a Strategy to Improve Both Efficacy and Pharmacokinetic Properties of the Complement Inhibitor Compstatin," ChemMedChem. 9(10):2223-6 (2014).
Huang et al., "Enhanced rapamycin production in *Streptomyces hygroscopicus* by integrative expression of aveR, a LAL family transcriptional regulator," World J Microbiol Biotechnol. 27:2103-9 (2011).
Hubler et al., "Synthetic routes to $NEtXaa^4$-cyclosporin A derivatives as potential anti-HIV I drugs," Tetrahedron Lett. 41:7193-6 (2000).
International Search Report and Written Opinion for PCT/US2022/077784, mailed Feb. 1, 2023 (9 pages).
International Search Report and Written Opinion for PCT/US2023/060288, dated Mar. 13, 2023 (15 pages).
Ishizawa et al., "TRAP display: a high-speed selection method for the generation of functional polypeptides," J Am Chem. 135(14):5433-40 (2013).
Janes et al., "Targeting KRAS Mutant Cancers with a Covalent G12C-Specific Inhibitor," Cell., 172(3):578-589.e17 (Jan. 2018).
Jarvis, "Have drug hunters finally cracked KRas?—After decades of failures, researchers see promise in fresh approaches to developing drugs that block cancer's toughest target," Chemical & Engineering News. 94(23):28-33. <https://cen.acs.org/articles/94/123/drug-hunters-finally-cracked-KRas.html>, retrieved on Oct. 14, 2018 (2016) (9 pages).
Kawakami et al., "In vitro selection of multiple libraries created by genetic code reprogramming to discover macrocyclic peptides that antagonize VEGFR2 activity in living cells," ACS Chem Biol. 8(6):1205-14 (2013).
Kelsey, "Approaches to Inhibiting RAS-Driven Tumors Beyond $KRAS^{G12C}$," RAS Targeted Drug Development, Revolution Medicines, Sep. 16, 2020 (24 pages).
Kelsey, "Discovery and Development of RAS(ON) Inhibitors Beyond $KRAS^{G12D}$," AACR-NCI-EORTC Virtual International Conference on Molecular Targets and Cancer Therapeutics, Oct. 7-10, Redwood City, California (Oct. 2021) (24 pages).
Kelsey, "Targeting RAS(ON) Beyond $KRAS^{G12D}$," 4th Annual RAS-Targeted Drug Development Summit, Sep. 28, Redwood City, California (Sep. 2022) (23 pages).
Kendrew et al., "Recombinant strains for the enhanced production of bioengineered rapalogs," Metab Eng. 15:167-73 (2013).
Knox, "RMC-9805 (RM-036), a First-in-Class, Orally-Bioavailable, Tri-Complex Covalent $KRAS^{G12D}$(ON) Inhibitor, Drives Profound Anti-Tumor Activity in $KRAS^{G12D}$ Mutant Tumor Models," AACR Annual Meeting, April 8-13, New Orleans, Louisiana (Apr. 2022) (Abstract Included) (13 pages).
Koltun et al., "Drugging the RAS(ON) Form of Diverse Oncogenic RAS Mutations," 21st RSC / SCI Medicinal Chemistry Symposium, Sep. 15, Cambridge, Massachusetts (Sep. 2021) (35 Pages).
Koltun et al., "First-in-class, orally bioavailable $KRAS^{G12V}$ (ON) tri-complex inhibitors, as single agents and in combinations, drive profound anti-tumor activity in preclinical models of $KRAS^{G12V}$ mutant cancers," American Association of Cancer Research, Meeting Abstract (Jul. 1, 2021) (1page).
Koltun et al., "First-in-class, orally bioavailable $KRAS^{G12V}$(ON)/$RAS^{MULTI}$(ON) tri-complex inhibitors, as single agents and in combinations, drive profound anti-tumor activity in preclinical models of $KRAS^{G12V}$ mutant cancers," Revolution Medicines (Apr. 2021) (1 Page).
Kuhn et al., "Synthesis of Functional Ras Lipoproteins and Fluorescent Derivatives," J Am Chem Soc. 123(6):1023-35 (2001).
Kuramochi et al., "Identification of Small Molecule Binding Molecules by Affinity Purification Using a Specific Ligand Immobilized on PEGA Resin," Bioconjug Chem. 19(12):2417-26 (2008).
Laureti et al., "Identification of a bioactive 51-membered macrolide complex by activation of a silent polyketide synthase in Streptomyces ambofaciens," Proc Natl Acad Sci USA. 108(15):6258-63 (2011).
Laureti et al., Supporting Material for "Identification of a bioactive 51-membered macrolide complex by activation of a silent polyketide synthase in Streptomyces ambofaciens," Proc Natl Acad Sci U.S.A. 108(15):6258-63 (2011), accessed via <https://www.pnas.org/content/suppl/2011/03/24/1019077108.DCSupplemental> (41 pages).
Lee et al., "Current implications of cyclophilins in human cancers," J Exp Clin Cancer Res. 29(1):97 (2010) (6 pages).

(56) References Cited

OTHER PUBLICATIONS

Leskiw et al., "TTA codons in some genes prevent their expression in a class of developmental, antibiotic-negative, *Streptomyces* mutants," Proc Natl Acad Sci USA. 88(6):2461-5 (1991).
Li et al., "A simple and efficient route to the FKBP-binding domain from rapamycin," available in PMC Sep. 28, 2012, published in final edited form as: Tetrahedron Lett. 52(39):5070-2 (2011) (7 pages).
Luengo et al., "Structure-activity studies of rapamycin analogs: evidence that the C-7 methoxy group is part of the effector domain and positioned at the FKBP12-FRAP interface," Chem Biol. 2(7):471-81 (1995).
Mackman et al., "Discovery of a Potent and Orally Bioavailable Cyclophilin Inhibitor Derived from the Sanglifehrin Macrocycle," J Med Chem. 61(21):9473-9499 (2018).
Majumder et al. "Interaction of aryl hydrocarbon receptor-interacting protein-like 1 with the farnesyl moiety," J Biol Chem. 288(29):21320-21328 (2013).
McGregor et al., "Expanding the Scope of Electrophiles Capable of Targeting K-Ras Oncogenes," Biochemistry. 56(25):3178-3183 (2017).
Meyer et al., "Selective palladation of a large (32 ring atom) macrocyclic ligand at a bis(N-heterocyclic carbene) coordination pocket through transmetallation of the corresponding mercury(II) derivative," Dalton Trans. 41(46): 14059-67 (2012) (10 pages).
Mo et al., "Interspecies Complementation of the LuxR Family Pathway-Specific Regulator Involved in Macrolide Biosynthesis," J Microbiol Biotechnol. 26(1):66-71 (2016).
Moore et al., "RAS-targeted therapies: is the undruggable drugged?" available in PMC Feb. 1, 2021, published in final edited form as: Nat Rev Drug Discov. 19(8):533-52 (Aug. 2020) (43 pages).
Mullard, "Cracking KRAS," Nat Rev Drug Discov. 18(12):887-91 (Nov. 2019) (14 pages).
Murphy et al., "Isolation and characterisation of amphotericin B analogues and truncated polyketide intermediates produced by genetic engineering of *Streptomyces nodosus*," Org Biomol Chem. 8(16):3758-70 (2010).
Ochi et al., "New strategies for drug discovery: activation of silent or weakly expressed microbial gene clusters," Appl Microbiol Biotechnol. 97(1):87-98 (2013).
Ostrem et al., "Direct small-molecule inhibitors of KRAS: from structural insights to mechanism-based design," Nat Rev Drug Discov. 15(11): 771-785 (2016).
Ostrem et al., "K-Ras(G12C) inhibitors allosterically control GTP affinity and effector interactions," Nature. 503(7477):548-51 (2013) (14 pages).
Papageorgiou et al., "Improved binding affinity for cyclophilin A by a cyclosporin derivative singly modified at its effector domain," J Med Chem. 37(22):3674-6 (1994).
Pfeifer et al., "Biosynthesis of complex polyketides in a metabolically engineered strain of *E. coli*," Science. 291(5509):1790-2 (2001) (4 pages).
Pollock et al., "Development of Inhibitors of the Activated Form of KRAS$^{G12O}$," AACR Targeting RAS-Driven Cancers, Dec. 9-12, San Diego, California (Dec. 2018) (Abstract Included) (2 pages).
Power et al., "Engineered Synthesis of 7-Oxo- and 15-Deoxy-15-Oxo-Amphotericins: Insights into Structure-Activity Relationships in Polyene Antibiotics," Chem Biol. 15(1): 78-86 (2008).
PubChem CID 130196149, <https://pubchem.ncbi.nlm.nih.gov/compound/130196149>, retrieved on Apr. 1, 2020 (10 pages).
Quesniaux et al., "Cyclophilin binds to the region of cyclosporine involved in its immunosuppressive activity," Eur J Immunol. 17(9):1359-65 (1987).
Quesniaux et al., "Study of the conformation of cyclosporine in aqueous medium by means of monoclonal antibodies," Int J Pept Protein Res. 31(2):173-85 (1988).
Ranganathan et al., "Knowledge-based design of bimodular and trimodular polyketide synthases based on domain and module swaps: a route to simple statin analogues," Chem Biol. 6(10):731-41 (1999).

Ray et al., "New Electrophiles and Strategies for Mechanism-Based and Targeted Covalent Inhibitor Design," Biochemistry. 58: 5234-5244 (Dec. 2019).
Reid et al. "A model of structure and catalysis for ketoreductase domains in modular polyketide synthases," Biochemistry. 42(1):72-79 (2003).
Revill et al., "Genetically engineered analogs of ascomycin for nerve regeneration," J Pharmacol Exp Ther. 302(3): 1278-85 (2002).
Revolution Medicines, "Corporate Overview Q1 2021," Translating Frontier Oncology Targets to Outsmart Cancer™ (Apr. 30, 2021) (35 pages).
Revolution Medicines, "Corporate Overview Q1 2021," Translating Frontier Oncology Targets to Outsmart Cancer™ (Mar. 2, 2021) (35 pages).
Revolution Medicines, "Corporate Overview Q1-2021," Translating Frontier Oncology Targets to Outsmart Cancer™ (Jan. 12, 2021) (34 pages).
Revolution Medicines, "Corporate Overview Q2 2021," Translating Frontier Oncology Targets to Outsmart Cancer™ (May 10, 2021) (34 pages).
Revolution Medicines, "Corporate Overview," Translating Frontier Oncology Targets to Outsmart Cancer™ (Aug. 11, 2021) (43 pages).
Revolution Medicines, "Corporate Overview," Translating Frontier Oncology Targets to Outsmart Cancer™ (Feb. 8, 2021) (35 pages).
Revolution Medicines, "Drugging the RAS(ON) Form of Diverse Oncogenic RAS Mutations," RAS Targeted Drug Discovery: Expanding RAS Druggability Beyond G12C (Feb. 2021) (24 pages).
Revolution Medicines, "RMC-6291: Biological Features of Targeting KRAS$^{G12C}$(ON) and Potential Application to Overcoming Drug Resistance in RAS-Addicted Tumors," dated May 26, 2021 (17 pages).
Revolution Medicines, "Translating Frontier Oncology Targets to Outsmart Cancer™: Corporate Overview Q4-2020," dated Nov. 12, 2020 (30 pages).
Ruan et al., "Binding of rapamycin analogs to calcium channels and FKBP52 contributes to their neuroprotective activities," Proc Natl Acad Sci U S A. 105(1):33-8 (2008).
Rudolph, "Covalent Modification In Drug Discovery—A Chemist's Perspective," Pharmaceutical & BioScience Society. Dated Feb. 7, 2019 (39 pages).
Schulze et al., "Tri-Complex Inhibitors of the Oncogenic, GTP-Bound Form of KRAS$^{G12O}$ Overcome RTK-Mediated Escape Mechanisms and Drive Tumor Regressions in Vivo," Revolution Medicines (Oct. 2019) (1 page).
Schutt, "Safety Considerations for Covalent Inhibitors," Pharmaceutical & BioScience Society. Dated Feb. 7, 2019 (36 pages).
Schwecke et al., "The biosynthetic gene cluster for the polyketide immunosuppressant rapamycin," Proc Natl Acad Sci U S A. 92(17):7839-43 (1995).
Sebastiano et al., "Impact of Dynamically Exposed Polarity on Permeability and Solubility of Chameleonic Drugs Beyond the Rule of 5," J Med Chem. 61:4189-4202 (2018).
Shigdel et al., "Genomic discovery of an evolutionarily programmed modality for small-molecule targeting of an intractable protein surface," Proc Natl Acad Sci U S A. 117(29): 17195-203 (Jul. 2020).
Sieber et al., "Novel inhibitors of the calcineurin/NFATc hub—alternatives to CsA and FK506?" Cell Commun Signal. 7:25 (2009) (19 pages).
Simanshu et al., "RAS Proteins and Their Regulators in Human Disease," available in PMC Jun. 29, 2018, published in final edited form as: Cell. 170(1): 17-33 (2017) (34 pages).
Smith, "Translating Frontier Oncology Targets to Outsmart Cancer," RAS-Targeted Drug Discovery Summit, Revolution Medicines, Sep. 19 (2019) (29 pages).
Smulik et al., "Synthesis of cyclosporin A-derived affinity reagents by olefin metathesis," Org Lett. 4(12):2051-4 (2002).
Steadman et al., "Discovery of Potent Cyclophilin Inhibitors Based on the Structural Simplification of Sanglifehrin A," J Med Chem. 60:1000-1017 (2017).
Stewart et al., "Development of Inhibitors of the Activated Form of KRAS$^{G12C}$," AACR Targeting RAS-Driven Cancers, Dec. 9-12, San Diego, California. Poster B37 (2018) (1 page).

(56) References Cited

OTHER PUBLICATIONS

STN record of WO 2014/009774, available online Jan. 16, 2014 (4 pages).
STN record of WO 98/12217, available online Mar. 26, 1998 (6 pages).
Summons to attend oral proceedings pursuant to Rule 115(1) EPC for European Patent Application No. 16735470.3, dated Feb. 18, 2020 (7 pages).
Sun et al. "Design and structure-based study of new potential FKBP12 inhibitors," Biophys J. 85(5):3194-3201 (2003).
Sweeney et al., "From chemical tools to clinical medicines: non-immunosuppressive cyclophilin inhibitors derived from the cyclosporin and sanglifehrin scaffolds," J Med Chem. 57(17):7145-59 (2014) (63 pages).
Sánchez-Tillo et al., "Cyclophilin A is required for M-CSF-dependent macrophage proliferation," Eur J Immunol. 36(9):2515-2524 (2006).
Takakusagi et al., "Efficient one-cycle affinity selection of binding proteins or peptides specific for a small-molecule using a T7 phage display pool," Bioorg Med Chem. 16(22):9837-46 (2008).
Tanaka et al., "Clinical Acquired Resistance to KRAS$^{G12O}$ Inhibition through a Novel KRAS Switch-II Pocket Mutation and Polyclonal Alterations Converging on RAS-MAPK Reactivation," Cancer Discov. 11(8):1913-1922 (Apr. 6, 2021).
Tang et al., "Generation of New Epothilones by Genetic Engineering of a Polyketide Synthase in Myxococcus xanthus," J Antibiot (Tokyo). 58(3): 178-184 (2005).
UniProtKB Accession No. A0A061A618, Sep. 3, 2014, available <http://www.uniprot.org/uniprot/A0A061A618>, (12 pages).
UniProtKB Accession No. Q54296, "Polyketide synthase," <https://www.uniprot.org/uniprot/A0A61A618.txt?version=14>, retrieved May 29, 2020 (12 pages).
UniProtKB Accession No. Q54296, Nov. 1, 1996, available <http://www.uniprot.org/uniprot/Q54296>, (12 pages).
UniProtKB Accession No. Q54297, Nov. 1, 1996, available <https://www.uniprot.org/uniprot/Q54297.txt>, (3 pages).
Upadhyaya et al., "Direct Ras Inhibitors Identified From a Structurally Rigidified Bicyclic Peptide Library," available in PMC Oct. 21, 2015, published in final edited form as: Tetrahedron. 70(42):7714-7720 (2014) (15 pages).
Vakiti et al., "Stereoselective synthesis of C17-C34 fragment of antascomicin A," Tetrahedron Lett. 55(47):6438-40 (2014).
Vignot et al., "mTOR-targeted therapy of cancer with rapamycin derivatives," Ann Oncol. 16(4):525-37 (2005).
Wagner et al., "New naturally occurring amino acids," Angew Chem Int Ed Engl. 22(11): 816-28 (1983).
Wang et al., "Thermodynamic analysis of cyclosporin a binding to cyclophilin a in a lung tumor tissue lysate," Anal Chem. 76(15):4343-8 (2004).
Weissman et al., "Combinatorial biosynthesis of reduced polyketides," Nat Rev Microbiol. 3(12):925-36 (2005).
Weissman, "Genetic engineering of modular PKSs: from combinatorial biosynthesis to synthetic biology," Nat Prod Rep. 33(2):203-230 (2016).
Wildes et al., "Inhibition of the Oncogenic, GTP-Bound Form of KRAS$^{G12C}$ by Second Generation, Tri-Complex Inhibitors Overcomes RTK-Mediated Escape Mechanisms," The FASEB Regulation and Function of Small GTPases Conference, Jun. 23-28, Olean, New York (Abstract Included) (Jun. 2019) (2 pages).
Wilson et al., "Comparative X-ray structures of the major binding protein for the immunosuppressant FK506 (tacrolimus) in unliganded form and in complex with FK506 and rapamycin," Acta Cryst. D51:511-21 (1995).
Wright et al., "Multivalent binding in the design of bioactive compounds," Curr Org Chem. 5(11):1107-31 (2001).
Wu et al., "Creating diverse target-binding surfaces on FKBP12: synthesis and evaluation of a rapamycin analogue library," available in PMC Sep. 12, 2012, published in final edited form as: ACS Comb Sci. 13(5):486-95 (2011) (22 pages).
Wu et al., "Inhibition of ras-effector interactions by cyclic peptides," Med Chem Commun. 4(2):378-82 (2013).
Wu et al., "Synthesis of Ketone Analogues of Prolyl and Pipecolyl Ester FKBP12 Ligands," J Med Chem. 45(16):3558-3568 (2002).
Zhang et al., "Bifunctional Small-Molecule Ligands of K-Ras Induce Its Association with Immunophilin Proteins," Angew Chem Int Ed Engl. 131:16460-5 (Nov. 2019).
Zhou et al., "Biophysical and biochemical characterization of KRAS$^{G12C}$ inhibition through a novel modality," AACR Targeting RAS-Driven Cancers, Dec. 9-12, San Diego, California. Poster A06 (2018) (1 page).
Saeidian et al. "Effect of aromaticity and ring strain on proton affinity of aziridine and amidine skeletons: a DFT study," Journal of the Iranian Chemical Society. 17:1731-1741 (Mar. 2020) (11 pages).
Vocadlo et al. "Mechanistic insights into glycosidase chemistry," Curr Opin Chem Biol. 12:539-555 (2008) (17 pages).
Kümmerer, "Pharmaceuticals in the Environment," Annual Review of Environment and Resources. 35:57-75 (Nov. 2010) (Epub Aug. 18, 2010).
Bastin et al., "Salt selection and optimisation procedures for pharmaceutical new chemical entities," Org Process Res Dev 4(5):427-35 (2000).
Sánchez-Tillo et al., "Cyclophilin A is required for M-CSF-dependent macrophage proliferation," Eur J Immunol. 36(9):2515-24 (Sep. 2006).
Sieburth et al., "SUR-8, a conserved Ras-binding protein with leucine-rich repeats, positively regulates Ras-mediated signaling in C. elegans," Cell. 94(1):119-30 (Jul. 1998).
Dyson et al., Chemistry of synthetic medicines. *May's Chemistry of Synthetic Drugs, Fifth Edition*. Moscow: Mir. pp. 12-19 (1964) (9 Pages).

\* cited by examiner

KRAS Target Engagement

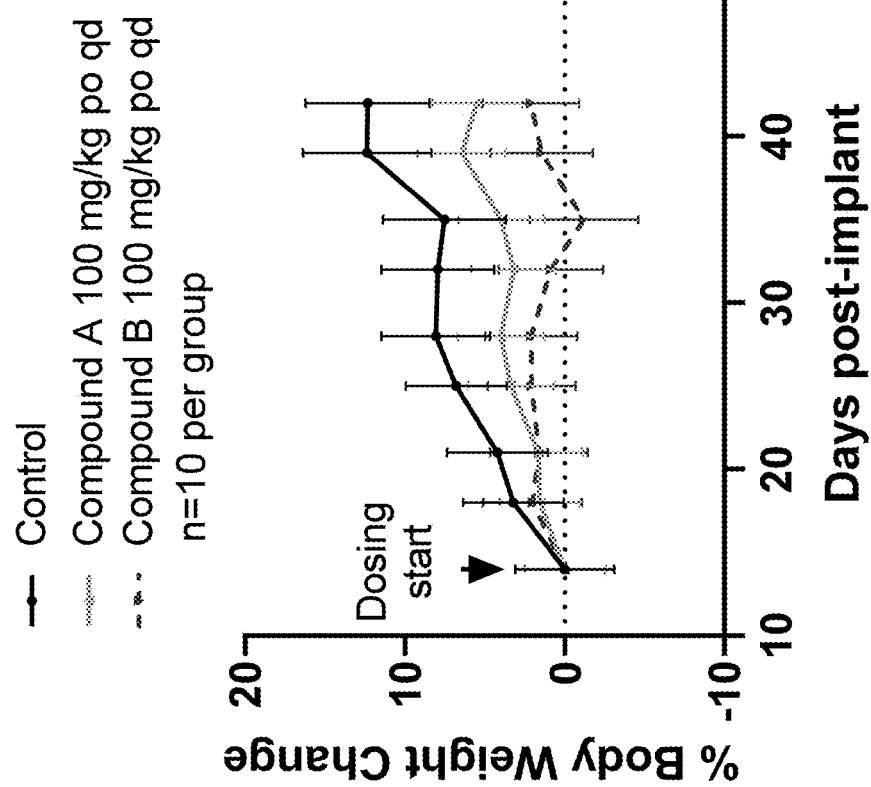

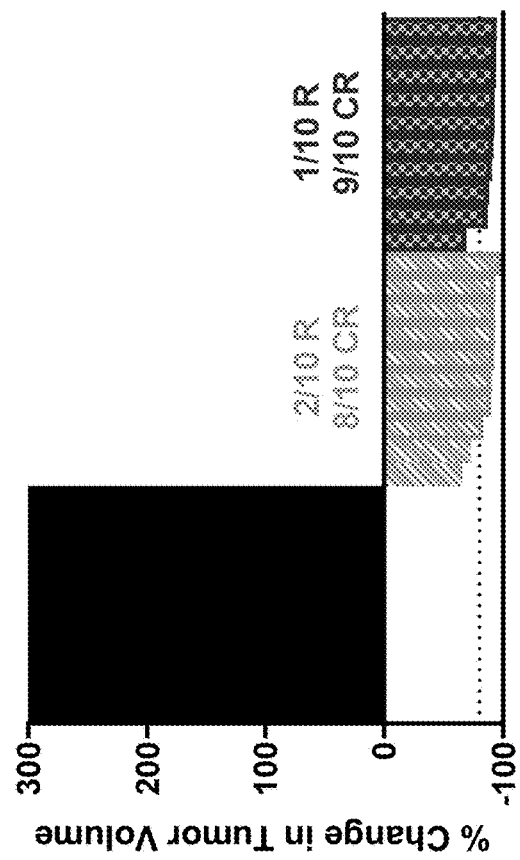

RAS INHIBITORS

BACKGROUND

The vast majority of small molecule drugs act by binding a functionally important pocket on a target protein, thereby modulating the activity of that protein. For example, cholesterol-lowering drugs known as statins bind the enzyme active site of HMG-COA reductase, thus preventing the enzyme from engaging with its substrates. The fact that many such drug/target interacting pairs are known may have misled some into believing that a small molecule modulator could be discovered for most, if not all, proteins provided a reasonable amount of time, effort, and resources. This is far from the case. Current estimates are that only about 10% of all human proteins are targetable by small molecules. Bojadzic and Buchwald, Curr Top Med Chem 18:674-699 (2019). The other 90% are currently considered refractory or intractable toward above-mentioned small molecule drug discovery. Such targets are commonly referred to as "undruggable." These undruggable targets include a vast and largely untapped reservoir of medically important human proteins. Thus, there exists a great deal of interest in discovering new molecular modalities capable of modulating the function of such undruggable targets.

It has been well established in literature that Ras proteins (K-Ras, H-Ras and N-Ras) play an essential role in various human cancers and are therefore appropriate targets for anticancer therapy. Indeed, mutations in Ras proteins account for approximately 30% of all human cancers in the United States, many of which are fatal. Dysregulation of Ras proteins by activating mutations, overexpression or upstream activation is common in human tumors, and activating mutations in Ras are frequently found in human cancer. For example, activating mutations at codon 12 in Ras proteins function by inhibiting both GTPase-activating protein (GAP)-dependent and intrinsic hydrolysis rates of GTP, significantly skewing the population of Ras mutant proteins to the "on" (GTP-bound) state (Ras (ON)), leading to oncogenic MAPK signaling. Notably, Ras exhibits a picomolar affinity for GTP, enabling Ras to be activated even in the presence of low concentrations of this nucleotide. Mutations at codons 13 (e.g., G13D) and 61 (e.g., Q61K) of Ras are also responsible for oncogenic activity in some cancers.

Despite extensive drug discovery efforts against Ras during the last several decades, only a drug targeting the K-Ras G12C mutant has been approved (sotorasib). Additional efforts are needed to uncover additional medicines for cancers driven by other Ras mutations.

SUMMARY

Provided herein are Ras inhibitors. The approach described herein entails formation of a high affinity three-component complex, or conjugate, between a synthetic ligand and two intracellular proteins which do not interact under normal physiological conditions: the target protein of interest (e.g., Ras), and a widely expressed cytosolic chaperone (presenter protein) in the cell (e.g., cyclophilin A). More specifically, in some embodiments, the inhibitors of Ras described herein induce a new binding pocket in Ras by driving formation of a high affinity tri-complex, or conjugate, between the Ras protein and the widely expressed cytosolic chaperone, cyclophilin A (CYPA). Without being bound by theory, the inventors believe that one way the inhibitory effect on Ras is effected by compounds of the invention and the complexes, or conjugates, they form is by steric occlusion of the interaction site between Ras and downstream effector molecules, such as RAF and PI3K, which are required for propagating the oncogenic signal.

As such, in some embodiments, the invention features a compound, or pharmaceutically acceptable salt thereof, of structural Formula I:

Formula I

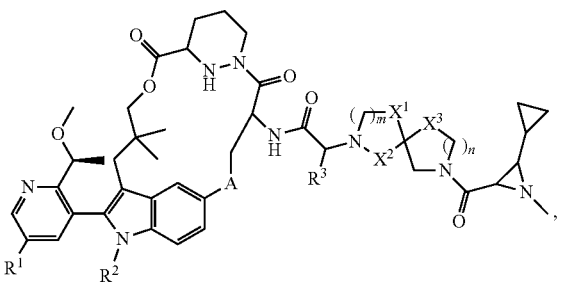

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$X^1$, $X^2$, and $X^3$ are each independently selected from $CH_2$, $CF_2$, C=O, or O;

m is 1 or 2;

n is 0 or 1;

$R^1$ is hydrogen, optionally substituted $C_1$-$C_6$ heteroalkyl, or optionally substituted 3 to 10-membered heterocycloalkyl;

$R^2$ is optionally substituted $C_1$-$C_6$ alkyl; and $R^3$ is optionally substituted $C_1$-$C_6$ alkyl, optionally substituted 3 to 6-membered cycloalkyl, or optionally substituted heterocycloalkyl, and wherein each hydrogen is independently, optionally, isotopically enriched for deuterium.

In some embodiments, the invention features a compound, or pharmaceutically acceptable salt thereof, of structural Formula II:

Formula II

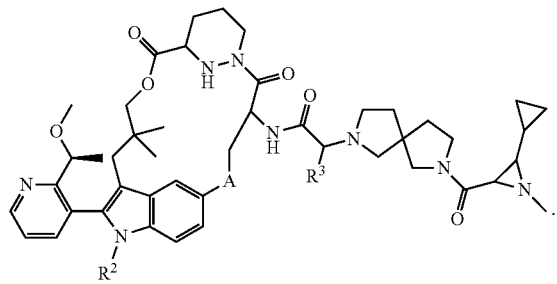

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$R^2$ is optionally substituted $C_1$-$C_6$ alkyl; and $R^3$ is optionally substituted $C_1$-$C_6$ alkyl, optionally substituted 3 to 6-membered cycloalkyl, or optionally substituted heterocycloalkyl, and wherein each hydrogen is independently, optionally, isotopically enriched for deuterium.

In some embodiments, the invention features a compound, or pharmaceutically acceptable salt thereof, of structural Formula V:

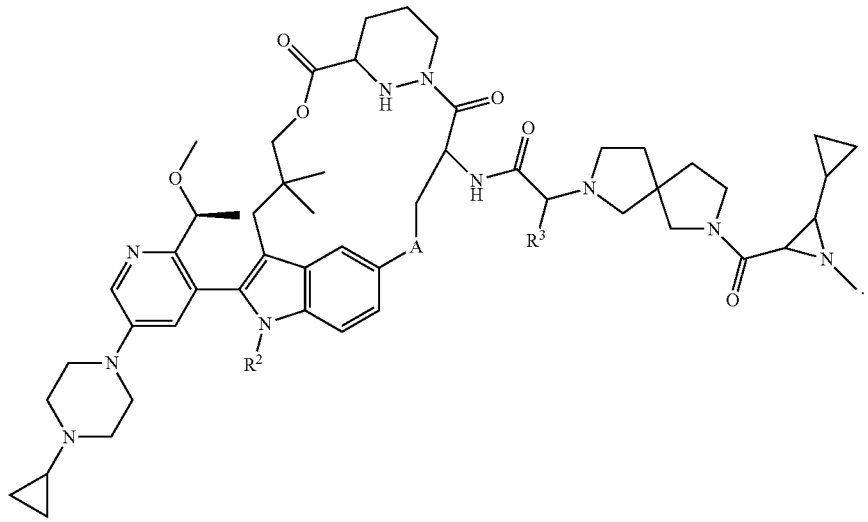

Formula V wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$R^2$ is optionally substituted $C_1$-$C_6$ alkyl; and $R^3$ is optionally substituted $C_1$-$C_6$ alkyl, optionally substituted 3 to 6-membered cycloalkyl, or optionally substituted heterocycloalkyl, and wherein each hydrogen is independently, optionally, isotopically enriched for deuterium.

In some embodiments, the invention features a compound, or pharmaceutically acceptable salt thereof, of structural Formula VI:

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$R^2$ is optionally substituted $C_1$-$C_6$ alkyl; and $R^3$ is optionally substituted $C_1$-$C_6$ alkyl, optionally substituted 3 to 6-membered cycloalkyl, or optionally substituted heterocycloalkyl, and wherein each hydrogen is independently, optionally, isotopically enriched for deuterium.

In some embodiments, the invention features a compound, or pharmaceutically acceptable salt thereof, of structural Formula VII:

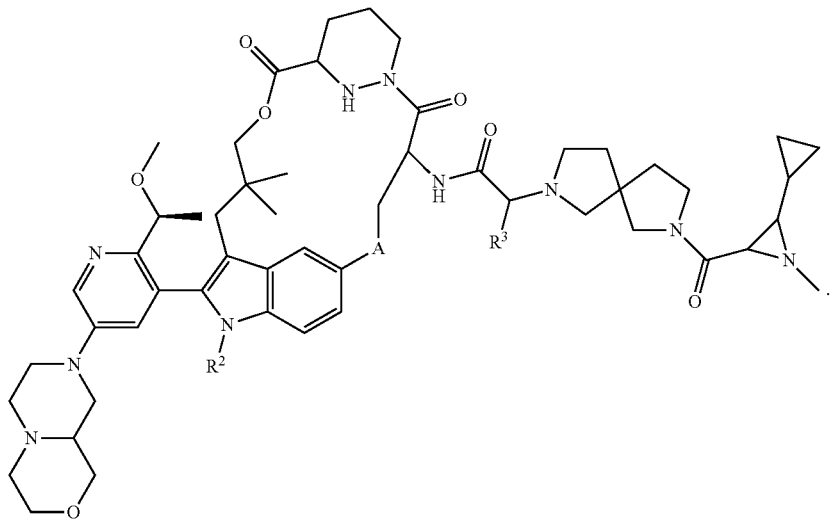

Formula VI

Formula VII

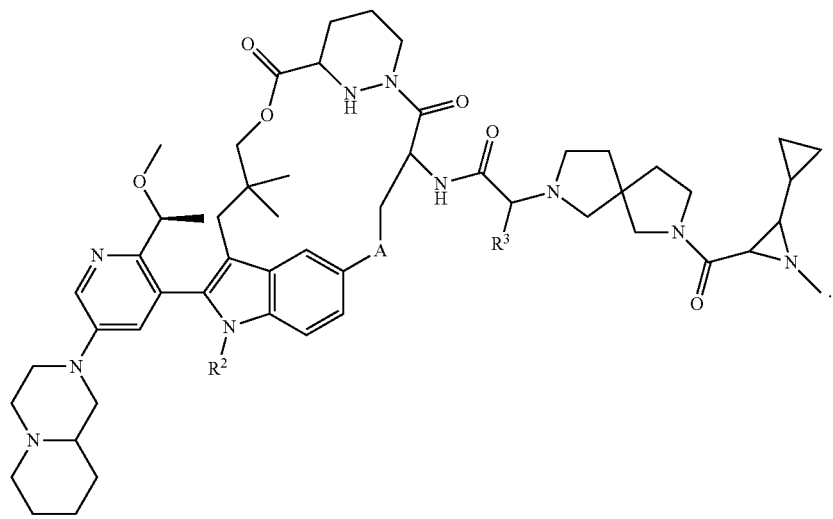

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$R^2$ is optionally substituted $C_1$-$C_6$ alkyl; and $R^3$ is optionally substituted $C_1$-$C_6$ alkyl, optionally substituted 3 to 6-membered cycloalkyl, or optionally substituted heterocycloalkyl, and wherein each hydrogen is independently, optionally, isotopically enriched for deuterium.

In some embodiments, the invention also features a compound, or pharmaceutically acceptable salt thereof, selected from Table 1 or Table 2.

Also provided are pharmaceutical compositions comprising a compound of Formula I, Formula II, Formula V, Formula VI, or Formula VII or a pharmaceutically acceptable salt thereof, and a pharmaceutically acceptable excipient. Also provided are pharmaceutical compositions comprising a compound of Table 1 or Table 2, or a pharmaceutically acceptable salt thereof, and a pharmaceutically acceptable excipient.

Also provided is a method of treating cancer in a subject in need thereof, the method comprising administering to the subject a therapeutically effective amount of a compound of the present invention, or a pharmaceutically acceptable salt thereof.

In some embodiments, a method is provided of treating a Ras protein-related disorder in a subject in need thereof, the method comprising administering to the subject a therapeutically effective amount of a compound of the present invention, or a pharmaceutically acceptable salt thereof.

Further provided is a method of inhibiting a Ras protein in a cell, the method comprising contacting the cell with an effective amount of a compound of the present invention, or a pharmaceutically acceptable salt thereof.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

Definitions and Chemical Terms

In this application, unless otherwise clear from context, (i) the term "a" means "one or more"; (ii) the term "or" is used to mean "and/or" unless explicitly indicated to refer to alternatives only or the alternative are mutually exclusive, although the invention supports a definition that refers to only alternatives and "and/or"; (iii) the terms "comprising" and "including" are understood to encompass itemized components or steps whether presented by themselves or together with one or more additional components or steps; and (iv) where ranges are provided, endpoints are included.

As used herein, the term "about" is used to indicate that a value includes the standard deviation of error for the device or method being employed to determine the value. In certain embodiments, the term "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of a stated value, unless otherwise stated or otherwise evident from the context (e.g., where such number would exceed 100% of a possible value).

As used herein, the term "adjacent" in the context of describing adjacent atoms refers to bivalent atoms that are directly connected by a covalent bond.

A "compound of the present invention" and similar terms as used herein, whether explicitly noted or not, refers to Ras inhibitors described herein, including compounds of any one of Formula I to Formula VII, or subformula thereof, and compounds of Table 1 or Table 2, as well as salts (e.g., pharmaceutically acceptable salts), solvates, hydrates, stereoisomers (including atropisomers), and tautomers thereof.

The term "wild-type" refers to an entity having a structure or activity as found in nature in a "normal" (as contrasted with mutant, diseased, altered, etc.) state or context. Those of ordinary skill in the art will appreciate that wild-type genes and polypeptides often exist in multiple different forms (e.g., alleles).

Those skilled in the art will appreciate that certain compounds described herein can exist in one or more different isomeric (e.g., stereoisomers, geometric isomers, atropisomers, tautomers) or isotopic (e.g., in which one or more atoms has been substituted with a different isotope of the atom, such as hydrogen substituted for deuterium) forms.

Unless otherwise indicated or clear from context, a depicted structure can be understood to represent any such isomeric or isotopic form, individually or in combination.

Compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

In some embodiments, one or more compounds depicted herein may exist in different tautomeric forms. As will be clear from context, unless explicitly excluded, references to such compounds encompass all such tautomeric forms. In some embodiments, tautomeric forms result from the swapping of a single bond with an adjacent double bond and the concomitant migration of a proton. In certain embodiments, a tautomeric form may be a prototropic tautomer, which is an isomeric protonation states having the same empirical formula and total charge as a reference form. Examples of moieties with prototropic tautomeric forms are ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. In some embodiments, tautomeric forms can be in equilibrium or sterically locked into one form by appropriate substitution. In certain embodiments, tautomeric forms result from acetal interconversion.

Unless otherwise stated, structures depicted herein are also meant to include compounds that differ only in the presence of one or more isotopically enriched atoms. Exemplary isotopes that can be incorporated into compounds of the present invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically-labeled compounds (e.g., those labeled with 3H and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Preparations of isotopically labelled compounds are known to those of skill in the art. For example, isotopically labeled compounds can generally be prepared by following procedures analogous to those disclosed for compounds of the present invention described herein, by substituting an isotopically labeled reagent for a non-isotopically labeled reagent.

As used interchangeably herein, "deuterium substituted," "deuterated," or "deuterium enriched," refer to a compound of the invention, or a moiety thereof, with a level of deuterium (D or $^{2}H$) that has been enriched to be greater than 0.015%, the natural abundance of deuterium. In certain embodiments, a composition of the invention has a minimum isotopic enrichment factor of at least 5 (0.075% deuterium incorporation), e.g., at least 10 (0.15% deuterium incorporation). In other embodiments, a composition has an isotopic enrichment factor of at least 50 (0.75% deuterium incorporation), at least 500 (7.5% deuterium incorporation), at least 2000 (30% deuterium incorporation), at least 3000 (45% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), or at least 6600 (99% deuterium incorporation).

Non-limiting examples of moieties that may contain one or more deuterium substitutions in compounds of the present invention, where any position "R" may be deuterium (D), include

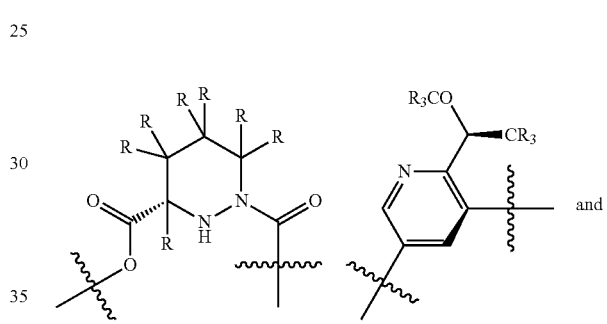

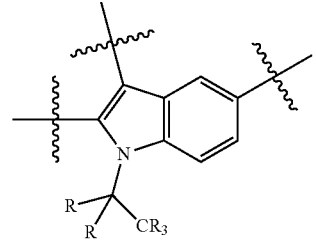

Additional examples include moieties such as

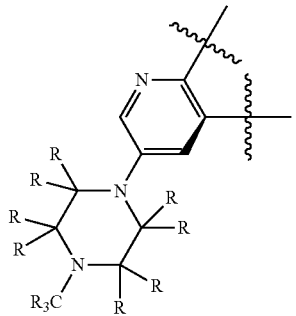

-continued

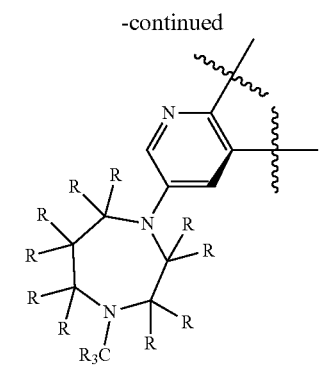

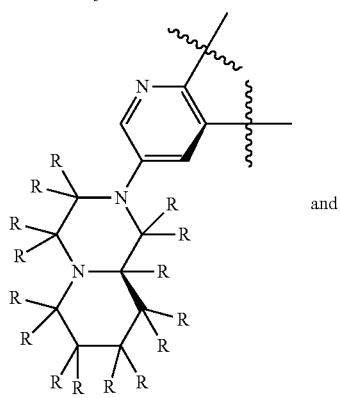
and

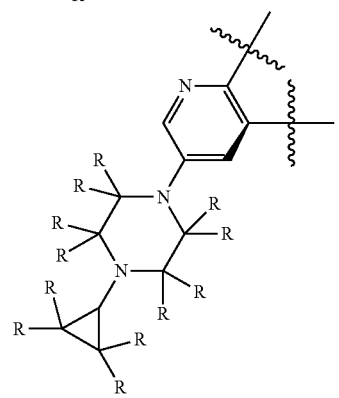

and deuteration of similar R¹-type moieties, wherein the definition of R¹ is found herein (e.g., in compounds of any one of Formulas I-VII). Deuteration of moieties within a cross-linking group (e.g., an optionally substituted aziridine moiety) in compounds of the present invention are also contemplated, where the cross-linking group is defined herein (see, e.g., generic Formulas I-VII and subformulas thereof as well as specific examples of W described herein, such as

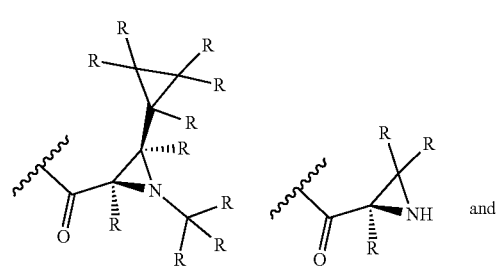
and

-continued

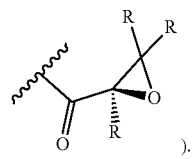
).

Moreover, deuteration of available positions in any A moiety of compounds of the Formulas described herein is also contemplated, such as

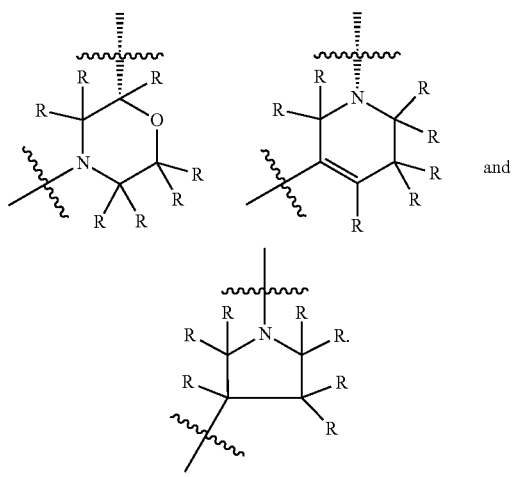
and

Further, deuterium substitution may also take place in compounds of the present invention at the linker position of compounds of the Formulas described herein, such as

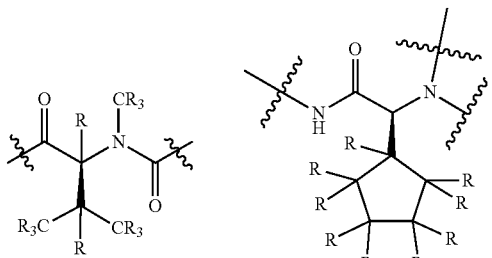

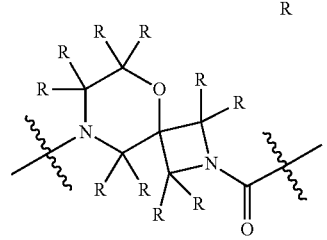

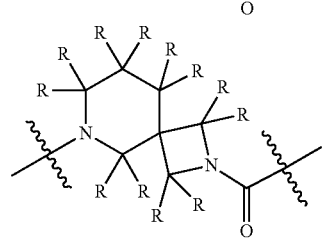

-continued

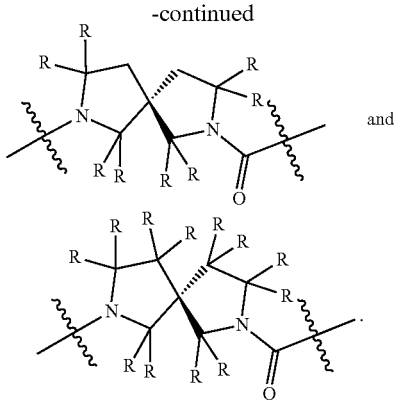

and

In a further embodiment, silylation substitution is also contemplated, such as in the linker position as follows:

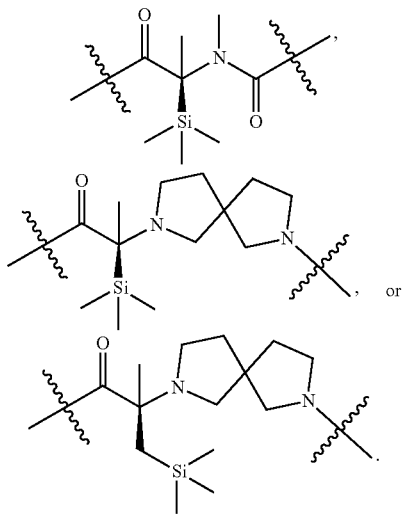

Additional examples of silylation include moieties such as

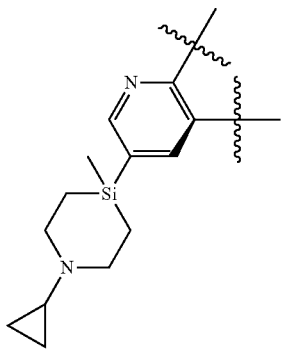

and silylation substitution of similar $R^1$-type moieties, wherein the definition of $R^1$ is found herein (e.g., in compounds of any one of Formulas I-VII).

As is known in the art, many chemical entities can adopt a variety of different solid forms such as, for example, amorphous forms or crystalline forms (e.g., polymorphs, hydrates, solvate). In some embodiments, compounds of the present invention may be utilized in any such form, including in any solid form. In some embodiments, compounds described or depicted herein may be provided or utilized in hydrate or solvate form.

At various places in the present specification, substituents of compounds of the present invention are disclosed in groups or in ranges. It is specifically intended that the present invention include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl. Furthermore, where a compound includes a plurality of positions at which substituents are disclosed in groups or in ranges, unless otherwise indicated, the present invention is intended to cover individual compounds and groups of compounds (e.g., genera and subgenera) containing each and every individual subcombination of members at each position.

The term "optionally substituted X" (e.g., "optionally substituted alkyl") is intended to be equivalent to "X, wherein X is optionally substituted" (e.g., "alkyl, wherein said alkyl is optionally substituted"). It is not intended to mean that the feature "X" (e.g., alkyl) per se is optional. As described herein, certain compounds of interest may contain one or more "optionally substituted" moieties. In general, the term "substituted", whether preceded by the term "optionally" or not, means that one or more hydrogens of the designated moiety are replaced with a suitable substituent, e.g., any of the substituents or groups described herein. Unless otherwise indicated, an "optionally substituted" group may have a suitable substituent at each substitutable position of the group, and when more than one position in any given structure may be substituted with more than one substituent selected from a specified group, the substituent may be either the same or different at every position. For example, in the term "optionally substituted $C_1$-$C_6$ alkyl-$C_2$-$C_9$ heteroaryl," the alkyl portion, the heteroaryl portion, or both, may be optionally substituted. Combinations of substituents envisioned by the present invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group may be, independently, deuterium; halogen; —$(CH_2)_{0-4}R°$; —$(CH_2)_{0-4}OR°$; —$O(CH_2)_{0-4}R°$; —$O$—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-1}(CH_2)_{0-1}Ph$ which may be substituted with $R°$; —$CH=CHPh$, which may be substituted with $R°$; —$(CH_2)_{0-4}O(CH_2)_{0-1}$-pyridyl which may be substituted with $R°$; 4 to 8-membered saturated or unsaturated heterocycloalkyl (e.g., pyridyl); 3 to 8-membered saturated or unsaturated cycloalkyl (e.g., cyclopropyl, cyclobutyl, or cyclopentyl); —$NO_2$; —$CN$; —$N_3$; —$(CH_2)_{0-4}$—$N(R°_2$; —$(CH_2)_{0-4}N(R°)C(O)R°$; —$N(R°C(S)R°$; —$(CH_2)_{0-4}N(R°C(O)$ $NR°_2$; —$N(R°C(S)NR°_2$; —$(CH_2)_{0-4}N(R°C(O)OR°$; —$N(R°N(R°C(O)R°$; —$N(R°N(R°C(O)NR°_2$; —$N(R°N(R°C(O)OR°$; —$(CH_2)_{0-4}C(O)R°$; —$C(S)R°$; —$(CH_2)_{0-4}C(O)OR°$; —$(CH_2)_{0-4}$—$C(O)$—$N(R°_2$; —$(CH_2)_{0-4}$—$C(O)$—$N(R°)$—$S(O)_2$—$R°$; —$C(NCN) NR°_2$; —$(CH_2)_{0-4}C(O)SR°$; —$(CH_2)_{0-4}C(O)OSi$ $R°_3$; —$(CH_2)_{0-4}OC(O)R°$; —$OC(O)(CH_2)_{0-4}SR°$; —$SC(S) SR°$; —$(CH_2)_{0-4}SC(O)R°$; —$(CH_2)_{0-4}C(O)NR°_2$; —$C(S) NR°_2$; —$C(S) SR°$; —$(CH_2)_{0-4}OC(O)NR°_2$; —$C(O)N(OR°)R°$;

—C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°S(O)$_2$NR°$_2$; —N(R°)S(O)$_2$R°; —N(OR°) R°; —C(NOR°)NR°$_2$; —C(NH) NR°$_2$; —P(O)$_2$R°; —P(O)R°$_2$; —P(O)(OR°)$_2$; —OP(O)R°$_2$; —OP(O)(OR°)$_2$; —OP(O)(OR°)R°, —SiR°$_3$; —(C$_1$-C$_4$ straight or branched) alkylene)O—N(R°)$_2$; or —(C$_1$-C$_4$ straight or branched) alkylene) C(O)O—N(R°)$_2$, wherein each R° may be substituted as defined below and is independently hydrogen, —C$_1$-C$_6$ aliphatic, —CH$_2$Ph, —O(CH$_2$)$_{0-1}$Ph, —CH$_2$-(5 to 6 membered heteroaryl ring), or a 3 to 6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3 to 12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), may be, independently, halogen, —(CH$_2$)$_{0-2}$R°, (haloR●), —(CH$_2$)$_{0-2}$OH, —(CH$_2$)$_{0-2}$OR●, —(CH$_2$)$_{0-2}$CH(OR●)$_2$, —O(haloR●), —CN, —N$_3$, —(CH$_2$)$_{0-2}$C(O)R°, —(CH$_2$)$_{0-2}$C(O)OH, —(CH$_2$)$_{0-2}$C(O)OR●, —(CH$_2$)$_{0-2}$SR●, —(CH$_2$)$_{0-2}$SH, —(CH$_2$)$_{0-2}$NH$_2$, —(CH$_2$)$_{0-2}$NHR●, —(CH$_2$)$_{0-2}$NR●$_2$, —NO$_2$, —SiR●$_3$, —OSiR●$_3$, —C(O)SR●—(C$_{1-4}$ straight or branched alkylene) C(O)OR●, or —SSR● wherein each R● is unsubstituted or where preceded by "halo" is substituted only with one or more halogens, and is independently selected from C$_1$-C$_4$ aliphatic, —CH$_2$Ph, —O(CH$_2$)$_{0-1}$Ph, or a 5 to 6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_1$-C$_6$ aliphatic which may be substituted as defined below, or an unsubstituted 5 to 6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_1$-C$_6$ aliphatic which may be substituted as defined below, or an unsubstituted 5 to 6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_1$-C$_4$ aliphatic, —CH$_2$Ph, —O(CH$_2$)$_{0-1}$Ph, or a 5 to 6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O) CH$_2$C(O) R†, —S(O)$_2$R†, —S(O)$_2$NR†$_2$, —C(S) NR†$_2$, —C(NH) NR†$_2$, or —N(R†)S(O)$_2$R†; wherein each R† is independently hydrogen, C$_1$-C$_6$ aliphatic which may be substituted as defined below, unsubstituted —OPh, or an unsubstituted 3 to 6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3 to 12-membered saturated, partially unsaturated, or aryl mono- or bicyclic ring having 0-4 heteroatoms independently selected from nitrogen, oxygen, or sulfur.

Suitable substituents on an aliphatic group of R† are independently halogen, —R●, -(haloR●), —OH, —OR●, —O (haloR●), —CN, —C(O) OH, —C(O)OR●, —NH$_2$, —NHR●, —NR●$_2$, or —NO$_2$, wherein each R● is unsubstituted or where preceded by "halo" is substituted only with one or more halogens, and is independently C$_1$-C$_4$ aliphatic, —CH$_2$Ph, —O(CH$_2$)$_{0-1}$Ph, or a 5 to 6-membered saturated, partially unsaturated, or aryl ring having 0-4 heteroatoms independently selected from nitrogen, oxygen, or sulfur. Suitable divalent substituents on a saturated carbon atom of R† include =O and =S.

The term "acetyl," as used herein, refers to the group —C(O)CH$_3$.

The term "alkoxy," as used herein, refers to a —O—C$_1$-C$_{20}$ alkyl group, wherein the alkoxy group is attached to the remainder of the compound through an oxygen atom.

The term "alkyl," as used herein, refers to a saturated, straight or branched monovalent hydrocarbon group containing from 1 to 20 (e.g., from 1 to 10 or from 1 to 6) carbons. In some embodiments, an alkyl group is unbranched (i.e., is linear); in some embodiments, an alkyl group is branched. Alkyl groups are exemplified by, but not limited to, methyl, ethyl, n- and iso-propyl, n-, sec-, iso- and tert-butyl, and neopentyl.

The term "alkylene," as used herein, represents a saturated divalent hydrocarbon group derived from a straight or branched chain saturated hydrocarbon by the removal of two hydrogen atoms, and is exemplified by methylene, ethylene, isopropylene, and the like. The term "C$_x$-C$_y$ alkylene" represents alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., C$_1$-C$_6$, C$_1$-C$_{10}$, C$_2$-C$_{20}$, C$_2$-C$_6$, C$_2$-C$_{10}$, or C$_2$-C$_{20}$ alkylene). In some embodiments, the alkylene can be further substituted with 1, 2, 3, or 4 substituent groups as defined herein.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, and 2-butenyl. Alkenyls include both cis and trans isomers. The term "alkenylene," as used herein, represents a divalent straight or branched chain groups of, unless otherwise specified, from 2 to 20 carbons (e.g., from 2 to 6 or from 2 to 10 carbons) containing one or more carbon-carbon double bonds.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, and 1-propynyl.

The term "amino," as used herein, represents -N(Rt) 2, e.g., —NH$_2$ and —N(CH$_3$)$_2$.

The term "aminoalkyl," as used herein, represents an alkyl moiety substituted on one or more carbon atoms with one or more amino moieties.

The term "amino acid," as described herein, refers to a molecule having a side chain, an amino group, and an acid group (e.g., —CO$_2$H or —SO$_3$H), wherein the amino acid is attached to the parent molecular group by the side chain, amino group, or acid group (e.g., the side chain). As used herein, the term "amino acid" in its broadest sense, refers to any compound or substance that can be incorporated into a polypeptide chain, e.g., through formation of one or more peptide bonds. In some embodiments, an amino acid has the general structure H$_2$N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. Exemplary amino acids include alanine, arginine, asparagine, aspartic acid, cysteine, glutamic acid, glutamine, glycine, histidine, optionally substituted hydroxylnorvaline, isoleucine, leucine, lysine, methionine, norvaline, ornithine, phenylalanine, proline, pyrrolysine, selenocysteine, serine, taurine, threonine, tryptophan, tyrosine, and valine.

The term "aryl," as used herein, represents a monovalent monocyclic, bicyclic, or multicyclic ring system formed by carbon atoms, wherein the ring attached to the pendant group is aromatic. Examples of aryl groups are phenyl, naphthyl, phenanthrenyl, and anthracenyl. An aryl ring can be attached to its pendant group at any heteroatom or carbon ring atom that results in a stable structure and any of the ring atoms can be optionally substituted unless otherwise specified.

The term "C$_0$," as used herein, represents a bond. For example, part of the term —N(C(O))—(C$_0$-C$_5$ alkylene-H)— includes —N(C(O))—(C$_0$ alkylene-H)—, which is also represented by —N(C(O))—H)—.

The terms "carbocyclic" and "carbocyclyl," as used herein, refer to a monovalent, optionally substituted 3 to 12-membered monocyclic, bicyclic, or tricyclic ring structure, which may be bridged, fused or spirocyclic, in which all the rings are formed by carbon atoms and at least one ring is non-aromatic. Carbocyclic structures include cycloalkyl, cycloalkenyl, and cycloalkynyl groups. Examples of carbocyclyl groups are cyclohexyl, cyclohexenyl, cyclooctynyl, 1,2-dihydronaphthyl, 1,2,3,4-tetrahydronaphthyl, fluorenyl, indenyl, indanyl, decalinyl, and the like. A carbocyclic ring can be attached to its pendant group at any ring atom that results in a stable structure and any of the ring atoms can be optionally substituted unless otherwise specified.

The term "carbonyl," as used herein, represents a C(O) group, which can also be represented as C=O.

The term "carboxyl," as used herein, means —CO$_2$H, (C=O)(OH), COOH, or C(O)OH or the unprotonated counterparts.

The term "cyano," as used herein, represents a —CN group.

The term "cycloalkyl," as used herein, represents a monovalent saturated cyclic hydrocarbon group, which may be bridged, fused, or spirocyclic having from three to eight ring carbons, unless otherwise specified, and is exemplified by cyclopropyl, cyclobutyl, cyclopentyl, cyclohexyl, cycloheptyl, and cycloheptyl.

The term "cycloalkenyl," as used herein, represents a monovalent, non-aromatic, saturated cyclic hydrocarbon group, which may be bridged, fused, or spirocyclic having from three to eight ring carbons, unless otherwise specified, and containing one or more carbon-carbon double bonds.

The term "diastereomer," as used herein, means stereoisomers that are not mirror images of one another and are non-superimposable on one another.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "haloacetyl," as used herein, refers to an acetyl group wherein at least one of the hydrogens has been replaced by a halogen.

The term "haloalkyl," as used herein, represents an alkyl moiety substituted on one or more carbon atoms with one or more of the same of different halogen moieties.

The term "halogen," as used herein, represents a halogen selected from bromine, chlorine, iodine, or fluorine.

The term "heteroalkyl," as used herein, refers to an "alkyl" group, as defined herein, in which at least one carbon atom has been replaced with a heteroatom (e.g., an O, N, or S atom). The heteroatom may appear in the middle or at the end of the radical.

The term "heteroaryl," as used herein, represents a monovalent, monocyclic or polycyclic ring structure that contains at least one fully aromatic ring: i.e., they contain 4n+2 pi electrons within the monocyclic or polycyclic ring system and contains at least one ring heteroatom selected from N, O, or S in that aromatic ring. Exemplary unsubstituted heteroaryl groups are of 1 to 12 (e.g., 1 to 11, 1 to 10, 1 to 9, 2 to 12, 2 to 11, 2 to 10, or 2 to 9) carbons. The term "heteroaryl" includes bicyclic, tricyclic, and tetracyclic groups in which any of the above heteroaromatic rings is fused to one or more, aryl or carbocyclic rings, e.g., a phenyl ring, or a cyclohexane ring. Examples of heteroaryl groups include, but are not limited to, pyridyl, pyrazolyl, benzoxazolyl, benzoimidazolyl, benzothiazolyl, imidazolyl, thiazolyl, quinolinyl, tetrahydroquinolinyl, and 4-azaindolyl. A heteroaryl ring can be attached to its pendant group at any ring atom that results in a stable structure and any of the ring atoms can be optionally substituted unless otherwise specified. In some embodiment, the heteroaryl is substituted with 1, 2, 3, or 4 substituents groups.

The term "heterocycloalkyl," as used herein, represents a monovalent, monocyclic, bicyclic or polycyclic ring system, which may be bridged, fused, or spirocyclic, wherein at least one ring is non-aromatic and wherein the non-aromatic ring contains one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocycloalkyl groups are of 1 to 12 (e.g., 1 to 11, 1 to 10, 1 to 9, 2 to 12, 2 to 11, 2 to 10, or 2 to 9) carbons. The term "heterocycloalkyl" also represents a heterocyclic compound having a bridged multicyclic structure in which one or more carbons or heteroatoms bridges two non-adjacent members of a monocyclic ring, e.g., a quinuclidinyl group. The term "heterocycloalkyl" includes bicyclic, tricyclic, and tetracyclic groups in which any of the above heterocyclic rings is fused to one or more aromatic, carbocyclic, heteroaromatic, or heterocyclic rings, e.g., an aryl ring, a cyclohexane ring, a cyclohexene ring, a cyclopentane ring, a cyclopentene ring, a pyridine ring, or a pyrrolidine ring. Examples of heterocycloalkyl groups are pyrrolidinyl, piperidinyl, 1,2,3,4-tetrahydroquinolinyl, decahydroquinolinyl, dihydropyrrolopyridine, and decahydronapthyridinyl. A heterocycloalkyl ring can be attached to its pendant group at any ring atom that results in a stable structure and any of the ring atoms can be optionally substituted unless otherwise specified.

The term "hydroxy," as used herein, represents a-OH group.

The term "hydroxyalkyl," as used herein, represents an alkyl moiety substituted on one or more carbon atoms with one or more-OH moieties.

The term "isomer," as used herein, means any tautomer, stereoisomer, atropiosmer, enantiomer, or diastereomer of any compound of the invention. It is recognized that the compounds of the invention can have one or more chiral centers or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

As used herein, a "monovalent organic moiety" is less than 500 kDa. In some embodiments, a "monovalent organic moiety" is less than 400 kDa. In some embodiments, a "monovalent organic moiety" is less than 300 kDa. In some embodiments, a "monovalent organic moiety" is less than 200 kDa. In some embodiments, a "monovalent organic moiety" is less than 100 kDa. In some embodiments, a "monovalent organic moiety" is less than 50 kDa. In some embodiments, a "monovalent organic moiety" is less than 25 kDa. In some embodiments, a "monovalent organic moiety" is less than 20 kDa. In some embodiments, a "monovalent organic moiety" is less than 15 kDa. In some embodiments, a "monovalent organic moiety" is less than 10 kDa. In some embodiments, a "monovalent organic moiety" is less than 1 kDa. In some embodiments, a "monovalent organic moiety" is less than 500 g/mol. In some embodiments, a "monovalent organic moiety" ranges between 500 g/mol and 500 kDa.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers or conformers of the basic molecular structure, including atropisomers. Some compounds of the present invention may exist in different tautomeric forms, all of the latter being included within the scope of the present invention.

The term "sulfonyl," as used herein, represents an —S(O)$_2$— group.

The term "thiocarbonyl," as used herein, refers to a —C(S)— group.

Those of ordinary skill in the art, reading the present invention, will appreciate that certain compounds described herein may be provided or utilized in any of a variety of forms such as, for example, salt forms, protected forms, pro-drug forms, ester forms, isomeric forms (e.g., optical or structural isomers), isotopic forms, etc. In some embodiments, reference to a particular compound may relate to a specific form of that compound. In some embodiments, reference to a particular compound may relate to that compound in any form. In some embodiments, for example, a preparation of a single stereoisomer of a compound may be considered to be a different form of the compound than a racemic mixture of the compound; a particular salt of a compound may be considered to be a different form from another salt form of the compound; a preparation containing one conformational isomer ((Z) or (E)) of a double bond may be considered to be a different form from one containing the other conformational isomer ((E) or (Z)) of the double bond; a preparation in which one or more atoms is a different isotope than is present in a reference preparation may be considered to be a different form.

BRIEF DESCRIPTION OF THE DRAWINGS

FIG. 3B shows that there was no body weight loss observed from either Compound A (100 mg/kg po qd) or Compound B (100 mg/kg po qd), indicating both compounds at 100 mg/kg are well tolerated in a human pancreatic adenocarcinoma HPAC KRASG12D/wt mouse xenograft model.

FIG. 3C shows that 8 out 10 tumors and 9 out 10 tumors reached complete regression (complete regression defined as >85% tumor regression from baseline) at Day 28 in Compound A (100 mg/kg po qd) and Compound B (100 mg/kg po qd) groups, respectively, in a human pancreatic adenocarcinoma HPAC KRASG12D/wt mouse xenograft model.

DETAILED DESCRIPTION

Compounds

Figure 1:
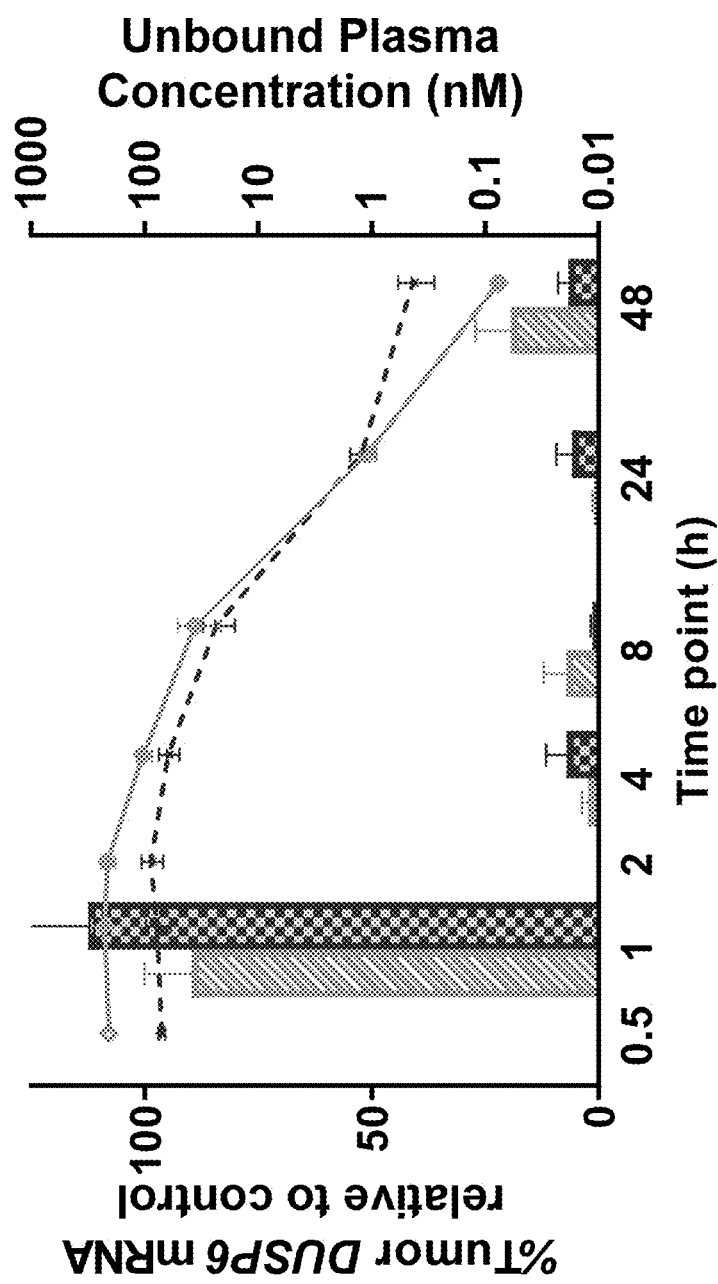
FIG. 1 shows that covalent KRAS G12D inhibitors, Compound A and Compound B, representative of compounds of the present invention, demonstrated strong, durable RAS pathway modulation in a human pancreatic adenocarcinoma HPAC KRAS$^{G12D/wt}$ mouse xenograft model. RAS/ERK signaling pathway modulation was assessed by measuring the mRNA level of human DUSP6 in a qPCR assay. Both Compound A and Compound B led to inhibition of DUSP6 mRNA levels in HPAC xenografted tumors by 4 h post dosing, indicating strong RAS pathway modulation.
Figure 1:

Provided herein are Ras inhibitors. The approach described herein entails formation of a high affinity three-component complex, or conjugate, between a synthetic ligand and two intracellular proteins which do not interact under normal physiological conditions: the target protein of interest (e.g., Ras), and a widely expressed cytosolic chaperone (presenter protein) in the cell (e.g., cyclophilin A). More specifically, in some embodiments, the inhibitors of Ras described herein induce a new binding pocket in Ras by driving formation of a high affinity tri-complex, or conjugate, between the Ras protein and the widely expressed cytosolic chaperone, cyclophilin A (CYPA). Without being bound by theory, the inventors believe that one way the inhibitory effect on Ras is effected by compounds of the invention and the complexes, or conjugates, they form is by steric occlusion of the interaction site between Ras and downstream effector molecules, such as RAF, which are required for propagating the oncogenic signal.

Without being bound by theory, the inventors postulate that both covalent and non-covalent interactions of a compound of the present invention with Ras and the chaperone protein (e.g., cyclophilin A) may contribute to the inhibition of Ras activity. In some embodiments, a compound of the present invention forms a covalent adduct with a side chain of a Ras protein (e.g., the —$CH_2$—COOH or —$CH_2$—COO— side chain of the aspartic acid at position 12 or 13 of a mutant Ras protein). Covalent adducts may also be formed with other side chains of Ras. In addition or alternatively, non-covalent interactions may be at play: for example, van der Waals, hydrophobic, hydrophilic, and hydrogen bond interactions, and combinations thereof, may contribute to the ability of the compounds of the present invention to form complexes and act as Ras inhibitors. Accordingly, a variety of Ras proteins may be inhibited by compounds of the present invention (e.g., K-Ras, N-Ras, H-Ras, and mutants thereof at positions 12, 13 and 61, such as G12C, G12D, G12V, G12S, G13C, G13D, and Q61L, and others described herein).

Methods of determining covalent adduct formation are known in the art. One method of determining covalent adduct formation is to perform a "cross-linking" assay, such as described below:

Note—the following protocol describes a procedure for monitoring cross-linking of K-Ras G12D (GMP-PNP) to a compound of the invention. This protocol may also be executed substituting other Ras proteins or nucleotides.

The purpose of this biochemical assay is to measure the ability of test compounds to covalently label nucleotide-loaded K-Ras isoforms. In assay buffer containing 12.5 mM HEPES pH 7.4, 75 mM NaCl, 1 mM $MgCl_2$, 5 μM Cyclophilin A and 2 μM test compound, a 5 μM stock of GMP-PNP-loaded K-Ras (1-169) G12D is diluted 10-fold to yield a final concentration of 0.5 μM; with final sample volume being 100 μL.

The sample is incubated at 25° C. for time period(s) of up to 24 hours prior to quenching by the addition of 10 μL of 5% Formic Acid. Quenched samples are centrifuged at 15000 rpm for 15 minutes in a benchtop centrifuge before injecting a 10 μL aliquot onto a reverse phase C4 column and eluting into the mass spectrometer with an increasing acetonitrile gradient in the mobile phase. Analysis of raw data may be carried out using Waters MassLynx MS software, with % bound calculated from the deconvoluted protein peaks for labeled and unlabeled K-Ras.

Accordingly, provided herein is a compound, or pharmaceutically acceptable salt thereof, having the structure of Formula 0:

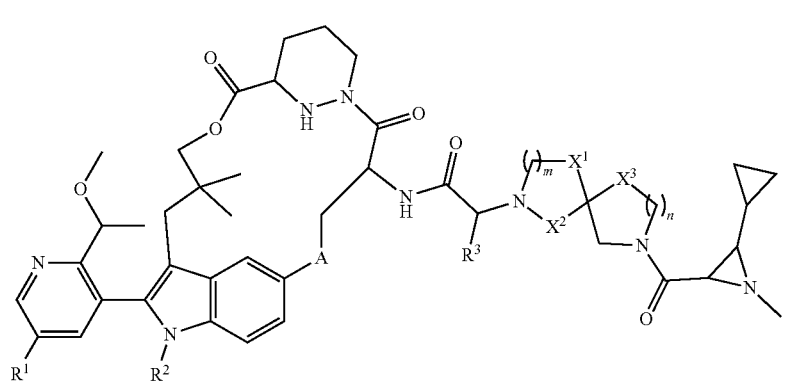

Formula 0 wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$X^1$, $X^2$, and $X^3$ are each independently selected from $CH_2$, $CF_2$, C=O, or O;

m is 1 or 2;

n is 0 or 1;

$R^1$ is hydrogen, optionally substituted $C_1$-$C_6$ heteroalkyl, or optionally substituted 3 to 10-membered heterocycloalkyl;

$R^2$ is optionally substituted $C_1$-$C_8$ alkyl; and $R^3$ is optionally substituted $C_1$-$C_6$ alkyl, optionally substituted 3 to 6-membered cycloalkyl, or optionally substituted heterocycloalkyl, and wherein each hydrogen is independently, optionally, isotopically enriched for deuterium.

In some embodiments, a compound of the present invention has the structure of Formula I, or a pharmaceutically acceptable salt thereof:

Formula I

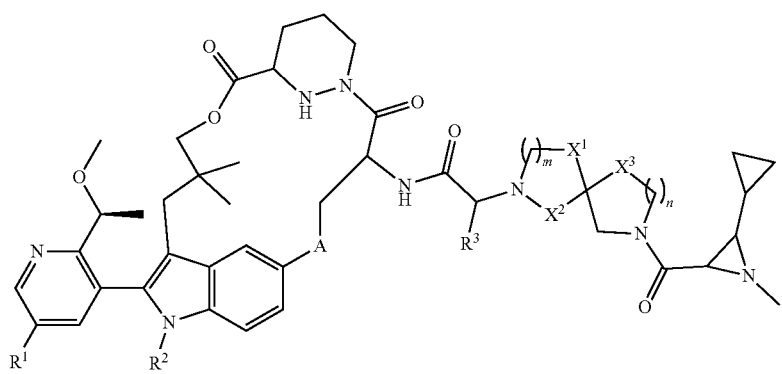

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$X^1$, $X^2$, and $X^3$ are each independently selected from $CH_2$, $CF_2$, C=O, or O;

m is 1 or 2;

n is 0 or 1;

$R^1$ is hydrogen, optionally substituted $C_1$-$C_6$ heteroalkyl, or optionally substituted 3 to 10-membered heterocycloalkyl;

$R^2$ is optionally substituted $C_1$-$C_6$ alkyl; and $R^3$ is optionally substituted $C_1$-$C_6$ alkyl, optionally substituted 3 to 6-membered cycloalkyl, or optionally substituted heterocycloalkyl, and wherein each hydrogen is independently, optionally, isotopically enriched for deuterium.

In some embodiments, a compound of the present invention has the structure of Formula Ia, Formula Ib, Formula Ic, or a pharmaceutically acceptable salt thereof:

Formula Ia

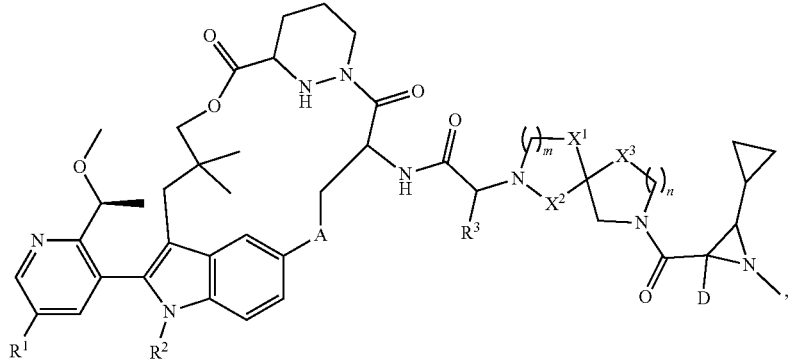

Formula Ib

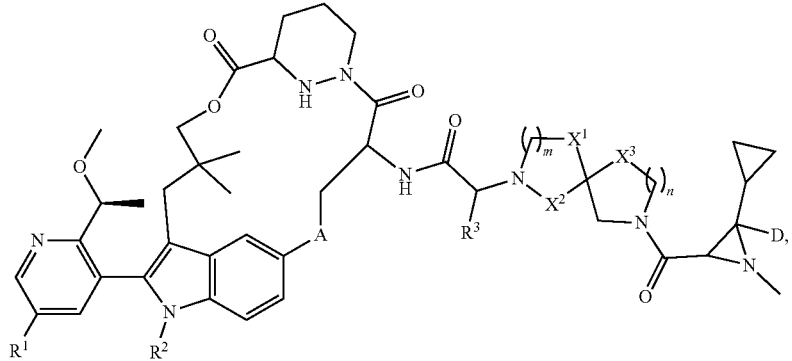

Formula Ic

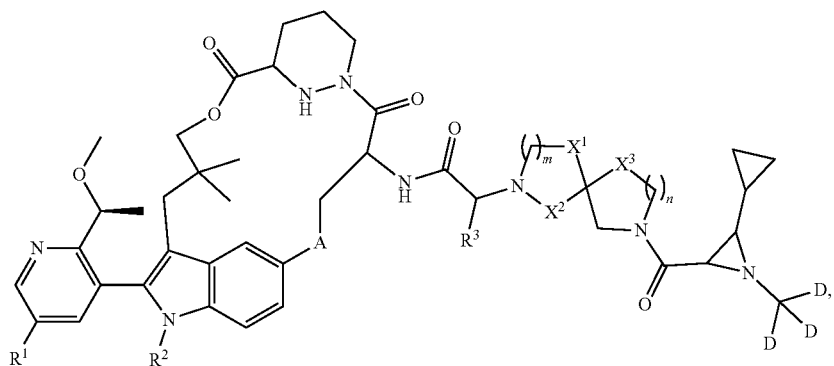

wherein each D indicates a hydrogen having an isotopic enrichment factor for deuterium of at least 5.

In some embodiments, a compound of the present invention has the structure of Formula II, or a pharmaceutically acceptable salt thereof.

Formula II

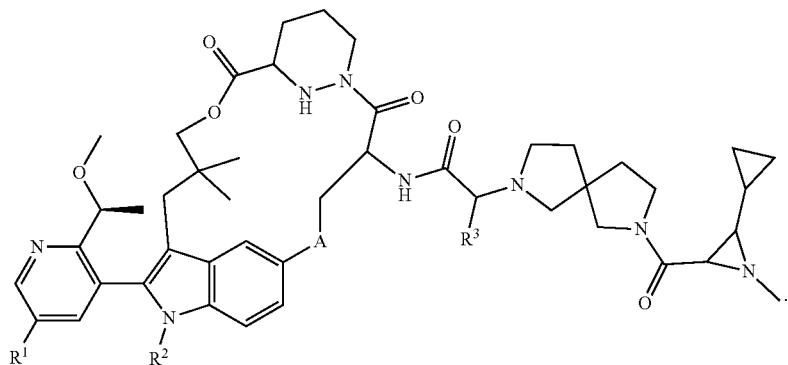

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$R^2$ is optionally substituted $C_1$-$C_6$ alkyl; and $R^3$ is optionally substituted $C_1$-$C_6$ alkyl, optionally substituted 3 to 6-membered cycloalkyl, or optionally substituted heterocycloalkyl, and wherein each hydrogen is independently, optionally, isotopically enriched for deuterium.

In some embodiments, a compound of the present invention has the structure of Formula V, or a pharmaceutically acceptable salt thereof:

Formula V

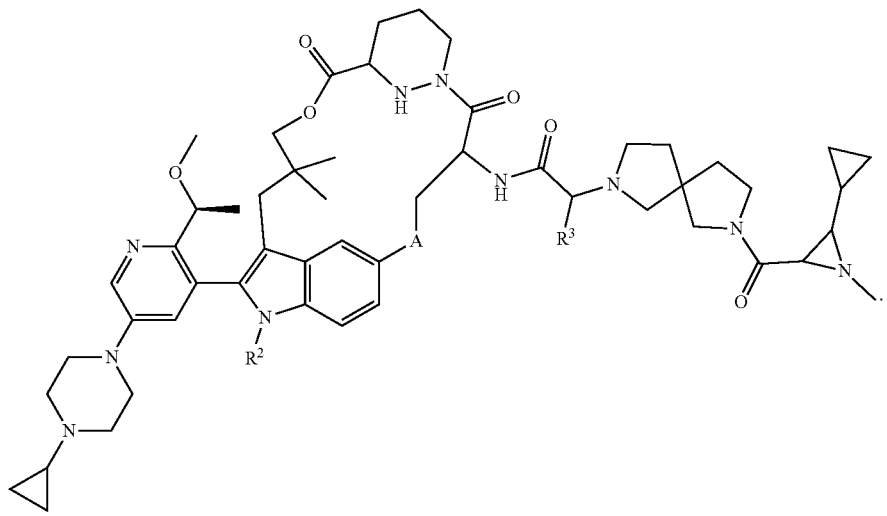

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$R^2$ is optionally substituted $C_1$-$C_6$ alkyl; and $R^3$ is optionally substituted $C_1$-$C_6$ alkyl, optionally substituted 3 to 6-membered cycloalkyl, or optionally substituted heterocycloalkyl, and wherein each hydrogen is independently, optionally, isotopically enriched for deuterium.

In some embodiments, a compound of the present invention has the structure of Formula VI, or a pharmaceutically acceptable salt thereof:

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$R^2$ is optionally substituted $C_1$-$C_6$ alkyl; and $R^3$ is optionally substituted $C_1$-$C_6$ alkyl, optionally substituted 3 to 6-membered cycloalkyl, or optionally substituted heterocycloalkyl, and wherein each hydrogen is independently, optionally, isotopically enriched for deuterium.

In some embodiments, a compound of the present invention has the structure of Formula VII, or a pharmaceutically acceptable salt thereof:

Formula VI

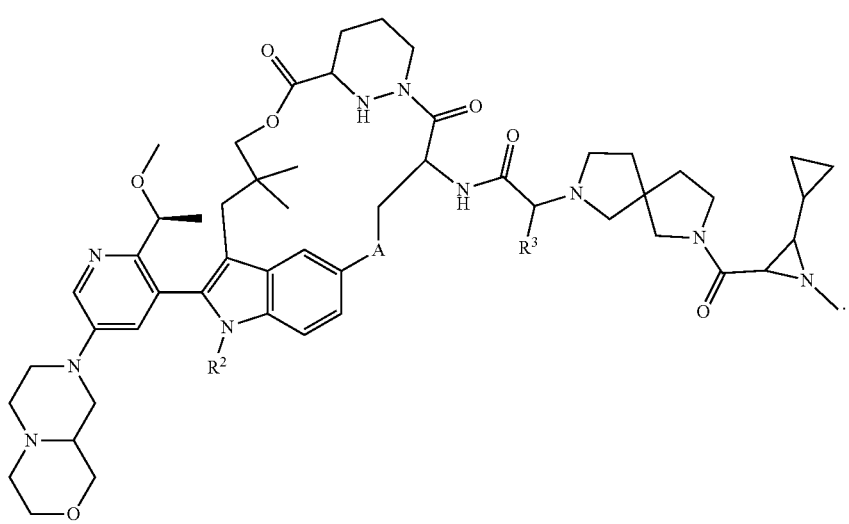

Formula VII

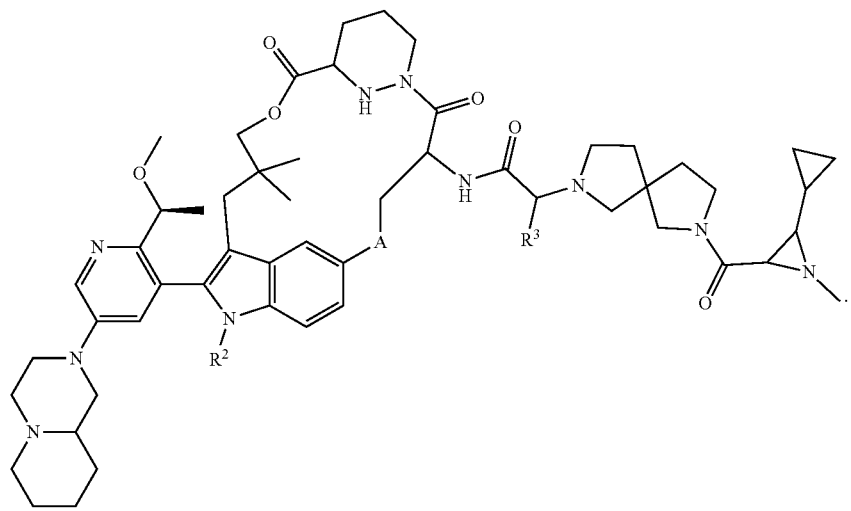

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

R² is optionally substituted C₁-C₆ alkyl; and

R³ is optionally substituted C₁-C₆ alkyl, optionally substituted 3 to 6-membered cycloalkyl, or optionally substituted heterocycloalkyl, and wherein each hydrogen is independently, optionally, isotopically enriched for deuterium.

In some embodiments, a compound of the present invention has the structure of Formula Va, Formula Vb, Formula Vc, or a pharmaceutically acceptable salt thereof:

Formula Va

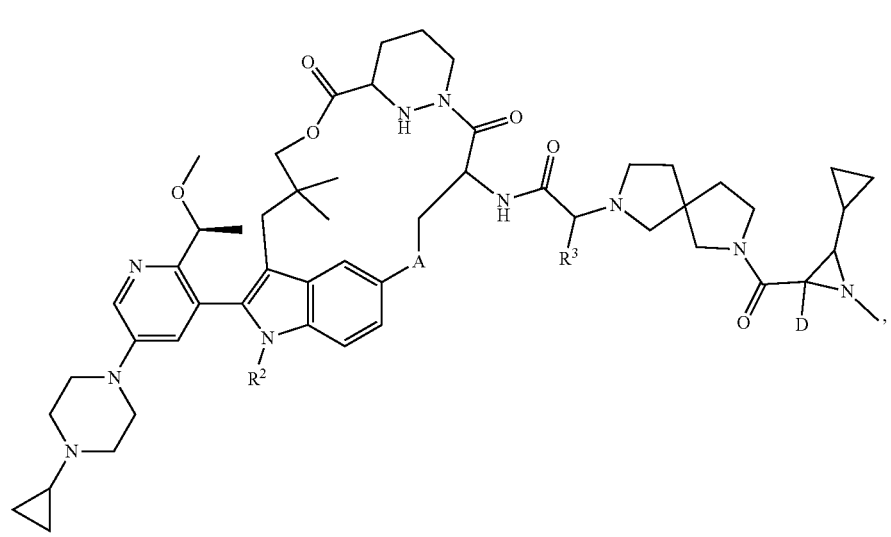

Formula Vb
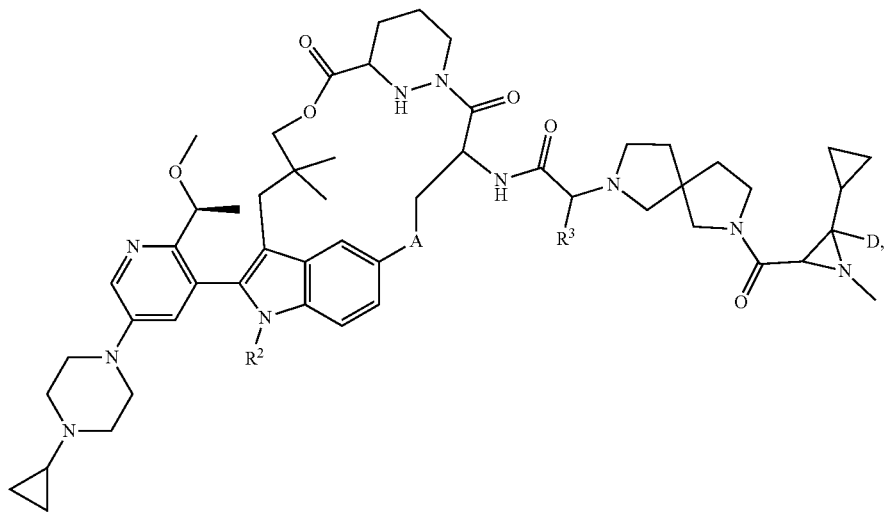
Formula Vc
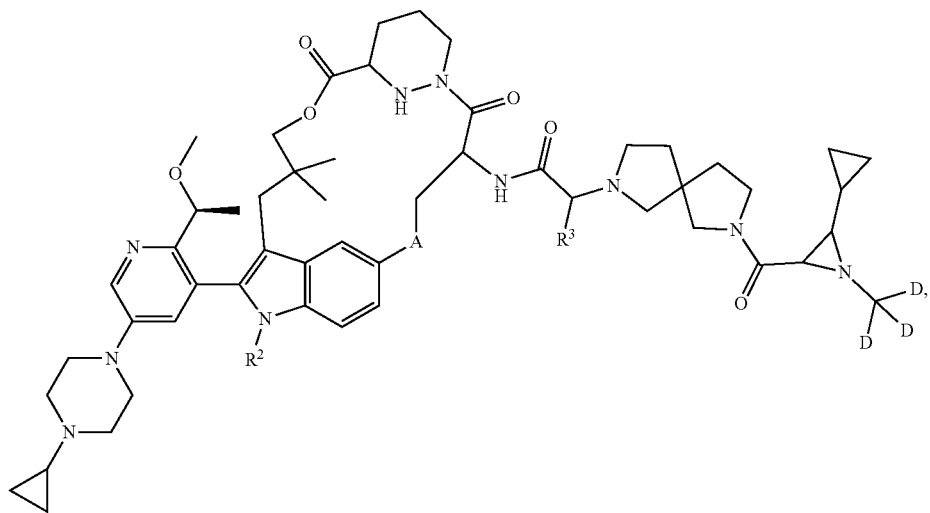

wherein each D indicates a hydrogen having an isotopic enrichment factor for deuterium of at least 5.
In some embodiments, a compound of the present invention has the structure of Formula Vd, Formula Ve, Formula Vf, or a pharmaceutically acceptable salt thereof:
Formula Vd
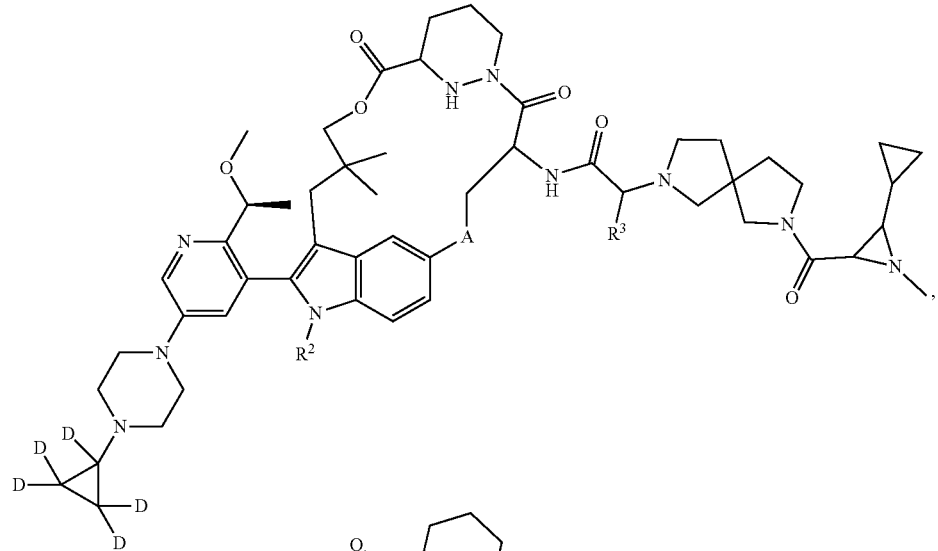
Formula Ve
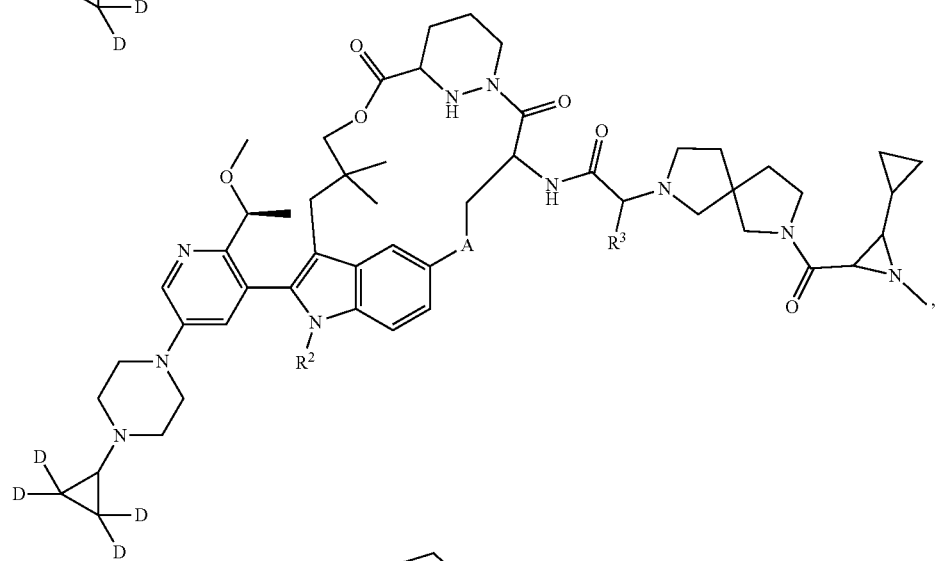
Formula Vf
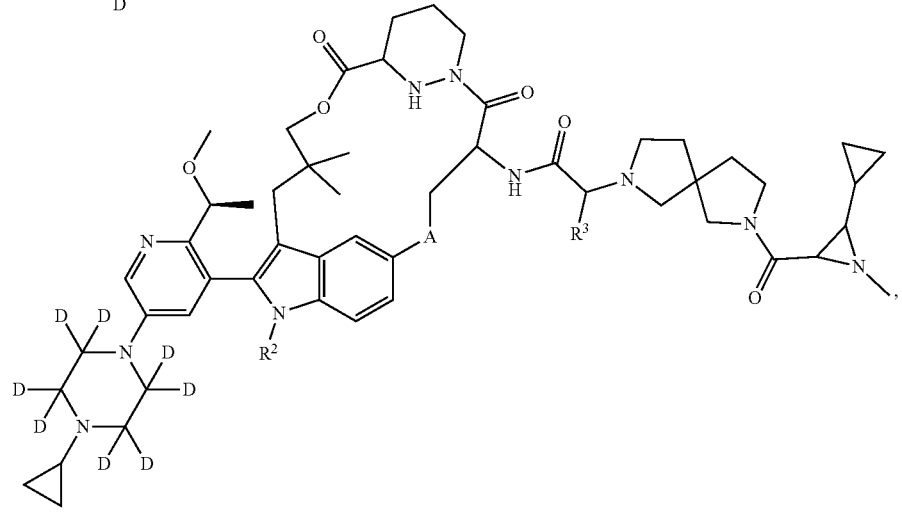

wherein each D indicates a hydrogen having an isotopic enrichment factor for deuterium of at least 5.

In some embodiments, A is optionally substituted thiazole-diyl, optionally substituted oxazole-diyl, optionally substituted morpholine-diyl, optionally substituted pyrrolidine-diyl, optionally substituted piperidine-diyl, or optionally substituted phenylene. In some embodiments, A is optionally substituted thiazole-diyl or optionally substituted morpholine-diyl. In some embodiments of a compound of the present invention, A is optionally substituted 5 to 10-membered heteroarylene. In some embodiments, A is

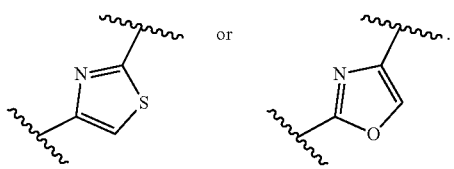 [SMILES: *c1csc(*)n1 ; *c1coc(*)n1]

In some embodiments, A is

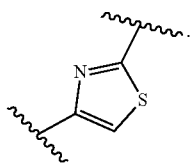 [SMILES: *c1csc(*)n1]

In some embodiments of a compound of the present invention, A is optionally substituted phenylene. In some embodiments, A is:

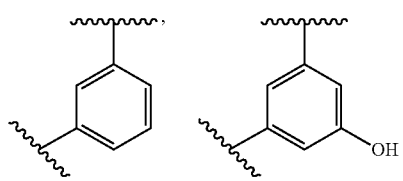

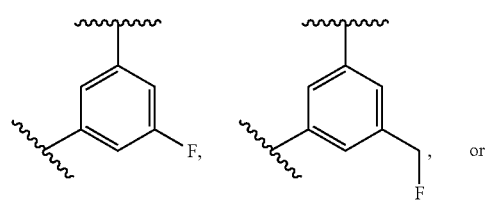

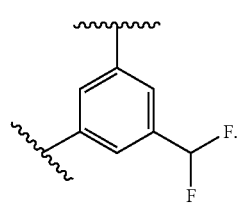

In some embodiments, A is

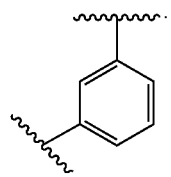 [SMILES: *c1cccc(*)c1]

In some embodiments of a compound of the present invention, A is optionally substituted 3 to 6-membered heterocycloalkylene. In some embodiments, A is optionally substituted 6-membered heterocycloalkylene. In some embodiments, A is selected from the following, or a stereoisomer thereof:

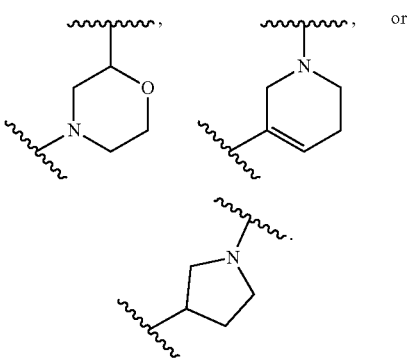

In some embodiments, A is selected from the following, or a stereoisomer thereof:

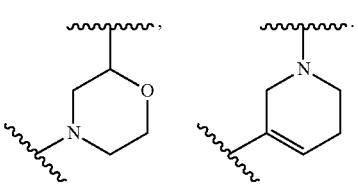 [SMILES: *C1CN(*)CCO1 ; *C1=CCCN(*)C1]

In some embodiments of a compound of the present invention, $R^1$ is hydrogen or optionally substituted 3 to 10-membered heterocycloalkyl. In some embodiments of a compound of the present invention, $R^1$ is optionally substituted 3 to 10-membered heterocycloalkyl. In some embodiments of a compound of the present invention, $R^1$ is:

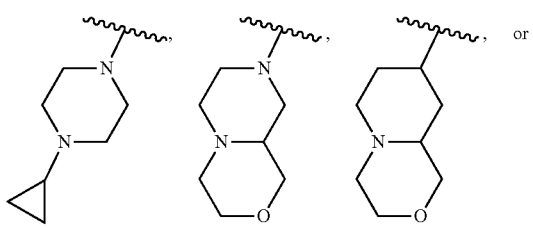

-continued

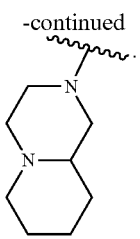

In some embodiments of a compound of the present invention, R¹ is:

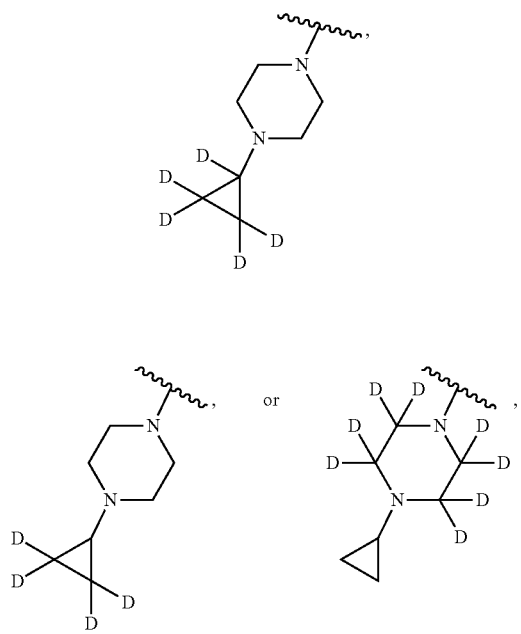

wherein each D indicates a hydrogen having an isotopic enrichment factor for deuterium of at least 5.

In some embodiments of a compound of the present invention, R² is:

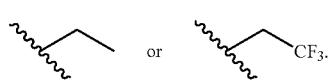

In some embodiments of a compound of the present invention, R² is:

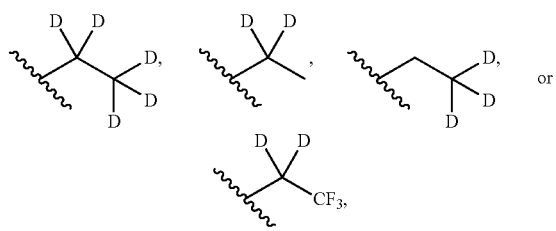

and wherein each D indicates a hydrogen having an isotopic enrichment factor for deuterium of at least 5.

In some embodiments of a compound of the present invention, R³ is optionally substituted $C_1$-$C_6$ alkyl or optionally substituted 3 to 6-membered cycloalkyl. In some embodiments of a compound of the present invention, R³ is optionally substituted $C_1$-$C_6$ alkyl. In some embodiments, R³ is:

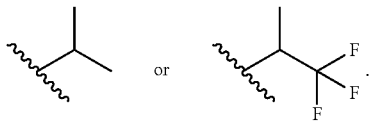

In some embodiments, R³ is:

In some embodiments, R³ is;

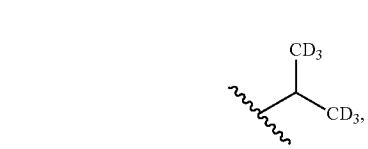

and wherein each D indicates a hydrogen having an isotopic enrichment factor for deuterium of at least 5.

In some embodiments of a compound of the present invention, R³ is or optionally substituted 3 to 6-membered cycloalkyl. In some embodiments, R³ is:

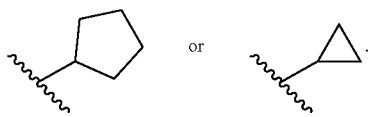

In some embodiments, R³ is:

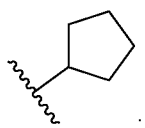 [SMILES: *C1CCCC1]

In some embodiments of a compound of the present invention,

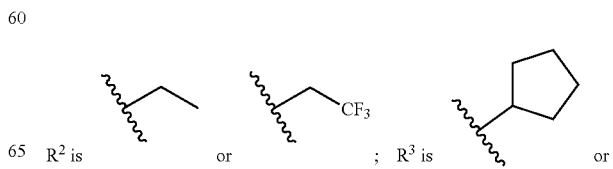

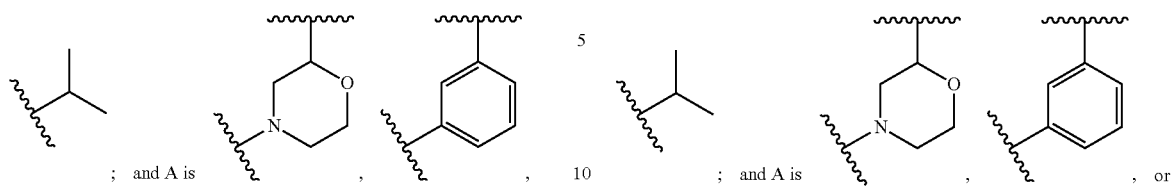

; and A is

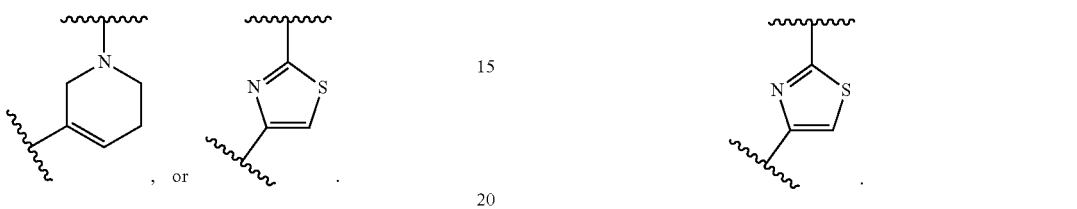

, or

In some embodiments, R² is

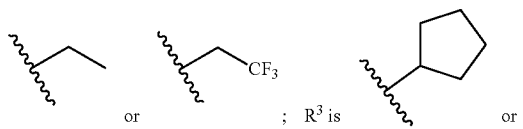

; R³ is

In some embodiments of a compound of the present invention, m is 1. In some embodiments, n is 1. In some embodiments, X¹ is CH₂. In some embodiments, X² is CH₂. In some embodiments, X³ is CH₂. In some embodiments, m is 1, n is 1, and each of X¹, X², and X³ is CH₂.

In some embodiments, a compound of the present invention is selected from Table 1, or a pharmaceutically acceptable salt or stereoisomer thereof. In some embodiments, a compound of the present invention is selected from Table 1, or a pharmaceutically acceptable salt or atropisomer thereof.

TABLE 1

| Ex# | Structure |
|---|---|
| | Certain Compounds of the Present Invention |

A1

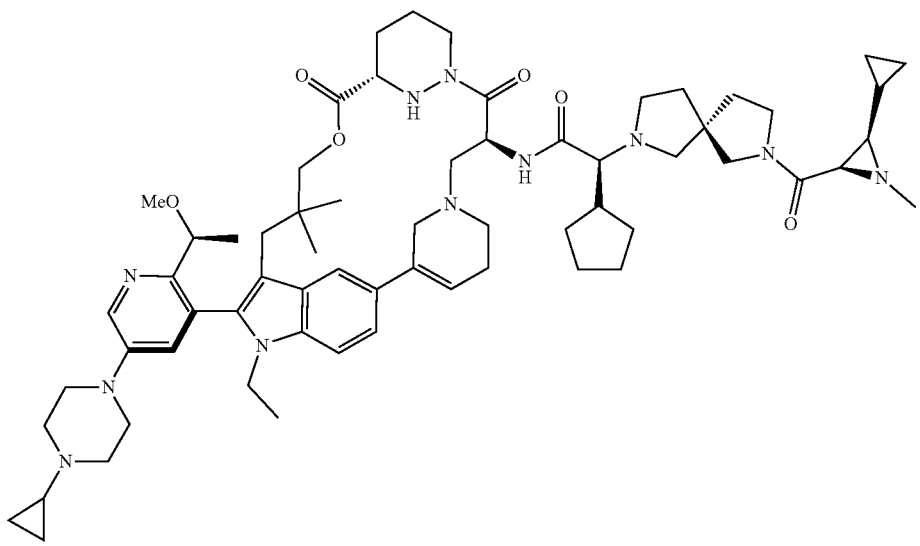

TABLE 1-continued
Certain Compounds of the Present Invention
| Ex# | Structure |
|---|---|
| A2 | 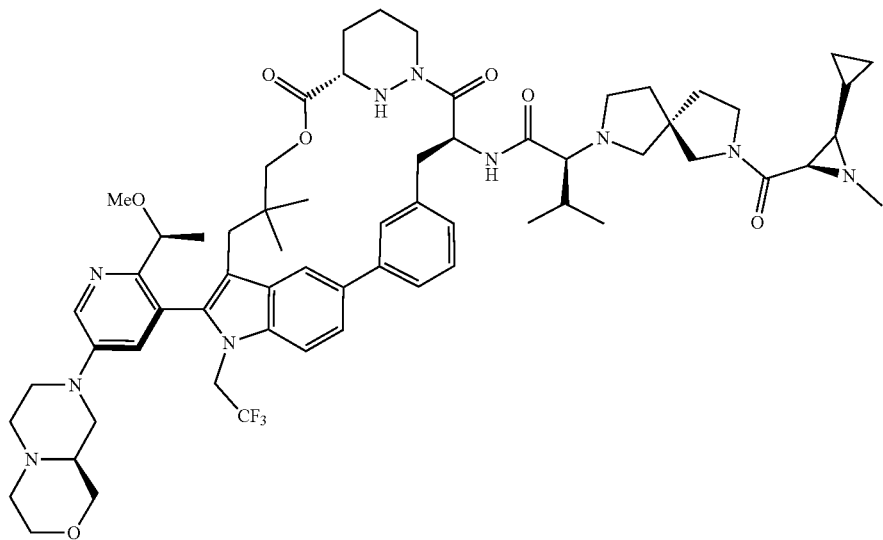 |
| A3 | 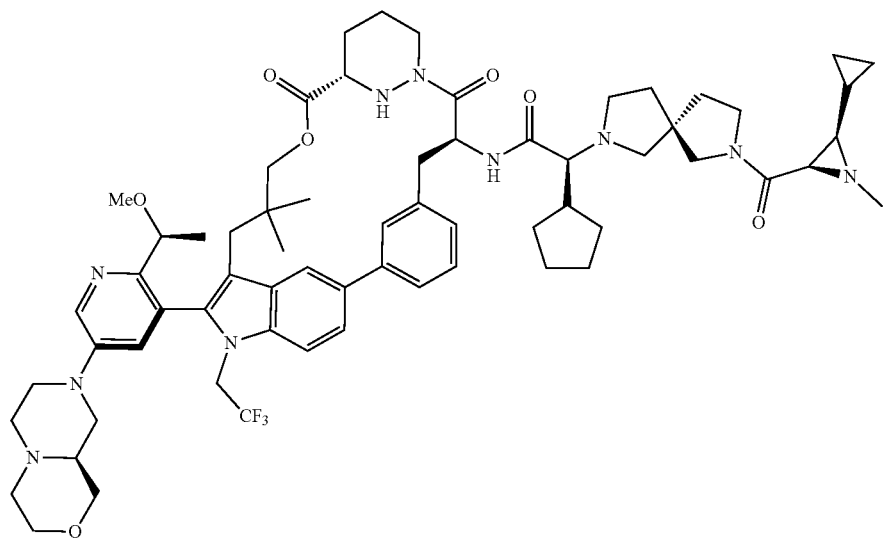 |

TABLE 1-continued
Certain Compounds of the Present Invention
| Ex# | Structure |
|---|---|
| A4 | 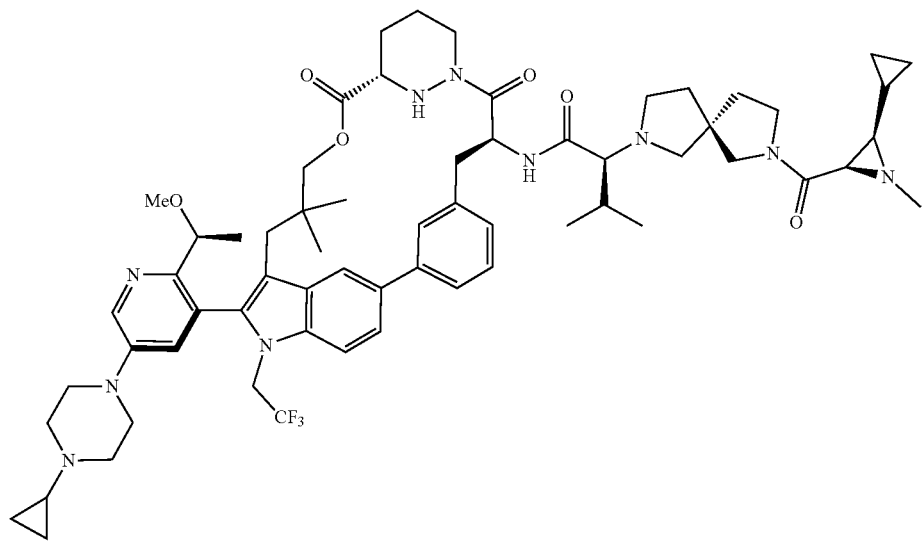 |
| A5 | 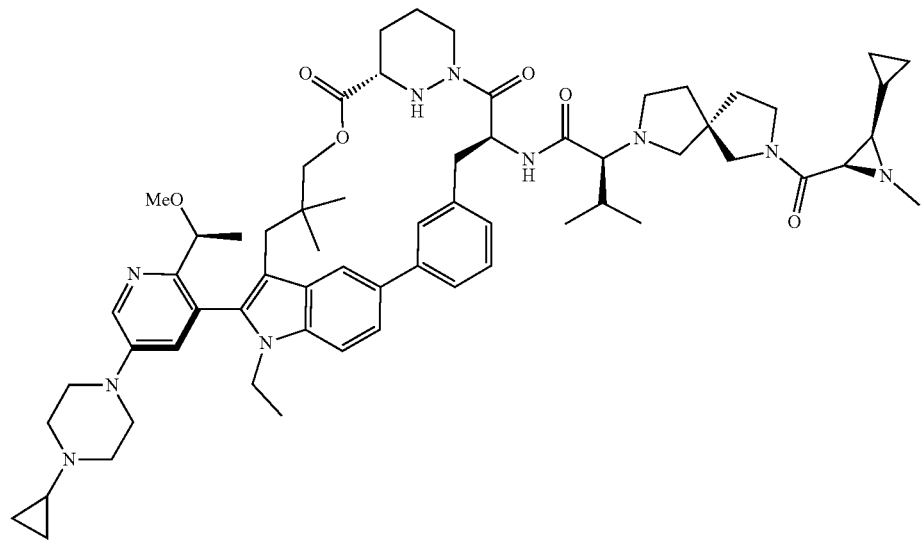 |

TABLE 1-continued
Certain Compounds of the Present Invention
| Ex# | Structure |
|---|---|
| A6 | 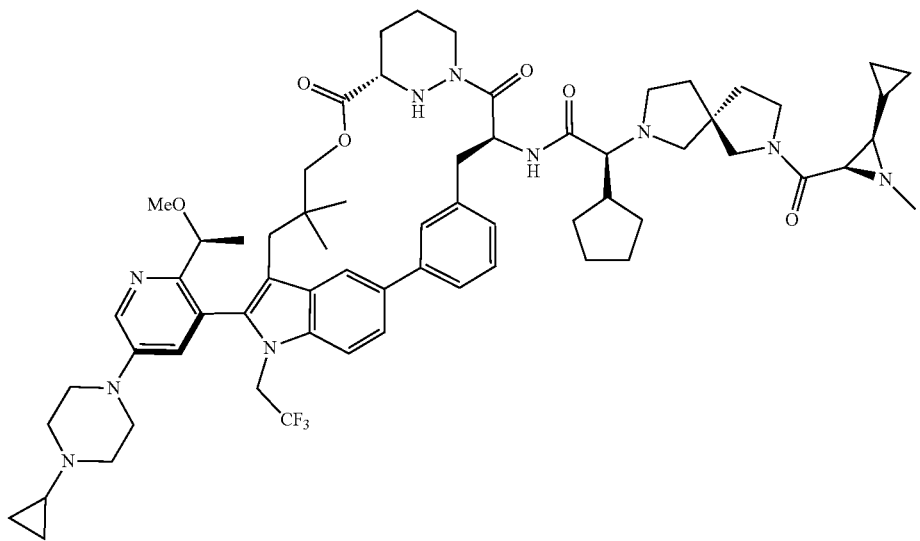 |
| A7 | 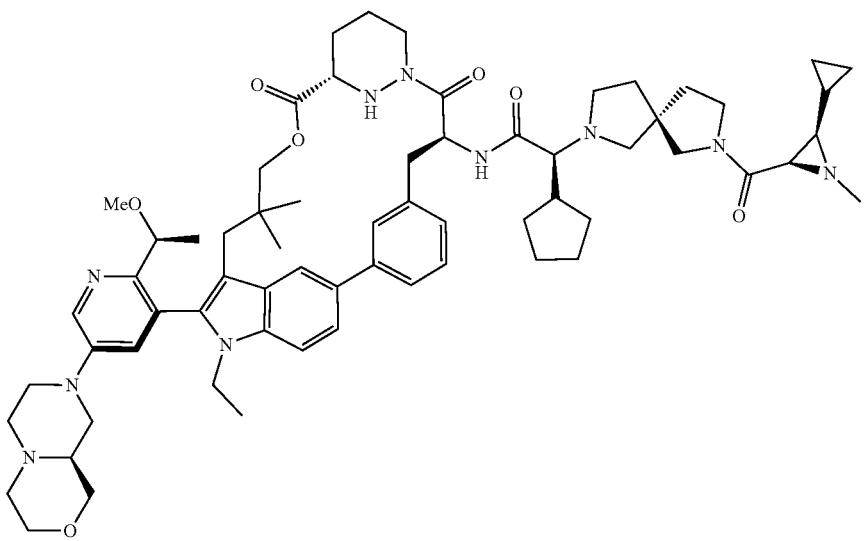 |

TABLE 1-continued
Certain Compounds of the Present Invention
| Ex# | Structure |
|---|---|
| A8 | 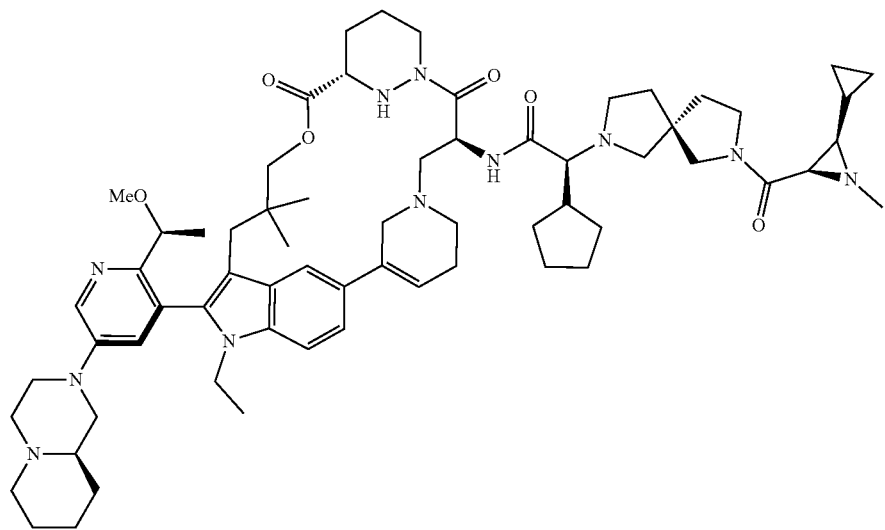 |
| A9 | 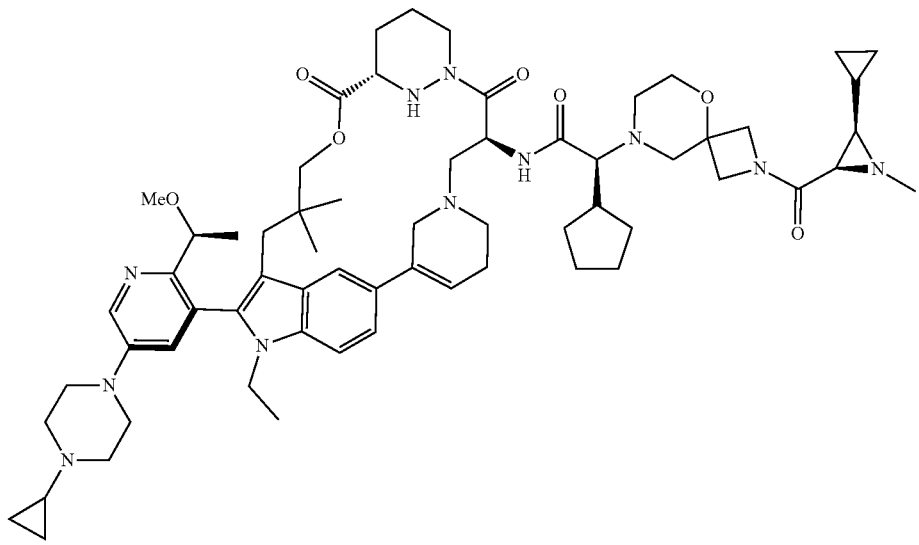 |

TABLE 1-continued
Certain Compounds of the Present Invention
| Ex# | Structure |
|---|---|
| A10 | 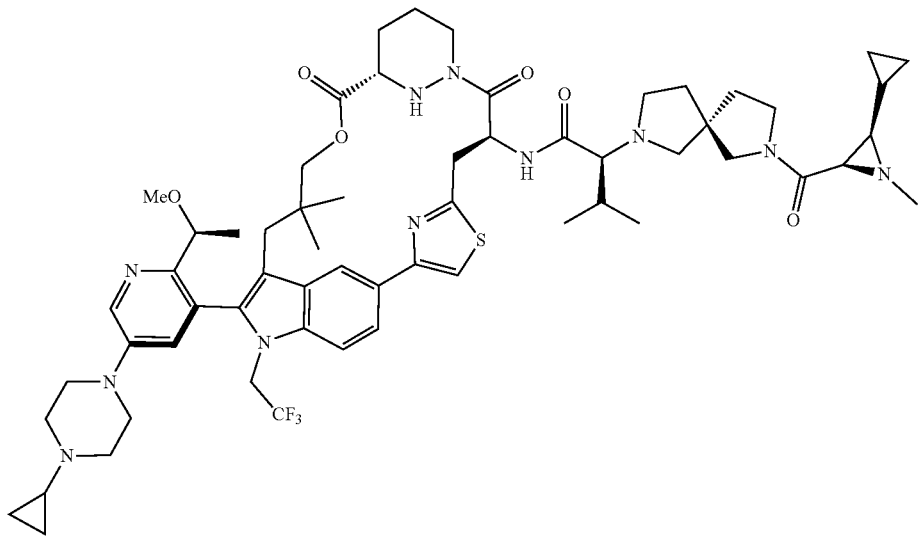 |
| A11 | 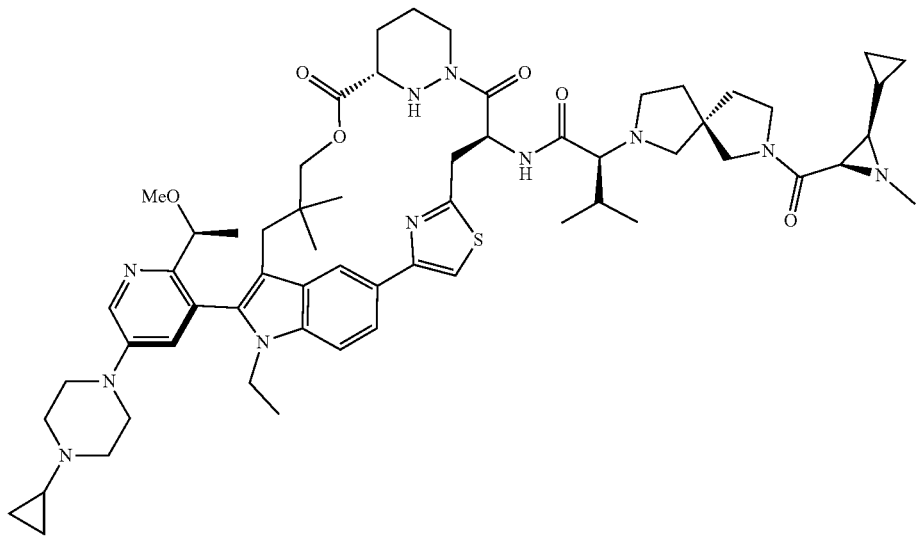 |

TABLE 1-continued
Certain Compounds of the Present Invention
| Ex# | Structure |
|---|---|
| A12 | 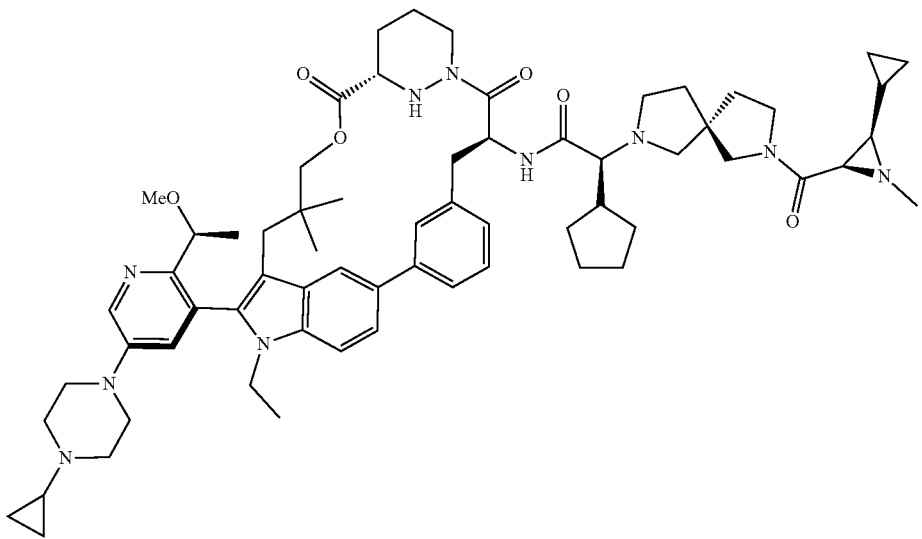 |
| A13 | 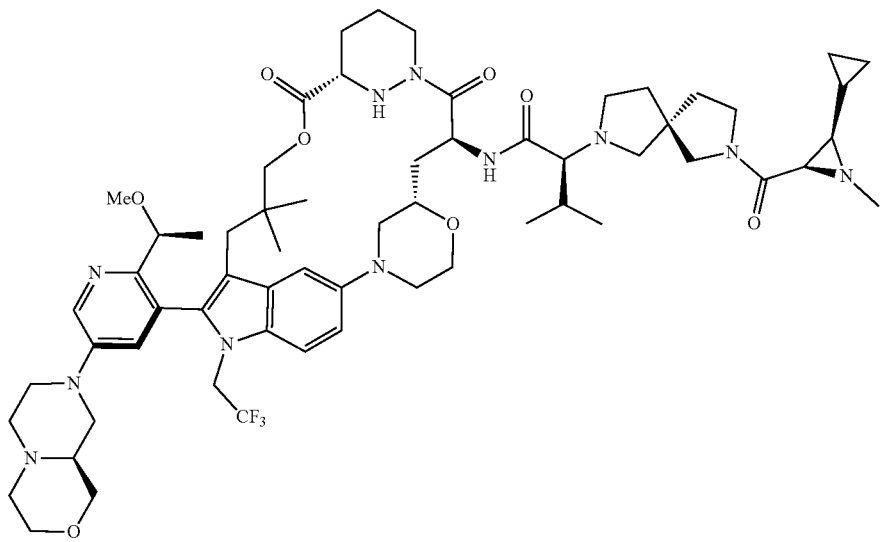 |

TABLE 1-continued
Certain Compounds of the Present Invention
| Ex# | Structure |
|---|---|
| A14 | 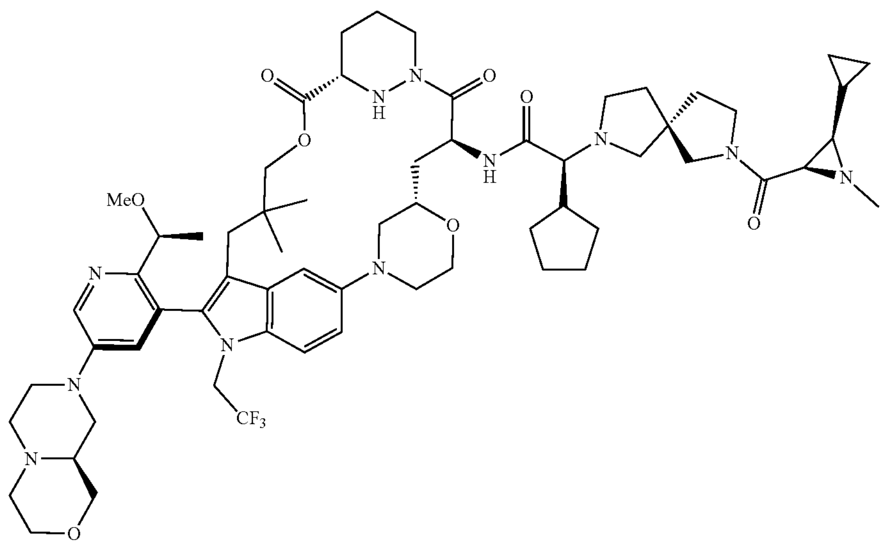 |
| A15 | 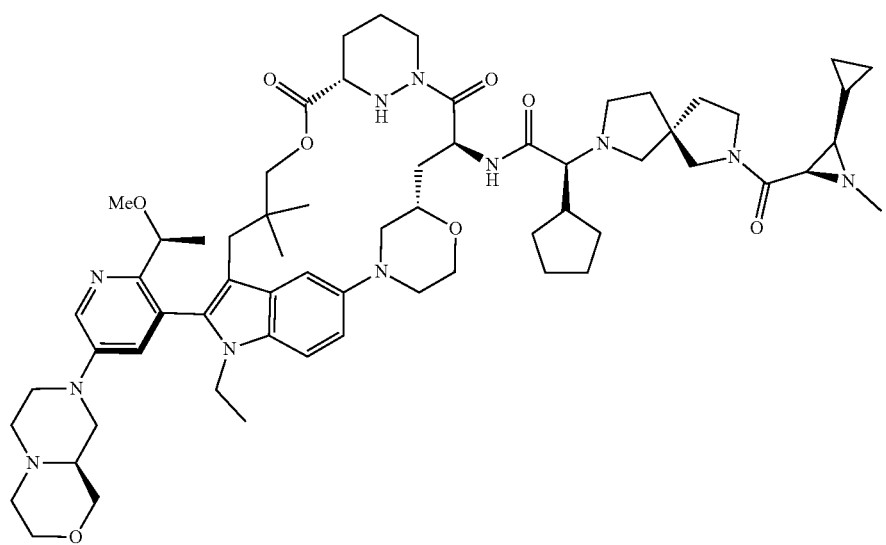 |

TABLE 1-continued
Certain Compounds of the Present Invention
| Ex# | Structure |
|---|---|
| A16 | 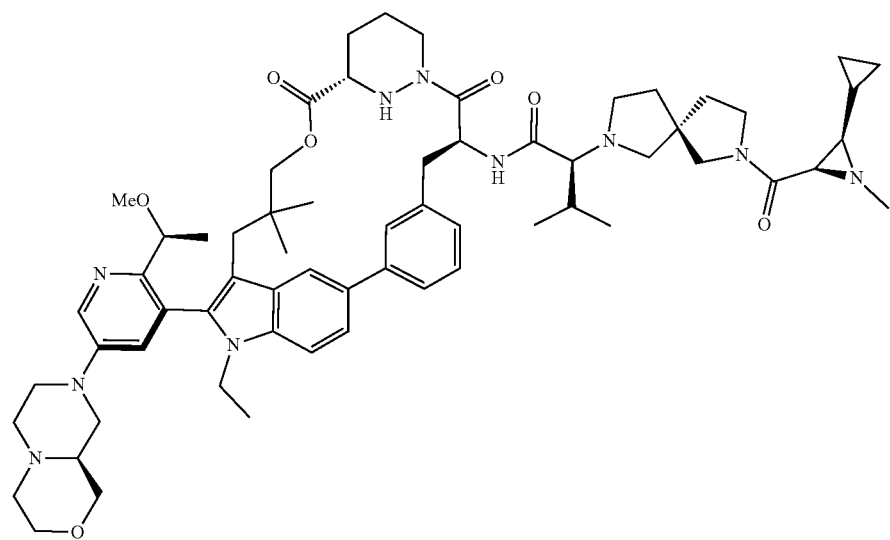 |
| A17 | 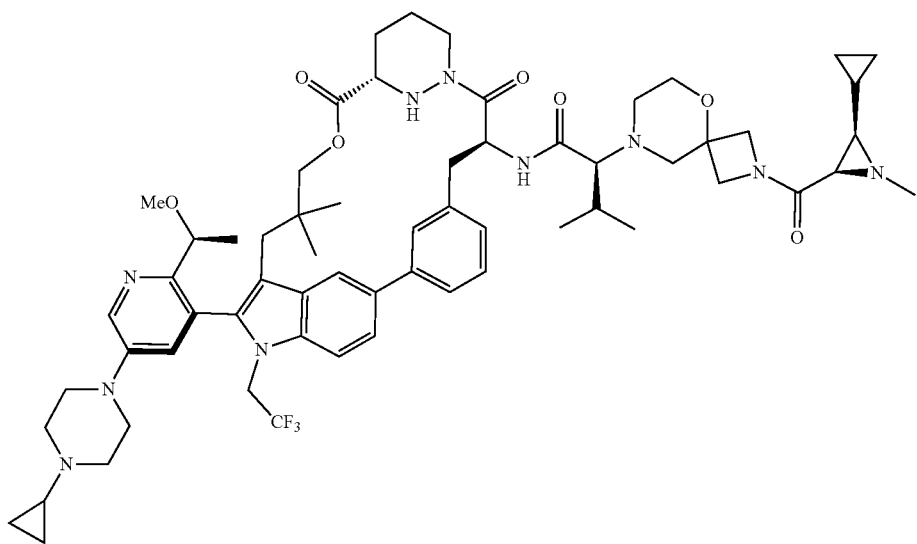 |

TABLE 1-continued
Certain Compounds of the Present Invention
| Ex# | Structure |
|---|---|
| A18 | 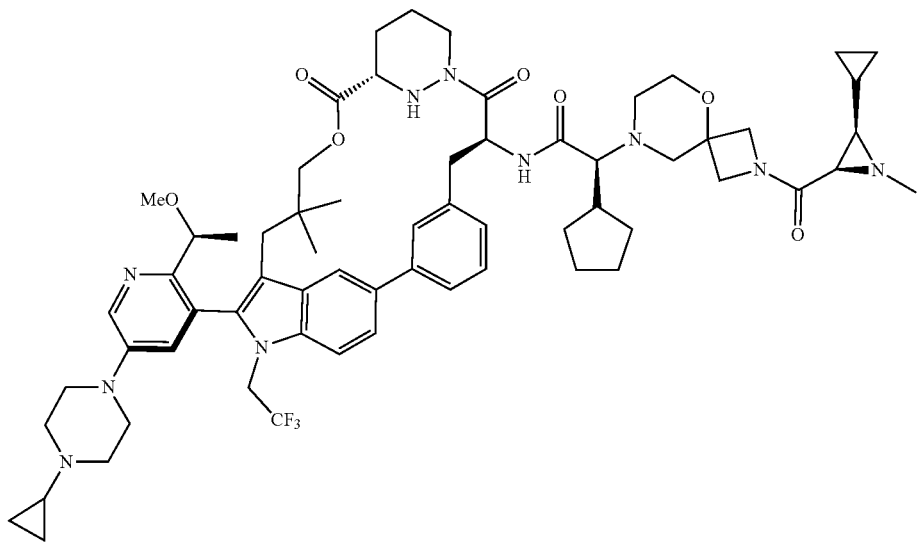 |
| A19 | 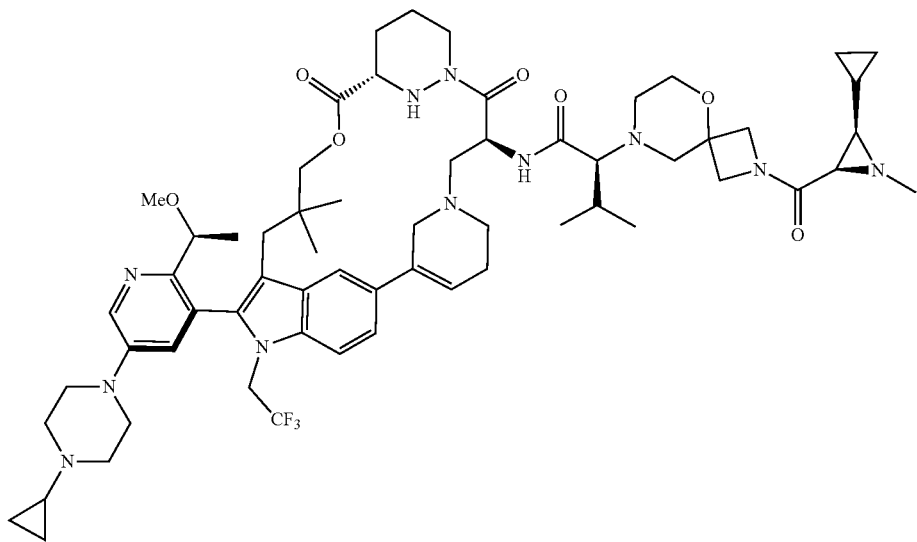 |

TABLE 1-continued
Certain Compounds of the Present Invention
| Ex# | Structure |
|---|---|
| A20 | 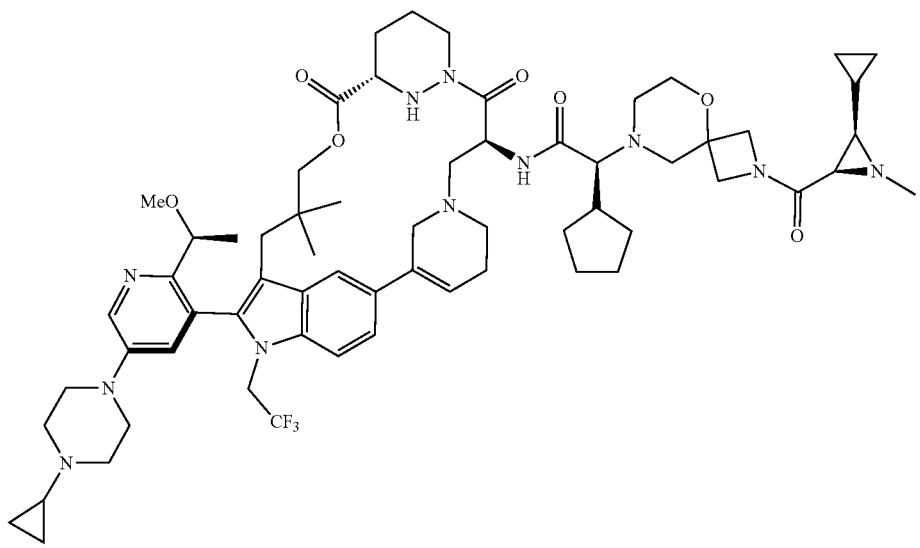 |
| A21 | 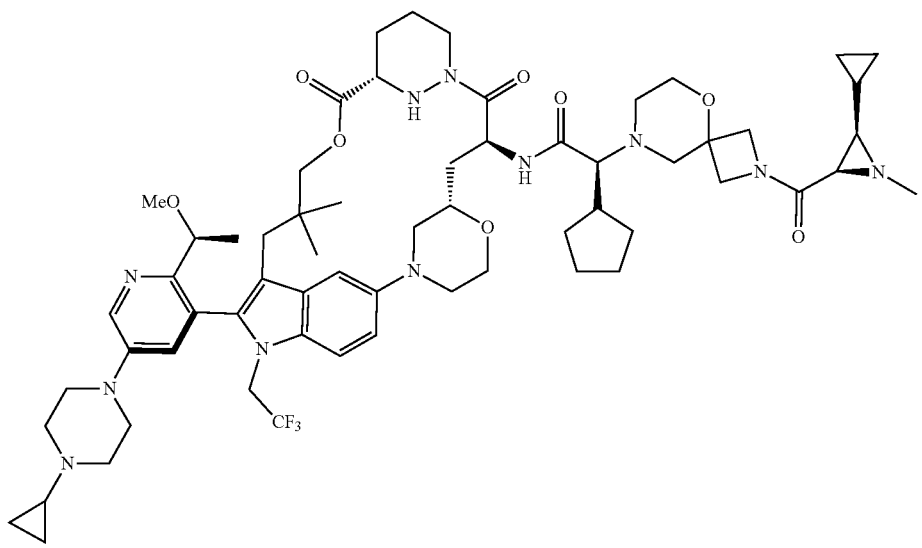 |

TABLE 1-continued
Certain Compounds of the Present Invention
| Ex# | Structure |
|---|---|
| A22 | 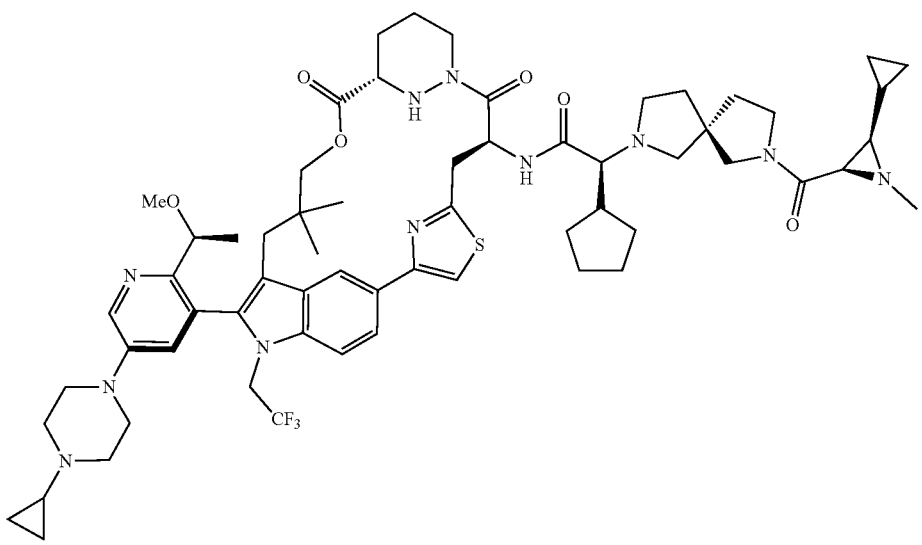 |
| A23 | 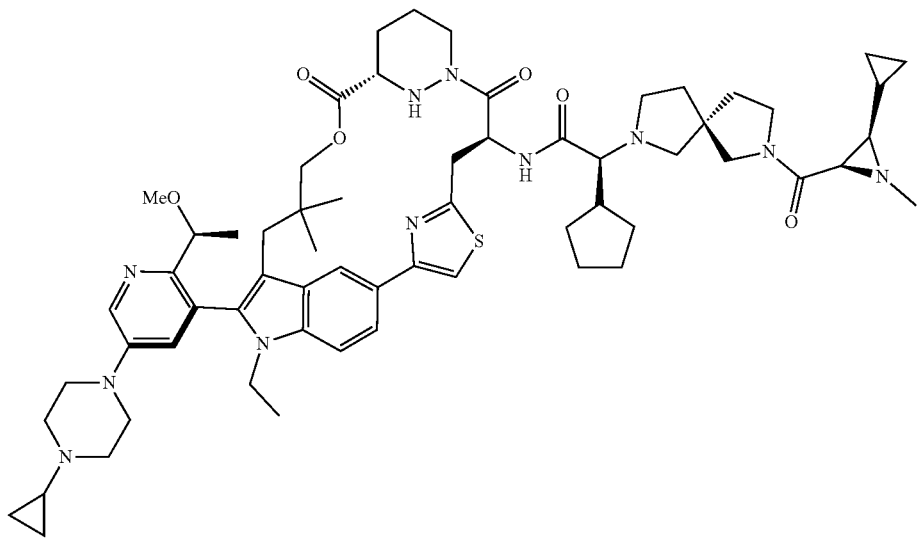 |

TABLE 1-continued
Certain Compounds of the Present Invention
| Ex# | Structure |
|---|---|
| A24 | 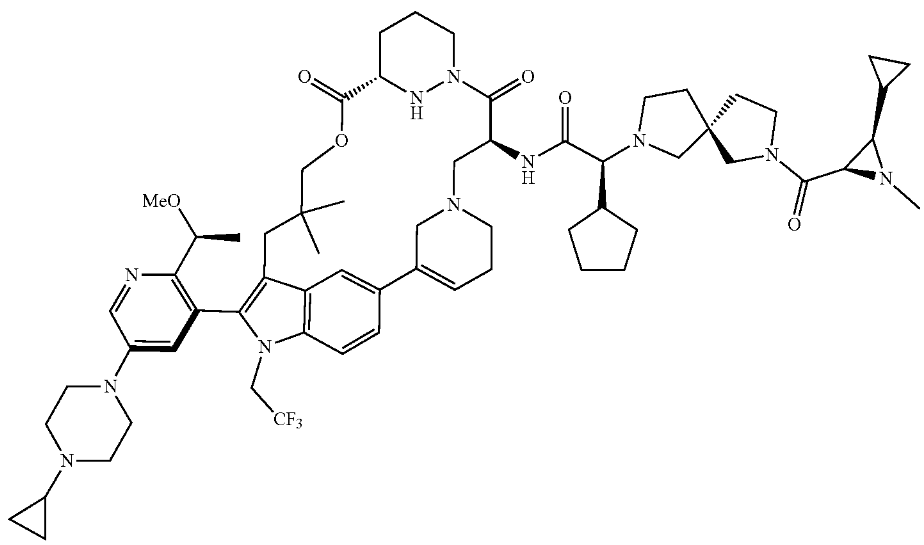 |
| A25 | 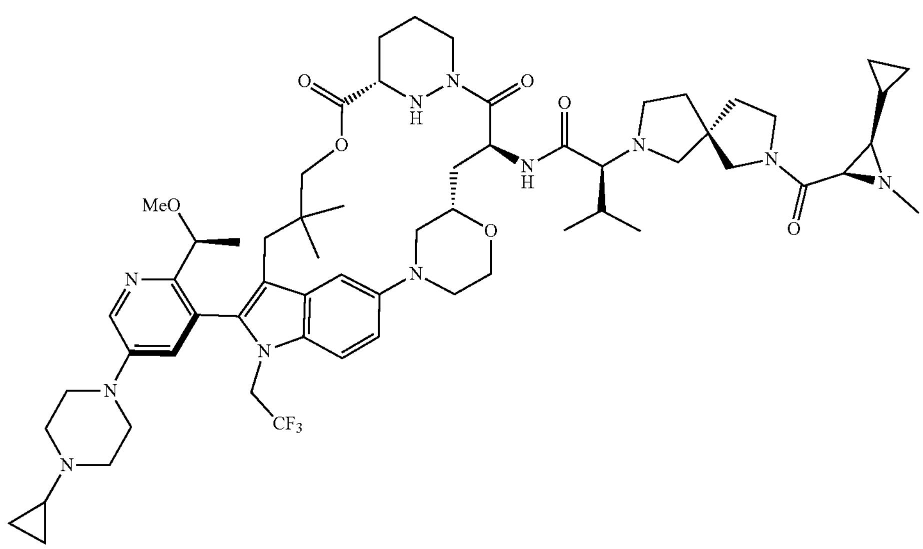 |
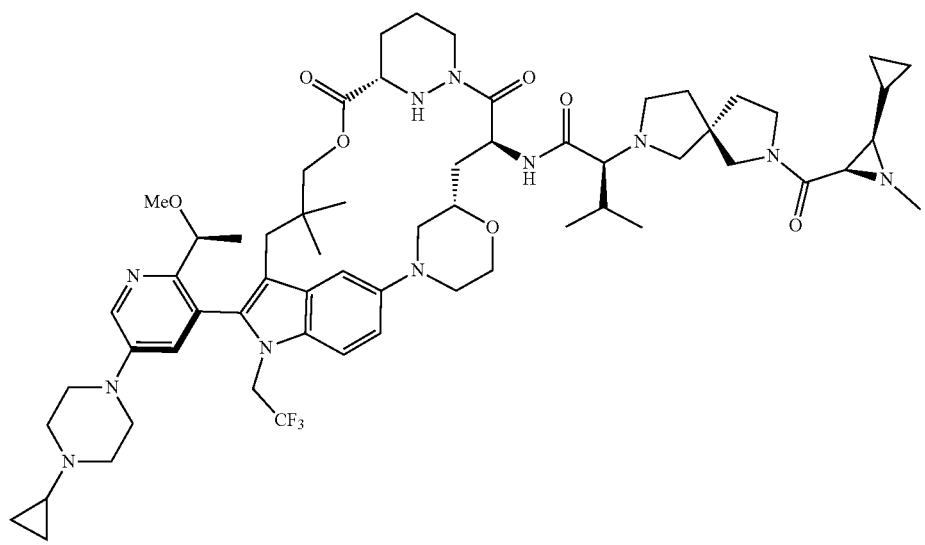

TABLE 1-continued
Certain Compounds of the Present Invention
| Ex# | Structure |
|---|---|
| A26 | 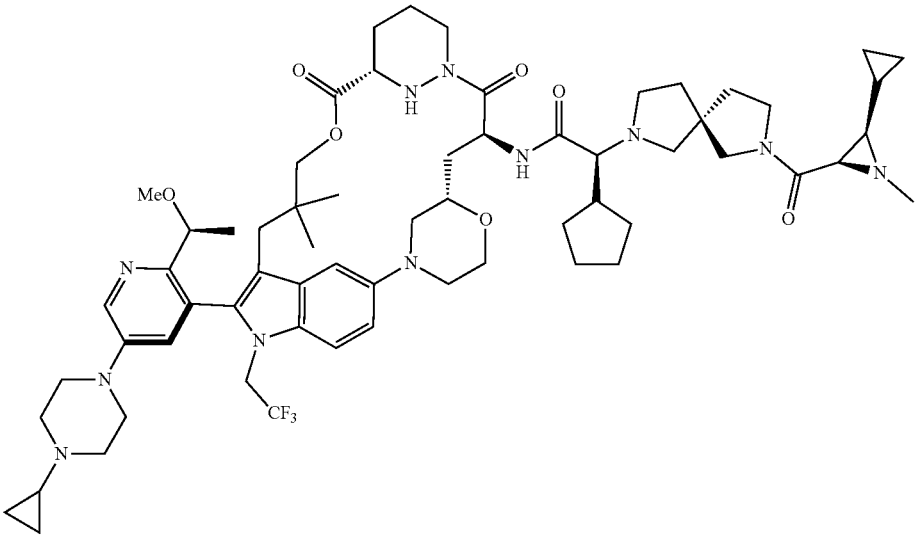 |
| A27 | 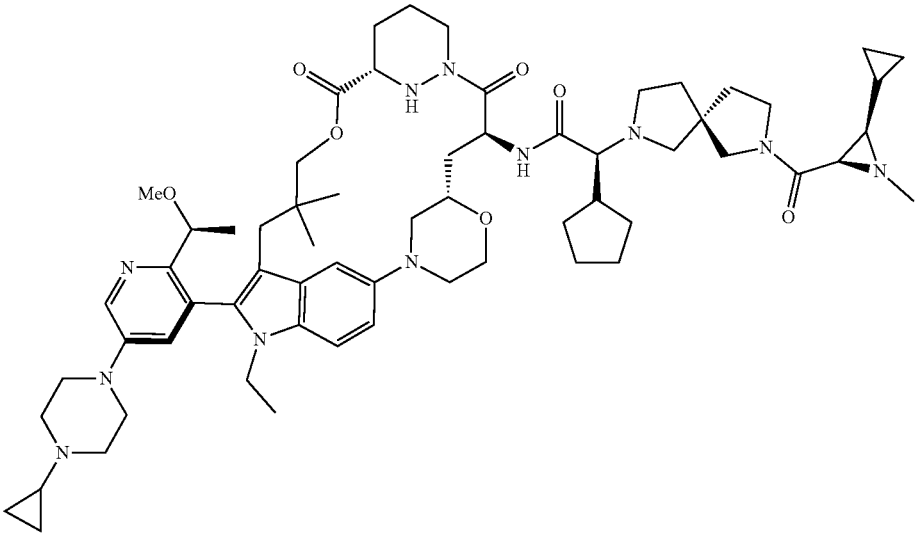 |
| A28 | 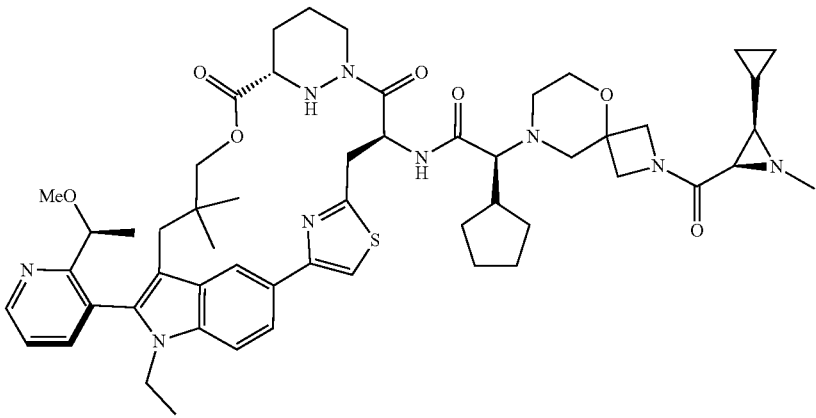 |

TABLE 1-continued
Certain Compounds of the Present Invention
| Ex# | Structure |
|---|---|
| A29 | 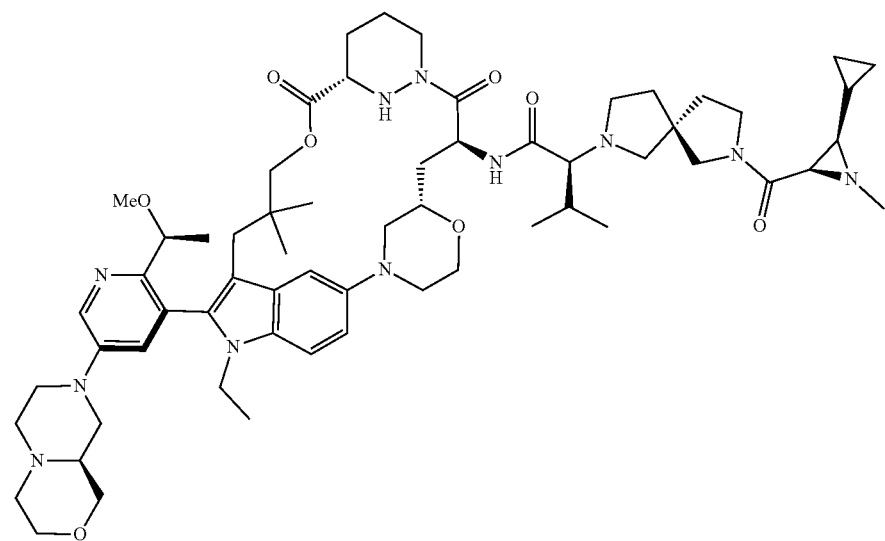 |
| A30 | 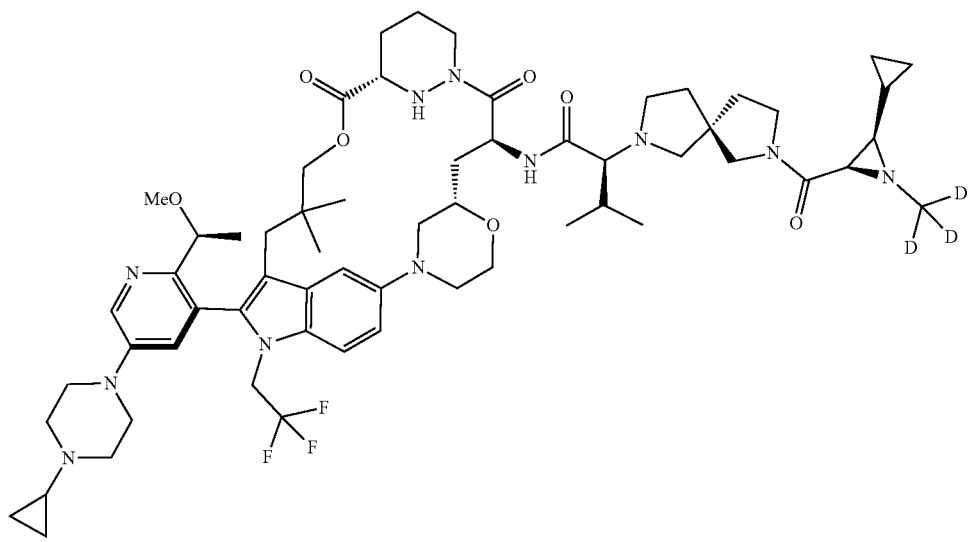 |

TABLE 1-continued
Certain Compounds of the Present Invention
| Ex# | Structure |
|---|---|
| A31 | 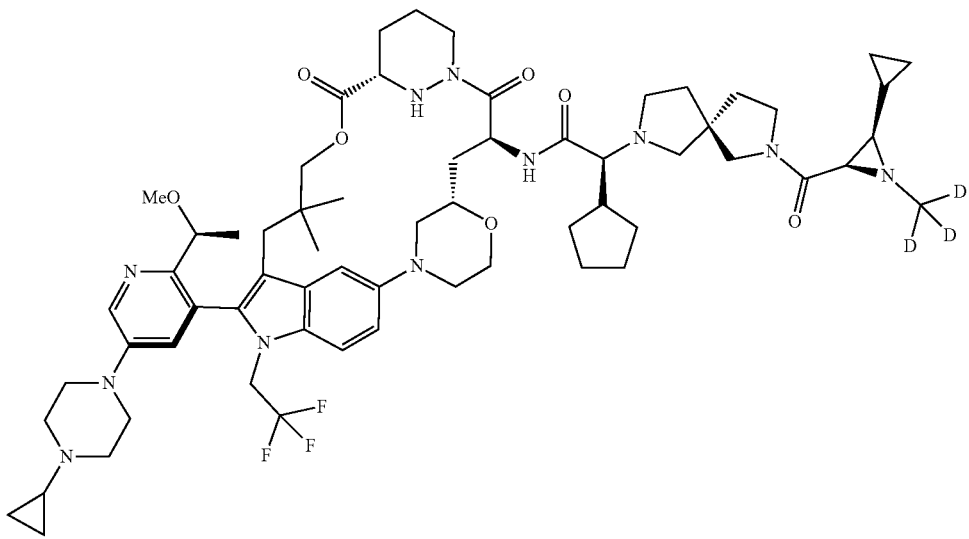 |
| A32 | 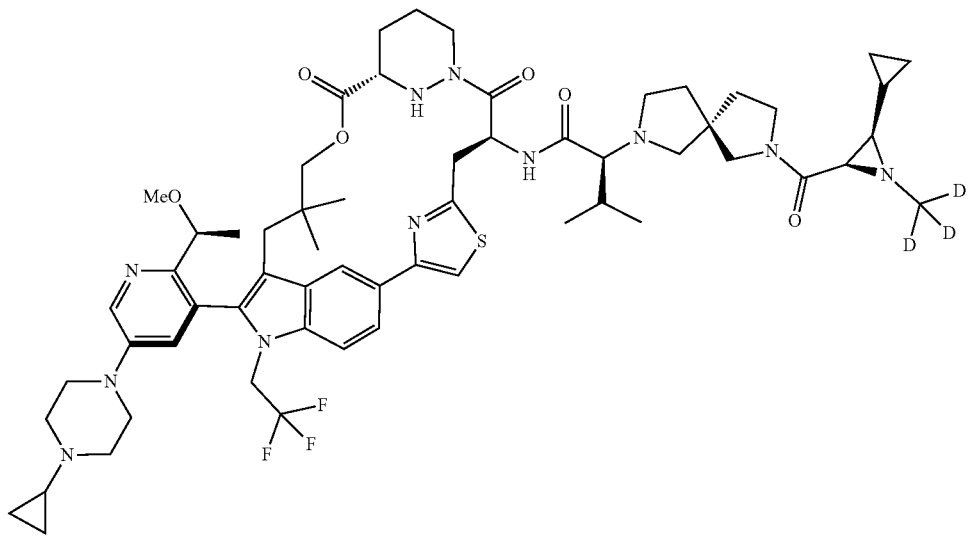 |

TABLE 1-continued
Certain Compounds of the Present Invention
| Ex# | Structure |
|---|---|
| A33 | 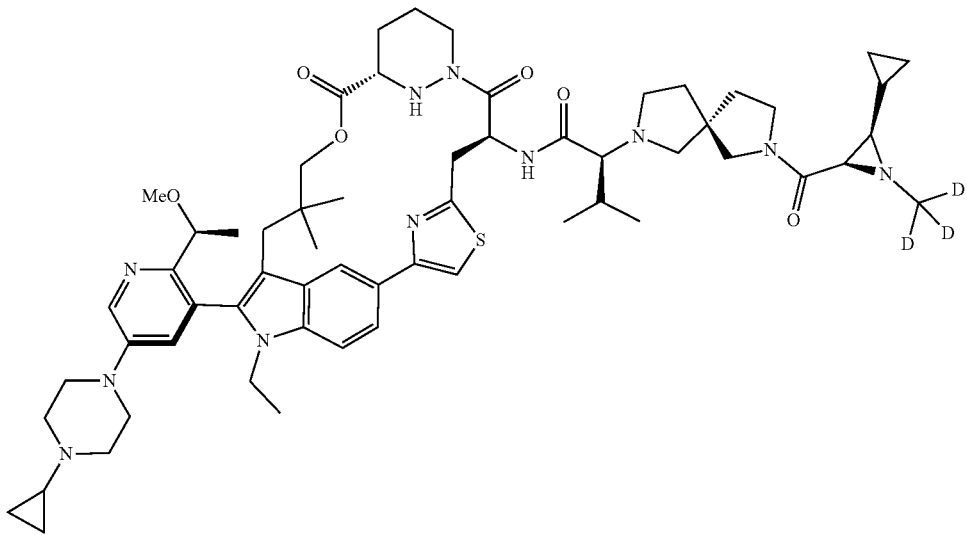 |
| A34 | 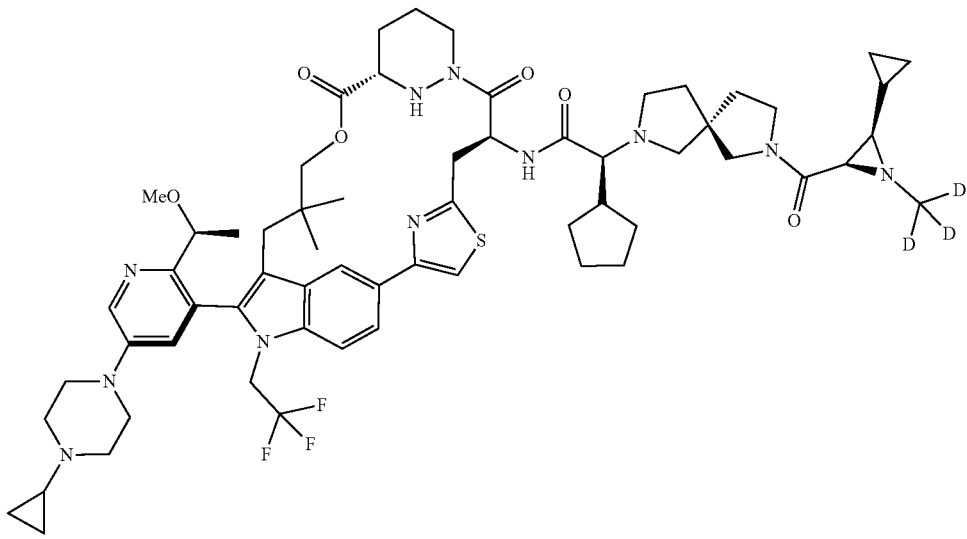 |

…
US 12,202,845 B2
TABLE 1-continued
Certain Compounds of the Present Invention
| Ex# | Structure |
|---|---|
| A35 | 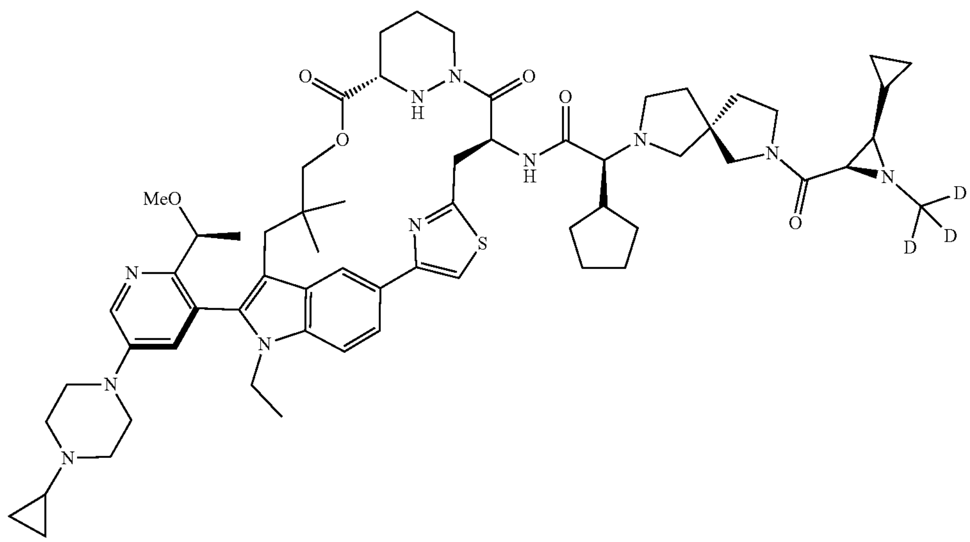 |
| A36 | 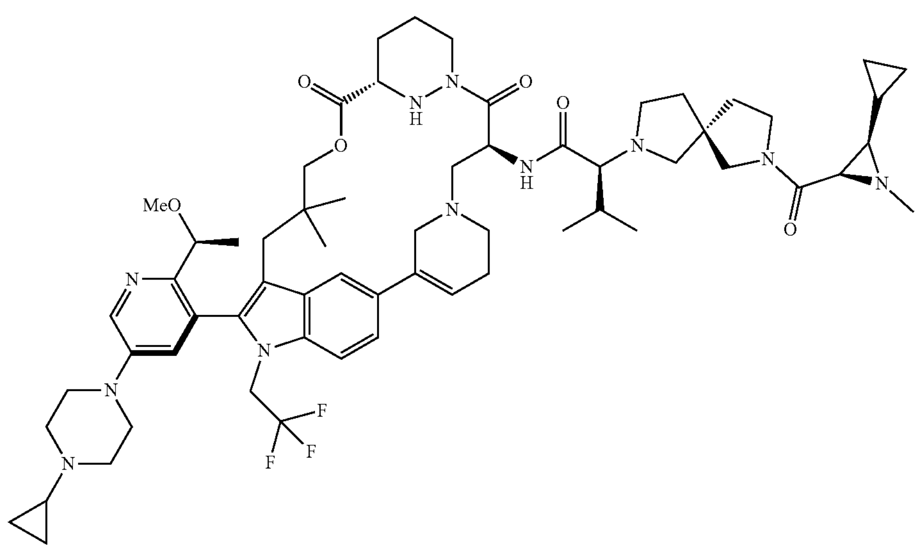 |
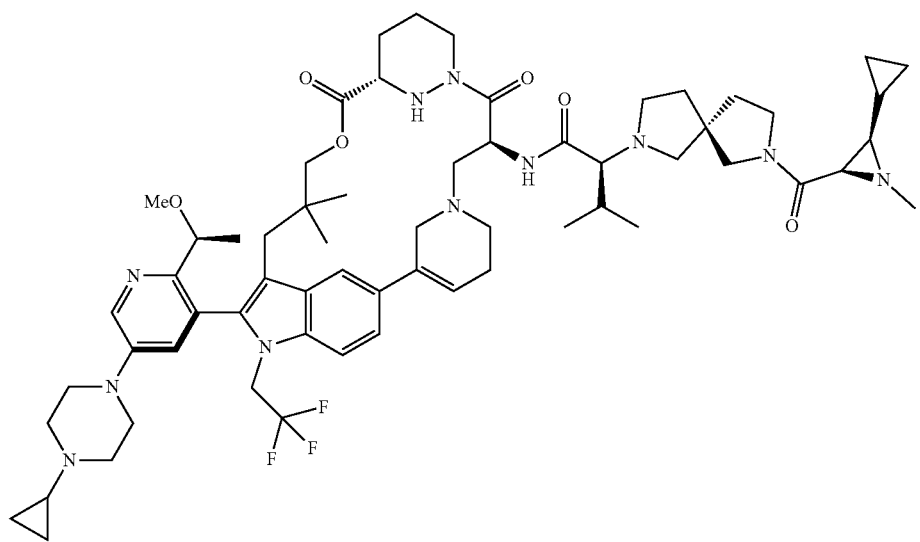

TABLE 1-continued
Certain Compounds of the Present Invention
| Ex# | Structure |
|---|---|
| A37 | 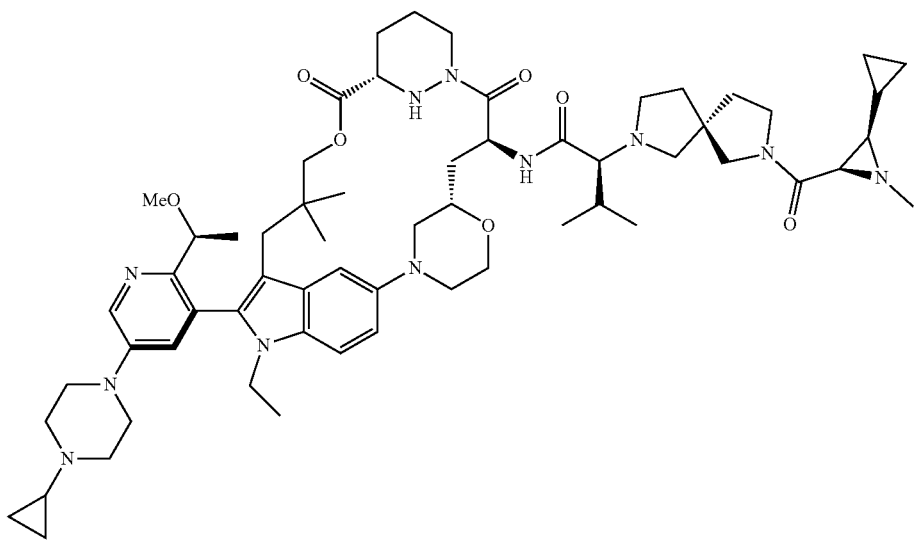 |
| A38 | 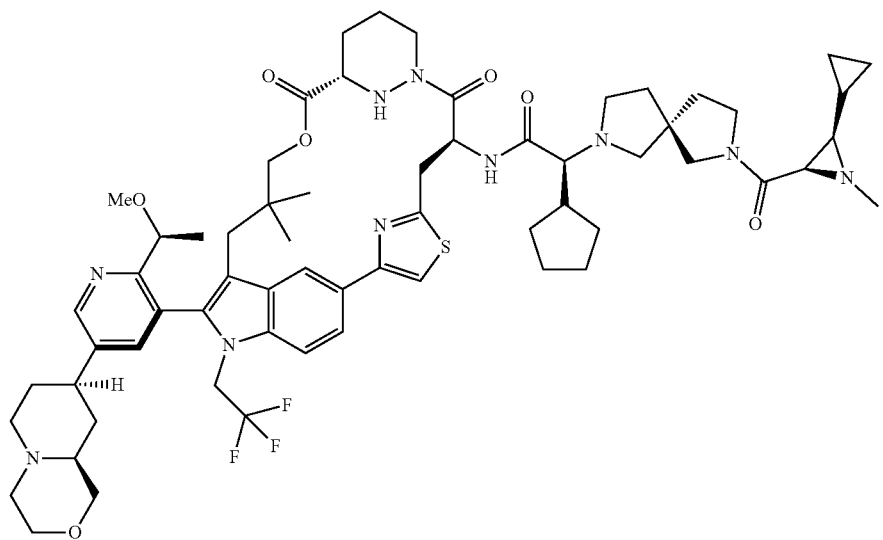 |

TABLE 1-continued
Certain Compounds of the Present Invention
| Ex# | Structure |
|---|---|
| A39 | 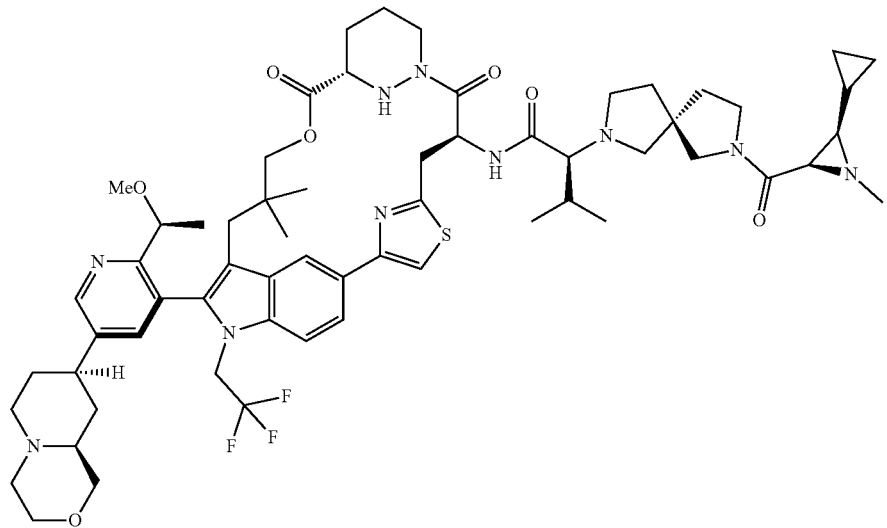 |
| A40 | 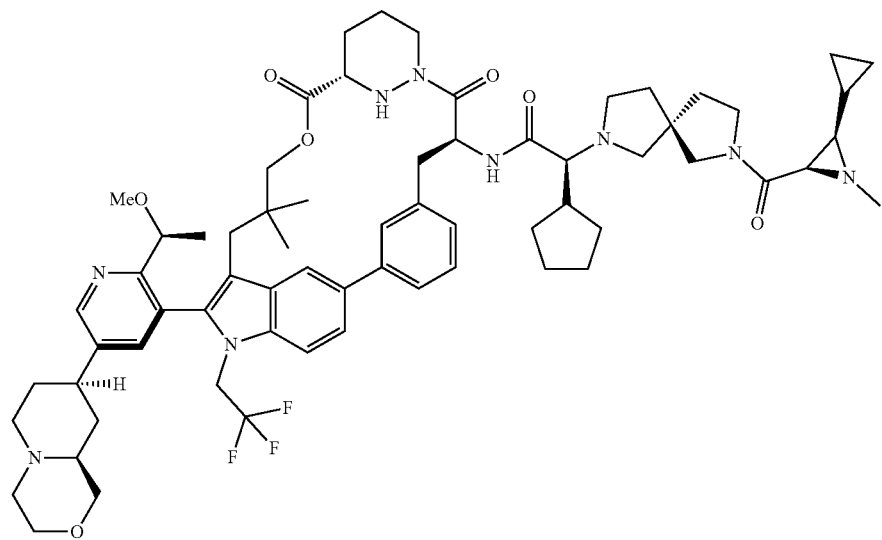 |

TABLE 1-continued
Certain Compounds of the Present Invention
| Ex# | Structure |
|---|---|
| A41 | 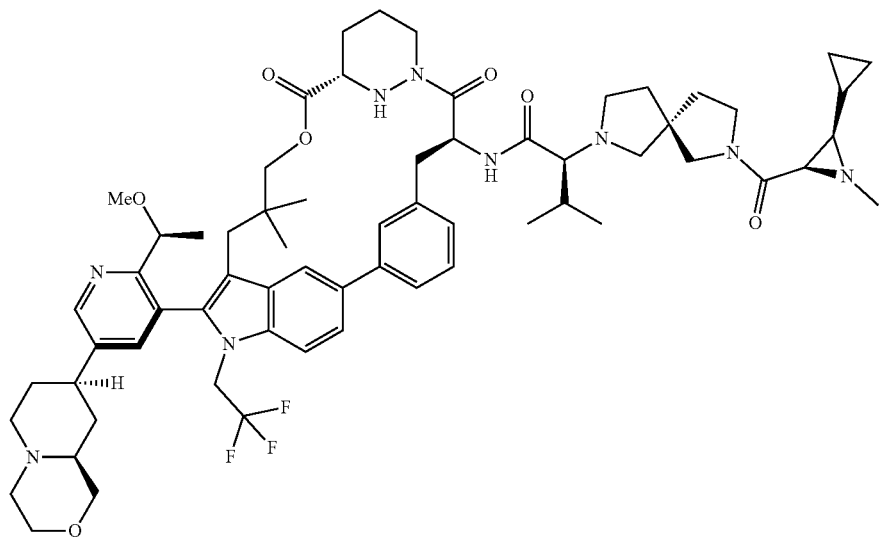 |
| A42 | 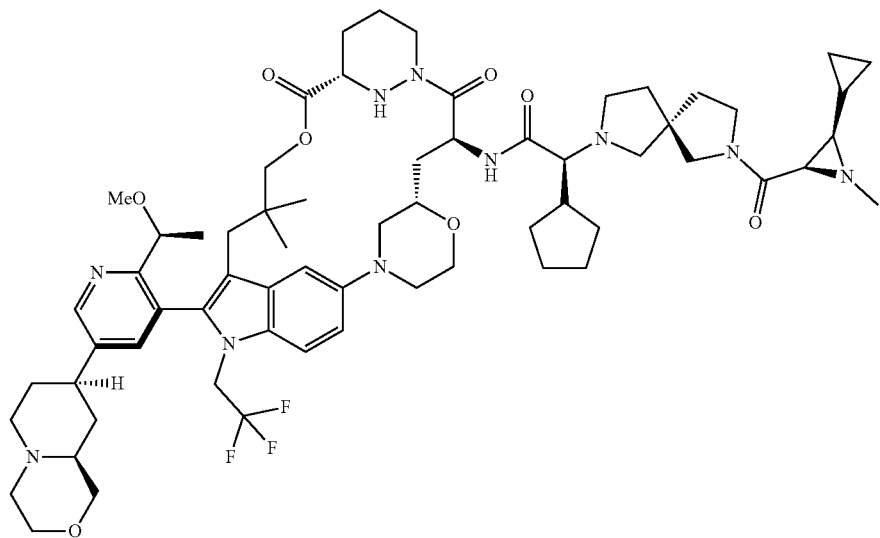 |

TABLE 1-continued
Certain Compounds of the Present Invention
| Ex# | Structure |
|---|---|
| A43 | 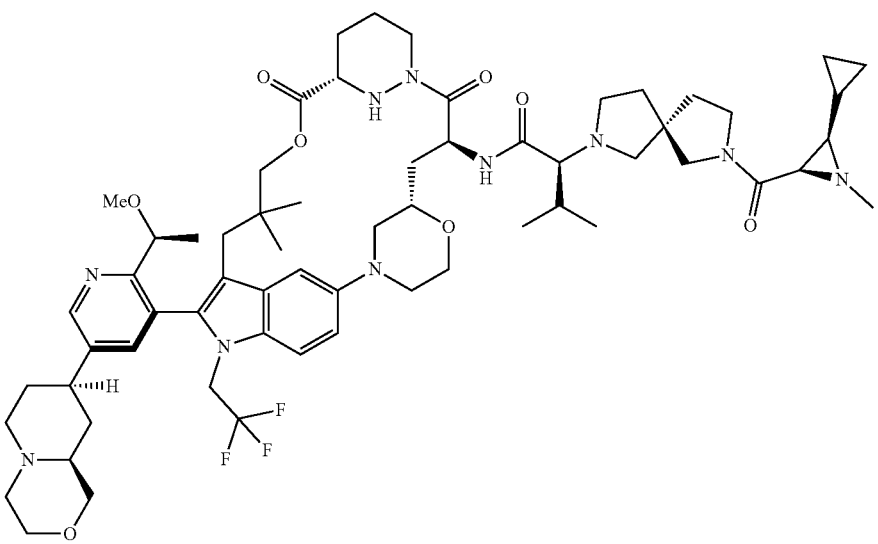 |
| A44 | 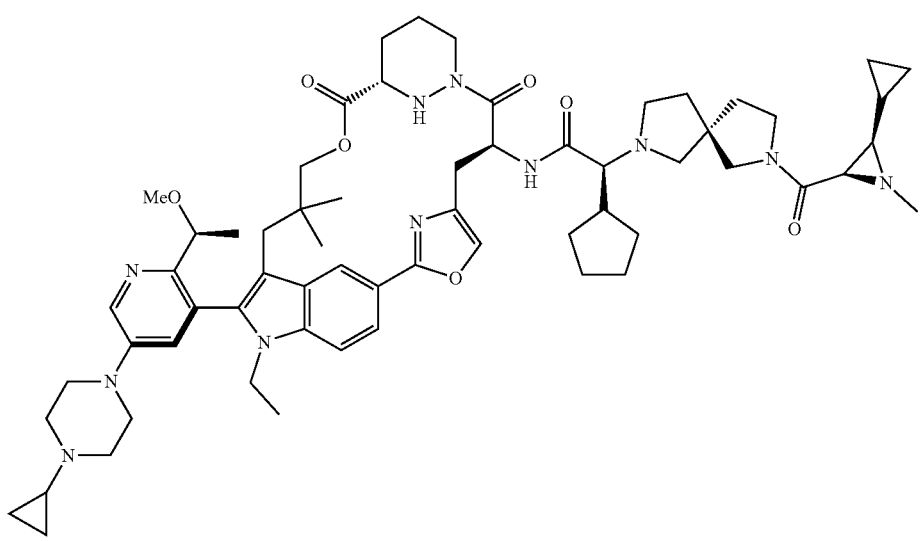 |

TABLE 1-continued
Certain Compounds of the Present Invention
| Ex# | Structure |
|---|---|
| B7 | 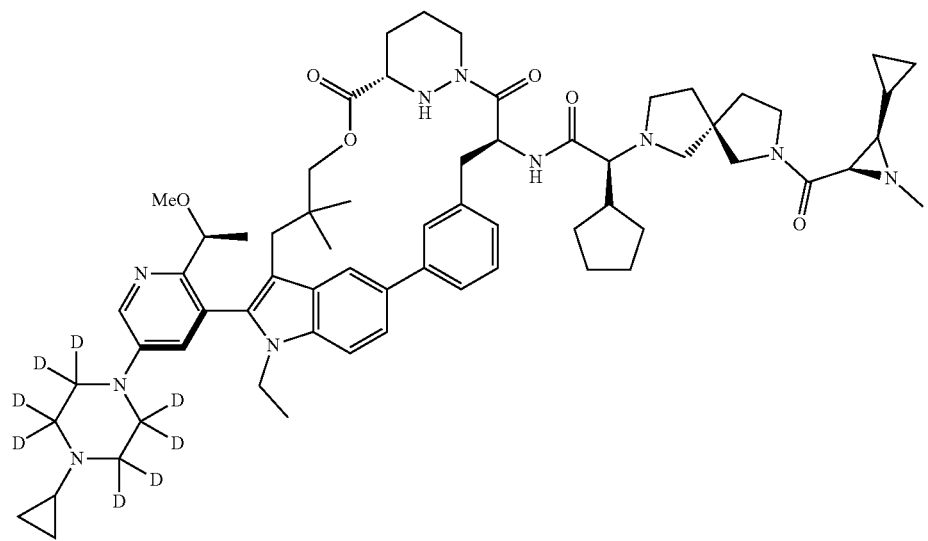 |
| B8 | 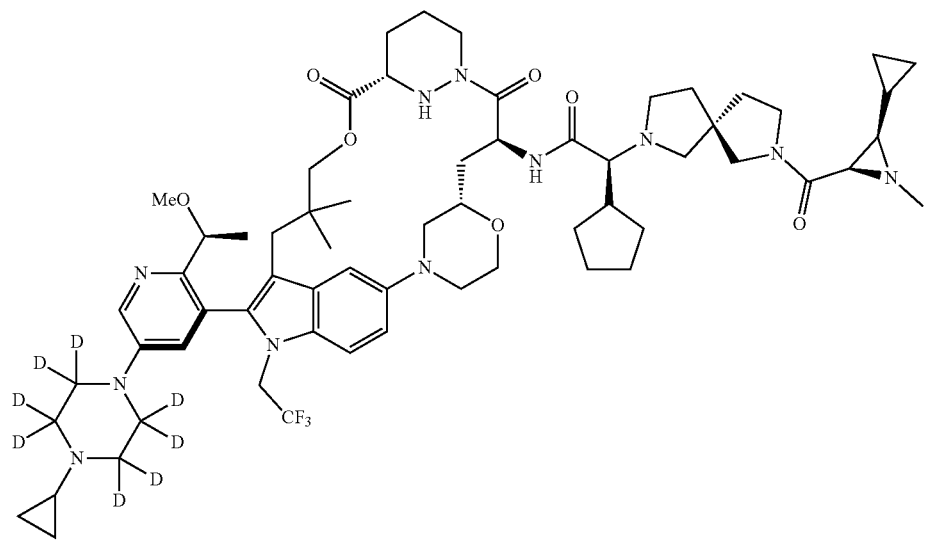 |

TABLE 1-continued
Certain Compounds of the Present Invention
| Ex# | Structure |
|---|---|
| B9 | 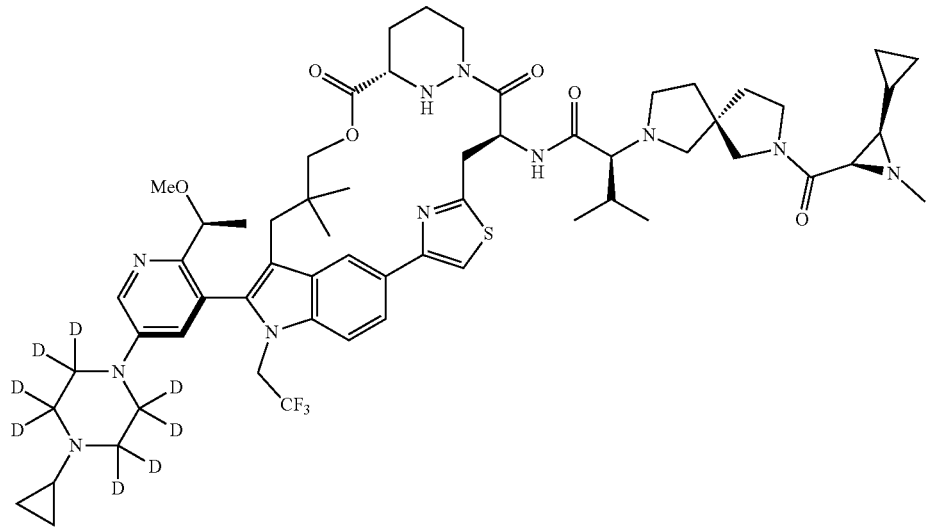 |
| B28 | 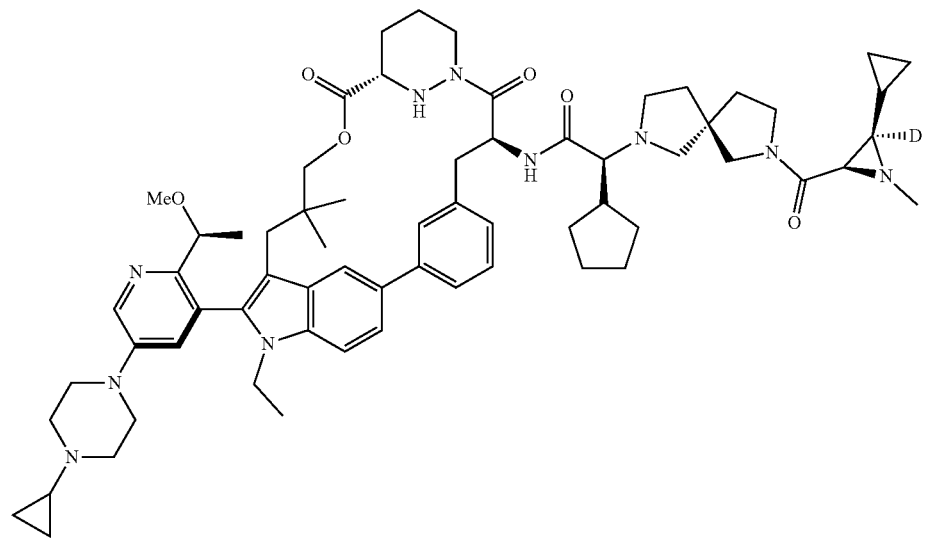 |

TABLE 1-continued

Certain Compounds of the Present Invention

| Ex# | Structure |
|---|---|
| B29 | 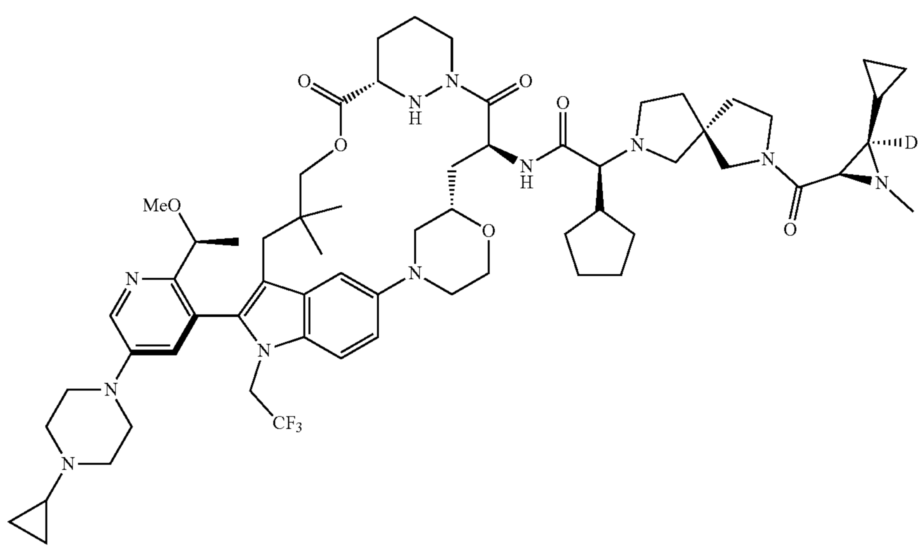 |
| B30 | 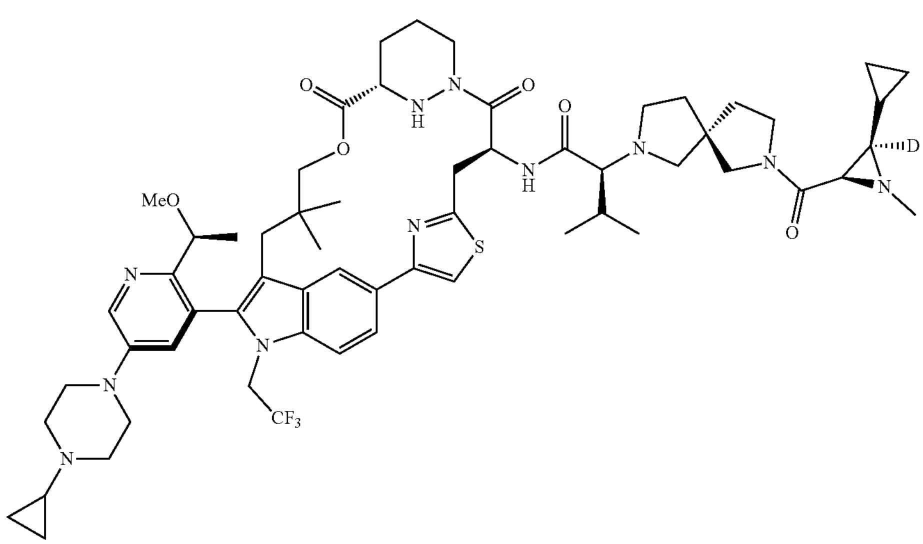 |

Note that some compounds are shown with bonds as flat or wedged. In some instances, the relative stereochemistry of stereoisomers has been determined; in some instances, the absolute stereochemistry has been determined. In some instances, a single Example number corresponds to a mixture of stereoisomers. All stereoisomers of the compounds of the foregoing table are contemplated by the present invention. In particular embodiments, an atropisomer of a compound of the foregoing table is contemplated.

In some embodiments, a compound of Table 2 is provided, or a pharmaceutically acceptable salt thereof. In some embodiments, a compound of the present invention is selected from Table 2, or a pharmaceutically acceptable salt or atropisomer thereof.

TABLE 2
Certain Compounds of the Present Invention
| Ex# | Structure |
|---|---|
| B1 | 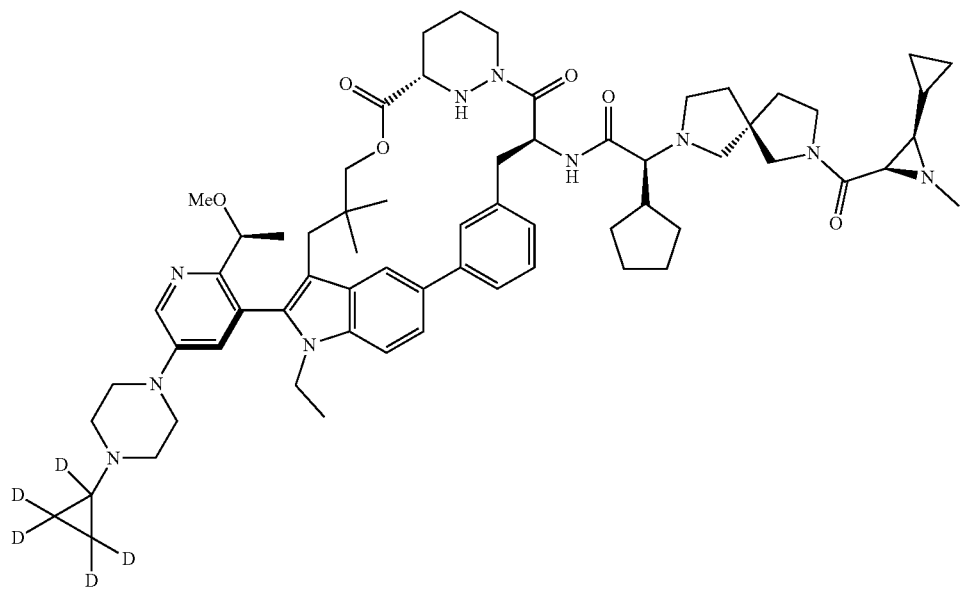 |
| B2 | 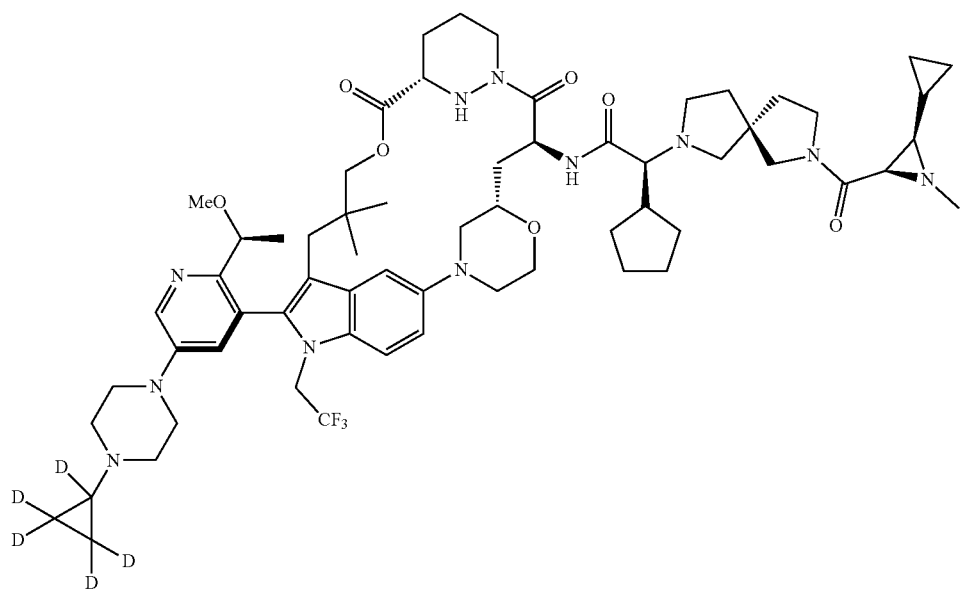 |

TABLE 2-continued
Certain Compounds of the Present Invention
| Ex# | Structure |
|---|---|
| B3 | 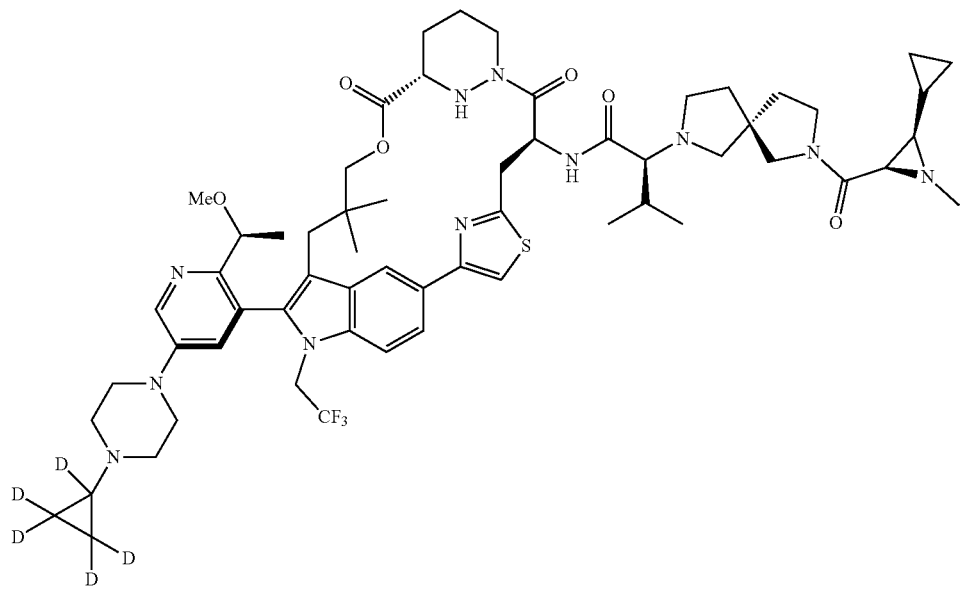 |
| B4 | 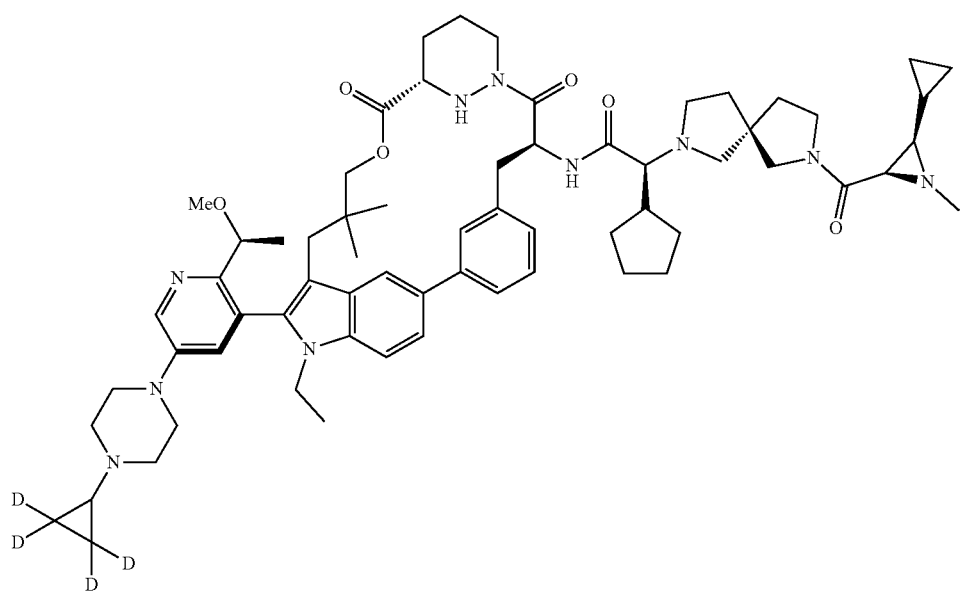 |

TABLE 2-continued
Certain Compounds of the Present Invention
| Ex# | Structure |
|---|---|
| B5 | 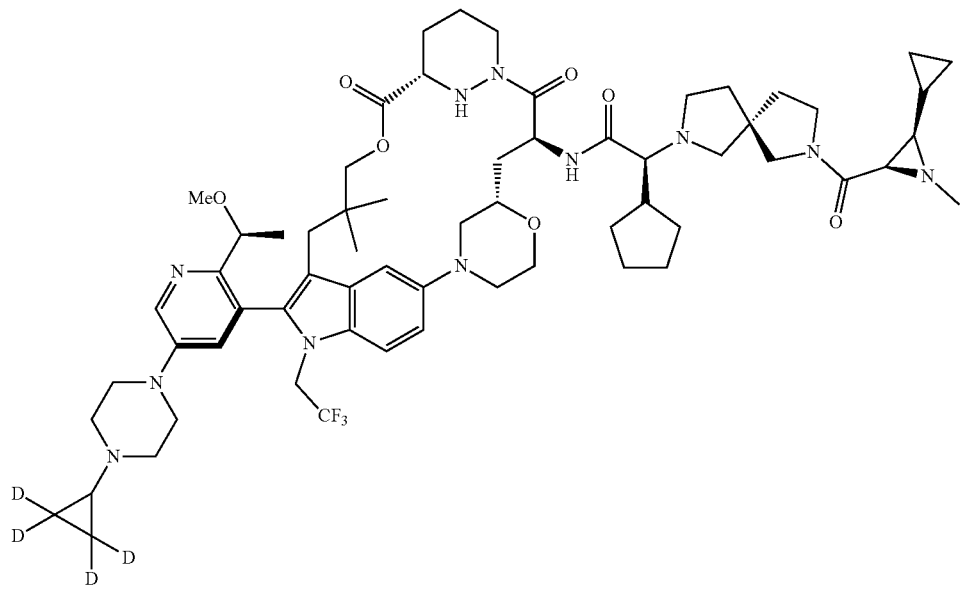 |
| B6 | 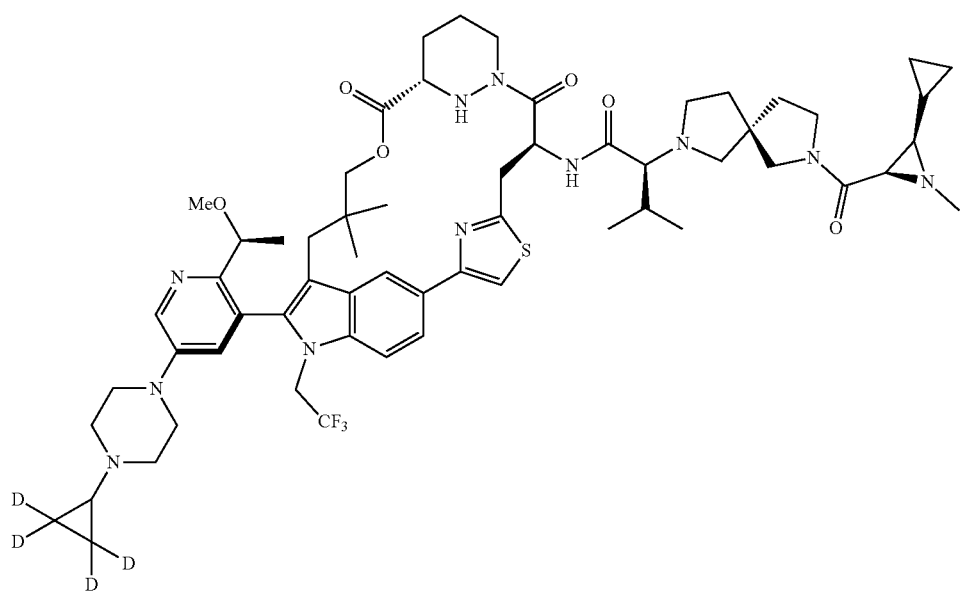 |

TABLE 2-continued
Certain Compounds of the Present Invention
| Ex# | Structure |
|---|---|
| B10 | 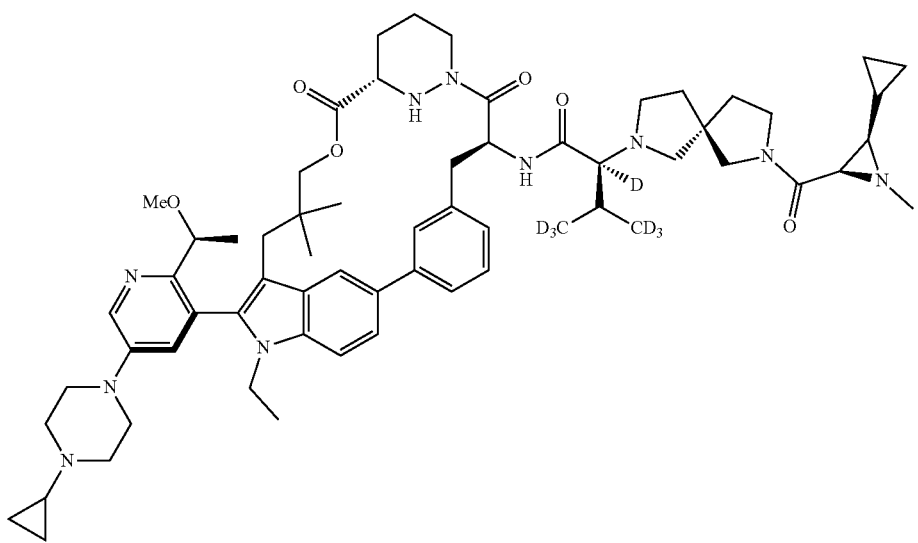 |
| B11 | 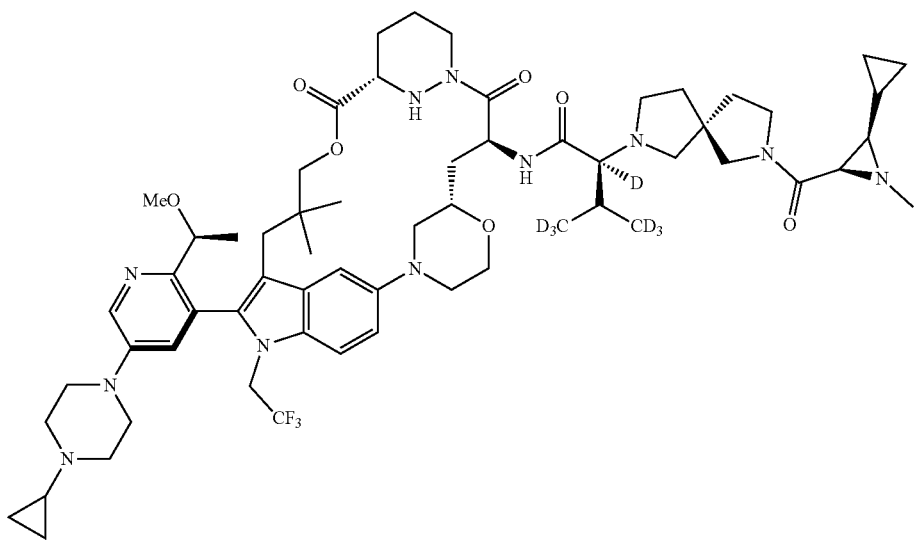 |

TABLE 2-continued
Certain Compounds of the Present Invention
| Ex# | Structure |
|---|---|
| B12 | 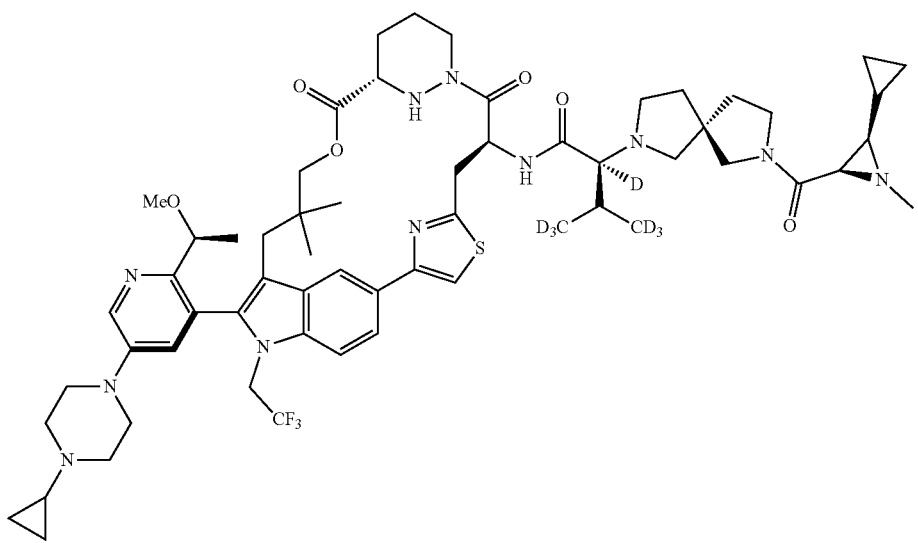 |
| B13 | 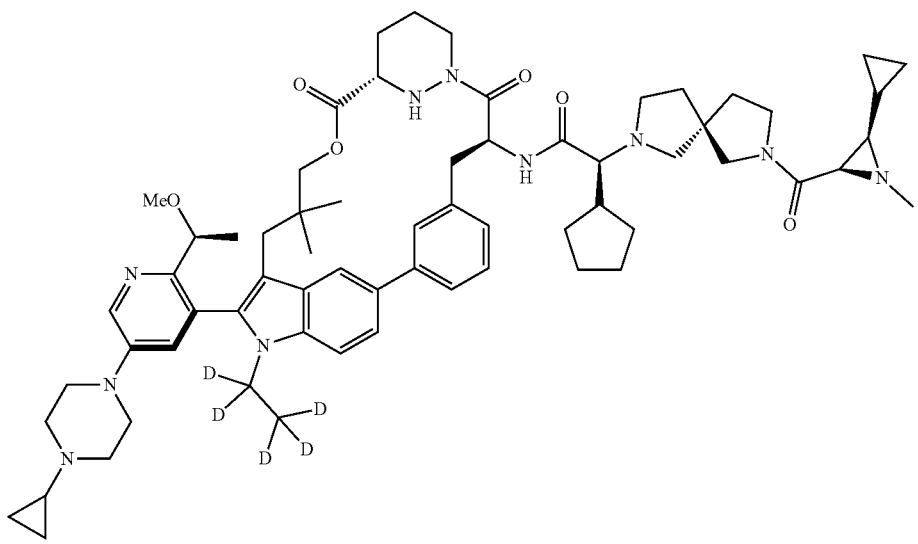 |

TABLE 2-continued
Certain Compounds of the Present Invention
| Ex# | Structure |
|---|---|
| B14 | 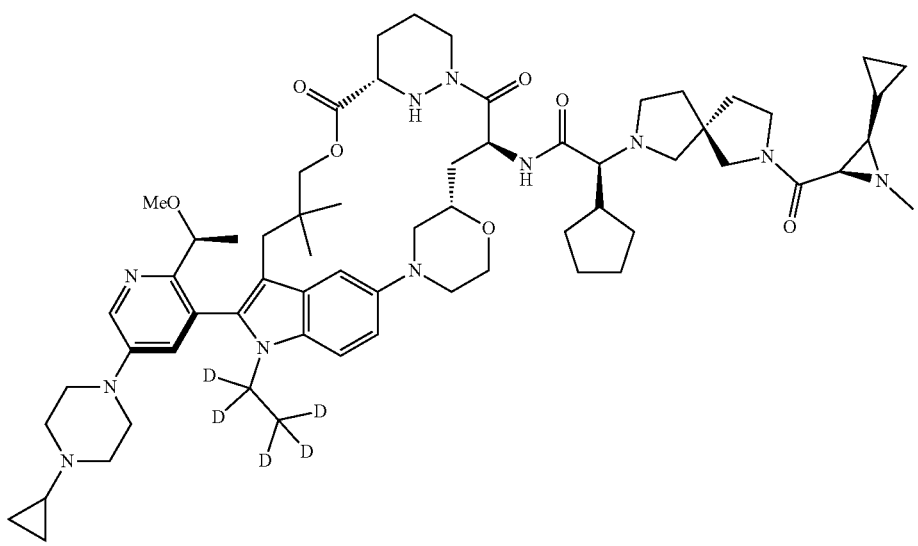 |
| B15 | 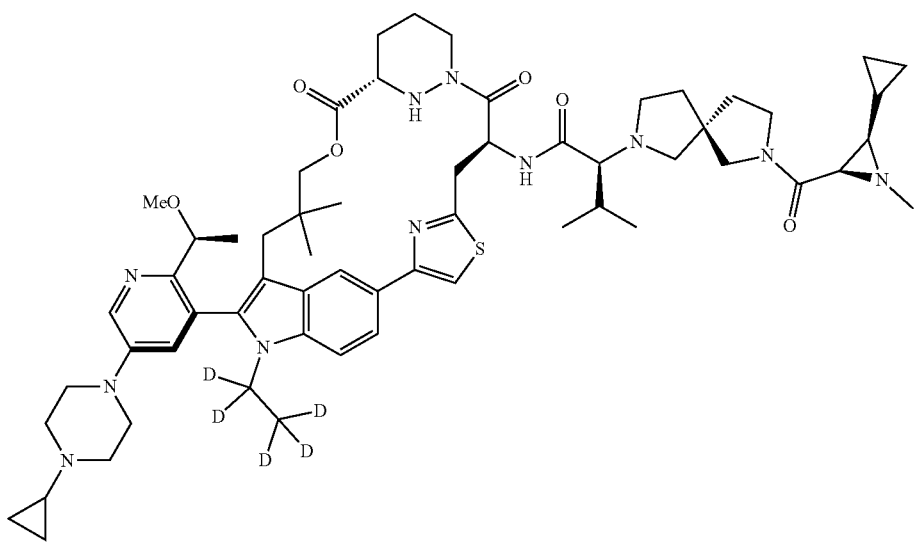 |

TABLE 2-continued
Certain Compounds of the Present Invention
| Ex# | Structure |
|---|---|
| B16 | 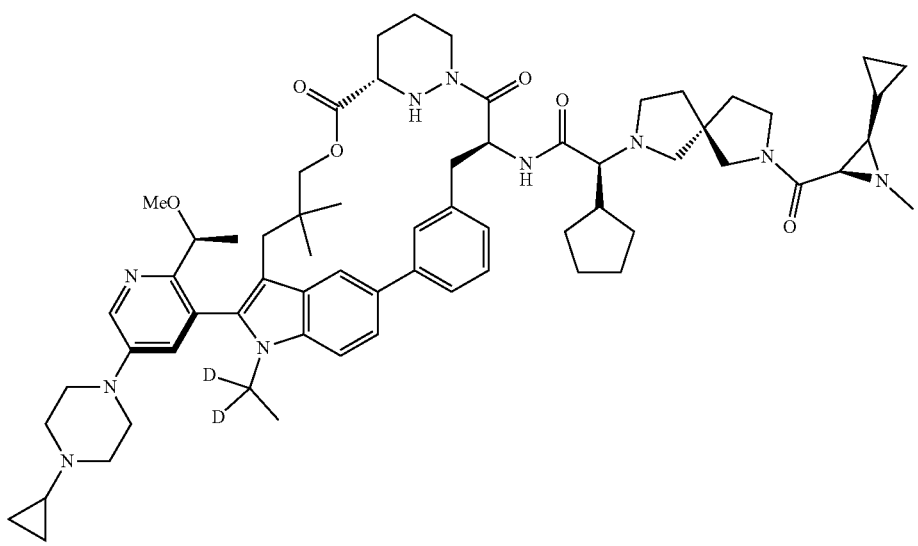 |
| B17 | 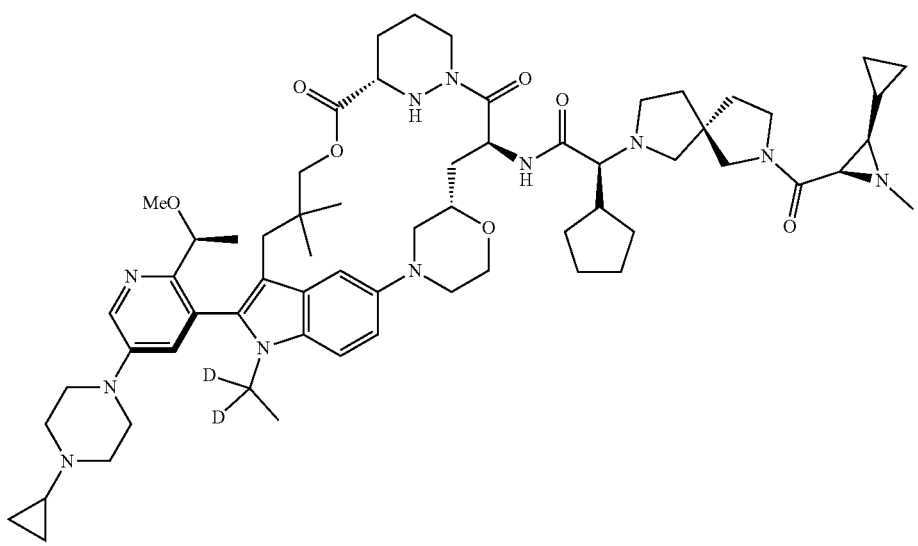 |

TABLE 2-continued
Certain Compounds of the Present Invention
| Ex# | Structure |
|---|---|
| B18 | 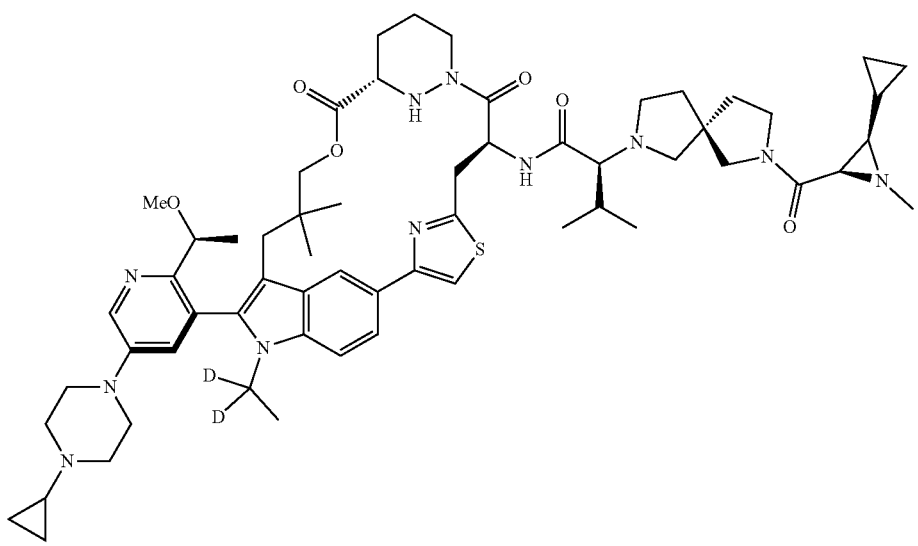 |
| B19 | 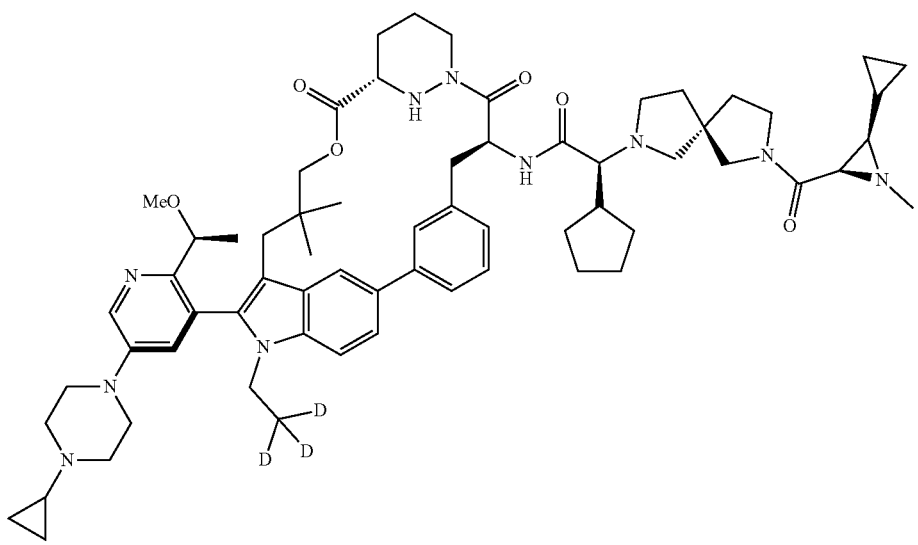 |

TABLE 2-continued
Certain Compounds of the Present Invention
| Ex# | Structure |
|---|---|
| B20 | 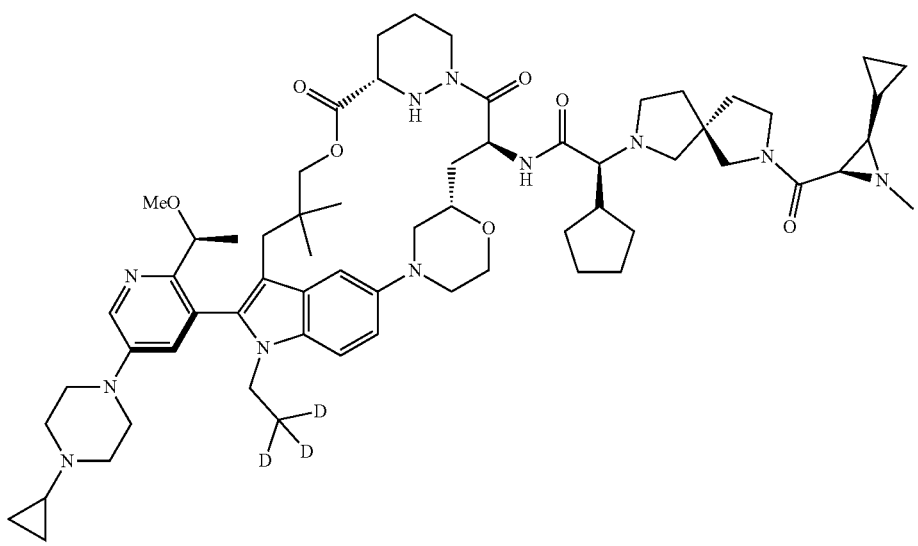 |
| B21 | 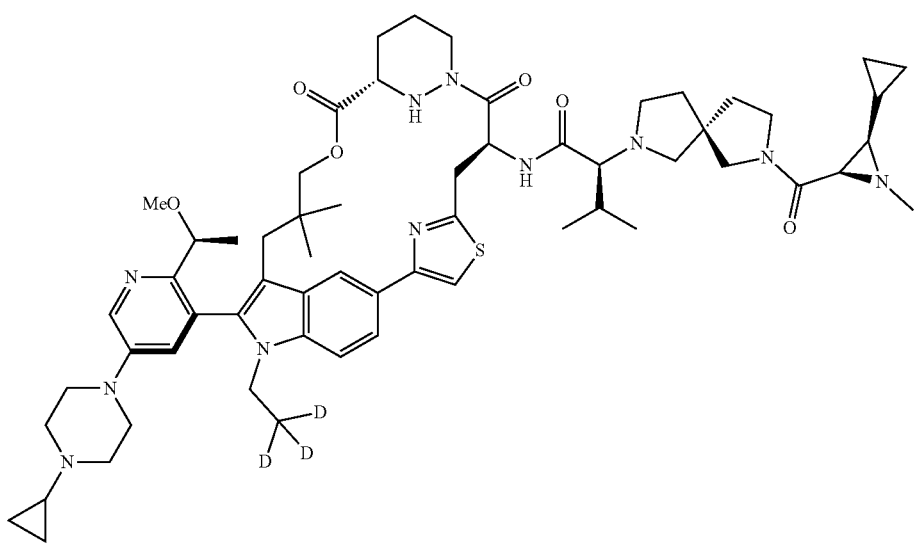 |

TABLE 2-continued
Certain Compounds of the Present Invention
| Ex# | Structure |
|---|---|
| B22 | 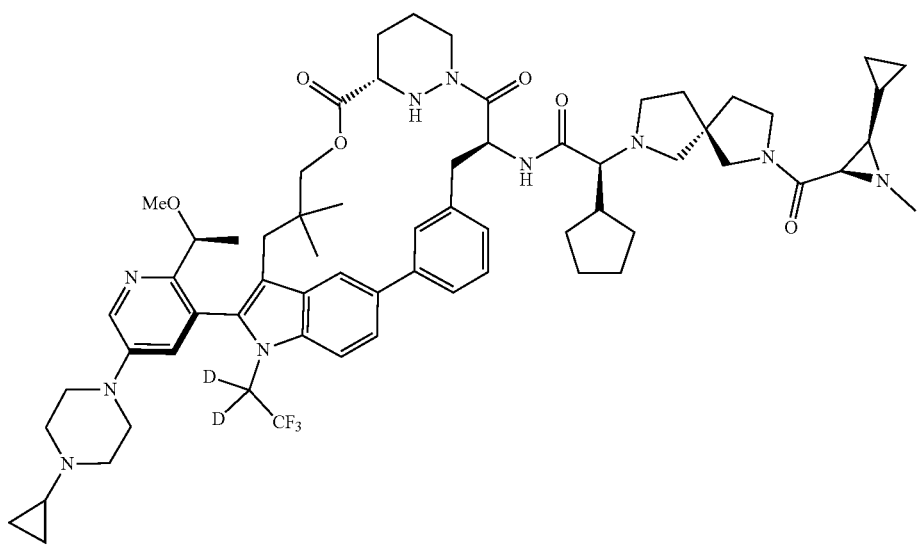 |
| B23 | 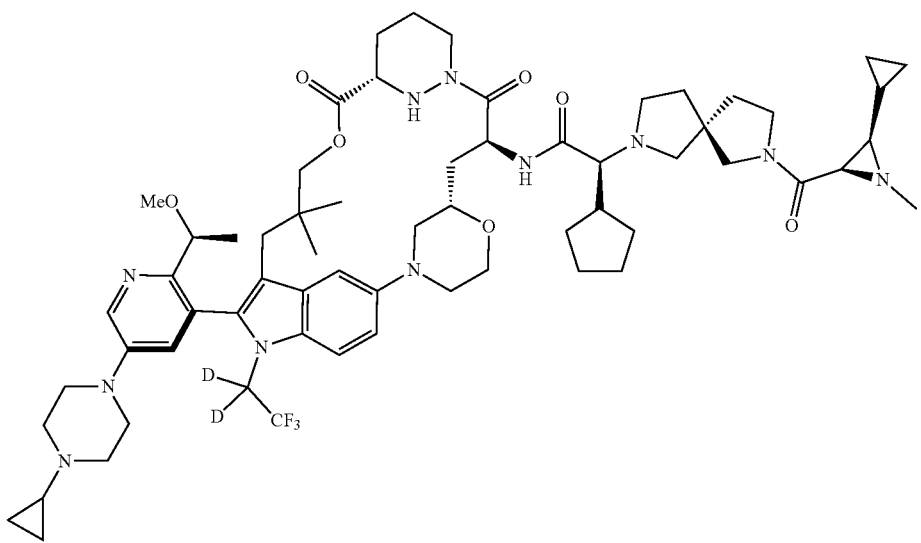 |

TABLE 2-continued
Certain Compounds of the Present Invention
| Ex# | Structure |
|---|---|
| B24 | 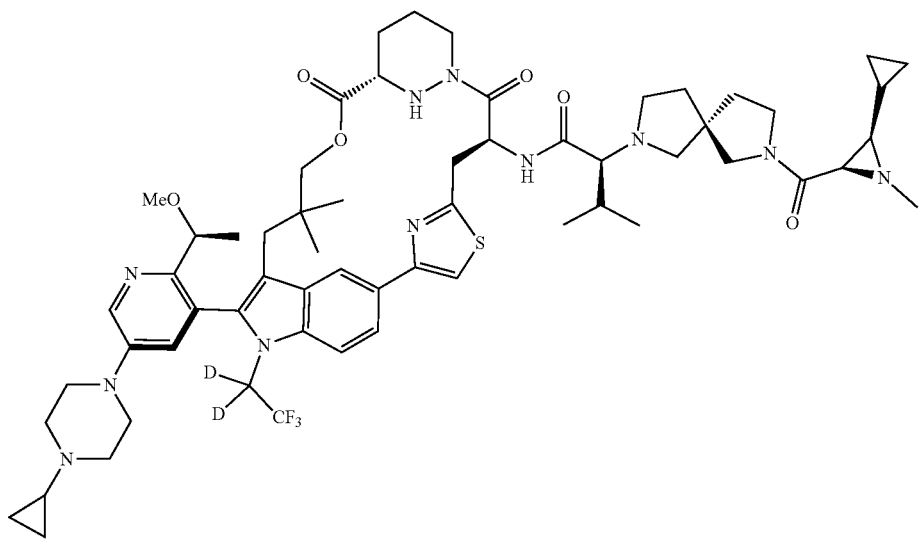 |
| B25 | 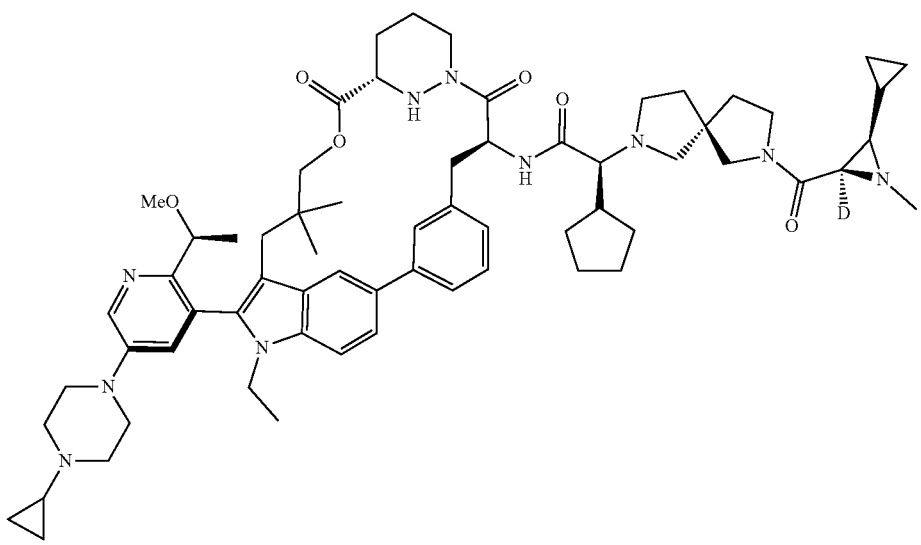 |

TABLE 2-continued

Certain Compounds of the Present Invention

| Ex# | Structure |
|---|---|
| B26 | 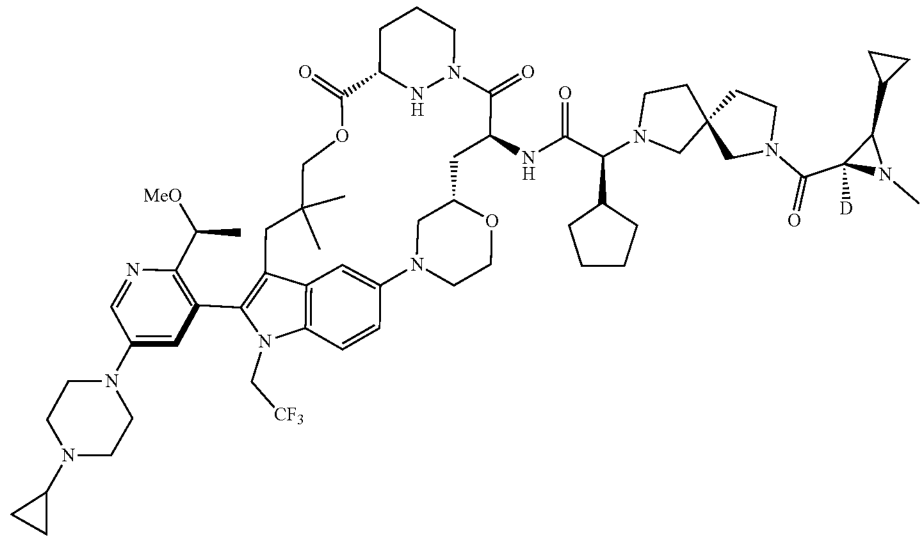 |
| B27 | 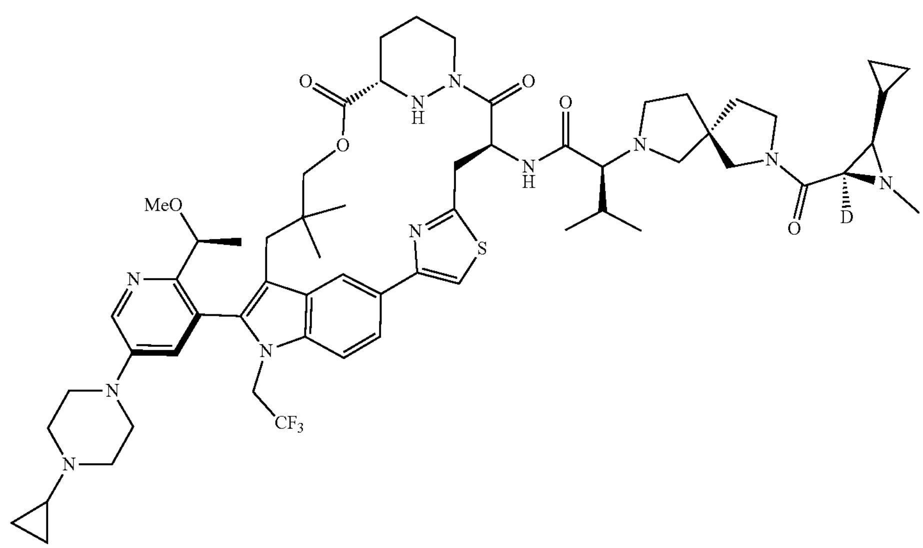 |

Note that some compounds are shown with bonds as flat or wedged. In some instances, a single Example number corresponds to a mixture of stereoisomers. All stereoisomers of the compounds of the foregoing table are contemplated by the present invention. In particular embodiments, an atropisomer of a compound of the foregoing table is contemplated.

In some embodiments, a compound of the present invention is a compound selected from Table 3, or a pharmaceutically acceptable salt or stereoisomer thereof. In some embodiments, a compound of the present invention is a compound selected from Table 3, or a pharmaceutically acceptable salt or atropisomer thereof.

In some embodiments, a compound of the present invention is not a compound selected from Table 3. In some embodiments, a compound of the present invention is not a compound selected from Table 3, or a pharmaceutically acceptable salt or stereoisomer thereof. In some embodiments, a compound of the present invention is not a compound selected from Table 3, or a pharmaceutically acceptable salt or atropisomer thereof.

TABLE 3
Certain Compounds
| Ex# | Structure |
|---|---|
| C1 | 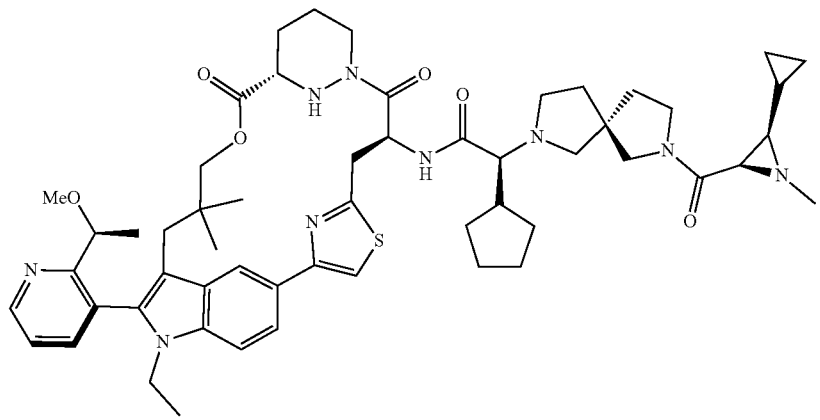 |
| C2 | 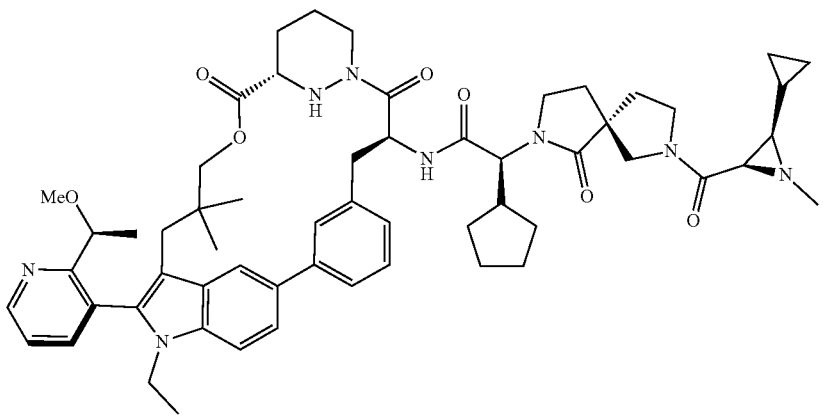 |
| C3 | 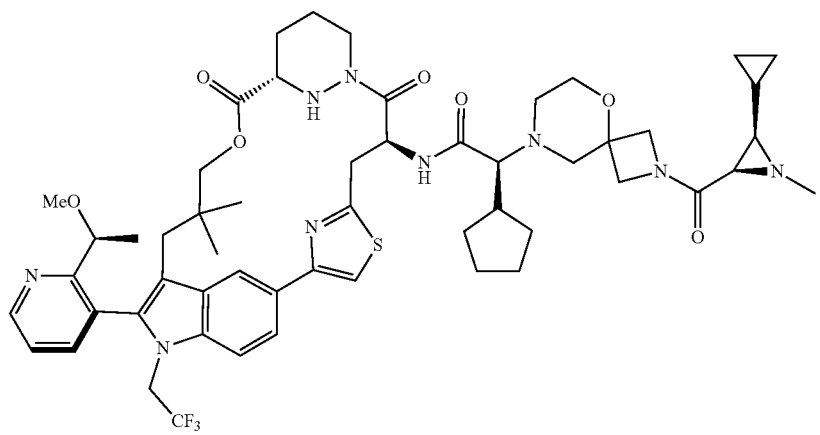 |

TABLE 3-continued
Certain Compounds
| Ex# | Structure |
|---|---|
| C4 | 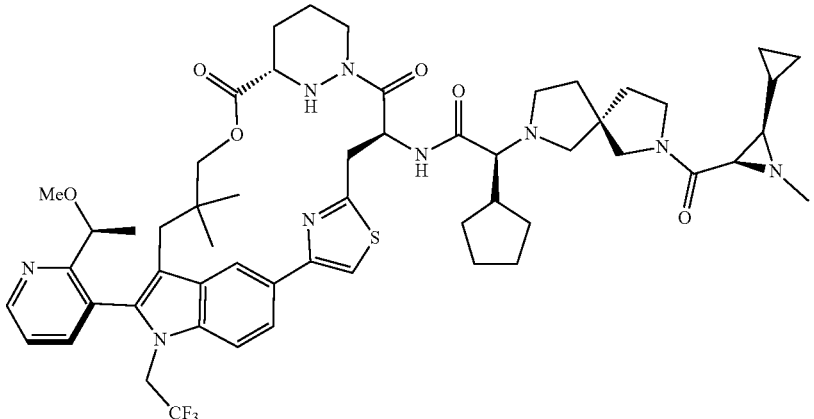 |
| C5 | 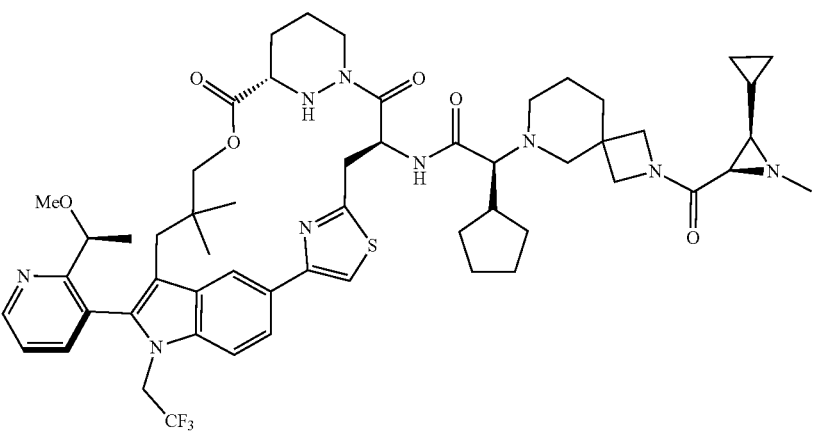 |
| C6 | 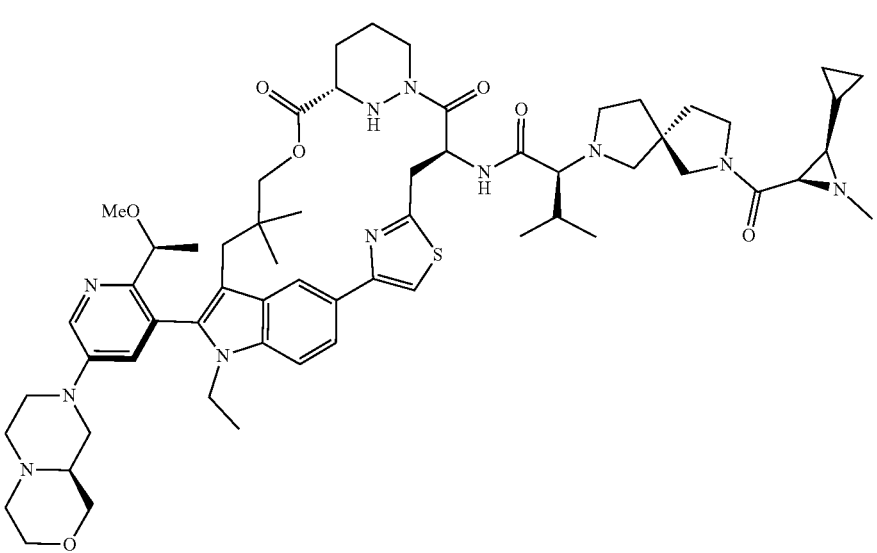 |

TABLE 3-continued
Certain Compounds
| Ex# | Structure |
|---|---|
| C7 | 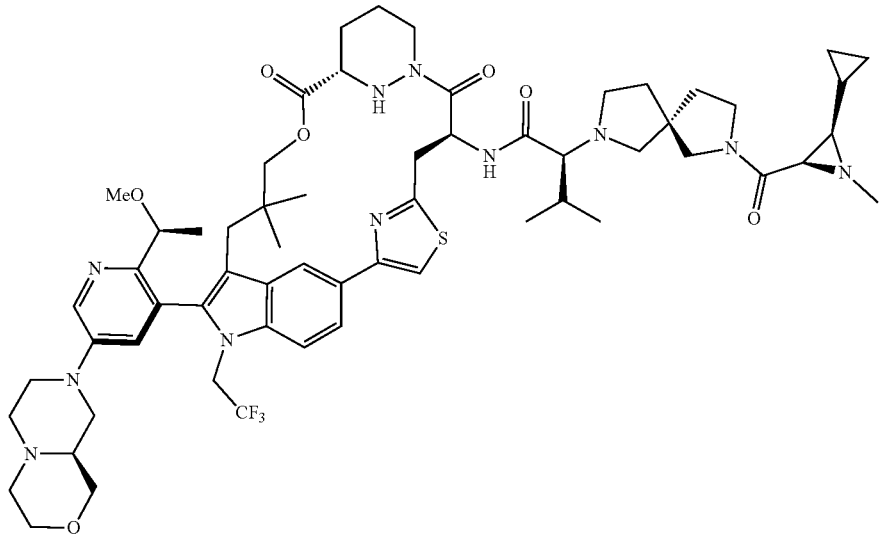 |
| C8 | 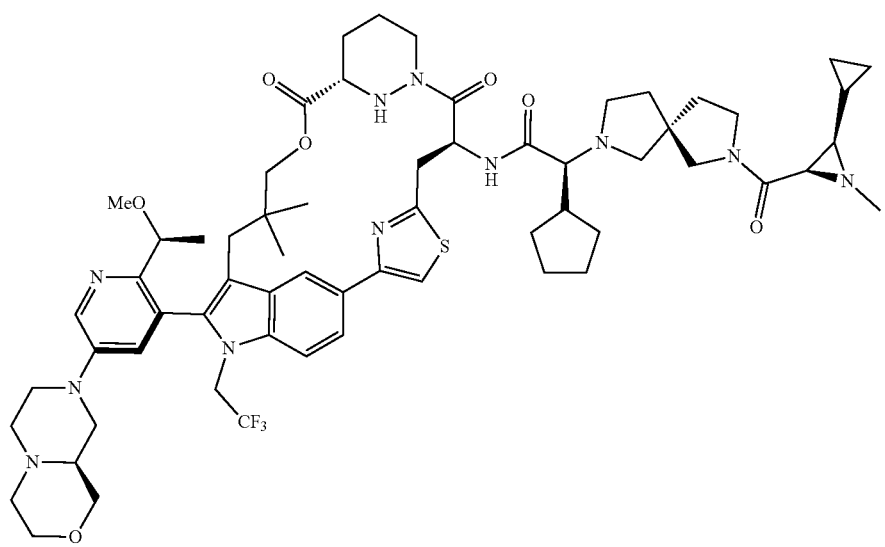 |

TABLE 3-continued

Certain Compounds

| Ex# | Structure |
|---|---|
| C9 | 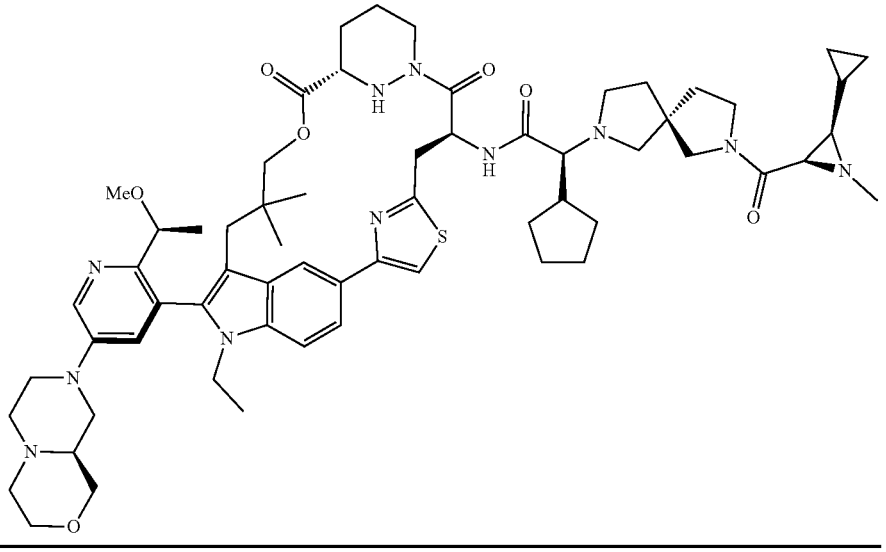 |

In some embodiments, a compound of the present invention includes a crossing-linking group (e.g., an optionally substituted aziridine moiety) bound to an organic moiety that is a Ras binding moiety wherein upon contact of the compound with a Ras protein, the compounds binds to the Ras protein to form a conjugate. For example, the crossing-linking group (e.g., an optionally substituted aziridine moiety) of the compound may bind, e.g., cross-link, with an amino acid of the Ras protein to form the conjugate. In some embodiments, the Ras binding moiety is a K-Ras binding moiety. In some embodiments, the K-Ras binding moiety binds to a residue of a K-Ras Switch-II binding pocket of the K-Ras protein. In some embodiments, the Ras binding moiety is an H-Ras binding moiety that binds to a residue of an H-Ras Switch-II binding pocket of an H-Ras protein. In some embodiments, the Ras binding moiety is an N-Ras binding moiety that binds to a residue of an N-Ras Switch-II binding pocket of an N-Ras protein. The Ras binding moiety typically has a molecular weight of under 1200 Da. See, e.g., see, e.g., Johnson et al., 292:12981-12993 (2017) for a description of Ras protein domains, incorporated herein by reference.

In some embodiments, a compound of the present invention is or acts as a prodrug, such as with respect to administration to a cell or to a subject in need thereof.

Also provided are pharmaceutical compositions comprising a compound of the present invention, or a pharmaceutically acceptable salt thereof, and a pharmaceutically acceptable excipient.

Further provided is a conjugate, or salt thereof, comprising the structure of Formula III:

$$M-P^1 \qquad \text{Formula III}$$

wherein $P^1$ is a monovalent organic moiety; and
M has the structure of Formula IV:

Formula IV

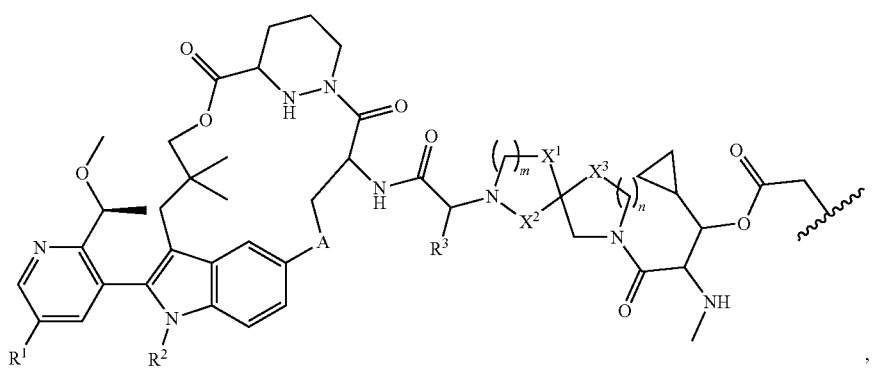

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$X^1$, $X^2$, and $X^3$ are each independently selected from $CH_2$, $CF_2$, C=O, or O;

m is 1 or 2;

n is 0 or 1;

$R^1$ is hydrogen, optionally substituted $C_1$-$C_6$ heteroalkyl, or optionally substituted 3 to 10-membered heterocycloalkyl;

$R^2$ is optionally substituted $C_1$-$C_6$ alkyl; and $R^3$ is optionally substituted $C_1$-$C_6$ alkyl, optionally substituted 3 to 6-membered cycloalkyl, or optionally substituted heterocycloalkyl, and wherein each hydrogen of Formula IV is independently, optionally, isotopically enriched for deuterium.

In some embodiments of conjugates of the present invention, the monovalent organic moiety is a protein. In some embodiments, the protein is a Ras protein. In some embodiments, the Ras protein is K-Ras G12D or K-Ras G13D. In some embodiments of conjugates of the present invention, M is bound to an amino acid residue of the monovalent organic moiety.

In some embodiments, a compound of the present invention has improved oral bioavailability (% F) compared to what is known in the art. Methods of measuring oral bioavailability are known in the art, and one such method is provided below:

Oral bioavailability may be determined in BALB/c mice. Following intravenous (IV) bolus and oral gavage (PO) administration of a test compound, about 30 µL of whole blood samples are collected at designated time points into tubes containing $K_2$EDTA. For some compounds, the blood samples are centrifuged at 4600 rpm at 4° C. for about 5 minutes and plasma samples are stored at −80° C. prior to bioanalysis. Either blood or plasma samples are extracted by protein precipitation and analyzed by tandem mass spectrometry (UPLC MS/MS) on, for example, an AB Sciex Triple Quad 6500+ mass spectrometry coupled with an Acquity UPLC system using electrospray positive ionization.

All PK parameters may be derived from blood (or plasma) concentration over time data with noncompartmental analysis using WinNonlin. The bioavailability (F %, also % F) is estimated using the following equation:

$$F\% = \frac{AUC_{inf,PO}}{AUC_{inf,IV}} \cdot \frac{Dose_{IV}}{Dose_{PO}}$$

$AUC_{inf,PO}$ is the area under the blood (or plasma) concentration over time from time zero to infinity following PO administration.

$AUC_{inf,IV}$ is the area under the blood (or plasma) concentration over time from time zero to infinity following IV administration.

$Dose_{IV}$ is the total dose of IV administration $Dose_{PO}$ is the total dose of PO administration In general, F % (or % F) values of over 10% are preferred.

Of 19 compounds of Table 1 described herein that were tested for oral bioavailability, all but three had % F greater than 10%. Furthermore, all but three cross-link the G12D residue of K-Ras greater than 60% over a 6-hour time period in the biochemical cross-linking assay described herein. Thirteen of the compounds tested had both % F greater than 10% and cross-linked the G12D residue of K-Ras greater than 60%. Without being bound by theory, the inventors purport that the N-methyl aziridine moiety of the compounds described herein is primarily responsible for this unexpected activity.

In some embodiments, a compound of the present invention is selective for one or more particular Ras mutants over other Ras mutants or wild-type compared to what is known in the art. Methods of measuring such selectivity are known in the art, such as the Ras-Raf binding assay, a protocol for which is provided here:

The purpose of this biochemical assay is to measure the ability of test compounds to facilitate ternary complex formation between a nucleotide-loaded Ras isoform and cyclophilin A; the resulting ternary complex disrupts binding to a $BRAF^{RBD}$ construct, inhibiting Ras signaling through a RAF effector.

In assay buffer containing 25 mM HEPES pH 7.3, 0.002% Tween20, 0.1% BSA, 100 mM NaCl and 5 mM $MgCl_2$, tagless Cyclophilin A, His6-K-Ras-GMPPNP (or other Ras variant), and GST-$BRAF^{RBD}$ are combined in a 384-well assay plate at final concentrations of 25 µM, 12.5 nM and 50 nM, respectively. Compound is present in plate wells as a 10-point 3-fold dilution series starting at a final concentration of 30 µM. After incubation at 25° C. for 3 hours, a mixture of Anti-His Eu-W1024 and anti-GST allophycocyanin is then added to assay sample wells at final concentrations of 10 nM and 50 nM, respectively, and the reaction incubated for an additional 1.5 hours. TR-FRET signal is read on a microplate reader (Ex 320 nm, Em 665/615 nm). Compounds that facilitate disruption of a Ras: RAF complex are identified as those eliciting a decrease in the TR-FRET ratio relative to DMSO control wells.

Accordingly, in some embodiments, compounds of the present invention are selective for $KRAS^{G12D}$ over other Ras mutants or over wild-type. Compounds of the present invention may also exhibit greater selectivity with respect to other RAS mutants disclosed herein, or combinations thereof.

In some embodiments, a compound of the present invention is more potent for one or more particular Ras mutants over other Ras mutants or wild-type compared to what is known in the art. Methods of measuring such potency are known in the art, such as the pERK assay, a protocol for which is provided in the Examples below. Accordingly, in some embodiments, compounds of the present invention exhibit greater potency with respect to $KRAS^{G12D}$ than what is known in the art. Compounds of the present invention may also exhibit greater potency with respect to other RAS mutants disclosed herein, or combinations thereof.

In some embodiments, a compound of the present invention exhibits a greater detrimental effect on cell viability with respect to one or more particular Ras mutants over other Ras mutants or wild-type compared to what is known in the art. Methods of measuring cell viability are known in the art, such as the CellTiter-Glo® Cell Viability Assay assay described here:

Note—The following protocol describes a procedure for monitoring cell viability of K-Ras mutant cancer cell lines in response to a compound of the invention. Other RAS isoforms may be employed, though the number of cells to be seeded will vary based on cell line used.

The purpose of this cellular assay is to determine the effects of test compounds on the proliferation of human Ras cancer cell lines (e.g., NCI-H358 (K-Ras G12C), AsPC-1 (K-Ras G12D), and Capan-1 (K-Ras G12V)) over a 5-day treatment period by quantifying the amount of ATP present at endpoint using the CellTiter-Glo® 2.0 Reagent (Promega).

Cells are seeded at 250 cells/well in 40 μL of growth medium in 384-well assay plates and incubated overnight in a humidified atmosphere of 5% $CO_2$ at 37° C. On the day of the assay, 10 mM stock solutions of test compounds are first diluted into 3 mM solutions with 100% DMSO. Well-mixed compound solutions (15 μL) are transferred to the next wells containing 30 μL of 100% DMSO, and repeated until a 9-concentration 3-fold serial dilution is made (starting assay concentration of 10 μM). Test compounds (132.5 nL) are directly dispensed into the assay plates containing cells. The plates are shaken for 15 seconds at 300 rpm, centrifuged, and incubated in a humidified atmosphere of 5% $CO_2$ at 37° C. for 5 days. On day 5, assay plates and their contents are equilibrated to room temperature for approximately 30 minutes. CellTiter-Glo® 2.0 Reagent (25 μL) is added, and plate contents are mixed for 2 minutes on an orbital shaker before incubation at room temperature for 10 minutes. Luminescence is measured using the PerkinElmer Enspire. Data are normalized by the following: (Sample signal/Avg. DMSO) *100. The data are fit using a four-parameter logistic fit. Accordingly, in some embodiments, compounds of the present invention exhibit a greater decrease in cell viability with respect to $KRAS^{G12D}$ compared to what is known in the art. Compounds of the present invention may also exhibit a greater decrease in cell viability respect to other RAS mutants disclosed herein, or combinations thereof.

In some embodiments, a compound of the present invention may exhibit greater metabolic stability, permeability, or solubility, or a combination thereof, versus what is known in the art. Compounds of the present invention may exhibit improved acid stability, such as in a simulated gastric fluid stability assay. Methods for measuring such properties are known in the art. A compound of the present invention may exhibit better Ras cross-linking than a compound known in the art. A method for measuring Ras cross-linking is provided herein. In some embodiments, a compound of the present invention may exhibit improvements with respect to any of the following properties, or a combination thereof, compared to what is known in the art: selectivity, potency, cell viability, metabolic stability, acid stability, cross-linking, permeability, or solubility.

Further provided is a method of treating cancer in a subject in need thereof, the method comprising administering to the subject a therapeutically effective amount of a compound of the present invention, or a pharmaceutically acceptable salt thereof. The cancer may, for example, be pancreatic cancer, colorectal cancer, non-small cell lung cancer, acute myeloid leukemia, multiple myeloma, thyroid gland adenocarcinoma, a myelodysplastic syndrome, or squamous cell lung carcinoma. In some embodiments, the cancer comprises a Ras mutation, such as K-Ras G12D or K-Ras G13D. Other Ras mutations are described herein.

Further provided is a method of treating a Ras protein-related disorder in a subject in need thereof, the method comprising administering to the subject a therapeutically effective amount of a compound of the present invention, or a pharmaceutically acceptable salt thereof.

Further provided is a method of inhibiting a Ras protein in a cell, the method comprising contacting the cell with an effective amount of a compound of the present invention, or a pharmaceutically acceptable salt thereof. For example, the Ras protein is K-Ras G12D or K-Ras G13D. Other Ras proteins are described herein. The cell may be a cancer cell, such as a pancreatic cancer cell, a colorectal cancer cell, a non-small cell lung cancer cell, an acute myeloid leukemia cell, a multiple myeloma cell, a thyroid gland adenocarcinoma cell, a myelodysplastic syndrome cell, or a squamous cell lung carcinoma cell. Other cancer types are described herein. The cell may be in vivo or in vitro. With respect to compounds of the present invention, one stereoisomer may exhibit better inhibition than another stereoisomer. For example, one atropisomer may exhibit inhibition, whereas the other atropisomer may exhibit little or no inhibition.

In some embodiments, a method or use described herein further comprises administering an additional anti-cancer therapy. In some embodiments, the additional anti-cancer therapy is an EGFR inhibitor, a second Ras inhibitor, a SHP2 inhibitor, a SOS1 inhibitor, a Raf inhibitor, a MEK inhibitor, an ERK inhibitor, a PI3K inhibitor, a PTEN inhibitor, an AKT inhibitor, an mTORC1 inhibitor, a BRAF inhibitor, a PD-L1 inhibitor, a PD-1 inhibitor, a CDK4/6 inhibitor, a HER2 inhibitor, or a combination thereof. In some embodiments, the additional anticancer therapy is a SHP2 inhibitor. Other additional anti-cancer therapies are described herein.

Methods of Synthesis

The compounds described herein may be made from commercially available starting materials or synthesized using known organic, inorganic, or enzymatic processes.

The compounds of the present invention can be prepared in a number of ways well known to those skilled in the art of organic synthesis. By way of example, compounds of the present invention can be synthesized using the methods described in the Schemes below, together with synthetic methods known in the art of synthetic organic chemistry, or variations thereon as appreciated by those skilled in the art. These methods include but are not limited to those methods described in the Schemes below.

Compounds of Table 1 herein were prepared using methods disclosed herein or were prepared using methods disclosed herein combined with the knowledge of one of skill in the art. Compounds of Table 2 may be prepared using methods disclosed herein or may be prepared using methods disclosed herein combined with the knowledge of one of skill in the art.

Scheme 1. General synthesis of aziridine containing macrocycles
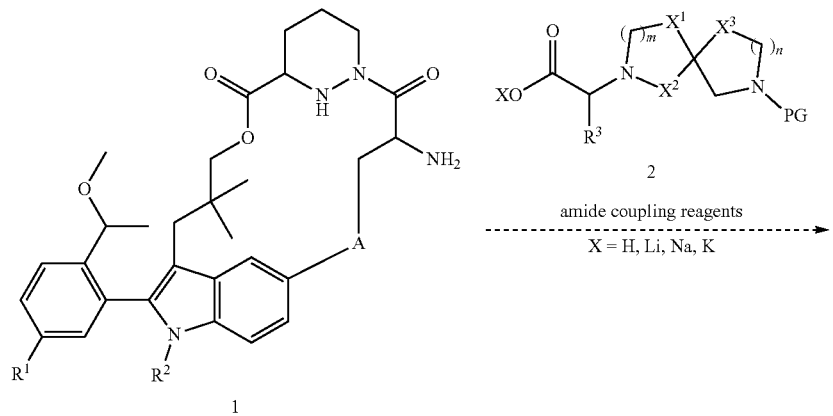
1
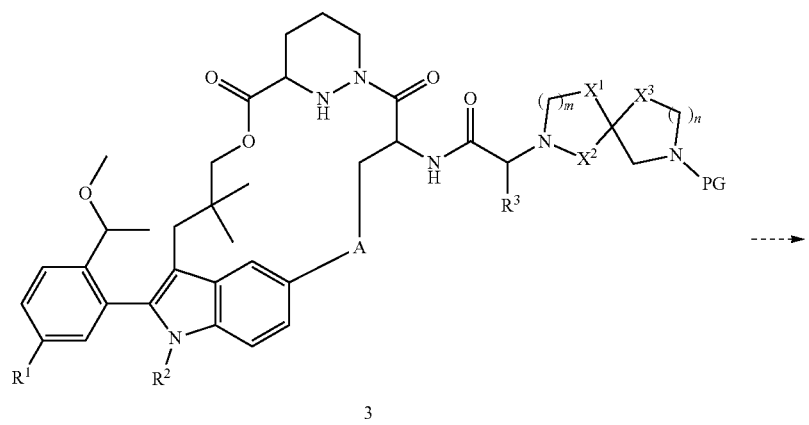
3
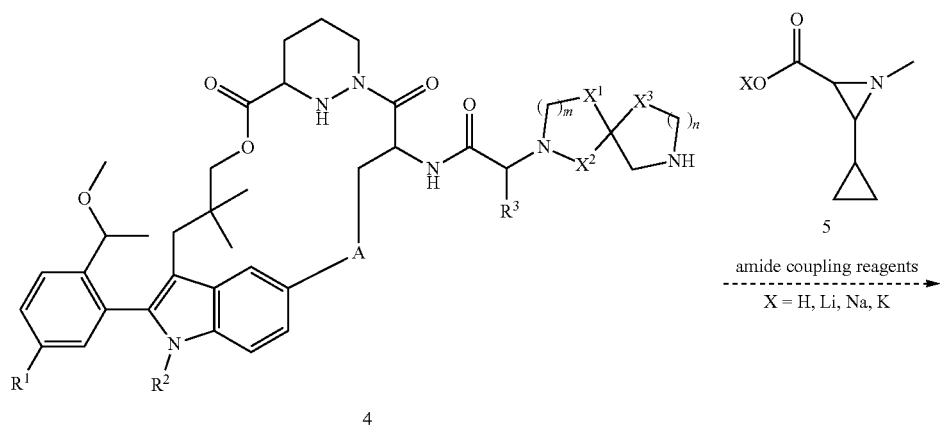
4

-continued

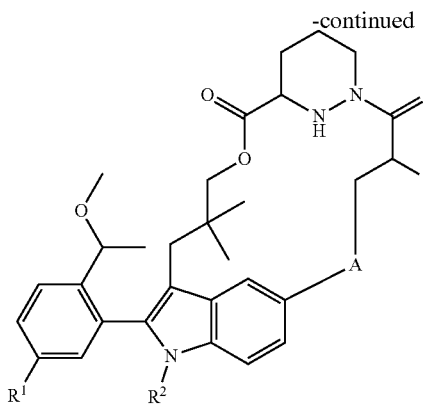 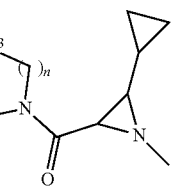

6

As shown in Scheme 1, compounds of this type may be prepared by the reaction of an appropriate amine (1) with a carboxylic acid containing protected amine (2) in the presence of standard amide coupling reagents to give 3, followed by deprotection of the amine to produce 4. Coupling of an aziridine carboxylate (5) in the presence of standard amide coupling reagents affords the final compound (6).

Pharmaceutical Compositions and Methods of Use
Pharmaceutical Compositions and Methods of Administration The compounds with which the invention is concerned are Ras inhibitors, and are useful in the treatment of cancer. Accordingly, one embodiment of the present invention provides pharmaceutical compositions containing a compound of the invention or a pharmaceutically acceptable salt thereof, and a pharmaceutically acceptable excipient, as well as methods of using the compounds of the invention to prepare such compositions.

As used herein, the term "pharmaceutical composition" refers to a compound, such as a compound of the present invention, or a pharmaceutically acceptable salt thereof, formulated together with a pharmaceutically acceptable excipient.

In some embodiments, a compound is present in a pharmaceutical composition in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

A "pharmaceutically acceptable excipient," as used herein, refers any inactive ingredient (for example, a vehicle capable of suspending or dissolving the active compound) having the properties of being nontoxic and non-inflammatory in a subject. Typical excipients include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Excipients include, but are not limited to: butylated optionally substituted hydroxyltoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, optionally substituted hydroxylpropyl cellulose, optionally substituted hydroxylpropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol. Those of ordinary skill in the art are familiar with a variety of agents and materials useful as excipients. See, e.g., e.g., Ansel, et al., Ansel's Pharmaceutical Dosage Forms and Drug Delivery Systems. Philadelphia: Lippincott, Williams & Wilkins, 2004; Gennaro, et al., Remington: The Science and Practice of Pharmacy. Philadelphia: Lippincott, Williams & Wilkins, 2000; and Rowe, Handbook of Pharmaceutical Excipients. Chicago, Pharmaceutical Press, 2005. In some embodiments, a composition includes at least two different pharmaceutically acceptable excipients.

Compounds described herein, whether expressly stated or not, may be provided or utilized in salt form, e.g., a pharmaceutically acceptable salt form, unless expressly stated to the contrary. The term "pharmaceutically acceptable salt," as use herein, refers to those salts of the compounds described herein that are, within the scope of sound medical judgment, suitable for use in contact with the tissues of humans and other animals without undue toxicity, irritation, allergic response and the like, and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention, be prepared from inorganic or organic bases. In some embodiments, the compounds are prepared or used as pharmaceutically acceptable salts prepared as addition products of pharmaceutically acceptable acids or bases. Suitable pharmaceutically acceptable acids and bases are well-known in the art, such as hydrochloric, sulfuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-optionally substituted hydroxyl-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

As used herein, the term "subject" refers to any member of the animal kingdom. In some embodiments, "subject" refers to humans, at any stage of development. In some embodiments, "subject" refers to a human patient. In some embodiments, "subject" refers to non-human animals. In some embodiments, the non-human animal is a mammal (e.g., a rodent, a mouse, a rat, a rabbit, a monkey, a dog, a cat, a sheep, cattle, a primate, or a pig). In some embodiments, subjects include, but are not limited to, mammals, birds, reptiles, amphibians, fish, or worms. In some embodiments, a subject may be a transgenic animal, genetically-engineered animal, or a clone.

As used herein, the term "dosage form" refers to a physically discrete unit of a compound (e.g., a compound of the present invention) for administration to a subject. Each unit contains a predetermined quantity of compound. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or compound administered to a particular subject is determined by one or more attending physicians and may involve administration of multiple dosage forms.

As used herein, the term "dosing regimen" refers to a set of unit doses (typically more than one) that are administered individually to a subject, typically separated by periods of time. In some embodiments, a given therapeutic compound (e.g., a compound of the present invention) has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

A "therapeutic regimen" refers to a dosing regimen whose administration across a relevant population is correlated with a desired or beneficial therapeutic outcome.

The term "treatment" (also "treat" or "treating"), in its broadest sense, refers to any administration of a substance (e.g., a compound of the present invention) that partially or completely alleviates, ameliorates, relieves, inhibits, delays onset of, reduces severity of, or reduces incidence of one or more symptoms, features, or causes of a particular disease, disorder, or condition. In some embodiments, such treatment may be administered to a subject who does not exhibit signs of the relevant disease, disorder or condition, or of a subject who exhibits only early signs of the disease, disorder, or condition. Alternatively, or additionally, in some embodiments, treatment may be administered to a subject who exhibits one or more established signs of the relevant disease, disorder, or condition. In some embodiments, treatment may be of a subject who has been diagnosed as suffering from the relevant disease, disorder, or condition. In some embodiments, treatment may be of a subject known to have one or more susceptibility factors that are statistically correlated with increased risk of development of the relevant disease, disorder, or condition.

The term "therapeutically effective amount" means an amount that is sufficient, when administered to a population suffering from or susceptible to a disease, disorder, or condition in accordance with a therapeutic dosing regimen, to treat the disease, disorder, or condition. In some embodiments, a therapeutically effective amount is one that reduces the incidence or severity of, or delays onset of, one or more symptoms of the disease, disorder, or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine). Those of ordinary skill in the art will appreciate that, in some embodiments, a therapeutically effective amount may be formulated or administered in a single dose. In some embodiments, a therapeutically effective amount may be formulated or administered in a plurality of doses, for example, as part of a dosing regimen.

For use as treatment of subjects, the compounds of the invention, or a pharmaceutically acceptable salt thereof, can be formulated as pharmaceutical or veterinary compositions. Depending on the subject to be treated, the mode of administration, and the type of treatment desired, e.g., prevention, prophylaxis, or therapy, the compounds, or a pharmaceutically acceptable salt thereof, are formulated in ways consonant with these parameters. A summary of such techniques may be found in *Remington: The Science and Practice of Pharmacy*, 21$^{st}$ *Edition*, Lippincott Williams & Wilkins, (2005); and *Encyclopedia of Pharmaceutical Technology*, eds. J. Swarbrick and J. C. Boylan, 1988-1999, Marcel Dekker, New York, each of which is incorporated herein by reference.

Compositions can be prepared according to conventional mixing, granulating, or coating methods, respectively, and the present pharmaceutical compositions can contain from about 0.1% to about 99%, from about 5% to about 90%, or from about 1% to about 20% of a compound of the present invention, or pharmaceutically acceptable salt thereof, by weight or volume. In some embodiments, compounds, or a pharmaceutically acceptable salt thereof, described herein may be present in amounts totaling 1-95% by weight of the total weight of a composition, such as a pharmaceutical composition.

The composition may be provided in a dosage form that is suitable for intraarticular, oral, parenteral (e.g., intravenous, intramuscular), rectal, cutaneous, subcutaneous, topical, transdermal, sublingual, nasal, vaginal, intravesicular, intraurethral, intrathecal, epidural, aural, or ocular administration, or by injection, inhalation, or direct contact with the nasal, genitourinary, reproductive, or oral mucosa. Thus, the pharmaceutical composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice.

As used herein, the term "administration" refers to the administration of a composition (e.g., a compound, or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal, or vitreal.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. A formulation will generally include a diluent as well as, in some cases, adjuvants, buffers, preservatives and the like. Compounds, or a pharmaceutically acceptable salt thereof, can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol, and the like. Such compositions may also contain amounts of nontoxic auxiliary substances such as wetting or emulsifying agents, pH buffering agents, and the like, such as, for example, sodium acetate, sorbitan monolaurate, and so forth.

Various sustained release systems for drugs have also been devised. See, for example, U.S. Pat. No. 5,624,677.

Systemic administration may also include relatively non-invasive methods such as the use of suppositories, transdermal patches, transmucosal delivery, and intranasal administration. Oral administration is also suitable for compounds of the invention, or pharmaceutically acceptable salts thereof. Suitable forms include syrups, capsules, and tablets, as is understood in the art.

Each compound, or a pharmaceutically acceptable salt thereof, as described herein, may be formulated in a variety of ways that are known in the art. For example, the first and second agents of the combination therapy may be formulated together or separately. Other modalities of combination therapy are described herein.

The individually or separately formulated agents can be packaged together as a kit. Non-limiting examples include, but are not limited to, kits that contain, e.g., two pills, a pill and a powder, a suppository and a liquid in a vial, two topical creams, etc. The kit can include optional components that aid in the administration of the unit dose to subjects, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one subject, multiple uses for a particular subject (at a constant dose or in which the individual compounds, or a pharmaceutically acceptable salt thereof, may vary in potency as therapy progresses); or the kit may contain multiple doses suitable for administration to multiple subjects ("bulk packaging"). The kit components may be assembled in cartons, blister packs, bottles, tubes, and the like.

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, optionally substituted hydroxylpropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Two or more compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion-controlled release can be achieved by appropriate coating of a tablet, capsule, pellet, or granulate formulation of compounds, or by incorporating the compound, or a pharmaceutically acceptable salt thereof, into an appropriate matrix. A controlled release coating may include one or more of the coating substances mentioned above or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-optionally substituted hydroxylmethacrylate, methacrylate hydrogels, 1,3 butylene glycol, ethylene glycol methacrylate, or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, or halogenated fluorocarbon.

The liquid forms in which the compounds, or a pharmaceutically acceptable salt thereof, and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Generally, when administered to a human, the oral dosage of any of the compounds of the invention, or a pharmaceutically acceptable salt thereof, will depend on the nature of the compound, and can readily be determined by one skilled in the art. A dosage may be, for example, about 0.001 mg to about 2000 mg per day, about 1 mg to about 1000 mg per day, about 5 mg to about 500 mg per day, about 100 mg to about 1500 mg per day, about 500 mg to about 1500 mg per day, about 500 mg to about 2000 mg per day, or any range derivable therein. In some embodiments, the daily dose range for oral administration, for example, may lie within the range of from about 0.001 mg to about 2000 mg per kg body weight of a human, in single or divided doses. On the other hand, it may be necessary to use dosages outside these limits in some cases.

In some embodiments, the pharmaceutical composition may further comprise an additional compound having antiproliferative activity. Depending on the mode of administration, compounds, or a pharmaceutically acceptable salt thereof, will be formulated into suitable compositions to permit facile delivery. Each compound, or a pharmaceutically acceptable salt thereof, of a combination therapy may be formulated in a variety of ways that are known in the art. For example, the first and second agents of the combination therapy may be formulated together or separately. Desirably, the first and second agents are formulated together for the simultaneous or near simultaneous administration of the agents.

It will be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics or procedures and the desired therapeutic effect to be achieved. It will also be appreciated that the therapies employed may achieve a desired effect for the same disorder, or they may achieve different effects (e.g., control of any adverse effects).

Administration of each drug in a combination therapy, as described herein, can, independently, be one to four times daily for one day to one year, and may even be for the life of the subject. Chronic, long-term administration may be indicated.

Methods of Use

In some embodiments, the invention discloses a method of treating a disease or disorder that is characterized by aberrant Ras activity due to a Ras mutant. In some embodiments, the disease or disorder is a cancer.

Accordingly, also provided is a method of treating cancer in a subject in need thereof, the method comprising administering to the subject a therapeutically effective amount of a compound of the present invention, or a pharmaceutically acceptable salt thereof, or a pharmaceutical composition comprising such a compound or salt. In some embodiments, the cancer is colorectal cancer, non-small cell lung cancer, small-cell lung cancer, pancreatic cancer, appendiceal cancer, melanoma, acute myeloid leukemia, small bowel cancer, ampullary cancer, germ cell cancer, cervical cancer, cancer of unknown primary origin, endometrial cancer, esophagogastric cancer, GI neuroendocrine cancer, ovarian cancer, sex cord stromal tumor cancer, hepatobiliary cancer, or bladder cancer. In some embodiments, the cancer is appendiceal, endometrial or melanoma. Also provided is a method of treating a Ras protein-related disorder in a subject in need thereof, the method comprising administering to the subject a therapeutically effective amount of a compound of the present invention, or a pharmaceutically acceptable salt thereof, or a pharmaceutical composition comprising such a compound or salt.

In some embodiments, the compounds of the present invention or pharmaceutically acceptable salts thereof, pharmaceutical compositions comprising such compounds or salts, and methods provided herein may be used for the treatment of a wide variety of cancers including tumors such as lung, prostate, breast, brain, skin, cervical carcinomas, testicular carcinomas, etc. More particularly, cancers that may be treated by the compounds or salts thereof, pharmaceutical compositions comprising such compounds or salts, and methods of the invention include, but are not limited to, tumor types such as astrocytic, breast, cervical, colorectal, endometrial, esophageal, gastric, head and neck, hepatocellular, laryngeal, lung, oral, ovarian, prostate, and thyroid carcinomas and sarcomas. Other cancers include, for example:

Cardiac, for example: sarcoma (angiosarcoma, fibrosarcoma, rhabdomyosarcoma, liposarcoma), myxoma, rhabdomyoma, fibroma, lipoma, and teratoma;

Lung, for example: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

Gastrointestinal, for example: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma);

Genitourinary tract, for example: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver, for example: hepatoma (hepatocellular carcinoma), cholangiocarcinoma, hepatoblastoma, angiosarcoma, hepatocellular adenoma, hemangioma;

Biliary tract, for example: gall bladder carcinoma, ampullary carcinoma, cholangiocarcinoma;

Bone, for example: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors;

Nervous system, for example: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, neurofibromatosis type 1, meningioma, glioma, sarcoma);

Gynecological, for example: uterus (endometrial carcinoma, uterine carcinoma, uterine corpus endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma);

Hematologic, for example: blood (myeloid leukemia (acute and chronic), acute lymphoblastic leukemia, chronic lymphocytic leukemia, myeloproliferative diseases (e.g., myelofibrosis and myeloproliferative neoplasms), multiple myeloma, myelodysplastic syndrome), Hodgkin's disease, non-Hodgkin's lymphoma (malignant lymphoma);

Skin, for example: malignant melanoma, basal cell carcinoma, squamous cell carcinoma, Kaposi's sarcoma, moles dysplastic nevi, lipoma, angioma, dermatofibroma, keloids, psoriasis; and Adrenal glands, for example: neuroblastoma.

In some embodiments, the Ras protein is wild-type ($Ras^{WT}$). Accordingly, in some embodiments, a compound of the present invention is employed in a method of treating a patient having a cancer comprising a $Ras^{WT}$ (e.g., K-$Ras^{WT}$, H-$Ras^{WT}$ or N-$Ras^{WT}$). In some embodiments, the Ras protein is Ras amplification (e.g., K-$Ras^{amp}$). Accordingly, in some embodiments, a compound of the present invention is employed in a method of treating a patient having a cancer comprising a $Ras^{amp}$ (K-$Ras^{amp}$, H-$Ras^{amp}$ or N-$Ras^{amp}$). In some embodiments, the cancer comprises a Ras mutation, such as a Ras mutation described herein. In some embodiments, a mutation is selected from:
  (a) the following K-Ras mutants: G12D, G12V, G12C, G13D, G12R, G12A, Q61H, G12S, A146T, G13C, Q61L, Q61R, K117N, A146V, G12F, Q61K, L19F, Q22K, V14I, A59T, A146P, G13R, G12L, or G13V, and combinations thereof;
  (b) the following H-Ras mutants: Q61R, G13R, Q61K, G12S, Q61L, G12D, G13V, G13D, G12C, K117N, A59T, G12V, G13C, Q61H, G13S, A18V, D119N, G13N, A146T, A66T, G12A, A146V, G12N, or G12R, and combinations thereof; and
  (c) the following N-Ras mutants: Q61R, Q61K, G12D, Q61L, Q61H, G13R, G13D, G12S, G12C, G12V, G12A, G13V, G12R, P185S, G13C, A146T, G60E, Q61P, A59D, E132K, E49K, T50I, A146V, or A59T, and combinations thereof;
or a combination of any of the foregoing. In some embodiments, a compound may inhibit both K-Ras G12C and K-Ras G12D. In some embodiments, a compound may inhibit both K-Ras G12D and K-Ras G13D. In some embodiments, a compound may inhibit both K-Ras G12V and K-Ras G12S. In some embodiments, a compound of the present invention inhibits $Ras^{WT}$ in addition to one or more additional Ras mutations (e.g., K, H or N-$Ras^{WT}$ and K-Ras G12D). In some embodiments, a compound of the present invention inhibits $Ras^{amp}$ in addition to one or more additional Ras mutations (e.g., K-, H- or N-$Ras^{amp}$ and K-Ras G12D).

Methods of detecting Ras mutations are known in the art. Such means include, but are not limited to direct sequencing, and utilization of a high-sensitivity diagnostic assay (with CE-IVD mark), e.g., as described in Domagala, et al., Pol J Pathol 3:145-164 (2012), incorporated herein by reference in its entirety, including TheraScreen PCR; AmoyDx; PNA-Clamp; RealQuality; EntroGen; LightMix; StripAssay; Hybcell plexA; Devyser; Surveyor; Cobas; and TheraScreen Pyro. See, also, e.g., WO 2020/106640.

In some embodiments, the cancer is non-small cell lung cancer and the Ras mutation comprises a K-Ras mutation, such as K-Ras G12D. In some embodiments, the cancer is colorectal cancer and the Ras mutation comprises a K-Ras mutation, such as K-Ras G12D. In some embodiments, the cancer is pancreatic cancer and the Ras mutation comprises an K-Ras mutation, such as K-Ras G12D. In some embodiments, the cancer is pancreatic cancer and the Ras mutation comprises an N-Ras mutation, such as N-Ras G12D. In any of the foregoing if not already specified, a compound may inhibit RasWI (e.g., K-, H- or N-$Ras^{WT}$) or $Ras^{amp}$ (e.g., K-, H- or N-$Ras^{amp}$) as well.

Also provided is a method of inhibiting a Ras protein in a cell, the method comprising contacting the cell with an effective amount of a compound of the present invention, or a pharmaceutically acceptable salt thereof. A compound, or a pharmaceutically acceptable salt thereof, may inhibit more than one type of Ras protein in a cell. A method of inhibiting RAF-Ras binding, the method comprising contacting the cell with an effective amount of a compound of the present invention, or a pharmaceutically acceptable salt thereof, is also provided. The cell may be a cancer cell. The cancer cell may be of any type of cancer described herein. The cell may be in vivo or in vitro.

Combination Therapy

The methods of the invention may include a compound of the invention used alone or in combination with one or more additional therapies (e.g., non-drug treatments or therapeutic agents). The dosages of one or more of the additional therapies (e.g., non-drug treatments or therapeutic agents) may be reduced from standard dosages when administered alone. For example, doses may be determined empirically from drug combinations and permutations or may be deduced by isobolographic analysis (e.g., Black et al., *Neurology* 65: S3-S6 (2005)).

A compound of the present invention may be administered before, after, or concurrently with one or more of such additional therapies. When combined, dosages of a compound of the invention and dosages of the one or more additional therapies (e.g., non-drug treatment or therapeutic agent) provide a therapeutic effect (e.g., synergistic or additive therapeutic effect). A compound of the present invention and an additional therapy, such as an anti-cancer agent, may be administered together, such as in a unitary pharmaceutical composition, or separately and, when administered separately, this may occur simultaneously or sequentially. Such sequential administration may be close or remote in time.

In some embodiments, the additional therapy is the administration of side-effect limiting agents (e.g., agents intended to lessen the occurrence or severity of side effects of treatment). For example, in some embodiments, the compounds of the present invention can also be used in combination with a therapeutic agent that treats nausea. Examples of agents that can be used to treat nausea include: dronabinol, granisetron, metoclopramide, ondansetron, and prochlorperazine, or pharmaceutically acceptable salts thereof.

In some embodiments, the one or more additional therapies includes a non-drug treatment (e.g., surgery or radiation therapy). In some embodiments, the one or more additional therapies includes a therapeutic agent (e.g., a compound or biologic that is an anti-angiogenic agent, signal transduction inhibitor, antiproliferative agent, glycolysis inhibitor, or autophagy inhibitor). In some embodiments, the one or more additional therapies includes a non-drug treatment (e.g., surgery or radiation therapy) and a therapeutic agent (e.g., a compound or biologic that is an anti-angiogenic agent, signal transduction inhibitor, antiproliferative agent, glycolysis inhibitor, or autophagy inhibitor). In other embodiments, the one or more additional therapies includes two therapeutic agents. In still other embodiments, the one or more additional therapies includes three therapeutic agents. In some embodiments, the one or more additional therapies includes four or more therapeutic agents.

In this Combination Therapy section, all references are incorporated by reference for the agents described, or a pharmaceutically acceptable salt, solvate, isomer (e.g., stereoisomer), prodrug, or tautomer thereof, whether explicitly stated as such or not.

Non-Drug Therapies

Examples of non-drug treatments include, but are not limited to, radiation therapy, cryotherapy, hyperthermia, surgery (e.g., surgical excision of tumor tissue), and T cell adoptive transfer (ACT) therapy.

In some embodiments, the compounds of the invention may be used as an adjuvant therapy after surgery. In some embodiments, the compounds of the invention may be used as a neo-adjuvant therapy prior to surgery.

Radiation therapy may be used for inhibiting abnormal cell growth or treating a hyperproliferative disorder, such as cancer, in a subject (e.g., mammal (e.g., human)). Techniques for administering radiation therapy are known in the art. Radiation therapy can be administered through one of several methods, or a combination of methods, including, without limitation, external-beam therapy, internal radiation therapy, implant radiation, stereotactic radiosurgery, systemic radiation therapy, radiotherapy, and permanent or temporary interstitial brachy therapy. The term "brachy therapy," as used herein, refers to radiation therapy delivered by a spatially confined radioactive material inserted into the body at or near a tumor or other proliferative tissue disease site. The term is intended, without limitation, to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, or Y-90. Moreover, the radionuclide(s) can be embodied in a gel or radioactive micro spheres.

In some embodiments, the compounds of the present invention can render abnormal cells more sensitive to treatment with radiation for purposes of killing or inhibiting the growth of such cells.

Accordingly, this invention further relates to a method for sensitizing abnormal cells in a mammal to treatment with radiation which comprises administering to the mammal an amount of a compound of the present invention, which amount is effective to sensitize abnormal cells to treatment with radiation. The amount of the compound in this method can be determined according to the means for ascertaining effective amounts of such compounds described herein. In some embodiments, the compounds of the present invention may be used as an adjuvant therapy after radiation therapy or as a neo-adjuvant therapy prior to radiation therapy.

In some embodiments, the non-drug treatment is a T cell adoptive transfer (ACT) therapy. In some embodiments, the T cell is an activated T cell. The T cell may be modified to express a chimeric antigen receptor (CAR). CAR modified T (CAR-T) cells can be generated by any method known in the art. For example, the CAR-T cells can be generated by introducing a suitable expression vector encoding the CAR to a T cell. Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art may be used. In some embodiments, the T cell is an autologous T cell. Whether prior to or after genetic modification of the T cells to express a desirable protein (e.g., a CAR), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 7,572,631; 5,883,223; 6,905,874; 6,797,514; and 6,867,041.

Therapeutic Agents

A therapeutic agent may be a compound used in the treatment of cancer or symptoms associated therewith. A compound of the present invention may be combined with a second, third, or fourth therapeutic agent, or more. A compound of the present invention may be combined with one or more therapeutic agents along with one or more non-drug therapies.

For example, a therapeutic agent may be a steroid. Steroids are known in the art. Accordingly, in some embodiments, the one or more additional therapies includes a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, fiucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts or derivatives thereof.

Further examples of therapeutic agents that may be used in combination therapy with a compound of the present invention include compounds described in the following patents: U.S. Pat. Nos. 6,258,812, 6,630,500, 6,515,004, 6,713,485, 5,521,184, 5,770,599, 5,747,498, 5,990,141, 6,235,764, and 8,623,885, and International Patent Applications WO01/37820, WO01/32651, WO02/68406, WO02/66470, WO02/55501, WO04/05279, WO04/07481, WO04/07458, WO04/09784, WO02/59110, WO99/45009, WO00/59509, WO99/61422, WO00/12089, and WO00/02871.

A therapeutic agent may be a biologic (e.g., cytokine (e.g., interferon or an interleukin such as IL-2)) used in treatment of cancer or symptoms associated therewith. Biologics are known in the art. In some embodiments, the biologic is an immunoglobulin-based biologic, e.g., a monoclonal antibody (e.g., a humanized antibody, a fully human antibody, an Fc fusion protein, or a functional fragment thereof) that agonizes a target to stimulate an anti-cancer response or antagonizes an antigen important for cancer. Also included are antibody-drug conjugates.

A therapeutic agent may be a T-cell checkpoint inhibitor. Such checkpoint inhibitors are known in the art. In one embodiment, the checkpoint inhibitor is an inhibitory antibody (e.g., a monospecific antibody such as a monoclonal antibody). The antibody may be, e.g., humanized or fully human. In some embodiments, the checkpoint inhibitor is a fusion protein, e.g., an Fc-receptor fusion protein. In some embodiments, the checkpoint inhibitor is an agent, such as an antibody, that interacts with a checkpoint protein. In some embodiments, the checkpoint inhibitor is an agent, such as an antibody, that interacts with the ligand of a checkpoint protein. In some embodiments, the checkpoint inhibitor is an inhibitor (e.g., an inhibitory antibody or small molecule inhibitor) of CTLA-4 (e.g., an anti-CTLA-4 antibody or fusion a protein). In some embodiments, the checkpoint inhibitor is an inhibitor or antagonist (e.g., an inhibitory antibody or small molecule inhibitor) of PD-1. In some embodiments, the checkpoint inhibitor is an inhibitor or antagonist (e.g., an inhibitory antibody or small molecule inhibitor) of PD-L1. In some embodiments, the checkpoint inhibitor is an inhibitor or antagonist (e.g., an inhibitory antibody or Fc fusion or small molecule inhibitor) of PD-L2 (e.g., a PD-L2/lg fusion protein). In some embodiments, the checkpoint inhibitor is an inhibitor or antagonist (e.g., an inhibitory antibody or small molecule inhibitor) of B7-H3, B7-H4, BTLA, HVEM, TIM3, GAL9, LAG3, VISTA, KIR, 2B4, CD160, CGEN-15049, CHK 1, CHK2, A2aR, B-7 family ligands, or a combination thereof. In some embodiments, the checkpoint inhibitor is pembrolizumab, nivolumab, PDR001 (NVS), REGN2810 (Sanofi/Regeneron), a PD-L1 antibody such as, e.g., avelumab, durvalumab, atezolizumab, pidilizumab, JNJ-63723283 (JNJ), BGB-A317 (BeiGene & Celgene), or a checkpoint inhibitor disclosed in Preusser, M. et al. (2015) Nat. Rev. Neurol., including, without limitation, ipilimumab, tremelimumab, nivolumab, pembrolizumab, AMP224, AMP514/MEDI0680, BMS936559, MEDI4736, MPDL3280A, MSB0010718C, BMS986016, IMP321, lirilumab, IPH2101, 1-7F9, and KW-6002.

A therapeutic agent may be an anti-TIGIT antibody, such as MBSA43, BMS-986207, MK-7684, COM902, AB154, MTIG7192A, or OMP-313M32 (etigilimab). Other anti-TIGIT antibodies are known in the art.

A therapeutic agent may be an agent that treats cancer or symptoms associated therewith (e.g., a cytotoxic agent, non-peptide small molecules, or other compound useful in the treatment of cancer or symptoms associated therewith, collectively, an "anti-cancer agent"). Anti-cancer agents can be, e.g., chemotherapeutics or targeted therapy agents. Such agents are known in the art.

Anti-cancer agents include mitotic inhibitors, intercalating antibiotics, growth factor inhibitors. cell cycle inhibitors, enzymes, topoisomerase inhibitors, biological response modifiers, alkylating agents, antimetabolites, folic acid analogs, pyrimidine analogs, purine analogs and related inhibitors, vinca alkaloids, epipodopyhllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Further anti-cancer agents include leucovorin (LV), irenotecan, oxaliplatin, capecitabine, paclitaxel, and doxetaxel. In some embodiments, the one or more additional therapies includes two or more anti-cancer agents. The two or more anti-cancer agents can be used in a cocktail to be administered in combination or administered separately. Suitable dosing regimens of combination anti-cancer agents are known in the art and described in, for example, Saltz et al., Proc. Am. Soc. Clin. Oncol. 18: 233a (1999), and Douillard et al., *Lancet* 355 (9209): 1041-1047 (2000).

Other non-limiting examples of anti-cancer agents include Gleevec® (Imatinib Mesylate); Kyprolis® (carfilzomib); Velcade® (bortezomib); Casodex (bicalutamide); Iressa® (gefitinib); alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; sarcodictyin A; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, such as calicheamicin gammaII and calicheamicin omegaII (see, e.g., Agnew, Chem. Intl. Ed Engl. 33:183-186 (1994)); dynemicin such as dynemicin A; bisphosphonates such as clodronate; an esperamicin; neocarzinostatin chromophore and related chromoprotein enediyne antiobiotic chromophores, aclacinomysins, actinomycin, authramycin, azaserine, bleomycins, cactinomycin, calicheamicin, carabicin, caminomycin, carminomycin, carzinophilin, chromomycins, dactinomycin, daunorubicin, detorubicin, 6-diazo-5-oxo-L-norleucine, adriamycin (doxorubicin), morpholino-doxorubicin, cyanomorpholino-doxorubicin, 2-pyrrolino-doxorubicin, deoxydoxorubicin, epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenishers such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone such as epothilone B; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes such as T-2 toxin, verracurin A, roridin A and anguidine; urethane; vindesine; dacarbazine; mannomustine; mitobronitol; mitolactol; pipobroman; gacytosine; arabinoside ("Ara-C"); cyclophosphamide; thiotepa; taxoids, e.g., Taxol® (paclitaxel), Abraxane® (cremophor-free, albumin-engineered nanoparticle formulation of paclitaxel), and Taxotere® (doxetaxel); chloranbucil; tamoxifen (Nolvadex™); raloxifene; aromatase inhibiting 4 (5)-imidazoles; 4-hydroxytamoxifen; trioxifene; keoxifene; LY 117018; onapristone; toremifene (Fareston®); flutamide, nilutamide, bicalutamide, leuprolide, goserelin; chlorambucil; Gemzar® gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; Navelbine® (vinorelbine); novantrone; teniposide; edatrexate; daunomycin; aminopterin; ibandronate; irinotecan (e.g., CPT-11); topoisomerase inhibitor RFS 2000; difluoromethylornithine (DMFO); retinoids such as retinoic acid; esperamicins; capecitabine (e.g., Xeloda®); and pharmaceutically acceptable salts of any of the above.

Additional non-limiting examples of anti-cancer agents include trastuzumab (Herceptin®), bevacizumab (Avastin®), cetuximab (Erbitux®), rituximab (Rituxan®), Taxol®, Arimidex®, ABVD, avicine, abagovomab, acridine carboxamide, adecatumumab, 17-N-allylamino-17-demethoxygeldanamycin, alpharadin, alvocidib, 3-aminopyridine-2-carboxaldehyde thiosemicarbazone, amonafide, anthracenedione, anti-CD22 immunotoxins, antineoplastics (e.g., cell-cycle nonspecific antineoplastic agents, and other antineoplastics described herein), antitumorigenic herbs, apaziquone, atiprimod, azathioprine, belotecan, bendamustine, BIBW 2992, biricodar, brostallicin, bryostatin, buthionine sulfoximine, CBV (chemotherapy), calyculin, dichloroacetic acid, discodermolide, elsamitrucin, enocitabine, eribulin, exatecan, exisulind, ferruginol, forodesine, fosfestrol, ICE chemotherapy regimen, IT-101, imexon, imiquimod, indolocarbazole, irofulven, laniquidar, larotaxel, lenalidomide, lucanthone, lurtotecan, mafosfamide, mitozolomide, nafoxidine, nedaplatin, olaparib, ortataxel, PAC-1, pawpaw, pixantrone, proteasome inhibitors, rebeccamycin, resiquimod, rubitecan, SN-38, salinosporamide A, sapacitabine, Stanford V, swainsonine, talaporfin, tariquidar, tegafur-uracil, temodar, tesetaxel, triplatin tetranitrate, tris(2-chloroethyl) amine, troxacitabine, uramustine, vadimezan, vinflunine, ZD6126, and zosuquidar.

Further non-limiting examples of anti-cancer agents include natural products such as vinca alkaloids (e.g., vinblastine, vincristine, and vinorelbine), epidipodophyllotoxins (e.g., etoposide and teniposide), antibiotics (e.g., dactinomycin (actinomycin D), daunorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., a CDK4/6 inhibitor such as abemaciclib, ribociclib, palbociclib; seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs, pyrimidine analogs (e.g., fluorouracil, floxuridine, and cytarabine), purine analogs and related inhibitors (e.g., mercaptopurine, thioguanine, pentostatin, and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, belinostat, LBH 589, romidepsin, ACY-1215, and panobinostat), mTOR inhibitors (e.g., vistusertib, temsirolimus, everolimus, ridaforolimus, and sirolimus), KSP (Eg5) inhibitors (e.g., Array 520), DNA binding agents (e.g., Zalypsis®), PI3K inhibitors such as PI3K delta inhibitor (e.g., GS-1101 and TGR-1202), PI3K delta and gamma inhibitor (e.g., CAL-130), copanlisib, alpelisib and idelalisib; multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163L), aurora kinase inhibitors (e.g., MLN8237), cell surface monoclonal antibodies (e.g., anti-CD38 (HUMAX-CD38), anti-CSI (e.g., elotuzumab), HSP90 inhibitors (e.g., 17 AAG and KOS 953), P13K/Akt inhibitors (e.g., perifosine), Akt inhibitors (e.g., GSK-2141795), PKC inhibitors (e.g., enzastaurin), FTIs (e.g., Zarnestra™), anti-CD138 (e.g., BT062), Torcl/2 specific kinase inhibitors (e.g., INK128), ER/UPR targeting agents (e.g., MKC-3946), cFMS inhibitors (e.g., ARRY-382), JAK1/2 inhibitors (e.g., CYT387), PARP inhibitors (e.g., olaparib and veliparib (ABT-888)), and BCL-2 antagonists.

In some embodiments, an anti-cancer agent is selected from mechlorethamine, camptothecin, ifosfamide, tamoxifen, raloxifene, gemcitabine, Navelbine®, sorafenib, or any analog or derivative variant of the foregoing.

In some embodiments, the anti-cancer agent is a HER2 inhibitor. HER2 inhibitors are known in the art. Non-limiting examples of HER2 inhibitors include monoclonal antibodies such as trastuzumab (Herceptin®) and pertuzumab (Perjeta®); small molecule tyrosine kinase inhibitors such as gefitinib (Iressa®), erlotinib (Tarceva®), pilitinib, CP-654577, CP-724714, canertinib (CI 1033), HKI-272, lapatinib (GW-572016; Tykerb®), PKI-166, AEE788, BMS-599626, HKI-357, BIBW 2992, ARRY-334543, and JNJ-26483327.

In some embodiments, an anti-cancer agent is an ALK inhibitor. ALK inhibitors are known in the art. Non-limiting examples of ALK inhibitors include ceritinib, TAE-684 (NVP-TAE694), PF02341066 (crizotinib or 1066), alectinib; brigatinib; entrectinib; ensartinib (X-396); lorlatinib; ASP3026; CEP-37440; 4SC-203; TL-398; PLB1003; TSR-011; CT-707; TPX-0005, and AP26113. Additional examples of ALK kinase inhibitors are described in examples 3-39 of WO05016894.

In some embodiments, an anti-cancer agent is an inhibitor of a member downstream of a Receptor Tyrosine Kinase (RTK)/Growth Factor Receptor (e.g., a SHP2 inhibitor (e.g., SHP099, TNO155, RMC-4550, RMC-4630, JAB-3068, JAB-3312, RLY-1971, ERAS-601, SH3809, PF-07284892, or BBP-398, or a pharmaceutically acceptable salt, solvate, isomer (e.g., stereoisomer), prodrug, or tautomer thereof), an SOS1 inhibitor (e.g., BI-1701963, BI-3406, SDR5, BAY-293 or RMC-5845, or a pharmaceutically acceptable salt, solvate, isomer (e.g., stereoisomer), prodrug, or tautomer thereof)), a Raf inhibitor, a MEK inhibitor, an ERK inhibitor, a PI3K inhibitor, a PTEN inhibitor, an AKT inhibitor, or an mTOR inhibitor (e.g., mTORC1 inhibitor or mTORC2 inhibitor). In some embodiments, the anti-cancer agent is JAB-3312.

In some embodiments, an anti-cancer agent is a SOS1 inhibitor. SOS1 inhibitors are known in the art. In some embodiments, the SOS1 inhibitor is selected from those disclosed in WO 2022146698, WO 2022081912, WO 2022058344, WO 2022026465, WO 2022017519, WO 2021173524, WO 2021130731, WO 2021127429, WO 2021092115, WO 2021105960, WO 2021074227, WO 2020180768, WO 2020180770, WO 2020173935, WO 2020146470, WO 2019201848, WO 2019122129, WO 2018172250, and WO 2018115380, or a pharmaceutically acceptable salt, solvate, isomer (e.g., stereoisomer), prodrug, or tautomer thereof. In some embodiments, a compound of the present invention is used in combination with a SOS1 inhibitor to treat a K-Ras G13D cancer.

In some embodiments, an anti-cancer agent is an additional Ras inhibitor or a Ras vaccine, or another therapeutic modality designed to directly or indirectly decrease the oncogenic activity of Ras. Such agents are known in the art. In some embodiments, an anti-cancer agent is an additional Ras inhibitor. In some embodiments, the Ras inhibitor targets Ras in its active, or GTP-bound state. In some embodiments, the Ras inhibitor targets Ras in its inactive, or GDP-bound state. In some embodiments, the Ras inhibitor is, such as an inhibitor of K-Ras G12C, such as AMG 510 (sotorasib), MRTX1257, MRTX849 (adagrasib), JNJ-74699157, LY3499446, ARS-1620, ARS-853, BPI-421286, LY3537982, JDQ443, AZ4625, JAB-21822, JAB-21000, IBI351, ERAS-3490, RMC-6291 or GDC-6036, or a pharmaceutically acceptable salt, solvate, isomer (e.g., stereoisomer), prodrug, or tautomer thereof. In some embodiments, the Ras inhibitor is an inhibitor of K-Ras G12D, such as MRTX1133 or JAB-22000, or a pharmaceutically acceptable salt, solvate, isomer (e.g., stereoisomer), prodrug, or tautomer thereof. In some embodiments, the Ras inhibitor is a K-Ras G12V inhibitor, such as JAB-23000, or a pharmaceutically acceptable salt, solvate, isomer (e.g., stereoisomer), prodrug, or tautomer thereof. In some embodiments, the Ras inhibitor is RMC-6236, or a pharmaceutically acceptable salt, solvate, isomer (e.g., stereoisomer), prodrug, or tautomer thereof. In some embodiments, the Ras inhibitor is selected from a Ras (ON) inhibitor disclosed in the following, incorporated herein by reference in their entireties, or a pharmaceutically acceptable salt, solvate, isomer (e.g., stereoisomer), prodrug, or tautomer thereof: WO 2021091982, WO 2021091967, WO 2021091956 and WO 2020132597. Other examples of Ras inhibitors are known in the art, such as in the following, incorporated herein by reference in their entireties: WO 20220133038, WO 2022133345, WO 2022132200, WO 2022119748, WO 2022109485, WO 2022109487, WO 2022066805, WO 2021190467, WO 2021185233, WO 2021180181, WO 2021175199, 2021173923, WO 2021169990, WO 2021169963, WO 2021168193, WO 2021158071, WO 2021155716, WO 2021152149, WO 2021150613, WO 2021147967, WO 2021147965, WO 2021143693, WO 2021142252, WO 2021141628, WO 2021139748, WO 2021139678, WO 2021129824, WO 2021129820, WO 2021127404, WO 2021126816, WO 2021126799, WO 2021124222, WO 2021121371, WO 2021121367, WO 2021121330, WO 2020050890, WO 2020047192, WO 2020035031, WO 2020028706, WO 2019241157, WO 2019232419, WO 2019217691, WO 2019217307, WO 2019215203, WO 2019213526, WO 2019213516, WO 2019155399, WO 2019150305, WO 2019110751, WO 2019099524, WO 2019051291, WO 2018218070, WO 2018217651, WO 2018218071, WO 2018218069, WO 2018206539, WO 2018143315, WO 2018140600, WO 2018140599, WO 2018140598, WO 2018140514, WO 2018140513, WO 2018140512, WO 2018119183, WO 2018112420, WO 2018068017, WO 2018064510, WO 2017201161, WO 2017172979, WO 2017100546, WO 2017087528, WO 2017058807, WO 2017058805, WO 2017058728, WO 2017058902, WO 2017058792, WO 2017058768, WO 2017058915, WO 2017015562, WO 2016168540, WO 2016164675, WO 2016049568, WO 2016049524, WO 2015054572, WO 2014152588, WO 2014143659, and WO 2013155223, or a pharmaceutically acceptable salt, solvate, isomer (e.g., stereoisomer), prodrug, or tautomer thereof.

In some embodiments, a therapeutic agent that may be combined with a compound of the present invention is an inhibitor of the MAP kinase (MAPK) pathway (or "MAPK inhibitor"). Such agents are known in the art. MAPK inhibitors include, but are not limited to, one or more MAPK inhibitor described in Cancers (Basel) 2015 September; 7 (3): 1758-1784. For example, the MAPK inhibitor may be selected from one or more of trametinib, binimetinib, selumetinib, cobimetinib, LErafAON (NeoPharm), ISIS 5132; vemurafenib, pimasertib, TAK733, RO4987655 (CH4987655); CI-1040; PD-0325901; $CH_{5126766}$; MAP855; AZD6244; refametinib (RDEA 119/BAY 86-9766); GDC-0973/XL581; AZD8330 (ARRY-424704/ARRY-704); RO5126766 (Roche, described in PLOS One. 2014 Nov. 25;9 (11)); and GSK1120212 (or JTP-74057, described in Clin Cancer Res. 2011 Mar. 1;17 (5): 989-1000). The MAPK inhibitor may be PLX8394, LXH254, GDC-5573, or LY3009120.

In some embodiments, an anti-cancer agent is a disrupter or inhibitor of the RAS-RAF-ERK or PI3K-AKT-TOR or PI3K-AKT signaling pathways. Such agents are known in the art. The PI3K/AKT inhibitor may include, but is not limited to, one or more PI3K/AKT inhibitor described in Cancers (Basel) 2015 September; 7 (3): 1758-1784. For example, the PI3K/AKT inhibitor may be selected from one or more of NVP-BEZ235; BGT226; XL765/SAR245409; SF1126; GDC-0980; PI-103; PF-04691502; PKI-587; GSK2126458.

In some embodiments, an anti-cancer agent is a PD-1 or PD-L1 antagonist. Such agents are known in the art.

In some embodiments, additional therapeutic agents include ALK inhibitors, HER2 inhibitors, EGFR inhibitors, IGF-1R inhibitors, MEK inhibitors, PI3K inhibitors, AKT inhibitors, TOR inhibitors, MCL-1 inhibitors, BCL-2 inhibitors, SHP2 inhibitors, proteasome inhibitors, and immune therapies. In some embodiments, additional therapeutic agents include FGFR inhibitors, PARP inhibitors, BET inhibitors, PRMT5i inhibitors, MAT2A inhibitors, VEGF inhibitors, and HDAC inhibitors. In some embodiments, a therapeutic agent may be a pan-RTK inhibitor, such as afatinib.

IGF-1R inhibitors are known in the art and include linsitinib, or a pharmaceutically acceptable salt thereof.

EGFR inhibitors are known in the art and include, but are not limited to, small molecule antagonists, antibody inhibitors, or specific antisense nucleotide or siRNA. Useful antibody inhibitors of EGFR include cetuximab (Erbitux®), panitumumab (Vectibix®), zalutumumab, nimotuzumab, and matuzumab. Further antibody-based EGFR inhibitors include any anti-EGFR antibody or antibody fragment that can partially or completely block EGFR activation by its natural ligand. Non-limiting examples of antibody-based EGFR inhibitors include those described in Modjtahedi et al., Br. J. Cancer 1993, 67:247-253; Teramoto et al., Cancer 1996, 77:639-645; Goldstein et al., Clin. Cancer Res. 1995, 1:1311-1318; Huang et al., 1999, Cancer Res. 15: 59 (8): 1935-40; and Yang et al., Cancer Res. 1999, 59:1236-1243. The EGFR inhibitor can be monoclonal antibody Mab E7.6.3 (Yang, 1999 supra), or Mab $C_{225}$ (ATCC Accession No. HB-8508), or an antibody or antibody fragment having the binding specificity thereof.

Small molecule antagonists of EGFR include gefitinib (Iressa®), erlotinib (Tarceva®), and lapatinib (TykerBR). See, e.g., Yan et al., Pharmacogenetics and Pharmacogenomics In Oncology Therapeutic Antibody Development, BioTechniques 2005, 39 (4): 565-8; and Paez et al., EGFR Mutations In Lung Cancer Correlation With Clinical Response To Gefitinib Therapy, Science 2004, 304 (5676): 1497-500. In some embodiments, the EGFR inhibitor is osimertinib (Tagrisso®). Further non-limiting examples of small molecule EGFR inhibitors include any of the EGFR inhibitors described in the following patent publications, and all pharmaceutically acceptable salts of such EGFR inhibitors: EP 0520722; EP 0566226; WO96/33980; U.S. Pat. No. 5,747,498; WO96/30347; EP 0787772; WO97/30034; WO97/30044; WO97/38994; WO97/49688; EP 837063; WO98/02434; WO97/38983; WO95/19774; WO95/19970; WO97/13771; WO98/02437; WO98/02438; WO97/32881; DE 19629652; WO98/33798; WO97/32880; WO97/32880; EP 682027; WO97/02266; WO97/27199; WO98/07726; WO97/34895; WO96/31510; WO98/14449; WO98/14450; WO98/14451; WO95/09847; WO97/19065; WO98/17662; U.S. Pat. Nos. 5,789,427; 5,650,415; 5,656,643; WO99/35146; WO99/35132; WO99/07701; and WO92/20642. Additional non-limiting examples of small molecule EGFR inhibitors include any of the EGFR inhibitors described in Traxler et al., Exp. Opin. Ther. Patents 1998, 8 (12): 1599-1625. In some embodiments, an EGFR inhibitor is an ERBB inhibitor. In humans, the ERBB family contains HER1 (EGFR, ERBB1), HER2 (NEU, ERBB2), HER3 (ERBB3), and HER (ERBB4).

MEK inhibitors are known in the art and include, but are not limited to, pimasertib, selumetinib, cobimetinib (Cotellic®), trametinib (Mekinist®), and binimetinib (Mektovi®). In some embodiments, a MEK inhibitor targets a MEK mutation that is a Class I MEK1 mutation selected from D67N; P124L; P124S; and L177V. In some embodiments, the MEK mutation is a Class II MEK1 mutation selected from ΔE51-Q58; ΔF53-Q58; E203K; L177M; C121S; F53L; K57E; Q56P; and K57N.

PI3K inhibitors are known in the art and include, but are not limited to, wortmannin; 17-hydroxywortmannin analogs described in WO06/044453; 4-[2-(1H-Indazol-4-yl)-6-[[4-(methylsulfonyl) piperazin-1-yl]methyl] thieno [3,2-d]pyrimidin-4-yl] morpholine (also known as pictilisib or GDC-0941 and described in WO09/036082 and WO09/055730); 2-methyl-2-[4-[3-methyl-2-oxo-8-(quinolin-3-yl)-2,3-dihydroimidazo[4,5-c]quinolin-1-yl]phenyl] propionitrile (also known as BEZ 235 or NVP-BEZ 235, and described in WO06/122806); (S)-I-(4-((2-(2-aminopyrimidin-5-yl)-7-methyl-4-morpholinothieno [3,2-d]pyrimidin-6-yl) methyl) piperazin-1-yl)-2-hydroxypropan-1-one (described in WO08/070740); LY294002 (2-(4-morpholinyl)-8-phenyl-4H-I-benzopyran-4-one (available from Axon Medchem); PI 103 hydrochloride (3-[4-(4-morpholinylpyrido-[3',2': 4,5] furo [3,2-d]pyrimidin-2-yl] phenol hydrochloride (available from Axon Medchem); PIK 75 (2-methyl-5-nitro-2-[(6-bromoimidazo[1,2-a]pyridin-3-yl) methylene]-1-methylhydrazide-benzenesulfonic acid, monohydrochloride) (available from Axon Medchem); PIK 90 (N-(7,8-dimethoxy-2, 3-dihydro-imidazo[1,2-c] quinazolin-5-yl)-nicotinamide (available from Axon Medchem); AS-252424 (5-[I-[5-(4-fluoro-2-hydroxy-phenyl)-furan-2-yl]-meth-(Z)-ylidene]-thiazolidine-2,4-dione (available from Axon Medchem); TGX-221 (7-methyl-2-(4-morpholinyl)-9-[1-(phenylamino) ethyl]-4H-pyrido-[1,2-a] pyrirnidin-4-one (available from Axon Medchem); XL-765; and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TGI 00-115, CAL263, PI-103, GNE-477, CUDC-907, and AEZS-136.

AKT inhibitors are known in the art and include, but are not limited to, Akt-1-1 (inhibits Aktl) (Barnett et al., Biochem. J. 2005, 385 (Pt. 2): 399-408); Akt-1-1,2 (inhibits Akl and 2) (Barnett et al., Biochem. J. 2005, 385 (Pt. 2): 399-408); API-59CJ-Ome (e.g., Jin et al., Br. J. Cancer 2004, 91:1808-12); 1-H-imidazo[4,5-c]pyridinyl compounds (e.g., WO 05/011700); indole-3-carbinol and derivatives thereof (e.g., U.S. Pat. No. 6,656,963; Sarkar and Li J Nutr. 2004, 134 (12 Suppl): 3493S-3498S); perifosine (e.g., interferes with Akt membrane localization; Dasmahapatra et al. Clin. Cancer Res. 2004, 10 (15): 5242-52); phosphatidylinositol ether lipid analogues (e.g., Gills and Dennis Expert. Opin. Investig. Drugs 2004, 13:787-97); and triciribine (TCN or API-2 or NCI identifier: NSC 154020; Yang et al., Cancer Res. 2004, 64:4394-9).

mTOR inhibitors are known in the art and include, but are not limited to, ATP-competitive mTORC1/mTORC2 inhibitors, e.g., PI-103, PP242, PP30; Torin 1; FKBP12 enhancers; 4H-1-benzopyran-4-one derivatives; and rapamycin (also known as sirolimus) and derivatives thereof, including: temsirolimus (Torisel®); everolimus (Afinitor®; WO94/09010); ridaforolimus (also known as deforolimus or AP23573); rapalogs, e.g., as disclosed in WO98/02441 and WO01/14387, e.g. AP23464 and AP23841; 40-(2-hydroxyethyl) rapamycin; 40-[3-hydroxy (hydroxymethyl) methylpropanoate]-rapamycin (also known as CC1779); 40-epi-(tetrazolyt)-rapamycin (also called ABT578); 32-deoxorapamycin; 16-pentynyloxy-32 (S)-dihydrorapanycin; derivatives disclosed in WO05/005434; derivatives disclosed in U.S. Pat. Nos. 5,258,389, 5,118,677, 5,118,678, 5,100,883, 5,151,413, 5,120,842, and 5,256,790, and in WO94/090101, WO92/05179, WO93/111130, WO94/02136, WO94/02485, WO95/14023, WO94/02136, WO95/16691, WO96/41807, WO96/41807, and WO2018204416; and phosphorus-containing rapamycin derivatives (e.g., WO05/016252). In some embodiments, the mTOR inhibitor is a bisteric inhibitor (see, e.g., WO2018204416, WO2019212990 and WO2019212991), such as RMC-5552, having the structure

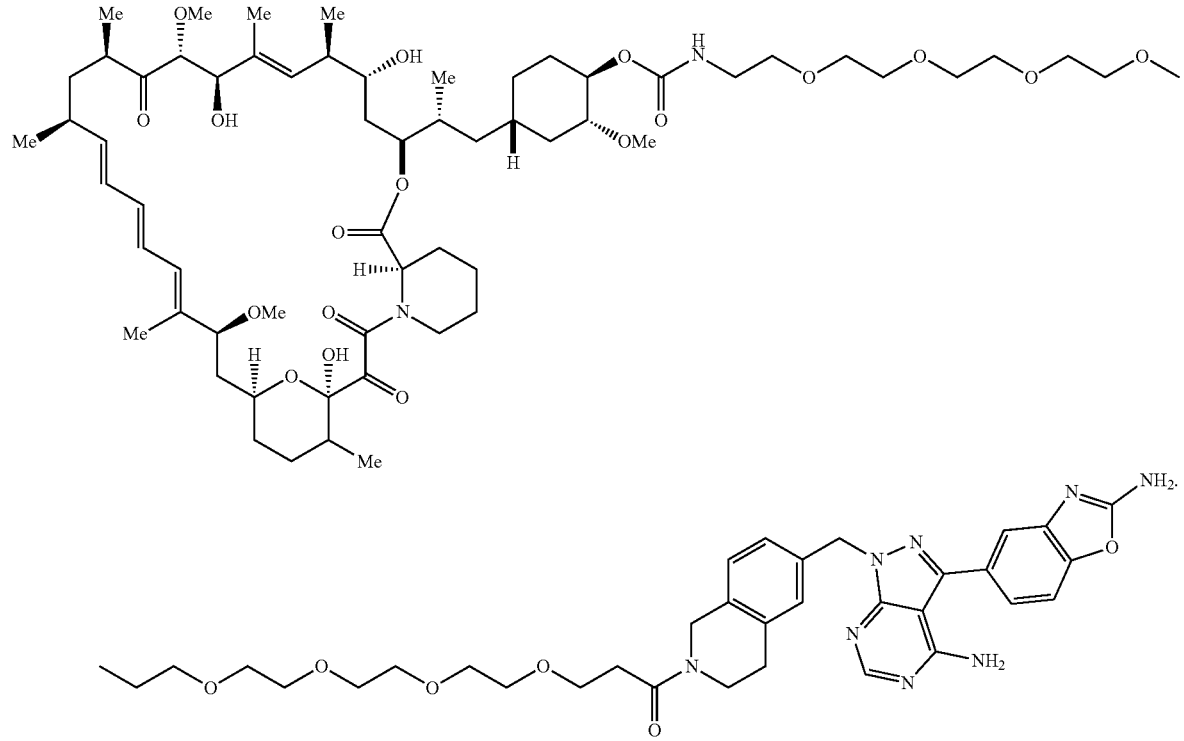

BRAF inhibitors that may be used in combination with compounds of the invention are known in the art and include, for example, vemurafenib, dabrafenib, and encorafenib. A BRAF may comprise a Class 3 BRAF mutation. In some embodiments, the Class 3 BRAF mutation is selected from one or more of the following amino acid substitutions in human BRAF: D287H; P367R; V459L; G466V; G466E; G466A; S467L; G469E; $N_{581}S$; $N_{581I}$; D594N; D594G; D594A; D594H; F595L; G596D; G596R; and A762E.

MCL-1 inhibitors are known in the art and include, but are not limited to, AMG-176, MIK665, and S63845. The myeloid cell leukemia-1 (MCL-1) protein is one of the key anti-apoptotic members of the B-cell lymphoma-2 (BCL-2) protein family. Over-expression of MCL-1 has been closely related to tumor progression as well as to resistance, not only to traditional chemotherapies but also to targeted therapeutics including BCL-2 inhibitors such as ABT-263.

In some embodiments, the additional therapeutic agent is a SHP2 inhibitor. SHP2 inhibitors are known in the art. SHP2 is a non-receptor protein tyrosine phosphatase encoded by the PTPN11 gene that contributes to multiple cellular functions including proliferation, differentiation, cell cycle maintenance and migration. SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N-SH2 and PTP domains.

Stimulation by, for example, cytokines or growth factors acting through receptor tyrosine kinases (RTKs) leads to exposure of the catalytic site resulting in enzymatic activation of SHP2.

SHP2 is involved in signaling through the RAS-mitogen-activated protein kinase (MAPK), the JAK-STAT or the phosphoinositol 3-kinase-AKT pathways. Mutations in the PTPN11 gene and subsequently in SHP2 have been identified in several human developmental diseases, such as Noonan Syndrome and Leopard Syndrome, as well as human cancers, such as juvenile myelomonocytic leukemia, neuroblastoma, melanoma, acute myeloid leukemia and cancers of the breast, lung and colon. Some of these mutations destabilize the auto-inhibited conformation of SHP2 and promote autoactivation or enhanced growth factor driven activation of SHP2. SHP2, therefore, represents a highly attractive target for the development of novel therapies for the treatment of various diseases including cancer. A SHP2 inhibitor (e.g., RMC-4550 or SHP099) in combination with a RAS pathway inhibitor (e.g., a MEK inhibitor) have been shown to inhibit the proliferation of multiple cancer cell lines in vitro (e.g., pancreas, lung, ovarian, and breast cancer). Thus, combination therapy involving a SHP2 inhibitor with a RAS pathway inhibitor could be a general strategy for preventing tumor resistance in a wide range of malignancies.

Non-limiting examples of such SHP2 inhibitors that are known in the art, include: Chen et al. Mol Pharmacol. 2006, 70, 562; Sarver et al., J. Med. Chem. 2017, 62, 1793; Xie et al., J. Med. Chem. 2017, 60, 113734; and Igbe et al., Oncotarget, 2017, 8, 113734; and PCT applications: WO 2022135568, WO 2021176072, WO 2021171261, WO 2021149817, WO 2021148010, WO 2021147879, WO 2021143823, WO 2021143701, WO 2021143680, WO 2021121397, WO 2021119525, WO 2021115286, WO 2021110796, WO 2021088945, WO 2021073439, WO 2021061706, WO 2021061515, WO 2021043077, WO 2021033153, WO 2021028362, WO 2021033153, WO 2021028362, WO 2021018287, WO 2020259679, WO 2020249079, WO 2020210384, WO 2020201991, WO 2020181283, WO 2020177653, WO 2020165734, WO 2020165733, WO 2020165732, WO 2020156243, WO 2020156242, WO 2020108590, WO 2020104635, WO 2020094104, WO 2020094018, WO 2020081848, WO 2020073949, WO 2020073945, WO 2020072656, WO 2020065453, WO 2020065452, WO 2020063760, WO 2020061103, WO 2020061101, WO 2020033828, WO 2020033286, WO 2020022323, WO 2019233810, WO 2019213318, WO 2019183367, WO 2019183364, WO 2019182960, WO 2019167000, WO 2019165073, WO 2019158019, WO 2019152454, WO 2019051469, WO 2019051084, WO 2018218133, WO 2018172984, WO 2018160731, WO 2018136265, WO 2018136264, WO 2018130928, WO 2018129402, WO 2018081091, WO 2018057884, WO 2018013597, WO 2017216706, WO 2017211303, WO 2017210134, WO 2017156397, WO 2017100279, WO 2017079723, WO 2017078499, WO 2016203406, WO 2016203405, WO 2016203404, WO 2016196591, WO 2016191328, WO 2015107495, WO 2015107494, WO 2015107493, WO 2014176488, WO 2014113584, US20210085677, U.S. Pat. Nos. 10,858,359, 10,934,302, 10,954,243, 10,988,466, 11,001,561, 11,033,547, 11,034,705, or U.S. Pat. No. 11,044,675, or a pharmaceutically acceptable salt, solvate, isomer (e.g., stereoisomer), prodrug, or tautomer thereof, each of which is incorporated herein by reference.

In some embodiments, a SHP2 inhibitor binds in the active site. In some embodiments, a SHP2 inhibitor is a mixed-type irreversible inhibitor. In some embodiments, a SHP2 inhibitor binds an allosteric site e.g., a non-covalent allosteric inhibitor. In some embodiments, a SHP2 inhibitor is a covalent SHP2 inhibitor, such as an inhibitor that targets the cysteine residue ($C_{333}$) that lies outside the phosphatase's active site. In some embodiments a SHP2 inhibitor is a reversible inhibitor. In some embodiments, a SHP2 inhibitor is an irreversible inhibitor. In some embodiments, the SHP2 inhibitor is SHP099. In some embodiments, the SHP2 inhibitor is TNO155, having the structure:

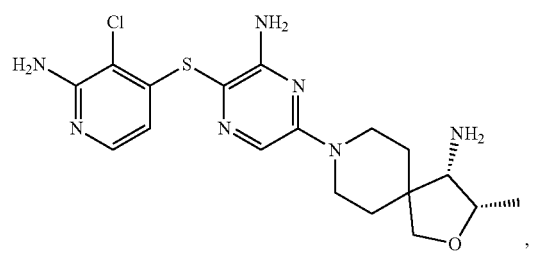 [SMILES: C[C@@H]1OCC2(CCN(c3cnc(Sc4ccnc(N)c4Cl)c(N)n3)CC2)[C@@H]1N]

or a pharmaceutically acceptable salt, solvate, isomer (e.g., stereoisomer), prodrug, or tautomer thereof. In some embodiments, the SHP2 inhibitor is RMC-4550, having the structure

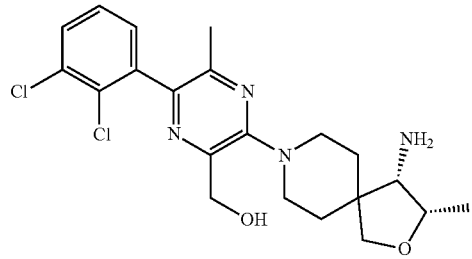 [SMILES: Cc1nc(N2CCC3(CC2)CO[C@@H](C)[C@H]3N)c(CO)nc1-c1cccc(Cl)c1Cl]

or a pharmaceutically acceptable salt, solvate, isomer (e.g., stereoisomer), prodrug, or tautomer thereof. In some embodiments, the SHP2 inhibitor is RMC-4630, having the structure:

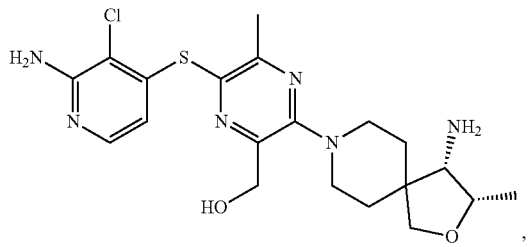 [SMILES: Cc1nc(N2CCC3(CC2)CO[C@@H](C)[C@H]3N)c(CO)nc1Sc1ccnc(N)c1Cl]

or a pharmaceutically acceptable salt, solvate, isomer (e.g., stereoisomer), prodrug, or tautomer thereof. In some embodiments, the SHP2 inhibitor is JAB-3068, having the structure

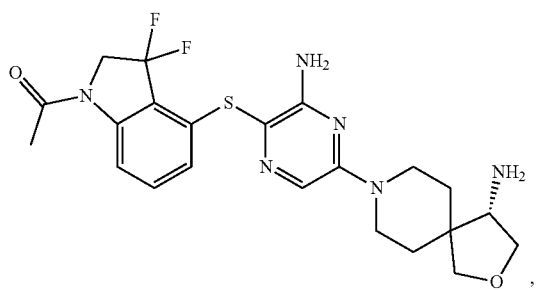 [SMILES: CC(=O)N1CC(F)(F)c2c(Sc3ncc(N4CCC5(CC4)COC[C@H]5N)nc3N)cccc21]

or a pharmaceutically acceptable salt, solvate, isomer (e.g., stereoisomer), prodrug, or tautomer thereof. In some embodiments, the SHP2 inhibitor is JAB-3312. In some embodiments, the SHP2 inhibitor is the following compound,

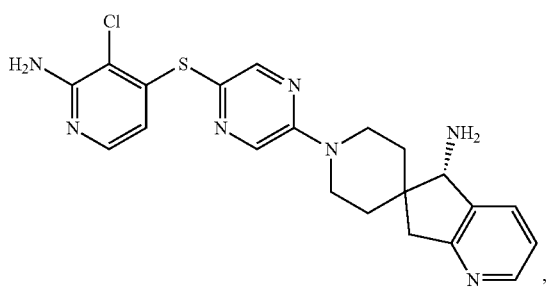 [SMILES: Nc1nccc(Sc2cnc(N3CCC4(CC3)Cc3ncccc3[C@H]4N)cn2)c1Cl]

or a pharmaceutically acceptable salt, solvate, isomer (e.g., stereoisomer), prodrug, or tautomer thereof. In some embodiments, the SHP2 inhibitor is RLY-1971, having the structure

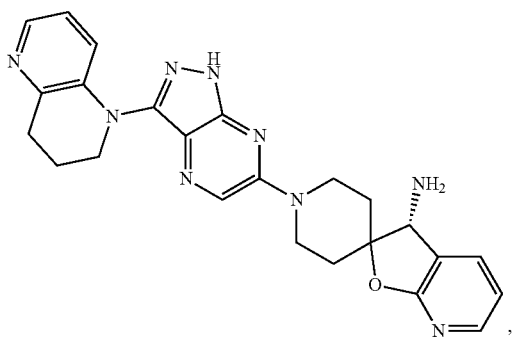 [SMILES: N[C@@H]1c2cccnc2OC12CCN(c1cnc3c(N4CCCc5ncccc54)n[nH]c3n1)CC2]

or a pharmaceutically acceptable salt, solvate, isomer (e.g., stereoisomer), prodrug, or tautomer thereof. In some embodiments, the SHP2 inhibitor is ERAS-601, or a pharmaceutically acceptable salt, solvate, isomer (e.g., stereoisomer), prodrug, or tautomer thereof. In some embodiments, the SHP2 inhibitor is BBP-398, or a pharmaceutically acceptable salt, solvate, isomer (e.g., stereoisomer), prodrug, or tautomer thereof. In some embodiments, the SHP2 inhibitor is SH3809. In some embodiments, the SHP2 inhibitor is PF-07284892, or a pharmaceutically acceptable salt, solvate, isomer (e.g., stereoisomer), prodrug, or tautomer thereof.

In some embodiments, the additional therapeutic agent is selected from the group consisting of a MEK inhibitor, a HER2 inhibitor, a SHP2 inhibitor, a CDK4/6 inhibitor, an mTOR inhibitor, a SOS1 inhibitor, and a PD-L1 inhibitor. In some embodiments, the additional therapeutic agent is selected from the group consisting of a MEK inhibitor, a SHP2 inhibitor, and a PD-L1 inhibitor. See, e.g., Hallin et al., Cancer Discovery, DOI: 10.1158/2159-8290 (Oct. 28, 2019) and Canon et al., Nature, 575:217 (2019). In some embodiments, a Ras inhibitor of the present invention is used in combination with a MEK inhibitor and a SOS1 inhibitor. In some embodiments, a Ras inhibitor of the present invention is used in combination with a PD-L1 inhibitor and a SOS1 inhibitor. In some embodiments, a Ras inhibitor of the present invention is used in combination with a PD-L1 inhibitor and a SHP2 inhibitor. In some embodiments, a Ras inhibitor of the present invention is used in combination with a MEK inhibitor and a SHP2 inhibitor. In some embodiments, a Ras inhibitor of the present invention is used in combination with a SHP2 inhibitor and a Ras inhibitor that inhibits multiple Ras isoforms and/or mutants (e.g., RMC-6236). In some embodiments, the cancer is colorectal cancer and the treatment comprises administration of a Ras inhibitor of the present invention in combination with a second or third therapeutic agent, such as a SHP2 inhibitor and a Ras inhibitor that inhibits multiple Ras isoforms and/or mutants. In some embodiments, the cancer is cholangiocarcinoma and the treatment comprises administration of a Ras inhibitor of the present invention, sorafenib and a chemotherapeutic agent. In some embodiments, the cancer is gastric cancer and the treatment comprises administration of a Ras inhibitor of the present invention and an FGFR inhibitor (e.g., FGFR2i or FGFR4i). In some embodiments, a Ras inhibitor of the present invention is used in combination with an immunotherapy, optionally in combination with a chemotherapeutic agent.

Proteasome inhibitors are known in the art and include, but are not limited to, carfilzomib (Kyprolis®), bortezomib (Velcade®), and oprozomib.

Immune therapies include, but are not limited to, monoclonal antibodies, immunomodulatory imides (IMiDs), GITR agonists, genetically engineered T-cells (e.g., CAR-T cells), bispecific antibodies (e.g., BiTEs), and anti-PD-1, anti-PD-L1, anti-CTLA4, anti-LAGI, and anti-OX40 agents). Other immune therapies are known in the art.

Immunomodulatory agents (IMiDs) are a class of immunomodulatory drugs (drugs that adjust immune responses) containing an imide group. The IMiD class includes thalidomide and its analogues (lenalidomide, pomalidomide, and apremilast).

Exemplary anti-PD-1 antibodies and methods for their use are described by Goldberg et al., Blood 2007, 110 (1): 186-192; Thompson et al., Clin. Cancer Res. 2007, 13 (6): 1757-1761; and WO06/121168 A1), as well as described elsewhere herein.

FGFR inhibitors are known in the art, such as pemigatinib and erdafitinib, including FGFR2 inhibitors and FGFR4 inhibitors. See, e.g., Cancers (Basel), 2021 June; 13 (12) 2968.

BET inhibitors are known in the art, such as romidepsin, panobinostat and belinostat. See, e.g., British J. Cancer 124:1478 (2021).

PRMT5i inhibitors are known in the art, such as PF-0693999, PJ-68 and MRTX1719. See, e.g., Biomed. Pharmacotherapy 144:112252 (2021).

MAT2A inhibitors are known in the art, such as AG-270 and IDE397. See, e.g., Exp Opin Ther Patents (2022) DOI: 10.1080/13543776.2022.2119127.

GITR agonists are known in the art and include, but are not limited to, GITR fusion proteins and anti-GITR antibodies (e.g., bivalent anti-GITR antibodies), such as, a GITR fusion protein described in U.S. Pat. Nos. 6,111,090, 8,586,023, WO2010/003118 and WO2011/090754; or an anti-GITR antibody described, e.g., in U.S. Pat. No. 7,025,962, EP 1947183, U.S. Pat. Nos. 7,812,135, 8,388,967, 8,591,886, 7,618,632, EP 1866339, and WO2011/028683, WO2013/039954, WO05/007190, WO07/133822, WO05/055808, WO99/40196, WO01/03720, WO99/20758, WO06/083289, WO05/115451, and WO2011/051726.

Another example of a therapeutic agent that may be used in combination with the compounds of the invention is an anti-angiogenic agent. Anti-angiogenic agents are known in the art and are inclusive of, but not limited to, in vitro synthetically prepared chemical compositions, antibodies, antigen binding regions, radionuclides, and combinations and conjugates thereof. An anti-angiogenic agent can be an agonist, antagonist, allosteric modulator, toxin or, more generally, may act to inhibit or stimulate its target (e.g., receptor or enzyme activation or inhibition), and thereby promote cell death or arrest cell growth. In some embodiments, the one or more additional therapies include an anti-angiogenic agent.

Anti-angiogenic agents can be MMP-2 (matrix-metalloproteinase 2) inhibitors, MMP-9 (matrix-metalloprotienase 9) inhibitors, and COX-II (cyclooxygenase 11) inhibitors. Non-limiting examples of anti-angiogenic agents include rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO96/33172, WO96/27583, WO98/07697, WO98/03516, WO98/34918, WO98/34915, WO98/33768, WO98/30566, WO90/05719, WO99/52910, WO99/52889, WO99/29667, WO99007675, EP0606046, EP0780386, EP1786785, EP1181017, EP0818442, EP1004578, and US20090012085, and U.S. Pat. Nos. 5,863,949 and 5,861,510. Preferred MMP-2 and MMP-9 inhibitors are those that have little or no activity inhibiting MMP-1. More preferred, are those that selectively inhibit MMP-2 or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors are AG-3340, RO 32-3555, and RS 13-0830.

Further exemplary anti-angiogenic agents include KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF (e.g., bevacizumab), or soluble VEGF receptors or a ligand binding region thereof) such as VEGF-TRAP™, and anti-VEGF receptor agents (e.g., antibodies or antigen binding regions that specifically bind thereto), VEGF inhibitors, EGFR inhibitory agents (e.g., antibodies or antigen binding regions that specifically bind thereto) such as Vectibix® (panitumumab), erlotinib (Tarceva®), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). Other anti-angiogenic agents include Campath, IL-8, B-FGF, Tek antagonists (US2003/0162712; U.S. Pat. No. 6,413,932), anti-TWEAK agents (e.g., specifically binding antibodies or antigen binding regions, or soluble TWEAK receptor antagonists; see U.S. Pat. No. 6,727,225), ADAM distintegrin domain to antagonize the binding of integrin to its ligands (US 2002/0042368), specifically binding anti-eph receptor or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto). Additional anti-angiogenic agents include: SD-7784 (Pfizer, USA); cilengitide (Merck KGaA, Germany, EPO 0770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol (EntreMed, USA); TLC ELL-12 (Elan, Ireland); anecortave acetate (Alcon, USA); alpha-D148 Mab (Amgen, USA); CEP-7055 (Cephalon, USA); anti-Vn Mab (Crucell, Netherlands), DACantiangiogenic (ConjuChem, Canada); Angiocidin (InKine Pharmaceutical, USA); KM-2550 (Kyowa Hakko, Japan); SU-0879 (Pfizer, USA); CGP-79787 (Novartis, Switzerland, EP 0970070); ARGENT technology (Ariad, USA); YIGSR-Stealth (Johnson & Johnson, USA); fibrinogen-E fragment (BioActa, UK); angiogenic inhibitor (Trigen, UK); TBC-1635 (Encysive Pharmaceuticals, USA); SC-236 (Pfizer, USA); ABT-567 (Abbott, USA); Metastatin (EntreMed, USA); maspin (Sosei, Japan); 2-methoxyestradiol (Oncology Sciences Corporation, USA); ER-68203-00 (IV AX, USA); BeneFin (Lane Labs, USA); Tz-93 (Tsumura, Japan); TAN-1120 (Takeda, Japan); FR-111142 (Fujisawa, Japan, JP 02233610); platelet factor 4 (RepliGen, USA, EP 407122); vascular endothelial growth factor antagonist (Borean, Denmark); bevacizumab (pINN) (Genentech, USA); angiogenic inhibitors (SUGEN, USA); XL 784 (Exelixis, USA); XL 647 (Exelixis, USA); MAb, alpha5beta3 integrin, second generation (Applied Molecular Evolution, USA and MedImmune, USA); enzastaurin hydrochloride (Lilly, USA); CEP 7055 (Cephalon, USA and Sanofi-Synthelabo, France); BC 1 (Genoa Institute of Cancer Research, Italy); rBPI 21 and BPI-derived antiangiogenic (XOMA, USA); PI 88 (Progen, Australia); cilengitide (Merck KGaA, German; Munich Technical University, Germany, Scripps Clinic and Research Foundation, USA); AVE 8062 (Ajinomoto, Japan); AS 1404 (Cancer Research Laboratory, New Zealand); SG 292, (Telios, USA); Endostatin (Boston Childrens Hospital, USA); ATN 161 (Attenuon, USA); 2-methoxyestradiol (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXIGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenic, (EntreMed, USA); urokinase plasminogen activator inhibitor, (Dendreon, USA); oglufanide (pINN), (Melmotte, USA); HIF-lalfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol; anginex (Maastricht University, Netherlands, and Minnesota University, USA); ABT 510 (Abbott, USA); AAL 993 (Novartis, Switzerland); VEGI (ProteomTech, USA); tumor necrosis factor-alpha inhibitors; SU 11248 (Pfizer, USA and SUGEN USA); ABT 518, (Abbott, USA); YH16 (Yantai Rongchang, China); S-3APG (Boston Childrens Hospital, USA and EntreMed, USA); MAb, KDR (ImClone Systems, USA); MAb, alpha5 beta (Protein Design, USA); KDR kinase inhibitor (Celltech Group, UK, and Johnson & Johnson, USA); GFB 116 (South Florida University, USA and Yale University, USA); CS 706 (Sankyo, Japan); combretastatin A4 prodrug (Arizona State University, USA); chondroitinase AC (IBEX, Canada); BAY RES 2690 (Bayer, Germany); AGM 1470 (Harvard University, USA, Takeda, Japan, and TAP, USA); AG 13925 (Agouron, USA); Tetrathiomolybdate (University of Michigan, USA); GCS 100 (Wayne State University, USA) CV 247 (Ivy Medical, UK); CKD 732 (Chong Kun Dang, South Korea); irsogladine, (Nippon Shinyaku, Japan); RG 13577 (Aventis, France); WX 360 (Wilex, Germany); squalamine, (Genaera, USA); RPI 4610 (Sirna, USA); heparanase inhibitors (InSight, Israel); KL 3106 (Kolon, South Korea); Honokiol (Emory University, USA); ZK CDK (Schering AG, Germany); ZK Angio (Schering AG, Germany); ZK 229561 (Novartis, Switzerland, and Schering AG, Germany); XMP 300 (XOMA, USA); VGA 1102 (Taisho, Japan); VE-cadherin-2 antagonists (ImClone Systems, USA); Vasostatin (National Institutes of Health, USA); Flk-1 (ImClone Systems, USA); TZ 93 (Tsumura, Japan); TumStatin (Beth Israel Hospital, USA); truncated soluble FLT 1 (vascular endothelial growth factor receptor 1) (Merck & Co, USA); Tie-2 ligands (Regeneron, USA); and thrombospondin 1 inhibitor (Allegheny Health, Education and Research Foundation, USA).

Further examples of therapeutic agents that may be used in combination with compounds of the invention include agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor, c-Met. Such agents are known in the art.

Another example of a therapeutic agent that may be used in combination with compounds of the invention is an autophagy inhibitor. Autophagy inhibitors are known in the art and include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of CAMP, and drugs which elevate CAMP levels such as adenosine, LY204002, N6-mercaptopurine riboside, and vinblastine. In addition, antisense or siRNA that inhibits expression of proteins including but not limited to ATG5 (which are implicated in autophagy), may also be used. In some embodiments, the one or more additional therapies include an autophagy inhibitor.

Another example of a therapeutic agent that may be used in combination with compounds of the invention is an anti-neoplastic agent, which are known in the art. In some embodiments, the one or more additional therapies include an anti-neoplastic agent. Non-limiting examples of anti-neoplastic agents include acemannan, aclarubicin, aldesleukin, alemtuzumab, alitretinoin, altretamine, amifostine, aminolevulinic acid, amrubicin, amsacrine, anagrelide, anastrozole, ancer, ancestim, arglabin, arsenic trioxide, BAM-002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-NI, interferon alfa-n3, interferon alfacon-1, interferon alpha, natural, interferon beta, interferon beta-la, interferon beta-lb, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit anti-thymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, virulizin, zinostatin stimalamer, or zoledronic acid; abarelix; AE 941 (Aeterna), ambamustine, antisense oligonucleotide, bcl-2 (Genta), APC 8015 (Dendreon), decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techni clone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Additional examples of therapeutic agents that may be used in combination with compounds of the invention include ipilimumab (Yervoy®); tremelimumab; galiximab; nivolumab, also known as BMS-936558 (Opdivo®); pembrolizumab (Keytruda®); avelumab (Bavencio®); AMP224; BMS-936559; MPDL3280A, also known as RG7446; MEDI-570; AMG557; MGA271; IMP321; BMS-663513; PF-05082566; CDX-1127; anti-OX40 (Providence Health Services); huMAbOX40L; atacicept; CP-870893; lucatumumab; dacetuzumab; muromonab-CD3; ipilumumab; MEDI4736 (Imfinzi®); MSB0010718C; AMP 224; adalimumab (Humira®); ado-trastuzumab emtansine (Kadcyla®); aflibercept (Eylea®); alemtuzumab (Campath®); basiliximab (Simulect®); belimumab (Benlysta®); basiliximab (Simulect®); belimumab (Benlysta®); brentuximab vedotin (Adcetris®); canakinumab (Ilaris®); certolizumab pegol (Cimzia®); daclizumab (Zenapax®); daratumumab (Darzalex®); denosumab (Prolia®); eculizumab (Soliris®); efalizumab (Raptiva®); gemtuzumab ozogamicin (Mylotarg®); golimumab (Simponi®); ibritumomab tiuxetan (Zevalin®); infliximab (Remicade®); motavizumab (Numax®); natalizumab (Tysabri®); obinutuzumab (Gazyva®); ofatumumab (Arzerra®); omalizumab (Xolair®); palivizumab (Synagis®); pertuzumab (Perjeta®); pertuzumab (Perjeta®); ranibizumab (Lucentis®); raxibacumab (Abthrax®); tocilizumab (Actemra®); tositumomab; tositumomab-i-131; tositumomab and tositumomab-i-131 (Bexxar®); ustekinumab (Stelara®); AMG 102; AMG 386; AMG 479; AMG 655; AMG 706; AMG 745; and AMG 951.

The compounds described herein can be used in combination with the agents disclosed herein or other suitable agents, depending on the condition being treated. Hence, in some embodiments the one or more compounds of the invention will be co-administered with other therapies as described herein. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described herein can be formulated together in the same dosage form and administered simultaneously. Alternatively, a compound of the invention and any of the therapies described herein can be simultaneously administered, wherein both the agents are present in separate formulations. In another alternative, a compound of the present invention can be administered and followed by any of the therapies described herein, or vice versa. In some embodiments of the separate administration protocol, a compound of the invention and any of the therapies described herein are administered a few minutes apart, or a few hours apart, or a few days apart.

In some embodiments of any of the methods described herein, the first therapy (e.g., a compound of the invention) and one or more additional therapies are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours, up to 24 hours, or up 10 to 1-7, 1-14, 1-21 or 1-30 days before or after the one or more additional therapies.

The invention also features kits including (a) a pharmaceutical composition including an agent (e.g., a compound of the invention) described herein, and (b) a package insert with instructions to perform any of the methods described herein. In some embodiments, the kit includes (a) a pharmaceutical composition including an agent (e.g., a compound of the invention) described herein, (b) one or more additional therapies (e.g., non-drug treatment or therapeutic agent), and (c) a package insert with instructions to perform any of the methods described herein.

As one aspect of the present invention contemplates the treatment of the disease or symptoms associated therewith with a combination of pharmaceutically active compounds that may be administered separately, the invention further relates to combining separate pharmaceutical compositions in kit form. The kit may comprise two separate pharmaceutical compositions: a compound of the present invention, and one or more additional therapies. The kit may comprise a container for containing the separate compositions such as a divided bottle or a divided foil packet. Additional examples of containers include syringes, boxes, and bags. In some embodiments, the kit may comprise directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

Numbered Embodiments

1. A compound, or a pharmaceutically acceptable salt thereof, having the structure of Formula I:

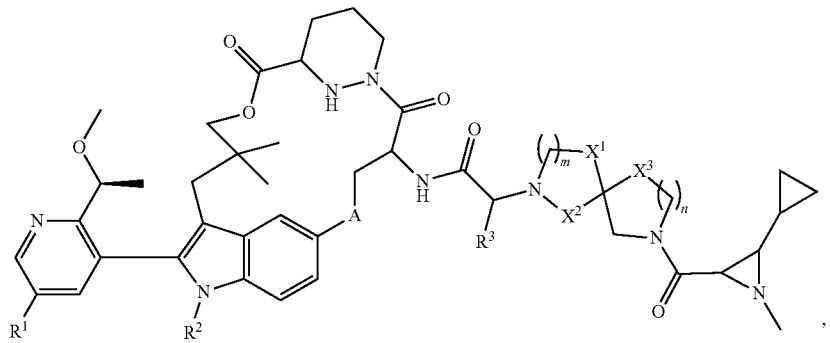

Formula I wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$X^1$, $X^2$, and $X^3$ are each independently selected from $CH_2$, CHF, $CF_2$, C=O, or O;

m is 1 or 2;

n is 0 or 1;

$R^1$ is hydrogen, optionally substituted $C_1$-$C_6$ heteroalkyl, or optionally substituted 3 to 10-membered heterocycloalkyl;

$R^2$ is optionally substituted $C_1$-$C_8$ alkyl; and $R^3$ is optionally substituted $C_1$-$C_8$ alkyl, optionally substituted $C_1$-$C_6$ heteroalkyl, optionally substituted 3 to 6-membered cycloalkyl, or optionally substituted heterocycloalkyl, and wherein each hydrogen is independently, optionally, isotopically enriched for deuterium.

2. A compound, or a pharmaceutically acceptable salt thereof, having the structure of Formula I:

wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$X^1$, $X^2$, and $X^3$ are each independently selected from $CH_2$, $CF_2$, C=O, or O;

m is 1 or 2;

n is 0 or 1;

$R^1$ is hydrogen, optionally substituted $C_1$-$C_6$ heteroalkyl, or optionally substituted 3 to 10-membered heterocycloalkyl;

$R^2$ is optionally substituted $C_1$-$C_6$ alkyl; and $R^3$ is optionally substituted $C_1$-$C_6$ alkyl, optionally substituted 3 to 6-membered cycloalkyl, or optionally substituted heterocycloalkyl, and wherein each hydrogen is independently, optionally, isotopically enriched for deuterium.

3. The compound of embodiment 1 or 2, or a pharmaceutically acceptable salt thereof, having the structure of any one of Formula Ia, Formula Ib, or Formula Ic:

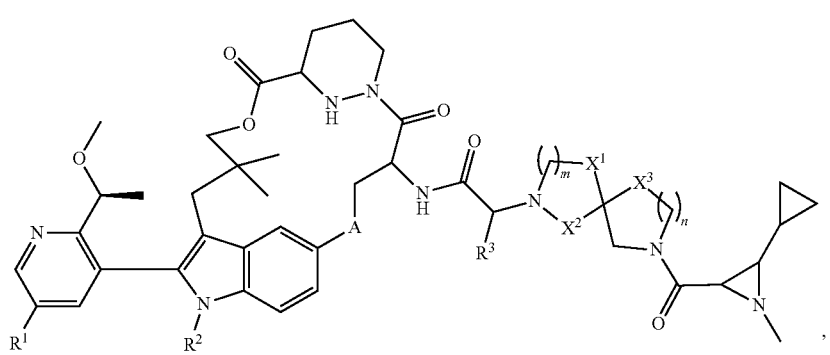

Formula I

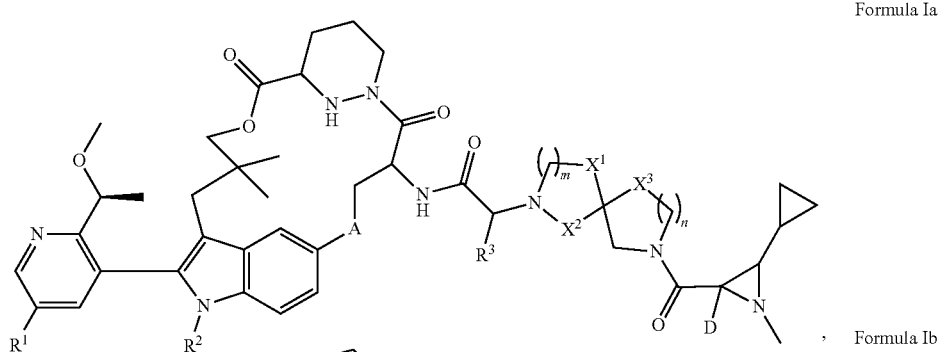

Formula Ia

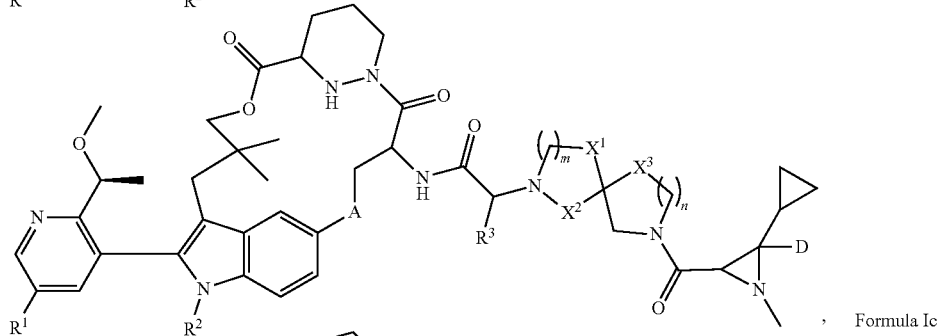

, Formula Ib

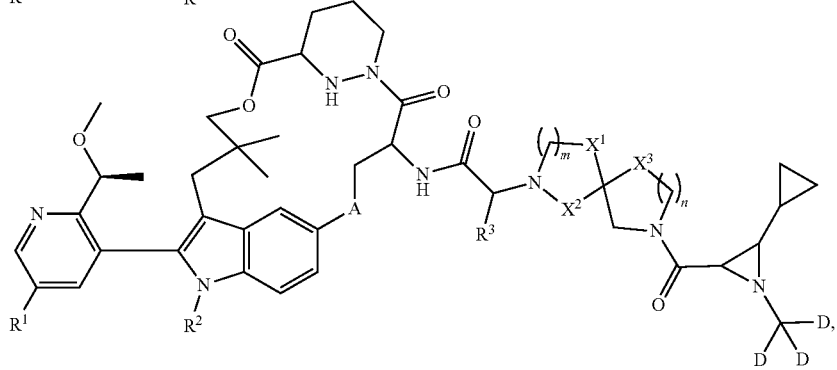

, Formula Ic wherein each D indicates a hydrogen having an isotopic enrichment factor for deuterium of at least 5.

4. The compound of any one of embodiments 1 to 3, or a pharmaceutically acceptable salt thereof, wherein $R^1$ is hydrogen or optionally substituted 3 to 10-membered heterocycloalkyl.

5. The compound of any one of embodiments 1 to 4, or a pharmaceutically acceptable salt thereof, wherein $R^1$ is optionally substituted 3 to 10-membered heterocycloalkyl.

6. The compound of embodiment 5, or a pharmaceutically acceptable salt thereof, wherein $R^1$ is:

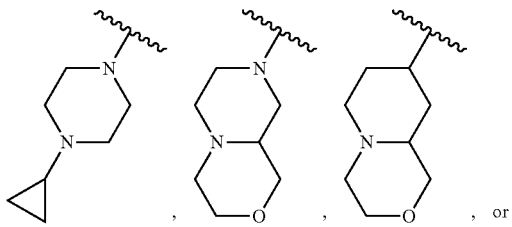

-continued

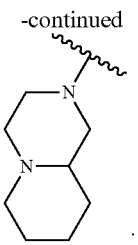

7. The compound of embodiment 5, or a pharmaceutically acceptable salt thereof, wherein $R^1$ is:

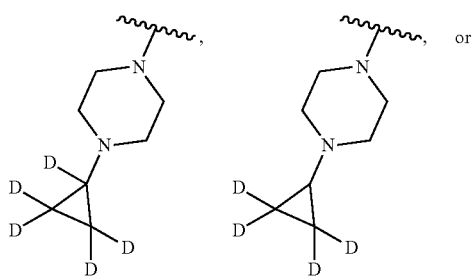

-continued

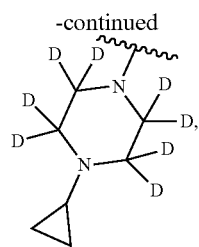

and wherein each D indicates a hydrogen having an isotopic enrichment factor for deuterium of at least 5.

8. The compound of any one of embodiments 1 to 7, or a pharmaceutically acceptable salt thereof, wherein m is 1.

9. The compound of any one of embodiments 1 to 8, or a pharmaceutically acceptable salt thereof, wherein n is 1.

10. The compound of any one of embodiments 1 to 9, or a pharmaceutically acceptable salt thereof, wherein each of $X^1$, $X^2$, and $X^3$ is $CH_2$.

11. The compound of embodiment 1, or a pharmaceutically acceptable salt thereof, having the structure of Formula II:

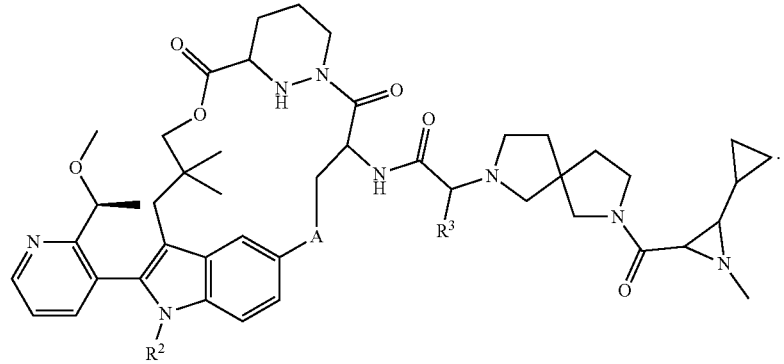

Formula II

12. The compound of embodiment 1, or a pharmaceutically acceptable salt thereof, having the structure of Formula V:

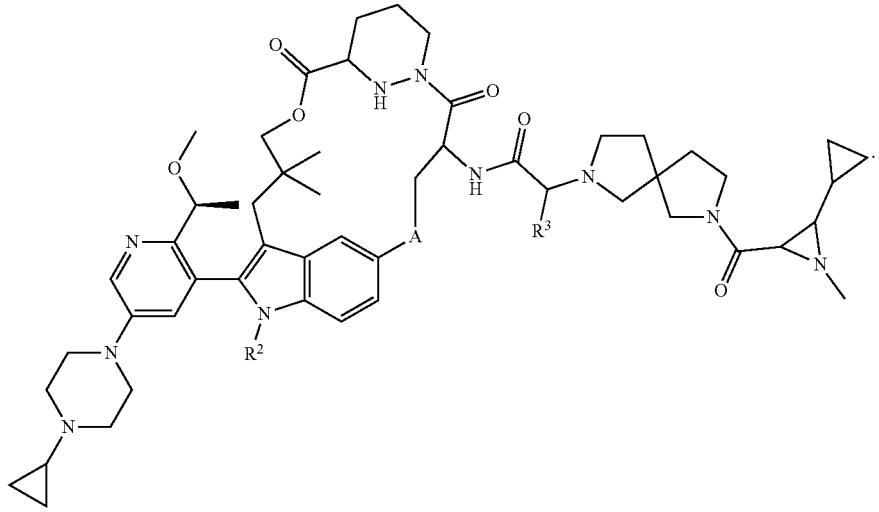

Formula V

13. The compound of embodiment 12, or a pharmaceutically acceptable salt thereof, having the structure of any one of Formula Va, Formula Vb, or Formula Vc:
Formula Va
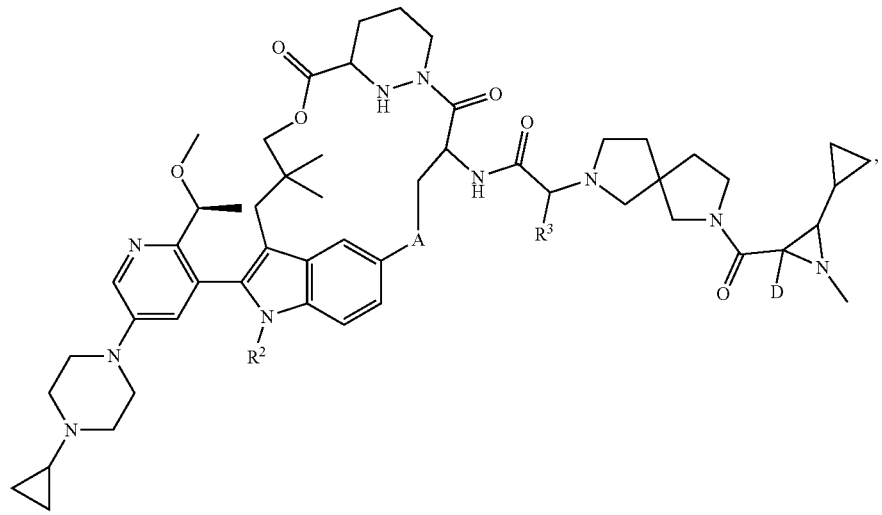
Formula Vb
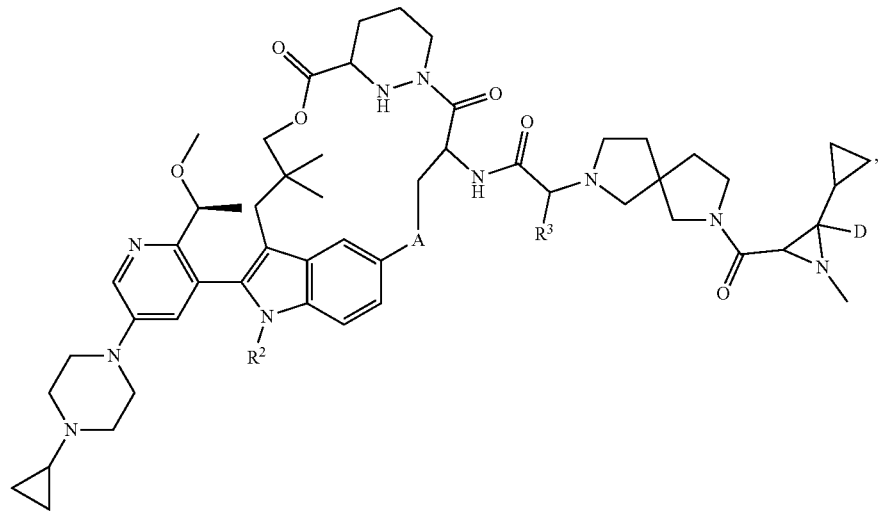
Formula Vc
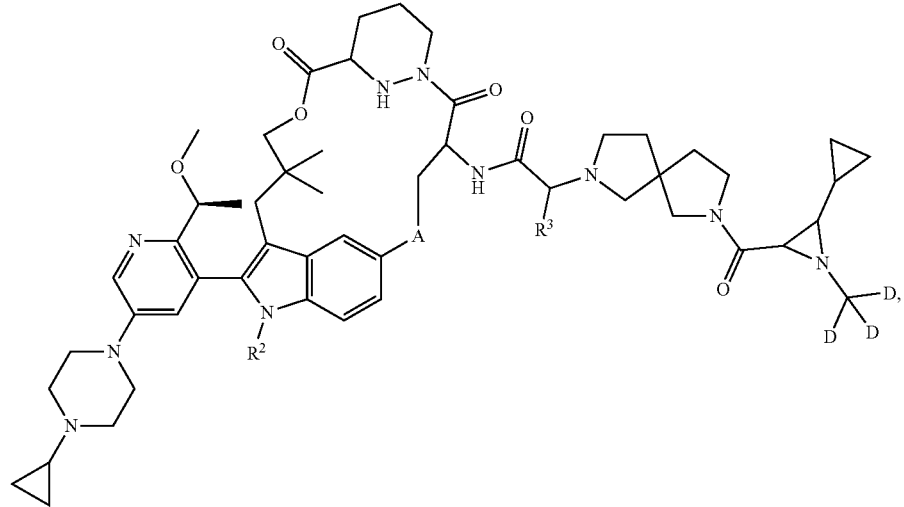

wherein each D indicates a hydrogen having an isotopic enrichment factor for deuterium of at least 5.
14. The compound of embodiment 12, or a pharmaceutically acceptable salt thereof, having the structure of any one of Formula Vd, Formula Ve, or Formula Vf:
Formula Vd
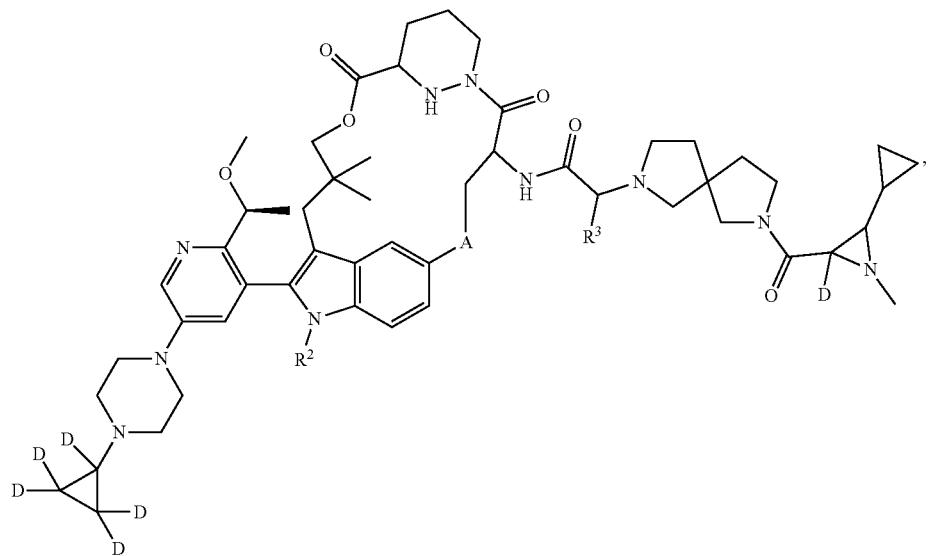
Formula Ve
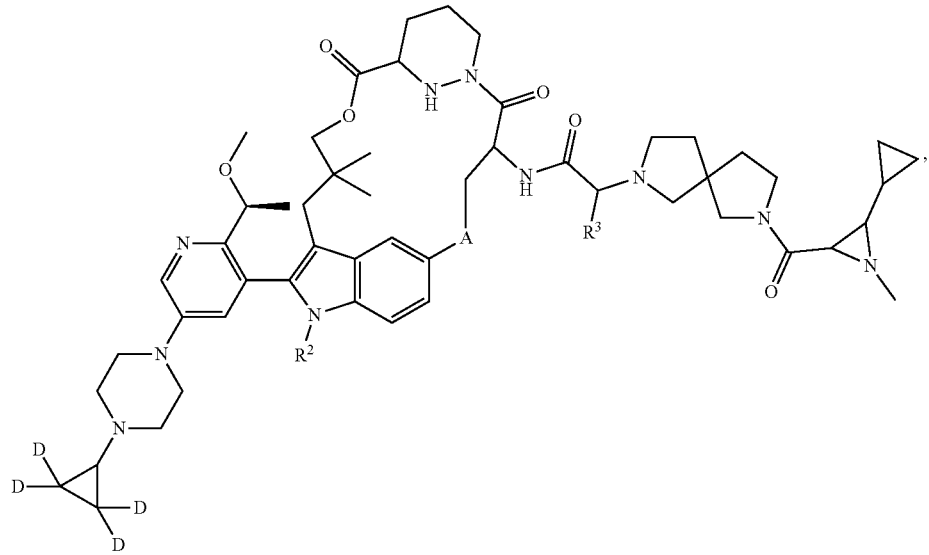

Formula Vf
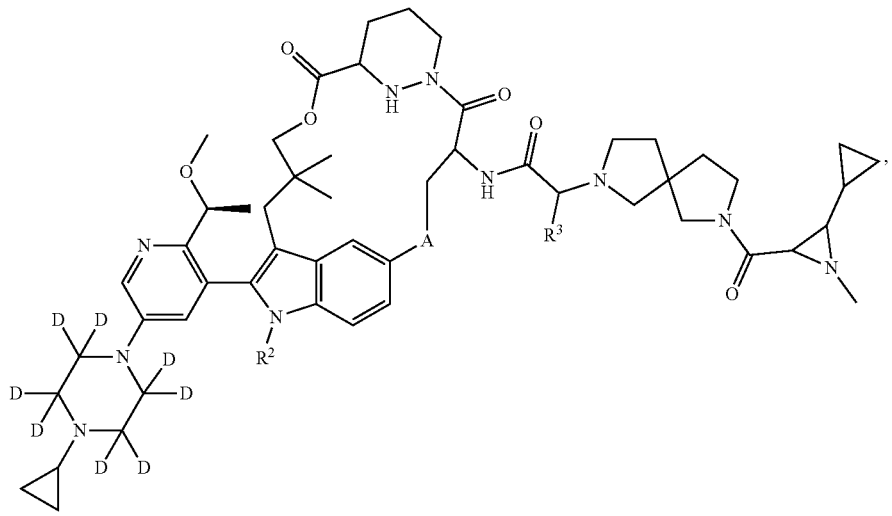
wherein each D indicates a hydrogen having an isotopic enrichment factor for deuterium of at least 5.
15. The compound of embodiment 1, or a pharmaceutically acceptable salt thereof, having the structure of Formula VI:
Formula VI
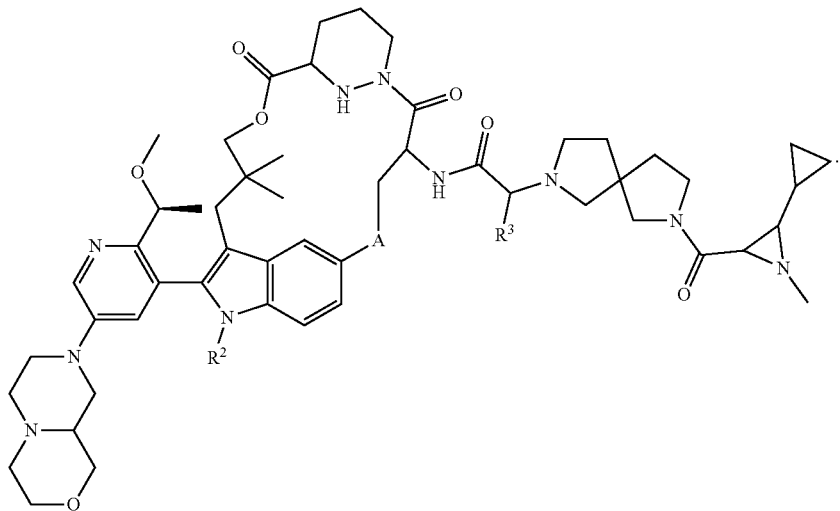

16. The compound of embodiment 1, or a pharmaceutically acceptable salt thereof, having the structure of Formula VII:

Formula VII

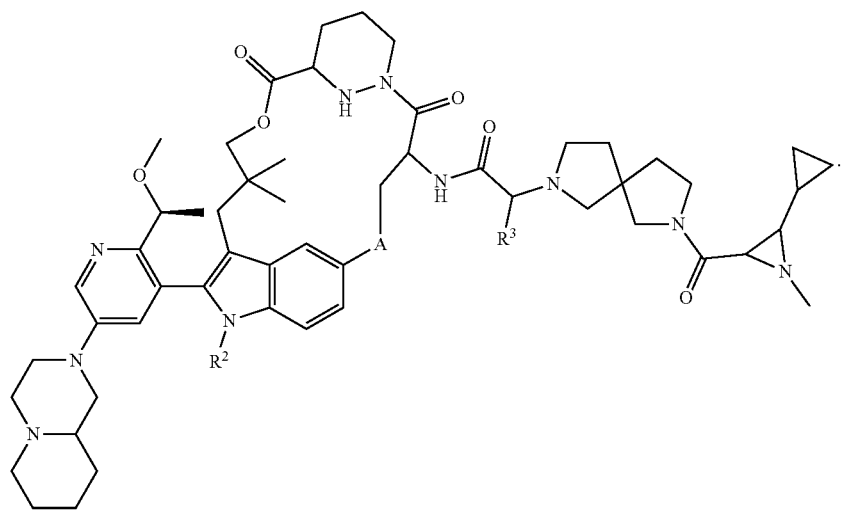

17. The compound of any one of embodiments 1 to 16, or a pharmaceutically acceptable salt thereof, wherein A is optionally substituted thiazole-diyl, optionally substituted oxazole-diyl, optionally substituted morpholine-diyl, optionally substituted pyrrolidine-diyl, optionally substituted piperidine-diyl, or optionally substituted phenylene.

18. The compound of embodiment 17, or a pharmaceutically acceptable salt thereof, wherein A is optionally substituted thiazole-diyl or optionally substituted morpholine-diyl.

19. The compound of any one of embodiments 1 to 16, or a pharmaceutically acceptable salt thereof, wherein A is optionally substituted 5 to 10-membered heteroarylene.

20. The compound of embodiment 19, or a pharmaceutically acceptable salt thereof, wherein A is:

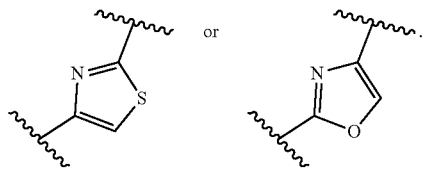 [SMILES: *c1csc(*)n1 ; *c1coc(*)n1]

21. The compound of embodiment 20, or a pharmaceutically acceptable salt thereof, wherein A is:

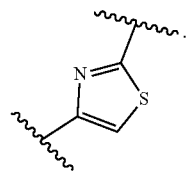 [SMILES: *c1csc(*)n1]

22. The compound of any one of embodiments 1 to 16, or a pharmaceutically acceptable salt thereof, wherein A is optionally substituted phenylene.

23. The compound of embodiment 22, or a pharmaceutically acceptable salt thereof, wherein A is:

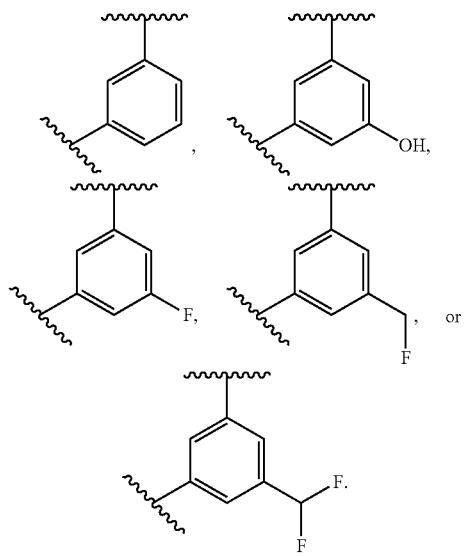

24. The compound of embodiment 23, or a pharmaceutically acceptable salt thereof, wherein A is:

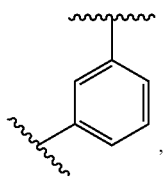 [SMILES: *c1cccc(*)c1]

25. The compound of any one of embodiments 1 to 16, or a pharmaceutically acceptable salt thereof, wherein A is optionally substituted 3 to 6-membered heterocycloalkylene.

26. The compound of embodiment 25, or a pharmaceutically acceptable salt thereof, wherein A is optionally substituted 6-membered heterocycloalkylene 27. The compound of embodiment 25, or a pharmaceutically acceptable salt thereof, wherein A is selected from the following, or a stereoisomer thereof:

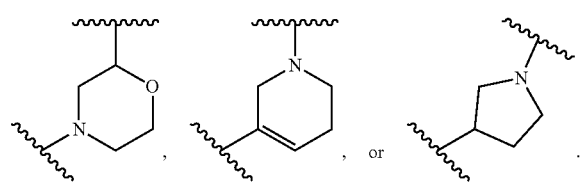 [SMILES: *C1CN(*)CCO1 ; *C1=CCCN(*)C1 ; *C1CCN(*)C1]

28. The compound of embodiment 26, or a pharmaceutically acceptable salt thereof, wherein A is selected from the following, or a stereoisomer thereof:

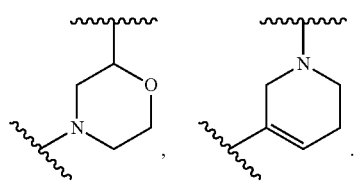 [SMILES: *C1CN(*)CCO1 ; *C1=CCCN(*)C1]

29. The compound of any one of embodiments 1 to 28, or a pharmaceutically acceptable salt thereof, wherein $R^2$ is:

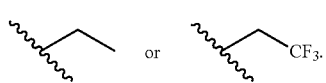

30. The compound of any one of embodiments 1 to 28, or a pharmaceutically acceptable salt thereof, wherein $R^2$ is:

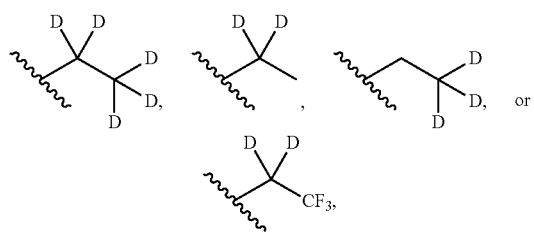

and wherein each D indicates a hydrogen having an isotopic enrichment factor for deuterium of at least 5.

31. The compound of any one of embodiments 1 to 30, or a pharmaceutically acceptable salt thereof, wherein $R^3$ is optionally substituted $C_1$-$C_6$ alkyl or optionally substituted 3 to 6-membered cycloalkyl.

32. The compound of any one of embodiments 1 to 31, or a pharmaceutically acceptable salt thereof, wherein $R^3$ is optionally substituted $C_1$-$C_6$ alkyl.

33. The compound of embodiment 32, or a pharmaceutically acceptable salt thereof, wherein $R^3$ is:

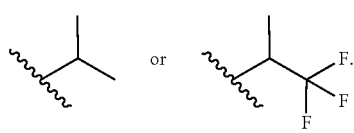

34. The compound of embodiment 33, or a pharmaceutically acceptable salt thereof, wherein $R^3$ is:

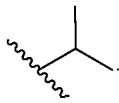

35. The compound of embodiment 32, or a pharmaceutically acceptable salt thereof, wherein $R^3$ is:

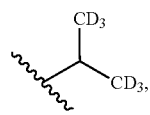

and wherein each D indicates a hydrogen having an isotopic enrichment factor for deuterium of at least 5.

36. The compound of any one of embodiments 1 to 31, or a pharmaceutically acceptable salt thereof, wherein $R^3$ is or optionally substituted 3 to 6-membered cycloalkyl.

37. The compound of embodiment 36, or a pharmaceutically acceptable salt thereof, wherein $R^3$ is:

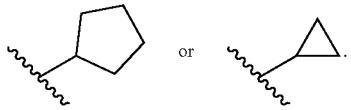

38. The compound of embodiment 36 or a pharmaceutically acceptable salt thereof, wherein $R^3$ is or optionally substituted 5-membered cycloalkyl.

39. The compound of embodiment 38, or a pharmaceutically acceptable salt thereof, wherein $R^3$ is:

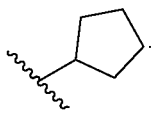 [SMILES: *C1CCCC1]

40. The compound of any one of embodiments 11 to 16, or a pharmaceutically acceptable salt thereof, wherein:

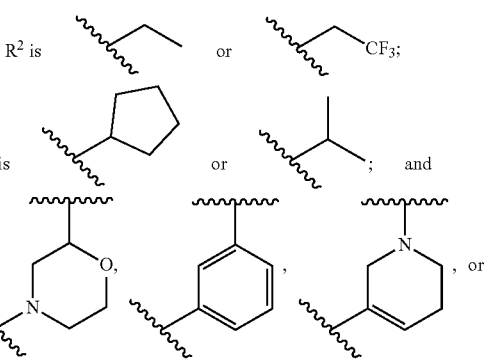

-continued

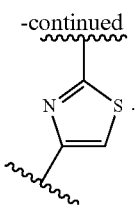

41. The compound of any one of embodiments 11 to 16, wherein:

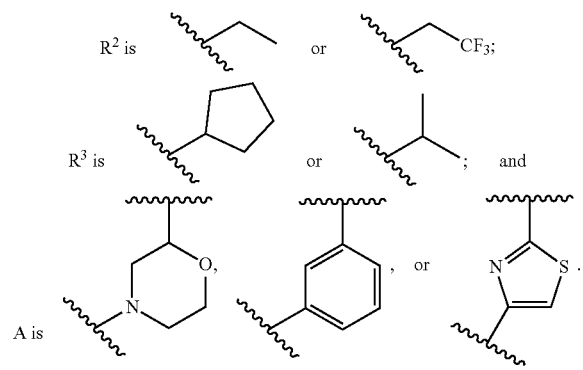

42. The compound of any one of embodiments 1 to 41, or a pharmaceutically acceptable salt thereof, wherein the compound is not a compound of Table 3.

43. A compound, or a pharmaceutically acceptable salt thereof, having the structure of a compound of Table 1 or Table 2.

44. A pharmaceutical composition comprising a compound, or a pharmaceutically acceptable salt thereof, of any one of embodiments 1 to 43 and a pharmaceutically acceptable excipient.

45. A method of treating cancer in a subject in need thereof, the method comprising administering to the subject a therapeutically effective amount of a compound, or a pharmaceutically acceptable salt thereof, of any one of embodiments 1 to 43 or a pharmaceutical composition of embodiment 44.

46. The method of embodiment 45, wherein the cancer is pancreatic cancer, non-small cell lung cancer, colorectal cancer or endometrial cancer.

47. The method of embodiment 45 or 46, wherein the cancer comprises a Ras mutation.

48. The method of embodiment 47, wherein the Ras mutation is K-Ras G12D or K-Ras G13D.

49. A method of treating a Ras protein-related disorder in a subject in need thereof, the method comprising administering to the subject a therapeutically effective amount of a compound, or a pharmaceutically acceptable salt thereof, of any one of embodiments 1 to 43 or a pharmaceutical composition of embodiment 44.

50. A method of inhibiting a Ras protein in a cell, the method comprising contacting the cell with an effective amount of a compound, or a pharmaceutically acceptable salt thereof, of any one of embodiments 1 to 43 or a pharmaceutical composition of embodiment 44.

51. The method of embodiment 49 or 50, wherein the Ras protein is K-Ras G12D or K-Ras G13D.

52. The method of embodiment 50 or 51, wherein the cell is a cancer cell.

53. The method of embodiment 52, wherein the cancer cell is a pancreatic cancer cell, a non-small cell lung cancer cell, a colorectal cancer cell, or an endometrial cell.

54. The method or use of any one of embodiments 45 to 53, wherein the method further comprises administering an additional anticancer therapy.

55. The method of embodiment 54, wherein the additional anticancer therapy is an EGFR inhibitor, a second Ras inhibitor, a SHP2 inhibitor, a SOS1 inhibitor, a Raf inhibitor, a MEK inhibitor, an ERK inhibitor, a PI3K inhibitor, a PTEN inhibitor, an AKT inhibitor, an mTORC1 inhibitor, a BRAF inhibitor, a PD-L1 inhibitor, a PD-1 inhibitor, a CDK4/6 inhibitor, a HER2 inhibitor, or a combination thereof.

56. The method of embodiment 54 or 55, wherein the additional anticancer therapy is a SHP2 inhibitor.

57. A conjugate, or a salt thereof, comprising the structure of Formula III:

M-P1        Formula III wherein $P^1$ is a monovalent organic moiety; and
M has the structure of Formula IV:

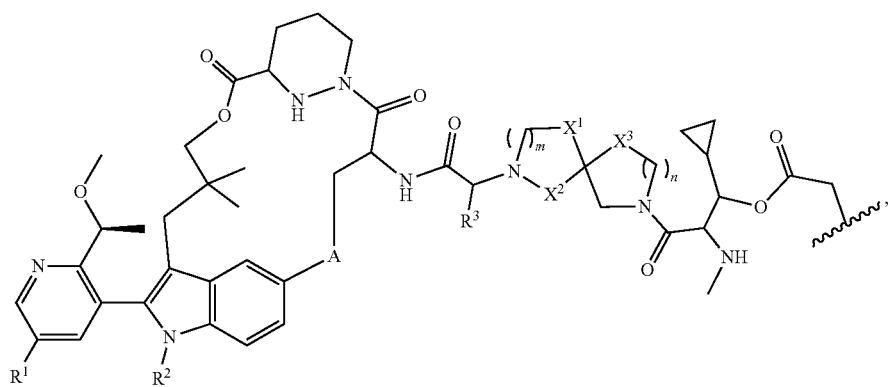

Formula IV wherein A is optionally substituted 3 to 6-membered heterocycloalkylene, optionally substituted 3 to 6-membered cycloalkylene, optionally substituted 6-membered arylene, or optionally substituted 5 to 10-membered heteroarylene;

$X^1$, $X^2$, and $X^3$ are each independently selected from $CH_2$, CHF, $CF_2$, C=O, or O;

m is 1 or 2;
n is 0 or 1;
R¹ is hydrogen, optionally substituted $C_1$-$C_6$ heteroalkyl, or optionally substituted 3 to 10-membered heterocycloalkyl;
R² is optionally substituted $C_1$-$C_6$ alkyl; and
R³ is optionally substituted $C_1$-$C_6$ alkyl, optionally substituted 3 to 6-membered cycloalkyl, optionally substituted $C_1$-$C_6$ heteroalkyl, or optionally substituted heterocycloalkyl,
and wherein each hydrogen of Formula IV is independently, optionally, isotopically enriched for deuterium.

58. The conjugate of embodiment 57, or a salt thereof, wherein A is optionally substituted thiazole-diyl, optionally substituted oxazole-diyl, optionally substituted morpholine-diyl, optionally substituted pyrrolidin-diyl, optionally substituted piperidine-diyl, or optionally substituted phenylene.

59. The conjugate of embodiment 57 or 58, or a salt thereof, wherein R¹ is:

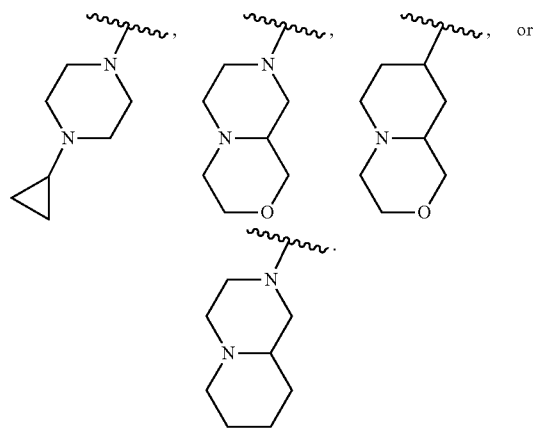

60. The conjugate of any one of embodiments 57 to 59, or a salt thereof, wherein m is 1, n is 1, and each of $X^1$, $X^2$, and $X^3$ is $CH_2$.

61. The conjugate of any one of embodiments 57 to 60, or a salt thereof, wherein the monovalent organic moiety is a protein.

62. The conjugate of embodiment 61, or a salt thereof, wherein the protein is a Ras protein.

63. The conjugate of embodiment 62, or a salt thereof, wherein the Ras protein is K-Ras G12D or K-Ras G13D.

64. The conjugate of any one of embodiments 57 to 63, wherein M is bound to an amino acid residue of the monovalent organic moiety.

EXAMPLES

The invention is further illustrated by the following examples and synthesis examples, which are not to be construed as limiting this invention in scope or spirit to the specific procedures herein described. It is to be understood that the examples are provided to illustrate certain embodiments and that no limitation to the scope of the invention is intended thereby. It is to be further understood that resort may be had to various other embodiments, modifications, and equivalents thereof which may suggest themselves to those skilled in the art without departing from the spirit of the present invention or scope of the appended claims.

Chemical Syntheses
Definitions used in the following examples and elsewhere herein are:

| | |
|---|---|
| $CH_2Cl_2$, DCM | Methylene chloride, Dichloromethane |
| $CH_3CN$, MeCN | Acetonitrile |
| CuI | Copper (I) iodide |
| DIPEA | Diisopropylethyl amine |
| DMF | N,N-Dimethylformamide |
| EtOAc | Ethyl acetate |
| h | hour |
| $H_2O$ | Water |
| HCl | Hydrochloric acid |
| $K_3PO_4$ | Potassium phosphate (tribasic) |
| MeOH | Methanol |
| $Na_2SO_4$ | Sodium sulfate |
| NMP | N-methyl pyrrolidone |
| Pd(dppf)$Cl_2$ | [1,1'-Bis(diphenylphosphino)ferrocene]dichloropalladium(II) |

Synthesis of Intermediates

Intermediate 1: Synthesis of 3-(5-bromo-1-ethyl-2-[2-[(1S)-1-methoxyethyl]pyridin-3-yl]indol-3-yl)-2,2-dimethylpropan-1-ol

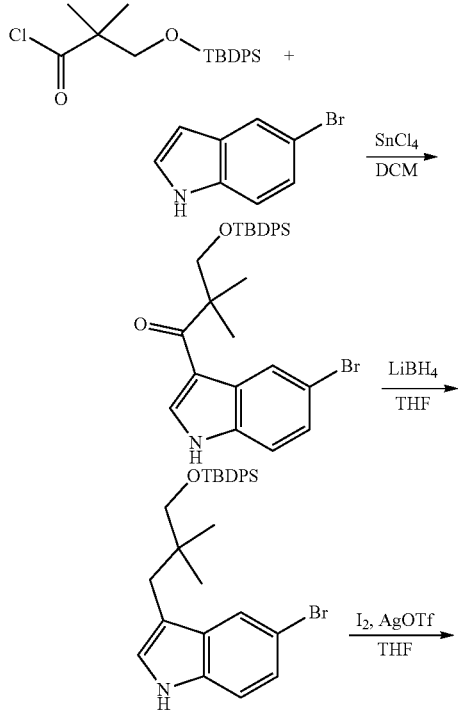

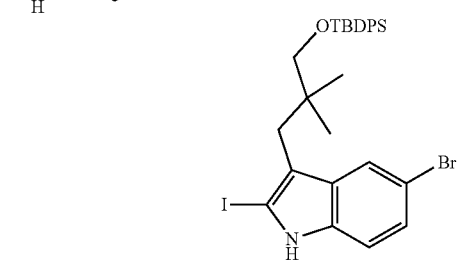

-continued

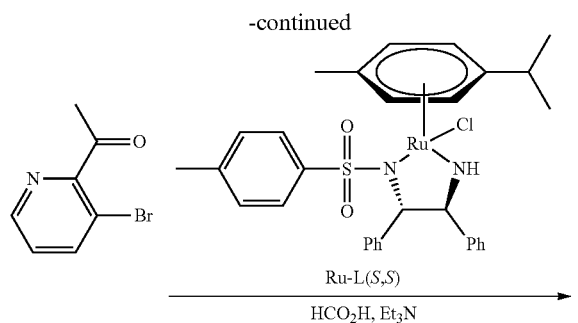

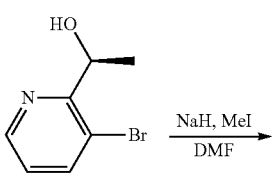

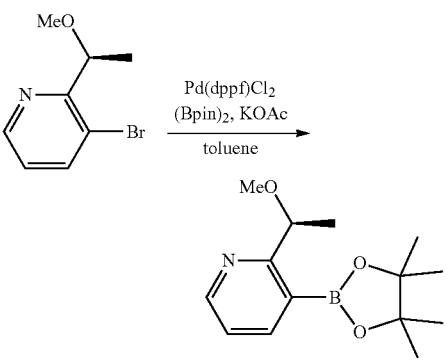

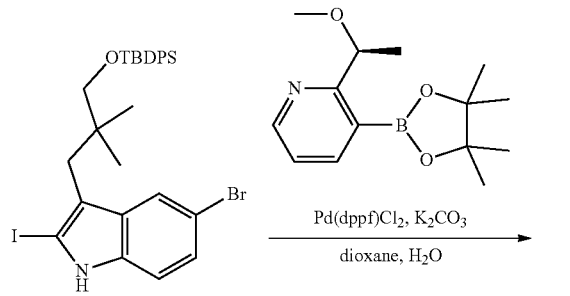

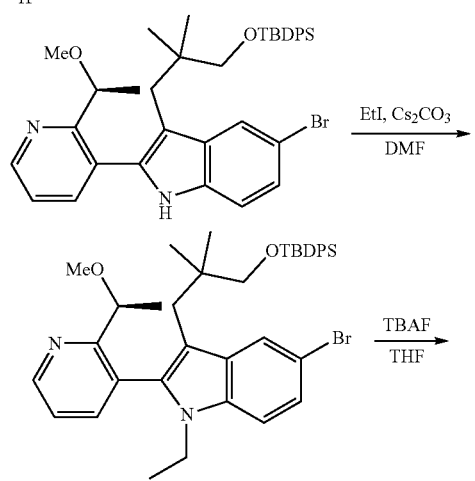

-continued

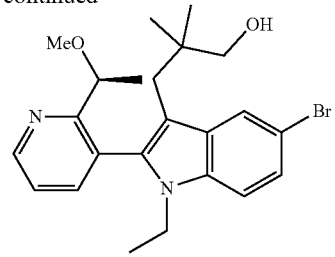

Step 1: Synthesis of 1-(5-bromo-1H-indol-3-yl)-3-((tert-butyldiphenylsilyl)oxy)-2,2-dimethylpropan-1-one To a mixture of 3-((tert-butyldiphenylsilyl)oxy)-2,2-dimethylpropanoyl chloride (65 g, 137 mmol, crude) in DCM (120 mL) at 0° C. under an atmosphere of $N_2$ was added 1 M $SnCl_4$ in DCM (137 mL, 137 mmol) slowly. The mixture was stirred at 0° C. for 30 min, then a solution of 5-bromo-1H-indole (26.8 g, 137 mmol) in DCM (40 mL) was added dropwise. The mixture was stirred at 0° C. for 45 min, then diluted with EtOAc (300 mL), washed with brine (4×100 mL), dried over $Na_2SO_4$ and filtered. The filtrate was concentrated under reduced pressure and the residue was purified by silica gel silica gel column chromatography to the product (55 g, 75% yield). LCMS (ESI) m/z [M+Na] calcd for $C_{29}H_{32}BrNO_2SiNa$ 556.1; found: 556.3.

Step 2: Synthesis of 1-(5-bromo-1H-indol-3-yl)-3-((tert-butyldiphenylsilyl)oxy)-2,2-dimethylpropan-1-one To a mixture of 1-(5-bromo-1H-indol-3-yl)-3-((tert-butyldiphenylsilyl)oxy)-2,2-dimethylpropan-1-one (50 g, 93.6 mmol) in THF (100 mL) at 0° C. under an atmosphere of $N_2$ was added $LiBH_4$ (6.1 g, 281 mmol). The mixture was heated to 60° C. and stirred for 20 h, then MeOH (10 mL) and EtOAc (100 mL) were added and the mixture washed with brine (50 mL), dried over $Na_2SO_4$, filtered and the filtrate concentrated under reduced pressure. The residue was diluted with DCM (50 mL), cooled to 10° C. and diludine (9.5 g, 37.4 mmol) and TsOH•$H_2O$ (890 mg, 4.7 mmol) were added. The mixture was stirred at 10° C. for 2 h, filtered, the filtrate concentrated under reduced pressure and the residue was purified by silica gel column chromatography to give the product (41 g, 84% yield). LCMS (ESI) m/z [M+H] calcd for $C_{29}H_{34}BrNOSi$: 519.2; found: 520.1

Step 3: Synthesis of 5-bromo-3-(3-((tert-butyldiphenylsilyl)oxy)-2,2-dimethylpropyl)-2-iodo-1H-indole To a mixture of 1-(5-bromo-1H-indol-3-yl)-3-((tert-butyldiphenylsilyl)oxy)-2,2-dimethylpropan-1-one (1.5 g, 2.9 mmol) and 12 (731 mg, 2.9 mmol) in THF (15 mL) at room temperature was added AgOTf (888 mg, 3.5 mmol). The mixture was stirred at room temperature for 2 h, then diluted with EtOAc (200 mL) and washed with sat. aq. $Na_2S_2O_3$ (100 mL), dried over anhydrous $Na_2SO_4$ and filtered. The filtrate was concentrated under reduced pressure and the residue was purified by silica gel column chromatography to afford the product (900 mg, 72% yield) as a solid.

Step 4: Synthesis of (1 S)-1-(3-bromopyridin-2-yl)ethanol

To a stirred mixture of $HCO_2H$ (66.3 g, 1.44 mol) in $Et_3N$ (728 g, 7.2 mol) at 0° C. under an atmosphere of Ar was added (4S,5S)-2-chloro-2-methyl-1-(4-methylbenzenesulfonyl)-4,5-diphenyl-1,3-diaza-2-ruthenacyclopentane cymene (3.9 g, 6.0 mmol) portion-wise. The mixture was heated to 40° C. and stirred for 15 min, then cooled to room temperature and 1-(3-bromopyridin-2-yl)ethanone (120 g, 600 mmol) added in portions. The mixture was heated to 40° C. and stirred for an additional 2 h, then the solvent was concentrated under reduced pressure. Brine (2 L) was added to the residue, the mixture was extracted with EtOAc (4×700 mL), dried over anhydrous $Na_2SO_4$ and filtered. The filtrate was concentrated under reduced pressure and the residue was purified by silica gel column chromatography to give the product (100 g, 74% yield) as an oil. LCMS (ESI) m/z [M+H] calcd for $C_7H_8BrNO$: 201.98; found: 201.9.

Step 5: Synthesis of 3-bromo-2-[(1 S)-1-methoxyethyl]pyridine

To a stirred mixture of (1S)-1-(3-bromopyridin-2-yl)ethanol (100 g, 495 mmol) in DMF (1 L) at 0° C. was added NaH, 60% dispersion in oil (14.25 g, 594 mmol) in portions. The mixture was stirred at 0° C. for 1 h. MeI (140.5 g, 990 mmol) was added dropwise at 0° C. and the mixture was warmed to room temperature and stirred for 2 h. The mixture was cooled to 0° C. and sat. aq. $NH_4Cl$ (5 L) was added. The mixture was extracted with EtOAc (3×1.5 L), dried over anhydrous $Na_2SO_4$ and filtered. The filtrate was concentrated under reduced pressure and the residue was purified by silica gel column chromatography to give the product (90 g, 75% yield) as an oil. LCMS (ESI) m/z [M+H] calcd for $C_8H_{10}BrNO$: 215.99; found: 215.9.

Step 6: Synthesis of 2-[(1 S)-1-methoxyethyl]-3-(4,4,5,5-tetramethyl-1,3,2-dioxaborolan-2-yl)pyridine To a stirred mixture of 3-bromo-2-[(1S)-1-methoxyethyl]pyridine (90 g, 417 mmol) in toluene (900 mL) at room temperature under an atmosphere of Ar was added bis(pinacolato)diboron (127 g, 500 mmol) and KOAc (81.8 g, 833 mmol) and $Pd(dppf)Cl_2$ (30.5 g, 41.7 mmol). The mixture was heated to 100° C. and stirred for 3 h. The filtrate was concentrated under reduced pressure and the residue was purified by $Al_2O_3$ column chromatography to give the product (100 g, 63% yield) as a semi-solid. LCMS (ESI) m/z [M+H] calcd for $C_{14}H_{22}BNO_3$: 264.17; found: 264.1.

Step 7: Synthesis of 5-bromo-3-[3-[(tert-butyldiphenylsilyl)oxy]-2,2-dimethylpropyl]-2-[2-[(1 S)-1-methoxyethyl]pyridin-3-yl]-1 H-indole To a stirred mixture of 5-bromo-3-[3-[(tert-butyldiphenylsilyl)oxy]-2,2-dimethylpropyl]-2-iodo-1H-indole (140 g, 217 mmol) and 2-[(1 S)-1-methoxyethyl]-3-(4,4,5,5-tetramethyl-1,3,2-dioxaborolan-2-yl)pyridine (100 g, 380 mmol) in dioxane (1.4 L) at room temperature under an atmosphere of Ar was added $K_2CO_3$ (74.8 g, 541 mmol), $Pd(dppf)Cl_2$ (15.9 g, 21.7 mmol) and $H_2O$ (280 mL) in portions. The mixture was heated to 85° C. and stirred for 4 h, then cold $H_2O$ (5 L) was added and the mixture extracted with EtOAc (3×2 L). The combined organic layers were washed with brine (2×1 L), dried over anhydrous $Na_2SO_4$ and filtered. The filtrate was concentrated under reduced pressure and the residue was purified by silica gel column chromatography to give the product (71 g, 45% yield) as a solid. LCMS (ESI) m/z [M+H] calcd for $C_{37}H_{43}BrN_2O_2Si$: 655.23; found: 655.1.

Step 8: Synthesis of 5-bromo-3-[3-[(tert-butyldiphenylsilyl)oxy]-2,2-dimethylpropyl]-1-ethyl-2-[2-[(1 S)-1-methoxyethyl]pyridin-3-yl]indole To a stirred mixture of 5-bromo-3-[3-[(tert-butyldiphenylsilyl)oxy]-2,2-dimethylpropyl]-2-[2-[(1 S)-1-methoxyethyl]pyridin-3-yl]-1 H-indole (71 g, 108 mmol) in DMF (0.8 L) at 0° C. under an atmosphere of $N_2$ was added $Cs_2CO_3$ (70.6 g, 217 mmol) and EtI (33.8 g, 217 mmol) in portions. The mixture was warmed to room temperature and stirred for 16 h then $H_2O$ (4 L) was added and the mixture extracted with EtOAc (3×1.5 L). The combined organic layers were washed with brine (2×1 L), dried over anhydrous $Na_2SO_4$ and filtered. The filtrate was concentrated under reduced pressure and the residue was purified by silica gel column chromatography to give the product (66 g, 80% yield) as an oil. LCMS (ESI) m/z [M+H] calcd for $C_{39}H_{47}BrN_2O_2Si$: 683.26; found: 683.3.

Step 9: Synthesis of 3-(5-bromo-1-ethyl-2-[2-[(1 S)-1-methoxyethyl]pyridin-3-yl]indol-3-yl)-2,2-dimethylpropan-1-ol To a stirred mixture of TBAF (172.6 g, 660 mmol) in THF (660 mL) at room temperature under an atmosphere of $N_2$ was added 5-bromo-3-[3-[(tert-butyldiphenylsilyl)oxy]-2,2-dimethylpropyl]-1-ethyl-2-[2-[(1 S)-1-methoxyethyl]pyridin-3-yl]indole (66 g, 97 mmol) in portions. The mixture was heated to 50° C. and stirred for 16 h, cooled, diluted with $H_2O$ (5 L) and extracted with EtOAc (3×1.5 L). The combined organic layers were washed with brine (2×1 L), dried over anhydrous $Na_2SO_4$ and filtered. After filtration, the filtrate was concentrated under reduced pressure and the residue was purified by silica gel column chromatography to give the product (30 g, 62% yield) as a solid. LCMS (ESI) m/z [M+H] calcd for $C_{23}H_{29}BrN_2O_2$: 445.14; found: 445.1.

Intermediate 2: Alternative Synthesis through Fisher Indole Route.

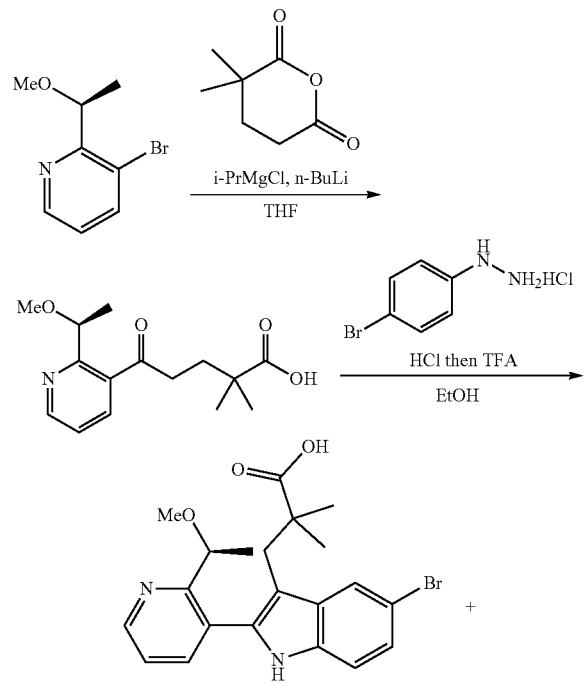

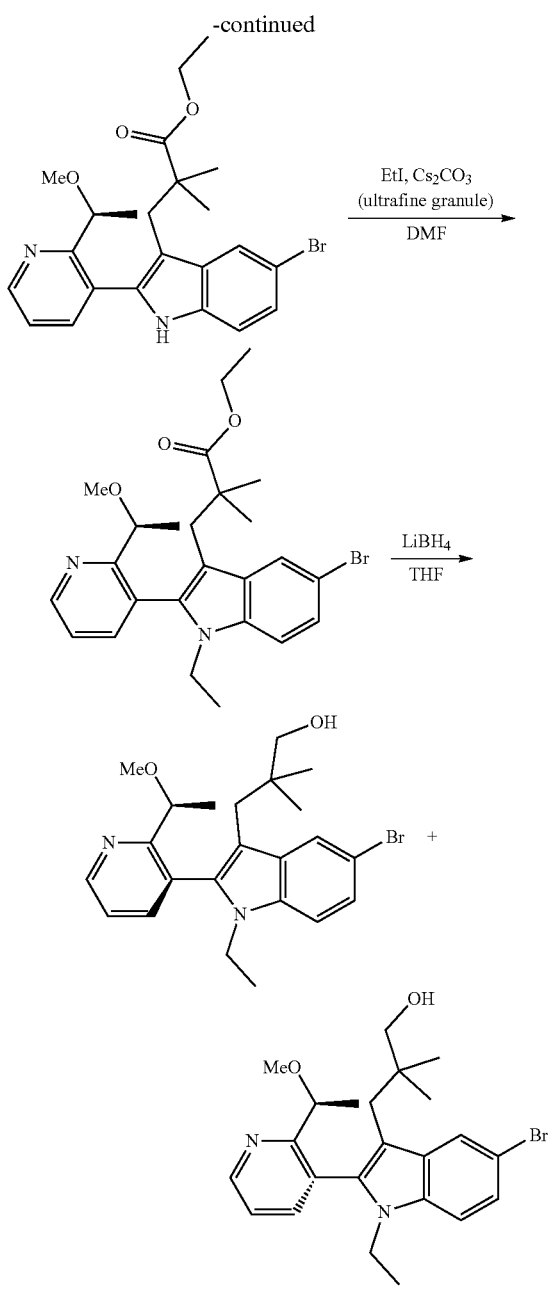

Step 1: Synthesis of 5-[2-[(1 S)-1-methoxyethyl]
pyridin-3-yl]-2,2-dimethyl-5-oxopentanoic acid To a mixture of i-PrMgCl (2M in in THF, 0.5 L) at −10° C. under an atmosphere of N$_2$ was added n-BuLi, 2.5 M in hexane (333 mL, 833 mmol) dropwise over 15 min. The mixture was stirred for 30 min at −10° C. then 3-bromo-2-[(1S)-1-methoxyethyl]pyridine (180 g, 833 mmol) in THF (0.5 L) added dropwise over 30 min at −10° C. The resulting mixture was warmed to −5° C. and stirred for 1 h, then 3,3-dimethyloxane-2,6-dione (118 g, 833 mmol) in THF (1.2 L) was added dropwise over 30 min at −5° C. The mixture was warmed to 0° C. and stirred for 1.5 h, then quenched with the addition of pre-cooled 4M HCl in dioxane (0.6 L) at 0° C. to adjust pH −5. The mixture was diluted with H$_2$O (3 L) at 0° C. and extracted with EtOAc (3×2.5 L). The combined organic layers were dried over anhydrous Na$_2$SO$_4$, filtered, the filtrate was concentrated under reduced pressure and the residue was purified by silica gel column chromatography to give the product (87 g, 34% yield) as a solid. LCMS (ESI) m/z [M+H] calcd for C$_{15}$H$_{21}$NO$_4$: 280.15; found: 280.1.

Step 2: Synthesis of 3-(5-bromo-2-[2-[(1S)-1-methoxyethyl]pyridin-3-yl]-1H-indol-3-yl)-2,2-dimethylpropanoicacid and ethyl (S)-3-(5-bromo-2-(2-(1-methoxyethyl)pyridin-3-yl)-1H-indol-3-yl)-2,2-dimethylpropanoate To a mixture of 5-[2-[(1 S)-1-methoxyethyl]pyridin-3-yl]-2,2-dimethyl-5-oxopentanoic acid (78 g, 279 mmol) in EtOH (0.78 L) at room temperature under an atmosphere of N$_2$ was added (4-bromophenyl)hydrazine HCl salt (68.7 g, 307 mmol) in portions. The mixture was heated to 85° C. and stirred for 2 h, cooled to room temperature, then 4M HCl in dioxane (69.8 mL, 279 mmol) added dropwise. The mixture was heated to 85° C. and stirred for an additional 3 h, then concentrated under reduced pressure and the residue was dissolved in TFA (0.78 L). The mixture was heated to 60° C. and stirred for 1.5 h, concentrated under reduced pressure and the residue adjusted to pH −5 with sat. aq. NaHCO$_3$, then extracted with EtOAc (3×1.5 L). The combined organic layers were dried over anhydrous Na$_2$SO$_4$, filtered, the filtrate concentrated under reduced pressure and the residue was purified by silica gel column chromatography to the product (78 g, crude). LCMS (ESI) m/z [M+H] calcd for C$_{21}$H$_{23}$BrN$_2$O$_3$: 430.1 and C$_{23}$H$_{27}$BrN$_2$O$_3$: 459.12; found: 431.1 (carboxylic acid) and 459.1.

Step 3: Synthesis of ethyl 3-(5-bromo-1-ethyl-2-[2-[(1 S)-1-methoxyethyl]pyridin-3-yl]indol-3-yl)-2,2-dimethylpropanoate To a mixture of 3-(5-bromo-2-[2-[(1 S)-1-methoxyethyl]pyridin-3-yl]-1 H-indol-3-yl)-2,2-dimethylpropanoic acid and ethyl (S)-3-(5-bromo-2-(2-(1-methoxyethyl)pyridin-3-yl)-1H-indol-3-yl)-2,2-dimethylpropanoate (198 g, 459 mmol) in DMF (1.8 L) at 0° C. under an atmosphere of N$_2$ was added Cs$_2$CO$_3$ (449 g, 1.38 mol) in portions. EtI (215 g, 1.38 mmol) in DMF (200 mL) was then added dropwise at 0° C. The mixture was warmed to room temperature and stirred for 4 h then diluted with brine (5 L) and extracted with EtOAc (3×2.5 L). The combined organic layers were washed with brine (2×1.5 L), dried over anhydrous Na$_2$SO$_4$ and filtered. The filtrate was concentrated under reduced pressure and the residue was purified by silica gel column chromatography to give the product (160 g, 57% yield) as a solid. LCMS (ESI) m/z [M+H] calcd for C$_{25}$H$_{31}$BrN$_2$O$_3$: 487.17; found: 487.2.

Step 4: Synthesis of 3-(5-bromo-1-ethyl-2-(2-((S)-1-methoxyethyl)pyridin-3-yl)-1H-indol-3-yl)-2,2-dimethylpropan-1-ol To a mixture of ethyl 3-(5-bromo-1-ethyl-2-[2-[(1 S)-1-methoxyethyl]pyridin-3-yl]indol-3-yl)-2,2-dimethylpropanoate (160 g, 328 mmol) in THF (1.6 L) at 0° C. under an atmosphere of N$_2$ was added LiBH$_4$ (28.6 g, 1.3 mol). The mixture was heated to 60° C. for 16 h, cooled, and quenched with pre-cooled (0° C.) sat. aq. NH$_4$Cl (5 L). The mixture was extracted with EtOAc (3×2 L) and the combined organic layers were washed with brine (2×1 L), dried over anhydrous Na$_2$SO$_4$ and filtered. The filtrate was concentrated under reduced pressure and the residue was purified by silica gel column chromatography to give to two atropisomers of 3-(5-bromo-1-ethyl-2-(2-((S)-1-methoxyethyl)pyridin-3-yl)-1H-indol-3-yl)-2,2-dimethylpropan-1-ol (as single atropisomers) (60 g, 38% yield) and (40 g, 26% yield) both as solids. LCMS (ESI) m/z [M+H] calcd for $C_{23}H_{29}BrN_2O_2$: 445.14; found: 445.2.

Intermediate 3: Synthesis of ($6^3$S,4S)-4-amino-$1^1$-ethyl-$1^2$-(2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-5,7-dione

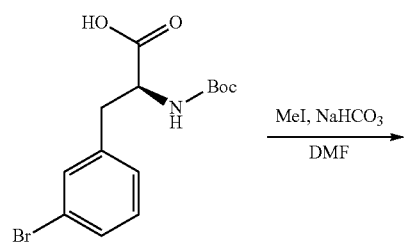

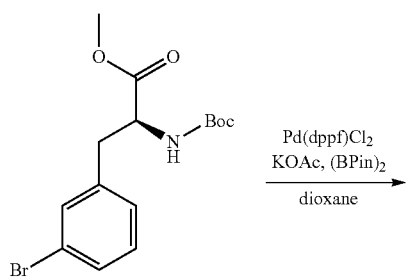

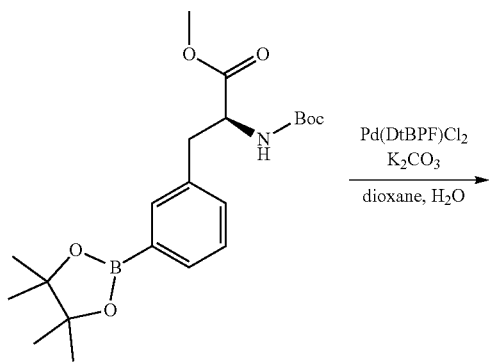

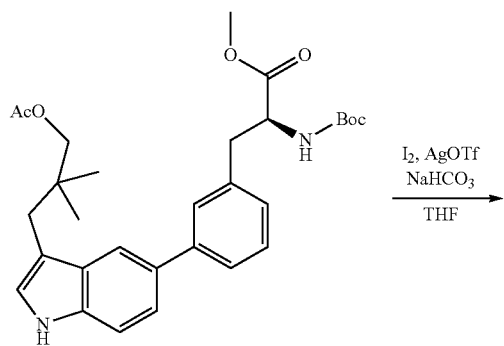

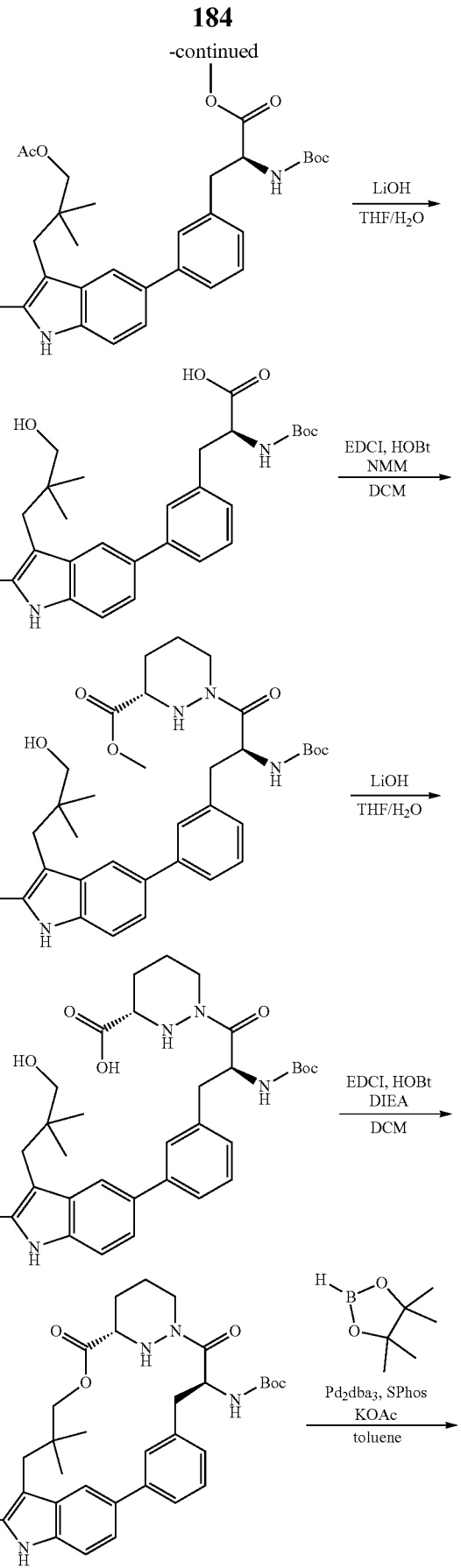

-continued

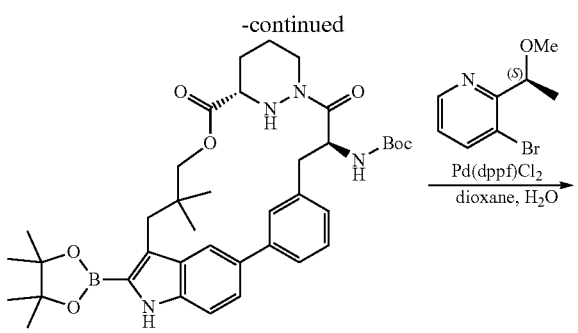

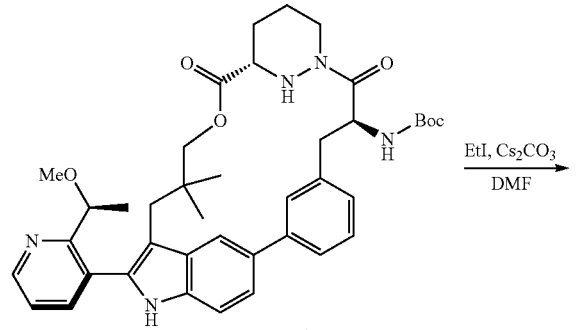

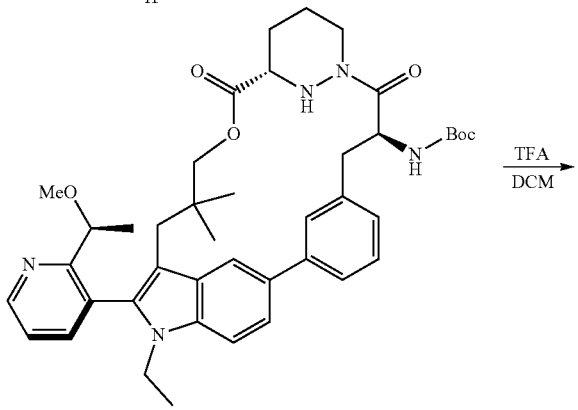

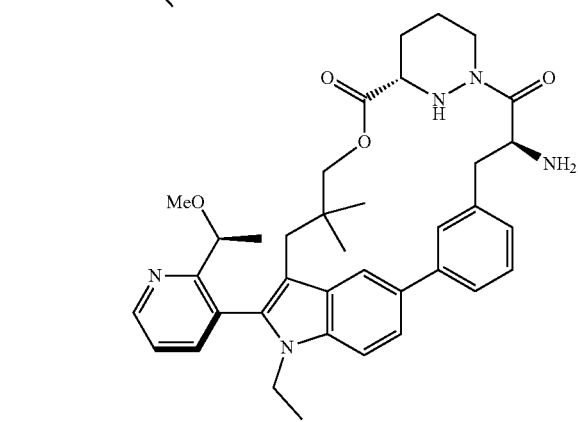

Step 1: Synthesis of methyl (S)-3-(3-bromophenyl)-2-((tert-butoxycarbonyl)amino)propanoate To a solution of (2S)-3-(3-bromophenyl)-2-[(tert-butoxycarbonyl)amino]propanoic acid (100 g, 290 mmol) in DMF (1 L) at room temperature was added NaHCO$_3$ (48.8 g, 581.1 mmol) and MeI (61.9 g, 435.8 mmol). The reaction mixture was stirred for 16 h and was then quenched with H$_2$O (1 L) and extracted with EtOAc (3×1 L). The combined organic layers were washed with brine (3×500 mL), dried over Na$_2$SO$_4$, filtered, and concentrated under reduced pressure. The residue was purified by silica gel column chromatography (13% EtOAc/pet. ether) to give the final product (109 g, crude). LCMS (ESI) m/z [M+Na] calcd for C$_{15}$H$_{20}$BrNO$_4$ 380.05; found: 380.0.

Step 2: Synthesis of methyl (S)-2-((tert-butoxycarbonyl)amino)-3-(3-(4,4,5,5-tetramethyl-1,3,2-dioxaborolan-2-yl)phenyl)propanoate To a stirred solution of methyl (2S)-3-(3-bromophenyl)-2-[(tert-butoxycarbonyl)amino]propanoate (108 g, 301.5 mmol) and bis(pinacolato)diboron (99.53 g, 391.93 mmol) in dioxane (3.2 L) was added KOAc (73.97 g, 753.70 mmol) and Pd(dppf)Cl$_2$ (22.06 g, 30.15 mmol). The reaction mixture was heated to 90° C. for 3 h and was then cooled to room temperature and extracted with EtOAc (2×3 L). The combined organic layers were washed with brine (3×800 mL), dried over Na$_2$SO$_4$, filtered, and concentrated under reduced pressure. The residue was purified by silica gel column chromatography (5% EtOAc/pet. ether) to afford the product (96 g, 78.6% yield). LCMS (ESI) m/z [M+Na] calcd for C$_{21}$H$_{32}$BNO$_6$ 428.22; found: 428.1.

Step 3: Synthesis of methyl (S)-3-(3-(3-(3-acetoxy-2,2-dimethylpropyl)-1H-indol-5-yl)phenyl)-2-((tert-butoxycarbonyl)amino)propanoate To a mixture of methyl (2S)-2-[(tert-butoxycarbonyl)amino]-3-[3-(4,4,5,5-tetramethyl-1,3,2-dioxaborolan-2-yl)phenyl]propanoate (94 g, 231.9 mmol) and 3-(5-bromo-1H-indol-3-yl)-2,2-dimethylpropyl acetate (75.19 g, 231.93 mmol) in dioxane (1.5 L) and H$_2$O (300 mL) was added K$_2$CO$_3$ (64.11 g, 463.85 mmol) and Pd(DtBPF)Cl$_2$ (15.12 g, 23.19 mmol). The reaction mixture was heated to 70° C. and stirred for 4 h. The reaction mixture was extracted with EtOAc (2×2 L) and the combined organic layers were washed with brine (3×600 mL), dried over Na$_2$SO$_4$, filtered, and concentrated under reduced pressure. The residue was purified by silica gel column chromatography (20% EtOAc/pet. ether) to give the product (130 g, crude). LCMS (ESI) m/z [M+H] calcd for C$_{30}$H$_{38}$N$_2$O$_6$ 523.28; found: 523.1.

Step 4: Synthesis of methyl (S)-3-(3-(3-(3-acetoxy-2,2-dimethylpropyl)-2-iodo-1H-indol-5-yl)phenyl)-2-((tert-butoxycarbonyl)amino)propanoate To a solution of methyl (2S)-3-(3-[3-[3-(acetyloxy)-2,2-dimethylpropyl]-1H-indol-5-yl]phenyl)-2-[(tert-butoxycarbonyl)amino]propanoate (95.0 g, 181.8 mmol) and iodine (36.91 g, 145.41 mmol) in THF (1 L) at −10° C. was added AgOTf (70.0 g, 272.7 mmol) and NaHCO$_3$ (22.9 g, 272.65 mmol). The reaction mixture was stirred for 30 min and was then quenched by the addition of sat. aq. Na$_2$S$_2$O$_3$ (100 mL) at 0 ° C. The resulting mixture was extracted with EtOAc (3×1 L) and the combined organic layers were washed with brine (3×500 mL), dried over Na$_2$SO$_4$, filtered, and concentrated under reduced pressure.

The residue was purified by silica gel column chromatography (50% EtOAc/pet. ether) to afford the desired product (49.3 g, 41.8% yield). LCMS (ESI) m/z [M+H] calcd for C$_{30}$H$_{37}$IN$_2$O$_6$: 649.18; found: 649.1.

Step 5: Synthesis of (S)-2-((tert-butoxycarbonyl)amino)-3-(3-(3-(3-hydroxy-2,2-dimethylpropyl)-2-iodo-1H-indol-5-yl)phenyl)propanoic acid To a solution of methyl (2S)-3-(3-[3-[3-(acetyloxy)-2,2-dimethylpropyl]-2-iodo-1H-indol-5-yl]phenyl)-2-[(tert-butoxycarbonyl)amino]propanoate (60 g, 92.5 mmol) in THF (600 mL) was added a solution of LiOH·H$_2$O (19.41 g, 462.5 mmol) in H$_2$O (460 mL). The resulting solution was stirred overnight and then the pH was adjusted to 6 with HCl (1 M). The resulting solution was extracted with EtOAc (2×500 mL) and the combined organic layers was washed with brine (2×500 mL), dried over Na$_2$SO$_4$, filtered, and concentrated under reduced pressure to give the product (45 g, 82.1% yield). LCMS (ESI) m/z [M+Na] calcd for C$_{27}$H$_{331}$N$_2$O$_6$ 615.13; found: 615.1.

Step 6: Synthesis of methyl (S)-1-((S)-2-((tert-butoxycarbonyl)amino)-3-(3-(3-(3-hydroxy-2,2-dimethylpropyl)-2-iodo-1H-indol-5-yl)phenyl)propanoyl)hexahydropyridazine-3-carboxylate To a solution of (2S)-2-[(tert-butoxycarbonyl)amino]-3-[3-[3-(3-hydroxy-2,2-dimethylpropyl)-2-iodo-1H-indol-5-yl]phenyl]propanoic acid (30 g, 50.6 mmol) and methyl (3S)-1,2-diazinane-3-carboxylate (10.9 g, 75.9 mmol) in DCM (400 mL) was added NMM (40.97 g, 405.08 mmol), HOBt (2.05 g, 15.19 mmol), and EDCI (19.41 g, 101.27 mmol). The reaction mixture was stirred overnight and then the mixture was washed with sat. aq. NH$_4$Cl (2×200 mL) and brine (2×200 mL), and the mixture was dried over Na$_2$SO$_4$, filtered, and concentrated under reduced pressure to give the product (14 g, 38.5% yield). LCMS (ESI) m/z [M+H] calcd for C$_{33}$H$_{431}$N$_4$O$_6$ 718.23; found: 719.4.

Step 7: Synthesis of (S)-1-((S)-2-((tert-butoxycarbonyl)amino)-3-(3-(3-(3-hydroxy-2,2-dimethylpropyl)-2-iodo-1H-indol-5-yl)phenyl)propanoyl)hexahydropyridazine-3-carboxylic acid To a solution of methyl (S)-1-((S)-2-((tert-butoxycarbonyl)amino)-3-(3-(3-(3-hydroxy-2,2-dimethylpropyl)-2-iodo-1H-indol-5-yl)phenyl)propanoyl)hexahydropyridazine-3-carboxylate (92 g, 128.0 mmol) in THF (920 mL) at 0° C. was added a solution of LiOH·H$_2$O (26.86 g, 640.10 mmol) in H$_2$O (640 mL). The reaction mixture was stirred for 2 h and was then concentrated under reduced pressure to give the product (90 g, crude). LCMS (ESI) m/z [M+H] calcd for C$_{32}$H$_{41}$IN$_4$O$_6$ 705.22; found: 705.1.

Step 8: Synthesis of tert-butyl ((6$^3$S,4S)-1$^2$-iodo-10,10-dimethyl-5,7-dioxo-6$^1$,6$^2$,6$^3$,6$^4$,6$^5$,6$^6$-hexahydro-1$^1$H-8-oxa-1 (5,3)-indola-6(1,3)-pyridazina-2(1,3)-benzenacycloundecaphane-4-yl)carbamate To a solution of (3S)-1-[(2S)-2-[(tert-butoxycarbonyl) amino]-3-[3-[3-(3-hydroxy-2,2-dimethylpropyl)-2-iodo-1H-indol-5-yl]phenyl]propanoyl]-1,2-diazinane-3-carboxylic acid (90 g, 127.73 mmol) in DCM (10 L) at 0° C. was added HOBt (34.52 g, 255.46 mmol), DIPEA (330.17 g, 2554.62 mmol) and EDCI (367.29 g, 1915.96 mmol). The reaction mixture was stirred for 16 h and was then concentrated under reduced pressure. The mixture was extracted with DCM (2×2 L) and the combined organic layers were washed with brine (3×1 L), dried over Na$_2$SO$_4$, filtered, and concentrated under reduced pressure. The residue was purified by silica gel column chromatography (50% EtOAc/pet. ether) to give the product (70 g, 79.8% yield). LCMS (ESI) m/z [M+H] calcd for C$_{32}$H$_{39}$IN$_4$O$_5$ 687.21; found: 687.1.

Step 9: Synthesis of tert-butyl ((6$^3$S,4S)-10,10-dimethyl-5,7-dioxo-12-(4,4,5,5-tetramethyl-1,3,2-dioxaborolan-2-yl)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)carbamate A 1 L round-bottom flask was charged with tert-butyl ((6$^3$S,4S)-1$^2$-iodo-10,10-dimethyl-5,7-dioxo-6$^1$,6$^2$,6$^3$,6$^4$,6$^5$, 6$^6$-hexahydro-1$^1$H-8-oxa-1(5,3)-indola-6(1,3)-pyridazina-2 (1,3)-benzenacycloundecaphane-4-yl)carbamate (22.0 g, 32.042 mmol), toluene (300.0 mL), Pd$_2$(dba)$_3$ (3.52 g, 3.845 mmol), S-Phos (3.95 g, 9.613 mmol), and KOAc (9.43 g, 96.127 mmol) at room temperature. To the mixture was added 4,4,5,5-tetramethyl-1,3,2-dioxaborolane (26.66 g, 208.275 mmol) dropwise with stirring at room temperature. The resulting solution was stirred for 3 h at 60° C. The resulting mixture was filtered, and the filter cake was washed with EtOAc. The filtrate was concentrated under reduced pressure and the remaining residue was purified by silica gel column chromatography to afford the product (22 g, 90% yield) as a solid. LCMS (ESI) m/z [M+H] calcd for C$_{38}$H$_{51}$BN$_4$O$_7$ 687.3; found: 687.4.

Step 10: Synthesis of tert-butyl ((6$^3$S,4S)-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)carbamate A mixture of tert-butyl ((6$^3$S,4S)-10,10-dimethyl-5,7-dioxo-1$^2$-(4,4,5,5-tetramethyl-1,3,2-dioxaborolan-2-yl)-6$^1$,6$^2$, 6$^3$,6$^4$,6$^5$,6$^6$-hexahydro-1$^1$H-8-oxa-1(5,3)-indola-6(1,3)-pyridazina-2(1,3)-benzenacycloundecaphane-4-yl) carbamate (2.0 g, 2.8 mmol), 3-bromo-2-[(1 S)-1-methoxyethyl]pyridine (0.60 g, 2.8 mmol), Pd(dppf)Cl$_2$ (0.39 g, 0.5 mmol), and K$_3$PO$_4$ (1.2 g, 6.0 mmol) in dioxane (50 mL) and H$_2$O (10 mL) under an atmosphere of N$_2$ was heated to 70° C. and stirred for 2 h. The mixture was diluted with H$_2$O (50 mL) and extracted with EtOAc (3×50 mL). The combined organic layers were washed with brine (3×50 mL), dried over anhydrous Na$_2$SO$_4$, and filtered. The filtrate was concentrated under reduced pressure and the residue was purified by silica gel column chromatography to afford the product (1.5 g, 74% yield) as a solid. LCMS (ESI) m/z [M+H] calcd for C$_{40}$H$_{49}$N$_5$O$_6$ 695.4; found: 696.5.

Step 11: Synthesis of tert-butyl ((6$^3$S,4S)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)carbamate To a solution of tert-butyl ((6$^3$S,4S)-1$^2$-(2-((S)-1-methoxyethyl) pyridin-3-yl)-10,10-dimethyl-5,7-dioxo-6$^1$, 6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl) carbamate (20 g, 28.7 mmol) and Cs$_2$CO$_3$ (18.7 g, 57.5 mmol) in DMF (150 mL) at 0° C. was added a solution of EtI (13.45 g, 86.22 mmol) in DMF (50 mL). The resulting mixture was stirred overnight at 35° C. and then diluted with H$_2$O (500 mL). The mixture was extracted with EtOAc (2×300 mL) and the combined organic layers were washed with brine (3×100 mL), dried over Na$_2$SO$_4$, filtered, and concentrated under reduced pressure. The residue was purified by silica gel column chromatography to afford the product (4.23 g, 18.8% yield) and the atropisomer (5.78 g, 25.7% yield) as solids. LCMS (ESI) m/z [M+H] calcd for C$_{42}$H$_{53}$N$_5$O$_6$ 724.4; found: 724.6.

Step 12: Synthesis of (6$^3$S,4S)-4-amino-1$^1$-ethyl-1$^2$-(2-((S)-1-methoxyethyl)pyridin-3-yl)-10,10-dimethyl-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-5,7-dione A mixture of tert-butyl ((6$^3$S,4S)-1$^1$-ethyl-1$^2$-(2-((S)-1-methoxyethyl)pyridin-3-yl)-10,10-dimethyl-5,7-dioxo-6$^1$, $6^2,6^3,6^4,6^5,6^6$-hexahydro-$1^1$H-8-oxa-1(5,3)-indola-6(1,3)-pyridazina-2(1,3)-benzenacycloundecaphane-4-yl) carbamate (1.3 g, 1.7 mmol) in TFA (10 mL) and DCM (20 mL) was stirred at 0° C. for 2 h. The mixture was concentrated under reduced pressure to afford the product (1.30 g, crude) as a solid. LCMS (ESI) m/z [M+H] calcd for $C_{37}H_{45}N_5O_4$ 623.3; found: 624.4.

Intermediate 4: Synthesis of tert-butyl (($6^3$S,4S,Z)-$1^1$-ethyl-$1^2$-(2-((S)-1-methoxyethyl)pyridin-3-yl)-10,10-dimethyl-5,7-dioxo-$6^1,6^2,6^3,6^4,6^5,6^6$-hexahydro-$1^1$H-8-oxa-2(4,2)-thiazola-1(5,3)-indola-6(1,3)-pyridazinacycloundecaphane-4-yl)carbamate

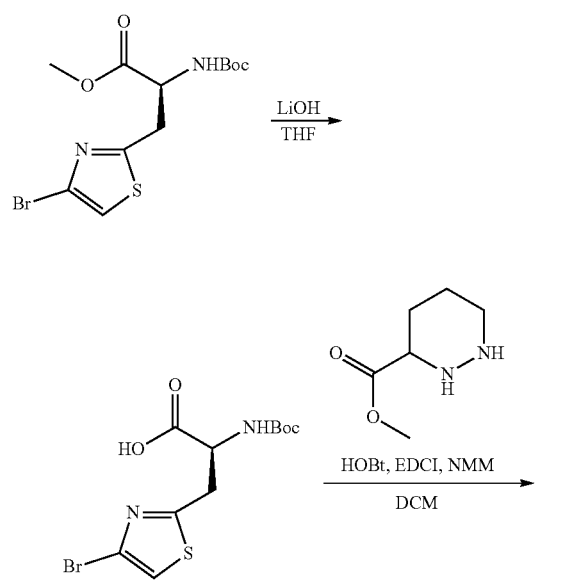

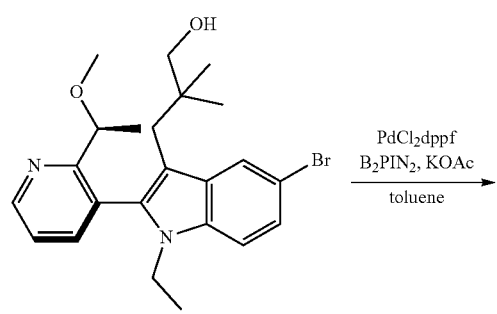

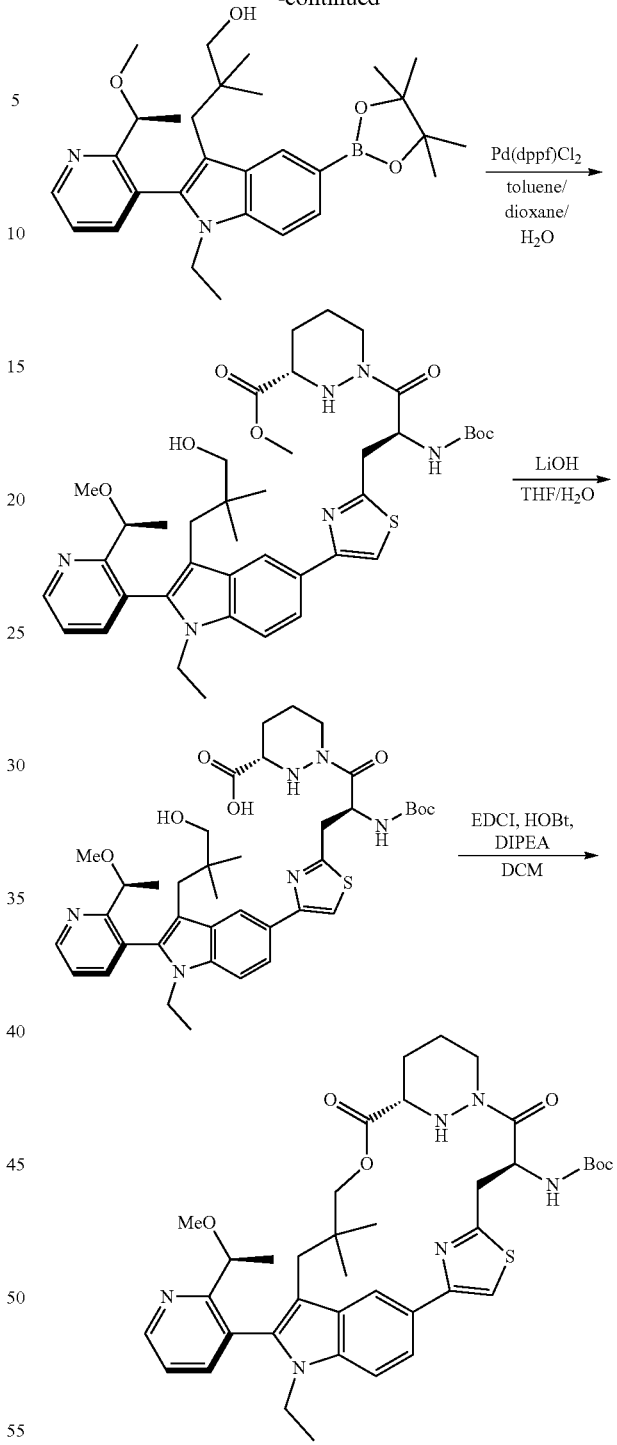

Step 1: Synthesis of (S)-3-(4-bromothiazol-2-yl)-2-((tert-butoxycarbonyl)amino)propanoic acid To a solution of methyl (2S)-3-(4-bromo-1,3-thiazol-2-yl)-2-[(tert-butoxycarbonyl)amino]propanoate (110 g, 301.2 mmol) in THF (500 mL) and H$_2$O (200 mL) at room temperature was added LiOH (21.64 g, 903.6 mmol). The resulting solution was stirred for 1 h and then concentrated under reduced pressure. The resulting residue was adjusted to pH 6 with 1 M HCl and then extracted with DCM (3×500 mL). The combined organic layers were, dried over $Na_2SO_4$, filtered, and concentrated under reduced pressure to afford the desired product (108 g, crude). LCMS (ESI) m/z [M+H] calcd for $C_{11}H_{15}BrN_2O_4S$: 351.00; found: 351.0.

Step 2: Synthesis of methyl (S)-1-((S)-3-(4-bromothiazol-2-yl)-2-((tert-butoxycarbonyl)amino)propanoyl)hexahydropyridazine-3-carboxylate To a solution of (S)-3-(4-bromothiazol-2-yl)-2-((tert-butoxycarbonyl)amino)propanoic acid (70 g, 199.3 mmol) in DCM (500 mL) at 0° C. was added methyl (3S)-1,2-diazinane-3-carboxylate bis(trifluoroacetic acid) salt (111.28 g, 298.96 mmol), NMM (219.12 mL. 1993.0 mmol), EDCI (76.41 g, 398.6 mmol) and HOBt (5.39 g, 39.89 mmol). The resulting solution was warmed to room temperature and stirred for 1 h. The reaction was then quenched with $H_2O$ (500 mL) and was extracted with EtOAc (3×500 mL). The combined organic layers were dried over $Na_2SO_4$, filtered, and concentrated under reduced pressured. The residue was purified by silica gel column chromatography (0→50% EtOAc/pet. ether) to afford the desired product (88.1 g, 93% yield). LCMS (ESI) m/z [M+H] calcd for $C_{17}H_{25}BrN_4O_5S$: 477.08; found: 477.1.

Step 3: Synthesis of (S)-3-(1-ethyl-2-(2-(1-methoxyethyl)pyridin-3-yl)-5-(4,4,5,5-tetramethyl-1,3,2-dioxaborolan-2-yl)-1H-indol-3-yl)-2,2-dimethylpropan-1-ol To a solution of 3-(5-bromo-1-ethyl-2-(2-((S)-1-methoxyethyl)pyridin-3-yl)-1H-indol-3-yl)-2,2-dimethylpropan-1-ol (60 g, 134.7 mmol) in toluene (500 mL) at room temperature was added bis(pinacolato)diboron (51.31 g, 202.1 mmol), Pd(dppf)Cl$_2$ (9.86 g, 13.48 mmol) and KOAc (26.44 g, 269.4 mmol). Then reaction mixture was then heated to 90° C. and stirred for 2 h. The reaction solution was then cooled to room temperature and concentrated under reduced pressure. Purification by silica gel column chromatography (0→50% EtOAc/pet. ether) afforded the desired product (60.6 g, 94% yield). LCMS (ESI) m/z [M+H] calcd for $C_{29}H_{41}BN_2O_4$: 493.32; found: 493.3.

Step 4: Synthesis of methyl (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-indol-5-yl)thiazol-2-yl)propanoyl)hexahydropyridazine-3-carboxylate To a solution of (S)-3-(1-ethyl-2-(2-(1-methoxyethyl)pyridin-3-yl)-5-(4,4,5,5-tetramethyl-1,3,2-dioxaborolan-2-yl)-1H-indol-3-yl)-2,2-dimethylpropan-1-ol (30 g, 60.9 mmol) in toluene (600 mL), dioxane (200 mL), and $H_2O$ (200 mL) at room temperature was added methyl (S)-1-((S)-3-(4-bromothiazol-2-yl)-2-((tert-butoxycarbonyl)amino)propanoyl)hexahydropyridazine-3-carboxylate (43.62 g, 91.4 mmol), $K_3PO_4$ (32.23 g, 152.3 mmol) and Pd(dppf)Cl$_2$ (8.91 g, 12.18 mmol). The resulting solution was heated to 70° C. and stirred overnight. The reaction mixture was then cooled to room temperature and was quenched with $H_2O$ (200 mL). The resulting mixture was extracted with EtOAc (3×1000 mL) and the combined organic layers were dried over $Na_2SO_4$, filtered, and concentrated under reduced pressure. The residue was purified by silica gel column chromatography (0→90% EtOAc/pet. ether) to afford the desired product (39.7 g, 85% yield). LCMS (ESI) m/z [M+H] calcd for $C_{40}H_{54}N_6O_7S$: 763.39; found: 763.3.

Step 5: Synthesis of (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-indol-5-yl)thiazol-2-yl)propanoyl)hexahydropyridazine-3-carboxylic acid To a solution of methyl (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-indol-5-yl)thiazol-2-yl)propanoyl)hexahydropyridazine-3-carboxylate (39.7 g, 52.0 mmol) in THF (400 mL) and $H_2O$ (100 mL) at room temperature was added LiOH·$H_2O$ (3.74 g, 156.2 mmol). The resulting mixture was stirred for 1.5 h and was then concentrated under reduced pressure. The residue was acidified to pH 6 with 1 M HCl and extracted with DCM (3×1000 mL). The combined organic layers were dried over $Na_2SO_4$, filtered, and concentrated under reduced pressure to afford the desired product (37.9 g, crude). LCMS (ESI) m/z [M+H] calcd for $C_{39}H_{52}N_6O_7S$: 749.37; found: 749.4.

Step 6: Synthesis of tert-butyl ((6$^3$S,4S,Z)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-11H-8-oxa-2(4,2)-thiazola-1(5,3)-indola-6(1,3)-pyridazinacycloundecaphane-4-yl)carbamate To a solution of (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-indol-5-yl)thiazol-2-yl)propanoyl)hexahydropyridazine-3-carboxylic acid (37.9 g, 50.6 mmol), HOBt (34.19 g, 253.0 mmol) and DIPEA (264.4 mL, 1518 mmol) in DCM (4 L) at 0° C. was added EDCI (271.63 g, 1416.9 mmol). The resulting mixture was warmed to room temperature and stirred overnight. The reaction mixture was then quenched with $H_2O$ and washed with 1 M HCl (4×1 L). The organic layer was separated and concentrated under reduced pressure. The residue was purified by silica gel column chromatography (0→70% EtOAc/pet. ether) to afford the desired product (30 g, 81% yield). LCMS (ESI) m/z [M+H] calcd for $C_{39}H_{50}N_6O_6S$: 731.36; found: 731.3.

Intermediate 5: Synthesis of (6$^3$S)-4-amino-1$^1$-ethyl-1$^2$-(2-((S)-1-methoxyethyl)pyridin-3-yl)-10,10-dimethyl-2$^1$,2$^2$,2$^3$,2$^6$,6$^1$,6$^2$,6$^3$,6$^4$,6$^5$,6$^6$-decahydro-1$^1$H-8-oxa-1(5,3)-indola-6(1,3)-pyridazina-2(5,1)-pyridinacycloundecaphane-5,7-dione

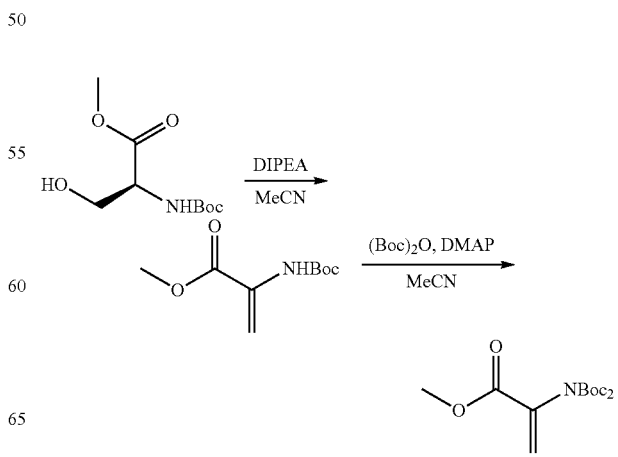

193 194
-continued -continued

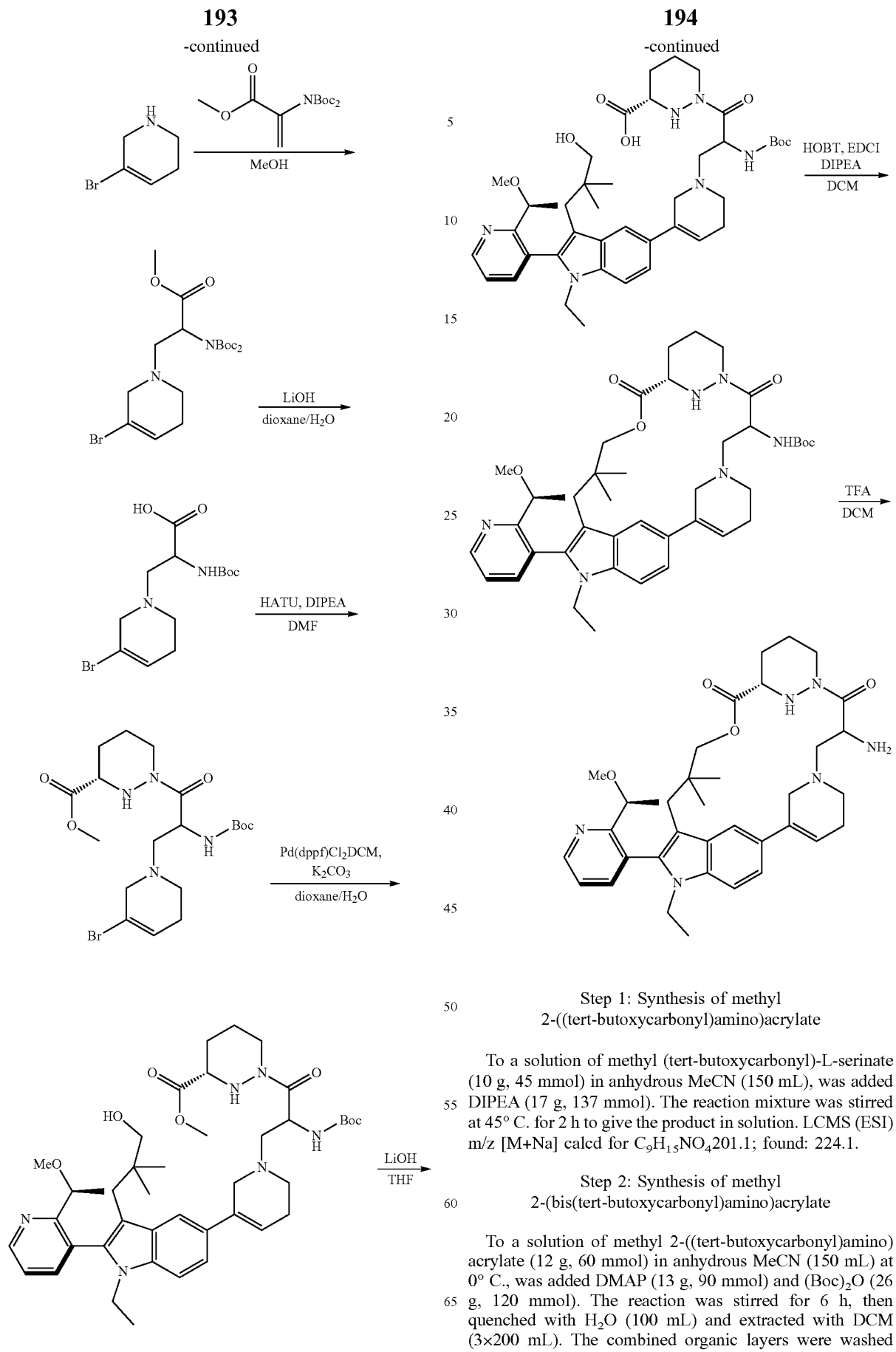

Step 1: Synthesis of methyl 2-((tert-butoxycarbonyl)amino)acrylate

To a solution of methyl (tert-butoxycarbonyl)-L-serinate (10 g, 45 mmol) in anhydrous MeCN (150 mL), was added DIPEA (17 g, 137 mmol). The reaction mixture was stirred at 45° C. for 2 h to give the product in solution. LCMS (ESI) m/z [M+Na] calcd for $C_9H_{15}NO_4$ 201.1; found: 224.1.

Step 2: Synthesis of methyl 2-(bis(tert-butoxycarbonyl)amino)acrylate

To a solution of methyl 2-((tert-butoxycarbonyl)amino) acrylate (12 g, 60 mmol) in anhydrous MeCN (150 mL) at 0° C., was added DMAP (13 g, 90 mmol) and $(Boc)_2O$ (26 g, 120 mmol). The reaction was stirred for 6 h, then quenched with $H_2O$ (100 mL) and extracted with DCM (3×200 mL). The combined organic layers were washed with brine (150 mL), dried over anhydrous $Na_2SO_4$, filtered and concentrated under reduced pressure. The residue was purified by silica gel column chromatography to give the product (12.5 g, 65% yield) as solid. LCMS (ESI) m/z [M+Na] calcd for $C_{14}H_{23}NO_6$ 301.2; found: 324.1.

Step 3: Synthesis of methyl 2-(bis(tert-butoxycarbonyl)amino)-3-(5-bromo-3,6-dihydropyridin-1(2H)-yl)propanoate To a mixture of 5-bromo-1,2,3,6-tetrahydropyridine (8.0 g, 49 mmol) in MeOH (120 mL) under an atmosphere ofArwas added methyl 2-{bis[(tert-butoxy)carbonyl]amino}prop-2-enoate (22 g, 74 mmol). The mixture was stirred for 16 h, then concentrated under reduced pressure and the residue was purified by silica gel column chromatography to give the product (12 g, 47% yield) as an oil. LCMS (ESI) m/z [M+H] calcd for $C_{19}H_{31}BrN_2O_6$ 462.1; found: 463.1.

Step 4: Synthesis of 3-(5-bromo-3,6-dihydropyridin-1(2H)-yl)-2-((tert-butoxycarbonyl)amino)propanoic acid To a mixture of methyl 2-(bis(tert-butoxycarbonyl)amino)-3-(5-bromo-3,6-dihydropyridin-1(2H)-yl)propanoate (14 g, 30 mmol) in dioxane (30 mL) and $H_2O$ (12 mL) was added LiOH (3.6 g, 151 mmol).
The mixture was heated to 35° C. and stirred for 12 h, then 1M HCl was added and the pH adjusted to ~3-4. The mixture was extracted with DCM (2×300 mL) and the combined organic layers were dried over anhydrous $Na_2SO_4$ and filtered. The filtrate was concentrated under reduced pressure to give the product (10 g, 85% yield) as a solid. LCMS (ESI) m/z [M+H] calcd for $C_{13}H_{21}BrN_2O_4$ 348.1; found: 349.0.

Step 5: Synthesis of methyl (3S)-1-(3-(5-bromo-3,6-dihydropyridin-1(2H)-yl)-2-((tert-butoxycarbonyl)amino)propanoyl)hexahydropyridazine-3-carboxylate To a mixture of 3-(5-bromo-3,6-dihydropyridin-1(2H)-yl)-2-((tert-butoxycarbonyl)amino)propanoic acid (10 g, 30 mmol), DIPEA (12 g, 93 mmol) and methyl (3S)-1,2-diazinane-3-carboxylate (5.4 g, 37 mmol) in DMF (100 mL) at 0° C. under an atmosphere of Ar was added HATU (13 g, 34 mmol). The mixture was stirred at 0° C. for 2 h, then $H_2O$ was added and the mixture extracted with EtOAc (2×300 mL). The combined organic layers were dried over anhydrous $Na_2SO_4$, filtered, the filtrate was concentrated under reduced pressure and the residue was purified by reverse phase chromatography to give the product (9.0 g, 55% yield) as a solid. LCMS (ESI) m/z [M+H] calcd for $C_{19}H_{31}BrN_4O_5$ 474.1; found: 475.1.

Step 6: Synthesis of methyl (3S)-1-(2-((tert-butoxycarbonyl)amino)-3-(5-(1-ethyl-3-(3-hydroxy-2,2-dimethylpropyl)-2-(2-((S)-1-methoxyethyl)pyridin-3-yl)-1H-indol-5-yl)-3,6-dihydropyridin-1(2H)-yl)propanoyl)hexahydropyridazine-3-carboxylate A mixture of methyl (3S)-1-(3-(5-bromo-3,6-dihydropyridin-1(2H)-yl)-2-((tert-butoxycarbonyl)amino)propanoyl)hexahydropyridazine-3-carboxylate (9.0 g, 18 mmol), $K_2CO_3$ (4.5 g, 32 mmol), Pd(dppf)$Cl_2$.DCM (1.4 g, 2 mmol), 3-(1-ethyl-2-{2-[(1S)-1-methoxyethyl]pyridin-3-yl}-5-(4,4,5,5-tetramethyl-1,3,2-dioxaborolan-2-yl)indol-3-yl)-2,2-dimethylpropan-1-ol (9.8 g, 20 mmol) in dioxane (90 mL) and $H_2O$ (10 mL) under an atmosphere of Ar was heated to 75° C. and stirred for 2 h. $H_2O$ was added and the mixture was extracted with EtOAc (3×200 mL). The combined organic layers were dried over $Na_2SO_4$, filtered, the filtrate was concentrated under reduced pressure and the residue was purified by silica gel column chromatography to give the product (4.0 g, 25% yield) as a solid. LCMS (ESI) m/z [M+H] calcd for $C_{42}H_{60}N_6O_7$ 760.5; found: 761.4.

Step 7: Synthesis of (3S)-1-(2-((tert-butoxycarbonyl)amino)-3-(5-(1-ethyl-3-(3-hydroxy-2,2-dimethylpropyl)-2-(2-((S)-1-methoxyethyl)pyridin-3-yl)-1H-indol-5-yl)-3,6-dihydropyridin-1(2H)-yl)propanoyl)hexahydropyridazine-3-carboxylic acid To a mixture of methyl (3S)-1-(2-((tert-butoxycarbonyl)amino)-3-(5-(1-ethyl-3-(3-hydroxy-2,2-dimethylpropyl)-2-(2-((S)-1-methoxyethyl)pyridin-3-yl)-1H-indol-5-yl)-3,6-dihydropyridin-1(2H)-yl)propanoyl)hexahydropyridazine-3-carboxylate (4.1 g, 5.0 mmol) in THF (35 mL) at 0° C. was added LiOH (0.60 g, 27 mmol). The mixture was stirred at 0° C. for 1.5 h, then 1 M HCl added to adjust pH to ~6-7 and the mixture was extracted with EtOAc (3×200 mL). The combined organic layers were dried over $Na_2SO_4$, filtered and the filtrate was concentrated under reduced pressure to give the product (3.6 g, 80% yield) as a solid. LCMS (ESI) m/z [M+H] calcd for $C_{41}H_{58}N_6O_7$ 746.4; found: 747.4.

Step 8: Synthesis of tert-butyl (($6^3$S)-$1^1$-ethyl-$1^2$-(2-((S)-1-methoxyethyl)pyridin-3-yl)-10,10-dimethyl-5,7-dioxo-$2^1$ $2^2,2^3,2^6,6^1,6^2,6^3,6^4,6^5,6^6$-decahydro-$1^1$H-8-oxa-1(5,3)-indola-6(1,3)-pyridazina-2(5,1)-pyridinacycloundecaphane-4-yl)carbamate To a mixture of (3S)-1-(2-((tert-butoxycarbonyl)amino)-3-(5-(1-ethyl-3-(3-hydroxy-2,2-dimethylpropyl)-2-(2-((S)-1-methoxyethyl)pyridin-3-yl)-1H-indol-5-yl)-3,6-dihydropyridin-1(2H)-yl)propanoyl)hexahydropyridazine-3-carboxylic acid (3.6 g, 5.0 mmol) and DIPEA (24 g,190 mmol) in DCM (700 mL) under an atmosphere ofAr was added EDClIHCI (28 g, 140 mmol) and HOBt (6.5 g, 50 mmol). The mixture was heated to 30° C. and stirred for 16 h at 30° C., then concentrated under reduced pressure. The residue was diluted with EtOAc (200 mL) and washed with $H_2O$ (2×200 mL), brine (200 mL), dried over $Na_2SO_4$ and filtered. The filtrate was concentrated under reduced pressure and the residue was purified by silica gel column chromatography to give the product (1.45 g, 40% yield) as a solid. LCMS (ESI) m/z [M+H] calcd for $C_{41}H_5NO_6$ 728.4; found: 729.4.

Step 9: Synthesis of ($6^3$S)-4-amino-$1^1$-ethyl-$1^2$-(2-((S)-1-methoxyethyl)pyridin-3-yl)-10,10-dimethyl-$2^1$ $2^2,2^3,2^6,6^1,6^2,6^3,6^4,6^{5},6^6$-decahydro-$1^1$H-8-oxa-1(5,3)-indola-6(1,3)-pyridazina-2(5,1)- pyridinacycloundecaphane-5,7-dione To a mixture of tert-butyl (($6^3$S)-$1^1$-ethyl-$1^2$-(2-((S)-1-methoxyethyl)pyridin-3-yl)-10,10-dimethyl-5,7-dioxo-$2^1$ $2^2,2^3,2^6,6^1,6^2,6^3,6^4,6^5,6^6$-decahydro-$1^1$H-8-oxa-1(5,3)-indola-6(1,3)-pyridazina-2(5,1)- pyridinacycloundecaphane-4-yl)carbamate (130 mg, 0.20 mmol) in DCM (1.0 mL) at 0° C. was added TFA (0.3 mL). The mixture was warmed to room temperature and stirred for 2 h, then concentrated under reduced pressure to give the product, which was used directly in the next step directly without further purification. LCMS (ESI) m/z [M+H] calcd for $C_{36}H_{48}N_6O_4$ 628.4; found: 629.4.
Intermediate 6: Synthesis of ($2^2S,6^3S,4S$)-4-amino-$1^1$-ethyl-$1^2$-(2-((S)-1-methoxyethyl)pyridin-3-yl)-10,10-dimethyl-$6^1,6^2,6^3,6^4,6^5,6^6$-hexahydro-$1^1$H-8-oxa-2(4,2)-morpholina-1(5,3)-indola-6(1,3)-pyridazinacycloundecaphane-5,7-dione
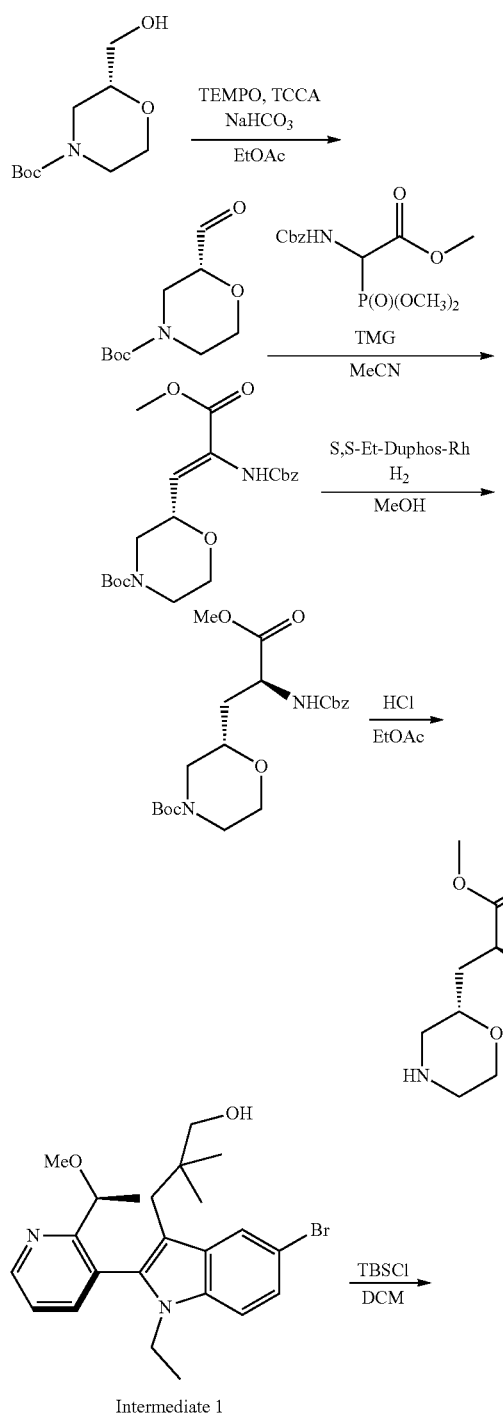
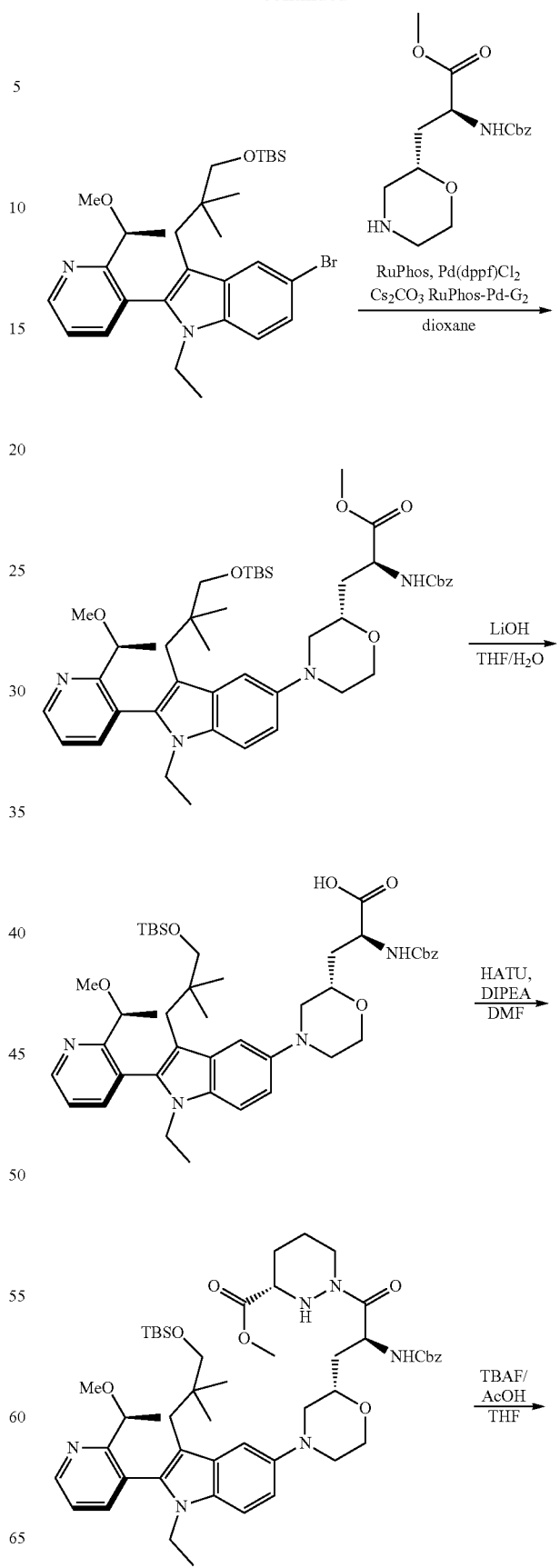
-continued -continued

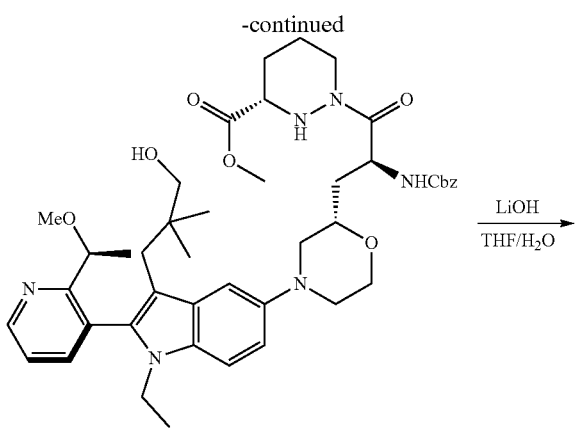

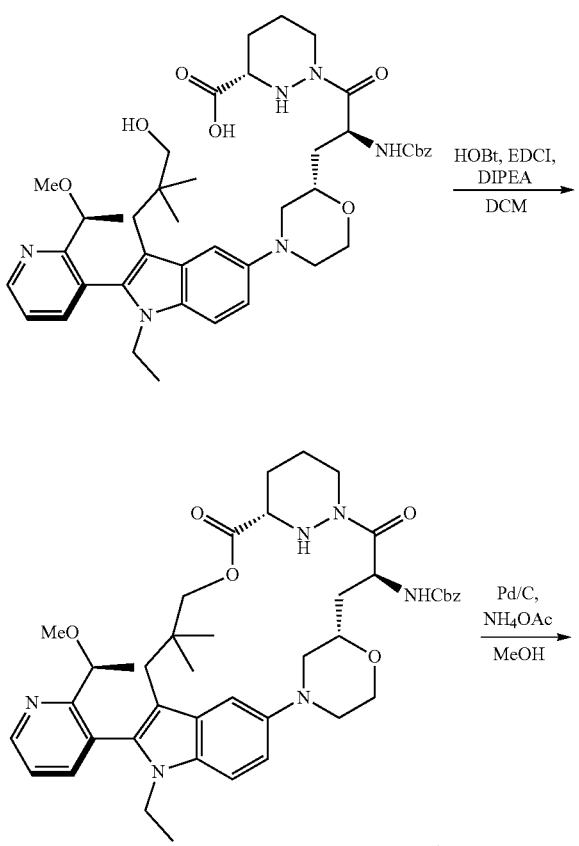

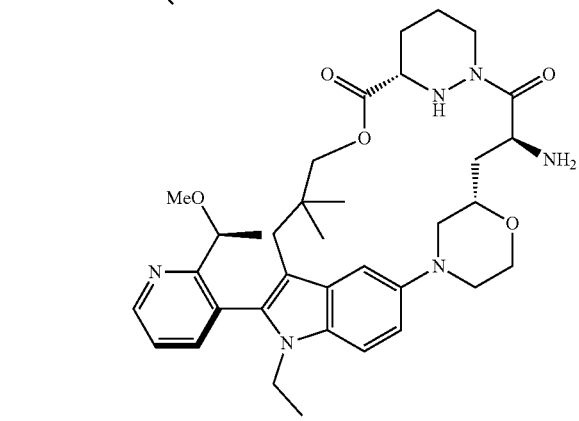

Step 1: Synthesis of tert-butyl (2R)-2-formylmorpholin-4-yl formate

To a solution of tert-butyl (2R)-2-(hydroxymethyl)morpholin-4-yl formate (50 g, 230 mmol) in EtOAc (1 L) was added TEMPO (715 mg, 4.6 mmol) and NaHCO$_3$ (58 g, 690 mmol) at room temperature.

The mixture was cooled to −50° C., then TCCA (56 g, 241 mmol) in EtOAc (100 mL) was added dropwise over 30 min. The reaction mixture was warmed to 5° C. for 2 h, then quenched with 10% Na$_2$S$_2$O$_3$ (200 mL) and stirred for 20 min. The resulting mixture was filtered and the organic phase was separated. The aqueous phase was extracted with EtOAc (2×100 mL). The combined organic layers were washed with H$_2$O (100 mL) and brine (100 mL), then dried over anhydrous Na$_2$SO$_4$. The organic layer was concentrated under reduced pressure to afford the product (50 g, crude) as an oil.

Step 2: Synthesis of afford tert-butyl (S,Z)-2-(2-(((benzyloxy)carbonyl)amino)-3-methoxy-3-oxo-prop-1-en-1-yl)morpholine-4-carboxylate To a solution of tert-butyl (2R)-2-formylmorpholin-4-yl formate (49 g, 153 mmol) and methyl 2-{[(benzyloxy)carbonyl]amino}-2-(dimethoxyphosphoryl)acetate (60 g, 183 mmol) in MeCN (300 mL) was added tetramethylguanidine (35 g, 306 mmol) at 0-10° C. The reaction mixture was stirred at 10° C. for 30 min then warmed to room temperature for 2 h. The reaction mixture was diluted with DCM (200 mL) and washed with 10% citric acid (200 mL) and 10% NaHCO$_3$ aq. (200 mL). The organic phase was concentrated under reduced pressure and purified by silica gel column chromatography to afford the product (36 g, 90% yield) as solid. LCMS (ESI) m/z [M+Na] calcd for C$_{21}$H$_{28}$N$_2$O$_4$ 420.2; found: 443.1

Step 3: Synthesis of tert-butyl (S)-2-((S)-2-(((benzyloxy)carbonyl)amino)-3-methoxy-3-oxopropyl)morpholine-4-carboxylate To a solution of tert-butyl (S,Z)-2-(2-(((benzyloxy)carbonyl)amino)-3-methoxy-3-oxoprop-1-en-1-yl)morpholine-4-carboxylate (49 g, 0.12 mol) in MeOH (500 mL) was added (S,S)-Et-DUPHOS-Rh (500 mg, 0.7 mmol). The mixture was stirred at room temperature under an H$_2$ (60 psi) atmosphere for 48 h.

The reaction was concentrated and purified by silica gel column chromatography to give the product (44 g, 90% yield) as solid. LCMS (ESI) m/z [M+Na] calcd for C$_{21}$H$_{30}$N$_2$O$_7$ 422.2; found: 445.2.

Step 4: Synthesis of methyl (S)-2-(((benzyloxy)carbonyl)amino)-3-((S)-morpholin-2-yl)propanoate To a stirred solution of tert-butyl (S)-2-((S)-2-(((benzyloxy)carbonyl)amino)-3-methoxy-3-oxopropyl)morpholine-4-carboxylate (2.2 g, 5.2 mmol) in EtOAc (2 mL) was added HCl/EtOAc (25 mL) at 15° C. The reaction was stirred at 15° C. for 2 h, then concentrated under reduced pressure to afford the product (1.51 g, 90% yield) as an oil. LCMS (ESI) m/z [M+H] calcd for C$_{16}$H$_{22}$N$_2$O$_5$ 322.1; found: 323.2.

Step 5: Synthesis of (S)-5-bromo-3-(3-((tert-butyldimethylsilyl)oxy)-2,2-dimethylpropyl)-1-ethyl-2-(2-(1-methoxyethyl)pyridin-3-yl)-1H-indole To a solution of 3-(5-bromo-1-ethyl-2-{2-[(1 S)-1-methoxyethyl]pyridin-3-yl}indol-3-yl)-2,2-dimethylpropan-1-ol (100 g, 0.22 mol) and imidazole (30.6 g, 0.45 mol) in DCM (800 mL) was added TBSCI (50.7 g, 0.34 mol) in DCM (200 mL) at 0° C. The reaction was stirred at room temperature for 2 h.

The resulting solution was washed with $H_2O$ (3×300 mL) and brine (2×200 mL), dried over anhydrous $Na_2SO_4$, filtered and concentrated under reduced pressure. The residue was purified with silica gel column chromatography to give the product (138 g, 90% yield) as a solid. LCMS (ESI) m/z [M+H] calcd for $C_{29}H_{43}BrN_2O_2Si$ 558.2; found: 559.2.

Step 6: Synthesis of methyl (2S)-2-{[(benzyloxy)carbonyl]amino}-3-[(2S)-4-(3-{3-[(tert-butyldimethylsilyl)oxy]-2,2-dimethylpropyl}-1-ethyl-2-{2-[(1 S)-1-methoxyethyl]pyridin-3-yl}indol-5-yl)morpholin-2-yl]propanoate To a stirred solution of (S)-5-bromo-3-(3-((tert-butyldimethylsilyl)oxy)-2,2-dimethylpropyl)-1-ethyl-2-(2-(1-methoxyethyl)pyridin-3-yl)-1H-indole (50 g, 89.3 mmol) in dioxane (500 mL) was added methyl (2S)-2-{[(benzyloxy)carbonyl]amino}-3-[(2S)-morpholin-2-yl]propanoate (31.7 g, 98.2 mmol), RuPhos (16.7 g, 35.7 mmol), di-p-chlorobis(2-amino-1,1-biphenyl-2-yl-C,N)dipalladium(II) (2.8 g, 4.4 mmol) and cesium carbonate (96 g, 295 mmol) followed by RuPhos-Pd-G2 (3.5 g, 4.4 mmol) at 105° C. under an $N_2$ atmosphere. The reaction mixture was stirred for 6 h at 105° C. under an $N_2$ atmosphere. The resulting mixture was filtered, and the filtrate was concentrated under reduced pressure. The residue was purified by prep-TLC chromatography to afford the product (55 g, 73% yield) as a solid. LCMS (ESI) m/z [M+H]calcd for $C_{45}H_{64}N_4O_7Si$ 800.5; found: 801.5.

Step 7: Synthesis of (2S)-2-{[(benzyloxy)carbonyl]amino}-3-[(2S)-4-(3-{3-[(tert-butyldimethylsilyl)oxy]-2,2-dimethylpropyl}-1-ethyl-2-{2-[(1 S)-1-methoxyethyl]pyridin-3-yl}indol-5-yl)morpholin-2-yl]propanoic acid To a solution of methyl (2S)-2-{[(benzyloxy)carbonyl]amino}-3-[(2S)-4-(3-{3-[(tert-butyldimethylsilyl)oxy]-2,2-dimethylpropyl}-1-ethyl-2-{2-[(1 S)-1-methoxyethyl]pyridin-3-yl}indol-5-yl)morpholin-2-yl]propanoate (10 g, 12 mmol) in THF (270 mL) was added LiOH (1.3 g, 31 mmol) in $H_2O$ (45 mL) at room temperature. The reaction was stirred at room temperature for 2 h, then treated with 1 N HCl to adjust pH to 4-5 at 0~5° C. The resulting mixture was extracted with EtOAc (2×50 mL). The combined organic layers were washed with brine and dried over anhydrous $Na_2SO_4$. The organic phase was then concentrated under reduced pressure to afford the product (9.5 g, 97% yield) as a solid. LCMS (ESI) m/z [M+H] calcd for $C_{44}H_{62}N_4O_7Si$ 786.4; found: 787.4.

Step 8: Synthesis of methyl (S)-1-((S)-2-(((benzyloxy)carbonyl)amino)-3-((S)-4-(3-(3-((tert-butyldimethylsilyl)oxy)-2,2-dimethylpropyl)-1-ethyl-2-(2-((S)-1-methoxyethyl)pyridin-3-yl)-1H-indol-5-yl)morpholin-2-yl)propanoyl)hexahydropyridazine-3-carboxylate To a stirred solution of (2S)-2-{[(benzyloxy)carbonyl]amino}-3-[(2S)-4-(3-{3-[(tert-butyldimethylsilyl)oxy]-2,2-dimethylpropyl}-1-ethyl-2-{2-[(1 S)-1-methoxyethyl]pyridin-3-yl}indol-5-yl)morpholin-2-yl]propanoic acid (10 g, 12.7 mmol) in DMF (150 mL), was added methyl (S)-hexahydropyridazine-3-carboxylate (2 g, 14 mmol), then cooled to 0° C., DIPEA (32.8 g, 254 mmol) was added followed by HATU (9.7 g, 25.4 mmol) at 0-5° C. The reaction mixture was stirred at 0-5° C. for 1 h. The resulting mixture was diluted with EtOAc (500 mL) and $H_2O$ (200 mL). The organic layer was separated and washed with $H_2O$ (2×100 mL) and brine (100 mL), dried over anhydrous sodium sulfate. The solution was filtered and concentrated under reduced pressure, and the residue was purified by silica gel column chromatography to afford the product. LCMS (ESI) m/z [M+H] calcd for $C_{50}H_{72}N_6O_8Si$ 912.5; found: 913.4.

Step 9: Synthesis of methyl (S)-1-((S)-2-(((benzyloxy)carbonyl)amino)-3-((S)-4-(1-ethyl-3-(3-hydroxy-2,2-dimethylpropyl)-2-(2-((S)-1-methoxyethyl)pyridin-3-yl)-1H-indol-5-yl)morpholin-2-yl)propanoyl)hexahydropyridazine-3-carboxylate A solution of methyl (S)-1-((S)-2-(((benzyloxy)carbonyl)amino)-3-((S)-4-(3-(3-((tert-butyldimethylsilyl)oxy)-2,2-dimethylpropyl)-1-ethyl-2-(2-((S)-1-methoxyethyl)pyridin-3-yl)-1H-indol-5-yl)morpholin-2-yl)propanoyl)hexahydropyridazine-3-carboxylate (8.5 g, 9 mmol) in THF (8 mL) was added a mixture of tetrabutylammonium fluoride (1M in THF, 180 mL, 180 mmol) and AcOH (11 g, 200 mmol) at room temperature. The reaction mixture was stirred at 75° C. for 3 h. The resulting mixture was diluted with EtOAc (150 mL) and washed with $H_2O$ (6×20 mL). The organic phase was concentrated under reduced pressure to give the product (7.4 g, 100% yield) as solid. LCMS (ESI) m/z [M+H] calcd for $C_{44}H_{58}N_6O_8$ 799.4; found: 798.4.

Step 10: Synthesis of (S)-1-((S)-2-(((benzyloxy)carbonyl)amino)-3-((S)-4-(1-ethyl-3-(3-hydroxy-2,2-dimethylpropyl)-2-(2-((S)-1-methoxyethyl)pyridin-3-yl)-1H-indol-5-yl)morpholin-2-yl)propanoyl)hexahydropyridazine-3-carboxylic acid To a solution of methyl (S)-1-((S)-2-(((benzyloxy)carbonyl)amino)-3-((S)-4-(1-ethyl-3-(3-hydroxy-2,2-dimethylpropyl)-2-(2-((S)-1-methoxyethyl)pyridin-3-yl)-1H-indol-5-yl)morpholin-2-yl)propanoyl)hexahydropyridazine-3-carboxylate (8 g, 10 mmol) in THF (200 mL) was added LiOH (600 mg, 25 mmol) in $H_2O$ (30 mL). The reaction mixture was stirred at room temperature for 1 h, then treated with 1 N HCl to adjust pH to 4-5 at 0-5° C., and extracted with EtOAc (2×500 mL). The organic phase was washed with brine and concentrated under reduced pressure to afford the product (8 g, crude) as a solid. LCMS (ESI) m/z [M+H] calcd for $C_{43}H_{56}N_6O_8$ 784.4; found: 785.4.

Step 11: Synthesis of afford benzyl ((2²S,6³S,4S)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹¹H-8-oxa-2(4,2)-morpholina-1(5,3)-indola-6(1,3)-pyridazinacycloundecaphane-4-yl)carbamate To a stirred solution of (S)-1-((S)-2-(((benzyloxy)carbonyl)amino)-3-((S)-4-(1-ethyl-3-(3-hydroxy-2,2-dimethylpropyl)-2-(2-((S)-1-methoxyethyl)pyridin-3-yl)-1H-indol-5-yl)morpholin-2-yl)propanoyl)hexahydropyridazine-3-carboxylic acid (8 g, 10.2 mmol) and DIPEA (59 g, 459 mmol) in DCM (800 mL) was added EDCI (88 g, 458 mmol) and HOBt (27.6 g, 204 mmol) at room temperature under an argon atmosphere. The reaction mixture was stirred at room temperature for 16 h. The resulting mixture was concentrated under reduced pressure, and the residue was purified by silica gel column chromatography to afford the product (5 g, 66% yield) as a solid; LCMS (ESI) m/z [M+H] calcd for $C_{43}H_{54}N_6O_7$ 766.4; found: 767.4.

Step 12: Synthesis of $(2^2S,6^3S,4S)$-4-amino-$1^1$-ethyl-$1^2$-(2-((S)-1-methoxyethyl)pyridin-3-yl)-10,10-dimethyl-$6^1,6^2,6^3,6^4,6^5,6^6$-hexahydro-$1^1$H-8-oxa-2(4,2)-morpholina-1(5,3)-indola-6(1,3)-pyridazinacycloundecaphane-5,7-dione To a solution of benzyl $((2^2S,6^3S,4S)$-$1^1$-ethyl-$1^2$-(2-((S)-1-methoxyethyl)pyridin-3-yl)-10,10-dimethyl-5,7-dioxo-$6^1,6^2,6^3,6^4,6^5,6^6$-hexahydro-$1^1$H-8-oxa-2(4,2)-morpholina-1(5,3)-indola-6(1,3)-pyridazinacycloundecaphane-4-yl)carbamate (400 mg, 0.5 mmol) in MeOH (20 mL) was added Pd/C (200 mg) and ammonium acetate (834 mg, 16 mmol) at room temperature under an $H_2$ atmosphere and the mixture was stirred for 2 h. The resulting mixture was filtered and concentrated under reduced pressure.

The residue was redissolved in DCM (20 mL) and washed with $H_2O$ (5 mL×2), then concentrated under reduced pressure to afford the product (320 mg, 97% yield) as a solid. LCMS (ESI) m/z [M+H] calcd for $C_{35}H_{48}N_6O_5$ 632.4; found: 633.3.

Intermediate 7: Synthesis of tert-butyl $((6^3S,4S,Z)$-11-ethyl-$1^2$-(2-((S)-1-methoxyethyl)-5-(4-methylpiperazin-1-yl)pyridin-3-yl)-10,10-dimethyl-5,7-dioxo-$6^1,6^2,6^3,6^4,6^5,6^6$-hexahydro-$1^1$H-8-oxa-2(4,2)-thiazola-1(5,3)-indola-6(1,3)-pyridazinacycloundecaphane-4-yl)carbamate

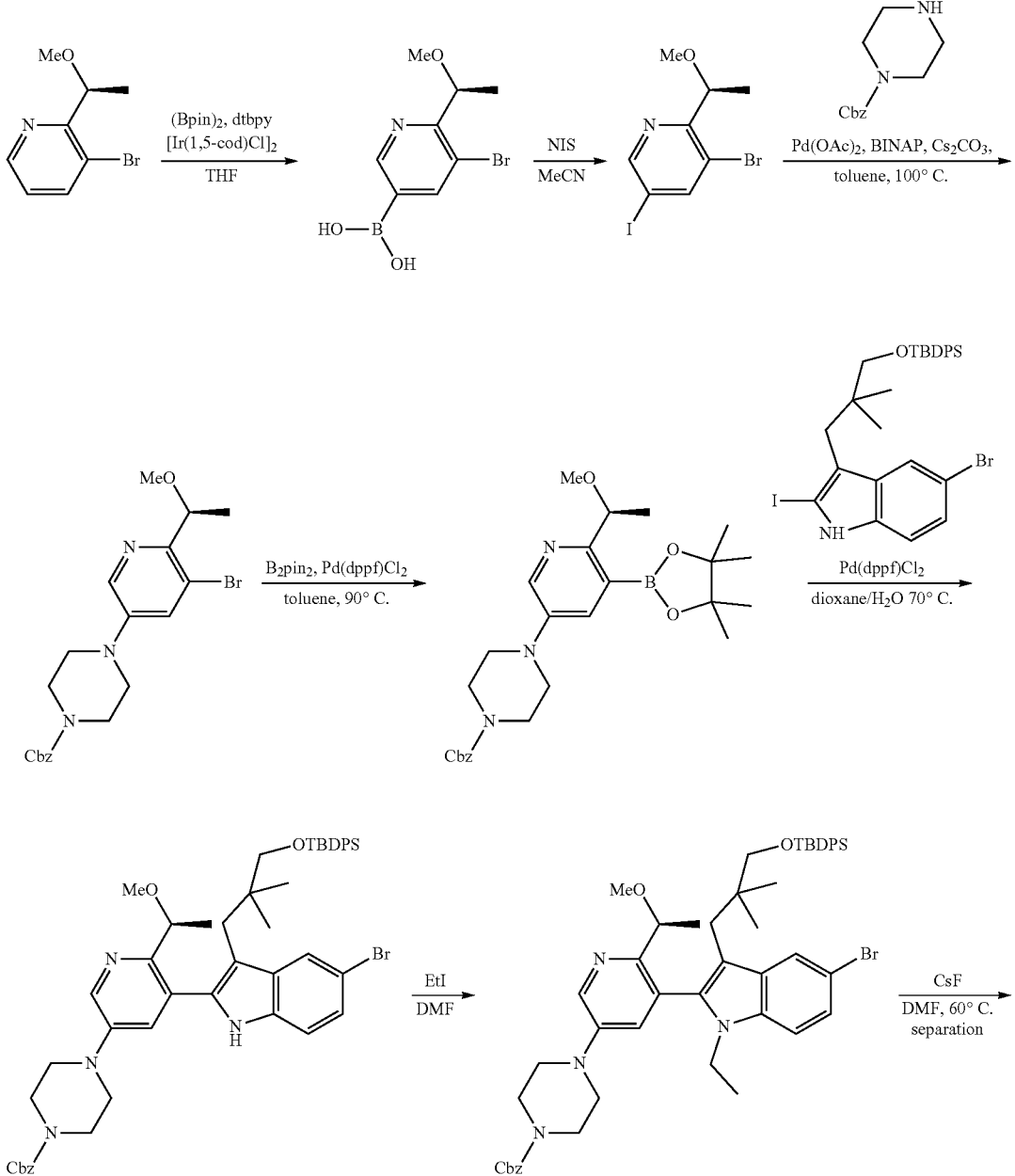

-continued
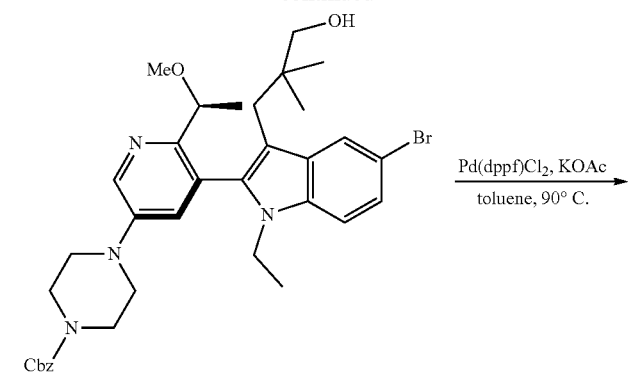
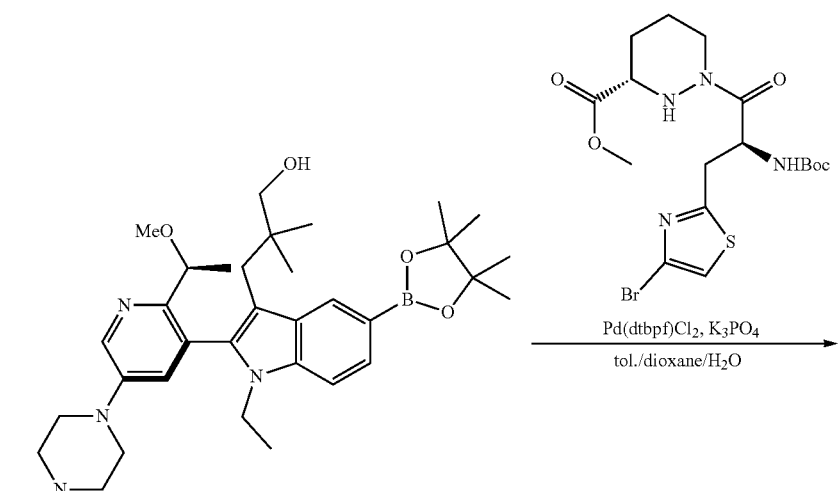
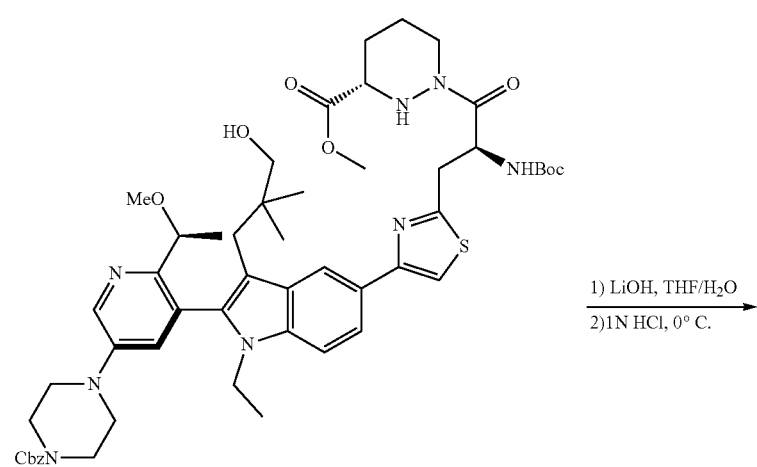

-continued
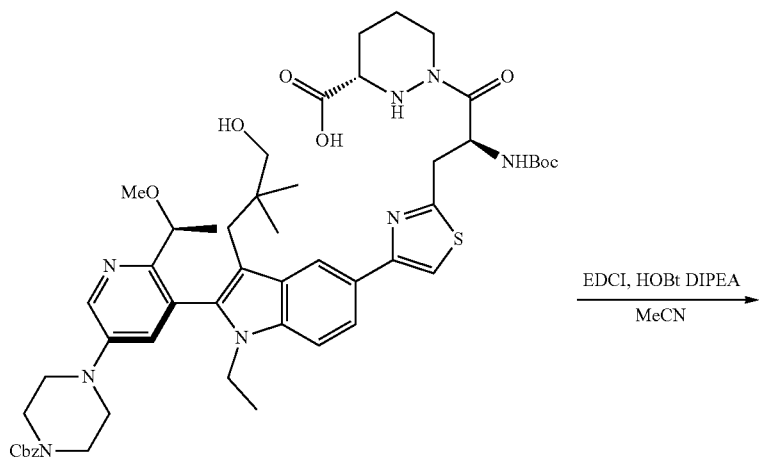
EDCI, HOBt DIPEA
―――――――――→
MeCN
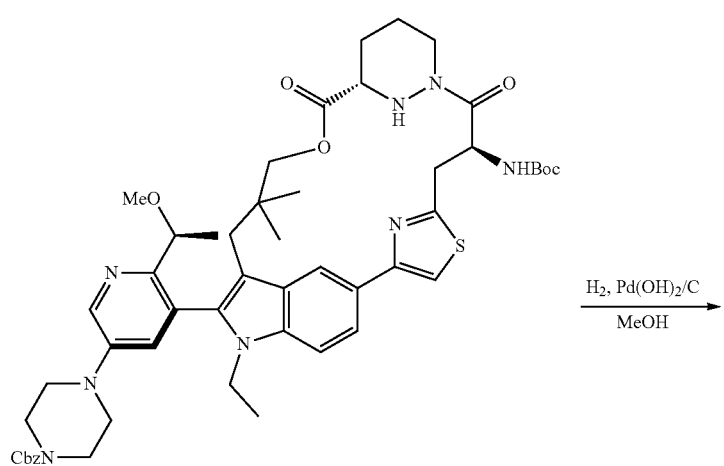
H₂, Pd(OH)₂/C
―――――――――→
MeOH
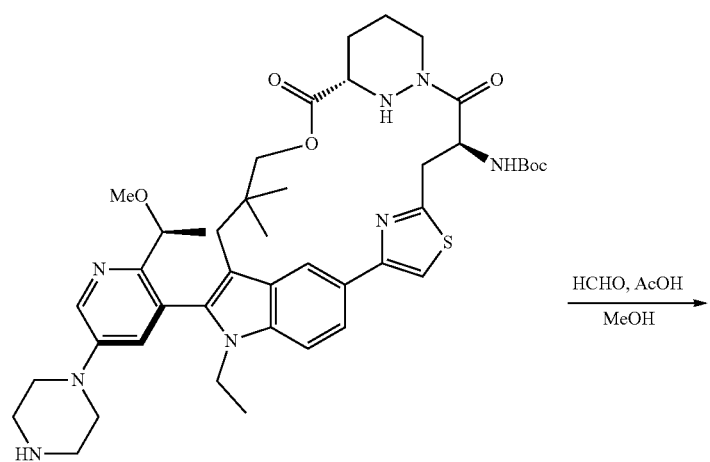
HCHO, AcOH
―――――――――→
MeOH

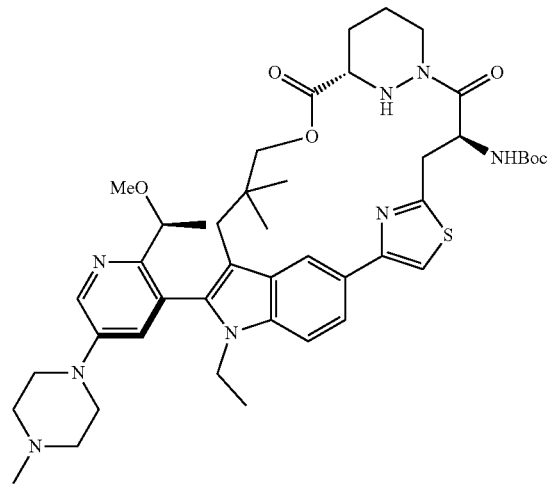

Step 1: Synthesis of (S)-(5-bromo-6-(1-methoxyethyl)pyridin-3-yl)boronic acid To a stirred solution of (S)-3-bromo-2-(1-methoxyethyl)pyridine (80.0 g, 370.24 mmol) and bis(pinacolato)diboron (141.03 g, 555.3 mmol) in THF (320 mL) was added dtbpy (14.91 g, 55.5 mmol) and chloro(1,5-cyclooctadiene)iridium (I) dimer (7.46 g, 11.1 mmol) under an argon atmosphere. The resulting mixture was stirred for 16 h at 75° C. The mixture was concentrated under reduced pressure and the resulting residue was dissolved in EtOAc (200 mL) and was adjusted to pH 10 with a solution of $Na_2CO_3$ (40 g) and NaOH (10 g) in $H_2O$ (600 mL). The aqueous layer was extracted with EtOAc (800 mL) and then the aqueous phase was acidified to pH 6 with HCl (6 N) to precipitate the desired product (50 g, 52% yield) as a solid. LCMS (ESI) m/z [M+H] calcd for $C_8H_{11}BBrNO_3$: 260.01; found: 260.0.

Step 2: Synthesis of (S)-3-bromo-5-iodo-2-(1-methoxyethyl)pyridine

To a stirred solution of (S)-(5-bromo-6-(1-methoxyethyl)pyridin-3-yl)boronic acid (23.0 g, 88.5 mmol) in MeCN (230 mL) at room temperature was added NIS (49.78 g, 221.2 mmol). The resulting mixture was stirred overnight at 80° C. under an argon atmosphere. The mixture was concentrated under reduced pressure and the residue was dissolved in DCM (2.1 L) and washed with $Na_2S_2O_3$ (3×500 mL). The organic layer was dried over anhydrous $Na_2SO_4$, filtered, and the filtrate was concentrated under reduced pressure. The residue was purified by silica gel column chromatography to afford the desired product (20 g, 66% yield). LCMS (ESI) m/z [M+H] calcd for $C_8H_9BrINO$: 341.90; found: 341.7.

Step 3: Synthesis of benzyl (S)-4-(5-bromo-6-(1-methoxyethyl)pyridin-3-yl)piperazine-1-carboxylate Into a 3L 3-necked round-bottom flask purged and maintained with an inert atmosphere of argon, was placed 3-bromo-5-iodo-2-[(1S)-1-methoxyethyl]pyridine (147 g, 429.8 mmol) and benzyl piperazine-1-carboxylate (94.69 g, 429.8 mmol), Pd(OAc)$_2$ (4.83 g, 21.4 mmol), BINAP (5.35 g, 8.6 mmol), Cs$_2$CO$_3$ (350.14 g, 1074.6 mmol), toluene (1 L). The resulting solution was stirred overnight at 100° C. in an oil bath. The reaction mixture was then cooled to room temperature. The resulting mixture was concentrated under reduced pressure. The residue was purified by silica gel column chromatography (50% EtOAc/hexanes) to afford the product (135 g, 65% yield) as a solid. LCMS (ESI) m/z [M+H] calcd for $C_{20}H_{24}BrN_3O_3$ 433.1; found: 434.1.

Step 4: Synthesis of benzyl (S)-4-(6-(1-methoxyethyl)-5-(4,4,5,5-tetramethyl-1,3,2-dioxaborolan-2-yl)pyridin-3-yl)piperazine-1-carboxylate Into a 3-L 3-necked round-bottom flask purged and maintained with an inert atmosphere of argon, was placed benzyl 4-[5-bromo-6-[(1S)-1-methoxyethyl]pyridin-3-yl]piperazine-1-carboxylate (135 g, 310.8 mmol), bis(pinacolato)diboron (86.82 g, 341.9 mmol), Pd(dppfCl$_2$ (22.74 g, 31.0 mmol), KOAc (76.26 g, 777.5 mmol), toluene (1 L). The resulting solution was stirred for 2 days at 90° C. in an oil bath. The reaction mixture was cooled to room temperature. The resulting mixture was concentrated under reduced pressure. The residue was purified by neutral alumina column chromatography (30% EtOAC//hexane) to afford the product (167 g, crude) as a solid. LCMS (ESI) m/z [M+H] calcd for $C_{26}H_{36}BN_3O_5$ 481.3; found: 482.1.

Step 5: Synthesis of benzyl (S)-4-(5-(5-bromo-3-(3-((tert-butyldiphenylsilyl)oxy)-2,2-dimethylpropyl)-1H-indol-2-yl)-6-(1-methoxyethyl)pyridin-3-yl)piperazine-1-carboxylate Into a 3-L 3-necked round-bottom flask purged and maintained with an inert atmosphere of argon, was placed (S)-4-(6-(1-methoxyethyl)-5-(4,4,5,5-tetramethyl-1,3,2-dioxaborolan-2-yl)pyridin-3-yl)piperazine-1-carboxylate (167 g, 346.9 mmol), 5-bromo-3-[3-[(tert-butyldiphenylsilyl)oxy]-2,2-dimethylpropyl]-2-iodo-1H-indole (224.27 g, 346.9 mmol), Pd(dppf)Cl$_2$ (25.38 g, 34.6 mmol), dioxane (600 mL), H$_2$O (200 mL), K$_3$PO$_4$ (184.09 g, 867.2 mmol), toluene (200 mL). The resulting solution was stirred overnight at 70° C. in an oil bath. The reaction mixture was then cooled to room temperature. The resulting mixture was concentrated under reduced pressure. The residue was purified by silica gel column chromatography (50% EtOAc/hexane) to afford the product (146 g, 48% yield) as a solid. LCMS (ESI) m/z [M+H] calcd for $C_{49}H_{57}BrN_4O_4Si$ 872.3; found: 873.3.

Step 6: Synthesis of benzyl (S)-4-(5-(5-bromo-3-(3-((tert-butyldiphenylsilyl)oxy)-2,2-dimethylpropyl)-1-ethyl-1H-indol-2-yl)-6-(1-methoxyethyl)pyridin-3-yl)piperazine-1-carboxylate To a stirred mixture of benzyl (S)-4-(5-(5-bromo-3-(3-((tert-butyldiphenylsilyl)oxy)-2,2-dimethylpropyl)-1H-indol-2-yl)-6-(1-methoxyethyl)pyridin-3-yl)piperazine-1-carboxylate (146 g, 167.0 mmol) and $Cs_2CO_3$ (163.28 g, 501.1 mmol) in DMF (1200 mL) was added ethyl iodide (52.11 g, 334.0 mmol) in portions at 0° C. under $N_2$ atmosphere. The final reaction mixture was stirred at room temperature for 12 h. The resulting mixture was diluted with EtOAc (1 L) and washed with brine (3×1.5L). The organic layers were dried over anhydrous $Na_2SO_4$. After filtration, the filtrate was concentrated under reduced pressure to give the product (143 g, crude) as a solid that was used directly for next step without further purification. LCMS (ESI) m/z [M+H] calcd for $C_{51}H_{61}BrN_4O_4Si$ 900.4; found: 901.4.

Step 7: Synthesis of benzyl (S)-4-(5-(5-bromo-1-ethyl-3-(3-hydroxy-2,2-dimethylpropyl)-1H-indol-2-yl)-6-(1-methoxyethyl)pyridin-3-yl)piperazine-1-carboxylate To a stirred mixture of benzyl (S)-4-(5-(5-bromo-3-(3-((tert-butyldiphenylsilyl)oxy)-2,2-dimethylpropyl)-1-ethyl-1H-indol-2-yl)-6-(1-methoxyethyl)pyridin-3-yl)piperazine-1-carboxylate (143 g, 158.5 mmol) in DMF (1250 mL) was added CsF (72.24 g, 475.5 mmol). Then the reaction mixture was stirred at 60° C. for 2 days under an $N_2$ atmosphere. The resulting mixture was diluted with EtOAc (1 L) and washed with brine (3×1 L). Then the organic phase was concentrated under reduced pressure. The residue was purified by silica gel column chromatography (30% EtOAc/pet. ether) to afford two atropisomers A (38 g, 36% yield) and B (34 g, 34% yield) both as solids. LCMS (ESI) m/z [M+H] calcd for $C_{35}H_{43}BrN_4O_4$ 663.2; found: 662.2.

Step 8: Synthesis of benzyl (S)-4-(5-(1-ethyl-3-(3-hydroxy-2,2-dimethylpropyl)-5-(4,4,5,5-tetramethyl-1,3,2-dioxaborolan-2-yl)-1H-indol-2-yl)-6-(1-methoxyethyl)pyridin-3-yl)piperazine-1-carboxylate Into a 500-mL 3-necked round-bottom flask purged and maintained with an inert atmosphere of nitrogen, was placed benzyl (S)-4-(5-(5-bromo-1-ethyl-3-(3-hydroxy-2,2-dimethylpropyl)-1H-indol-2-yl)-6-(1-methoxyethyl)pyridin-3-yl)piperazine-1-carboxylate (14 g, 21.1 mmol), bis(pinacolato)diboron (5.89 g, 23.21 mmol), $Pd(dppf)Cl_2$ (1.54 g, 2.1 mmol), KOAc (5.18 g, 52.7 mmol), toluene (150 mL). The resulting solution was stirred for 5 h at 90° C. in an oil bath. The reaction mixture was cooled to room temperature then concentrated under reduced pressure. The residue was purified by silica gel column chromatography (30% EtOAc/pet. ether) to give the product (12 g, 76% yield) as a solid. LCMS (ESI) m/z [M+H] calcd for $C_{41}H_{55}BN_4O_6$ 710.4; found: 711.3.

Step 9: Synthesis of methyl (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl)hexahydropyridazine-3-carboxylate Into a 250-mL round-bottom flask purged and maintained with an inert atmosphere of argon, was placed benzyl (S)-4-(5-(1-ethyl-3-(3-hydroxy-2,2-dimethylpropyl)-5-(4,4,5,5-tetramethyl-1,3,2-dioxaborolan-2-yl)-1H-indol-2-yl)-6-(1-methoxyethyl)pyridin-3-yl)piperazine-1-carboxylate (10.8 g, 15.2 mmol), methyl (3S)-1-[(2S)-3-(4-bromo-1,3-thiazol-2-yl)-2-[(tert-butoxycarbonyl)amino]propanoyl]-1,2-diazinane-3-carboxylate (7.98 g, 16.7 mmol), $Pd(dtbpf)Cl_2$ (0.99 g, 1.52 mmol), $K_3PO_4$ (8.06 g, 37.9 mmol), toluene (60 mL), dioxane (20 mL), $H_2O$ (20 mL). The resulting solution was stirred for 3 h at 70° C. in an oil bath. The reaction mixture was cooled to room temperature. The resulting solution was extracted with EtOAc (2×50 mL) and concentrated under reduced pressure. The residue was purified by silica gel column chromatography (10% EtOAc/hexane). The solvent was removed under reduced pressure to give the product (8 g, 51% yield) as a solid. LCMS (ESI) m/z [M+H] calcd for $C_{52}H_{68}N_8O_9S$ 980.5; found: 980.9.

Step 10: Synthesis of (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl)hexahydropyridazine-3-carboxylic acid To a stirred mixture of methyl (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl)hexahydropyridazine-3-carboxylate (12 g, 12.23 mmol) in THF (100 mL)/$H_2O$ (100 mL) was added LiOH (2.45 g, 61.1 mmol) under an $N_2$ atmosphere and the resulting mixture was stirred for 2 h at room temperature. THF was removed under reduced pressure. The pH of the aqueous phase was acidified to 5 with 1 N HCl at 0° C. The aqueous layer was extracted with DCM (3×100 mL). The organic phase was concentrated under reduced pressure to give the product (10 g, 85% yield) as a solid. LCMS (ESI) m/z [M+H] calcd for $C_{51}H_{66}N_8O_9S$ 966.5; found: 967.0.

Step 11: Synthesis of benzyl 4-(5-((6³S,4S,2)-4-((tert-butoxycarbonyl)amino)-1¹-ethyl-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-1²-yl)-6-((S)-1-methoxyethyl)pyridin-3-yl)piperazine-1-carboxylate Into a 3-L round-bottom flask purged and maintained with an inert atmosphere of nitrogen, was placed (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl)hexahydropyridazine-3-carboxylic acid (18 g, 18.61 mmol), MeCN (1.8 L), DIPEA (96.21 g, 744.4 mmol), EDCI (107.03 g, 558.3 mmol), and HOBt (25.15 g, 186.1 mmol). The resulting solution was stirred overnight at room temperature then concentrated under reduced pressure.

The resulting solution was diluted with DCM (1 L) and washed with 1 M HCl (3×1 L,) and $H_2O$ (3×1 L).

Then the organic layer was concentrated under reduced pressure and purified by silica gel column chromatography (50% EtOAc/hexane) to afford the product (10.4 g, 55% yield) as a solid. LCMS (ESI) m/z [M+H] calcd for $C_{51}H_{64}N_8O_8S$ 948.5; found: 949.3.

Step 12: Synthesis of tert-butyl ((6³S,4S,2)-11-ethyl-1²-(2-((S)-1-methoxyethyl)-5-(piperazin-1-yl)pyridin-3-yl)-10,10-dimethyl-5,7-dioxo-6¹,6²,6³,6⁴,6⁵,6⁶-hexahydro-11H-8-oxa-2(4,2)-thiazola-1(5,3)-indola-6(1,3)-pyridazinacycloundecaphane-4-yl)carbamate Into a 250-mL round-bottom flask purged and maintained with an inert atmosphere of nitrogen, was placed benzyl 4-(5-((6³S,4S,2)-4-((tert-butoxycarbonyl)amino)-1¹-ethyl-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazina-cycloundecaphane-1²-yl)-6-((S)-1-methoxyethyl)pyridin-3-yl)piperazine-1-carboxylate (10.40 g, 10.9 mmol), Pd(OH)2/C (5 g, 46.9 mmol), MeOH (100 mL). The resulting solution was stirred for 3 h at room temperature under a 2 atm H₂ atmosphere. The solids were filtered out and the filter cake was washed with MeOH (3×100 mL). The combined organic phases were concentrated under reduced pressure to give the product (8.5 g, 90% yield) as a solid. LCMS (ESI) m/z [M+H] calcd for $C_{43}H_{58}N_8O_6S$ 814.4; found: 815.3.

Step 13: Synthesis of tert-butyl ((6³S,4S,Z)-1¹-ethyl-1²-(2-((S)-1-methoxyethyl)-5-(4-methylpiperazin-1-yl)pyridin-3-yl)-10,10-dimethyl-5,7-dioxo-6¹,6²,6³,6⁴,6⁵,6⁶-hexahydro-1¹H-8-oxa-2(4,2)-thiazola-1 (5,3)-indola-6(1,3)-pyridazinacycloundecaphane-4-yl)carbamate Into a 1000-mL round-bottom flask purged and maintained with an inert atmosphere of nitrogen, was placed tert-butyl ((6³S,4S,Z)-1¹-ethyl-1²-(2-((S)-1-methoxyethyl)-5-(piperazin-1-yl)pyridin-3-yl)-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)carbamate (8.5 g, 10.4 mmol), MeOH (100 mL), AcOH (1.88 g, 31.2 mmol). The solution was stirred for 15 min and then HCHO (1.88 g, 23.15 mmol, 37% aqueous solution) and NaBH₃CN (788 mg, 12.5 mmol) were added at room temperature. The resulting solution was stirred for 3 h. The mixture was then quenched with H₂O (100 mL) and concentrated under reduced pressure to remove MeOH. The resulting solution was diluted with DCM (300 mL) and washed with H₂O (3×100 mL). The solution was concentrated under reduced pressure to afford the product (8.2 g, 90% yield) as a solid. LCMS (ESI) m/z [M+H] calcd for $C_{44}H_{60}N_8O_6S$ 828.4; found: 829.3.

Intermediate 8: Synthesis of (6³S,4S,Z)-4-amino-1¹-ethyl-1²-(5-((S)-hexahydropyrazino[2,1-c][1,4]oxazin-8(1H)-yl)-2-((S)-1-methoxyethyl)pyridin-3-yl)-10,10-dimethyl-6¹,6²,6³,6⁴,6⁵,6⁶-hexahydro-1¹H-8-oxa-2(4,2)-thiazola-1(5,3)-indola-6(1,3)-pyridazinacycloundecaphane-5,7-dione

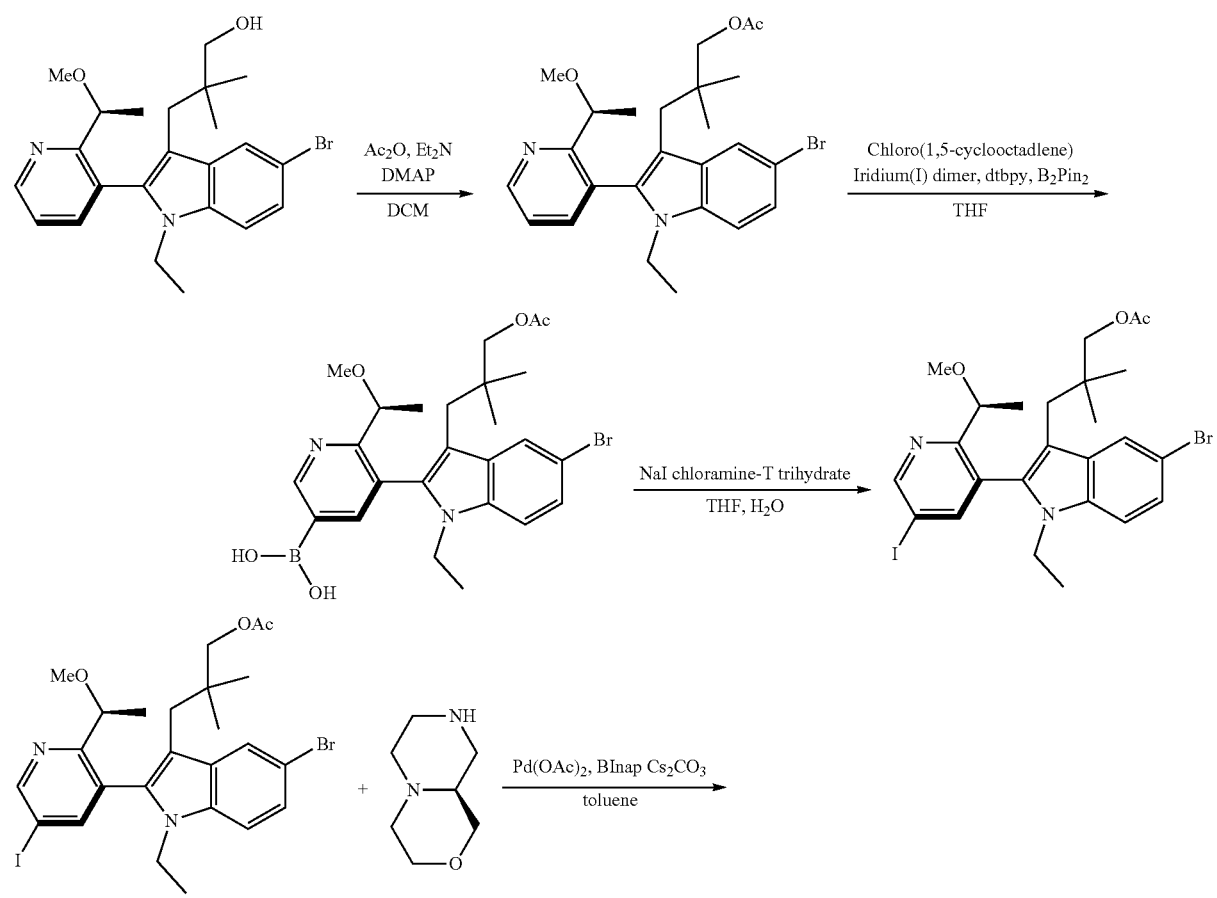

-continued
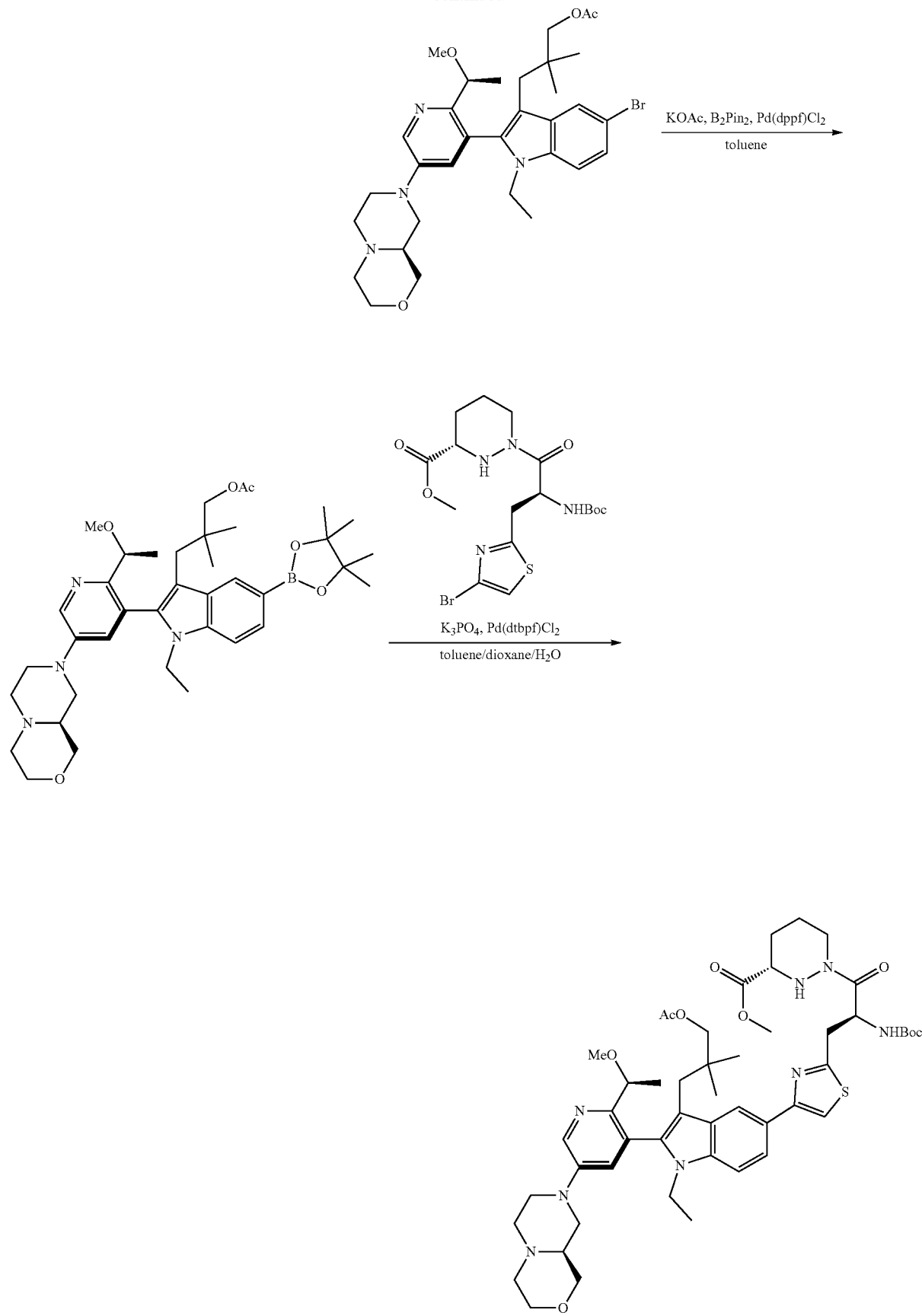

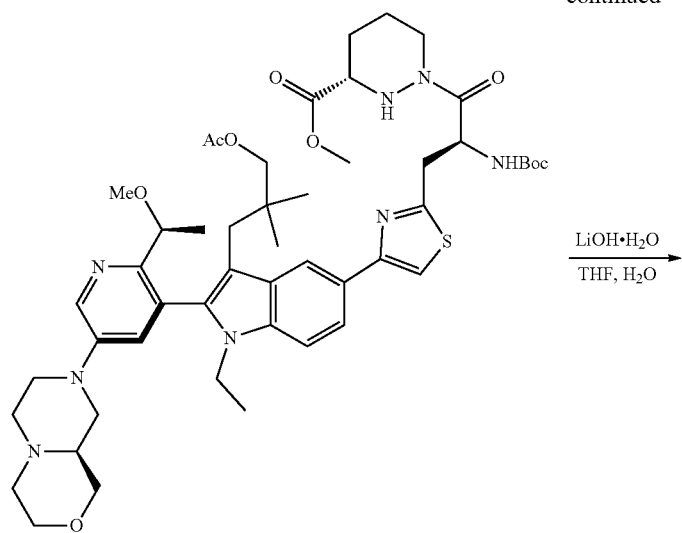
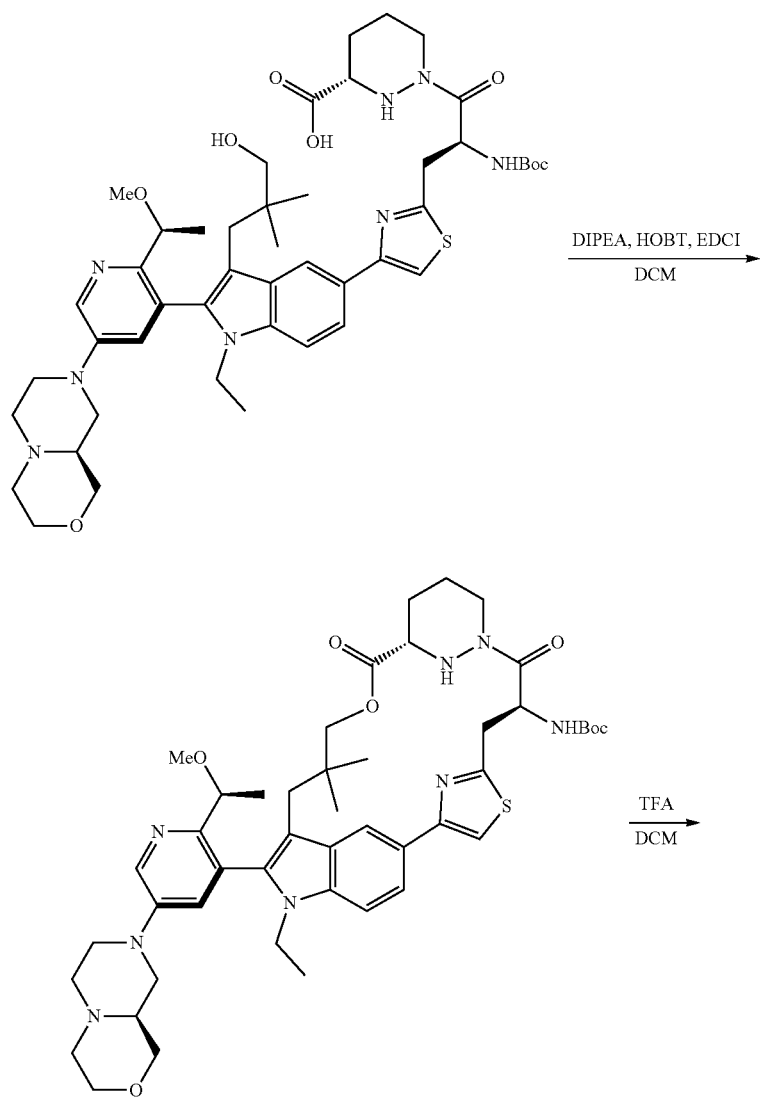

-continued

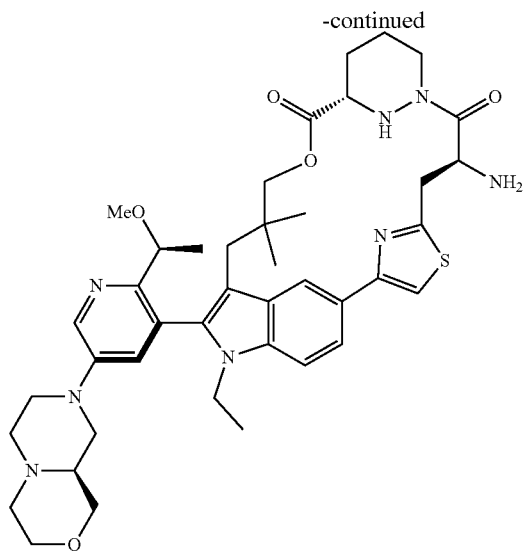

Step 1: Synthesis of (S)-3-(5-bromo-1-ethyl-2-(2-(1-methoxyethyl)pyridin-3-yl)-1H-indol-3-yl)-2,2-dimethylpropyl acetate To a stirred solution of (S)-3-(5-bromo-1-ethyl-2-(2-(1-methoxyethyl)pyridin-3-yl)-1H-indol-3-yl)-2,2-dimethylpropan-1-ol (100 g, 224.517 mmol) and Et$_3$N (45.44 g, 449.034 mmol) in DCM (1 L) was added DMAP (2.74 g, 22.452 mmol) and AC2O (27.50 g, 269.420 mmol) in portions at 0° C. under an argon atmosphere. The resulting mixture was stirred for 3 h at room temperature. The resulting mixture was concentrated under reduced pressure then diluted with EtOAc (1000 mL). The resulting mixture was washed with 1 M HCl (500 mL) then washed with sat. NaHCO$_3$ (500 mL) and brine (500 mL) dried over anhydrous Na$_2$SO$_4$. After filtration, the filtrate was concentrated under reduced pressure. The residue was purified by trituration with pet. ether (500 mL) to afford the product (93.3 g, 85% yield) as a white solid. LCMS (ESI) m/z [M+H] calcd for C$_{25}$H$_{31}$BrN$_2$O$_3$: 487.16; found: 489.2

Step 2: Synthesis of (S)-(5-(3-(3-acetoxy-2,2-dimethylpropyl)-5-bromo-1-ethyl-1H-indol-2-yl)-6-(1-methoxyethyl)pyridin-3-yl)boronic acid To a stirred solution of (S)-3-(5-bromo-1-ethyl-2-(2-(1-methoxyethyl)pyridin-3-yl)-1H-indol-3-yl)-2,2-dimethylpropyl acetate (93.3 g, 191.409 mmol) and B$_2$PIN$_2$ (72.91 g, 287.113 mmol) in THF (370 mL) was added dtbpy (7.71 g, 28.711 mmol) and chloro(1,5-cyclooctadiene)iridium(I) dimer (6.43 g, 9.570 mmol) in portions at room temperature under an argon atmosphere. The resulting mixture was stirred overnight at 75° C. The resulting mixture was concentrated under reduced pressure to afford the product (190 g, crude) as an oil. LCMS(ESI) m/z [M+H]; calcd for C$_{25}$H$_{32}$BBrN$_2$O$_5$: 531.17; found: 533.3

Step 3: Synthesis of (S)-3-(5-bromo-1-ethyl-2-(5-iodo-2-(1-methoxyethyl)pyridin-3-yl)-1H-indol-3-yl)-2,2-dimethylpropyl acetate To a stirred solution of (S)-(5-(3-(3-acetoxy-2,2-dimethylpropyl)-5-bromo-1-ethyl-1H-indol-2-yl)-6-(1-methoxyethyl)pyridin-3-yl)boronic acid (110 g, 207.059 mmol) and chloramine-T trihydrate (349.96 g, 1242.354 mmol) in THF (550 mL) was added a solution of NaI (186.22 g, 1242.354 mmol) in H$_2$O (225 mL) in portions at 0° C. under an air atmosphere. The resulting mixture was stirred overnight at 50° C. under an argon atmosphere. The resulting mixture was concentrated under reduced pressure then washed with CHCl$_3$ (500 mL). The resulting mixture was filtered, the filter cake was washed with CHCl$_3$ (3×250 mL). The filtrate was extracted with CHCl$_3$ (3×500 mL). The combined organic layers were washed with Na$_2$S$_2$O$_3$ (500 mL), washed with brine (2×200 mL) dried over anhydrous Na$_2$SO$_4$. After filtration, the filtrate was concentrated under reduced pressure. The residue was purified by silica gel column chromatography, (18% EtOAc/pet. ether) to afford the product (24 g, 18% yield) as a solid. LCMS(ESI) m/z [M+H]; calcd for C$_{25}$H$_{30}$BrIN$_2$O$_3$: 613.06; found: 614.7

Step 4: Synthesis of 3-(5-bromo-1-ethyl-2-(5-((S)-hexahydropyrazino[2,1-c][1,4]oxazin-8(1H)-yl)-2-((S)-1-methoxyethyl)pyridin-3-yl)-1H-indol-3-yl)-2,2-dimethylpropyl acetate To a stirred solution of 3-(5-bromo-1-ethyl-2-{5-iodo-2-[(1 S)-1-methoxyethyl]pyridin-3-yl}indol-3-yl)-2,2-dimethylpropyl acetate (9 g, 14.674 mmol), (S)-octahydropyrazino[2,1-c][1,4]oxazine (2.469 g, 17.609 mmol), Cs$_2$CO$_3$ (11.953 g, 36.685 mmol,) and BINAP (456.9 mg, 0.734 mmol) in toluene (63 mL) was added Pd(OAc)$_2$ (329.44 mg, 1.467 mmol) at room temperature under an argon atmosphere. The resulting mixture was stirred for 6 h at 100° C. After filtration, the filter cake was washed with EtOAc (100 mL). The filtrate was concentrated under reduced pressure. The residue was purified by prep-TLC (8% MeOH/DCM) to afford the product (6.9 g, 75% yield) as a solid. LCMS (ESI) m/z [M+H] calcd for C$_{32}$H$_{43}$BrN$_4$O$_4$: 627.25; found: 627.4.

Step 5: Synthesis of 3-(1-ethyl-2-(5-((S)-hexahydropyrazino[2,1-c][1,4]oxazin-8(1H)-yl)-2-((S)-1-methoxyethyl)pyridin-3-yl)-5-(4,4,5,5-tetramethyl-1,3,2-dioxaborolan-2-yl)-1H-indol-3-yl)-2,2-dimethylpropyl acetate To a stirred solution of 3-(5-bromo-1-ethyl-2-(5-((S)-hexahydropyrazino[2,1-c][1,4]oxazin-8(1H)-yl)-2-((S)-1-methoxyethyl)pyridin-3-yl)-1H-indol-3-yl)-2,2-dimethylpropyl acetate (3.2 g, 5.115 mmol), KOAc (1.51 g, 15.345 mmol) and 4,4,5,5-tetramethyl-2-(tetramethyl-1,3,2-dioxaborolan-2-yl)-1,3,2-dioxaborolane (2.60 g, 10.230 mmol) in toluene (48 mL) was added Pd(dppf)C$_{12}$ (0.37 g, 0.512 mmol) in portions at room temperature under an argon atmosphere. The resulting mixture was stirred for 1.5 h at 90° C. The resulting mixture was filtered, the filter cake was washed with EtOAc (100 mL). The filtrate was concentrated under reduced pressure. The residue was purified by prep-TLC (8% MeOH/DCM) to afford the product (3.0 g, 88% yield) as a solid. LCMS (ESI) m/z [M+H] calcd for C$_{38}$H$_{55}$BN$_4$O$_6$: 675.43; found: 675.1

Step 6: Synthesis of methyl (S)-1-((S)-3-(4-(3-(3-acetoxy-2,2-dimethylpropyl)-1-ethyl-2-(5-((S)-hexahydropyrazino[2,1-c][1,4]oxazin-8(1H)-yl)-2-((S)-1-methoxyethyl)pyridin-3-yl)-1H-indol-5-yl)thiazol-2-yl)-2-((tert-butoxycarbonyl)amino)propanoyl)hexahydropyridazine-3-carboxylate To a stirred mixture of 3-(1-ethyl-2-(5-((S)-hexahydropyrazino[2,1-c][1,4]oxazin-8(1H)-yl)-2-((S)-1-methoxyethyl)pyridin-3-yl)-5-(4,4,5,5-tetramethyl-1,3,2-dioxaborolan-2-yl)-1H-indol-3-yl)-2,2-dimethylpropyl acetate (5 g, 7.433 mmol) and K$_3$PO$_4$ (4.26 g, 20.067 mmol) in toluene (54 mL) were added dioxane (17.82 mL, 210.307 mmol) and H$_2$O (17.82 mL) at room temperature under an argon atmosphere. The resulting mixture was stirred for 2 h at 70° C. The resulting mixture was filtered, the filter cake was washed with EtOAc (100 mL). The filtrate was concentrated under reduced pressure. The resulting mixture was extracted with EtOAc (200 mL). The combined organic layers were washed with brine (100 mL), dried over anhydrous Na$_2$SO$_4$. After filtration, the filtrate was concentrated under reduced pressure. The residue was purified by prep-TLC (8% MeOH/DCM) to afford the product (4.6 g, 66% yield) as a solid. LCMS (ESI) m/z [M+H] calcd for C$_{49}$H$_{68}$N$_8$O$_9$S: 945.49; found: 945.7

Step 7: Synthesis of (S)-1-((S)-2-((tert-butoxycarbonyl)amino)-3-(4-(1-ethyl-2-(5-((S)-hexahydropyrazino[2,1-c][1,4]oxazin-8(1H)-yl)-2-((S)-1-methoxyethyl)pyridin-3-yl)-3-(3-hydroxy-2,2-dimethylpropyl)-1H-indol-5-yl)thiazol-2-yl)propanoyl)hexahydropyridazine-3-carboxylic acid To a stirred solution of methyl (S)-1-((S)-3-(4-(3-(3-acetoxy-2,2-dimethylpropyl)-1-ethyl-2-(5-((S)-hexahydropyrazino[2,1-c][1,4]oxazin-8(1H)-yl)-2-((S)-1-methoxyethyl)pyridin-3-yl)-1H-indol-5-yl)thiazol-2-yl)-2-((tert-butoxycarbonyl)amino)propanoyl)hexahydropyridazine-3-carboxylate (6 g, 6.361 mmol) in THF (43 mL) was added LiOH·H$_2$O (573.92 mg, 13.677 mmol) at 0° C. The resulting mixture was stirred for 16 h at room temperature. The mixture was acidified to pH 6 with HCl (aq.). The resulting mixture was extracted with EtOAc (3×100 mL). The combined organic layers were washed with brine, dried over anhydrous Na$_2$SO$_4$. After filtration, the filtrate was concentrated under reduced pressure to afford the product (4 g, crude) as a solid. LCMS (ESI) m/z [M+H] calcd for C$_{45}$H$_{60}$N$_8$O$_9$S: 889.43; found: 889.7

Step 8: Synthesis of tert-butyl ((6$^3$S,4S,Z)-1$^1$-ethyl-1$^2$-(5-((S)-hexahydropyrazino[2,1-c][1,4]oxazin-8(1H)-yl)-2-((S)-1-methoxyethyl)pyridin-3-yl)-10,10-dimethyl-5,7-dioxo-6,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)carbamate To a stirred solution of (S)-1-((S)-2-((tert-butoxycarbonyl)amino)-3-(4-(1-ethyl-2-(5-((S)-hexahydropyrazino[2,1-c][1,4]oxazin-8(1H)-yl)-2-((S)-1-methoxyethyl)pyridin-3-yl)-3-(3-hydroxy-2,2-dimethylpropyl)-1H-indol-5-yl)thiazol-2-yl)propanoyl)hexahydropyridazine-3-carboxylic acid (4 g, 4.51 mmol), HOBt (6.09 g, 45.09 mmol) and DIPEA (23.31 g, 180.36 mmol) in DCM (200 mL) was added EDCI (25.93 g, 135.27 mmol) in DCM (200 mL) dropwise at 0° C. under an argon atmosphere. The resulting mixture was stirred for 16 h at room temperature then concentrated under reduced pressure. The reaction was quenched with H$_2$O at 0° C. and extracted with EtOAc (500 mL). The combined organic layers were washed with brine, dried over anhydrous Na$_2$SO$_4$. After filtration, the filtrate was concentrated under reduced pressure. The residue was purified by prep-TLC (8% MeOH/DCM) to afford the product (2.0 g, 52% yield) as a solid. LCMS (ESI) m/z [M+H] calcd for C$_{46}$H$_{62}$N$_8$O$_7$S: 870.4; found:871.8

Step 9: Synthesis of (6$^3$S,4S,Z)-4-amino-1$^1$-ethyl-1$^2$-(5-((S)-hexahydropyrazino[2,1-c][1,4]oxazin-8(1H)-yl)-2-((S)-1-methoxyethyl)pyridin-3-yl)-10,10-dimethyl-6$^1$,6$^2$,6$^3$,6$^4$,6$^5$,6$^6$-hexahydro-1'H-8-oxa-2(4,2)-thiazola-1(5,3)-indola-6(1,3)-pyridazinacycloundecaphane-5,7-dione To a stirred solution of tert-butyl ((6$^3$S,4S,Z)-1$^1$-ethyl-1$^2$-(5-((S)-hexahydropyrazino[2,1-c][1,4]oxazin-8(1H)-yl)-2-((S)-1-methoxyethyl)pyridin-3-yl)-10,10-dimethyl-5,7-dioxo-6,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)carbamate (316 mg, 0.345 mmol) in DCM (3 mL,) was added TFA (1 mL) dropwise at 0° C. under an argon atmosphere. The resulting mixture was stirred for 2 h at room temperature. The mixture was basified to pH 8 with sat. aq. NaHCO$_3$. The resulting mixture was extracted with EtOAc (3×80 mL). The combined organic layers were washed with brine (3×40 mL), dried over anhydrous Na$_2$SO$_4$. After filtration, the filtrate was concentrated under reduced pressure. The crude product mixture was used in the next step directly without further purification. LCMS (ESI) m/z [M+H] calcd for C$_{41}$H$_{54}$N$_8$O$_5$S: 771.4; found: 771.6 Intermediate 9: Synthesis of (6$^3$S,4S,Z)-4-amino-1$^1$-ethyl-1$^2$-(2-((S)-1-methoxyethyl)-5-((R)-octahydro-2H-pyrido[1,2-a]pyrazin-2-yl)pyridin-3-yl)-10,10-dimethyl-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-5,7-dione

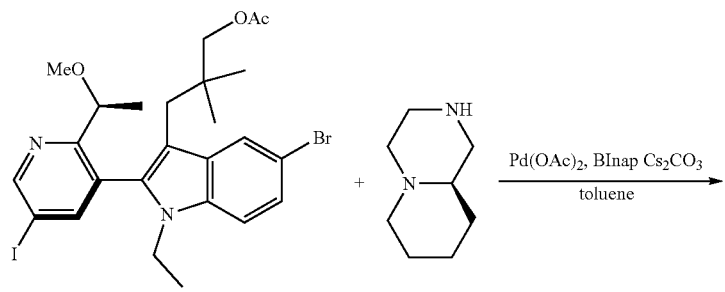
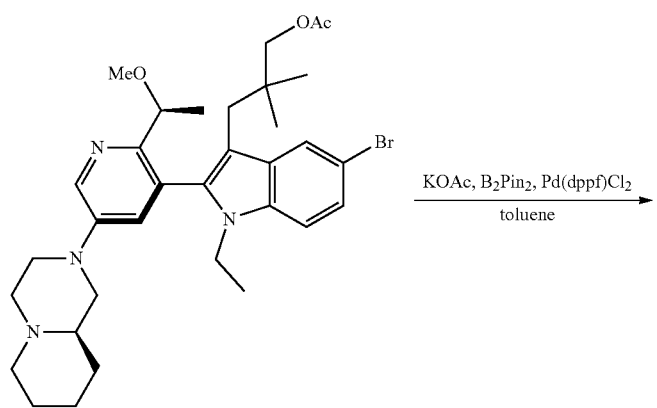
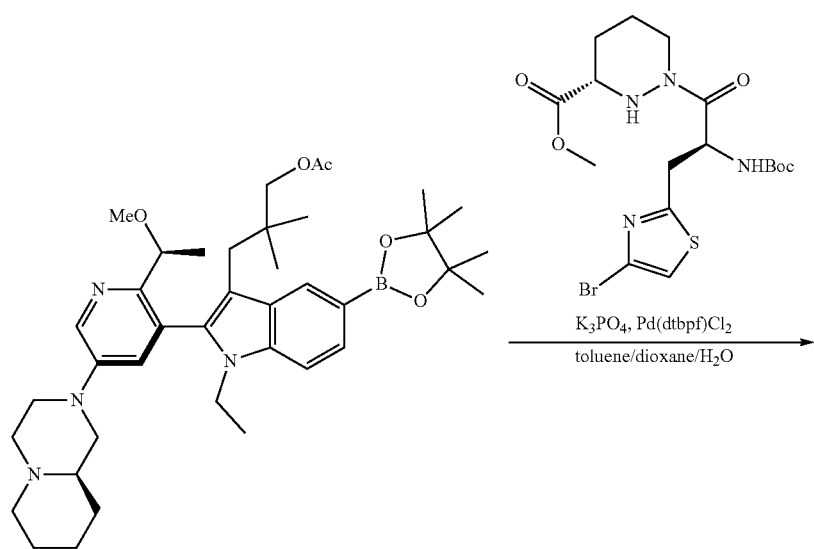

-continued
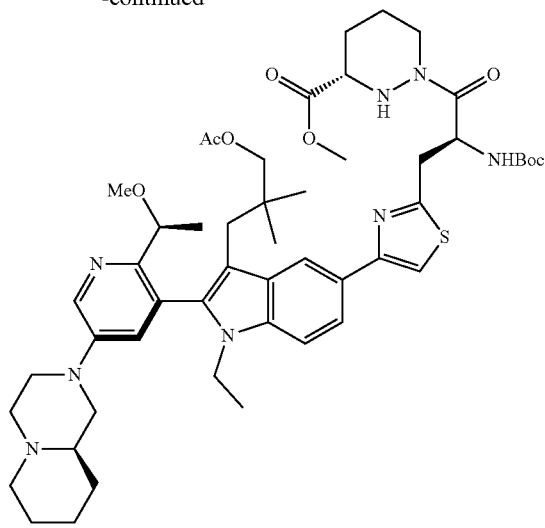
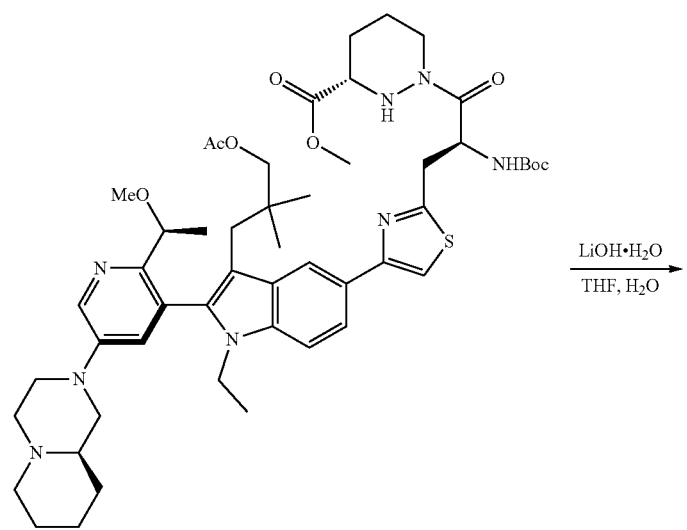
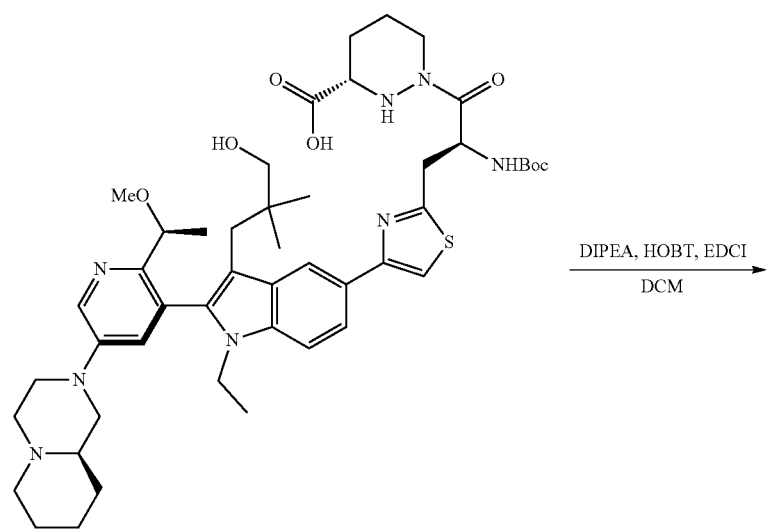

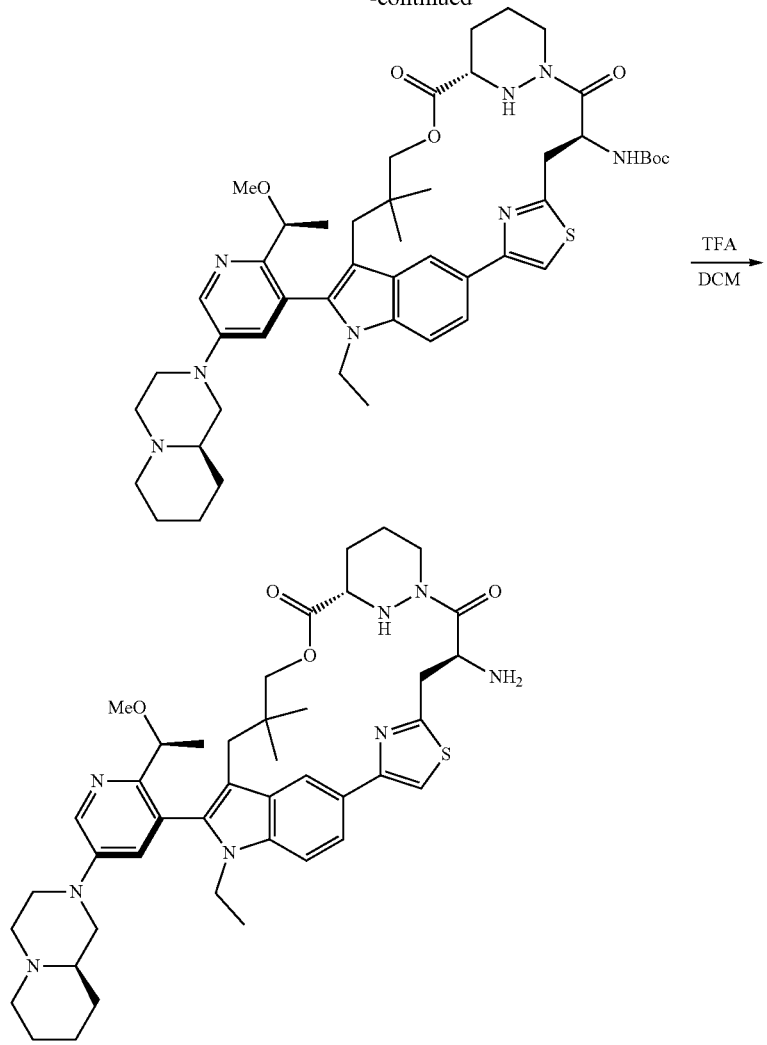

Step 1: Synthesis of 3-(5-bromo-1-ethyl-2-(2-((S)-1-methoxyethyl)-5-((R)-octahydro-2H-pyrido[1,2-a]pyrazin-2-yl)pyridin-3-yl)-1H-indol-3-yl)-2,2-dimethylpropyl acetate To a stirred solution of 3-(5-bromo-1-ethyl-2-{5-iodo-2-[(1 S)-1-methoxyethyl]pyridin-3-yl}indol-3-yl)-2,2-dimethylpropyl acetate (9 g, 14.674 mmol), (R)-octahydro-2H-pyrido[1,2-a]pyrazine (2.469 g, 17.609 mmol), $Cs_2CO_3$ (11.9523 g, 36.685 mmol) and BINAP (456.85 mg, 0.734 mmol) in toluene (63 mL) was added $Pd(OAc)_2$ (329.44 mg, 1.467 mmol) in portions at room temperature under an argon atmosphere. The resulting mixture was stirred for 6 h at 100° C. then the mixture was filtered, the filter cake was washed with EtOAc (100 mL). The filtrate was concentrated under reduced pressure. The residue was purified by prep-TLC (8% MeOH/DCM) to afford the product (6 g, 65% yield) as a solid. LCMS (ESI) m/z [M+H] calcd $C_{33}H_{45}BrN_4O_3$: 625.28; found: 627.4.

Step 2: Synthesis of 3-(1-ethyl-2-(2-((S)-1-methoxyethyl)-5-((R)-octahydro-2H-pyrido[1,2-a]pyrazin-2-yl)pyridin-3-yl)-5-(4,4,5,5-tetramethyl-1,3,2-dioxaborolan-2-yl)-1H-indol-3-yl)-2,2-dimethylpropyl acetate To a stirred solution of 3-(5-bromo-1-ethyl-2-(2-((S)-1-methoxyethyl)-5-((R)-octahydro-2H-pyrido[1,2-a]pyrazin-2-yl)pyridin-3-yl)-1H-indol-3-yl)-2,2-dimethylpropyl acetate (3.2 g, 5.115 mmol), KOAc (1.51 g, 15.345 mmol) and 4,4,5,5-tetramethyl-2-(tetramethyl-1,3,2-dioxaborolan-2-yl)-1,3,2-dioxaborolane (2.60 g, 10.230 mmol) in toluene (48 mL) was added $Pd(dppfCl_2$ (0.37 g, 0.512 mmol) in portions at room temperature under an argon atmosphere. The resulting mixture was stirred for 1.5 h at 90° C. The resulting mixture was filtered, the filter cake was washed with EtOAc (100 mL). The filtrate was concentrated under reduced pressure and purified by prep-TLC (8% MeOH/DCM) to afford the product (3.1 g, 81% yield) as a solid. LCMS (ESI) m/z [M+H] calcd $C_{39}H_{57}BN_4O_5$: 673.45; found: 673.4

Step 3: Synthesis for methyl (S)-1-((S)-3-(4-(3-(3-acetoxy-2,2-dimethylpropyl)-1-ethyl-2-(2-((S)-1-methoxyethyl)-5-((R)-octahydro-2H-pyrido[1,2-a]pyrazin-2-yl)pyridin-3-yl)-1H-indol-5-yl)thiazol-2-yl)-2-((tert-butoxycarbonyl)amino)propanoyl) hexahydropyridazine-3-carboxylate To a stirred mixture of 3-(1-ethyl-2-(2-((S)-1-methoxyethyl)-5-((R)-octahydro-2H-pyrido[1,2-a]pyrazin-2-yl)pyridin-3-yl)-5-(4,4,5,5-tetramethyl-1,3,2-dioxaborolan-2-yl)-

1H-indol-3-yl)-2,2-dimethylpropyl acetate (5 g, 7.433 mmol), methyl (S)-1-((S)-3-(4-bromothiazol-2-yl)-2-((tert-butoxycarbonyl)amino)propanoyl)hexahydropyridazine-3-carboxylate (3.89 g, 8.176 mmol) and $K_3PO_4$ (4.26 g, 20.067 mmol) in toluene (54 mL), dioxane (18 mL) and $H_2O$ (18 mL) was added $Pd(dtbpf)Cl_2$ (969 mg, 1.486 mmol) at room temperature under an argon atmosphere. The resulting mixture was stirred for 2 h at 70° C. The mixture was filtered, the filter cake was washed with EtOAc (100 mL). The filtrate was concentrated under reduced pressure and the resulting mixture was extracted with EtOAc (200 mL). The combined organic layers were washed with brine (100 mL), dried over anhydrous $Na_2SO_4$. After filtration, the filtrate was concentrated under reduced pressure. The residue was purified by prep-TLC (8% MeOH/DCM) to afford the product (6.8 g, 83% yield) as a solid. LCMS (ESI) m/z [M+H] calcd $C_{50}H_{70}N_8O_8S$: 943.51; found: 943.4

Step 4: Synthesis of (S)-1-((S)-2-((tert-butoxycarbonyl)amino)-3-(4-(1-ethyl-3-(3-hydroxy-2,2-dimethylpropyl)-2-(2-((S)-1-methoxyethyl)-5-((R)-octahydro-2H-pyrido[1,2-a]pyrazin-2-yl)pyridin-3-yl)-1H-indol-5-yl)thiazol-2-yl)propanoyl)hexahydropyridazine-3-carboxylic acid To a stirred solution of methyl (S)-1-((S)-3-(4-(3-(3-acetoxy-2,2-dimethylpropyl)-1-ethyl-2-(2-((S)-1-methoxyethyl)-5-((R)-octahydro-2H-pyrido[1,2-a]pyrazin-2-yl)pyridin-3-yl)-1H-indol-5-yl)thiazol-2-yl)-2-((tert-butoxycarbonyl)amino)propanoyl)hexahydropyridazine-3-carboxylate (6 g, 6.361 mmol) in THF (43 mL) was added $LiOH \cdot H_2O$ (573.92 mg, 13.677 mmol) dropwise at 0° C. under an argon atmosphere. The resulting mixture was stirred for 16 h at room temperature. The mixture was acidified to pH 6 with HCl (aq.). The resulting mixture was extracted with EtOAc (3×150 mL). The combined organic layers were washed with brine, dried over anhydrous $Na_2SO_4$. After filtration, the filtrate was concentrated under reduced pressure to afford the product (4 g, crude) as a solid. LCMS (ESI) m/z [M+H] calcd $C_{47}H_{66}N_8O_7S$: 887.49; found: 887.6

Step 5: Synthesis of tert-butyl (($6^3$S,4S,Z)-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate To a stirred solution of (S)-1-((S)-2-((tert-butoxycarbonyl)amino)-3-(4-(1-ethyl-3-(3-hydroxy-2,2-dimethylpropyl)-2-(2-((S)-1-methoxyethyl)-5-((R)-octahydro-2H-pyrido[1,2-a]pyrazin-2-yl)pyridin-3-yl)-1H-indol-5-yl)thiazol-2-yl)propanoyl)hexahydropyridazine-3-carboxylic acid (4 g, 4.509 mmol), HOBt (6.09 g, 45.090 mmol) and DIPEA (23.31 g, 180.360 mmol) in DCM (200 mL) was added EDCI (25.93 g, 135.270 mmol) in DCM (200 mL) dropwise at 0° C. under an argon atmosphere. The resulting mixture was stirred for 16 h at room temperature. The resulting mixture was concentrated under reduced pressure and quenched with $H_2O$ at 0° C. and extracted with EtOAc (500 mL). The combined organic layers were washed with brine, dried over anhydrous $Na_2SO_4$. After filtration, the filtrate was concentrated under reduced pressure. The residue was purified by prep-TLC (8% MeOH/DCM) to afford the product (2.0 g, 49% yield) as a solid. LCMS (ESI) m/z [M+H] calcd for $C_{47}H_{64}N_8O_6S$: 869.47; found: 869.8

Step 6: Synthesis of ($6^3$S,4S,Z)-4-amino-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione To a stirred solution of tert-butyl (($6^3$S,4S,Z)-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (900 mg, 1.035 mmol) in DCM (9 mL) was added TFA (3 mL) dropwise at 0° C. The resulting mixture was stirred for 2 h at room temperature. The mixture was basified to pH=8 with sat. aq. $NaHCO_3$. and extracted with EtOAc (3×100 mL). The combined organic layers were washed with brine (3×50 mL), dried over anhydrous $Na_2SO_4$. After filtration, the filtrate was concentrated under reduced pressure to afford the product (800 mg), which was used in the next step directly without further purification. LCMS (ESI) m/z [M+H] calcd for $C_{42}H_{56}N_8O_4S$: 769.42; found: 769.5

Intermediate 10: Synthesis of ($6^3$S,4S)-4-amino-$1^2$-(5-((S)-hexahydropyrazino[2,1-c][1,4]oxazin-8(1H)-yl)-2-((S)-1-methoxyethyl)pyridin-3-yl)-10,10-dimethyl-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-5,7-dione

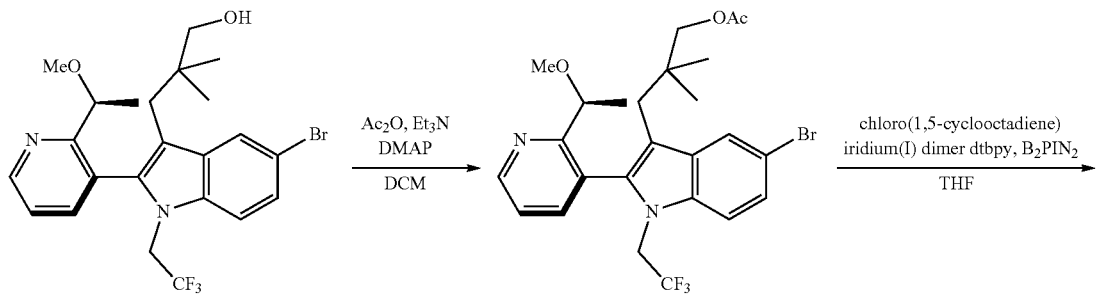

231 232
-continued
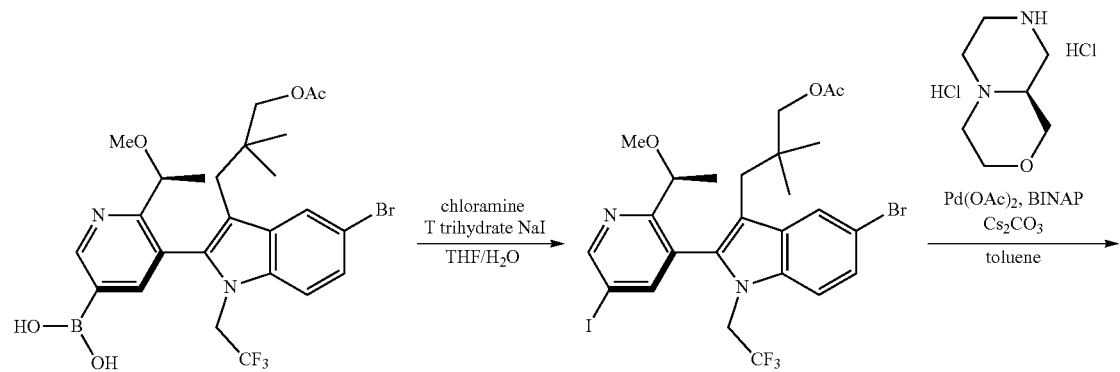
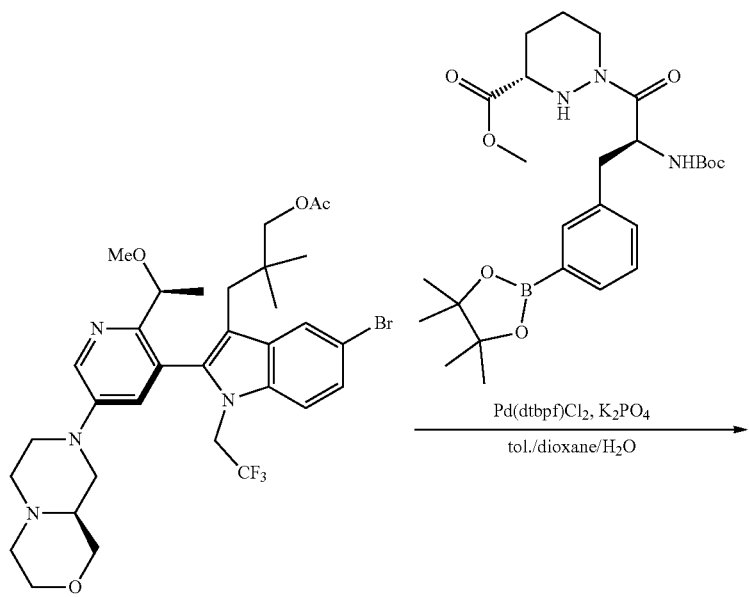
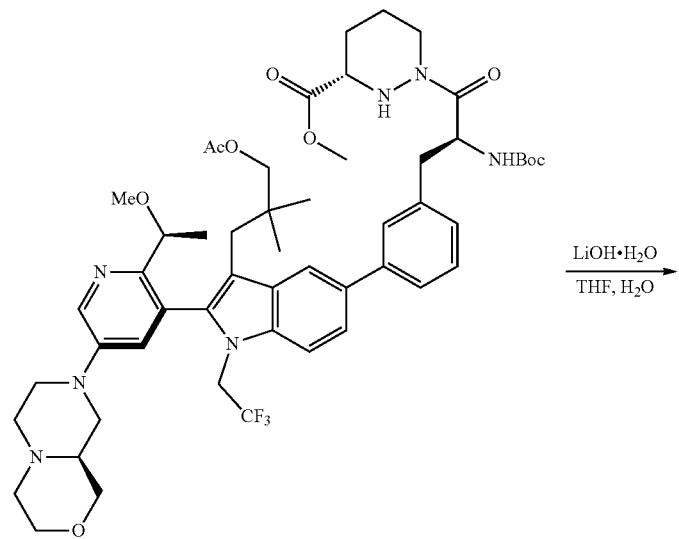

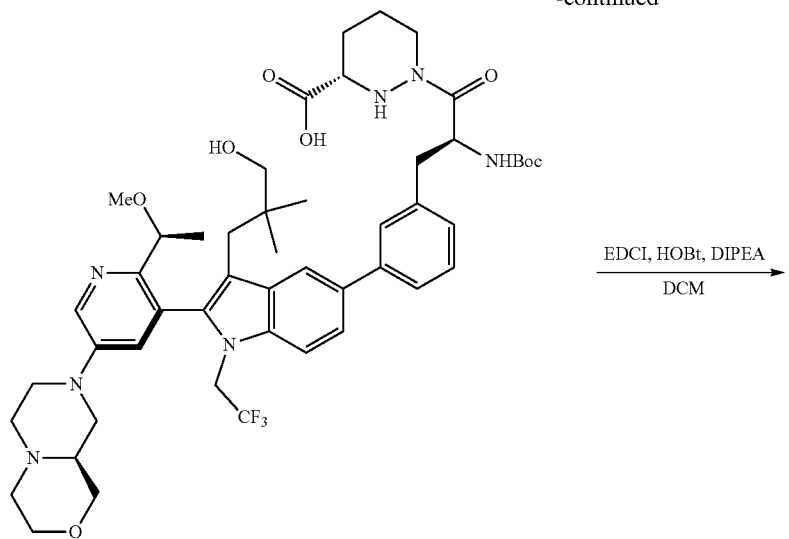
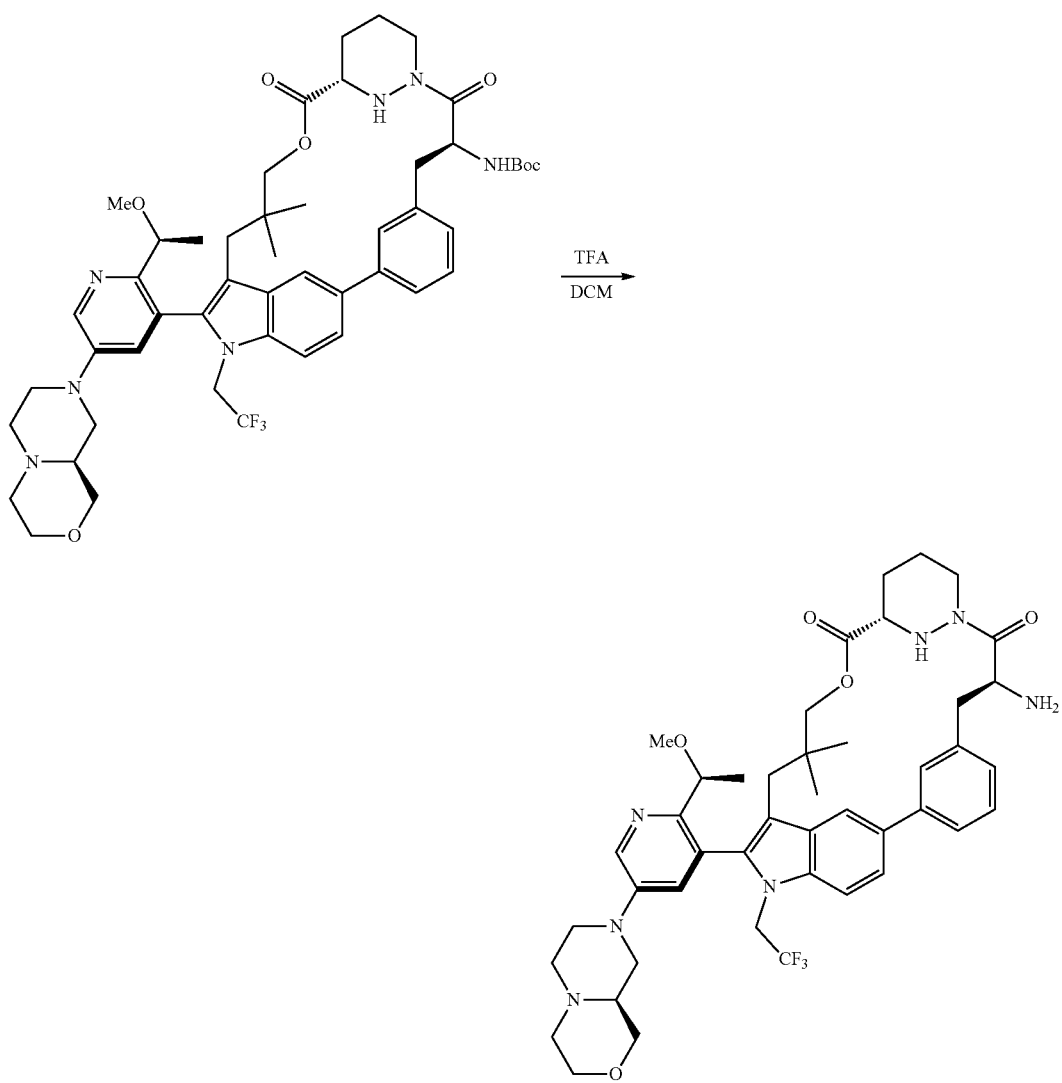

Step 1: Synthesis of (S)-3-(5-bromo-2-(2-(1-methoxyethyl)pyridin-3-yl)-1-(2,2,2-trifluoroethyl)-1H-indol-3-yl)-2,2-dimethylpropyl acetate To a stirred solution of (S)-3-(5-bromo-2-(2-(1-methoxyethyl)pyridin-3-yl)-1-(2,2,2-trifluoroethyl)-1H-indol-3-yl)-2,2-dimethylpropan-1-ol (60 g, 0.12 mol) and Et$_3$N (24.33 g, 0.24 mol) in DCM (600 mL) were added DMAP (1.46 g, 0.012 mol) and acetic anhydride (14.7 g, 144 mmol) dropwise at 0° C. under an argon atmosphere. The resulting mixture was stirred for 2 h at room temperature. The resulting mixture was concentrated under reduced pressure and washed with of HCl (500 mL). The resulting mixture was washed with of sat. aq. NaHCO$_3$ (500 mL). The combined organic layers were washed with brine (500 mL), dried over anhydrous Na$_2$SO$_4$. After filtration, the filtrate was concentrated under reduced pressure to afford the product (59.6 g, 92% yield) as a n oil. LCMS (ESI) m/z [M+H] calcd C$_{25}$H$_{28}$BrF$_3$N$_2$O$_3$: 541.13; found: 543.2

Step 2: Synthesis of (S)-(5-(3-(3-acetoxy-2,2-dimethylpropyl)-5-bromo-1-(2,2,2-trifluoroethyl)-1H-indol-2-yl)-6-(1-methoxyethyl)pyridin-3-yl)boronic acid To a stirred mixture of (S)-3-(5-bromo-2-(2-(1-methoxyethyl)pyridin-3-yl)-1-(2,2,2-trifluoroethyl)-1H-indol-3-yl)-2,2-dimethylpropyl acetate (55.1 g, 101.771 mmol) and 4,4,5,5-tetramethyl-2-(tetramethyl-1,3,2-dioxaborolan-2-yl)-1,3,2-dioxaborolane (38.77 g, 152.656 mmol) in THF (40 mL) were added dtbpy (4.10 g, 15.266 mmol) and Chloro(1,5-cyclooctadiene)iridium(I) dimer (3.42 g, 5.089 mmol) in portions at room temperature under an argon atmosphere. The resulting mixture was stirred for 5 h at 75° C. The resulting mixture was concentrated under reduced pressure to afford the product (102.4 g, crude) as an oil. LCMS (ESI) m/z [M+H] calcd C$_{25}$H$_{29}$BBrF$_3$N$_2$O$_5$: 585.14; found: 585.2

Step 3: Synthesis of (S)-3-(5-bromo-2-(5-iodo-2-(1-methoxyethyl)pyridin-3-yl)-1-(2,2,2-trifluoroethyl)-1H-indol-3-yl)-2,2-dimethylpropyl acetate To a stirred solution of (S)-(5-(3-(3-acetoxy-2,2-dimethylpropyl)-5-bromo-1-(2,2,2-trifluoroethyl)-1H-indol-2-yl)-6-(1-methoxyethyl)pyridin-3-yl)boronic acid (51.2 g, 87.487 mmol) and sodium chloro[(4-methylbenzene)sulfonyl]azanide (197 g, 699.896 mmol) in THF (258 mL) was added NaI (104.91 g, 699.896 mmol) in H$_2$O (129 mL) dropwise at 0° C. under an argon atmosphere. The resulting mixture was stirred for 16 h at 55° C. The resulting mixture was concentrated under reduced pressure and extracted with CH$_3$Cl (2×200 mL). The combined organic layers were washed with brine (2×20 mL), dried over anhydrous Na$_2$SO$_4$. After filtration, the filtrate was concentrated under reduced pressure. The residue was purified by silica gel column chromatography (20% EtOAc/pet. ether) to afford the product (15.3 g, 26% yield) as a solid. LCMS (ESI) m/z [M+H] calcd C$_{32}$H$_{40}$BrF$_3$N$_4$O$_4$: 666.0; found: 667.3

Step 4: Synthesis of methyl (S)-1-((S)-3-(3-(3-(3-acetoxy-2,2-dimethylpropyl)-2-(5-((S)-hexahydropyrazino[2,1-c][1,4]oxazin-8(1 H)-yl)-2-((S)-1-methoxyethyl)pyridin-3-yl)-1-(2,2,2-trifluoroethyl)-1H-indol-5-yl)phenyl)-2-((tert-butoxycarbonyl)amino)propanoyl)hexahydropyridazine-3-carboxylate To a stirred mixture of (S)-3-(5-bromo-2-(5-iodo-2-(1-methoxyethyl)pyridin-3-yl)-1-(2,2,2-trifluoroethyl)-1H-indol-3-yl)-2,2-dimethylpropyl acetate (2.70 g, 4.046 mmol) and (S)-octahydropyrazino[2,1-c][1,4]oxazine dihydrochloride (1.044 g, 4.855 mmol) in toluene(18.9 mL) was added Cs$_2$CO$_3$ (5932.38 mg, 18.207 mmol) and BINAP (125.97 mg, 0.202 mmol) in portions at room temperature under an argon atmosphere. To the above mixture was added Pd(OAc)$_2$ (90.84 mg, 0.405 mmol) in portions. The resulting mixture was stirred for additional 16 h at 90° C. The mixture was cooled to room temperature then filtered, the filter cake was washed with EtOAc (2×20 mL). The filtrate was concentrated under reduced pressure. The residue was purified by silica gel column chromatography (10% MeOH/DCM) to afford the product (2.3 g, 83% yield) as a solid. LCMS (ESI) m/z [M+H] calcd C$_{32}$H$_{40}$BrF$_3$N$_4$O$_4$: 681.23; found: 681.4

Step 5: Synthesis of methyl (S)-1-((S)-3-(3-(3-(3-acetoxy-2,2-dimethylpropyl)-2-(5-((S)-hexahydropyrazino[2,1-c][1,4]oxazin-8(1 H)-yl)-2-((S)-1-methoxyethyl)pyridin-3-yl)-1-(2,2,2-trifluoroethyl)-1H-indol-5-yl)phenyl)-2-((tert-butoxycarbonyl)amino)propanoyl)hexahydropyridazine-3-carboxylate Into a 250 mL 3-necked round-bottom flask was added methyl (S)-1-((S)-3-(3-(3-(3-acetoxy-2,2-dimethylpropyl)-2-(5-((S)-hexahydropyrazino[2,1-c][1,4]oxazin-8(1 H)-yl)-2-((S)-1-methoxyethyl)pyridin-3-yl)-1-(2,2,2-trifluoroethyl)-1H-indol-5-yl)phenyl)-2-((tert-butoxycarbonyl)amino)propanoyl)hexahydropyridazine-3-carboxylate (2.33 g, 4.512 mmol) and K$_3$PO$_4$ (1.59 g, 7.490 mmol) at room temperature under an air atmosphere. To a stirred mixture of H$_2$O (8.20 mL), and dioxane (8.20 mL) in toluene was added Pd(dtbpf)Cl$_2$ (0.29 g, 0.451 mmol) in portions at room temperature. The resulting mixture was stirred for 3 h at 65° C. The resulting mixture was filtered, the filter cake was washed with EtOAc (2×100 mL). The filtrate was concentrated under reduced pressure. The resulting mixture was extracted with EtOAc (2×100 mL). The combined organic layers were washed with brine (2×150 mL), dried over anhydrous Na$_2$SO$_4$. After filtration, the filtrate was concentrated under reduced pressure. The residue was purified by silica gel column chromatography (3→4% MeOH/DCM) to afford the product (2.7 g, 90% yield) as a solid. LCMS (ESI) m/z [M+H] calcd C$_{52}$H$_{68}$F$_3$N$_7$O$_9$: 991.5; found: 992.7

Step 6: Synthesis of (S)-1-((S)-2-((tert-butoxycarbonyl)amino)-3-(3-(2-(5-((S)-hexahydropyrazino[2,1-c][1,4]oxazin-8(1 H)-yl)-2-((S)-1-methoxyethyl)pyridin-3-yl)-3-(3-hydroxy-2,2-dimethylpropyl)-1-(2,2,2-trifluoroethyl)-1H-indol-5-yl)phenyl)propanoyl)hexahydropyridazine-3-carboxylic acid Into a 100 mL 3-necked round-bottom flask were added methyl (S)-1-((S)-3-(3-(3-(3-acetoxy-2,2-dimethylpropyl)-2-(5-((S)-hexahydropyrazino[2,1-c][1,4]oxazin-8(1 H)-yl)-2-((S)-1-methoxyethyl)pyridin-3-yl)-1-(2,2,2-trifluoroethyl)-1H-indol-5-yl)phenyl)-2-((tert-butoxycarbonyl)amino)propanoyl)hexahydropyridazine-3-carboxylate (3 g, 3.024 mmol) and THF (30 mL) at room temperature. Followed by LiOH (0.30 g, 12.701 mmol) in H$_2$O (12.7 mL) in portions at 0° C. The resulting mixture was stirred for 16 h at room temperature. The mixture was acidified to pH 5 with 1 N HCl. The resulting mixture was extracted with EtOAc (2×100 mL). The combined organic layers were washed with brine (2×100 mL), dried over anhydrous Na$_2$SO$_4$. After filtration, the filtrate was concentrated under reduced pressure to afford the product (2.7 g, crude) as a solid. LCMS (ESI) m/z [M+H] calcd for $C_{49}H_{64}F_3N_7O_8$: 936.48; found: 936.7

Step 7: synthesis of tert-butyl ((6$^3$S,4S)-12-(5-((S)-hexahydropyrazino[2,1-c][1,4]oxazin-8(1H)-yl)-2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)carbamate Into a 2 L 3-necked round-bottom flask were added (S)-1-((S)-2-((tert-butoxycarbonyl)amino)-3-(3-(2-(5-((S)-hexahydropyrazino[2,1-c][1,4]oxazin-8(1H)-yl)-2-((S)-1-methoxyethyl)pyridin-3-yl)-3-(3-hydroxy-2,2-dimethylpropyl)-1-(2,2,2-trifluoroethyl)-1H-indol-5-yl)phenyl)propanoyl)hexahydropyridazine-3-carboxylic acid (3.12 g, 3.333 mmol) and DCM (624 mL) at room temperature. To the above mixture was added DIPEA (17.23 g, 133.320 mmol) and HOBt (4.50 g, 33.330 mmol) in portions at 0° C. The resulting mixture was stirred for additional 30 min. To the above mixture was added EDCI (19.17 g, 99.990 mmol) in portions over 16 h at room temperature. The resulting mixture was concentrated under reduced pressure. The reaction was quenched with $H_2O$ at 0° C. The resulting mixture was extracted with EtOAc (3×100 mL). The combined organic layers were washed with brine (3×100 mL), dried over anhydrous $Na_2SO_4$. After filtration, the filtrate was concentrated under reduced pressure. The residue was purified by silica gel column chromatography (3→4% MeOH/DCM) to afford the product (3 g, 98% yield) as a solid. LCMS (ESI) m/z [M+H] calcd $C_{49}H_{62}F_3N_7O_7$: 918.47; found: 918.8

Step 8: Synthesis of (6$^3$S,4S)-4-amino-1$^2$-(5-((S)-hexahydropyrazino[2,1-c][1,4]oxazin-8(1H)-yl)-2-((S)-1-methoxyethyl)pyridin-3-yl)-10,10-dimethyl-1$^1$-(2,2,2-trifluoroethyl)-6$^1$,6$^2$,6$^3$,6$^4$,6$^5$,6$^6$-hexahydro-1 $^1$H-8-oxa-1(5,3)-indola-6(1,3)-pyridazina-2(1,3)-benzenacycloundecaphane-5,7-dione To a stirred solution of tert-butyl ((6$^3$S,4S)-12-(5-((S)-hexahydropyrazino[2,1-c][1,4]oxazin-8(1H)-yl)-2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)carbamate (930 mg, 1.013 mmol) in DCM (15 mL) was added TFA (5 mL, 67.315 mmol) dissolved in DCM (5 mL) dropwise at 0° C. under an argon atmosphere. The resulting mixture was stirred for 2 h at 0° C. The residue was basified to pH 8 with sat. aq. $NaHCO_3$. The resulting mixture was extracted with DCM, the combined organic layers were washed with brine, dried over anhydrous $Na_2SO_4$. After filtration, the filtrate was concentrated under reduced pressure to afford the product (880 mg, crude) as a solid. LCMS (ESI) m/z [M+H] calcd for $C_{44}H_{54}F_3N_7O_5$: 818.42; found: 818.6

Intermediate 11: Synthesis of (6$^3$S,4S)-4-amino-12-(2-((S)-1-methoxyethyl)-5-((R)-octahydro-2H-pyrido[1,2-a]pyrazin-2-yl)pyridin-3-yl)-10,10-dimethyl-1$^1$-(2,2,2-trifluoroethyl)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-5,7-dione

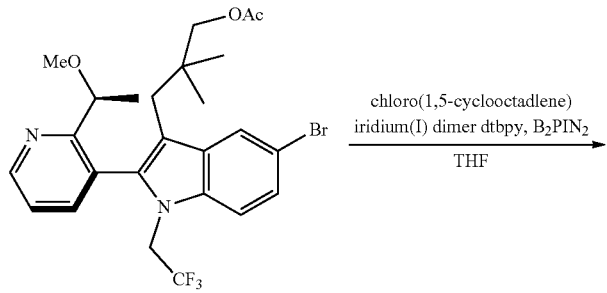

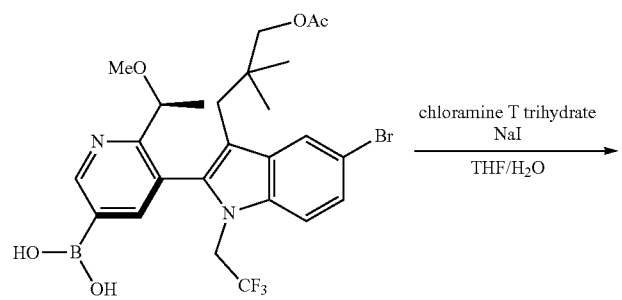

-continued
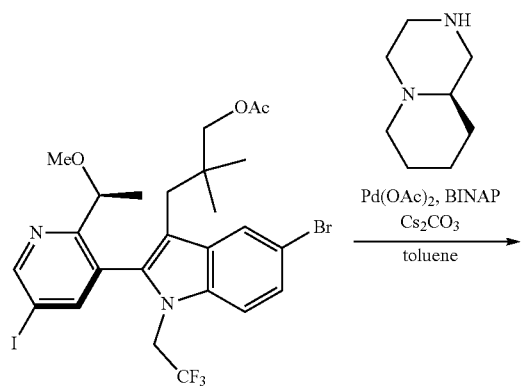
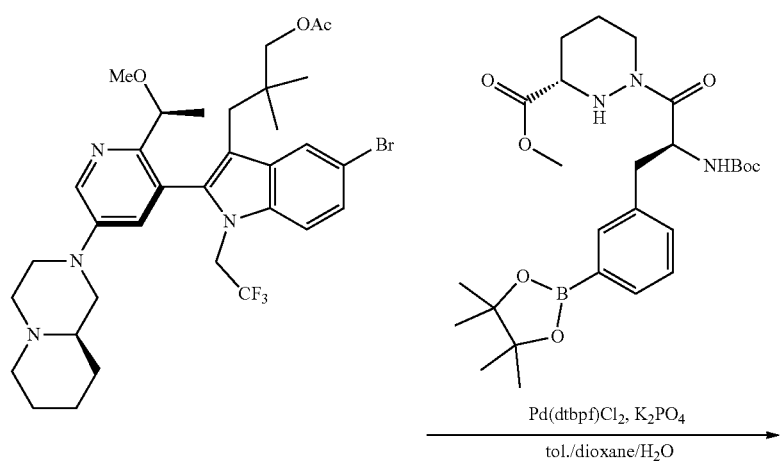
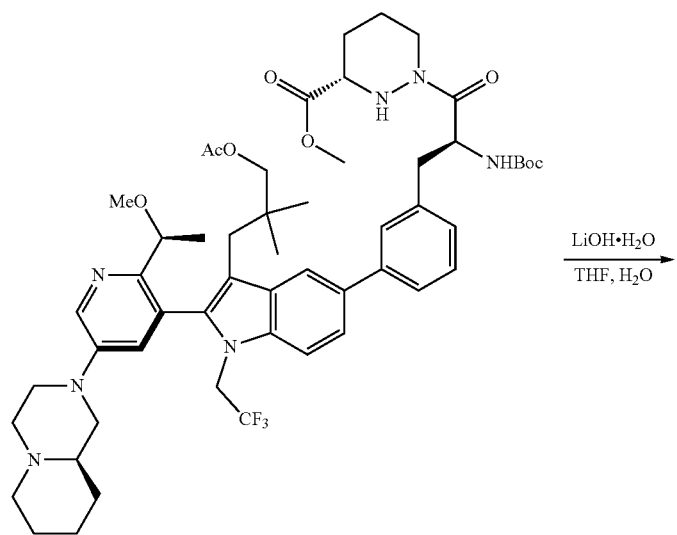

-continued
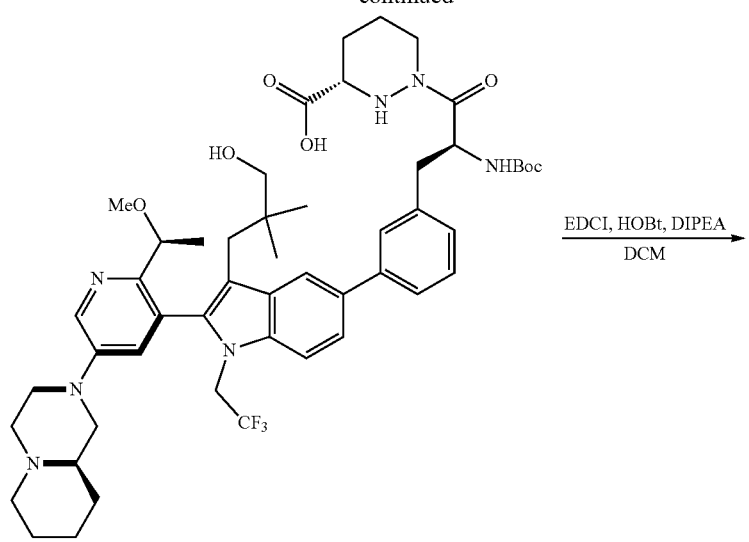
EDCI, HOBt, DIPEA
―――――――――→
DCM
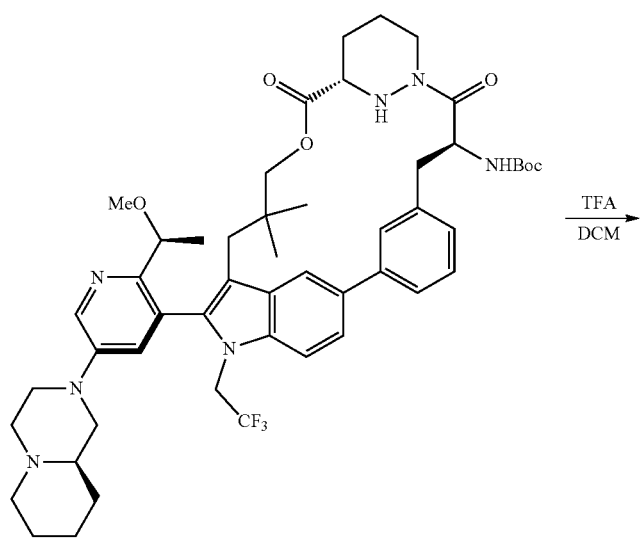
TFA
――→
DCM
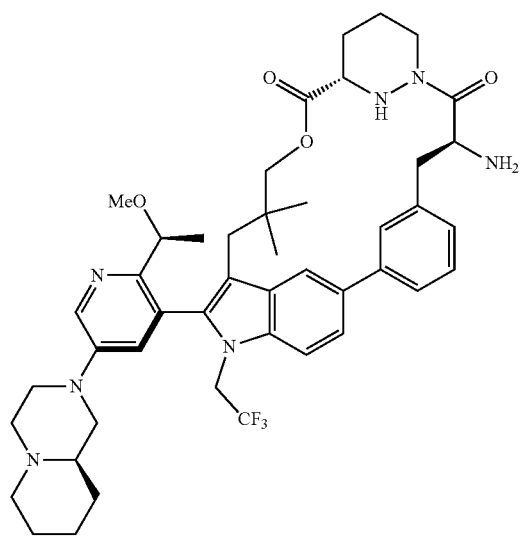

Step 1: Synthesis of (S)-(5-(3-(3-acetoxy-2,2-dimethylpropyl)-5-bromo-1-(2,2,2-trifluoroethyl)-1H-indol-2-yl)-6-(1-methoxyethyl)pyridin-3-yl)boronic acid Into a 100 mL 3-necked round-bottom flask were added 3-(5-bromo-2-{2-[(1S)-1-methoxyethyl]pyridin-3-yl}-1-(2,2,2-trifluoroethyl)indol-3-yl)-2,2-dimethylpropyl acetate (10 g, 18.470 mmol), 4,4,5,5-tetramethyl-2-(tetramethyl-1,3,2-dioxaborolan-2-yl)-1,3,2-dioxaborolane (8.44 g, 33.25 mmol) and dtbpy (0.89 g, 3.325 mmol) at room temperature. To the above mixture was added chloro(1,5-cyclooctadiene)iridium(I) dimer (0.74 g, 1.108 mmol) and THF (40 mL). The resulting mixture was stirred for additional 16 h at 80° C. The resulting mixture was concentrated under reduced pressure. The crude product was used in the next step directly without further purification. LCMS (ESI) m/z [M+H] calcd for $C_{25}H_{29}BBrF_3N_2O_5$: 585.14; found: 585.0

Step 2: Synthesis of (S)-3-(5-bromo-2-(5-iodo-2-(1-methoxyethyl)pyridin-3-yl)-1-(2,2,2-trifluoroethyl)-1H-indol-3-yl)-2,2-dimethylpropyl acetate To a stirred solution of (S)-(5-(3-(3-acetoxy-2,2-dimethylpropyl)-5-bromo-1-(2,2,2-trifluoroethyl)-1H-indol-2-yl)-6-(1-methoxyethyl)pyridin-3-yl)boronic acid (17.9 g, 30.586 mmol) in THF (89.5 mL,) were added sodium chloro[(4-methylbenzene)sulfonyl]azanide (68.93 g, 244.688 mmol) and NaI (36.68 g, 244.688 mmol) in $H_2O$ (44.75 mL) dropwise at 0° C. under a nitrogen atmosphere. The resulting mixture was stirred for additional 20 min at room temperature then heated to 50° C. for 16 h. The resulting mixture was concentrated under reduced pressure and washed with $CHCl_3$ (300 mL). After filtration, the filter cake was washed with $CHCl_3$ (3×100 mL). The filtrate was extracted with $CHCl_3$ (3×200 mL). The combined organic layers were washed with $Na_2S_2O_3$ (300 mL), and brine (2×150 mL), dried over anhydrous $Na_2SO_4$. After filtration, the filtrate was concentrated under reduced pressure. The residue was purified by silica gel column chromatography (16% EtOAc/pet. ether) to afford the product (6.6 g, 32% yield) as a solid. LCMS (ESI) m/z [M+H] calcd for $C_{25}H_{27}BrF_3IN_2O_3$: 667.03; found: 668.7

Step 3: Synthesis of 3-(5-bromo-2-(2-((S)-1-methoxyethyl)-5-((R)-octahydro-2H-pyrido[1,2-a]pyrazin-2-yl)pyridin-3-yl)-1-(2,2,2-trifluoroethyl)-1H-indol-3-yl)-2,2-dimethylpropyl acetate To a stirred mixture of (S)-3-(5-bromo-2-(5-iodo-2-(1-methoxyethyl)pyridin-3-yl)-1-(2,2,2-trifluoroethyl)-1H-indol-3-yl)-2,2-dimethylpropyl acetate (1.4 g, 2.098 mmol) and (R)-octahydro-2H-pyrido[1,2-a]pyrazine (353.04 mg, 2.518 mmol) in toluene (10 mL) was added $Cs_2CO_3$ (3076.05 mg, 9.441 mmol), BINAP (65.32 mg, 0.105 mmol) and Pd(OAc)$_2$ (47.10 mg, 0.210 mmol). The resulting mixture was stirred overnight at 90° C. under an argon atmosphere. The reaction was quenched with $H_2O$ (100 mL). The resulting mixture was extracted with DCM (3×100 mL). The combined organic layers were washed with $H_2O$ (3×100 mL), dried over anhydrous $Na_2SO_4$. After filtration, the filtrate was concentrated under reduced pressure. The residue was purified by silica gel column chromatography (5% MeOH/DCM) to afford the product (1 g, 49% yield) as an oil. LCMS (ESI) m/z [M+H] calcd for $C_{33}H_{42}BrF_3N_4O_3$: 679.25; found: 679.5

Step 4: Synthesis of methyl (S)-1-((S)-3-(3-(3-acetoxy-2,2-dimethylpropyl)-2-(2-((S)-1-methoxyethyl)-5-((R)-octahydro-2H-pyrido[1,2-a]pyrazin-2-yl)pyridin-3-yl)-1-(2,2,2-trifluoroethyl)-1H-indol-5-yl)phenyl)-2-((tert-butoxycarbonyl)amino)propanoyl)hexahydropyridazine-3-carboxylate To a stirred mixture of 3-(5-bromo-2-(2-((S)-1-methoxyethyl)-5-((R)-octahydro-2H-pyrido[1,2-a]pyrazin-2-yl)pyridin-3-yl)-1-(2,2,2-trifluoroethyl)-1H-indol-3-yl)-2,2-dimethylpropyl acetate (1 g, 1.471 mmol) and methyl (S)-1-((S)-2-((tert-butoxycarbonyl)amino)-3-(3-(4,4,5,5-tetramethyl-1,3,2-dioxaborolan-2-yl)phenyl)propanoyl)hexahydropyridazine-3-carboxylate (913.62 mg, 1.765 mmol) in toluene (9 mL) were added dioxane (6 mL), $H_2O$ (3 mL), $K_3PO_4$ (780.82 mg, 3.678 mmol) and Pd(dtbpf)Cl$_2$ (95.90 mg, 0.147 mmol), the resulting mixture was stirred for 2 h at 70° C. under a nitrogen atmosphere. The mixture was basified to pH 8 with sat. aq. NaHCO$_3$. The resulting mixture was extracted with DCM (3×30 mL). The combined organic layers were washed with $H_2O$ (3×30 mL), dried over anhydrous $Na_2SO_4$. After filtration, the filtrate was concentrated under reduced pressure. The residue was purified by silica gel column chromatography (20% EtOAc/pet. ether) to afford the product (1.2 g, 74% yield) as a solid. LCMS (ESI) m/z [M+H] calcd for $C_{53}H_{70}F_3N_7O_8$: 990.53; found: 990.8

Step 5: Synthesis of (S)-1-((S)-2-((tert-butoxycarbonyl)amino)-3-(3-(3-(3-hydroxy-2,2-dimethylpropyl)-2-(2-((S)-1-methoxyethyl)-5-((R)-octahydro-2H-pyrido[1,2-a]pyrazin-2-yl)pyridin-3-yl)-1-(2,2,2-trifluoroethyl)-1H-indol-5-yl)phenyl)propanoyl)hexahydropyridazine-3-carboxylic acid To a stirred mixture of methyl (S)-1-((S)-3-(3-(3-(3-acetoxy-2,2-dimethylpropyl)-2-(2-((S)-1-methoxyethyl)-5-((R)-octahydro-2H-pyrido[1,2-a]pyrazin-2-yl)pyridin-3-yl)-1-(2,2,2-trifluoroethyl)-1H-indol-5-yl)phenyl)-2-((tert-butoxycarbonyl)amino)propanoyl)hexahydropyridazine-3-carboxylate (1.2 g, 1.212 mmol) and LiOH (252 mg, 10.523 mmol) in THF (6 mL) was added $H_2O$ (6 mL) in portions at 0° C. The resulting mixture was stirred overnight at 0° C. The mixture was acidified to pH 7 with 1 N HCl (aq.). The aqueous layer was extracted with DCM (3×30 mL). The combined organic layers were washed with $H_2O$ (30 mL), dried over anhydrous $Na_2SO_4$. After filtration, the filtrate was concentrated under reduced pressure to afford the product (1.2 g, 84% yield) as a solid. LCMS (ESI) m/z [M+H] calcd for $C_{50}H_{66}F_3N_7O_7$: 934.51; found: 935.0

Step 6: Synthesis of tert-butyl ((6$^3$S,4S)-12-(2-((S)-1-methoxyethyl)-5-((R)-octahydro-2H-pyrido[1,2-a]pyrazin-2-yl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)carbamate To a stirred mixture of (S)-1-((S)-2-((tert-butoxycarbonyl)amino)-3-(3-(3-(3-hydroxy-2,2-dimethylpropyl)-2-(2-((S)-1-methoxyethyl)-5-((R)-octahydro-2H-pyrido[1,2-a]pyrazin-2-yl)pyridin-3-yl)-1-(2,2,2-trifluoroethyl)-1H-indol-5-yl)phenyl)propanoyl)hexahydropyridazine-3-carboxylic acid (1.2 g, 1.285 mmol) and DIPEA (7.83 mL, 44.975 mmol) in DCM (100 mL) were added HOBt (0.87 g, 6.425 mmol) and EDCI•HCl (5.58 g, 35.980 mmol) in portions at 0° C. The resulting mixture was stirred overnight at 0° C. The mixture was diluted with DCM (30 mL). The combined organic layers were washed with H₂O (3×30 mL), dried over anhydrous Na₂SO₄. After filtration, the filtrate was concentrated under reduced pressure. The residue was purified by silica gel column chromatography (5% MeOH/DCM) to afford the product (850 mg, 65% yield) as a solid. LCMS (ESI) m/z [M+H] calcd for C₅₀H₆₄F₃N₇O₆: 916.49; found: 917.0

Step 7: Synthesis of (6³S,4S)-4-amino-12-(2-((S)-1-methoxyethyl)-5-((R)-octahydro-2H-pyrido[1,2-a]pyrazin-2-yl)pyridin-3-yl)-10,10-dimethyl-1¹-(2,2,2-trifluoroethyl)-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione To a stirred mixture tert-butyl ((6³S,4S)-12-(2-((S)-1-methoxyethyl)-5-((R)-octahydro-2H-pyrido[1,2-a]pyrazin-2-yl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate (1000 mg, 1.092 mmol) in DCM (4 mL) was added TFA (4 mL) at 0° C. The resulting mixture was stirred for 1 h at 0° C. under a nitrogen atmosphere. The resulting mixture was concentrated under reduced pressure. The residue was basified to pH 8 with sat. aq. NaHCO₃. The aqueous layer was extracted with DCM (3×30 mL). The combined organic layers dried over anhydrous Na₂SO₄. After filtration, the filtrate was concentrated under reduced pressure to afford the product (800 mg, 80% yield) as a solid. LCMS (ESI) m/z [M+H] calcd for C₄₅H₅₆F₃N₇O₄: 816.44 found: 816.6

Intermediate 12: Synthesis of (6³S,4S)-4-amino-1¹-ethyl-1²-(5-((S)-hexahydropyrazino[2,1-c][1,4]oxazin-8(1H)-yl)-2-((S)-1-methoxyethyl)pyridin-3-yl)-10,10-dimethyl-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione

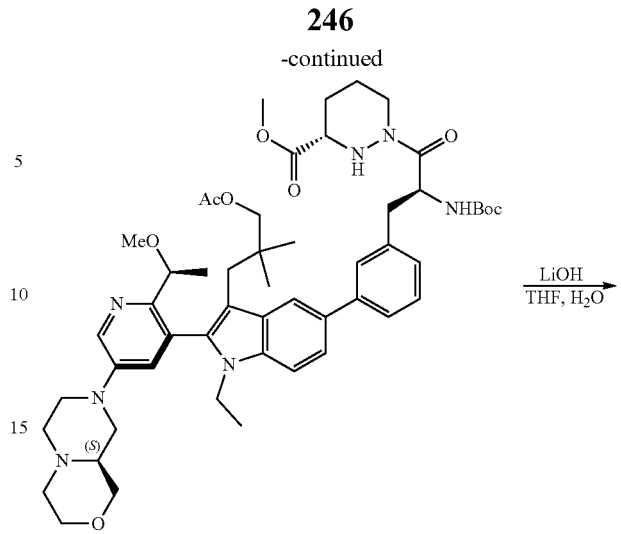

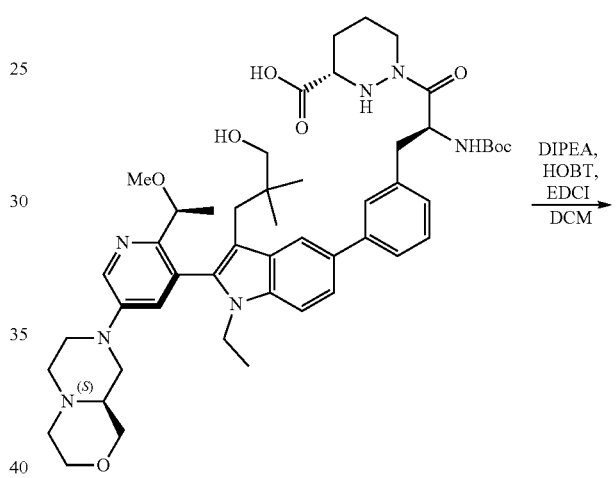

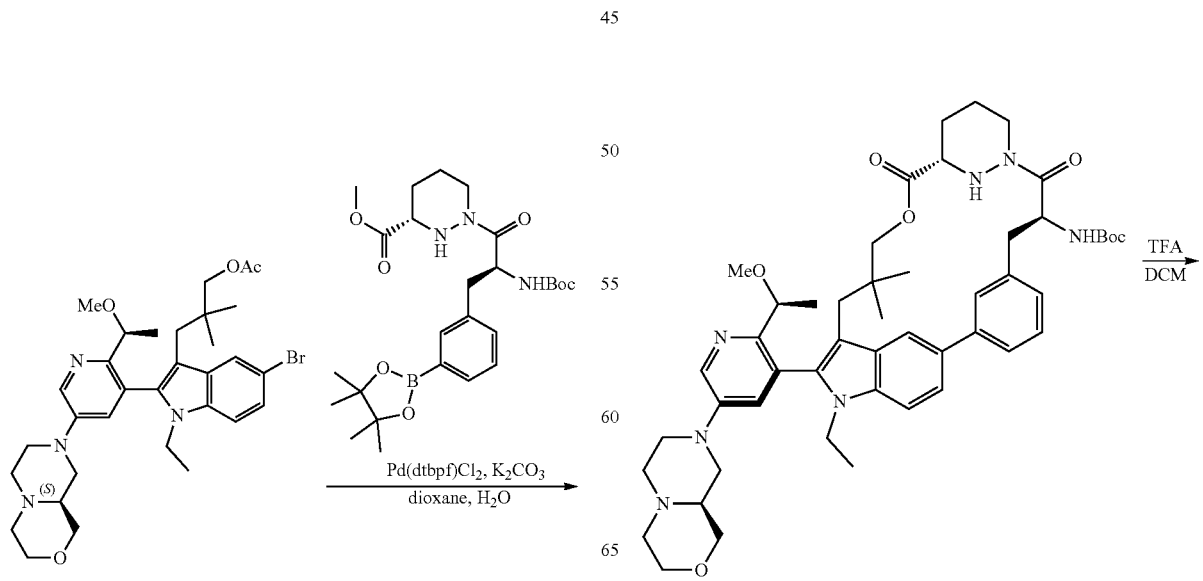

-continued

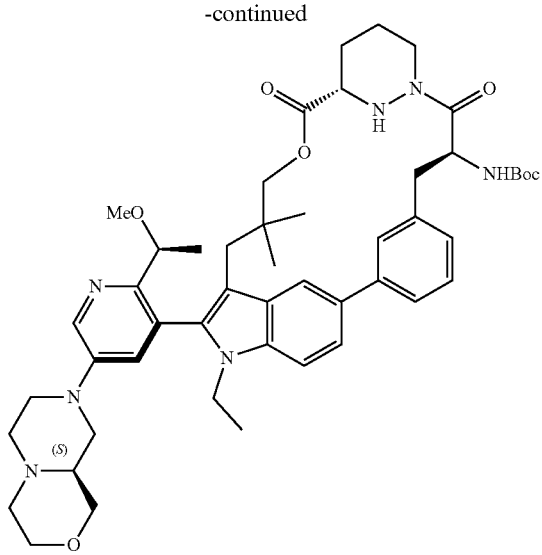

Step 1: Synthesis of methyl (S)-1-((S)-3-(3-(3-(3-acetoxy-2,2-dimethylpropyl)-1-ethyl-2-(5-((S)-hexahydropyrazino[2,1-c][1,4]oxazin-8(1 H)-yl)-2-((S)-1-methoxyethyl)pyridin-3-yl)-1H-indol-5-yl)phenyl)-2-((tert-butoxycarbonyl)amino)propanoyl)hexahydropyridazine-3-carboxylate Into a 500 mL 3-necked round-bottom flask were added 3-(5-bromo-1-ethyl-2-(5-((S)-hexahydropyrazino[2,1-c][1,4]oxazin-8(1 H)-yl)-2-((S)-1-methoxyethyl)pyridin-3-yl)-1H-indol-3-yl)-2,2-dimethylpropyl acetate (14.2 g, 22.625 mmol), methyl (S)-1-((S)-2-((tert-butoxycarbonyl)amino)-3-(3-(4,4,5,5-tetramethyl-1,3,2-dioxaborolan-2-yl)phenyl)propanoyl)hexahydropyridazine-3-carboxylate (17.56 g, 33.938 mmol), H$_2$O (30 mL,) in dioxane (150 mL), Pd(dtbpf)Cl$_2$ (1.47 g, 2.263 mmol) at room temperature under an argon atmosphere. The resulting mixture was stirred for 3 h at 65° C. and then cooled to room temperature. The mixture was filtered, the filter cake was washed with EtOAc (2×200 mL). The filtrate was concentrated under reduced pressure and was then extracted with EtOAc (2×200 mL). The combined organic layers were washed with brine (2×250 mL) and dried over anhydrous Na$_2$SO$_4$. After filtration, the filtrate was concentrated under reduced pressure. The residue was purified by silica gel column chromatography (3→4% MeOH/DCM) to afford the product (17.2 g, 81% yield) as a solid. LCMS (ESI) m/z [M+H] calcd for C$_{52}$H$_{71}$N$_7$O$_9$: 938.54; found: 938.8

Step 2: Synthesis of (S)-1-((S)-2-((tert-butoxycarbonyl)amino)-3-(3-(1-ethyl-2-(5-((S)-hexahydropyrazino[2,1-c][1,4]oxazin-8(1 H)-yl)-2-((S)-1-methoxyethyl)pyridin-3-yl)-3-(3-hydroxy-2,2-dimethylpropyl)-1H-indol-5-yl)phenyl)propanoyl)hexahydropyridazine-3-carboxylic acid Into a 250 mL 3-necked round-bottom flask were added methyl (S)-1-((S)-3-(3-(3-(3-acetoxy-2,2-dimethylpropyl)-1-ethyl-2-(5-((S)-hexahydropyrazino[2,1-c][1,4]oxazin-8(1 H)-yl)-2-((S)-1-methoxyethyl)pyridin-3-yl)-1H-indol-5-yl)phenyl)-2-((tert-butoxycarbonyl)amino)propanoyl)hexahydropyridazine-3-carboxylate (17.2 g, 18.33 mmol) and THF (175 mL) at room temperature. To a stirred mixture of LiOH (1.88 g, 78.343 mmol) in H$_2$O (78.34 mL, 4348.526 mmol) in portions at 0° C. The resulting mixture was stirred for 16 h at room temperature. The mixture was acidified to pH 5 with 1 N HCl. The resulting mixture was extracted with EtOAc (2×200 mL). The combined organic layers were washed with brine (2×200 mL), dried over anhydrous Na$_2$SO$_4$. After filtration, the filtrate was concentrated under reduced pressure. The crude mixture (17 g, crude) as a solid was used in the next step directly without further purification. LCMS (ESI) m/z [M+H] calcd for C$_{49}$H$_{67}$N$_7$O$_8$: 882.51; found: 882.8.

Step 3: Synthesis of tert-butyl ((6$^3$S,4S)-1$^1$-ethyl-1$^2$-(5-((S)-hexahydropyrazino[2,1-c][1,4]oxazin-8(1 H)-yl)-2-((S)-1-methoxyethyl)pyridin-3-yl)-10,10-dimethyl-5,7-dioxo-6$^1$,6$^2$,6$^3$,6$^4$,6$^5$,6$^6$-hexahydro-11H-8-oxa-1(5,3)-indola-6(1,3)-pyridazina-2(1,3)-benzenacycloundecaphane-4-yl)carbamate Into a 5 L 3-necked round-bottom flask were added (S)-1-((S)-2-((tert-butoxycarbonyl)amino)-3-(3-(1-ethyl-2-(5-((S)-hexahydropyrazino[2,1-c][1,4]oxazin-8(1 H)-yl)-2-((S)-1-methoxyethyl)pyridin-3-yl)-3-(3-hydroxy-2,2-dimethylpropyl)-1H-indol-5-yl)phenyl)propanoyl)hexahydropyridazine-3-carboxylic acid (16.8 g, 19.045 mmol) and DCM (2.52 L) at room temperature. To the above mixture was added DIPEA (98.46 g, 761.800 mmol) and HOBt (25.73 g, 190.450 mmol) in portions 0° C. The resulting mixture was stirred for additional 30 min at 0° C. Followed by the addition of EDCI (109.53 g, 571.350 mmol) in portions at 0° C. The mixture was stirred for 16 h at room temperature then concentrated under reduced pressure. The reaction was quenched with cold H$_2$O (500 mL) at 0° C. and extracted with EtOAc (3×500 mL). The combined organic layers were washed with brine (3×500 mL), dried over anhydrous Na$_2$SO$_4$.

After filtration, the filtrate was concentrated under reduced pressure and purified by silica gel column chromatography (3→4% MeOH/DCM) to afford the product (13.4 g, 81% yield) as a solid. LCMS (ESI) m/z [M+H] calcd for C$_{49}$H$_{65}$N$_7$O$_7$: 864.50; found: 864.8.

Step 4: Synthesis of (6$^3$S,4S)-4-amino-1$^1$-ethyl-1$^2$-(5-((S)-hexahydropyrazino[2,1-c][1,4]oxazin-8(1 H)-yl)-2-((S)-1-methoxyethyl)pyridin-3-yl)-10,10-dimethyl-6$^1$,6$^2$,6$^3$,6$^4$,6$^5$,6$^6$-hexahydro-1'H-8-oxa-1(5,3)-indola-6(1,3)-pyridazina-2(1,3)-benzenacycloundecaphane-5,7-dione Into a 100 mL round-bottom flask were added tert-butyl ((6$^3$S,4S)-11-ethyl-1$^2$-(5-((S)-hexahydropyrazino[2,1-c][1,4]oxazin-8(1 H)-yl)-2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)carbamatebutyl (300 mg, 0.347 mmol) and DCM (3 mL), TFA (1.5 mL) was added to the above solution at 0° C. After 1 h, the mixture was basified to pH 9 with sat. aq. NaHCO$_3$. The resulting mixture was extracted with DCM (3×50 mL). The combined organic layers were washed with brine (3×50 mL), dried over anhydrous Na$_2$SO$_4$. After filtration, the filtrate was concentrated under reduced pressure to afford the product (242 mg, crude) as a solid. The crude product was used in the next step directly without further purification. LCMS (ESI) m/z [M+H] calcd for C$_{44}$H$_{57}$N$_7$O$_5$: 764.45; found: 764.4

249

Intermediate 13: Synthesis of (6³S,4S)-4-amino-1¹-ethyl-1²-(2-((S)-1-methoxyethyl)-5-((R)-octahydro-2H-pyrido[1,2-a]pyrazin-2-yl)pyridin-3-yl)-10,10-dimethyl-6,6²,6³,6⁴,6⁵,6⁶-hexahydro-1¹H-8-oxa-1(5,3)-indola-6(1,3)-pyridazina-2(1,3)-benzenacycloundecaphane-5,7-dione

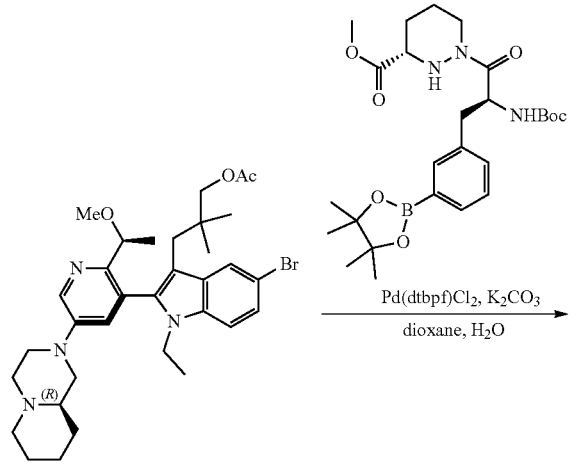

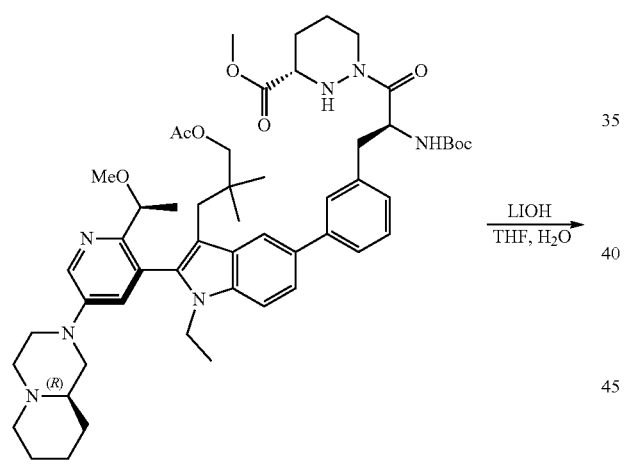

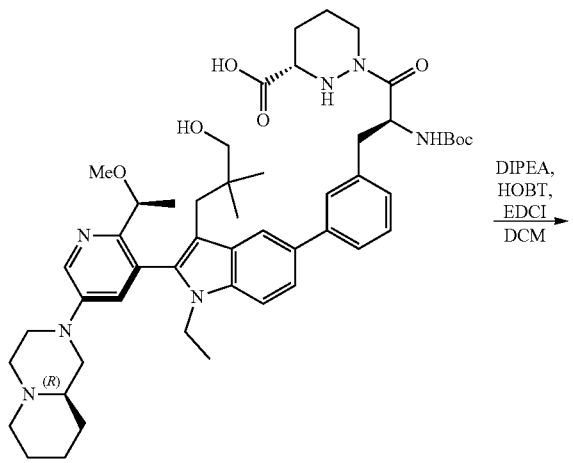

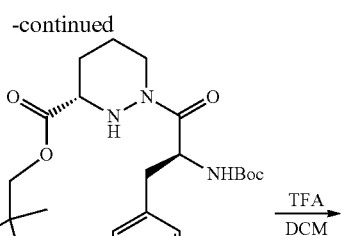

Step 1: Synthesis of methyl (S)-1-((S)-3-(3-(3-(3-acetoxy-2,2-dimethylpropyl)-1-ethyl-2-(2-((S)-1-methoxyethyl)-5-((R)-octahydro-2H-pyrido[1,2-a]pyrazin-2-yl)pyridin-3-yl)-1H-indol-5-yl)phenyl)-2-((tert-butoxycarbonyl)amino)propanoyl)hexahydropyridazine-3-carboxylate Into a 40 mL vial were added 3-(5-bromo-1-ethyl-2-(2-((S)-1-methoxyethyl)-5-((R)-octahydro-2H-pyrido[1,2-a]pyrazin-2-yl)pyridin-3-yl)-1H-indol-3-yl)-2,2-dimethylpropyl acetate (2 g, 3.196 mmol), methyl (3S)-1-[(2S)-2-[(tert-butoxycarbonyl)amino]-3-[3-(4,4,5,5-tetramethyl-1,3,2-dioxaborolan-2-yl)phenyl]propanoyl]-1,2-diazinane-3-carboxylate (1.98 g, 3.836 mmol) and H₂O (5 mL) in dioxane (20 mL) at room temperature. To the above mixture was added K₂CO₃ (883 mg, 6.392 mmol) and Pd(dtbpfCl₂ (208 mg, 0.32 mmol) in portions. The resulting mixture was stirred for additional 4 h at 65° C., then filtered, and the filter cake was washed with EtOAc (2×200 mL). The filtrate was concentrated under reduced pressure. The resulting mixture was extracted with EtOAc (3×100 mL). The combined organic layers were washed with brine (2×100 mL), dried over anhydrous Na₂SO₄. After filtration, the filtrate was concentrated under reduced pressure. The residue was purified by prep-TLC (50% MeOH/DCM) to afford the product (2.11 g, 70% yield) as a solid. LCMS (ESI) m/z [M+H] calcd for $C_{53}H_{73}N_7O_8$: 936.56; found: 936.7

Step 2: Synthesis of (S)-1-((S)-2-((tert-butoxycarbonyl)amino)-3-(3-(1-ethyl-3-(3-hydroxy-2,2-dimethylpropyl)-2-(2-((S)-1-methoxyethyl)-5-((R)-octahydro-2H-pyrido[1,2-a]pyrazin-2-yl)pyridin-3-yl)-1H-indol-5-yl)phenyl)propanoyl)hexahydropyridazine-3-carboxylic acid Into a 100 mL 3-necked round-bottom flask were added methyl (S)-1-((S)-3-(3-(3-(3-acetoxy-2,2-dimethylpropyl)-1-ethyl-2-(2-((S)-1-methoxyethyl)-5-((R)-octahydro-2H-pyrido[1,2-a]pyrazin-2-yl)pyridin-3-yl)-1H-indol-5-yl)phenyl)-2-((tert-butoxycarbonyl)amino)propanoyl)hexahydropyridazine-3-carboxylate (2.1 g, 2.245 mmol) and THF (21 mL) at room temperature. To the above mixture was added LiOH●$H_2O$ (283 mg, 6.735 mmol) in $H_2O$ (7 mL) in portions at 0° C. The resulting mixture was stirred overnight at room temperature. The mixture was acidified to pH 5 with 1 N HCl. The resulting mixture was extracted with EtOAc (3×150 mL). The combined organic layers were washed with brine (2×150 mL), dried over anhydrous $Na_2SO_4$. After filtration, the filtrate was concentrated under reduced pressure to afford the product (1.8 g, crude). LCMS (ESI) m/z [M+H] calcd for $C_{50}H_{69}N_7O_7$: 880.53; found: 880.8 Step 3: Synthesis of tert-butyl (($6^3$S,4S)-$1^1$-ethyl-$1^2$-(2-((S)-1-methoxyethyl)-5-((R)-octahydro-2H-pyrido[1,2-a]pyrazin-2-yl)phenyl)-10,10-dimethyl-5,7-dioxo-$6^1,6^2,6^3,6^4,6^5,6^6$-hexahydro-$1^1$H-8-oxa-1(5,3)-indola-6(1,3)-pyridazina-2(1,3)-benzenacycloundecaphane-4-yl)carbamate Into a 2 L 3-necked round-bottom flask were added (S)-1-((S)-2-((tert-butoxycarbonyl)amino)-3-(3-(1-ethyl-3-(3-hydroxy-2,2-dimethylpropyl)-2-(2-((S)-1-methoxyethyl)-5-((R)-octahydro-2H-pyrido[1,2-a]pyrazin-2-yl)pyridin-3-yl)-1H-indol-5-yl)phenyl)propanoyl)hexahydropyridazine-3-carboxylic acid (1.8 g, 2.09 mmol) and DCM (360 mL) at room temperature followed by DIPEA (24.28 mL, 139.394 mmol) and HOBt (4.71 g, 34.857 mmol) in portions at 0° C. The resulting mixture was stirred for additional 30 min at 0° C. To the above mixture was added EDCI (8.67 g, 37.63 mmol) in portions over 5 min at 0° C. The resulting mixture was stirred overnight at room temperature then concentrated under reduced pressure. The reaction was quenched with $H_2O$ at 0° C. The resulting mixture was extracted with EtOAc (3×300 mL). The combined organic layers were washed with brine (2×250 mL), dried over anhydrous $Na_2SO_4$. After filtration, the filtrate was concentrated under reduced pressure. The residue was purified by silica gel column chromatography (10% MeOH/DCM) to the product (623 mg, 34% yield) as a solid. LCMS (ESI) m/z [M+H] calcd for $C_{51}H_{68}N_6O_6$: 861.53; found: 862.8

Step 4: Synthesis of ($6^3$S,4S)-4-amino-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-$6^1,6^2,6^3,6^4,6^5,6^6$-hexahydro-$1^1$H-8-oxa-1(5,3)-indola-6(1,3)-pyridazina-2(1,3)-benzenacycloundecaphane-5,7-dione Into a 100 mL round-bottom flask were added tert-butyl (($6^3$S,4S)-$1^1$-ethyl-$1^2$-(2-((S)-1-methoxyethyl)-5-((R)-octahydro-2H-pyrido[1,2-a]pyrazin-2-yl)phenyl)-10,10-dimethyl-5,7-dioxo-$6^1,6^2,6^3,6^4,6^5,6^6$-hexahydro-$1^1$H-8-oxa-1(5,3)-indola-6(1,3)-pyridazina-2(1,3)-benzenacycloundecaphane-4-yl)carbamate (350 mg, 0.406 mmol) and DCM (4 mL) at 0° C. Then TFA (1 mL) was added into above mixture. After 1 h, the mixture was basified to pH 9 with sat. aq. $NaHCO_3$. The resulting mixture was extracted with DCM (3×5 mL). The combined organic layers were washed with brine (3×30 mL), dried over anhydrous $Na_2SO_4$. After filtration, the filtrate was concentrated under reduced pressure to afford the product (300 mg, crude). LCMS (ESI) m/z [M+H] calcd for $C_{45}H_{59}N_7O_4$: 762.47; found: 762.3

Intermediate 14: Synthesis of ($6^3$S,4S)-4-amino-$1^1$-ethyl-$1^2$-(5-((R)-hexahydropyrrolo[1,2-a]pyrazin-2(1H)-yl)-2-((S)-1-methoxyethyl)pyridin-3-yl)-10,10-dimethyl-$6^1,6^2,6^3,6^4,6^5,6^6$-hexahydro-$1^1$H-8-oxa-1(5,3)-indola-6(1,3)-pyridazina-2(1,3)-benzenacycloundecaphane-5,7-dione

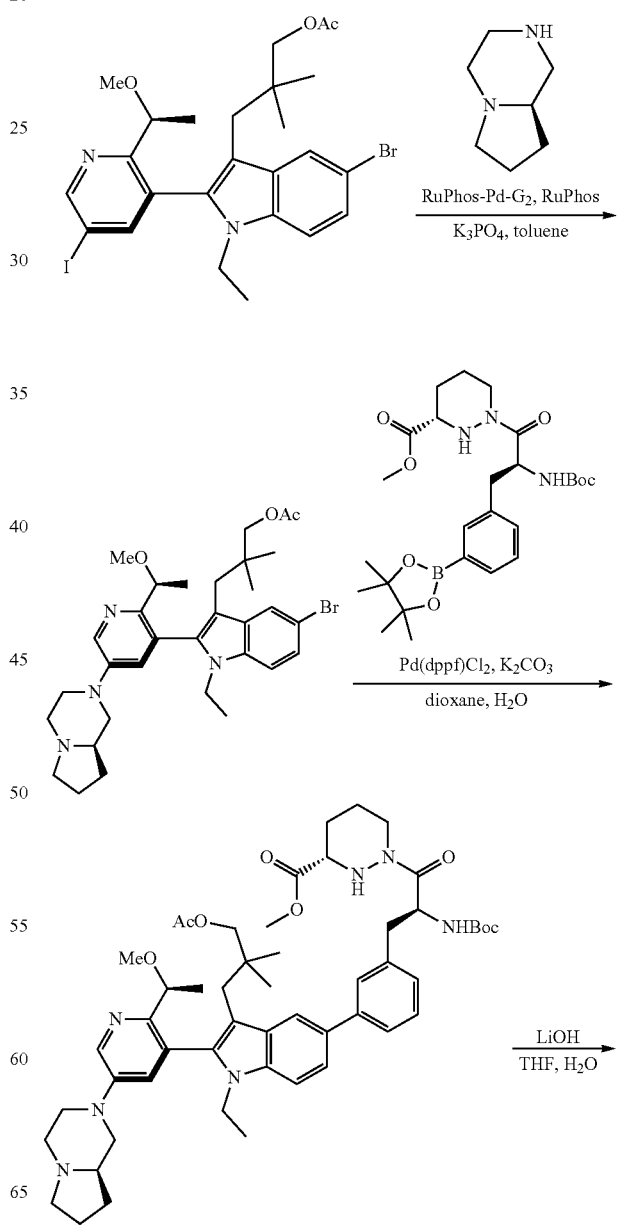

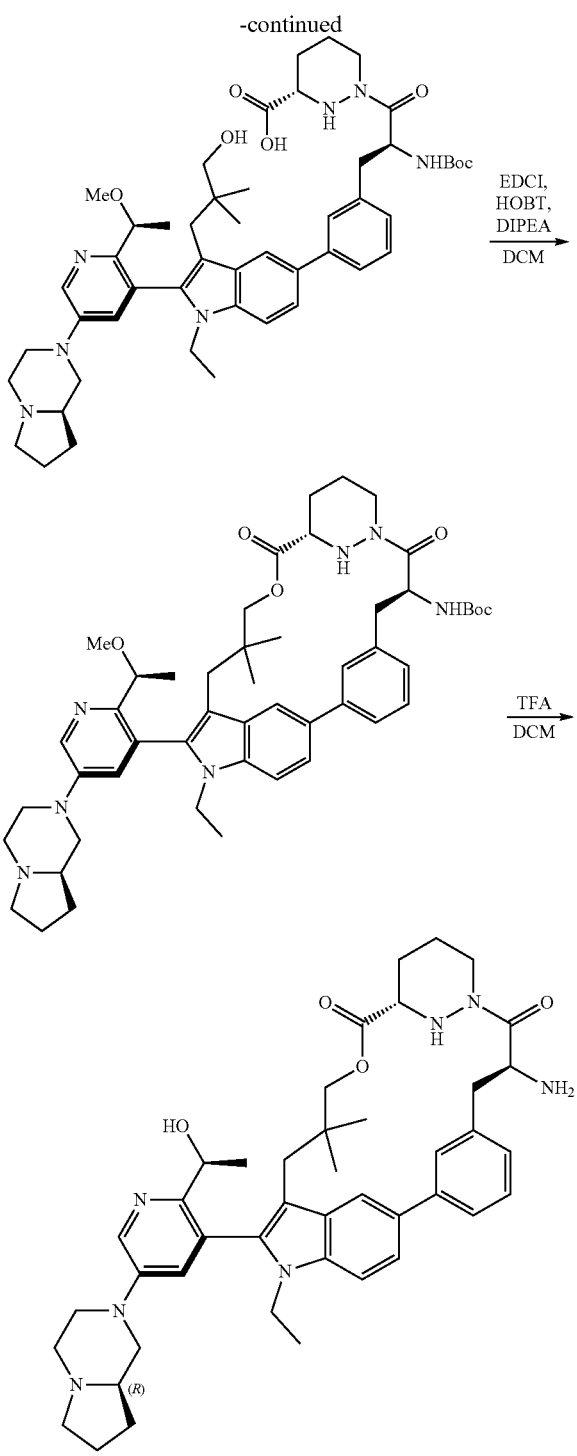

(100 mL) at room temperature. To the above mixture was added RuPhos-Pd-G2 (2.53 g, 3.261 mmol), RuPhos (2.28 g, 4.891 mmol) in portions over 1 min. The resulting mixture was stirred for additional 3 h at 90° C. The reaction was quenched by the addition of H₂O (50 mL) at room temperature. The aqueous layer was extracted with EtOAc (3×600 mL). The resulting mixture was concentrated under reduced pressure. The residue was purified by silica gel column chromatography (12% MeOH/DCM) to afford the product (7 g, 70% yield) as a solid. LCMS (ESI) m/z [M+H] calcd for $C_{32}H_{43}BrN_4O_3$: 611.26; found: 611.3

Step 2: Synthesis of methyl (S)-1-((S)-3-(3-(3-(3-acetoxy-2,2-dimethylpropyl)-1-ethyl-2-(5-((R)-hexahydropyrrolo[1,2-a]pyrazin-2(1 H)-yl)-2-((S)-1-methoxyethyl)pyridin-3-yl)-1H-indol-5-yl)phenyl)-2-((tert-butoxycarbonyl)amino)propanoyl) hexahydropyridazine-3-carboxylate To a solution of 3-(5-bromo-1-ethyl-2-(5-((R)-hexahydropyrrolo[1,2-a]pyrazin-2(1H)-yl)-2-((S)-1-methoxyethyl) pyridin-3-yl)-1H-indol-3-yl)-2,2-dimethylpropyl acetate (5 g, 8.175 mmol) and methyl (3S)-1-[(2S)-2-[(tert-butoxycarbonyl)amino]-3-[3-(4,4,5,5-tetramethyl-1,3,2-dioxaborolan-2-yl)phenyl]propanoyl]-1,2-diazinane-3-carboxylate (5.07 g, 9.81 mmol) in dioxane (125 mL) and H₂O (25 mL) were added K₂CO₃ (2824 mg, 20.438 mmol) and Pd(dppf)Cl₂ (1196 mg, 1.635 mmol). After stirring for 2 h at 70° C. under a nitrogen atmosphere. The precipitated solids were collected by filtration and washed with EtOAc (3×100 mL). The resulting mixture was concentrated under reduced pressure. The residue was purified by silica gel column chromatography (13% MeOH/DCM) to afford the product (4 g, 53% yield) as a solid. LCMS (ESI) m/z [M+H] calcd for $C_{52}H_{71}N_7O_8$: 922.54; found: 922.6

Step 3: Synthesis of (S)-1-((S)-2-((tert-butoxycarbonyl)amino)-3-(3-(1-ethyl-2-(5-((R)-hexahydropyrrolo[1,2-a]pyrazin-2(1 H)-yl)-2-((S)-1-methoxyethyl)pyridin-3-yl)-3-(3-hydroxy-2,2-dimethylpropyl)-1H-indol-5-yl)phenyl)propanoyl) hexahydropyridazine-3-carboxylic acid Into a 100 mL round-bottom flask were added methyl (S)-1-((S)-3-(3-(3-(3-acetoxy-2,2-dimethylpropyl)-1-ethyl-2-(5-((R)-hexahydropyrrolo[1,2-a]pyrazin-2(1 H)-yl)-2-((S)-1-methoxyethyl)pyridin-3-yl)-1H-indol-5-yl)phenyl)-2-((tert-butoxycarbonyl)amino) propanoyl)hexahydropyridazine-3-carboxylate (3 g, 3.2501 mmol) and THF (30 mL) and LiOH●H₂O (0.55 g, 13.012 mmol) at 0° C. The resulting mixture was stirred overnight at room temperature under an argon atmosphere. The mixture was acidified to pH 6 with HCl (aq.). The aqueous layer was extracted with EtOAc (3×100 mL). The resulting mixture was concentrated under reduced pressure to afford the product (2.96 g, 92% yield) as a solid. LCMS (ESI) m/z [M+H] calcd for $C_{49}H_{67}N_7O_7$: 866.52; found: 866.6

Step 4: Synthesis of tert-butyl ((6³S,4S)-1¹-ethyl-1²-(5-((R)-hexahydropyrrolo[1,2-a]pyrazin-2(1 H)-yl)-2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate Into a 500 mL round-bottom flask were added (S)-1-((S)-2-((tert-butoxycarbonyl)amino)-3-(3-(1-ethyl-2-(5-((R)-

Step 1: Synthesis of 3-(5-bromo-1-ethyl-2-(5-((R)-hexahydropyrrolo[1,2-a]pyrazin-2(1H)-yl)-2-((S)-1-methoxyethyl)pyridin-3-yl)-1H-indol-3-yl)-2,2-dimethylpropyl acetate Into a 100 mL 3-necked round-bottom flask were added (S)-3-(5-bromo-1-ethyl-2-(5-iodo-2-(1-methoxyethyl)pyridin-3-yl)-1H-indol-3-yl)-2,2-dimethylpropyl acetate (10 g, 16.304 mmol), K₃PO₄ (8.65 g, 40.760 mmol), (R)-octahydropyrrolo[1,2-a]pyrazine (2.67 g, 21.195 mmol) in toluene hexahydropyrrolo[1,2-a]pyrazin-2(1 H)-yl)-2-((S)-1-methoxyethyl)pyridin-3-yl)-3-(3-hydroxy-2,2-dimethylpropyl)-1H-indol-5-yl)phenyl)propanoyl)hexahydropyridazine-3-carboxylic acid (2.9 g, 3.348 mmol), DCM (200 mL), and DIPEA (8.65 g, 66.960 mmol) in at 0° C. To the above mixture was added HOBt (2.26 g, 16.740 mmol), EDCI (6.42 g, 33.480 mmol) in portions over 5 min at 0° C. The resulting mixture was stirred overnight at room temperature. The resulting mixture was washed with H$_2$O (3×200 mL). The aqueous layer was extracted with EtOAc (3×20 mL). The resulting mixture was concentrated under reduced pressure. The residue was purified by silica gel column chromatography (10% MeOH/DCM) to afford the product (1.2 g, 42% yield) as a solid. LCMS (ESI) m/z [M+H] calcd for C$_{49}$H$_{65}$N$_7$O$_6$: 848.51; found: 847.6

Step 5: Synthesis of (6$^3$S,4S)-4-amino-1$^1$-ethyl-1$^2$-(5-((R)-hexahydropyrrolo[1,2-a]pyrazin-2(1$^1$H)-yl)-2-((S)-1-methoxyethyl)pyridin-3-yl)-10,10-dimethyl-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-5,7-dione Into a 40 mL vial were added tert-butyl ((6$^3$S,4S)-1$^1$-ethyl-1$^2$-(5-((R)-hexahydropyrrolo[1,2-a]pyrazin-2(1 H)-yl)-2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-1 (5,3)-indola-6(1,3)-pyridazina-2(1,3)-benzenacycloundecaphane-4-yl)carbamate (400 mg, 0.472 mmol) DCM (8 mL), and TFA (4 mL) at 0° C. The resulting mixture was stirred for 3 h at 0° C. The resulting mixture was concentrated under reduced pressure to afford the product (300 mg, 85% yield) as a solid. LCMS (ESI) m/z [M+H] calcd for C$_{44}$H$_{57}$N$_7$O$_4$: 747.4; found: 748.4

Intermediate 15: Synthesis of (2$^2$S,6$^3$S,4S)-4-amino-1$^1$-ethyl-1$^2$-(2-((S)-1-methoxyethyl)-5-((R)-octahydro-2H-pyrido[1,2-a]pyrazin-2-yl)pyridin-3-yl)-10,10-dimethyl-6$^1$,6$^2$,6$^3$,6$^4$,6$^5$,6$^6$-hexahydro-11 H-8-oxa-2(4,2)-morpholina-1(5,3)-indola-6(1,3)-pyridazinacycloundecaphane-5,7-dione

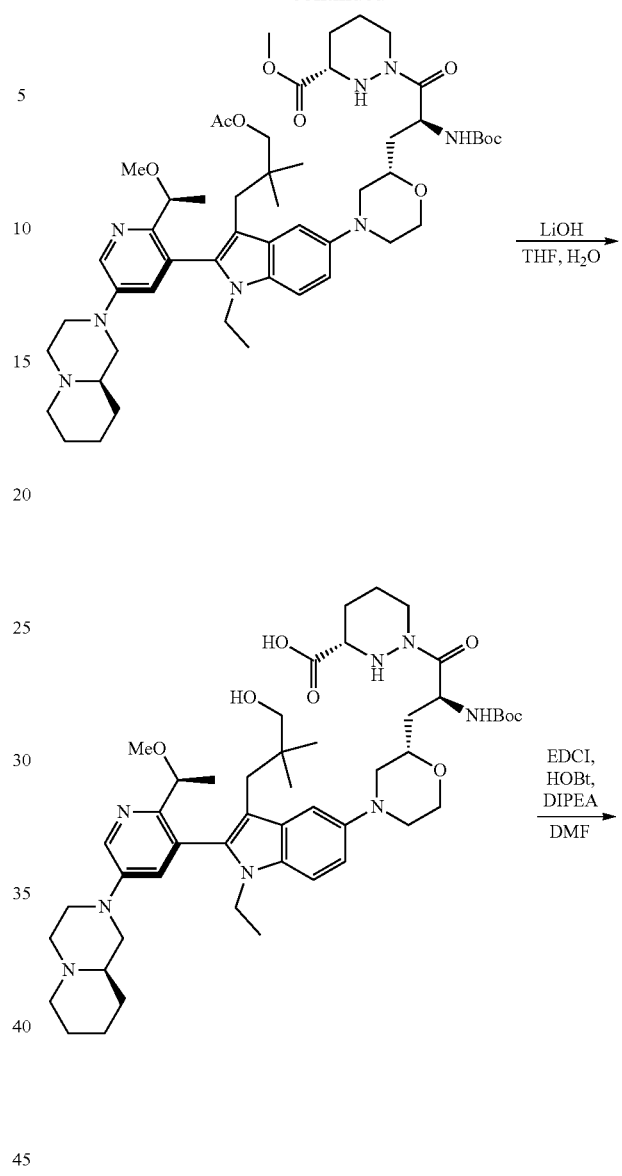

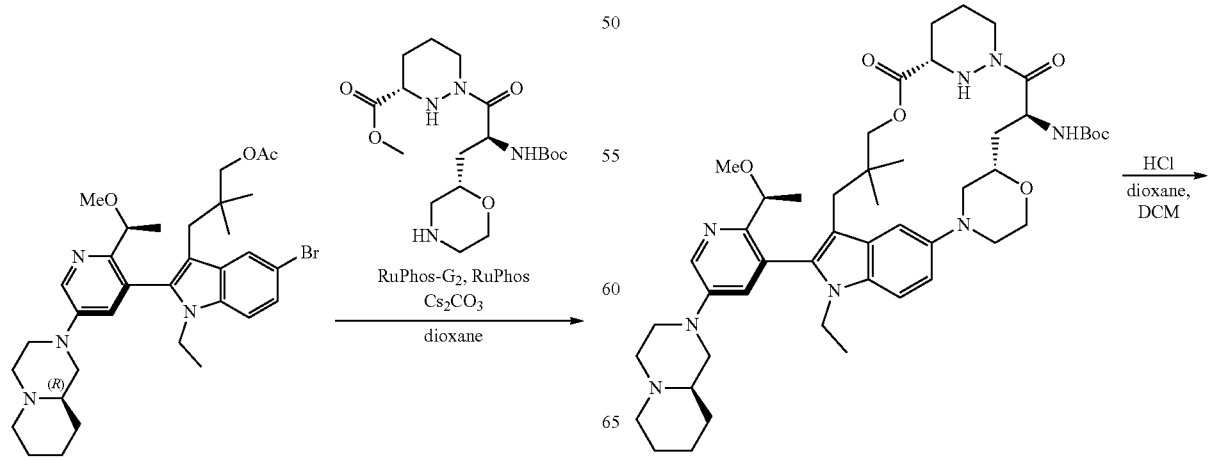

-continued

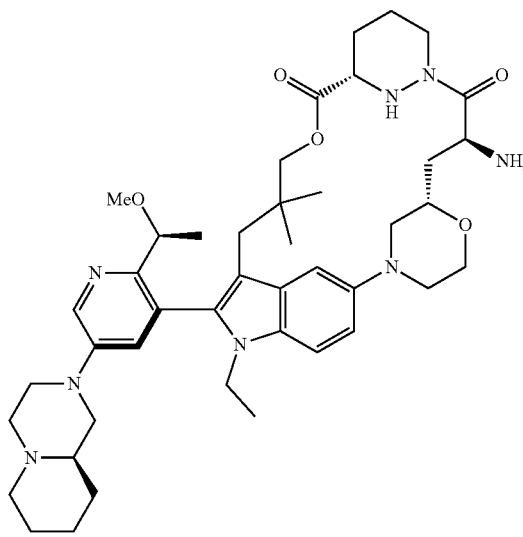

Step 1: Synthesis of methyl (S)-1-((S)-3-((S)-1-(3-(3-acetoxy-2,2-dimethylpropyl)-1-ethyl-2-(2-((S)-1-methoxyethyl)-5-((R)-octahydro-2H-pyrido[1,2-a]pyrazin-2-yl)pyridin-3-yl)-1H-indol-5-yl)piperidin-3-yl)-2-((tert-butoxycarbonyl)amino)propanoyl)hexahydropyridazine-3-carboxylate To a stirred solution of 3-(5-bromo-1-ethyl-2-(2-((S)-1-methoxyethyl)-5-((R)-octahydro-2H-pyrido[1,2-a]pyrazin-2-yl)pyridin-3-yl)-1H-indol-3-yl)-2,2-dimethylpropyl acetate (13 g, 20.778 mmol) and methyl (S)-1-((S)-2-((tert-butoxycarbonyl)amino)-3-((S)-morpholin-2-yl)propanoyl)hexahydropyridazine-3-carboxylate (10.82 g, 27.011 mmol) in dioxane (130 mL) were added chloro(2-dicyclohexylphosphino-2',6'-diisopropoxy-1,1'-biphenyl)[2-(2'-amino-1,1'-biphenyl)]palladium(II) (1.61 g, 2.078 mmol), RuPhos (1.94 g, 4.156 mmol) and Cs$_2$CO$_3$ (13.54 g, 41.556 mmol) at room temperature under a nitrogen atmosphere. The resulting mixture was stirred for 3 h at 80° C. The resulting mixture was diluted with H$_2$O (300 mL) and extracted with EtOAc (3×200 mL). The combined organic layers were washed with brine (2 20×100 mL), dried over anhydrous Na$_2$SO$_4$. After filtration, the filtrate was concentrated under reduced pressure. The residue was purified by silica gel column chromatography (8% MeOH/DCM) to afford the product (18.8 g, 95% yield) as a solid. LCMS (ESI) m/z [M+H] calcd for C$_{52}$H$_{78}$N$_8$O$_8$: 945.58; found: 945.5

Step 2: Synthesis of (S)-1-((S)-2-((tert-butoxycarbonyl)amino)-3-((S)-4-(1-ethyl-3-(3-hydroxy-2,2-dimethylpropyl)-2-(2-((S)-1-methoxyethyl)-5-((R)-octahydro-2H-pyrido[1,2-a]pyrazin-2-yl)pyridin-3-yl)-1H-indol-5-yl)morpholin-2-yl)propanoyl)hexahydropyridazine-3-carboxylic acid To a stirred solution of methyl (S)-1-((S)-3-((S)-1-(3-(3-acetoxy-2,2-dimethylpropyl)-1-ethyl-2-(2-((S)-1-methoxy-ethyl)-5-((R)-octahydro-2H-pyrido[1,2-a]pyrazin-2-yl)pyridin-3-yl)-1H-indol-5-yl)piperidin-3-yl)-2-((tert-butoxycarbonyl)amino)propanoyl)hexahydropyridazine-3-carboxylate (18.8 g, 19.890 mmol) in THF (85 mL) and H$_2$O (85 mL) was added LiOH•H$_2$O (4.17 g, 99.450 mmol) at 0° C. The resulting mixture was stirred at room temperature then diluted with H$_2$O (300 mL). The resulting mixture was washed with MTBE (3×100 mL) and extracted with DCM (3×200 mL). The combined organic layers were washed with H$_2$O (200 mL), dried over anhydrous Na$_2$SO$_4$. After filtration, the filtrate was concentrated under reduced pressure to afford the product (11.2 g, crude) as a solid. The crude product was used in the next step directly without further purification. LCMS (ESI) m/z [M+H] calcd for C$_{48}$H$_{72}$N$_8$O$_8$: 889.56; found: 889.5 Step 3: Synthesis of tert-butyl ((2$^2$S,6$^3$S,4S)-1$^1$-ethyl-1$^2$-(2-((S)-1-methoxyethyl)-5-((R)-octahydro-2H-pyrido[1,2-a]pyrazin-2-yl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-4-yl)carbamate To a stirred solution of (S)-1-((S)-2-((tert-butoxycarbonyl)amino)-3-((S)-4-(1-ethyl-3-(3-hydroxy-2,2-dimethylpropyl)-2-(2-((S)-1-methoxyethyl)-5-((R)-octahydro-2H-pyrido[1,2-a]pyrazin-2-yl)pyridin-3-yl)-1H-indol-5-yl)morpholin-2-yl)propanoyl)hexahydropyridazine-3-carboxylic acid (5.57 g, 6.264 mmol) and DIPEA (64.77 g, 501.120 mmol) in DMF (557 mL) were added HOBt (33.86 g, 250.560 mmol) and EDCI (72.05 g, 375.840 mmol) at 0° C. under a nitrogen atmosphere. The resulting mixture was stirred overnight at room temperature. The resulting mixture was diluted with H$_2$O (1 L). The resulting mixture was extracted with EtOAc (3×1 L). The combined organic layers were washed with brine (5×1 L), dried over anhydrous Na$_2$SO$_4$. After filtration, the filtrate was concentrated under reduced pressure. The residue was purified by silica gel column chromatography (10% MeOH/DCM) to afford the product (4 g, 73% yield) as a solid. LCMS (ESI) m/z [M+H] calcd for C$_{48}$H$_{70}$N$_8$O$_7$: 871.54; found: 871.6

Step 4: Synthesis of (2$^2$S,6$^3$S,4S)-4-amino-1$^1$-ethyl-1$^2$-(2-((S)-1-methoxyethyl)-5-((R)-octahydro-2H-pyrido[1,2-a]pyrazin-2-yl)pyridin-3-yl)-10,10-dimethyl-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-5,7-dione To a stirred mixture of tert-butyl ((2$^2$S,6$^3$S,4S)-1$^1$-ethyl-1$^2$-(2-((S)-1-methoxyethyl)-5-((R)-octahydro-2H-pyrido[1,2-a]pyrazin-2-yl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-4-yl)carbamate (750 mg, 0.861 mmol) in DCM (5 mL) was added HCl (4 M in dioxane) (5 mL) dropwise at 0° C. The resulting mixture was stirred for 2 h at room temperature then concentrated under reduced pressure. This resulted in the product (830 mg, crude) as a solid. LCMS (ESI) m/z [M+H] calcd for C$_{43}$H$_{62}$N$_8$O$_5$: 771.49; found: 771.7

Intermediate 16: Synthesis of (6³S,4S)-4-amino-1'-ethyl-12-(5-((S)-hexahydropyrazino[2,1-c][1,4]oxazin-8(1H)-yl)-2-((S)-1-methoxyethyl)pyridin-3-yl)-10,10-dimethyl-2¹,2²,2³,2⁶,6¹,6²,6³,6⁴,6,⁶6-decahydro-1¹H-8-oxa-1(5,3)-indola-6(1,3)-pyridazina-2(5,1)-pyridinacycloundecaphane-5,7-dione
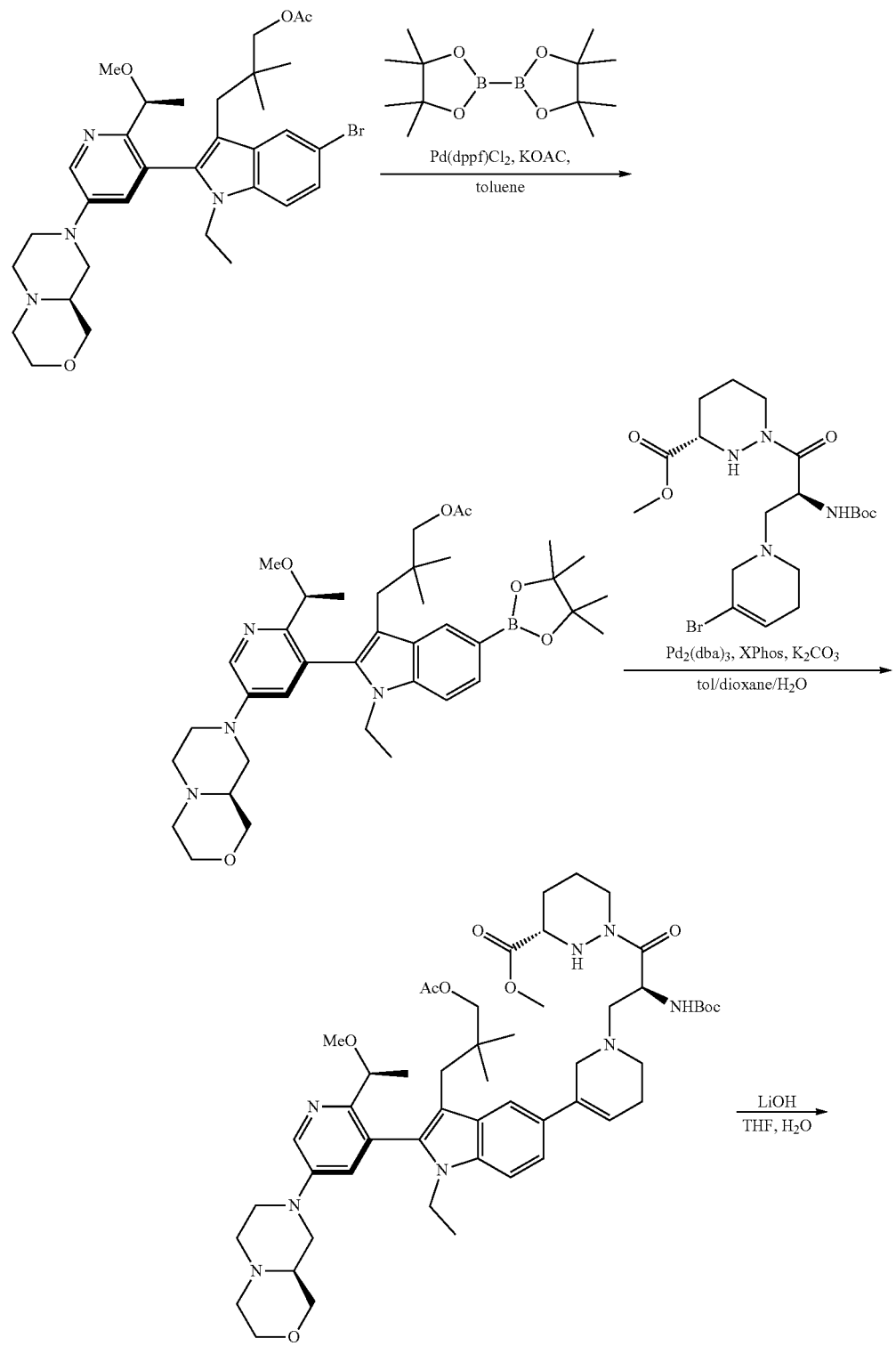

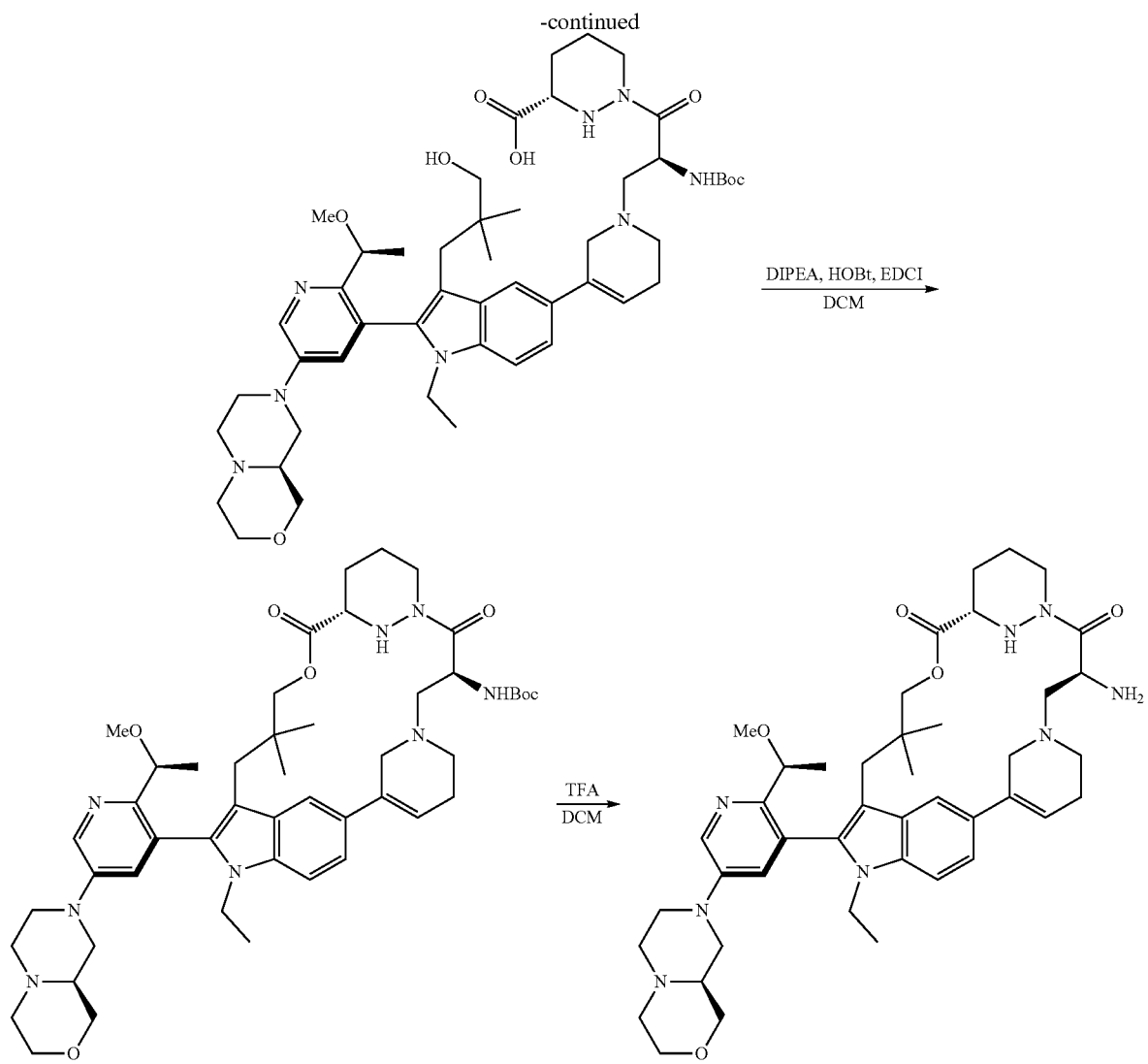

Step 1: Synthesis of 3-(1-ethyl-2-(5-((S)-hexahydropyrazino[2,1-c][1,4]oxazin-8(1H)-yl)-2-((S)-1-methoxyethyl)pyridin-3-yl)-5-(4,4,5,5-tetramethyl-1,3,2-dioxaborolan-2-yl)-1H-indol-3-yl)-2,2-dimethylpropyl acetate To a stirred solution of 3-(5-bromo-1-ethyl-2-(5-((S)-hexahydropyrazino[2,1-c][1,4]oxazin-8(1H)-yl)-2-((S)-1-methoxyethyl)pyridin-3-yl)-1H-indol-3-yl)-2,2-dimethylpropyl acetate (2.16 g, 3.45 mmol) in toluene (40 mL) was added KOAc (0.78 g, 7.967 mmol), 4,4,4',4',5,5,5',5'-octamethyl-2,2'-bi(1,3,2-dioxaborolane (1.314 g, 5.175 mmol) and Pd(dppf)Cl$_2$ (0.23 g, 0.319 mmol, 0). The resulting mixture was stirred for 2 h at 90° C. under a nitrogen atmosphere. The mixture was basified to pH 8 with sat. aq. NaHCO$_3$. The resulting mixture was extracted with DCM (3×100 mL) and the combined organic layers were washed with brine (3×40 mL) and dried over anhydrous Na$_2$SO$_4$. After filtration, the filtrate was concentrated under reduced pressure. The residue was purified by silica gel column chromatography (2% MeOH/DCM) to afford the product (2 g, 86% yield) as a solid. LCMS (ESI) m/z [M+H] calcd for C$_{38}$H$_{55}$BN$_4$O$_6$: 675.43; found: 675.5

Step 2: Synthesis of methyl (S)-1-((S)-3-(5-(3-(3-acetoxy-2,2-dimethylpropyl)-1-ethyl-2-(5-((S)-hexahydropyrazino[2,1-c][1,4]oxazin-8(1 H)-yl)-2-((S)-1-methoxyethyl)pyridin-3-yl)-1H-indol-5-yl)-3,6-dihydropyridin-1(2H)-yl)-2-((tert-butoxycarbonyl)amino)propanoyl)hexahydropyridazine-3-carboxylate To a stirred solution of 3-(1-ethyl-2-(5-((S)-hexahydropyrazino[2,1-c][1,4]oxazin-8(1H)-yl)-2-((S)-1-methoxyethyl)pyridin-3-yl)-5-(4,4,5,5-tetramethyl-1,3,2-dioxaborolan-2-yl)-1H-indol-3-yl)-2,2-dimethylpropyl acetate (2 g, 2.964 mmol) and methyl (S)-1-((S)-3-(5-bromo-3,6-dihydropyridin-1(2H)-yl)-2-((tert-butoxycarbonyl)amino)propanoyl)hexahydropyridazine-3-carboxylate (2.25 g, 4.742 mmol) in toluene (12.5 mL), dioxane (8.3 mL), and H$_2$O (4.1 mL) was added K$_2$CO$_3$ (1.02 g, 7.410 mmol), X-Phos (0.57 g, 1.186 mmol), and Pd$_2$(dba)$_3$ (0.81 g, 0.889 mmol). The resulting mixture was stirred for 2 h at 70° C. under a nitrogen atmosphere. The mixture was basified to pH 8 with sat. aq. NaHCO$_3$. The resulting mixture was extracted with DCM (3×100 mL). and the combined organic layers were washed with brine (3×100 mL) and dried over anhydrous Na₂SO₄. After filtration, the filtrate was concentrated under reduced pressure. The residue was purified by silica gel column chromatography (2% MeOH/DCM) to afford the product (1.7 g, 55% yield) as a solid. LCMS (ESI) m/z [M+H] calcd for $C_{51}H_{74}N_8O_9$: 943.57; found: 943.7

Step 3: Synthesis of (S)-1-((S)-2-((tert-butoxycarbonyl)amino)-3-(5-(1-ethyl-2-(5-((S)-hexahydropyrazino[2,1-c][1,4]oxazin-8(1 H)-yl)-2-((S)-1-methoxyethyl)pyridin-3-yl)-3-(3-hydroxy-2,2-dimethylpropyl)-1H-indol-5-yl)-3,6-dihydropyridin-1(2H)-yl)propanoyl)hexahydropyridazine-3-carboxylic acid To a stirred solution of methyl (S)-1-((S)-3-(5-(3-(3-acetoxy-2,2-dimethylpropyl)-1-ethyl-2-(5-((S)-hexahydropyrazino[2,1-c][1,4]oxazin-8(1 H)-yl)-2-((S)-1-methoxyethyl)pyridin-3-yl)-1H-indol-5-yl)-3,6-dihydropyridin-1(2H)-yl)-2-((tert-butoxycarbonyl)amino)propanoyl)hexahydropyridazine-3-carboxylate (1.7 g, 1.802 mmol) in THF (9 mL) and H₂O (9 mL) was added LiOH (0.19 g, 8.109 mmol) at 0° C. The resulting mixture was stirred for 2 h at 0° C. The mixture was acidified to pH 6 with conc. HCl. The mixture was then extracted with DCM (3×50 mL) and dried over anhydrous Na₂SO₄. After filtration, the filtrate was concentrated under reduced pressure to afford the crude product (1.2 g, 67% yield) as a solid, which was used in the next step directly without further purification. LCMS (ESI) m/z [M+H] calcd for $C_{48}H_{70}N_8O_8$: 887.54; found: 887.6

Step 4: Synthesis of tert-butyl ((6³S,4S)-1¹-ethyl-1²-(5-((S)-hexahydropyrazino[2,1-c][1,4]oxazin-8(1 H)-yl)-2-((S)-1-methoxyethyl)pyridin-3-yl)-10,10-dimethyl-5,7-dioxo-2¹ 2²,2³,2⁶,6¹,6²,6³,6⁴,6⁵,6⁶-decahydro-1¹H-8-oxa-1(5,3)-indola-6(1,3)-pyridazina-2(5,1)-pyridinacycloundecaphane-4-yl)carbamate To a stirred solution of (S)-1-((S)-2-((tert-butoxycarbonyl)amino)-3-(5-(1-ethyl-2-(5-((S)-hexahydropyrazino[2,1-c][1,4]oxazin-8(1H)-yl)-2-((S)-1-methoxyethyl)pyridin-3-yl)-3-(3-hydroxy-2,2-dimethylpropyl)-1H-indol-5-yl)-3,6-dihydropyridin-1(2H)-yl)propanoyl)hexahydropyridazine-3-carboxylic acid (1.2 g, 1.353 mmol) and HOBt (0.91 g, 6.765 mmol) in DCM (120 mL) was added EDC●HCl (7.26 g, 37.884 mmol) and DIPEA (6.12 g, 47.355 mmol) dropwise at 0° C. under a nitrogen atmosphere. The resulting mixture was stirred for 2 h at 0° C. The mixture was basified to pH 8 with sat. aq. NaHCO₃. The resulting mixture was extracted with DCM (3×100 mL). The combined organic layers were washed with brine (3×100 mL) and dried over anhydrous Na₂SO₄. After filtration, the filtrate was concentrated under reduced pressure. The residue was purified by silica gel column chromatography (3% MeOH/DCM) to afford the product (880 mg, 67% yield) as a solid. LCMS (ESI) m/z [M+H] calcd for $C_{48}H_{68}N_8O_7$: 869.53; found: 869.4

Step 5: Synthesis of (6³S,4S)-4-amino-1'-ethyl-12-(5-((S)-hexahydropyrazino[2,1-c][1,4]oxazin-8(1H)-yl)-2-((S)-1-methoxyethyl)pyridin-3-yl)-10,10-dimethyl-2¹ 2²,2³,2⁶,6¹,6²,6³,6⁴,6⁵,6⁶-decahydro-1¹H-8-oxa-1(5,3)-indola-6(1,3)-pyridazina-2(5,1)-pyridinacycloundecaphane-5,7-dione To a stirred solution of tert-butyl ((6³S,4S)-1¹-ethyl-1²-(5-((S)-hexahydropyrazino[2,1-c][1,4]oxazin-8(1 H)-yl)-2-((S)-1-methoxyethyl)pyridin-3-yl)-10,10-dimethyl-5,7-dioxo-2¹,2²,2³,2⁶,6¹,6²,6³,6⁴,⁶⁵,6⁶-decahydro-1 ¹H-8-oxa-1(5,3)-indola-6(1,3)-pyridazina-2(5,1)- pyridinacycloundecaphane-4-yl)carbamate (880 mg, 1.013 mmol) in DCM (8 mL) was added TFA (8 mL) dropwise at 0° C. The resulting mixture was stirred for 1 h at 0° C. The mixture was basified to pH 8 with sat. aq. NaHCO₃. The resulting mixture was extracted with DCM (3×50 mL) and the combined organic layers were washed with brine (3×50 mL) and dried over anhydrous Na₂SO₄. After filtration, the filtrate was concentrated under reduced pressure to afford the crude product (720 mg, 83% yield) as a solid, which was used in the next step directly without further purification. LCMS (ESI) m/z [M+H] calcd for $C_{43}H_{60}N_8O_5$: 769.48; found: 769.6

Intermediate 17: Synthesis of (6³S,4S)-4-amino-1¹-ethyl-1²-(2-((S)-1-methoxyethyl)-5-((R)-octahydro-2H-pyrido[1,2-a]pyrazin-2-yl)pyridin-3-yl)-10,10-dimethyl-2,2²,2³,2⁶,6,6²,6³,6⁴,6⁵,6⁶-decahydro-1¹H-8-oxa-1(5,3)-indola-6(1,3)-pyridazina-2(5,1)-pyridinacycloundecaphane-5,7-dione

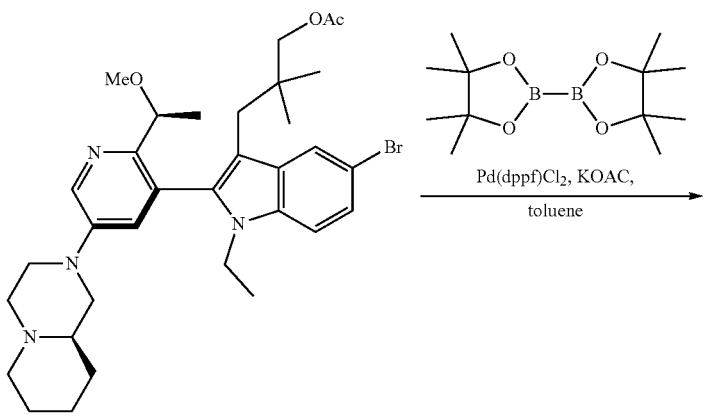

-continued
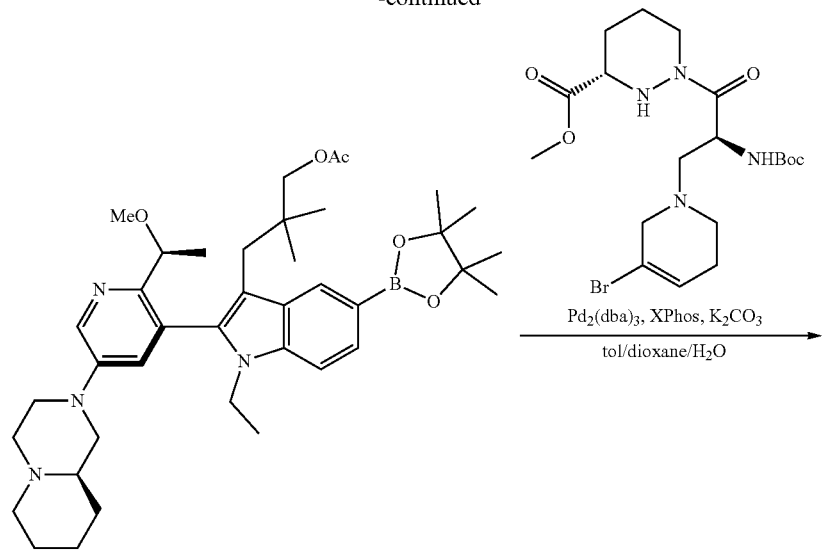
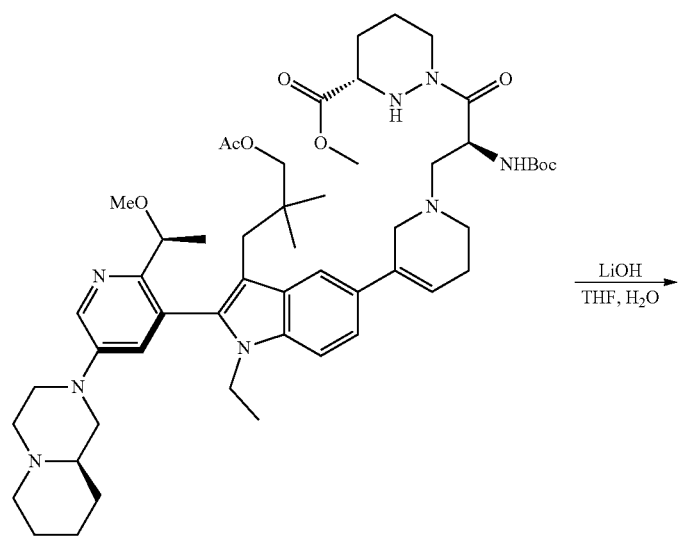
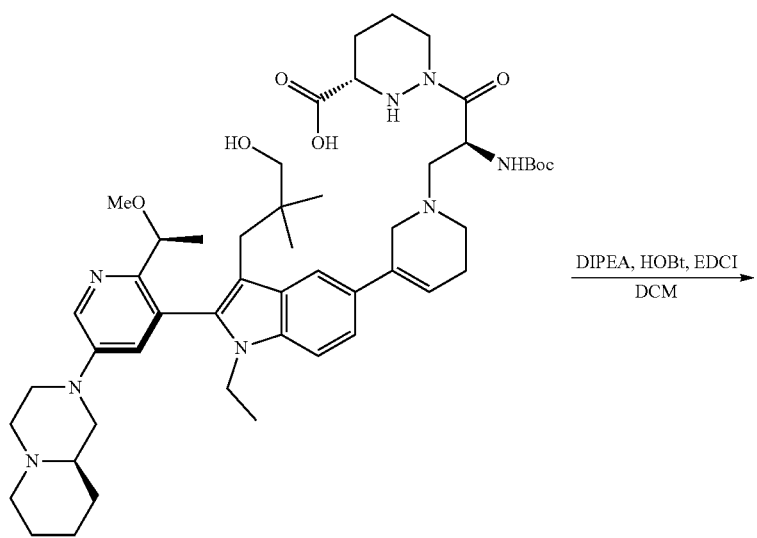

267 268

-continued

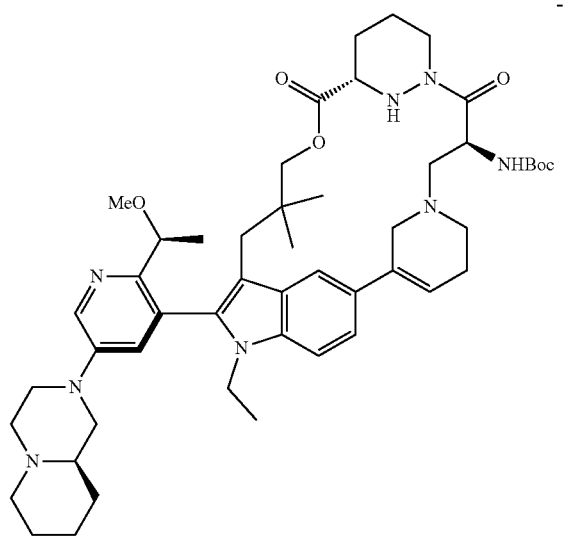

TFA
/
DCM

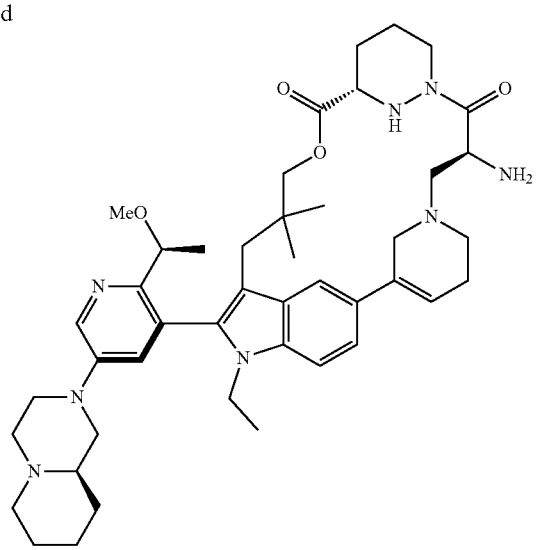

Step 1: Synthesis of 3-(1-ethyl-2-(2-((S)-1-methoxyethyl)-5-((R)-octahydro-2H-pyrido[1,2-a]pyrazin-2-yl)pyridin-3-yl)-5-(4,4,5,5-tetramethyl-1,3,2-dioxaborolan-2-yl)-1H-indol-3-yl)-2,2-dimethylpropyl acetate To a stirred solution of 3-(5-bromo-1-ethyl-2-(2-((S)-1-methoxyethyl)-5-((R)-octahydro-2H-pyrido[1,2-a]pyrazin-2-yl)pyridin-3-yl)-1H-indol-3-yl)-2,2-dimethylpropyl acetate (1 g, 1.598 mmol) and $B_2Pin_2$ (0.81 g, 3.196 mmol) in toluene (20 mL) was added KOAc (0.39 g, 3.995 mmol) and Pd(dppf)Cl$_2$ (0.12 g, 0.16 mmol). The mixture was stirred for 2 h at 90° C. under a nitrogen atmosphere. The mixture was then basified to pH 8 with sat. aq. NaHCO$_3$. The resulting mixture was extracted with DCM (3×40 mL) and the combined organic layers were washed with brine (3×40 mL) and dried over anhydrous Na$_2$SO$_4$. After filtration, the filtrate was concentrated under reduced pressure. The residue was purified by silica gel column chromatography (2% MeOH/DCM) to afford the product (0.9 g, 83% yield) as a solid. LCMS (ESI) m/z [M+H] calcd for $C_{39}H_{57}BN_4O_5$: 673.45; found: 673.6

Step 2: Synthesis of methyl (S)-1-((S)-3-(5-(3-(3-acetoxy-2,2-dimethylpropyl)-1-ethyl-2-(2-((S)-1-methoxyethyl)-5-((R)-octahydro-2H-pyrido[1,2-a]pyrazin-2-yl)pyridin-3-yl)-1H-indol-5-yl)-3,6-dihydropyridin-1(2H)-yl)-2-((tert-butoxycarbonyl)amino)propanoyl)hexahydropyridazine-3-carboxylate To a stirred solution of 3-(1-ethyl-2-(2-((S)-1-methoxyethyl)-5-((R)-octahydro-2H-pyrido[1,2-a]pyrazin-2-yl)pyridin-3-yl)-5-(4,4,5,5-tetramethyl-1,3,2-dioxaborolan-2-yl)-1H-indol-3-yl)-2,2-dimethylpropyl acetate (0.9 g, 1.338 mmol), methyl (3S)-1-[(2S)-3-(3-bromo-5,6-dihydro-2H-pyridin-1-yl)-2-[(tert-butoxycarbonyl)amino]propanoyl]-1,2-diazinane-3-carboxylate (1.02 g, 2.141 mmol), K$_2$CO$_3$ (0.46 g, 3.345 mmol), and X-Phos (0.26 g, 0.535 mmol) in toluene (13.5 mL), dioxane (90 mL), and H$_2$O (4.5 mL) was added Pd$_2$(dba)$_3$ (0.37 g, 0.401 mmol). The mixture was stirred for 2 h at 70° C. under a nitrogen atmosphere. The mixture was then basified to pH 8 with sat. aq. NaHCO$_3$. The resulting mixture was extracted with DCM (3×100 mL) and the combined organic layers were washed with brine (3×100 mL) and dried over anhydrous Na$_2$SO$_4$. After filtration, the filtrate was concentrated under reduced pressure. The residue was purified by silica gel column chromatography (2% MeOH/DCM) to afford the product (1.1 g, 87% yield) as a solid. LCMS (ESI) m/z [M+H] calcd for $C_{52}H_{76}N_8O_8$: 941.59; found: 941.8

Step 3: Synthesis of (S)-1-((S)-2-((tert-butoxycarbonyl)amino)-3-(5-(1-ethyl-3-(3-hydroxy-2,2-dimethylpropyl)-2-(2-((S)-1-methoxyethyl)-5-((R)-octahydro-2H-pyrido[1,2-a]pyrazin-2-yl)pyridin-3-yl)-1H-indol-5-yl)-3,6-dihydropyridin-1(2H)-yl)propanoyl)hexahydropyridazine-3-carboxylic acid To a stirred solution of methyl (S)-1-((S)-3-(5-(3-(3-acetoxy-2,2-dimethylpropyl)-1-ethyl-2-(2-((S)-1-methoxyethyl)-5-((R)-octahydro-2H-pyrido[1,2-a]pyrazin-2-yl)pyridin-3-yl)-1H-indol-5-yl)-3,6-dihydropyridin-1(2H)-yl)-2-((tert-butoxycarbonyl)amino)propanoyl)hexahydropyridazine-3-carboxylate (1.1 g, 1.169 mmol) in THF (8 mL) was added a solution of LiOH (0.14 g, 5.845 mmol) in H$_2$O (8 mL) dropwise at 0° C. under a nitrogen atmosphere. The reaction mixture was stirred for 16 h. The mixture was then acidified to pH 6 with conc. HCl. The resulting mixture was extracted with DCM (3×50 mL) and dried over anhydrous Na$_2$SO$_4$. After filtration, the filtrate was concentrated under reduced pressure to afford the product (1.0 g, 96% yield) as a solid, which was used in the next step directly without further purification. LCMS (ESI) m/z [M+H] calcd for $C_{49}H_{72}N_8O_7$: 885.56; found: 885.5

Step 4: Synthesis of tert-butyl (($6^3$S,4S)-$1^1$-ethyl-$1^2$-(2-((S)-1-methoxyethyl)-5-((R)-octahydro-2H-pyrido[1,2-a]pyrazin-2-yl)pyridin-3-yl)-10,10-dimethyl-5,7-dioxo-$2^1$,$2^2$,$2^3$,$2^6$,$6^1$,$6^2$,$6^3$,$6^4$,$6^5$,$6^6$-decahydro-$1^1$H-8-oxa-1(5,3)-indola-6(1,3)-pyridazina-2(5,1)-pyridinacycloundecaphane-4-yl) carbamate To a stirred solution of (S)-1-((S)-2-((tert-butoxycarbonyl)amino)-3-(5-(1-ethyl-3-(3-hydroxy-2,2-dimethylpropyl)-2-(2-((S)-1-methoxyethyl)-5-((R)-octahydro-2H- pyrido[1,2-a]pyrazin-2-yl)pyridin-3-yl)-1H-indol-5-yl)-3,6-dihydropyridin-1(2H)-yl)propanoyl)hexahydropyridazine-3-carboxylic acid (1.0 g, 1.13 mmol) and HOBt (0.76 g, 5.65 mmol) in DCM (100 mL) was added EDC●HCl (6.06 g, 31.64 mmol) and DIPEA (5.11 g, 39.55 mmol) dropwise at 0° C. under a nitrogen atmosphere. The reaction mixture was stirred for 16 h. The mixture was then basified to pH 8 with sat. aq. NaHCO$_3$. The resulting mixture was extracted with DCM (3×100 mL) and the combined organic layers were washed with brine (3×100 mL) and dried over anhydrous Na$_2$SO$_4$. After filtration, the filtrate was concentrated under reduced pressure. The residue was purified by silica gel column chromatography (3% MeOH/DCM) to afford the product (650 mg, 66% yield) as a solid. LCMS (ESI) m/z [M+H] calcd for $C_{49}H_{70}N_8O_6$: 867.55; found: 867.5

Step 5: Synthesis of (6$^3$S,4S)-4-amino-1$^1$-ethyl-1$^2$-(2-((S)-1-methoxyethyl)-5-((R)-octahydro-2H-pyrido[1,2-a]pyrazin-2-yl)pyridin-3-yl)-10,10-dimethyl-2$^1$ 2$^2$,2$^3$,2$^6$,6$^{17}$,6$^2$,6$^3$,6$^4$,6$^5$, 6$^6$-decahydro-1$^1$H-8-oxa-1(5,3)-indola-6(1,3)-pyridazina-2(5,1)-pyridinacycloundecaphane-5,7-dione To a stirred solution of tert-butyl ((6$^3$S,4S)-1$^1$-ethyl-1$^2$-(2-((S)-1-methoxyethyl)-5-((R)-octahydro-2H-pyrido[1,2-a]pyrazin-2-yl)pyridin-3-yl)-10,10-dimethyl-5,7-dioxo-2$^1$ 2$^2$,2$^3$,2$^6$,6,6$^2$,6$^3$,6$^4$,6$^5$,6$^6$-decahydro-1$^1$H-8-oxa-1(5,3)-indola-6(1,3)-pyridazina-2(5,1)-pyridinacycloundecaphane-4-yl)carbamate (300 mg, 0.346 mmol) in DCM (3 mL) was added TFA (3 mL) dropwise at 0° C. under a nitrogen atmosphere. The resulting mixture was stirred for 1 h at 0° C. The mixture was then basified to pH 8 with sat. aq. NaHCO$_3$. The resulting mixture was extracted with DCM (3×50 mL) and the combined organic layers were washed with brine (3×50 mL) and dried over anhydrous Na$_2$SO$_4$. After filtration, the filtrate was concentrated under reduced pressure to afford the product (260 mg, 98% yield) as a solid, which was used in the next step directly without further purification. LCMS (ESI) m/z [M+H] calcd for $C_{44}H_{62}N_8O_4$: 767.50; found: 767.2

Intermediate 18: Synthesis of (2$^2$S,6$^3$S,4S)-4-amino-1$^2$-(5-(4-cyclopropylpiperazin-1-yl)-2-((S)-1-methoxyethyl)pyridin-3-yl)-1$^1$-ethyl-10,10-dimethyl-6,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-5,7-dione

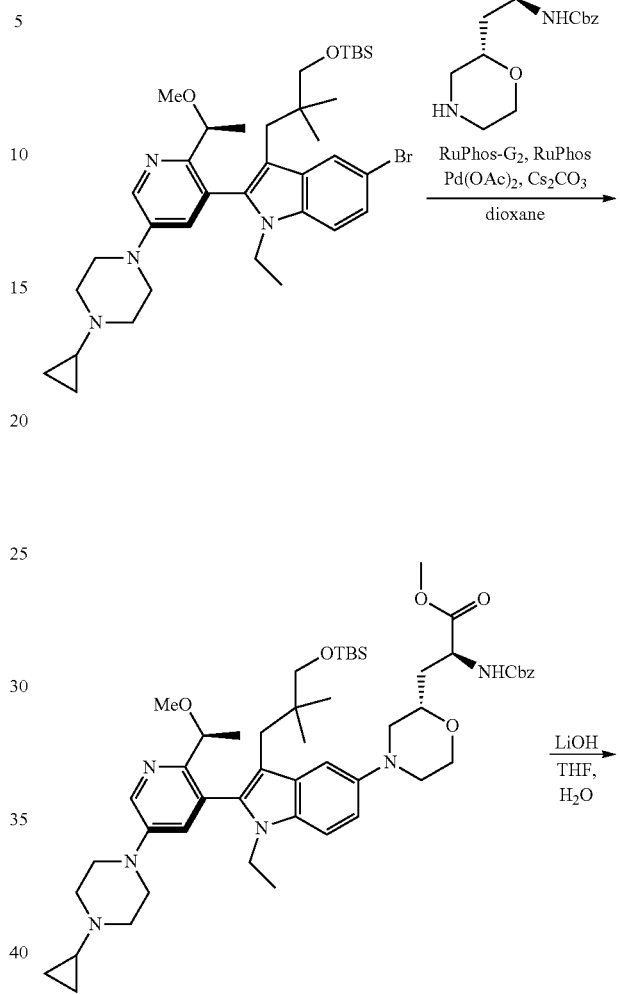

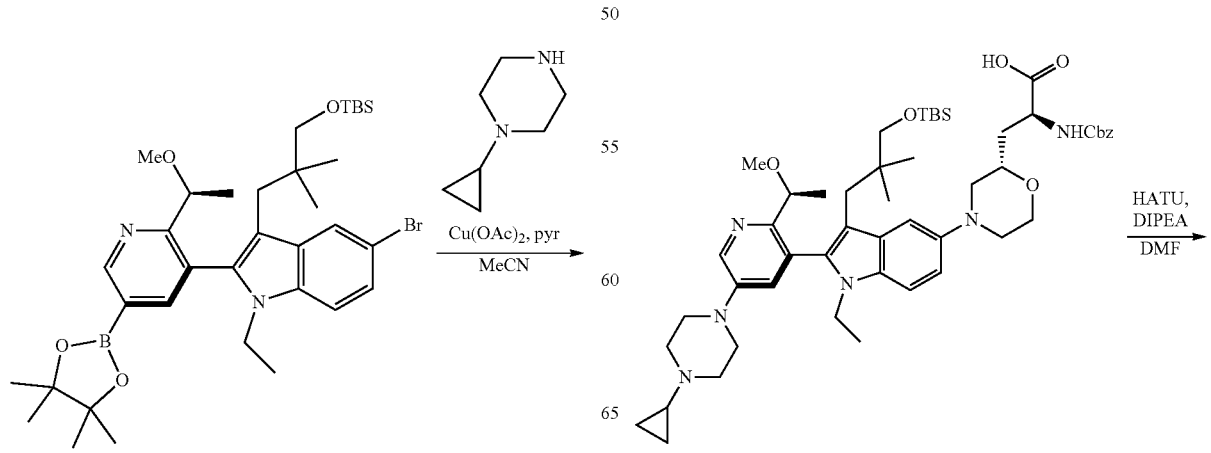

271
-continued

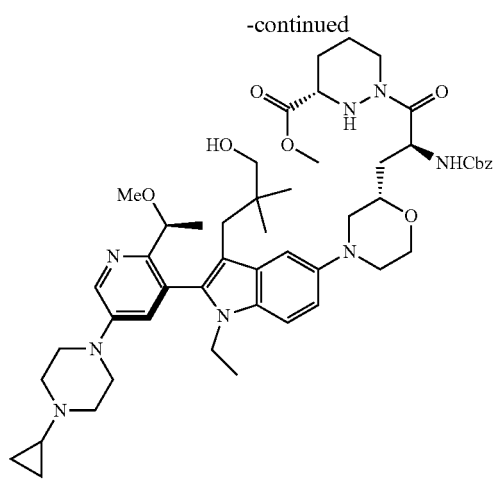

272
-continued

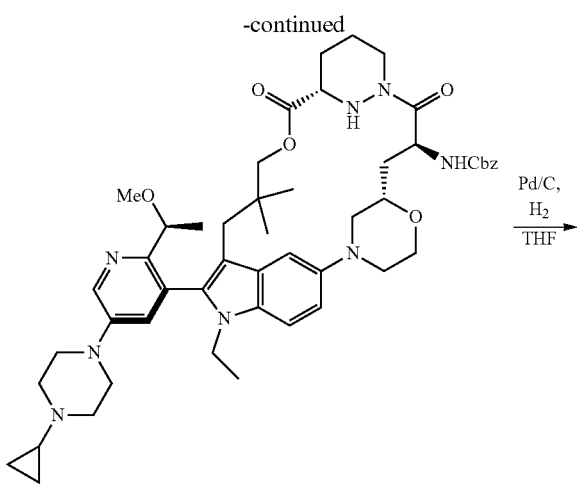

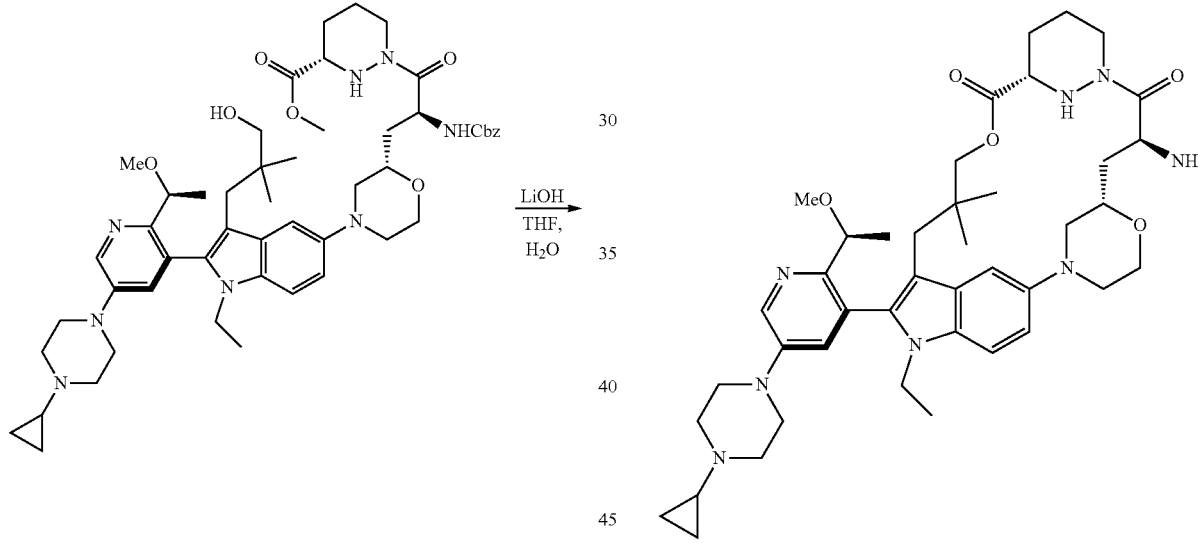

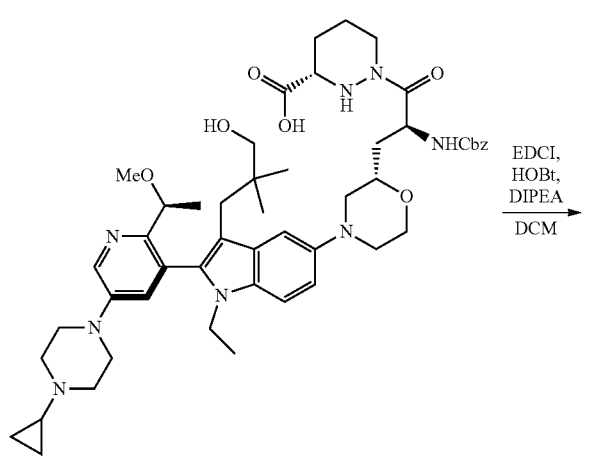

Step 1: Synthesis of (S)-5-bromo-3-(3-((tert-butyldimethylsilyl)oxy)-2,2-dimethylpropyl)-2-(5-(4-cyclopropylpiperazin-1-yl)-2-(1-methoxyethyl)pyridin-3-yl)-1-ethyl-1H-indole To a solution of (S)-5-bromo-3-(3-((tert-butyldimethylsilyl)oxy)-2,2-dimethylpropyl)-1-ethyl-2-(2-(1-methoxyethyl)-5-(4,4,5,5-tetramethyl-1,3,2-dioxaborolan-2-yl)pyridin-3-yl)-1H-indole (20 g, 29.2 mmol) in MeCN (100 mL) was added 1-cyclopropylpiperazine (5.53 g, 43.8 mmol), pyridine (6.93 g, 87.6 mmol) and Cu(OAC)$_2$ (10.61 g, 58.4 mmol), followed by the addition of 4A MS (20 g). The reaction was stirred at 60° C. for 16 h under O$_2$. The mixture was then filtered and concentrated under reduced pressure. The residue was purified by silica gel column chromatography (EtOAc/Pet. ether 2:1 then EtOAc/MeOH 10:1) to afford the desired product (6 g, 30% yield) as a solid. LCMS (ESI) m/z [M+H] calcd for C$_{36}$H$_{55}$BrN$_4$O$_2$Si: 683.34; found: 683.3.

Step 2: Synthesis of methyl (S)-2-(((benzyloxy) carbonyl)amino)-3-((S)-4-(3-(3-((tert-butyldimethylsilyl)oxy)-2,2-dimethylpropyl)-2-(5-(4-cyclopropylpiperazin-1-yl)-2-((S)-1-methoxyethyl)pyridin-3-yl)-1-ethyl-1H-indol-5-yl)morpholin-2-yl) propanoate To a solution of (S)-5-bromo-3-(3-((tert-butyldimethylsilyl)oxy)-2,2-dimethylpropyl)-2-(5-(4-cyclopropylpiperazin-1-yl)-2-(1-methoxyethyl)pyridin-3-yl)-1-ethyl-1H-indole (4 g, 5.8 mmol) in dioxane (40 mL) was added methyl (S)-2-(((benzyloxy)carbonyl)amino)-3-((S)-morpholin-2-yl)propanoate (2.8 g, 8.7 mmol), RuPhos (0.81 g, 1.7 mmol), $Cs_2CO_3$ (5.67 g, 17.4 mmol), Ruphos Pd G2 (0.45 g, 0.6 mmol) and $Pd(OAc)_2$ (0.13 g, 0.6 mmol). The reaction was stirred at 105° C. for 4 h under $N_2$. The mixture was concentrated under reduced pressure and the residue was purified by column chromatography (basic $Al_2O_3$, EtOAc/pet. ether 1:1) to afford the desired product (2 g, 38% yield) as a solid. LCMS (ESI) m/z [M+H] calcd for $C_{52}H_{76}N_6O_7Si$: 925.56; found: 925.5.

Step 3: Synthesis of (S)-2-(((benzyloxy)carbonyl) amino)-3-((S)-4-(3-(3-((tert-butyldimethylsilyl)oxy)-2,2-dimethylpropyl)-2-(5-(4-cyclopropylpiperazin-1-yl)-2-((S)-1-methoxyethyl)pyridin-3-yl)-1-ethyl-1H-indol-5-yl)morpholin-2-yl)propanoic acid To a solution of methyl (S)-2-(((benzyloxy)carbonyl)amino)-3-((S)-4-(3-(3-((tert-butyldimethylsilyl)oxy)-2,2-dimethylpropyl)-2-(5-(4-cyclopropylpiperazin-1-yl)-2-((S)-1-methoxyethyl)pyridin-3-yl)-1-ethyl-1H-indol-5-yl)morpholin-2-yl)propanoate (2 g, 2.2 mmol) in THF (20 mL) and $H_2O$ (6 mL) was added LiOH (0.26 g. 11 mmol) at 0° C. The reaction was stirred at room temperature for 3 h. The mixture was adjusted to pH 6 with 1 N HCl and extracted with EtOAc (2×30 mL). The combined organic layers were washed with brine, dried over $Na_2SO_4$, filtered and concentrated under reduced pressure to afford (1.8 g crude) as a solid, which was used in the next step directly without further purification. LCMS (ESI) m/z [M+H] calcd for $C_{51}H_{74}N_6O_7Si$: 911.55; found: 911.5.

Step 4: Synthesis of methyl (S)-1-((S)-2-(((benzyloxy)carbonyl)amino)-3-((S)-4-(3-(3-((tert-butyldimethylsilyl)oxy)-2,2-dimethylpropyl)-2-(5-(4-cyclopropylpiperazin-1-yl)-2-((S)-1-methoxyethyl) pyridin-3-yl)-1-ethyl-1H-indol-5-yl)morpholin-2-yl) propanoyl)hexahydropyridazine-3-carboxylate To a solution of (S)-2-(((benzyloxy)carbonyl)amino)-3-((S)-4-(3-(3-((tert-butyldimethylsilyl)oxy)-2,2-dimethylpropyl)-2-(5-(4-cyclopropylpiperazin-1-yl)-2-((S)-1-methoxyethyl)pyridin-3-yl)-1-ethyl-1H-indol-5-yl)morpholin-2-yl)propanoic acid (1.8 g, 2.0 mmol) in DMF (15 mL) was added a solution of methyl (3S)-1,2-diazinane-3-carboxylate (0.43 g, 3 mmol) and DIPEA (1.3 g, 10 mmol) at 0° C. in DMF (5 mL), followed by HATU (0.91 g, 2.4 mmol). The reaction was stirred at 0° C. for 2 h. The mixture was diluted with EtOAc (40 mL) and quenched with $H_2O$ (30 mL). The organic layer was washed with $H_2O$ (2×30 mL) and brine (30 mL), dried over $Na_2SO_4$, filtered, and concentrated under reduced pressure. The residue was purified by normal phase column chromatography (EtOAc/MeOH 20:1) to afford the desired product (1.8 g, 85% yield) as a solid. LCMS (ESI) m/z [M/2+H] calcd for $C_{57}H_{84}N_8O_8Si$: 519.32; found: 519.4.

Step 5: Synthesis of methyl (S)-1-((S)-2-(((benzyloxy)carbonyl)amino)-3-((S)-4-(2-(5-(4-cyclopropylpiperazin-1-yl)-2-((S)-1-methoxyethyl)pyridin-3-yl)-1-ethyl-3-(3-hydroxy-2,2-dimethylpropyl)-1H-indol-5-yl)morpholin-2-yl)propanoyl) hexahydropyridazine-3-carboxylate To a solution of methyl (S)-1-((S)-2-(((benzyloxy)carbonyl)amino)-3-((S)-4-(3-(3-((tert-butyldimethylsilyl)oxy)-2,2-dimethylpropyl)-2-(5-(4-cyclopropylpiperazin-1-yl)-2-((S)-1-methoxyethyl)pyridin-3-yl)-1-ethyl-1H-indol-5-yl)morpholin-2-yl)propanoyl)hexahydropyridazine-3-carboxylate (1.8 g, 1.7 mmol) in MeOH (20 mL) was added $NH_4F$ (2.52 g, 67.9 mmol). The reaction was stirred at 80° C. for 16 h. The mixture was concentrated under reduced pressure, and the residue was diluted with DCM (30 mL). After filtration, the filtrate was concentrated under reduced pressure to afford the dired product (1.7 g crude) as a solid, which was used in the next step directly without further purification. LCMS (ESI) m/z [M+H] calcd for $C_{51}H_{70}N_8O_8$: 923.54; found: 923.4.

Step 6: Synthesis of (S)-1-((S)-2-(((benzyloxy)carbonyl)amino)-3-((S)-4-(2-(5-(4-cyclopropylpiperazin-1-yl)-2-((S)-1-methoxyethyl)pyridin-3-yl)-1-ethyl-3-(3-hydroxy-2,2-dimethylpropyl)-1H-indol-5-yl)morpholin-2-yl)propanoyl)hexahydropyridazine-3-carboxylic acid To a solution of methyl (S)-1-((S)-2-(((benzyloxy)carbonyl)amino)-3-((S)-4-(2-(5-(4-cyclopropylpiperazin-1-yl)-2-((S)-1-methoxyethyl)pyridin-3-yl)-1-ethyl-3-(3-hydroxy-2,2-dimethylpropyl)-1H-indol-5-yl)morpholin-2-yl)propanoyl)hexahydropyridazine-3-carboxylate (1.8 g, 1.9 mmol) in THF (20 mL) and $H_2O$ (5 mL) was added LiOH (0.23 g, 9.5 mmol) at 0° C. The reaction was stirred at room temperature for 3 h. The mixture was adjusted to pH-7 with 1 N HCl. The resulting solution was concentrated under reduced pressure to afford the desired product (1.8 g crude) as a solid, which was used in the next step directly without further purification. LCMS (ESI) m/z [M+H] calcd for $C_{50}H_{68}N_8O_8$: 909.53; found: 909.5.

Step 7: Synthesis of benzyl ((2²S,6³S,4S)-1²-(5-(4-cyclopropylpiperazin-1-yl)-2-((S)-1-methoxyethyl) pyridin-3-yl)-1¹-ethyl-10,10-dimethyl-5,7-dioxo-6¹, 6²,6³,6⁴,6⁵,6⁶-hexahydro-1¹H-8-oxa-2(4,2)-morpholina-1(5,3)-indola-6(1,3)-pyridazinacycloundecaphane-4-yl)carbamate To a solution of (S)-1-((S)-2-(((benzyloxy)carbonyl) amino)-3-((S)-4-(2-(5-(4-cyclopropylpiperazin-1-yl)-2-((S)-1-methoxyethyl)pyridin-3-yl)-1-ethyl-3-(3-hydroxy-2,2-dimethylpropyl)-1H-indol-5-yl)morpholin-2-yl) propanoyl)hexahydropyridazine-3-carboxylic acid (1.6 g, 1.8 mmol) in DCM (160 mL) was added DIPEA (6.98 g, 54 mmol), HOBt (2.43 g, 18 mmol) and EDCI (10.4 g, 54 mmol). The reaction was stirred at 30° C. for 16 h. The mixture was concentrated under reduced pressure, the residue was diluted with EtOAc (50 mL). The organic layer was washed with $H_2O$ (2×40 mL) and brine (40 mL), dried over $Na_2SO_4$, filtered and concentrated under reduced pressure. The residue was purified by normal phase column chromatography (EtOAc/MeOH 10:1) to afford the desired product (0.8 g, 50% yield) as a solid. LCMS (ESI) m/z [M+H] calcd for $C_{50}H_{66}N_8O_7$: 891.52; found: 891.6.

Step 8: Synthesis of (2²S,6³S,4S)-4-amino-1²-(5-(4-cyclopropylpiperazin-1-yl)-2-((S)-1-methoxyethyl)pyridin-3-yl)-1¹-ethyl-10,10-dimethyl-6¹,6²,6³,6⁴,6⁵,6⁶-hexahydro-1¹H-8-oxa-2(4,2)-morpholina-1(5,3)-indola-6(1,3)-pyridazinacycloundecaphane-5,7-dione To a solution of benzyl ((2²S,6³S,4S)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)carbamate (700 mg, 0.79 mmol) in THF (10 mL) was added 10% Pd/C (350 mg). The reaction was stirred for 6 h under $H_2$ (1 atm). The mixture was filtered and concentrated under reduced pressure. The residue was purified by normal phase column chromatography (EtOAc (1% $NH_3H_2O$)/MeOH (1% $NH_3H_2O$) 10:1) to afford the desired product (420 mg, 71% yield) as a solid. LCMS (ESI) m/z [M+H] calcd for $C_{42}H_{60}N_8O_5$: 757.48; found: 757.5.

Intermediate 19: Synthesis of (6³S,4S)-4-amino-1²-(5-(4-cyclopropylpiperazin-1-yl)-2-((S)-1-methoxyethyl)pyridin-3-yl)-1¹-ethyl-10,10-dimethyl-2,22,2³,2⁶,6¹,6²,6³,6⁴,6⁵,6⁶-decahydro-1¹H-8-oxa-1(5,3)-indola-6(1,3)-pyridazina-2(5,1)-pyridinacycloundecaphane-5,7-dione

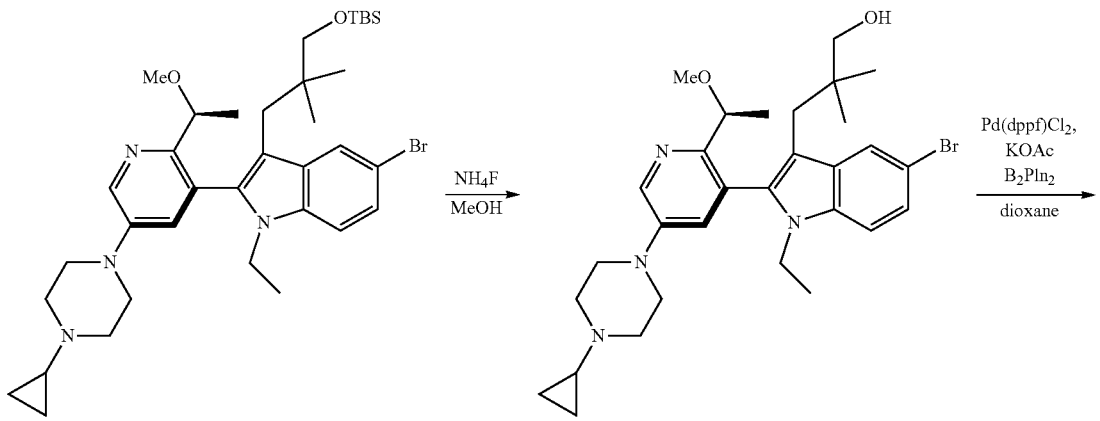

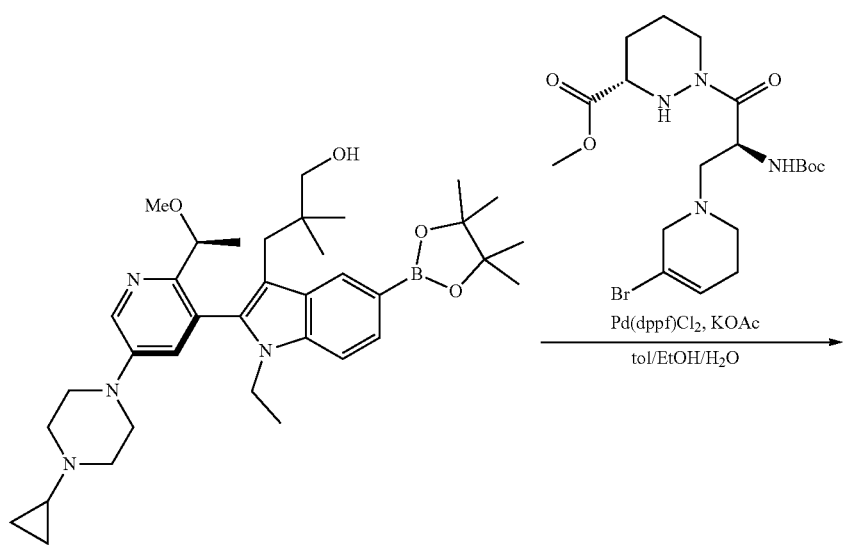

-continued
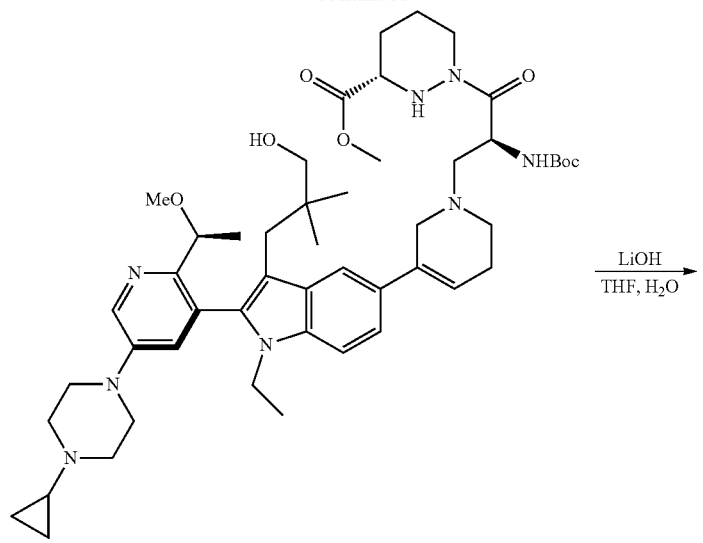
LiOH
THF, H₂O
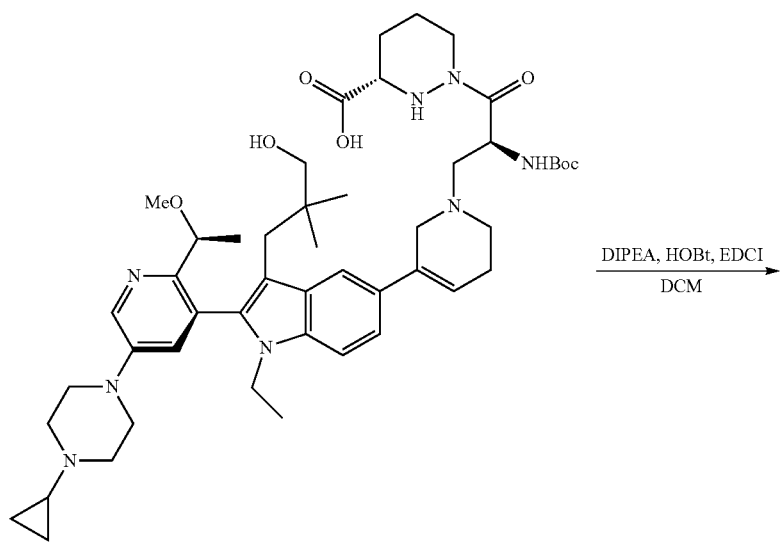
DIPEA, HOBt, EDCI
DCM
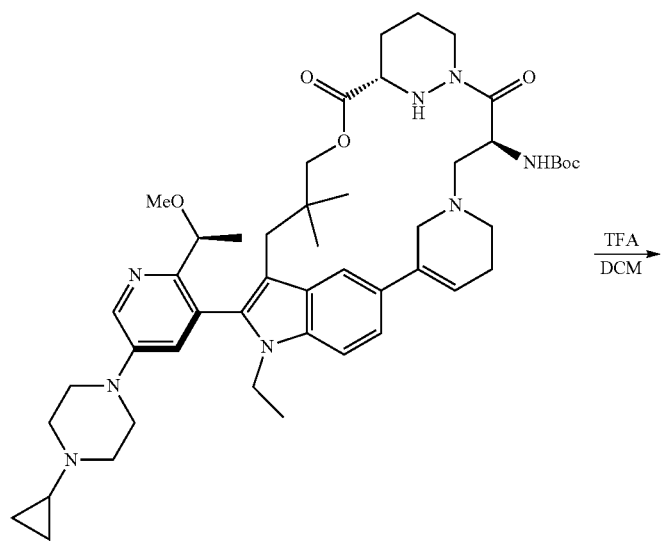
TFA
DCM

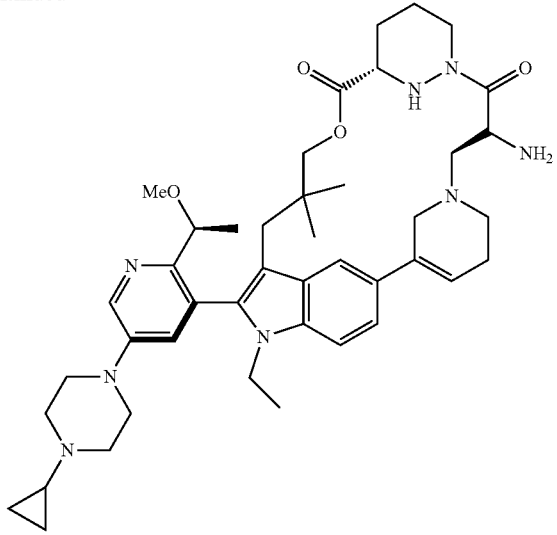

Step 1: Synthesis of (S)-3-(5-bromo-2-(5-(4-cyclopropylpiperazin-1-yl)-2-(1-methoxyethyl)pyridin-3-yl)-1-ethyl-1H-indol-3-yl)-2,2-dimethylpropan-1-ol A solution of (S)-5-bromo-3-(3-((tert-butyldimethylsilyl)oxy)-2,2-dimethylpropyl)-2-(5-(4-cyclopropylpiperazin-1-yl)-2-(1-methoxyethyl)pyridin-3-yl)-1-ethyl-1H-indole (3 g, 4 mmol) and $NH_4F$ (6.5 g, 176 mmol, 40 eq) in MeOH (30 mL) was stirred for 16h at 80° C. The reaction mixture was diluted with EtOAc (50 mL) and washed with $H_2O$ (2×50 mL). The organic phase was concentrated under reduced pressure to afford (4.2 g, 95% yield) as a solid. LCMS (ESI) m/z [M+H] calcd for $C_{30}H_{41}BrN_4O_2$: 569.25; found: 569.3.

Step 2: Synthesis of (S)-3-(2-(5-(4-cyclopropylpiperazin-1-yl)-2-(1-methoxyethyl)pyridin-3-yl)-1-ethyl-5-(4,4,5,5-tetramethyl-1,3,2-dioxaborolan-2-yl)-1H-indol-3-yl)-2,2-dimethylpropan-1-ol To a solution of (S)-3-(5-bromo-2-(5-(4-cyclopropylpiperazin-1-yl)-2-(1-methoxyethyl)pyridin-3-yl)-1-ethyl-1H-indol-3-yl)-2,2-dimethylpropan-1-ol (3 g, 5.3 mmol) and 4,4,5,5-tetramethyl-2-(4,4,5,5-tetramethyl-1,3,2-dioxaborolan-2-yl)-1,3,2-dioxaborolane (1.5 g, 5.8 mmol) in 1,4-dioxane (30 mL) was added KOAc (1 g, 10.5 mmol) followed by Pd(dppf)Cl$_2$●DCM (860 mg, 1.1 mmol) under $N_2$ atmosphere. The resulting mixture was stirred for 6 hours at 85° C. The mixture was concentrated under pressure to give a residue. The residue was purified by normal phase column chromatography (EtOAc/pet. ether 5:1) to afford the desired product (2 g, 61% yield) as an oil. LCMS (ESI) m/z [M+H] calcd for $C_{36}H_{53}BN_4O_4$: 617.43; found: 617.3.

Step 3: Synthesis of methyl (S)-1-((S)-2-((tert-butoxycarbonyl)amino)-3-(5-(2-(5-(4-cyclopropylpiperazin-1-yl)-2-((S)-1-methoxyethyl)pyridin-3-yl)-1-ethyl-3-(3-hydroxy-2,2-dimethylpropyl)-1H-indol-5-yl)-3,6-dihydropyridin-1(2H)-yl)propanoyl)hexahydropyridazine-3-carboxylate To a solution of (S)-3-(2-(5-(4-cyclopropylpiperazin-1-yl)-2-(1-methoxyethyl)pyridin-3-yl)-1-ethyl-5-(4,4,5,5-tetramethyl-1,3,2-dioxaborolan-2-yl)-1H-indol-3-yl)-2,2-dimethylpropan-1-ol (1.7 g, 2.8 mmol) and methyl (S)-1-((S)-3-(5-bromo-3,6-dihydropyridin-1(2H)-yl)-2-((tert-butoxycarbonyl)amino)propanoyl)hexahydropyridazine-3-carboxylate (1.4 g, 3 mmol) in toluene (20 mL), EtOH (4 mL), and $H_2O$ (1 mL) was added $K_2CO_3$ (1.2 g, 8.4 mmol) followed by Pd(dppf)Cl$_2$●DCM (230 mg, 0.28 mmol) under $N_2$ atmosphere. The resulting mixture was stirred for 6 hours at 85° C. under $N_2$ atmosphere. The mixture was concentrated under reduced pressure to give a residue. The residue was purified by normal phase column chromatography (EtOAc/pet. ether 5:1) to afford the desired product (1 g, 40% yield) as a solid. LCMS (ESI) m/z [M+H] calcd for $C_{49}H_{72}N_8O_7$: 885.56; found: 885.5.

Step 4: Synthesis of (S)-1-((S)-2-((tert-butoxycarbonyl)amino)-3-(5-(2-(5-(4-cyclopropylpiperazin-1-yl)-2-((S)-1-methoxyethyl)pyridin-3-yl)-1-ethyl-3-(3-hydroxy-2,2-dimethylpropyl)-1H-indol-5-yl)-3,6-dihydropyridin-1(2H)-yl)propanoyl)hexahydropyridazine-3-carboxylic acid To a solution of methyl (S)-1-((S)-2-((tert-butoxycarbonyl)amino)-3-(5-(2-(5-(4-cyclopropylpiperazin-1-yl)-2-((S)-1-methoxyethyl)pyridin-3-yl)-1-ethyl-3-(3-hydroxy-2,2-dimethylpropyl)-1H-indol-5-yl)-3,6-dihydropyridin-1(2H)-yl)propanoyl)hexahydropyridazine-3-carboxylate (900 mg, 1 mmol) in THF (4 mL) was added a solution of lithium hydroxide (260 mg, 6.1 mmol) in $H_2O$ (1 mL). The resulting mixture was stirred for 3 hours. The reaction mixture was treated with 1 N HCl to pH to 4 at 0° C. The mixture was extracted with DCM (2×20 mL) and the organic layer was washed with brine. The solution was concentrated under reduced pressure to afford the desired product (1.0 g) as a solid, which was used directly in the next step. LCMS (ESI) m/z [M+H] calcd for $C_{48}H_{70}N_8O_7$: 871.55; found: 871.5.

Step 5: Synthesis of tert-butyl ((6$^3$S,4S)-1$^2$-(5-(4-cyclopropylpiperazin-1-yl)-2-((S)-1-methoxyethyl)pyridin-3-yl)-1$^1$-ethyl-10,10-dimethyl-5,7-dioxo-2$^1$2$^2$,2$^3$,2$^6$,6$^1$,6$^2$,6$^3$,6$^4$,6$^5$,6$^6$-decahydro-1$^1$H-8-oxa-1(5,3)-indola-6(1,3)-pyridazina-2(5,1)-pyridinacycloundecaphane-4-yl)carbamate To a stirred solution of (S)-1-((S)-2-((tert-butoxycarbonyl)amino)-3-(5-(2-(5-(4-cyclopropylpiperazin-1-yl)-2-

((S)-1-methoxyethyl)pyridin-3-yl)-1-ethyl-3-(3-hydroxy-2,2-dimethylpropyl)-1H-indol-5-yl)-3,6-dihydropyridin-1(2H)-yl)propanoyl)hexahydropyridazine-3-carboxylic acid (900 mg, 1 mmol) and DIPEA (4 g, 30 mmol) in DCM (100 mL) was added EDCI (5.9 g, 30 mmol) and HOBt (1.4 g, 10 mmol). The resulting mixture was stirred for 16 hours at 35° C. under an argon atmosphere. The resulting mixture was concentrated under reduced pressure and the residue was purified by normal phase column chromatography (pet. ether/EtOAc/NH$_3$·H$_2$O(1:5:0.05) to afford the desired product (450 mg, 53% yield) as a solid. LCMS (ESI) m/z [M+H] calcd for $C_{48}H_{68}N_8O_6$: 853.54; found: 853.4.

Step 6: Synthesis of (6$^3$S,4S)-4-amino-1$^2$-(5-(4-cyclopropylpiperazin-1-yl)-2-((S)-1-methoxyethyl)pyridin-3-yl)-1$^1$-ethyl-10,10-dimethyl-2$^1$ 2$^2$,2$^3$,2$^6$,6$^1$,6$^2$,6$^3$,6$^4$,6$^5$,6$^6$-decahydro-1$^1$H-8-oxa-1(5,3)-indola-6(1,3)-pyridazina-2(5,1)-pyridinacycloundecaphane-5,7-dione To a solution of tert-butyl ((6$^3$S,4S)-1$^2$-(5-(4-cyclopropylpiperazin-1-yl)-2-((S)-1-methoxyethyl)pyridin-3-yl)-1$^1$-ethyl-10,10-dimethyl-5,7-dioxo-2$^1$ 2$^2$,2$^3$,2$^6$,6$^1$,6$^2$,6$^3$,6$^4$,6$^5$,6$^6$-decahydro-1$^1$H-8-oxa-1(5,3)-indola-6(1,3)-pyridazina-2(5,1)-pyridinacycloundecaphane-4-yl)carbamate (230 mg, 0.024 mmol) in DCM (1.5 mL) was added TFA (0.5 mL). The solution was stirred for 1 h and was then concentrated under reduced pressure to afford the desired product (280 mg). LCMS (ESI) m/z [M+H]calcd for $C_{43}H_{60}N_8O_4$: 753.48; found: 753.5.

Intermediate 20: Synthesis of (6$^3$S,4S,Z)-4-amino-1$^2$-(5-(4-cyclopropylpiperazin-1-yl)-2-((S)-1-methoxyethyl)pyridin-3-yl)-10,10-dimethyl-1-(2,2,2-trifluoroethyl)-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-5,7-dione

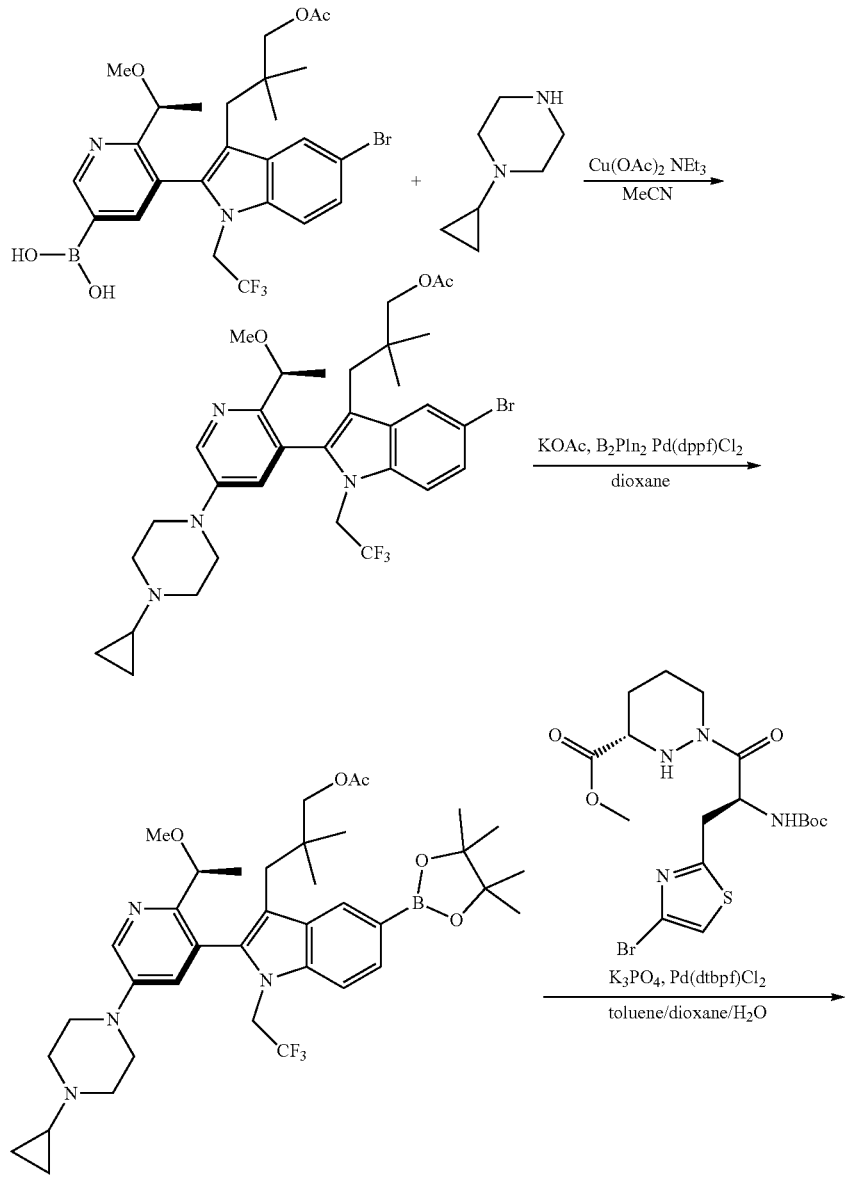

-continued
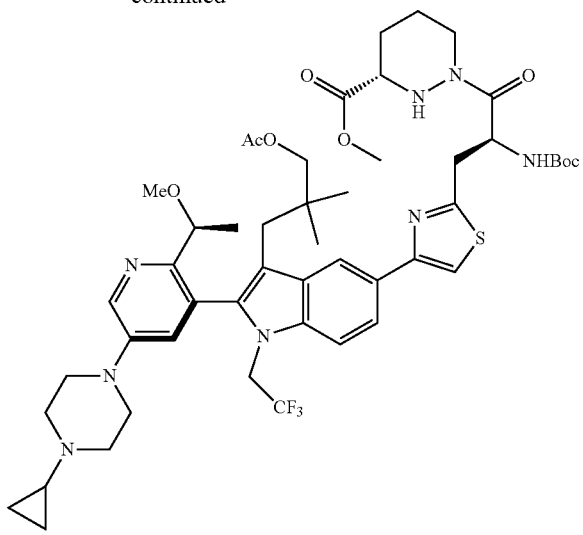
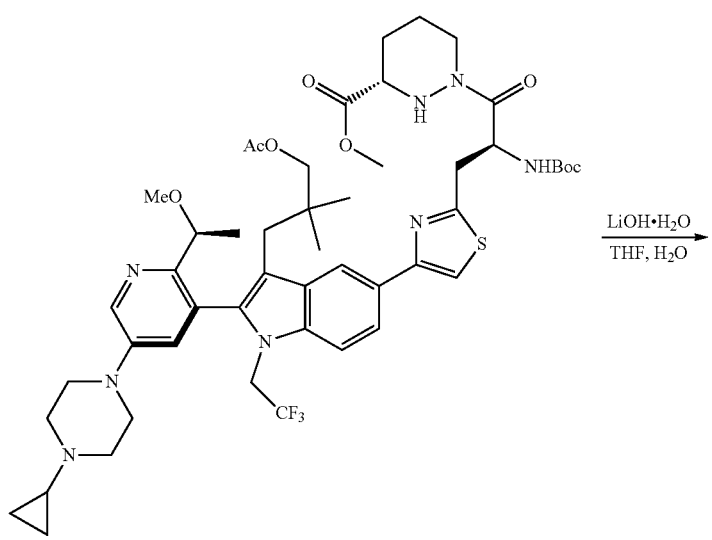
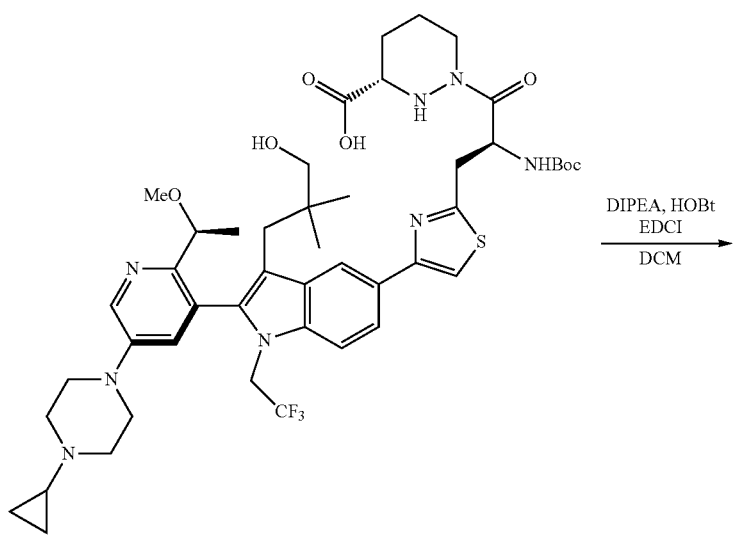

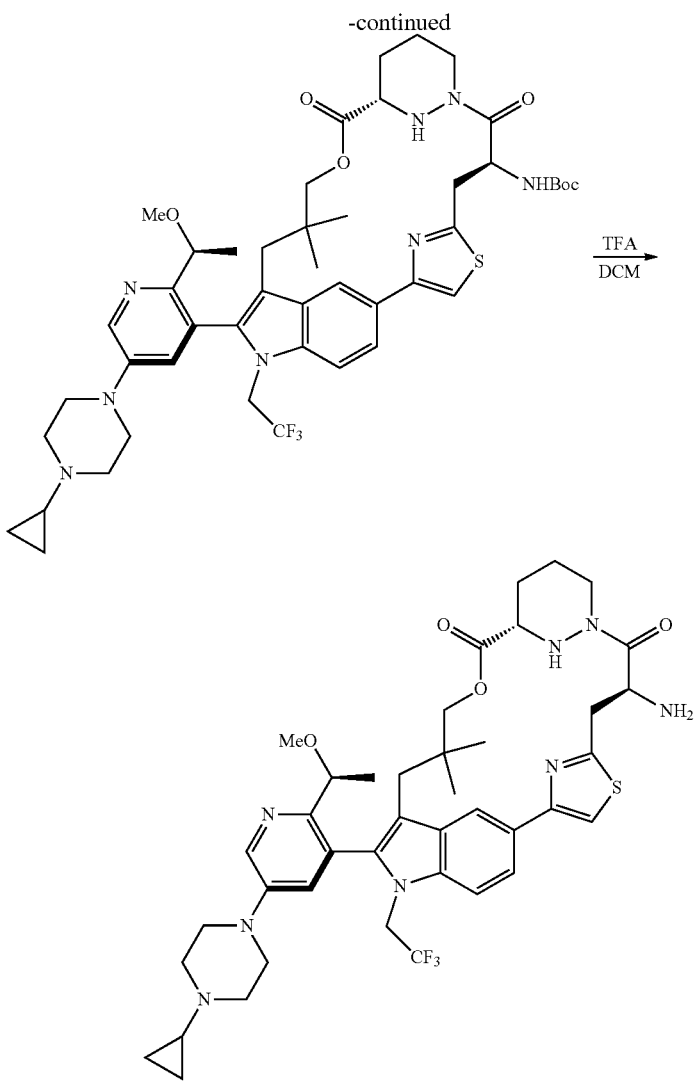

Step 1: Synthesis of (S)-3-(5-bromo-2-(5-(4-cyclopropylpiperazin-1-yl)-2-(1-methoxyethyl)pyridin-3-yl)-1-(2,2,2-trifluoroethyl)-1H-indol-3-yl)-2,2-dimethylpropyl acetate To a stirred solution of (S)-(5-(3-(3-acetoxy-2,2-dimethylpropyl)-5-bromo-1-(2,2,2-trifluoroethyl)-1H-indol-2-yl)-6-(1-methoxyethyl)pyridin-3-yl)boronic acid (40 g, 61.514 mmol) and NEt3 (12.45 g, 123.028 mmol) in MeCN (1000 mL) was added 4A MS (8 g) and 1-cyclopropylpiperazine (38.82 g, 307.570 mmol) in portions under an oxygen atmosphere. The resulting mixture was stirred for 1 h at room temperature under an oxygen atmosphere. To the above mixture was added Cu(OAc)$_2$ (22.35 g, 123.028 mmol) and then the vessel was evacuated, backfilled with oxygen, and then stirred overnight at room temperature. The resulting mixture was filtered and was concentrated under reduced pressure. The residue was diluted with EtOAc (300 mL) and the organic layer was washed with NH$_3$·H$_2$O (4×100 mL), dried over Na$_2$SO$_4$, and concentrated under reduce pressure. The residue was purified by column chromatography (50% EtOAc/pet. ether) to afford the desired product (23.7 g, 56% yield) as a solid. LCMS (ESI) m/z [M+H] calcd for C$_{32}$H$_{40}$BrF$_3$N$_4$O$_3$ 665.23; found: 666.0.

Step 2: Synthesis of (S)-3-(2-(5-(4-cyclopropylpiperazin-1-yl)-2-(1-methoxyethyl)pyridin-3-yl)-5-(4,4,5,5-tetramethyl-1,3,2-dioxaborolan-2-yl)-1-(2,2,2-trifluoroethyl)-1H-indol-3-yl)-2,2-dimethylpropyl acetate To a solution of (S)-3-(5-bromo-2-(5-(4-cyclopropylpiperazin-1-yl)-2-(1-methoxyethyl)pyridin-3-yl)-1-(2,2,2-trifluoroethyl)-1H-indol-3-yl)-2,2-dimethylpropyl acetate (26 g, 39.063 mmol) and KOAc (13.42 g, 136.721 mmol) in dioxane (260 mL) was added B$_2$Pin$_2$ (37.7 g, 148.4 mmol) and Pd(dppf)Cl$_2$ (2.86 g, 3.906 mmol). The resulting mixture was evacuated and backfilled with argon then stirred at 90° C. for 3 h. The resulting mixture was filtered, the filter cake was washed with EtOAc (2×200 mL), and the filtrate was concentrated under reduced pressure. The residue was purified by silica gel column chromatography, (80% EtOAc/pet. ether) to afford the desired product (17 g, 61% yield) as a solid. LCMS (ESI) m/z [M+H]calcd for C$_{38}$H$_{52}$BF$_3$N$_4$O$_5$ 713.41; found: 713.3.

Step 3: Synthesis of methyl (S)-1-((S)-3-(4-(3-(3-acetoxy-2,2-dimethylpropyl)-2-(5-(4-cyclopropylpiperazin-1-yl)-2-((S)-1-methoxyethyl)pyridin-3-yl)-1-(2,2,2-trifluoroethyl)-1H-indol-5-yl)thiazol-2-yl)-2-((tert-butoxycarbonyl)amino)propanoyl) hexahydropyridazine-3-carboxylate To a solution of (S)-3-(2-(5-(4-cyclopropylpiperazin-1-yl)-2-(1-methoxyethyl)pyridin-3-yl)-5-(4,4,5,5-tetramethyl-1,3,2-dioxaborolan-2-yl)-1-(2,2,2-trifluoroethyl)-1H-indol-3-yl)-2,2-dimethylpropyl acetate (17 g, 23.854 mmol), methyl (S)-1-((S)-3-(4-bromothiazol-2-yl)-2-((tert-butoxycarbonyl)amino)propanoyl)hexahydropyridazine-3-carboxylate (13.66 g, 28.625 mmol) and $K_3PO_4$ (12.66 g, 59.635 mmol) in toluene (170 mL), dioxane (57 mL) and $H_2O$ (57 mL) was added 1,1'-bis(di-tert-butylphosphino)ferrocene palladium dichloride (1.55 g, 2.385 mmol) in portions under an argon atmosphere. To the mixture was added. The resulting mixture was stirred at 70° C. for 2 h. The mixture was filtered, the filter cake was washed with EtOAc (3×100 mL). The aqueous layer was extracted with EtOAc (3×200 mL), and the combined organic layers were washed with brine (2×200 mL), dried over $Na_2SO_4$, filtered, and concentrated under reduced pressure. The residue was purified by silica gel column chromatography (3% MeOH/DCM) to afford the desired product (20.4 g, 87% yield) as a solid. LCMS (ESI) m/z [M+H] calcd for $C_{49}H_{65}F_3N_8O_8S$ 983.47; found: 983.6.

Step 4: Synthesis of (S)-1-((S)-2-((tert-butoxycarbonyl)amino)-3-(4-(2-(5-(4-cyclopropylpiperazin-1-yl)-2-((S)-1-methoxyethyl)pyridin-3-yl)-3-(3-hydroxy-2,2-dimethylpropyl)-1-(2,2,2-trifluoroethyl)-1H-indol-5-yl)thiazol-2-yl)propanoyl) hexahydropyridazine-3-carboxylic acid To a solution of methyl (S)-1-((S)-3-(4-(3-(3-acetoxy-2,2-dimethylpropyl)-2-(5-(4-cyclopropylpiperazin-1-yl)-2-((S)-1-methoxyethyl)pyridin-3-yl)-1-(2,2,2-trifluoroethyl)-1H-indol-5-yl)thiazol-2-yl)-2-((tert-butoxycarbonyl)amino)propanoyl)hexahydropyridazine-3-carboxylate (20 g, 20.343 mmol) in THF (200 mL) was added a solution of LiOH (2.56 g, 61.029 mmol) in $H_2O$ (61 mL) at 0° C. The resulting mixture was stirred overnight at room temperature. The mixture was then acidified to pH 6 with 1 N HCl (aq.) and was then extracted with EtOAc (3×100 mL). The combined organic layers were washed with brine (2×100 mL), dried over $Na_2SO_4$, filtered, and concentrated under reduced pressure to afford the crude product (18.8 g), which was used directly in the next step without purification. LCMS (ESI) m/z [M+H] calcd for $C_{46}H_{61}F_3N_8O_7S$ 927.44; found: 927.3.

Step 5: Synthesis of tert-butyl ((6$^3$S,4S,Z)-1$^2$-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)carbamate To a solution of (S)-1-((S)-2-((tert-butoxycarbonyl)amino)-3-(4-(2-(5-(4-cyclopropylpiperazin-1-yl)-2-((S)-1-methoxyethyl)pyridin-3-yl)-3-(3-hydroxy-2,2-dimethylpropyl)-1-(2,2,2-trifluoroethyl)-1H-indol-5-yl)thiazol-2-yl)propanoyl)hexahydropyridazine-3-carboxylic acid (15 g, 16.179 mmol), DIPEA (112.73 mL, 647.160 mmol), and HOBt (43.72 g, 323.580 mmol) in DCM (768 mL) at 0° C.
was added EDCI (93.05 g, 485.370 mmol). The resulting mixture was stirred overnight at room temperature. The reaction mixture was quenched by the addition of cold $H_2O$ (500 mL). The resulting mixture was extracted with EtOAc (3 x 500 mL), and the combined organic layers were washed with brine (2×500 mL), dried over $Na_2SO_4$, filtered, and concentrated under reduced pressure. The residue was purified by silica gel column chromatography (3% MeOH/DCM) to afford the desired product (7.5 g, 51% yield) as a solid. LCMS (ESI) m/z [M+H] calcd for $C_{46}H_{59}F_3N_8O_6S$ 909.43; found: 909.3.

Step 6: Synthesis of (6$^3$S,4S,Z)-4-amino-1$^2$-(5-(4-cyclopropylpiperazin-1-yl)-2-((S)-1-methoxyethyl)pyridin-3-yl)-10,10-dimethyl-1$^1$-(2,2,2-trifluoroethyl)-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-5,7-dione To a solution of tert-butyl ((6$^3$S,4S,2)-1$^2$-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)carbamate (8.2 g, 9.02 mmol) in DCM (80 mL) at 0° C. was added TFA (40 mL, 538.52 mmol). The resulting mixture was stirred for 2 h at room temperature. The mixture was then concentrated under reduced pressure and the residue was adjusted to pH 8 with sat. $NaHCO_3$ (aq.). The resulting mixture was extracted with EtOAc (3×300 mL), and the combined organic layers were washed with brine (300 mL), dried over $Na_2SO_4$, filtered, and concentrated under reduced pressure to afford the desired product (8.0 g, 98% yield) as a solid. LCMS (ESI) m/z [M+H] calcd for $C_{41}H_{51}F_3N_8O_4S$ 809.38; found: 809.5.

Intermediate 21: Synthesis of (2$^2$S,6$^3$S,4S)-4-amino-1$^2$-(5-(4-cyclopropylpiperazin-1-yl)-2-((S)-1-methoxyethyl)pyridin-3-yl)-10,10-dimethyl-1$^1$-(2,2,2-trifluoroethyl)-6$^1$,6$^2$,6$^3$,6$^4$,6$^5$,6$^6$-hexahydro-11H-8-oxa-2(4,2)-morpholina-1(5,3)-indola-6(1,3)-pyridazinacycloundecaphane-5,7-dione

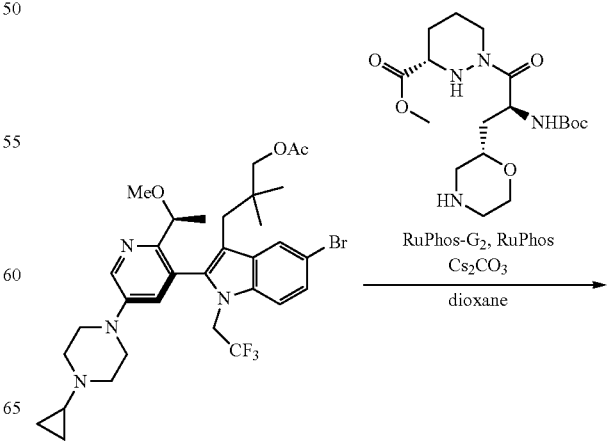

289
-continued

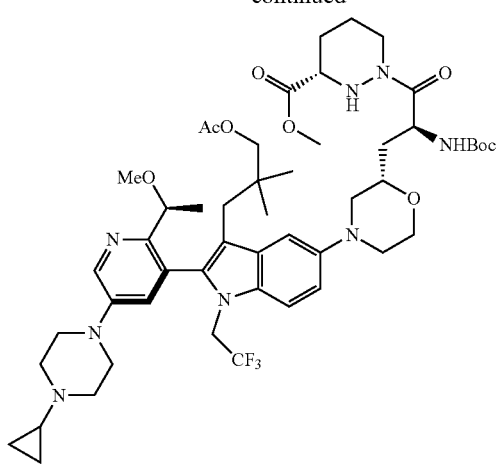

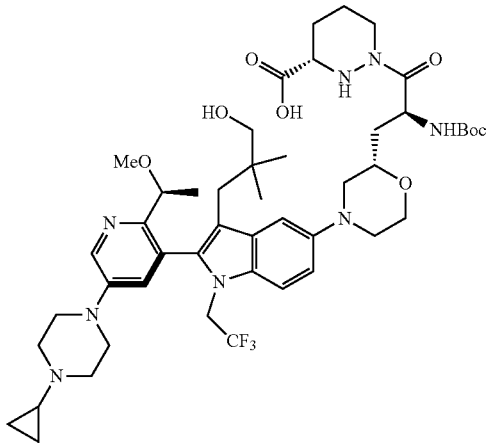

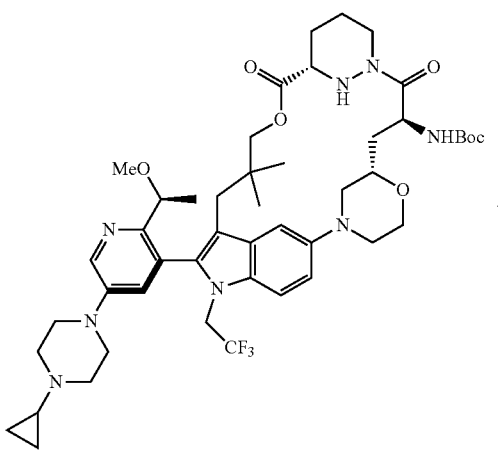

290
-continued

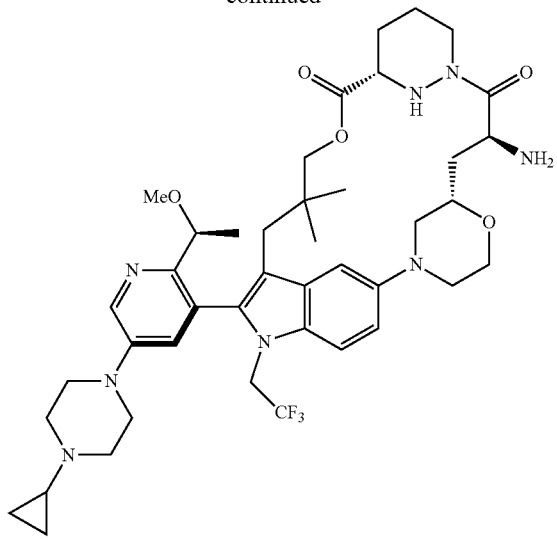

Step 1: Synthesis of methyl (S)-1-((S)-3-((S)-4-(3-(3-acetoxy-2,2-dimethylpropyl)-2-(5-(4-cyclopropylpiperazin-1-yl)-2-((S)-1-methoxyethyl)pyridin-3-yl)-1-(2,2,2-trifluoroethyl)-1H-indol-5-yl)morpholin-2-yl)-2-((tert-butoxycarbonyl)amino)propanoyl)hexahydropyridazine-3-carboxylate To a solution of 3(S)-3-(5-bromo-2-(5-(4-cyclopropylpiperazin-1-yl)-2-(1-methoxyethyl)pyridin-3-yl)-1-(2,2,2-trifluoroethyl)-1H-indol-3-yl)-2,2-dimethylpropyl acetate (65.0 g, 97.66 mmol) and methyl (S)-1-((S)-2-((tert-butoxycarbonyl)amino)-3-((S)-morpholin-2-yl)propanoyl)hexahydropyridazine-3-carboxylate (78.2 g, 0.195 mol) in dioxane (650 mL) was added RuPhos (27.3 g, 58.60 mmol), RuPhos-G2-Pd (22.7 g, 29.30 mmol), and $Cs_2CO_3$ (95.5 g, 0.29 mol). The resulting mixture was stirred overnight at 80° C. The reaction mixture was then filtered, the filter cake was washed with EtOAc (3×300 mL), and the filtrate was concentrated under reduced pressure. The residue was purified by silica gel column chromatography to afford the desired product (63 g, 65% yield) as a solid. LCMS (ESI) m/z [M+H] calcd for $C_{50}H_{71}F_3NaO_9$ 985.54; found: 985.8.

Step 2: Synthesis of (S)-1-((S)-2-((tert-butoxycarbonyl)amino)-3-((S)-4-(2-(5-(4-cyclopropylpiperazin-1-yl)-2-((S)-1-methoxyethyl)pyridin-3-yl)-3-(3-hydroxy-2,2-dimethylpropyl)-1-(2,2,2-trifluoroethyl)-1H-indol-5-yl)morpholin-2-yl)propanoyl)hexahydropyridazine-3-carboxylic acid To a solution of methyl (S)-1-((S)-3-((S)-4-(3-(3-acetoxy-2,2-dimethylpropyl)-2-(5-(4-cyclopropylpiperazin-1-yl)-2-((S)-1-methoxyethyl)pyridin-3-yl)-1-(2,2,2-trifluoroethyl)-1H-indol-5-yl)morpholin-2-yl)-2-((tert-butoxycarbonyl)amino)propanoyl)hexahydropyridazine-3-carboxylate (79 g, 80.19 mmol) in THF (700 mL) was added a solution of LiOH•$H_2O$ (16.7 g, 0.398 mol) in $H_2O$ (150 mL) at 0° C. The resulting mixture was stirred for 5 h at room temperature. The mixture was then acidified to pH 5 with 1 M HCl. The aqueous layer was extracted with DCM (3×500 mL) and the organic layer was dried over $Na_2SO_4$, filtered, and Step 3: Synthesis of tert-butyl ((2²S,6³S,4S)-1²-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6¹,6²,6³,6⁴,6⁵,6⁶-hexahydro-1'H-8-oxa-2(4,2)-morpholina-1(5,3)-indola-6(1,3)-pyridazinacycloundecaphane-4-yl)carbamate To a solution of (S)-1-((S)-2-((tert-butoxycarbonyl)amino)-3-((S)-4-(2-(5-(4-cyclopropylpiperazin-1-yl)-2-((S)-1-methoxyethyl)pyridin-3-yl)-3-(3-hydroxy-2,2-dimethylpropyl)-1-(2,2,2-trifluoroethyl)-1H-indol-5-yl)morpholin-2-yl)propanoyl)hexahydropyridazine-3-carboxylic acid (55.7 g, 59.95 mmol) and DIPEA (208.8 mL, 1.199 mol) in DCM (6500 mL) at 0° C. was added EDCI (229.9 g, 1.199 mol) and HOBt (40.5 g, 0.299 mol). The resulting mixture was stirred overnight at room temperature. The reaction mixture was quenched by the addition of cold H₂O (500 mL) and the aqueous layer was extracted with EtOAc (3×800 mL). The combined organic layers were washed with brine (2×500 mL), dried over Na₂SO₄, filtered, and concentrated under reduced pressure. The residue was purified by silica gel column chromatography to afford the desired product (35.0 g, 64% yield) as a solid. LCMS (ESI) m/z [M+H] calcd for $C_{47}H_{65}F_3N_8O_7$ 911.50; found: 911.3.

Step 4: Synthesis of (2²S,6³S,4S)-4-amino-1²-(5-(4-cyclopropylpiperazin-1-yl)-2-((S)-1-methoxyethyl)pyridin-3-yl)-10,10-dimethyl-1¹-(2,2,2-trifluoroethyl)-6¹,6²,6³,6⁴,6⁵,6⁶-hexahydro-1¹H-8-oxa-2(4,2)-morpholina-1(5,3)-indola-6(1,3)-pyridazinacycloundecaphane-5,7-dione To a solution of tert-butyl ((2²S,6³S,4S)-1²-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)carbamate (33 g, 36.07 mmol) in DCM (180 mL) at 0° C. was added HCl in 1,4-dioxane (180 mL). The resulting mixture was stirred for 2 h at room temperature and then the mixture was concentrated under reduced pressure to afford the desired product (33 g, crude) as a solid. LCMS (ESI) m/z [M+H] calcd for $C_{42}H_{57}F_3N_8O_5$ 811.45; found: 811.3.

Intermediate 24: Synthesis of (6³S,4S)-4-amino-1²-(5-(4-cyclopropylpiperazin-1-yl)-2-((S)-1-methoxyethyl)pyridin-3-yl)-10,10-dimethyl-1¹-(2,2,2-trifluoroethyl)-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione

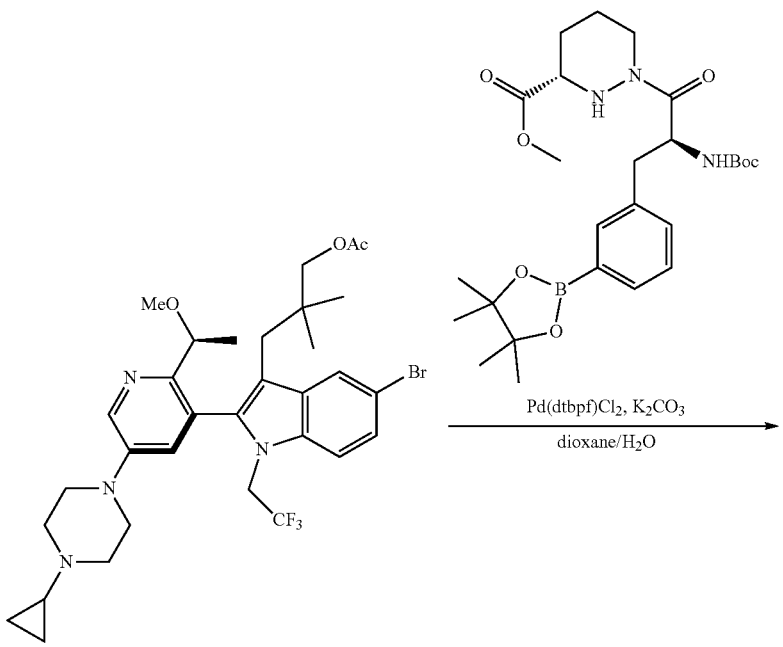

-continued
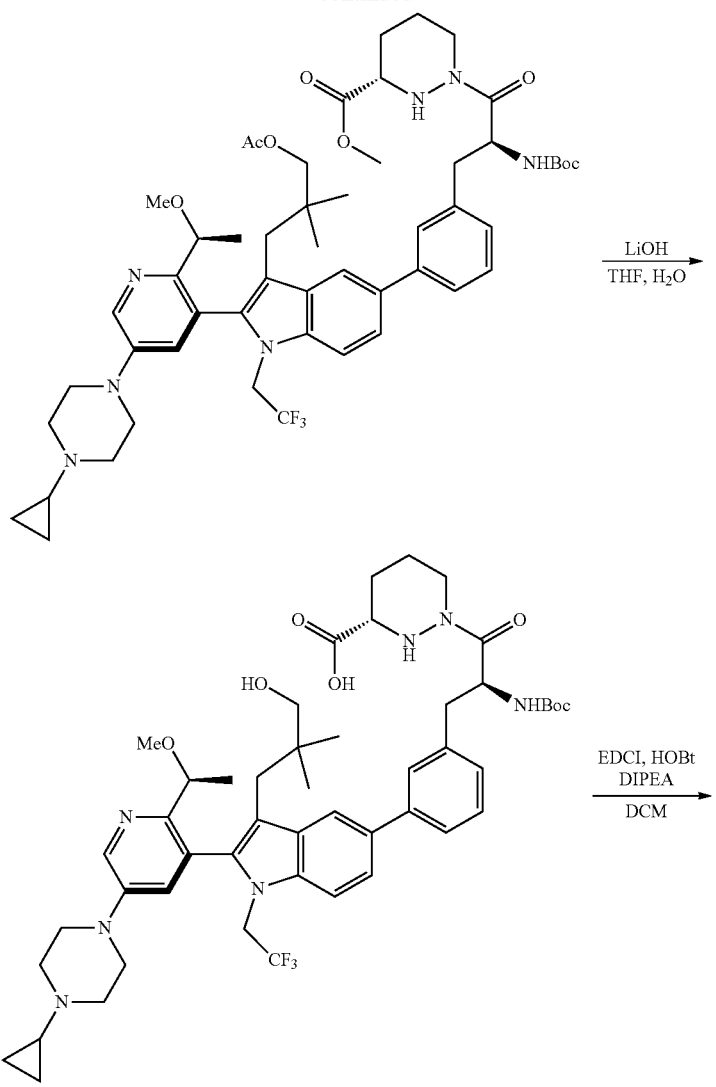
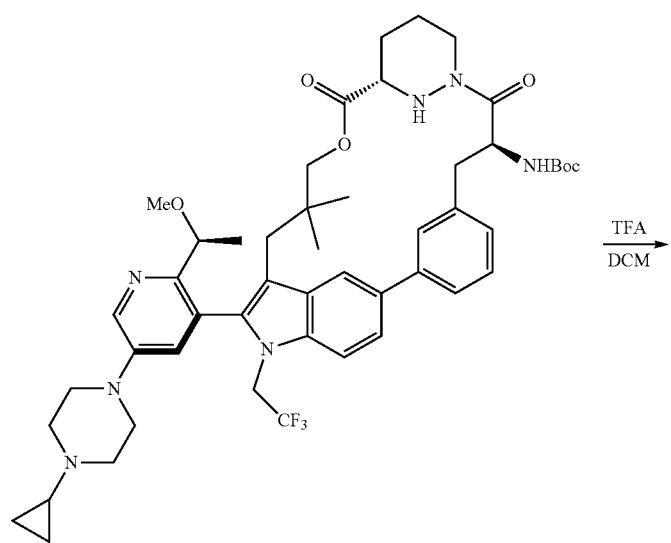

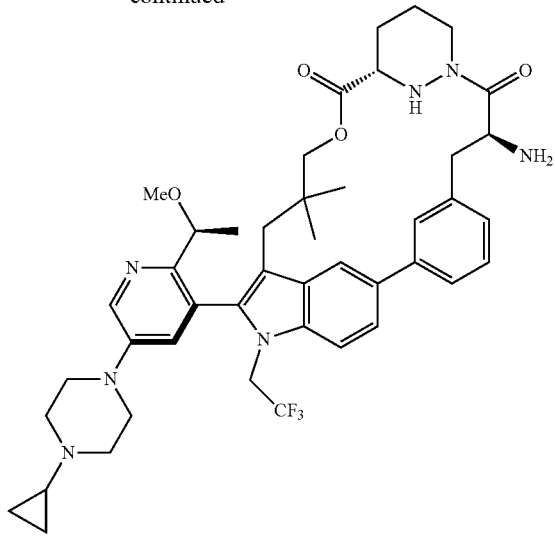

Step 1: Synthesis of methyl (S)-1-((S)-3-(3-(3-(3-acetoxy-2,2-dimethylpropyl)-2-(5-(4-cyclopropylpiperazin-1-yl)-2-((S)-1-methoxyethyl)pyridin-3-yl)-1-(2,2,2-trifluoroethyl)-1H-indol-5-yl)phenyl)-2-((tert-butoxycarbonyl)amino)propanoyl)hexahydropyridazine-3-carboxylate To a solution of 3(S)-3-(5-bromo-2-(5-(4-cyclopropylpiperazin-1-yl)-2-(1-methoxyethyl)pyridin-3-yl)-1-(2,2,2-trifluoroethyl)-1H-indol-3-yl)-2,2-dimethylpropyl acetate (1 g, 1.502 mmol) methyl (S)-1-((S)-2-((tert-butoxycarbonyl)amino)-3-(3-(4,4,5,5-tetramethyl-1,3,2-dioxaborolan-2-yl)phenyl)propanoyl)hexahydropyridazine-3-carboxylate (1.14 g, 2.253 mmol) in 1,4-dioxane (10 mL) and H$_2$O (2 mL) was added K$_2$CO$_3$ (415.28 mg, 3.004 mmol) and Pd(dtbpf)Cl$_2$ (97.92 mg, 0.150 mmol). The resulting mixture was stirred for 3 h at 65° C. The precipitated solids were collected by filtration and washed with DCM (30 mL). The resulting mixture was extracted with EtOAc (3×50 mL). The combined organic layers were washed with brine (2×20 mL), dried over Na$_2$SO$_4$, filtered, and concentrated under reduced pressure. The residue was purified by silica gel column chromatography (10% MeOH/DCM) to afford the desired product (860 mg, 90% yield) as a solid. LCMS (ESI) m/z [M+H] calcd for C$_{52}$H$_{68}$F$_3$N$_7$O$_8$ 976.52; found: 976.9.

Step 2: Synthesis of (S)-1-((S)-2-((tert-butoxycarbonyl)amino)-3-(3-(2-(5-(4-cyclopropylpiperazin-1-yl)-2-((S)-1-methoxyethyl)pyridin-3-yl)-3-(3-hydroxy-2,2-dimethylpropyl)-1-(2,2,2-trifluoroethyl)-1H-indol-5-yl)phenyl)propanoyl)hexahydropyridazine-3-carboxylic acid To a solution of methyl (S)-1-((S)-3-(3-(3-(3-acetoxy-2,2-dimethylpropyl)-2-(5-(4-cyclopropylpiperazin-1-yl)-2-((S)-1-methoxyethyl)pyridin-3-yl)-1-(2,2,2-trifluoroethyl)-1H-indol-5-yl)phenyl)-2-((tert-butoxycarbonyl)amino)propanoyl)hexahydropyridazine-3-carboxylate (6.8 g, 6.963 mmol) in THF (68 mL) was added a solution of LiOH●H$_2$O (4.096 mmol) in H$_2$O (13.9 mL) at 0° C. The resulting mixture was stirred overnight and was then acidified to pH 5 with 1 M HCl. The resulting mixture was extracted with DCM (3×50 mL) and the combined organic layers were washed with brine (2×50 mL), dried over Na$_2$SO$_4$, filtered, and concentrated under reduced pressure to afford the desired product (6 g, 90% yield) as a solid. LCMS (ESI) m/z [M+H] calcd for C$_{49}$H$_{64}$F$_3$N$_7$O$_7$ 920.49; found: 920.9.

Step 3: Synthesis of tert-butyl ((6$^3$S,4S)-1$^2$-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)carbamate To a solution of (S)-1-((S)-2-((tert-butoxycarbonyl)amino)-3-(3-(2-(5-(4-cyclopropylpiperazin-1-yl)-2-((S)-1-methoxyethyl)pyridin-3-yl)-3-(3-hydroxy-2,2-dimethylpropyl)-1-(2,2,2-trifluoroethyl)-1H-indol-5-yl)phenyl)propanoyl)hexahydropyridazine-3-carboxylic acid (5 g, 5.434 mmol) in DCM (40 mL) at 0° C. was added DIPEA (28.09 g, 217.360 mmol) and HOBt (7.34 g, 54.34 mmol). To the mixture was added a solution of EDCI (31.25 g, 163.020 mmol) in DCM (10 mL). The resulting mixture was warmed to room temperature and stirred overnight. The mixture was concentrated under reduced pressure and the residue was taken up in EtOAc (100 mL). The organic layer was washed with brine (2×100 mL), dried over Na$_2$SO$_4$, filtered, and concentrated under reduced pressure. The residue was purified by silica gel column chromatography (3% MeOH/DCM) to afford the desired product (4.2 g, 79% yield) as a solid. LCMS (ESI) m/z [M+H] calcd for C$_{49}$H$_{62}$F$_3$N$_7$O$_6$ 902.48; found: 902.1.

Step 4: Synthesis of (6$^3$S,4S)-4-amino-1$^2$-(5-(4-cyclopropylpiperazin-1-yl)-2-((S)-1-methoxyethyl)pyridin-3-yl)-10,10-dimethyl-1$^1$-(2,2,2-trifluoroethyl)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-5,7-dione To a solution of tert-butyl ((6$^3$S,4S)-1$^2$-(5-(4-cyclopropylpiperazin-1-yl)-2-((S)-1-methoxyethyl)pyridin-3-yl)-10, 10-dimethyl-5,7-dioxo-1'-(2,2,2-trifluoroethyl)-$6^1,6^2,6^3,6^4$, $6^5,6^6$-hexahydro-$1^1$H-8-oxa-1(5,3)-indola-6(1,3)-pyridazina-2(1,3)-benzenacycloundecaphane-4-yl)carbamate (1.8 g, 1.995 mmol) in DCM (16 mL) at 0° C. was added TFA (4 mL). The resulting mixture was stirred at 0° C. for 1 h and then the mixture was neutralized to pH 7 with sat. NaHCO$_3$ (aq). The resulting mixture was extracted with DCM (100 mL) and the combined organic layers were washed with brine (2×100 mL), dried over Na$_2$SO$_4$, filtered, and concentrated under reduced pressure to afford the desired product (1.5 g, 89% yield) as a solid. LCMS (ESI) m/z [M+H] calcd for $C_{44}H_{54}F_3N_7O_4$ 802.43; found: 802.8.

Intermediate 25: Synthesis of ($6^3$S,4S,Z)-4-amino-$1^2$-(5-(4-cyclopropylpiperazin-1-yl)-2-((S)-1-methoxyethyl)pyridin-3-yl)-$1^1$-ethyl-10,10-dimethy-$6^1,6^2,6^3,6^4,6^5,6^6$-hexahydro-$1^1$H-8-oxa-2(4,2)-thiazola-1(5,3)-indola-6(1,3)-pyridazinacycloundecaphane-5,7-dione

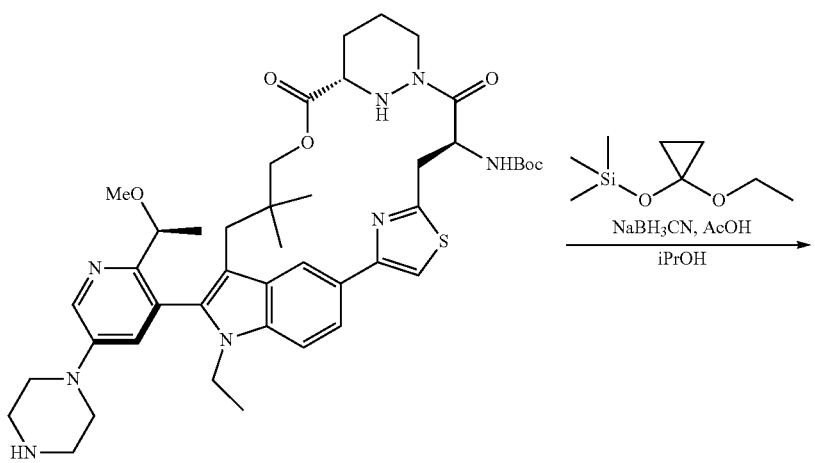

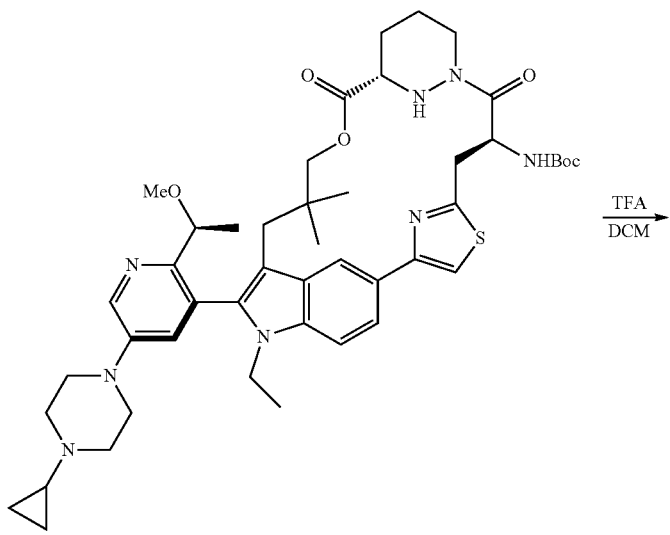

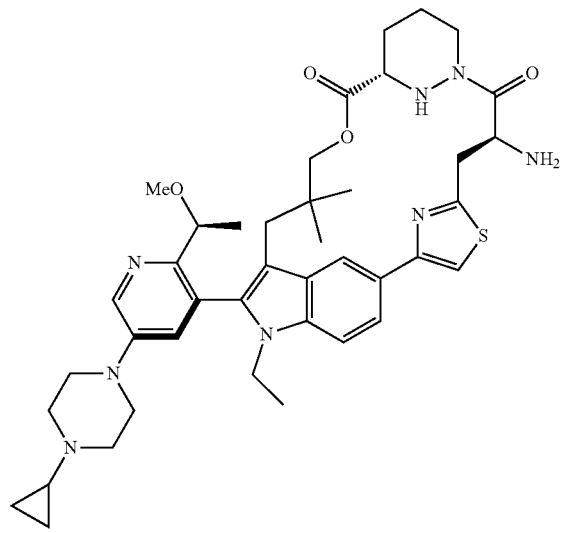

Step 1: Synthesis of tert-butyl ((6³S,4S,Z)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)carbamate To a solution of tert-butyl ((6³S,4S,Z)-1¹-ethyl-1²-(2-((S)-1-methoxyethyl)-5-(piperazin-1-yl)pyridin-3-yl)-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)carbamate (2 g, 2.454 mmol) and (1-ethoxycyclopropoxy)trimethylsilane (0.86 g, 4.908 mmol) in 2-propanol (20 mL) at room temperature was added NaBH₃CN (0.46 g, 7.362 mmol) and AcOH (0.28 mL, 4.908 mmol). The resulting mixture was stirred at 50° C. for 16 h and then reaction mixture was cooled to 0° C. and sat. NH₄Cl (30 mL) was added. The resulting mixture was extracted with EtOAc (2×20 mL) and the combined organic layers were washed with brine (2×20 mL), dried over Na₂SO₄, filtered, and concentrated under reduced pressure. The residue was purified by silica gel column chromatography (3% MeOH/DCM) to afford the desired product (1.5 g, 71% yield) as a solid. LCMS (ESI) m/z [M+H] calcd for C₄₆H₆₂N₈O₆S 855.46; found: 856.4.

Step 2: Synthesis of (6³S,4S,Z)-4-amino-1²-(5-(4-cyclopropylpiperazin-1-yl)-2-((S)-1-methoxyethyl)pyridin-3-yl)-1¹-ethyl-10,10-dimethyl-6¹,6²,6³,6⁴,6⁵,6⁶-hexahydro-1¹H-8-oxa-2(4,2)-thiazola-1(5,3)-indola-6(1,3)-pyridazinacycloundecaphane-5,7-dione A solution of tert-butyl ((6³S,4S,Z)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)carbamate (1.56 g, 1.824 mmol) and TFA (4 mL) in DCM (16 mL) was stirred at room temperature for 2 h and was then concentrated under reduced pressure. The residue was dissolved in EtOAc (30 mL) and the mixture was basified to pH 8 with sat. NaHCO₃ (aq). The aqueous layer was extracted with EtOAc (3×40 mL) and the combined organic layers were washed with brine (2×20 mL), dried over Na₂SO₄, filtered, and concentrated under reduced pressure to afford the desired product (1.36 g, crude) as a solid. LCMS (ESI) m/z [M+H] calcd for C₄₁H₅₄NaO₄S 755.41; found: 755.3.

Intermediate 26: Synthesis of (2²S,6³S,4S)-4-amino-1¹-ethyl-1²-(5-((S)-hexahydropyrazino[2,1-c][1,4]oxazin-8(1H)-yl)-2-((S)-1-methoxyethyl)pyridin-3-yl)-10,10-dimethyl-6¹,6²,6³,6⁴,6⁵,6⁶-hexahydro-1¹H-8-oxa-2(4,2)-morpholina-1(5,3)-indola-6(1,3)-pyridazinacycloundecaphane-5,7-dione

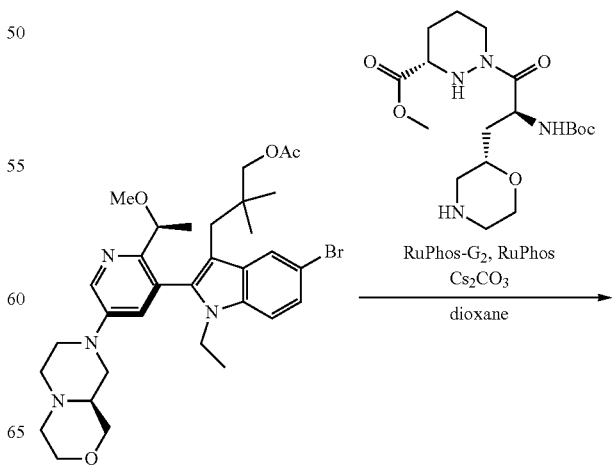

301
-continued

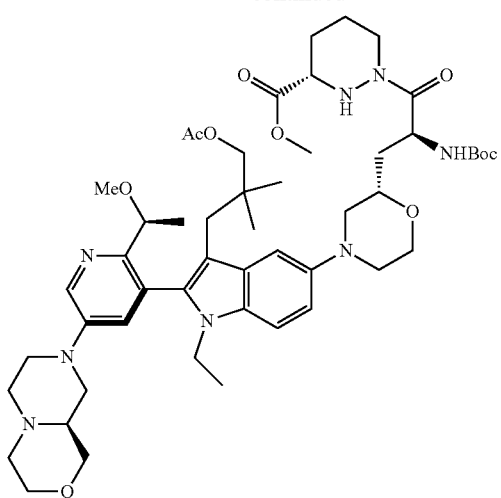

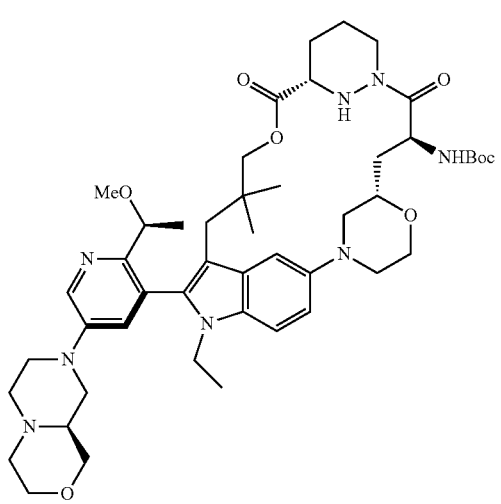

302
-continued

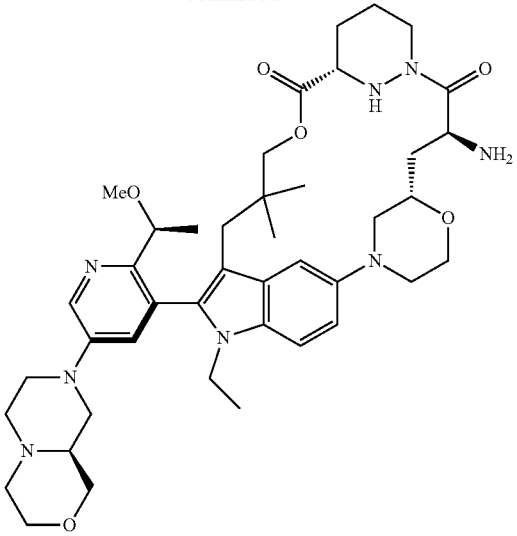

Step 1: Synthesis of methyl (S)-1-((S)-3-((S)-4-(3-(3-acetoxy-2,2-dimethylpropyl)-1-ethyl-2-(5-((S)-hexahydropyrazino[2,1-c][1,4]oxazin-8(1H)-yl)-2-((S)-1-methoxyethyl)pyridin-3-yl)-1H-indol-5-yl)morpholin-2-yl)-2-((tert-butoxycarbonyl)amino)propanoyl)hexahydropyridazine-3-carboxylate To a solution of 3-(5-bromo-1-ethyl-2-(5-((S)-hexahydropyrazino[2,1-c][1,4]oxazin-8(1H)-yl)-2-((S)-1-methoxyethyl)pyridin-3-yl)-1H-indol-3-yl)-2,2-dimethylpropyl acetate (15 g, 23.900 mmol) and methyl (S)-1-((S)-2-((tert-butoxycarbonyl)amino)-3-((S)-morpholin-2-yl)propanoyl)hexahydropyridazine-3-carboxylate (12.44 g, 31.070 mmol) in dioxane (150 mL) was added RuPhos (2.23 g, 4.780 mmol), RuPhos-G2-Pd (1.86 g, 2.390 mmol), and $Cs_2CO_3$ (3.64 g, 47.800 mmol). The resulting mixture was stirred overnight at 90° C. The reaction mixture was then filtered, the filter cake was washed with EtOAc (3×100 mL), and the filtrate was concentrated under reduced pressure. The residue was purified by silica gel column chromatography (9% MeOH/DCM) to afford the desired product (15.3 g, 33% yield) as a solid. LCMS (ESI) m/z [M+H] calcd for $C_{50}H_{74}N_8O_{10}$ 947.56; found: 947.4.

Step 2: Synthesis of (S)-1-((S)-2-((tert-butoxycarbonyl)amino)-3-((S)-4-(1-ethyl-2-(5-((S)-hexahydropyrazino[2,1-c][1,4]oxazin-8(1H)-yl)-2-((S)-1-methoxyethyl)pyridin-3-yl)-3-(3-hydroxy-2,2-dimethylpropyl)-1H-indol-5-yl)morpholin-2-yl)propanoyl)hexahydropyridazine-3-carboxylic acid To a solution of methyl (S)-1-((S)-3-((S)-4-(3-(3-acetoxy-2,2-dimethylpropyl)-1-ethyl-2-(5-((S)-hexahydropyrazino[2,1-c][1,4]oxazin-8(1H)-yl)-2-((S)-1-methoxyethyl)pyridin-3-yl)-1H-indol-5-yl)morpholin-2-yl)-2-((tert-butoxycarbonyl)amino)propanoyl)hexahydropyridazine-3-carboxylate (7.6 g, 8.024 mmol) in THF (34 mL) and $H_2O$ (34) was added LiOH•$H_2O$ (0.96 g, 40.120 mmol). The resulting mixture was stirred overnight at room temperature.

The mixture was then acidified to pH 5 with HCl (1 M). The aqueous layer was extracted with DCM (3×100 mL) and the organic layer was washed with brine (3×100 mL), dried over $Na_2SO_4$, filtered, and concentrated under reduced pressure to afford the desired product (6.4 g, 89% yield) as a solid. LCMS (ESI) m/z [M+H] calcd for $C_{47}H_{70}N_8O_9$ 891.54; found: 891.5.

Step 3: Synthesis of tert-butyl ((2$^2$S,6$^3$S,4S)-1$^1$-ethyl-1$^2$-(5-((S)-hexahydropyrazino[2,1-c][1,4]oxazin-8(1 H)-yl)-2-((S)-1-methoxyethyl)pyridin-3-yl)-10,10-dimethyl-5,7-dioxo-6,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-4-yl)carbamate To a solution of (S)-1-((S)-2-((tert-butoxycarbonyl)amino)-3-((S)-4-(1-ethyl-2-(5-((S)-hexahydropyrazino[2,1-c][1,4]oxazin-8(1 H)-yl)-2-((S)-1-methoxyethyl)pyridin-3-yl)-3-(3-hydroxy-2,2-dimethylpropyl)-1H-indol-5-yl)morpholin-2-yl)propanoyl)hexahydropyridazine-3-carboxylic acid (6.4 g, 7.182 mmol) and NMM (58.11 g, 574.560 mmol) in DCM (640 mL) at 0° C. was added EDCI (82.61 g, 430.920 mmol) and HOBt (14.6 g, 75.9 mmol). The resulting mixture was stirred overnight at room temperature. The reaction mixture was concentrated under reduced pressure and taken up in EtOAc (3×300 mL). The organic layer was washed with brine (3×200 mL), dried over $Na_2SO_4$, filtered, and concentrated under reduced pressure. The residue was purified by silica gel column chromatography (8% MeOH/DCM) to afford the desired product (3.2 g, 51% yield) as a solid. LCMS (ESI) m/z [M+H] calcd for $C_{47}H_{68}N_8O_8$ 873.53; found: 873.4.

Step 4: Synthesis of (2$^2$S,6$^3$S,4S)-4-amino-1$^1$-ethyl-1$^2$-(5-((S)-hexahydropyrazino[2,1-c][1,4]oxazin-8(1 H)-yl)-2-((S)-1-methoxyethyl)pyridin-3-yl)-10,10-dimethyl-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-5,7-dione To a solution tert-butyl ((2$^2$S,6$^3$S,4S)-1$^1$-ethyl-1$^2$-(5-((S)-hexahydropyrazino[2,1-c][1,4]oxazin-8(1 H)-yl)-2-((S)-1-methoxyethyl)pyridin-3-yl)-10,10-dimethyl-5,7-dioxo-6$^1$,6$^2$,6$^3$,6$^4$,6$^5$,6$^6$-hexahydro-1' H-8-oxa-2(4,2)-morpholina-1(5,3)-indola-6(1,3)-pyridazinacycloundecaphane-4-yl)carbamate (1 g, 1.145 mmol) in DCM (20 mL) at 0° C. was added TFA (10 mL). The resulting mixture was stirred at 0° C. for 3 h and was then concentrated under reduced to afford the desired product as a solid. LCMS (ESI) m/z [M+H] calcd for $C_{42}H_{60}N_8O_6$ 773.47; found: 773.5.

Intermediate 27: Synthesis of (6$^3$S,4S)-4-amino-1$^2$-(5-(4-cyclopropylpiperazin-1-yl)-2-((S)-1-methoxyethyl)pyridin-3-yl)-1$^1$-ethyl-10,10-dimethyl-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-5,7-dione

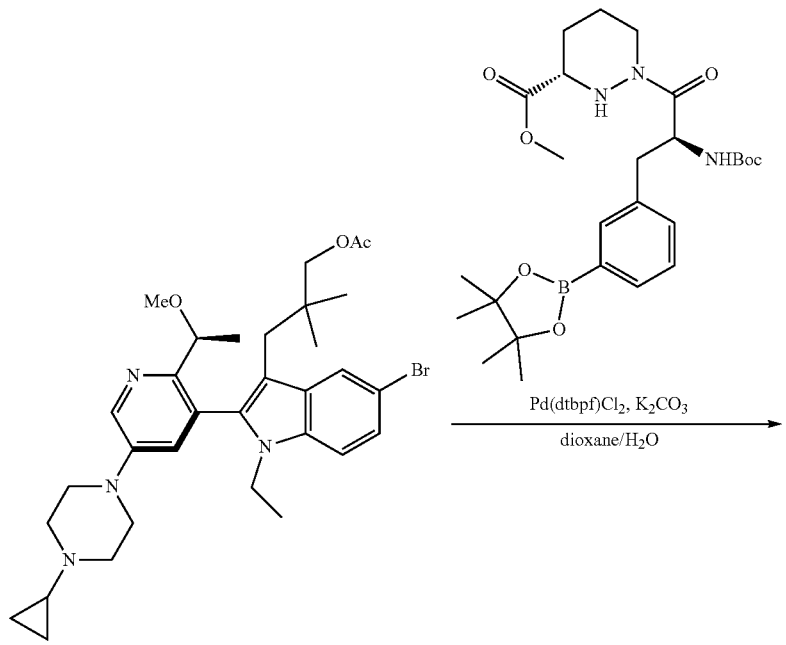

-continued
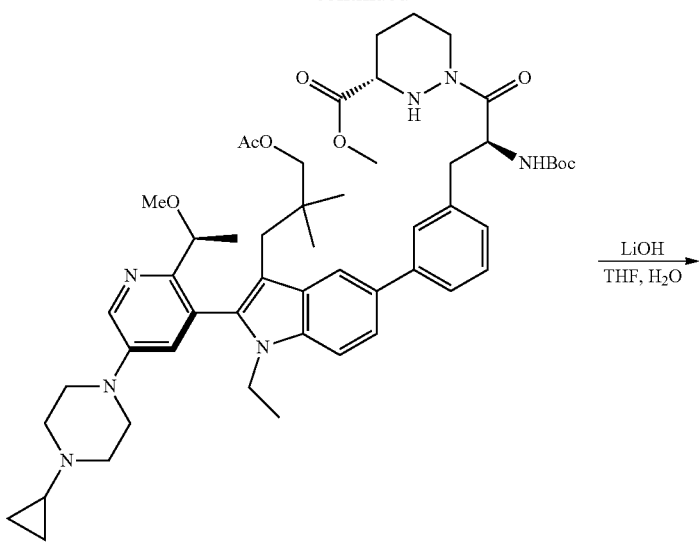
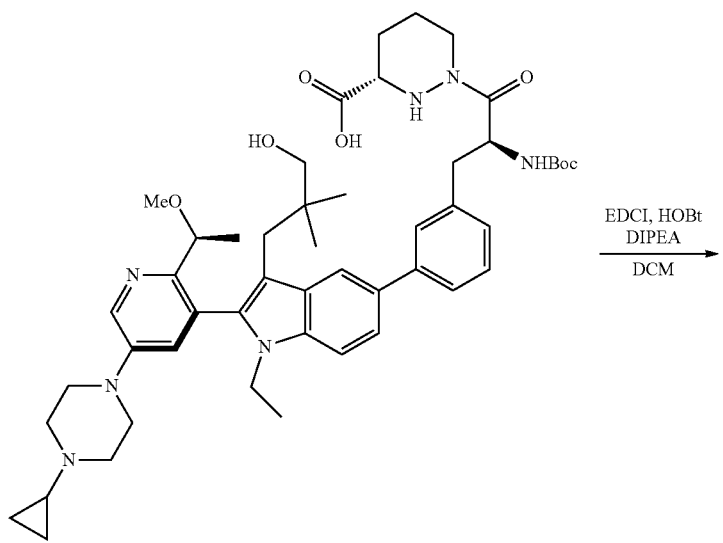
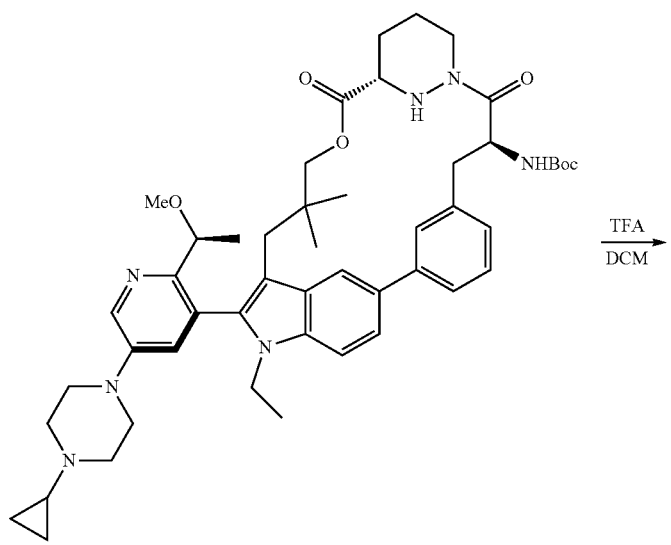

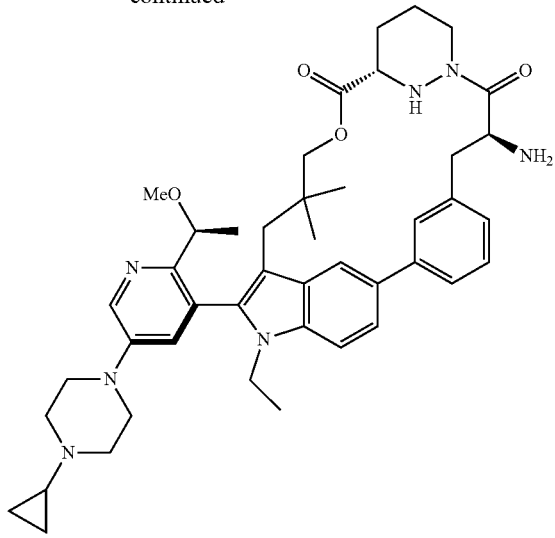

Step 1: Synthesis of methyl (S)-1-((S)-3-(3-(3-(3-acetoxy-2,2-dimethylpropyl)-2-(5-(4-cyclopropylpiperazin-1-yl)-2-((S)-1-methoxyethyl)pyridin-3-yl)-1-ethyl-1H-indol-5-yl)phenyl)-2-((tert-butoxycarbonyl)amino)propanoyl)hexahydropyridazine-3-carboxylate To a solution of (S)-3-(5-bromo-2-(5-(4-cyclopropylpiperazin-1-yl)-2-(1-methoxyethyl)pyridin-3-yl)-1-ethyl-1H-indol-3-yl)-2,2-dimethylpropyl acetate (10 g, 16.350 mmol) and methyl (S)-1-((S)-2-((tert-butoxycarbonyl)amino)-3-(3-(4,4,5,5-tetramethyl-1,3,2-dioxaborolan-2-yl)phenyl)propanoyl)hexahydropyridazine-3-carboxylate (12.69 g, 24.525 mmol) in 1,4-dioxane (110 mL) and H$_2$O (20 mL) was added K$_2$CO$_3$ (4.52 g, 32.700 mmol) and Pd(dtbpf)Cl$_2$ (1.07 g, 1.635 mmol). The resulting mixture was stirred for 3 h at 70° C. The precipitated solids were collected by filtration and washed with DCM (2×200 mL). The resulting mixture was extracted with EtOAc (100 mL). The combined organic layers were washed with brine (2×100 mL), dried over Na$_2$SO$_4$, filtered, and concentrated under reduced pressure. The residue was purified by silica gel column chromatography (10% MeOH/DCM) to afford the desired product (8.5 g, 56% yield) as a solid. LCMS (ESI) m/z [M+H] calcd for C$_{52}$H$_{71}$N$_7$O$_8$ 922.55; found: 922.7.

Step 2: Synthesis of (S)-1-((S)-2-((tert-butoxycarbonyl)amino)-3-(3-(2-(5-(4-cyclopropylpiperazin-1-yl)-2-((S)-1-methoxyethyl)pyridin-3-yl)-1-ethyl-3-(3-hydroxy-2,2-dimethylpropyl)-1H-indol-5-yl)phenyl)propanoyl)hexahydropyridazine-3-carboxylic acid To a solution of methyl (S)-1-((S)-3-(3-(3-(3-acetoxy-2,2-dimethylpropyl)-2-(5-(4-cyclopropylpiperazin-1-yl)-2-((S)-1-methoxyethyl)pyridin-3-yl)-1-ethyl-1H-indol-5-yl)phenyl)-2-((tert-butoxycarbonyl)amino)propanoyl)hexahydropyridazine-3-carboxylate (7 g, 7.591 mmol) in THF (70 mL) was added a solution of LiOH●H$_2$O (0.96 g, 22.773) in H$_2$O (22 mL) at 0° C. The resulting mixture was stirred overnight and was then acidified to pH 6 with 1 M HCl. The resulting mixture was extracted with DCM (2×100 mL) and the combined organic layers were washed with brine (2×100 mL), dried over Na$_2$SO$_4$, filtered, and concentrated under reduced pressure to afford the desired product as a solid. LCMS (ESI) m/z [M+H] calcd for C$_{49}$H$_{67}$N$_7$O$_7$ 866.52; found: 866.4.

Step 3: Synthesis of tert-butyl ((6$^3$S,4S)-1$^2$-(5-(4-cyclopropylpiperazin-1-yl)-2-((S)-1-methoxyethyl)pyridin-3-yl)-1$^1$-ethyl-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)carbamate To a solution of (S)-1-((S)-2-((tert-butoxycarbonyl)amino)-3-(3-(2-(5-(4-cyclopropylpiperazin-1-yl)-2-((S)-1-methoxyethyl)pyridin-3-yl)-1-ethyl-3-(3-hydroxy-2,2-dimethylpropyl)-1H-indol-5-yl)phenyl)propanoyl)hexahydropyridazine-3-carboxylic acid (6 g, 6.927 mmol) in DCM (240 mL) at 0° C. was added DIPEA (35.81 g, 277.080 mmol) and HOBt (9.36 g, 69.270 mmol). To the mixture was added a solution of EDCI (39.84 g, 207.810 mmol) in DCM (240 mL). The resulting mixture was warmed to room temperature and stirred overnight. The mixture was concentrated under reduced pressure and the residue was taken up in EtOAc (200 mL). The organic layer was washed with brine, dried over Na$_2$SO$_4$, filtered, and concentrated under reduced pressure. The residue was purified by prep-TLC (8% MeOH/DCM) to afford the desired product (43.8 g, 64% yield) as a solid. LCMS (ESI) m/z [M+H] calcd for C$_{49}$H$_{65}$N$_7$O$_6$ 848.51; found: 848.7.

Step 4: Synthesis of (6$^3$S,4S)-4-amino-1$^2$-(5-(4-cyclopropylpiperazin-1-yl)-2-((S)-1-methoxyethyl)pyridin-3-yl)-1$^1$-ethyl-10,10-dimethyl-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-5,7-dione To a solution of tert-butyl ((6$^3$S,4S)-1$^2$-(5-(4-cyclopropylpiperazin-1-yl)-2-((S)-1-methoxyethyl)pyridin-3-yl)-1$^1$-ethyl-10,10-dimethyl-5,7-dioxo-6$^1$,6$^2$,6$^3$,6$^4$,6$^5$,6$^6$-hexahydro-1$^1$H-8-oxa-1 (5,3)-indola-6(1,3)-pyridazina-2(1,3)-benzenacycloundecaphane-4-yl)carbamate (1.5 g, 1.769 mmol) in DCM (15 mL) at 0° C. was added TFA (7 mL). The resulting mixture was stirred at 0° C. for 1 h and then the mixture was neutralized to pH 8 with sat. NaHCO$_3$ (aq). The resulting mixture was extracted with DCM (3×100 mL) and the combined organic layers were washed with brine (3×100 mL), dried over Na$_2$SO$_4$, filtered, and concentrated under reduced pressure to afford the desired product as a solid. LCMS (ESI) m/z [M+H] calcd for C$_{44}$H$_{57}$N$_7$O$_4$ 748.45; found: 748.4.

Intermediate 28: Synthesis of (6$^3$S,4S,Z)-4-amino-1$^2$-(5-((S)-hexahydropyrazino[2,1-c][1,4]oxazin-8(1H)-yl)-2-((S)-1-methoxyethyl)pyridin-3-yl)-10,10-dimethyl-1$^1$-(2,2,2-trifluoroethyl)-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-5,7-dione

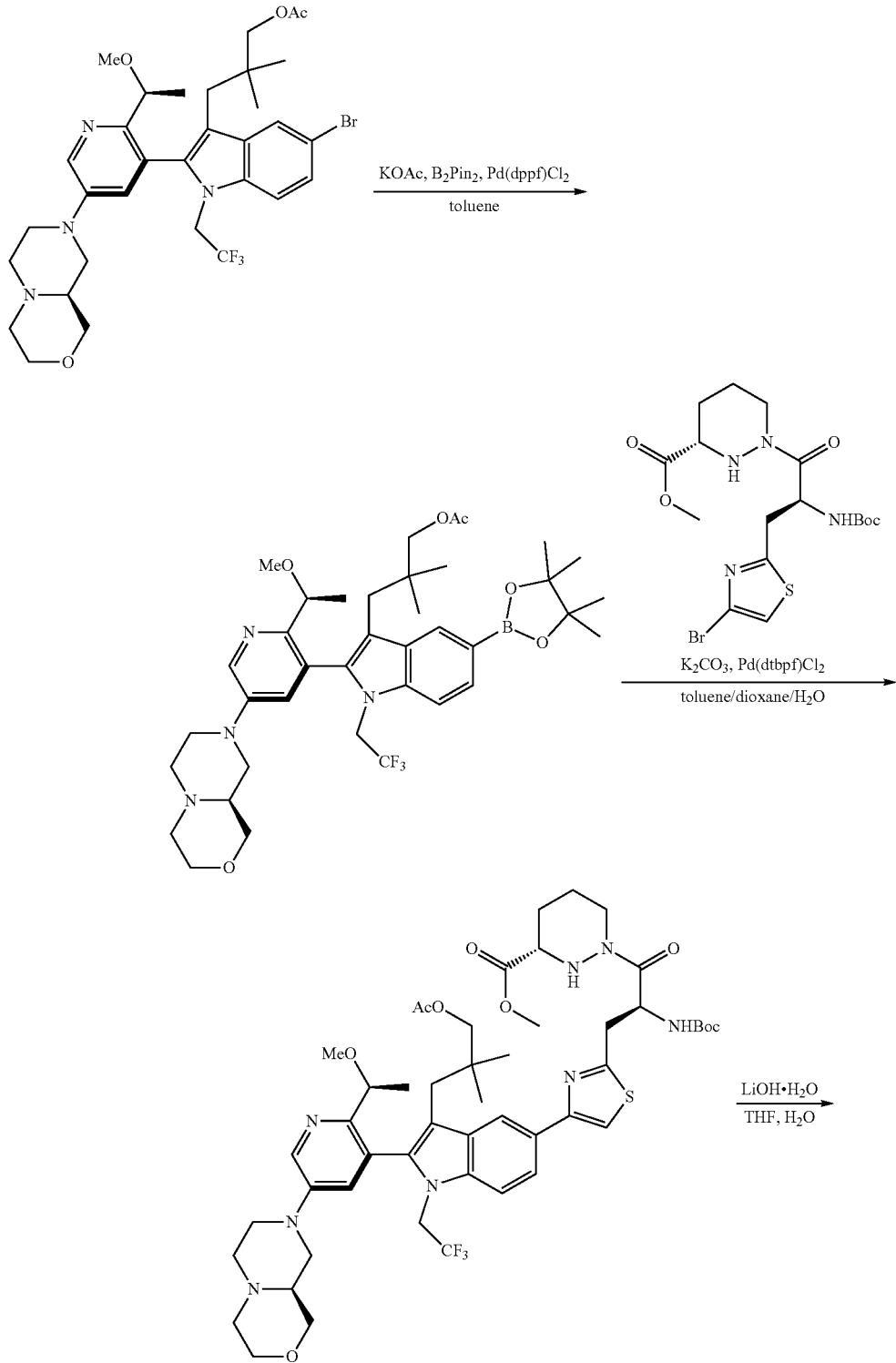

-continued

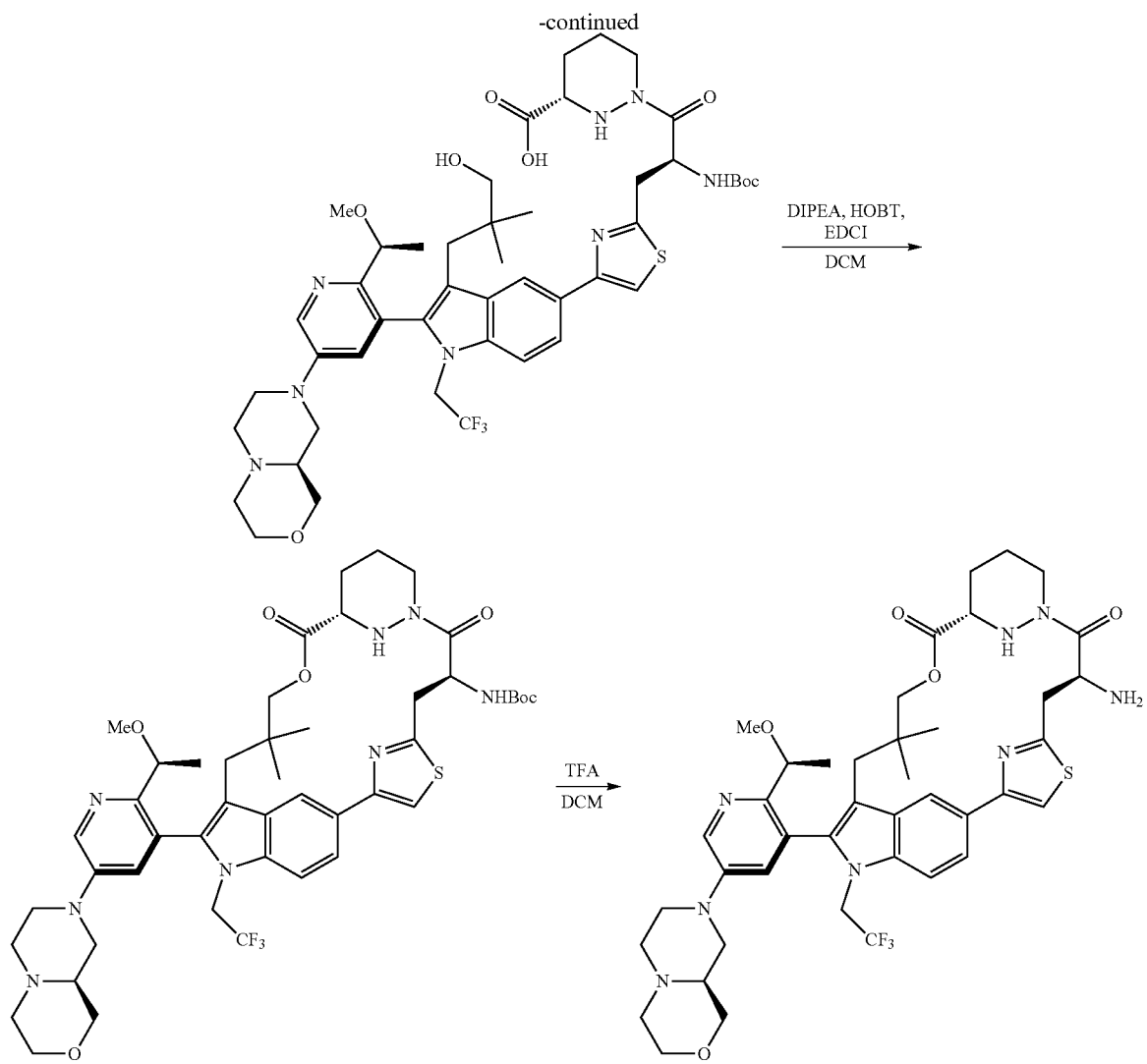

Step 1: Synthesis of 3-(2-(5-((S)-hexahydropyrazino[2,1-c][1,4]oxazin-8(1H)-yl)-2-((S)-1-methoxyethyl)pyridin-3-yl)-5-(4,4,5,5-tetramethyl-1,3,2-dioxaborolan-2-yl)-1-(2,2,2-trifluoroethyl)-1H-indol-3-yl)-2,2-dimethylpropyl acetate To a solution of 3-(5-bromo-2-(5-((S)-hexahydropyrazino[2,1-c][1,4]oxazin-8(1H)-yl)-2-((S)-1-methoxyethyl)pyridin-3-yl)-1-(2,2,2-trifluoroethyl)-1H-indol-3-yl)-2,2-dimethylpropyl acetate (26.5 g, 38.879 mmol), KOAc (9.54 g, 97.197 mmol) and 4,4,5,5-tetramethyl-2-(tetramethyl-1,3,2-dioxaborolan-2-yl)-1,3,2-dioxaborolane (19.75 g, 77.758 mmol) in toluene (300 mL) was added Pd(dppf)Cl$_2$ (2.84 g, 3.888 mmol) in portions at room temperature under an argon atmosphere. The resulting mixture was stirred for 3 h at 90° C. The resulting mixture was filtered, the filter cake was washed with DCM (3×500 mL). The filtrate was concentrated under reduced pressure. The residue was purified by silica gel column chromatography (20% EtOAc/pet. ether) to afford the product (325 g, 83% yield) as a solid. LCMS (ESI) m/z [M+H] calcd for C$_{38}$H$_{52}$BF$_3$N$_4$O$_6$: 729.40; found: 729.5.

Step 2: Synthesis of methyl (S)-1-((S)-3-(4-(3-(3-acetoxy-2,2-dimethylpropyl)-2-(5-((S)-hexahydropyrazino[2,1-c][1,4]oxazin-8(1 H)-yl)-2-((S)-1-methoxyethyl)pyridin-3-yl)-1-(2,2,2-trifluoroethyl)-1H-indol-5-yl)thiazol-2-yl)-2-((tert-butoxycarbonyl)amino)propanoyl)hexahydropyridazine-3-carboxylate To a stirred mixture of 3-(2-(5-((S)-hexahydropyrazino[2,1-c][1,4]oxazin-8(1H)-yl)-2-((S)-1-methoxyethyl)pyridin-3-yl)-5-(4,4,5,5-tetramethyl-1,3,2-dioxaborolan-2-yl)-1-(2,2,2-trifluoroethyl)-1H-indol-3-yl)-2,2-dimethylpropyl acetate (25 g, 34.310 mmol), methyl (S)-1-((S)-3-(4-bromothiazol-2-yl)-2-((tert-butoxycarbonyl)amino)propanoyl)hexahydropyridazine-3-carboxylate (19.65 g, 41.172 mmol), and K$_2$CO$_3$ (11.85 g, 85.775 mmol) in toluene (200 mL) were added dioxane (100 mL) and H$_2$O (50 mL) was added Pd(dtbpf)Cl$_2$ (2.24 g, 3.431 mmol). The resulting mixture was stirred for 2 h at 70° C. The resulting mixture was filtered, the filter cake was washed with DCM (3×500 mL). The filtrate was concentrated under reduced pressure. The resulting mixture was extracted with DCM (3×200 mL). The combined organic layers were washed with brine, dried over anhydrous Na$_2$SO$_4$. After filtration, the filtrate was concentrated under reduced pressure. The residue was purified by silica gel column chromatography (20% EtOAc/pet. ether) to afford the desired product (32 g, 84% yield) as a solid. LCMS (ESI) m/z [M+H]calcd for $C_{49}H_{65}F_3N_8O_9S$: 999.46; found: 999.8.

Step 3: Synthesis of (S)-1-((S)-2-((tert-butoxycarbonyl)amino)-3-(4-(2-(5-((S)-hexahydropyrazino[2,1-c][1,4]oxazin-8(1 H)-yl)-2-((S)-1-methoxyethyl)pyridin-3-yl)-3-(3-hydroxy-2,2-dimethylpropyl)-1-(2,2,2-trifluoroethyl)-1H-indol-5-yl)thiazol-2-yl)propanoyl)hexahydropyridazine-3-carboxylic acid To a solution of methyl (S)-1-((S)-3-(4-(3-(3-acetoxy-2,2-dimethylpropyl)-2-(5-((S)-hexahydropyrazino[2,1-c][1,4]oxazin-8(1 H)-yl)-2-((S)-1-methoxyethyl)pyridin-3-yl)-1-(2,2,2-trifluoroethyl)-1H-indol-5-yl)thiazol-2-yl)-2-((tert-butoxycarbonyl)amino)propanoyl)hexahydropyridazine-3-carboxylate (32 g, 32.027 mmol) in THF (320 mL) and $H_2O$ (300 mL) at 0° C. was added LiOH•$H_2O$ (5.38 g, 128.108 mmol). The resulting mixture was stirred overnight at room temperature. The mixture was neutralized to pH 7 with HCl (aq.). The resulting mixture was extracted with DCM (3×500 mL). The combined organic layers were washed with brine (3×500 mL), dried over anhydrous $Na_2SO_4$. After filtration, the filtrate was concentrated under reduced pressure to afford the product (30 g, 89% yield) as a solid. LCMS (ESI) m/z [M+H] calcd for $C_{46}H_{61}F_3N_8O_8S$: 943.43; found: 943.8

Step 4: Synthesis of tert-butyl (($6^3$S,4S,Z)-12-(5-((S)-hexahydropyrazino[2,1-c][1,4]oxazin-8(1H)-yl)-2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-11H-8-oxa-2(4,2)-thiazola-1(5,3)-indola-6(1,3)-pyridazinacycloundecaphane-4-yl)carbamate To a solution of (S)-1-((S)-2-((tert-butoxycarbonyl)amino)-3-(4-(2-(5-((S)-hexahydropyrazino[2,1-c][1,4]oxazin-8(1H)-yl)-2-((S)-1-methoxyethyl)pyridin-3-yl)-3-(3-hydroxy-2,2-dimethylpropyl)-1-(2,2,2-trifluoroethyl)-1H-indol-5-yl)thiazol-2-yl)propanoyl)hexahydropyridazine-3-carboxylic acid (30 g, 31.810 mmol), HOBt (25.79 g, 190.860 mmol) and DIPEA (164.45 g, 1272.400 mmol) in DCM (3 L) at 0° C. was added EDCI (182.94 g, 954.300 mmol) under an argon atmosphere. The resulting mixture was stirred for overnight at room temperature and then cold $H_2O$ (5 L) was added. Then the mixture was extracted with DCM (3×1 L) and the combined organic layers were washed with brine (3×1 L), dried over $Na_2SO_4$, filtered, and concentrated under reduced pressure. The residue was purified by silica gel column chromatography (20% EtOAc/pet. ether) to afford the desired product (20 g, 64% yield) as a solid. LCMS (ESI) m/z [M+H] calcd for $C_{46}H_{59}F_3N_8O_7S$: 925.43; found: 925.5

Step 5: Synthesis of ($6^3$S,4S,Z)-4-amino-$1^2$-(5-((S)-hexahydropyrazino[2,1-c][1,4]oxazin-8(1H)-yl)-2-((S)-1-methoxyethyl)pyridin-3-yl)-10,10-dimethyl-$1^1$-(2,2,2-trifluoroethyl)-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-5,7-dione To a solution of tert-butyl (($6^3$S,4S,Z)-12-(5-((S)-hexahydropyrazino[2,1-c][1,4]oxazin-8(1 H)-yl)-2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-2(4,2)-thiazola-1(5,3)-indola-6(1,3)-pyridazinacycloundecaphane-4-yl)carbamate (977 mg, 0.843 mmol) in DCM (8 mL,) was added TFA (8 mL) dropwise at 0° C. under an argon atmosphere. The resulting mixture was stirred at 0° C. for 1 h. The mixture was basified to pH 8 with sat. aq. $NaHCO_3$. The resulting mixture was extracted with DCM (3×50 mL). The combined organic layers were washed with brine (3×50 mL), dried over $Na_2SO_4$, filtered, and concentrated under reduced pressure to afford the desired product (766 mg, 88% yield) as a solid. LCMS (ESI) m/z [M+H] calcd for $C_{41}H_{51}F_3NaO_5S$: 825.38; found: 825.6.

Intermediate 29: Synthesis of ($2^2$S,$6^3$S,4S)-4-amino-$1^2$-(5-((S)-hexahydropyrazino[2,1-c][1,4]oxazin-8(1H)-yl)-2-((S)-1-methoxyethyl)pyridin-3-yl)-10,10-dimethyl-$1^1$-(2,2,2-trifluoroethyl)-$6^1$,$6^2$,$6^3$,$6^4$,$6^5$,$6^6$-hexahydro-$1^1$H-8-oxa-2(4,2)-morpholina-1(5,3)-indola-6(1,3)-pyridazinacycloundecaphane-5,7-dione

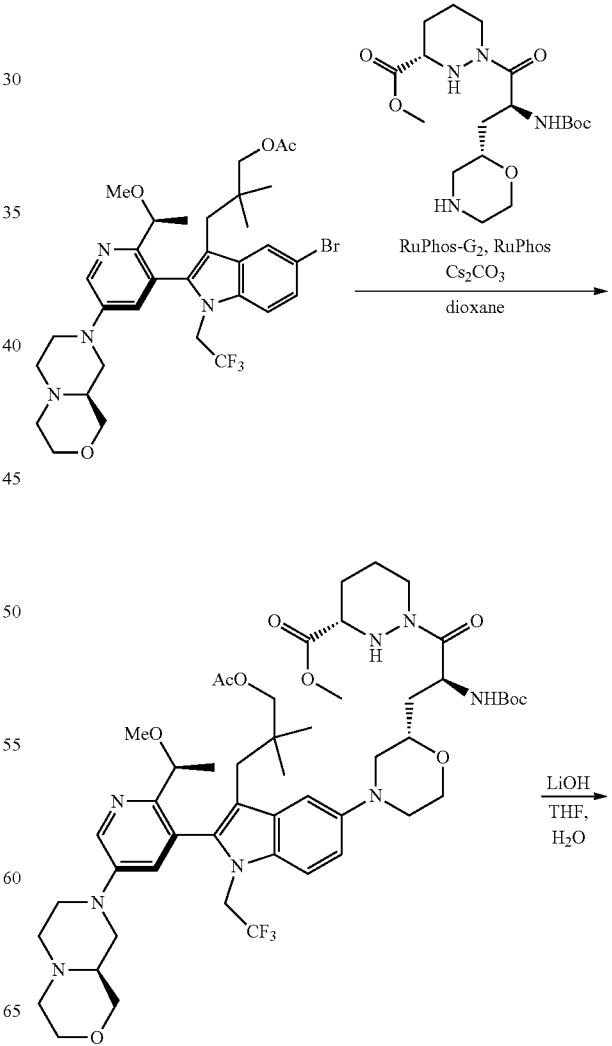

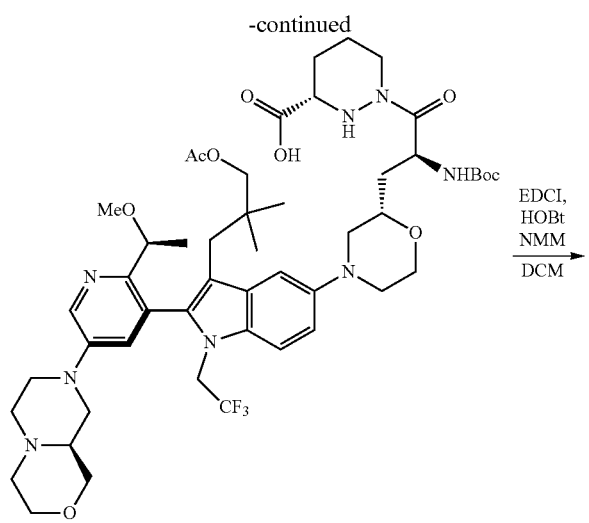
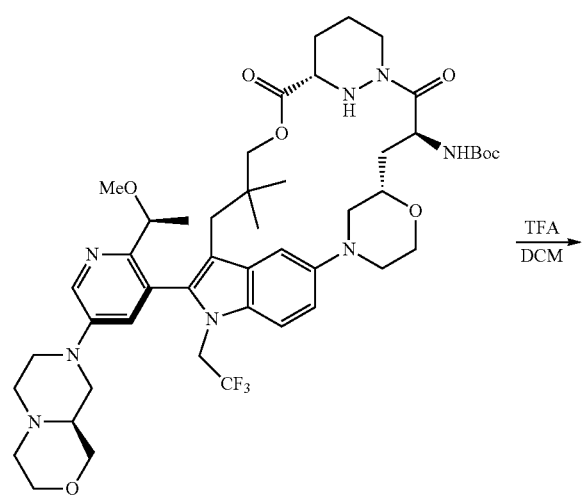
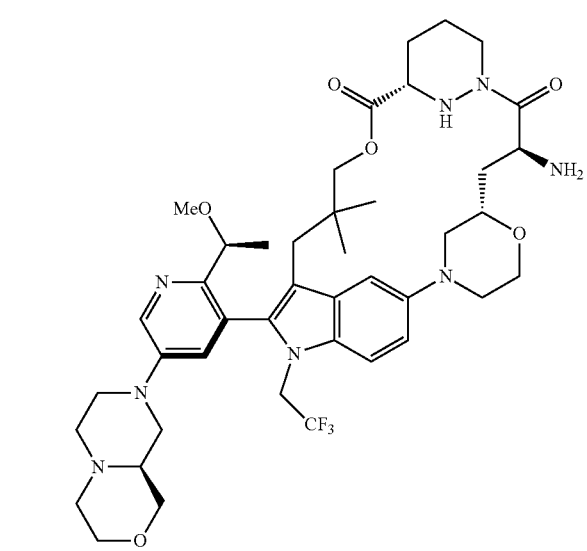

Step 1: Synthesis of methyl (S)-1-((S)-3-((S)-4-(3-(3-acetoxy-2,2-dimethylpropyl)-2-(5-((S)-hexahydropyrazino[2,1-c][1,4]oxazin-8(1H)-yl)-2-((S)-1-methoxyethyl)pyridin-3-yl)-1-(2,2,2-trifluoroethyl)-1H-indol-5-yl)morpholin-2-yl)-2-((tert-butoxycarbonyl)amino)propanoyl)hexahydropyridazine-3-carboxylate To a solution of 3-(5-bromo-2-(5-((S)-hexahydropyrazino[2,1-c][1,4]oxazin-8(1H)-yl)-2-((S)-1-methoxyethyl)pyridin-3-yl)-1-(2,2,2-trifluoroethyl)-1H-indol-3-yl)-2,2-dimethylpropyl acetate (9.5 g, 13.938 mmol) and methyl (S)-1-((S)-2-((tert-butoxycarbonyl)amino)-3-((S)-morpholin-2-yl)propanoyl)hexahydropyridazine-3-carboxylate (11.16 g, 27.876 mmol) in dioxane (95 mL) was added RuPhos (1.30 g, 2.788 mmol), RuPhos-G2-Pd (1.08 g, 1.394 mmol), and $Cs_2CO_3$ (9.08 g, 27.876 mmol). The resulting mixture was at 80° C. for 3 h. The reaction mixture was then filtered, the filter cake was washed with EtOAc (3×300 mL), and the filtrate was washed with brine (3×100 mL), dried over $Na_2SO_4$, filtered, and concentrated under reduced pressure. The residue was purified by silica gel column chromatography (5% MeOH/DCM) to afford the desired product (10 g, 70% yield) as a solid. LCMS (ESI) m/z [M+H] calcd for $C_{50}H_{71}F_3N_8O_{10}$ 1001.53; found: 1001.7.

Step 2: Synthesis of (S)-1-((S)-2-((tert-butoxycarbonyl)amino)-3-((S)-4-(2-(5-((S)-hexahydropyrazino[2,1-c][1,4]oxazin-8(1H)-yl)-2-((S)-1-methoxyethyl)pyridin-3-yl)-3-(3-hydroxy-2,2-dimethylpropyl)-1-(2,2,2-trifluoroethyl)-1H-indol-5-yl)morpholin-2-yl)propanoyl)hexahydropyridazine-3-carboxylic acid To a solution of methyl (S)-1-((S)-3-((S)-4-(3-(3-acetoxy-2,2-dimethylpropyl)-2-(5-((S)-hexahydropyrazino[2,1-c][1,4]oxazin-8(1H)-yl)-2-((S)-1-methoxyethyl)pyridin-3-yl)-1-(2,2,2-trifluoroethyl)-1H-indol-5-yl)morpholin-2-yl)-2-((tert-butoxycarbonyl)amino)propanoyl)hexahydropyridazine-3-carboxylate (10 g, 9.988 mmol) in THF (50 mL) and $H_2O$ (50 mL) at 0° C. was added LiOH•$H_2O$ (2.10 g, 49.940 mmol). The resulting mixture was stirred overnight at room temperature and then $H_2O$ (100 mL) was added. The aqueous layer was extracted with MTBE (3×300 mL) and then the aqueous layer was acidified to pH 6 with HCl (1 M) and extracted with DCM (3×500 mL). The combined organic layers were washed with brine (3×200 mL), dried over $Na_2SO_4$, filtered, and concentrated under reduced pressure to afford the desired product (7.1 g) as a solid. LCMS (ESI) m/z [M+H] calcd for $C_{47}H_{67}F_3N_8O_9$ 945.51; found: 945.3.

Step 3: Synthesis of tert-butyl (($2^2$S,$6^3$S,4S)-$1^2$-(5-((S)-hexahydropyrazino[2,1-c][1,4]oxazin-8(1H)-yl)-2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-2(4,2)-morpholina-1(5,3)-indola-6(1,3)-pyridazinacycloundecaphane-4-yl)carbamate To a solution of (S)-1-((S)-2-((tert-butoxycarbonyl)amino)-3-((S)-4-(2-(5-((S)-hexahydropyrazino[2,1-c][1,4]oxazin-8(1H)-yl)-2-((S)-1-methoxyethyl)pyridin-3-yl)-3-(3-hydroxy-2,2-dimethylpropyl)-1-(2,2,2-trifluoroethyl)-1H-indol-5-yl)morpholin-2-yl)propanoyl)hexahydropyridazine-3-carboxylic acid (7.1 g, 7.512 mmol) and NMM (12.16 g, 120.192 mmol) in DCM (710 mL) at 0°

C. was added EDCI (11.52 g, 60.096 mmol) and HOBt (4.06 g, 30.048 mmol). The resulting mixture was stirred at room temperature overnight and then H$_2$O (500 mL) was added. The resulting mixture was extracted with DCM (3×500 mL) and the combined organic layers were washed with brine (3×1 L), dried over Na$_2$SO$_4$, filtered, and concentrated under reduced pressure. The residue was purified by silica gel column chromatography (8% MeOH/DCM) to afford the desired product (3 g, 48% yield) as a solid. LCMS (ESI) m/z [M+H] calcd for C$_{47}$H$_{65}$F$_3$N$_8$O$_8$ 927.50; found: 927.3.

Step 4: Synthesis of (2$^2$S,6$^3$S,4S)-4-amino-1$^2$-(5-((S)-hexahydropyrazino[2,1-c][1,4]oxazin-8(1H)-yl)-2-((S)-1-methoxyethyl)pyridin-3-yl)-10,10-dimethyl-1$^{11}$-(2,2,2-trifluoroethyl)-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-5,7-dione To a solution tert-butyl ((2$^2$S,6$^3$S,4S)-1$^2$-(5-((S)-hexahydropyrazino[2,1-c][1,4]oxazin-8(1H)-yl)-2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-4-yl)carbamate (3 g, 3.236 mmol) in DCM (30 mL) at 0° C. was added TFA (15 mL). The resulting mixture was stirred at 0° C. for 2 h and was then basified to pH 8 with sat. NaHCO$_3$ (aq.). The resulting mixture was extracted with DCM (3×100 mL). The combined organic layers were washed with brine (3×100 mL), dried over Na$_2$SO$_4$, filtered, and concentrated under reduced pressure to afford the desired product as a solid. LCMS (ESI) m/z [M+H] calcd for C$_{42}$H$_{57}$F$_3$N$_8$O$_6$ 827.45; found: 827.5.

Intermediate 30: Synthesis of (6$^3$S,4S)-4-amino-1$^2$-(5-(4-cyclopropylpiperazin-1-yl)-2-((S)-1-methoxyethyl)pyridin-3-yl)-10,10-dimethyl-1$^1$-(2,2,2-trifluoroethyl)-2$^1$,2$^2$,2$^3$,2$^6$,6$^1$,6$^2$,6$^3$,6$^4$,6$^5$,6$^6$-decahydro-1$^1$H-8-oxa-1(5,3)-indola-6(1,3)-pyridazina-2(5,1)-pyridinacycloundecaphane-5,7-dione

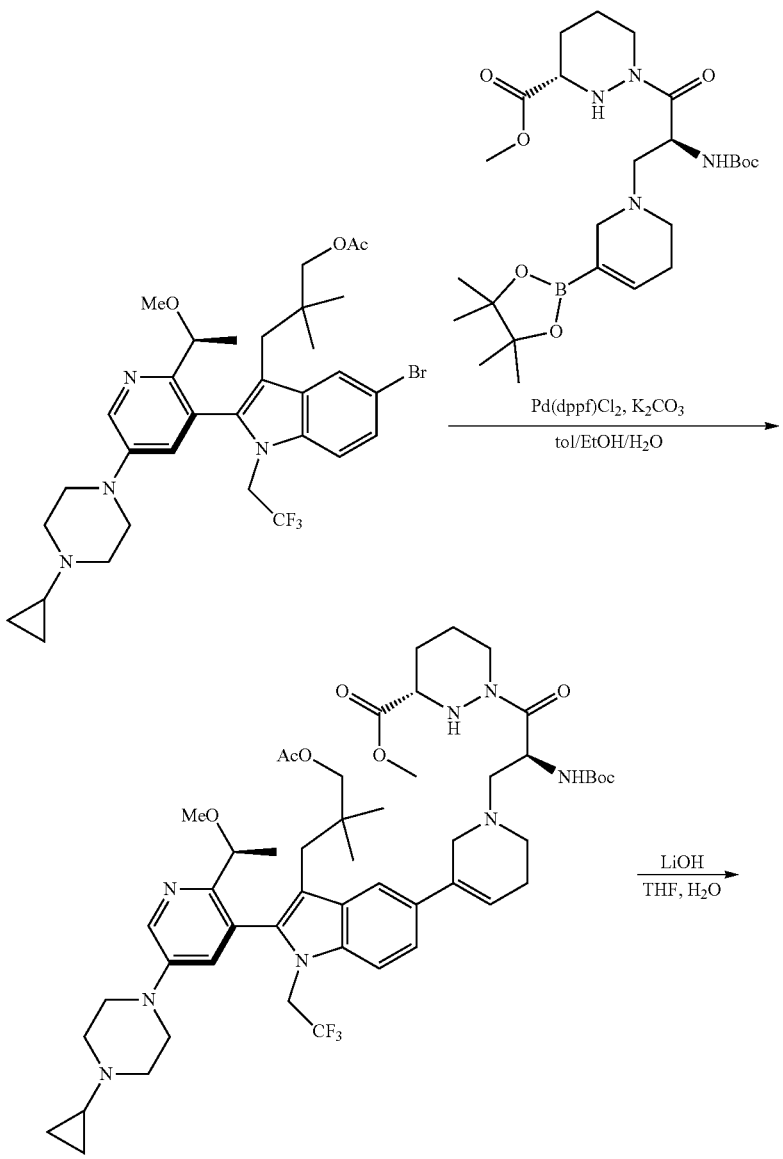

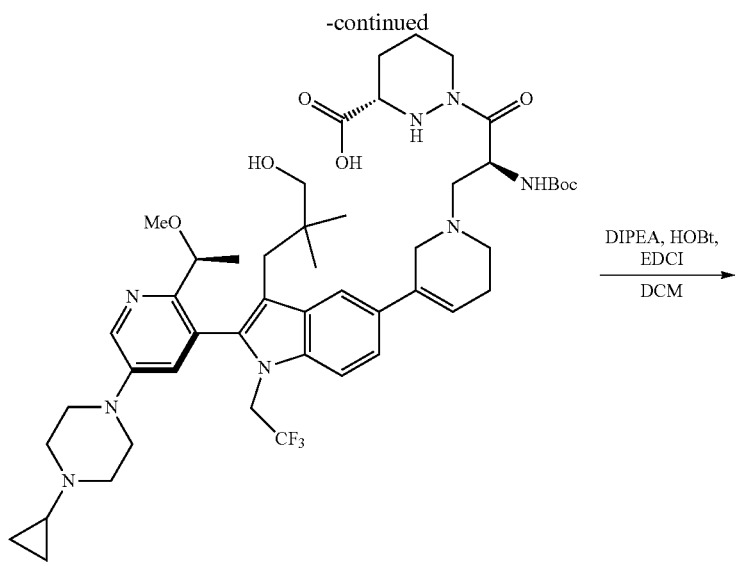
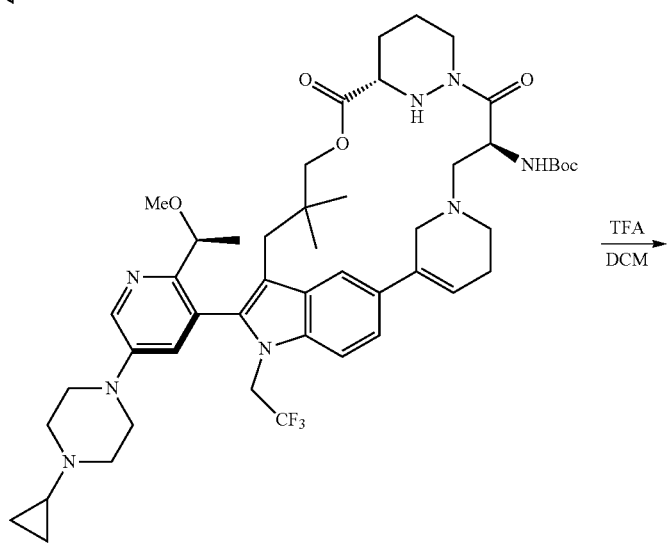
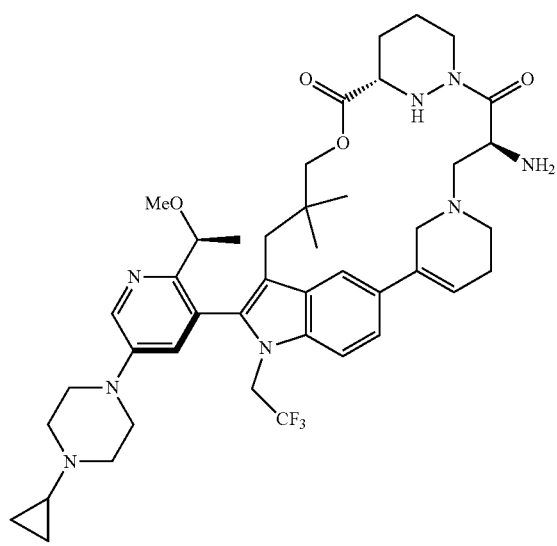

Step 1: Synthesis of methyl (S)-1-((S)-3-(5-(3-(3-acetoxy-2,2-dimethylpropyl)-2-(5-(4-cyclopropylpiperazin-1-yl)-2-((S)-1-methoxyethyl)pyridin-3-yl)-1-(2,2,2-trifluoroethyl)-1H-indol-5-yl)-3,6-dihydropyridin-1(2H)-yl)-2-((tert-butoxycarbonyl)amino)propanoyl)hexahydropyridazine-3-carboxylate To a solution of (S)-3-(5-bromo-2-(5-(4-cyclopropylpiperazin-1-yl)-2-(1-methoxyethyl)pyridin-3-yl)-1-(2,2,2-trifluoroethyl)-1H-indol-3-yl)-2,2-dimethylpropyl acetate (9 g, 13.522 mmol), methyl (S)-1-((S)-2-((tert-butoxycarbonyl)amino)-3-(5-(4,4,5,5-tetramethyl-1,3,2-dioxaborolan-2-yl)-3,6-dihydropyridin-1(2H)-yl)propanoyl)hexahydropyridazine-3-carboxylate (7.14 g, 16.226 mmol), and $K_2CO_3$ (8.41 g, 60.849 mmol) in toluene (90 mL), dioxane (60 mL), and $H_2O$ (30 mL) was added and $Pd(dtbpf)Cl_2$ (2.97 g, 4.057 mmol). The resulting mixture was stirred at 70° C. for 3 h and then cold $H_2O$ (1 L). The resulting mixture was extracted with DCM (3×500 mL) and the combined organic layers were washed with brine (3×300 mL), dried over $Na_2SO_4$, filtered, and concentrated under reduced pressure. The residue was purified by silica gel column chromatography (5% MeOH/DCM) to afford the desired product (9 g, 67% yield) as a solid. LCMS (ESI) m/z [M+H] calcd for $C_{51}H_{71}F_3N_8O_8$: 981.54; found: 981.3.

Step 2: Synthesis of (S)-1-((S)-2-((tert-butoxycarbonyl)amino)-3-(5-(2-(5-(4-cyclopropylpiperazin-1-yl)-2-((S)-1-methoxyethyl)pyridin-3-yl)-3-(3-hydroxy-2,2-dimethylpropyl)-1-(2,2,2-trifluoroethyl)-1H-indol-5-yl)-3,6-dihydropyridin-1(2H)-yl)propanoyl)hexahydropyridazine-3-carboxylic acid To a solution of methyl (S)-1-((S)-3-(5-(3-(3-acetoxy-2,2-dimethylpropyl)-2-(5-(4-cyclopropylpiperazin-1-yl)-2-((S)-1-methoxyethyl)pyridin-3-yl)-1-(2,2,2-trifluoroethyl)-1H-indol-5-yl)-3,6-dihydropyridin-1(2H)-yl)-2-((tert-butoxycarbonyl)amino)propanoyl)hexahydropyridazine-3-carboxylate (9 g, 9.173 mmol) in THF (70 mL) and $H_2O$ (50 mL) at 0° C. was added LiOH•$H_2O$ (0.88 g, 36.692 mmol). The resulting mixture was stirred overnight at room temperature and was then neutralized to pH 7 with HCl (aq.). The resulting mixture was extracted with DCM (3×200 mL) and the combined organic layers were washed with brine (3×200 mL), dried over $Na_2SO_4$, filtered, and concentrated under reduced pressure to afford the desired product (7.5 g, 88% yield) as a solid. LCMS (ESI) m/z [M+H] calcd for $C_{48}H_{67}F_3N_8O_7$: 925.52; found: 925.6.

Step 3: Synthesis of tert-butyl ((6$^3$S,4S)-1$^2$-(5-(4-cyclopropylpiperazin-1-yl)-2-((S)-1-methoxyethyl)pyridin-3-yl)-10,10-dimethyl-5,7-dioxo-1$^1$-(2,2,2-trifluoroethyl)-2$^1$,2$^2$,2$^3$,2$^6$,6$^1$,6$^2$,6$^3$,6$^4$,6$^5$,6$^6$-decahydro-1$^1$H-8-oxa-1(5,3)-indola-6(1,3)-pyridazina-2(5,1)-pyridinacycloundecaphane-4-yl)carbamate To a solution of (S)-1-((S)-2-((tert-butoxycarbonyl)amino)-3-(5-(2-(5-(4-cyclopropylpiperazin-1-yl)-2-((S)-1-methoxyethyl)pyridin-3-yl)-3-(3-hydroxy-2,2-dimethylpropyl)-1-(2,2,2-trifluoroethyl)-1H-indol-5-yl)-3,6-dihydropyridin-1(2H)-yl)propanoyl)hexahydropyridazine-3-carboxylic acid (7.5 g, 8.107 mmol) and DIPEA (41.91 g, 324.280 mmol) in DCM (750 mL) at 0° C. was added EDCI (46.62 g, 243.210 mmol) and HOBt (16.57 g, 48.642 mmol). The resulting mixture was stirred overnight at room temperature and then cold $H_2O$ (1 L) was added. The resulting mixture was extracted with DCM (3×500 mL) and the combined organic layers were washed with brine (3×500 mL), dried over $Na_2SO_4$, filtered, and concentrated under reduced pressure. The residue was purified by silica gel column chromatography (20% EtOAc/pet. ether) to afford the desired product (6 g, 73% yield) as a solid. LCMS (ESI) m/z [M+H] calcd for $C_{48}H_{65}F_3N_8O_6$: 907.51; found: 907.6

Step 4: Synthesis of (6$^3$S,4S)-4-amino-1$^2$-(5-(4-cyclopropylpiperazin-1-yl)-2-((S)-1-methoxyethyl)pyridin-3-yl)-10,10-dimethyl-1$^1$-(2,2,2-trifluoroethyl)-2$^1$ 2$^2$,2$^3$,2$^6$,6$^1$,6$^2$,6$^3$,6$^4$,6$^5$,6$^6$-decahydro-1$^1$H-8-oxa-1(5,3)-indola-6(1,3)-pyridazina-2(5,1)-pyridinacycloundecaphane-5,7-dione To a solution of tert-butyl ((6$^3$S,4S)-1$^2$-(5-(4-cyclopropylpiperazin-1-yl)-2-((S)-1-methoxyethyl)pyridin-3-yl)-10,10-dimethyl-5,7-dioxo-1$^1$-(2,2,2-trifluoroethyl)-2$^1$ 2$^2$,2$^3$,2$^6$,6$^1$,6$^2$,6$^3$,6$^4$,6$^5$,6$^6$-decahydro-1$^1$H-8-oxa-1(5,3)-indola-6(1,3)-pyridazina-2(5,1)-pyridinacycloundecaphane-4-yl)carbamate (2 g, 2.205 mmol) in DCM (15 mL) at 0° C. was added TFA (15 mL). The resulting mixture was stirred at 0° C. for 1 h and then the mixture was basified to pH 8 with sat. $NaHCO_3$ (aq.). The resulting mixture was extracted with DCM (3×100 mL) and the combined organic layers were washed with brine (3×100 mL), dried over $Na_2SO_4$, filtered, and concentrated under reduced pressure to afford the desired product (1.65 g, 83% yield) as a solid. LCMS (ESI) m/z [M+H] calcd for $C_{43}H_{57}F_3N_8O_4$: 807.46; found: 807.7.

Intermediate 31. Synthesis of (3-(3-acetoxy-2,2-dimethylpropyl)-2-(2-((S)-1-methoxyethyl)-5-((8R,9aS)-octahydropyrido[2,1-c][1,4]oxazin-8-yl)pyridin-3-yl)-1-(2,2,2-trifluoroethyl)-1H-indol-5-yl)boronic acid

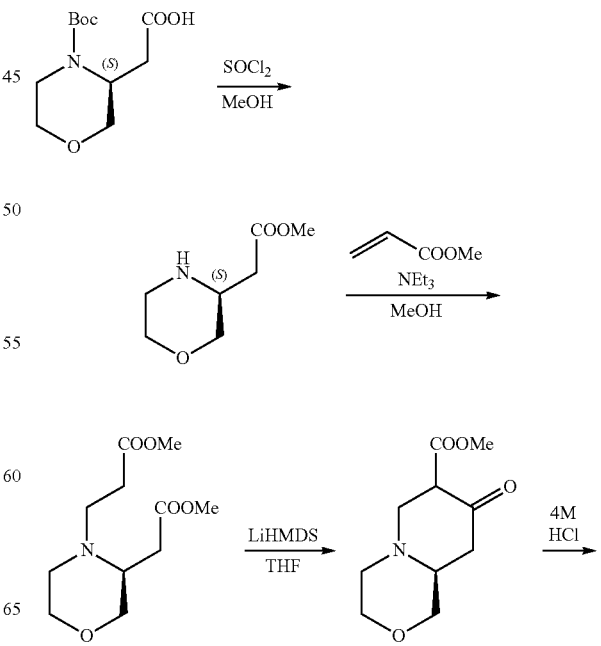

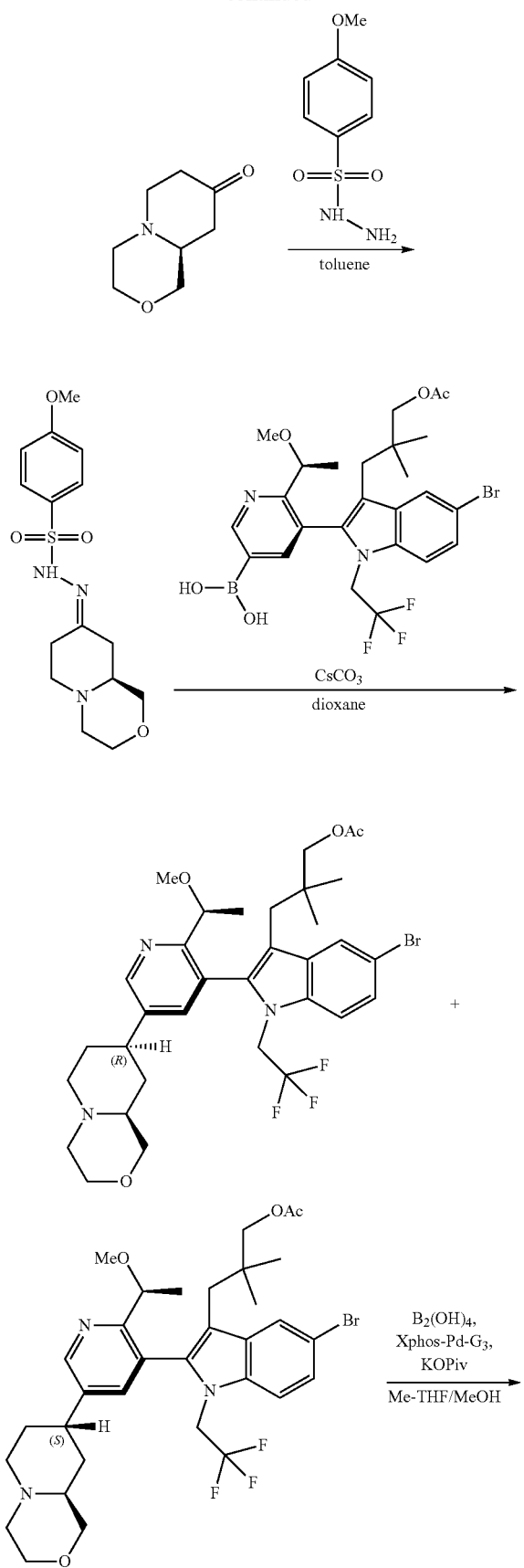

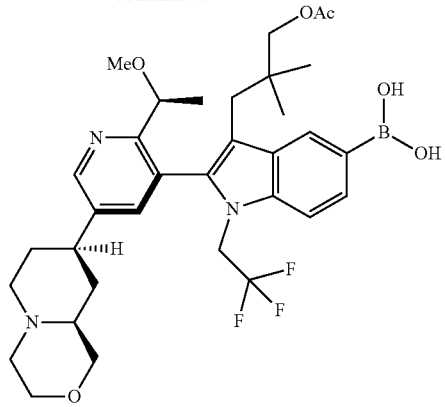

Step 1: Synthesis of methyl (S)-2-(morpholin-3-yl)acetate

To a solution of (S)-2-(4-(tert-butoxycarbonyl)morpholin-3-yl)acetic acid (41.5 g, 169.198 mmol) in MeOH (415 mL) at room temperature was added $SOCl_2$ (415 mL, 5721.251 mmol) dropwise. The reaction mixture was stirred for 2 h and was then concentrated under reduced pressure to afford the desired product (38 g, crude) as a solid. LCMS (ESI) m/z [M+H] calcd for $C_7H_{13}NO_3$: 160.10; found: 160.0.

Step 2: Synthesis of methyl (S)-3-(3-(2-methoxy-2-oxoethyl)morpholino)propanoate To a solution of methyl (S)-2-(morpholin-3-yl)acetate (38 g, 238.716 mmol) and $NEt_3$ (72.47 g, 716.148 mmol) in MeOH (380 mL) at room temperature was added methyl acrylate (41.10 g, 477.432 mmol) dropwise. The reaction mixture was warmed to 40° C. and stirred overnight. The reaction mixture was then concentrated under reduced pressure to afford the desired product (75 g, crude) as a solid. LCMS (ESI) m/z [M+H] calcd for $C_{11}H_{20}NO_5$: 246.13; found: 246.0.

Step 3: Synthesis of methyl (9aS)-8-oxooctahydropyrido[2,1-c][1,4]oxazine-7-carboxylate To a solution of methyl (S)-3-(3-(2-methoxy-2-oxoethyl)morpholino)propanoate (75 g, 305.779 mmol) in 750 mL THF at −78° C. was added LiHMDS (611 mL, 611.558 mmol) dropwise. The resulting mixture was stirred for additional 3 h at −78° C. The reaction was quenched by the addition of sat. $NH_4Cl$ (500 mL) at 0° C. The resulting mixture was extracted with EtOAc (3×500 mL) and the combined organic layers were washed with brine (3×200 mL), dried over $Na_2SO_4$, filtered, and concentrated under reduced pressure to afford the desired product (38 g, crude) as a solid. LCMS (ESI) m/z [M+H] calcd for $C_{10}H_{18}NO_4$: 214.11; found: 214.0.

Step 4: Synthesis of (S)-hexahydropyrido[2,1-c][1,4]oxazin-8($1^1$H)-one

A solution of methyl (9aS)-8-oxooctahydropyrido[2,1-c][1,4]oxazine-7-carboxylate (38 g, 178.209 mmol, 1 equiv) in 4M HCl (380 mL) was stirred for 3 h at 100° C. The reaction mixture was cooled to room temperature and was then neutralized to pH 7 with $NaHCO_3$ (aq.). The resulting mixture was extracted with EtOAc (4×500 mL) and the combined organic layers were washed with brine (3×200 mL), dried over Na$_2$SO$_4$, filtered, and concentrated under reduced pressure to afford the desired product (22.4 g, crude) as a solid. LCMS (ESI) m/z [M+H] calcd for C$_8$H$_{14}$NO$_2$: 156.10; found: 155.9.

Step 5: Synthesis of (S,E)-N'-(hexahydropyrido[2,1-c][1,4]oxazin-8(1H)-ylidene)-4-methoxybenzenesulfonohydrazide To a solution of (S)-hexahydropyrido[2,1-c][1,4]oxazin-8(1H)-one (22.4 g, 144.333 mmol) in toluene (224 mL) was added 4-methoxybenzenesulfonohydrazide (29.19 g, 144.333 mmol). The reaction mixture was heated to 110° C. and stirred for 1 h and was then cooled to room temperature and concentrated under reduced pressure. The residue was purified by silica gel column chromatography (50% EtOAc/pet. ether) to afford the desired product (31 g, 66% yield) as an oil. LCMS (ESI) m/z [M+H]calcd for C$_{15}$H$_{21}$N$_3$O$_4$S: 340.13; found: 340.0.

Step 6: Synthesis of 3-(5-bromo-2-(2-((S)-1-methoxyethyl)-5-((8R,9aS)-octahydropyrido[2,1-c][1,4]oxazin-8-yl)pyridin-3-yl)-1-(2,2,2-trifluoroethyl)-1H-indol-3-yl)-2,2-dimethylpropyl acetate and 3-(5-bromo-2-(2-((S)-1-methoxyethyl)-5-((8S,9aS)-octahydropyrido[2,1-c][1,4]oxazin-8-yl)pyridin-3-yl)-1-(2,2,2-trifluoroethyl)-1H-indol-3-yl)-2,2-dimethylpropyl acetate To a solution of (S,E)-N'-(hexahydropyrido[2,1-c][1,4]oxazin-8(1H)-ylidene)-4-methoxybenzenesulfonohydrazide (31 g, 100.174 mmol) and Cs$_2$CO$_3$ (48.96 g, 150.261 mmol) in dioxane (290 mL) was added (S)-(5-(3-(3-acetoxy-2,2-dimethylpropyl)-5-bromo-1-(2,2,2-trifluoroethyl)-1H-indol-2-yl)-6-(1-methoxyethyl)pyridin-3-yl)boronic acid (117.25 g, 200.348 mmol). The reaction mixture was stirred overnight at 110° C. The reaction mixture was then cooled to room temperature and quenched with H$_2$O (500 mL). The mixture was extracted with EtOAc (3×500 mL) and the combined organic layers were washed with brine (3×200 mL), dried over Na$_2$SO$_4$, filtered, and concentrated under reduced pressure. The residue was purified by silica gel column chromatography (20% MeOH/DCM) to afford a mixture of diastereomers (38 g, 61% yield) as an oil. The residue was purified by reverse phase chromatography (10→50% MeCN/H$_2$O (10 mmol/L NH$_4$HCO$_3$)) to afford 3-(5-bromo-2-(2-((S)-1-methoxyethyl)-5-((8R,9aS)-octahydropyrido[2,1-c][1,4]oxazin-8-yl)pyridin-3-yl)-1-(2,2,2-trifluoroethyl)-1H-indol-3-yl)-2,2-dimethylpropyl acetate (26 g) and 3-(5-bromo-2-(2-((S)-1-methoxyethyl)-5-((8S,9aS)-octahydropyrido[2,1-c][1,4]oxazin-8-yl)pyridin-3-yl)-1-(2,2,2-trifluoroethyl)-1H-indol-3-yl)-2,2-dimethylpropyl acetate (11 g) as oils. LCMS (ESI) m/z [M+H] calcd for C$_{33}$H$_{42}$BrF$_3$N$_3$O$_4$: 680.23; found: 680.3.

Step 7: Synthesis of (3-(3-acetoxy-2,2-dimethylpropyl)-2-(2-((S)-1-methoxyethyl)-5-((8R,9aS)-octahydropyrido[2,1-c][1,4]oxazi-8-yl)pyridin-3-yl)-1-(2,2,2-trifluoroethyl)-1H-indol-5-yl)boronic acid To a solution of 3-(5-bromo-2-(2-((S)-1-methoxyethyl)-5-((8R,9aS)-octahydropyrido[2,1-c][1,4]oxazin-8-yl)pyridin-3-yl)-1-(2,2,2-trifluoroethyl)-1H-indol-3-yl)-2,2-dimethylpropyl acetate (4.29 g, 6.303 mmol) and B$_2$(OH)$_4$ (0.68 g, 7.564 mmol) in 2-methylTHF (26.4 mL) and MeOH (8.8 mL) at room temperature was added XPhos Pd G3 (0.16 g, 0.189 mmol) and KOPiv (1.77 g, 12.606 mmol). The resulting mixture was stirred for 2 h at room temperature. The reaction mixture was then washed with H$_2$O (3×100 mL), dried over Na$_2$SO$_4$, filtered, and concentrated under reduced pressure to afford the desired product (5.2 g, crude) as a solid. LCMS (ESI) m/z [M+H] calcd for C$_{33}$H$_{43}$BF$_3$N$_3$O$_6$: 646.33; found: 646.0.

Intermediate 32. Synthesis of (S)-(3-(3-acetoxy-2,2-dimethylpropyl)-2-(5-(4-cyclopropylpiperazin-1-yl-2,2,3,3,5,5,6,6-da)-2-(1-methoxyethyl)pyridin-3-yl)-1-(2,2,2-trifluoroethyl)-1H-indol-5-yl)boronic acid

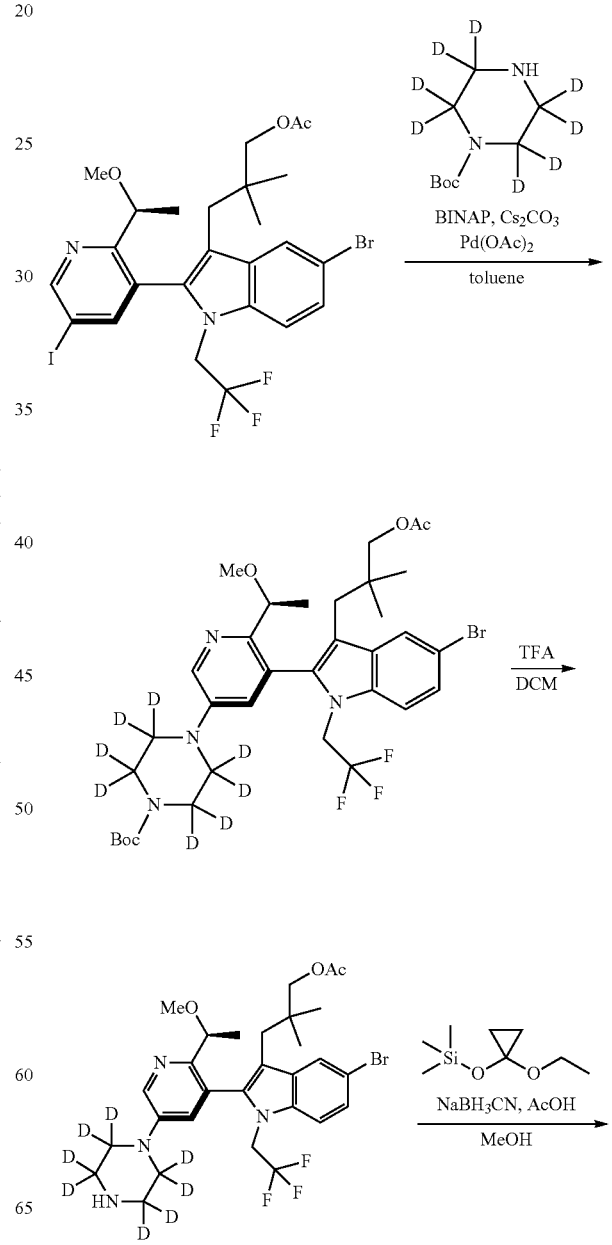

-continued

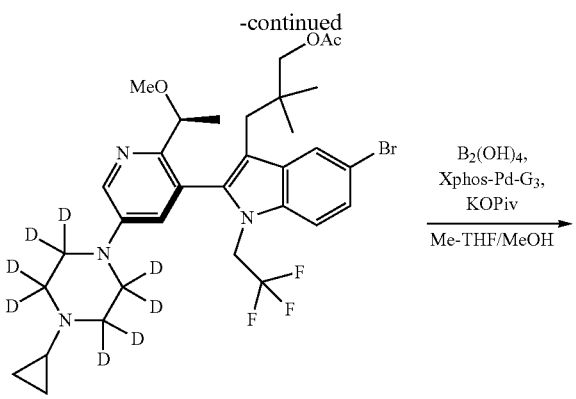

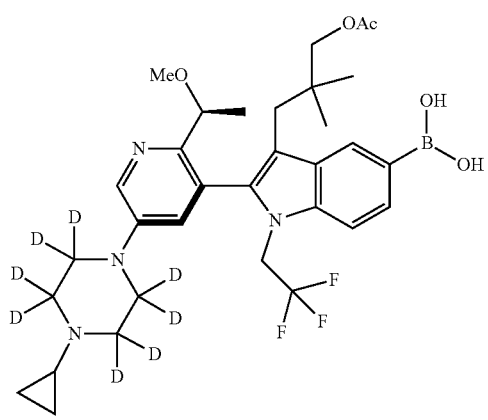

Step 1: Synthesis of tert-butyl (S)-4-(5-(3-(3-acetoxy-2,2-dimethylpropyl)-5-bromo-1-(2,2,2-trifluoroethyl)-1H-indol-2-yl)-6-(1-methoxyethyl)pyridin-3-yl)piperazine-1-carboxylate-2,2,3,3,5,5,6,6-d To a solution of (S)-3-(5-bromo-2-(5-iodo-2-(1-methoxyethyl)pyridin-3-yl)-1-(2,2,2-trifluoroethyl)-1H-indol-3-yl)-2,2-dimethylpropyl acetate (5 g, 7.493 mmol) and tert-butyl piperazine-1-carboxylate-2,2,3,3,5,5,6,6-$d_8$ (1.31 g, 6.744 mmol) and Pd(OAc)$_2$ (168.22 mg, 0.749 mmol) in toluene (35 mL) at room temperature was added BINAP (233.28 mg, 0.375 mmol) and Cs$_2$CO$_3$ (8.54 g, 26.226 mmol). The resulting mixture was stirred overnight at 82° C. The mixture was then cooled to room temperature, quenched with H$_2$O (300 mL) at 0° C., and the resulting mixture was extracted with DCM (3×100 mL). The combined organic layers were washed with brine (3×100 mL), dried over Na$_2$SO$_4$, filtered, and concentrated under reduced pressure. The residue was purified by silica gel column chromatography (70% EtOAc/pet. ether) to afford the desired product (4.2 g, 69% yield) as a solid. LCMS (ESI) m/z [M+H] calcd for C$_{34}$H$_{36}$D$_8$BrF$_3$N$_4$O$_5$: 733.30; found: 735.2

Step 2: Synthesis of (S)-3-(5-bromo-2-(2-(1-methoxyethyl)-5-(piperazin-1-yl-2,2,3,3,5,5,6,6-d8)pyridin-3-yl)-1-(2,2,2-trifluoroethyl)-1H-indol-3-yl)-2,2-dimethylpropyl acetate To a solution of tert-butyl (S)-4-(5-(3-(3-acetoxy-2,2-dimethylpropyl)-5-bromo-1-(2,2,2-trifluoroethyl)-1H-indol-2-yl)-6-(1-methoxyethyl)pyridin-3-yl)piperazine-1-carboxylate-2,2,3,3,5,5,6,6-d (2 g, 2.726 mmol) in DCM (14 mL) at 0° C. was added TFA (7 mL). The resulting mixture was stirred for 30 min and was then basified to pH 8 with sat. NaHCO$_3$ (aq.). The resulting mixture was extracted with DCM (3×50 mL) and the combined organic layers were washed with H$_2$O (3×30 mL), dried over Na$_2$SO$_4$, filtered, and concentrated under reduced pressure to afford the desired crude product (1.8 g, 70% yield) as a solid, which was used in the next step directly without further purification. LCMS (ESI) m/z [M+H]calcd for C$_{29}$H$_{28}$D$_8$BrF$_3$N$_4$O$_3$: 633.25; found: 633.3

Step 3: Synthesis of (S)-3-(5-bromo-2-(5-(4-cyclopropylpiperazin-1-yl-2,2,3,3,5,5,6,6-da)-2-(1-methoxyethyl)pyridin-3-yl)-1-(2,2,2-trifluoroethyl)-1H-indol-3-yl)-2,2-dimethylpropyl acetate To a solution of (S)-3-(5-bromo-2-(2-(1-methoxyethyl)-5-(piperazin-1-yl-2,2,3,3,5,5,6,6-da)pyridin-3-yl)-1-(2,2,2-trifluoroethyl)-1H-indol-3-yl)-2,2-dimethylpropyl acetate (1.6 g, 2.525 mmol) in MeOH (16 mL) at 0° C. was added AcOH (0.45 g, 7.575 mmol) and (1-ethoxycyclopropoxy)trimethylsilane (1.10 g, 6.313 mmol). The solution was stirred for 1 h at 0° C. and then NaBH$_3$CN (0.48 g, 7.575 mmol) was added. The resulting mixture was stirred for 2 h at 0° C. and then sat. NH$_4$Cl was added. The resulting mixture was extracted with DCM (3×50 mL) and the combined organic layers were washed with H$_2$O (3×50 mL), dried over Na$_2$SO$_4$, filtered, and concentrated under reduced pressure. The residue was purified by silica gel column chromatography (5% MeOH/DCM) to afford the desired product (1.4 g, 82% yield) as a solid. LCMS (ESI) m/z [M+H] calcd for C$_{32}$H$_{32}$D8BrF$_3$N$_4$O$_3$: 673.28; found: 673.3.

Step 4: Synthesis of (S)-(3-(3-acetoxy-2,2-dimethylpropyl)-2-(5-(4-cyclopropylpiperazin-1-yl-2,2,3,3,5,5,6,6-da)-2-(1-methoxyethyl)pyridin-3-yl)-1-(2,2,2-trifluoroethyl)-1H-indol-5-yl)boronic acid To a solution of (S)-3-(5-bromo-2-(5-(4-cyclopropylpiperazin-1-yl-2,2,3,3,5,5,6,6-da)-2-(1-methoxyethyl)pyridin-3-yl)-1-(2,2,2-trifluoroethyl)-1H-indol-3-yl)-2,2-dimethylpropyl acetate (1.56 g, 2.316 mmol) and B$_2$(OH)$_4$ (249.13 mg, 2.779 mmol) in MeOH (3 mL) and 2-methylTHF (9 mL) at room temperature was added XPhos Pd G3 (117.61 mg, 0.139 mmol) and KOPiv (648.41 mg, 4.632 mmol). The resulting mixture was stirred for 2 h at room temperature and was then quenched by the addition of H$_2$O (10 mL) at 0° C. The resulting mixture was extracted with DCM (3×50 mL) and the combined organic layers were washed with H$_2$O (3×30 mL), dried over Na$_2$SO$_4$, filtered, and concentrated under reduced pressure. The residue was purified by silica gel column chromatography (2% MeOH/DCM) to afford the desired product (1.72 g, 70% yield) as a solid. LCMS (ESI) m/z [M+H] calcd for C$_{32}$H$_{34}$D$_6$BF$_3$N$_4$O$_5$:639.38; found: 639.4.

Intermediate 33. Synthesis of (S)-3-(5-bromo-2-(5-(4-cyclopropylpiperazin-1-yl-2,2,3,3,5,5,6,6-da)-2-(1-methoxyethyl)pyridin-3-yl)-1-ethyl-1H-indol-3-yl)-2,2-dimethylpropyl acetate

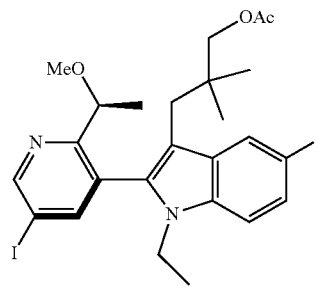

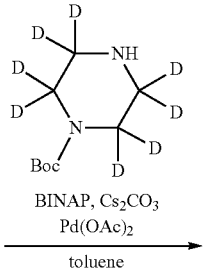

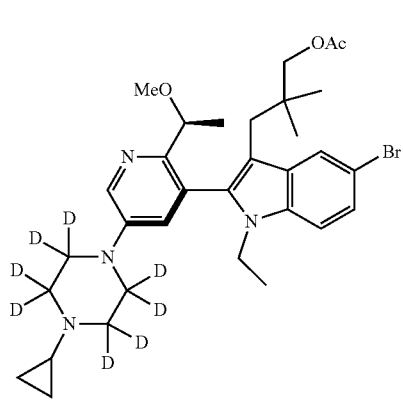

Step 1: Synthesis of tert-butyl (S)-4-(5-(3-(3-acetoxy-2,2-dimethylpropyl)-5-bromo-1-ethyl-1H-indol-2-yl)-6-(1-methoxyethyl)pyridin-3-yl)piperazine-1-carboxylate-2,2,3,3,5,5,6,6-d To a solution of (S)-3-(5-bromo-1-ethyl-2-(5-iodo-2-(1-methoxyethyl)pyridin-3-yl)-1H-indol-3-yl)-2,2-dimethylpropyl acetate (5 g, 7.493 mmol) and tert-butyl piperazine-1-carboxylate-2,2,3,3,5,5,6,6-d$_8$ (0.51 g, 2.609 mmol) and Pd(OAc)$_2$ (0.03 g, 0.130 mmol) in toluene (16 mL) at room temperature was added BINAP (0.16 g, 0.261 mmol) and Cs$_2$CO$_3$ (2.55 g, 7.827 mmol). The reaction mixture was stirred for 3 h at 75° C. and was then cooled to room temperature, quenched with H$_2$O (500 mL) at 0° C., and was extracted with DCM (3×200 mL). The combined organic layers were washed with brine (2×200 mL), dried over Na$_2$SO$_4$, filtered, and concentrated under reduced pressure. The residue was purified by prep-TLC (8% MeOH/DCM) to afford the desired product (1.20 g, 62% yield) as a solid. LCMS (ESI) m/z [M+H] calcd for C$_{34}$H$_{39}$D$_8$BrN$_4$O$_5$: 679.33; found: 379.3.

Step 2: Synthesis of (S)-3-(5-bromo-1-ethyl-2-(2-(1-methoxyethyl)-5-(piperazin-1-yl-2,2,3,3,5,5,6,6-da)pyridin-3-yl)-1H-indol-3-yl)-2,2-dimethylpropyl acetate To a solution of tert-butyl (S)-4-(5-(3-(3-acetoxy-2,2-dimethylpropyl)-5-bromo-1-ethyl-1H-indol-2-yl)-6-(1-methoxyethyl)pyridin-3-yl)piperazine-1-carboxylate-2,2,3,3,5,5,6,6-da (1.2 g, 1.765 mmol) in DCM (6 mL) at 0° C. was added TFA (2.7 mL). The resulting mixture was stirred for 3 h and was then concentrated under reduced pressure. The residue was basified to pH 8 with sat. NaHCO$_3$ (aq.). The resulting mixture was extracted with DCM (3×50 mL) and the combined organic layers were washed with brine (50 mL), dried over Na$_2$SO$_4$, filtered, and concentrated under reduced pressure. Purification by prep-TLC (9% MeOH/DCM) afforded the desired product (1.0 g, 88% yield) as a solid. LCMS (ESI) m/z [M+H] calcd for C$_{29}$H$_{31}$D8BrN$_4$O$_3$: 579.28; found: 579.3.

Step 3: Synthesis of (S)-3-(5-bromo-2-(5-(4-cyclopropylpiperazin-1-yl-2,2,3,3,5,5,6,6-da)-2-(1-methoxyethyl)pyridin-3-yl)-1-ethyl-1H-indol-3-yl)-2,2-dimethylpropyl acetate To a solution of (S)-3-(5-bromo-1-ethyl-2-(2-(1-methoxyethyl)-5-(piperazin-1-yl-2,2,3,3,5,5,6,6-d8)pyridin-3-yl)-1H-indol-3-yl)-2,2-dimethylpropyl acetate (1.2 g, 2.070 mmol) in MeOH (12 mL) at 0° C. was added AcOH (1.24 g, 20.70 mmol), (1-ethoxycyclopropoxy)trimethylsilane (541.34 mg, 3.105 mmol), and NaBH$_3$CN (1.30 g, 20.700 mmol). The resulting mixture was stirred for 4 h at room temperature and then sat. NH$_4$Cl was added at 0° C. The resulting mixture was extracted with EtOAc (3×200 mL) and the combined organic layers were washed with brine (1200 mL), dried over Na$_2$SO$_4$, filtered, and concentrated under reduced pressure. The residue was purified by prep-TLC (9% MeOH/DCM) to afford the desired product (1.0 g, 78% yield) as a solid. LCMS (ESI) m/z [M+H] calcd for C$_{32}$H$_{35}$D$_8$BrN$_4$O$_3$: 619.31; found: 619.3.

Intermediate A-1 and A-2: Synthesis of (S)-2-((R)-7-(tert-butoxycarbonyl)-2,7-diazaspiro[4.4]nonan-2-yl)-2-cyclopentylacetic acid and (S)-2-((S)-7-(tert-butoxycarbonyl)-2,7-diazaspiro[4.4]nonan-2-yl)-2-cyclopentylacetic acid

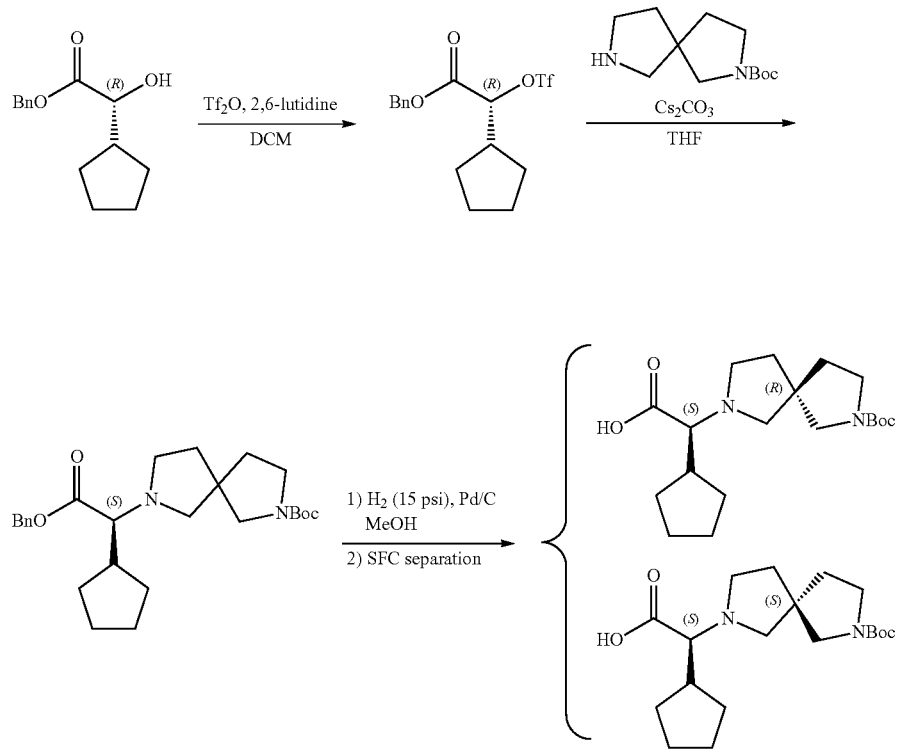

Step 1: Synthesis of benzyl (R)-2-cyclopentyl-2-(((trifluoromethyl)sulfonyl)oxy)acetate To a solution of benzyl (R)-2-cyclopentyl-2-hydroxyacetate (3 g, 12.8 mmol) in DCM (50 mL) was added Tf$_2$O (3.79 g, 13.44 mmol) and 2,6-lutidine (1.51 g, 14.09 mmol) at 0° C. under N$_2$ and the mixture was stirred at 0° C. for 2 h. The residue was diluted with H$_2$O (30 mL) and extracted with DCM (3×50 mL). The combined organic layers were washed with brine (2×50 mL), dried over Na$_2$SO$_4$, filtered and the filtrate was concentrated under reduced pressure to give the product, which was used directly without further purification.

Step 2: Synthesis of tert-butyl 7-((S)-2-(benzyloxy)-1-cyclopentyl-2-oxoethyl)-2,7-diazaspiro[4.4]nonane-2-carboxylate To a solution of benzyl (R)-2-cyclopentyl-2-(((trifluoromethyl)sulfonyl)oxy)acetate (4.86 g, 13.26 mmol) in THF (20 mL) was added tert-butyl 2,7-diazaspiro[4.4]nonane-2-carboxylate (2 g, 8.84 mmol) and Cs$_2$CO$_3$ (8.64 g, 26.51 mmol). The mixture was stirred at room temperature for 30 min. The residue was diluted with H$_2$O (30 mL) and extracted with EtOAc (3×30 mL) and the combined organic layers were washed with brine (2×40 mL), dried over Na$_2$SO$_4$, filtered, and concentrated under reduced pressure. The residue was purified by silica gel column chromatography (20→100% EtOAc/pet. ether) to give the product (2.6 g, 66% yield) as a solid. LCMS (ESI) m/z [M+H] calcd for C$_{26}$H$_{38}$N$_2$O$_4$:443.3; found: 443.2.

Step 3: Synthesis of (S)-2-((R)-7-(tert-butoxycarbonyl)-2,7-diazaspiro[4.4]nonan-2-yl)-2-cyclopentylacetic acid and (S)-2-((S)-7-(tert-butoxycarbonyl)-2,7-diazaspiro[4.4]nonan-2-yl)-2-cyclopentylacetic acid To a solution of tert-butyl 7-((S)-2-(benzyloxy)-1-cyclopentyl-2-oxoethyl)-2,7-diazaspiro[4.4]nonane-2-carboxylate (2.6 g, 5.87 mmol) in MeOH (30 mL) was added Pd/C (0.5 g, 10% on carbon w/w) under a N$_2$ atmosphere. The suspension was degassed and purged with H$_2$. The mixture was stirred under H$_2$ (15 psi) at room temperature for 4 h. The mixture was filtered and the filtrate was concentrated under reduced pressure to give residue. The residue was dissolved in EtOAc (5 mL) and the mixture was stirred for 10 min. Then the mixture was filtered and the filter cake was dried under reduced pressure. The solid was purified by SFC-separation (CO$_2$/MeOH (0.1% NH$_4$0)) to give (S)-2-((R)-7-(tert-butoxycarbonyl)-2,7-diazaspiro[4.4]nonan-2-yl)-2-cyclopentylacetic acid (450 mg, 22% yield) and (S)-2-((S)-7-(tert-butoxycarbonyl)-2,7-diazaspiro[4.4]nonan-2-yl)-2-cyclopentylacetic acid (450 mg, 22% yield).

Intermediate A-3 and A-4: (S)-2-((S)-7-(tert-butoxycarbonyl)-2,7-diazaspiro[4.4]nonan-2-yl)-3-methylbutanoic acid and (S)-2-((R)-7-(tert-butoxycarbonyl)-2,7diazaspiro[4.4]nonan-2-yl)-3-methylbutanoic acid

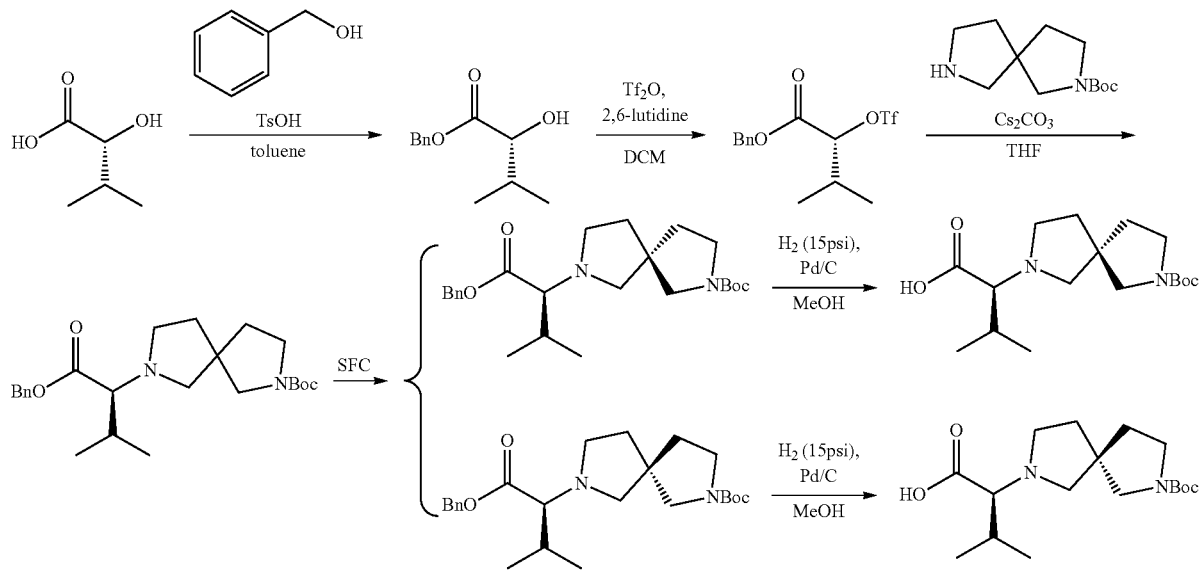

Step 1: Synthesis of benzyl (R)-2-hydroxy-3-methylbutanoate

To a stirred solution of benzyl alcohol (19.22 g, 177.77 mmol) in toluene (200 mL) was added TsOH•H$_2$O (2.92 g, 16.93 mmol) in portions at room temperature under N$_2$. The mixture was stirred at 80° C. for 30 min, the mixture then cooled to room temperature and (R)-2-hydroxy-3-methylbutanoic acid (20 g, 169.30 mmol, 1 eq) was added. The resultant mixture was stirred at 80° C. for 3 h. The reaction mixture was concentrated under reduced pressure to give the crude product as colorless oil. The crude product was purified by silica gel column chromatography (20→100% EtOAc/pet. ether) to afford the product (25 g, 71% yield) as an oil.

Step 2: Synthesis of benzyl (R)-3-methyl-2-(((trifluoromethyl)sulfonyl)oxy)butanoate A solution of benzyl (R)-2-hydroxy-3-methylbutanoate (15 g, 72.03 mmol) in DCM (225 mL) was cooled to 0° C. and then treated with Tf$_2$O (21.34 g, 75.63 mmol) and 2,6-lutidine (8.49 g, 79.23 mmol) under N$_2$. The resultant mixture was stirred for 1 h at 0° C. The reaction mixture was added into H$_2$O (300 mL). The mixture was extracted with DCM (3×100 mL) and the combined organic layers were washed with brine (400 mL), filtered and concentrated under reduced pressure to give the crude product. The crude product was purified by silica gel column chromatography (5→10% EtOAc/pet. ether: EtOAc) to afford the product (20 g, 82% yield) as an oil.

Step 3: Synthesis of tert-butyl 7-((S)-1-(benzyloxy)-3-methyl-1-oxobutan-2-yl)-2,7-diazaspiro[4.4]nonane-2-carboxylate To a solution of benzyl (R)-3-methyl-2-(((trifluoromethyl)sulfonyl)oxy)butanoate (20 g, 58.77 mmol) and tert-butyl 2,7-diazaspiro[4.4]nonane-2-carboxylate (11.08 g, 48.97 mmol), Cs$_2$CO$_3$ (47.87 g, 146.92 mmol) in THF (300 mL) at 0° C. The resultant mixture was stirred for 2 h at room temperature. The reaction mixture was filtered and the filter cake washed with THF (3×100 mL). Then the filtrate was concentrated under reduced pressure to give the crude product as an oil. The oil was purified by silica gel column chromatography (10→30% EtOAc/pet. ether) to give the product (13.2 g, 64% yield). LCMS (ESI) m/z [M+H] calcd for C$_{24}$H$_{37}$N$_2$O$_4$: 417.27; found: 417.2

Step 4: Synthesis tert-butyl (S)-7-((S)-1-(benzyloxy)-3-methyl-1-oxobutan-2-yl)-2,7-diazaspiro[4.4]nonane-2-carboxylate and tert-butyl (R)-7-((S)-1-(benzyloxy)-3-methyl-1-oxobutan-2-yl)-2,7-diazaspiro[4.4]nonane-2-carboxylate The tert-butyl 7-((S)-1-(benzyloxy)-3-methyl-1-oxobutan-2-yl)-2,7-diazaspiro[4.4]nonane-2-carboxylate (10 g) was purified by SFC separation to afford tert-butyl (S)-7-((S)-1-(benzyloxy)-3-methyl-1-oxobutan-2-yl)-2,7-diazaspiro[4.4]nonane-2-carboxylate (3.4 g) and tert-butyl (R)-7-((S)-1-(benzyloxy)-3-methyl-1-oxobutan-2-yl)-2,7-diazaspiro[4.4]nonane-2-carboxylate (3.9 g).

Step 5: Synthesis of (S)-2-((R)-7-(tert-butoxycarbonyl)-2,7-diazaspiro[4.4]nonan-2-yl)-3-methylbutanoic acid To a solution of tert-butyl (R)-7-((S)-1-(benzyloxy)-3-methyl-1-oxobutan-2-yl)-2,7-diazaspiro[4.4]nonane-2-carboxylate (2.5 g, 6.00 mmol) in MeOH (25 mL) was added Pd/C (1.5 g, 10% purity) under Ar. The suspension was degassed under reduced pressure and purged with H$_2$ several times. The mixture was stirred under H$_2$ (15 psi) at room temperature for 1 h. The reaction mixture was filtered and then the filtrate was concentrated under reduced pressure to give the product (1.9 g, crude) as a solid.

Step 6: Synthesis of (S)-2-((S)-7-(tert-butoxycarbonyl)-2,7-diazaspiro[4.4]nonan-2-yl)-3-methylbutanoic acid To a solution of tert-butyl (S)-7-((S)-1-(benzyloxy)-3-methyl-1-oxobutan-2-yl)-2,7-diazaspiro[4.4]nonane-2-carboxylate (3 g, 7.20 mmol) in MeOH (5 mL) was added Pd/C (1 g, 10% purity) under Ar. The suspension was degassed under reduced pressure and purged with H₂ several times. The mixture was stirred under H₂ (15 psi) at room temperature for 1 h. The reaction mixture was filtered and then the filtrate was concentrated under reduced pressure to give the product (2.3 g, 98% yield) as solid.

Intermediate B-1: Synthesis of lithium (2R,3R)-3-cyclopropyl-1-methylaziridine-2-carboxylate

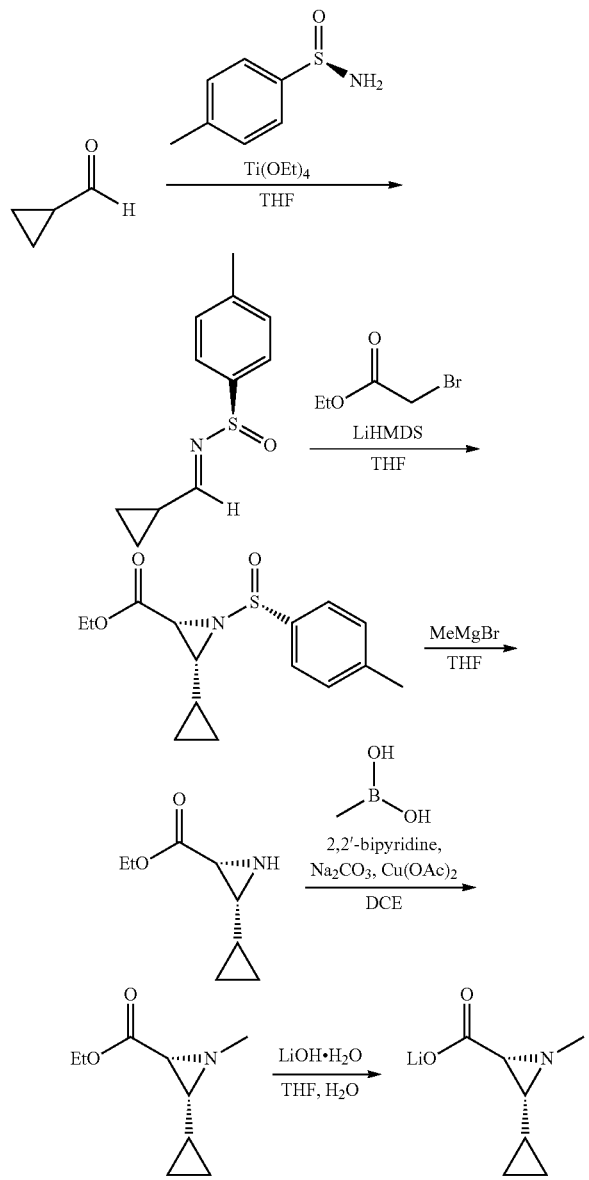

Step 1: Synthesis of (R,E)-N-(cyclopropylmethylene)-4-methylbenzenesulfinamide

To a solution of cyclopropanecarbaldehyde (6 g, 85.60 mmol) in THF (120 mL) was added (R)-4-methylbenzenesulfinamide (13.29 g, 85.60 mmol) and Ti(OEt)₄ (39.05 g, 171.21 mmol) at room temperature under N₂. The mixture was stirred at 75 0C for 2 h. The reaction mixture was poured into brine/H₂O (1:1, 600 mL) at 0-15° C. The mixture was filtered through a pad of Celite and the pad was washed with EtOAc (6×200 mL). The combined filtrates were extracted with EtOAc (2×200 mL). The combined organic layers were washed with brine (200 mL), dried over Na₂SO₄, filtered and concentrated under reduced pressure to give a residue. The crude product was purified by silica gel column chromatography. (0→10% EtOAc/pet. ether) to give the product (14.6 g, 82% yield) as a solid.

Step 2: Synthesis of ethyl (2R,3R)-3-cyclopropyl-1-((R)-p-tolylsulfinyl)aziridine-2-carboxylate To a solution of ethyl 2-bromoacetate (23.52 g, 140.86 mmol) in THF (700 mL) was added LiHMDS (1 M, 140.86 mL) at −70 0C over 10 min under N₂. The mixture was stirred at −70 0C for 20 min. A solution of (R,E)-N-(cyclopropylmethylene)-4-methylbenzenesulfinamide (14.6 g, 70.43 mmol) in THE (150 mL) was added into the reaction solution at −70 0C for 10 min. Then the mixture was stirred at −70 0C for 1 h 20 min under N₂. The reaction mixture was poured into cold H₂O (1.2 L) and stirred at room temperature for 5 min. The aqueous layer was extracted with EtOAc (3×300 mL). The combined organic layers were washed with brine (300 mL), dried over Na₂SO₄, filtered and concentrated under reduced pressure to give a residue. The crude product was purified by silica gel column chromatography. (0→10% EtOAc/pet. ether) to give the product (11 g, 53% yield) as an oil. LCMS (ESI) m/z [M+H] calcd for C₁₅H₂₀NO₃S: 294.11; found: 294.1.

Step 3: Synthesis of ethyl (2R,3R)-3-cyclopropylaziridine-2-carboxylate

Ethyl (2R,3R)-3-cyclopropyl-1-[(R)-p-tolylsulfinyl]aziridine-2-carboxylate (6 g, 20.45 mmol) was dissolved in anhydrous THE (300 mL). MeMgBr (3 M, 13.63 mL) was added dropwise at −65 0C over 40 min under N₂. The reaction mixture was stirred for 5 min. Sat. aq. NH₄Cl (90 mL) was added dropwise at −65° C. The cooling bath was removed, and the reaction mixture was warmed to room temperature. EtOAc (300 mL) was added and the organic layer was separated and concentrated under reduced pressure. The residue was purified by silica gel column chromatography (0→50% EtOAC/pet. ether) to afford the product as an oil.

Step 4: ethyl (2R,3R)-3-cyclopropyl-1-methylaziridine-2-carboxylate

To a solution of ethyl (2R,3R)-3-cyclopropylaziridine-2-carboxylate (400 mg, 2.58 mmol) in DCE (8 mL) was added methylboronic acid (462.85 mg, 7.73 mmol), 2,2'-bipyridine (402.54 mg, 2.58 mmol), Cu(OAc)₂ (468.14 mg, 2.58 mmol), and Na₂CO₃ (819.54 mg, 7.73 mmol). The reaction mixture was stirred at 45° C. for 40 h. The mixture was poured into aq. NH₄Cl (15 mL) and extracted with DCM (3×15 mL), the combined organic phases were washed with brine (20 mL), dried with anhydrous Na₂SO₄, filtered and concentrated under reduced pressure. The residue was purified by silica gel column chromatography (0→50% EtOAc/pet. ether) to give the product (230 mg, 53% yield) as an oil. LCMS (ESI) m/z [M+H] calcd for C₉H₁₆NO₂: 170.1; found: 170.1.

Step 5: lithium (2R,3R)-3-cyclopropyl-1-methyl-aziridine-2-carboxylate

To a solution of ethyl (2R,3R)-3-cyclopropyl-1-methyl-aziridine-2-carboxylate (230 mg, 1.36 mmol) in THF (2 mL) was added a solution of LiOH•H$_2$O (114.07 mg, 2.72 mmol) in H$_2$O (1 mL). The reaction mixture was stirred at room temperature for 1 h. The pH was adjusted to about 8 with 0.5 N HCl at 0° C., and the solution was lyophilized directly to give the product (230 mg, crude) as a solid.

Intermediate B-2: Synthesis of lithium (2R,3R)-3-cyclopropyl-1-(methyl-d$_3$)aziridine-2-carboxylate

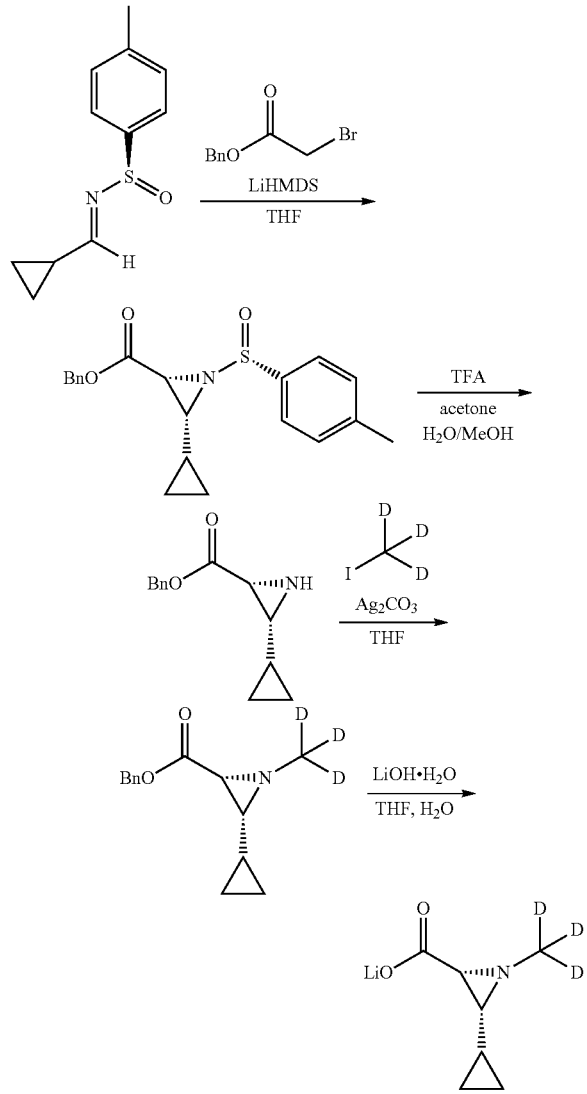

Step 1: Synthesis of benzyl (2R,3R)-3-cyclopropyl-1-((R)-p-tolylsulfinyl)aziridine-2-carboxylate Preparation of benzyl (2R,3R)-3-cyclopropyl-1-((R)-p-tolylsulfinyl)aziridine-2-carboxylate may be achieved using a comparable procedure as described for Intermediate B-1, Step 2, using commercially available starting materials.

To a solution of (R)-N-(cyclopropylmethylidene)-4-methylbenzenesulfinamide (100 g, 482.4 mmol) and benzyl 2-bromoacetate (143.66 g, 627.1 mmol) in THF (1 L) at −60 0C was added LiHMDS (627.1 mL, 627.1 mmol) dropwise over 30 min. The resulting mixture was stirred at −40 0C for 1.5 h and then cold H$_2$O (1.5 L) was added. The aqueous layer was extracted with EtOAc (2×1 L) and the combined organic layers were washed with H$_2$O (2×2 L) and brine (2 L), dried over Na$_2$SO$_4$, filtered, and concentrated under reduced pressure. The residue was purified by silica gel column chromatography (5% EtOAc/Pet. ether) to afford the desired product (137 g, 80% yield) as an oil.

Step 2: Synthesis of benzyl (2R,3R)-3-cyclopropylaziridine-2-carboxylate

To a solution of benzyl (2R,3R)-3-cyclopropyl-1-((R)-p-tolylsulfinyl)aziridine-2-carboxylate (60 g, 168.80 mmol) in acetone (786 mL), H$_2$O (131 mL) and MeOH (102 mL) at 0° C. was added TFA (96.24 g, 844.0 mmol). The resulting mixture was stirred at 0° C. for 60 min and then the reaction mixture was added to NH$_3$•H$_2$O (500 mL of 28% NH$_3$•H$_2$O in 1 L of H$_2$O) at 0° C. The resulting mixture was extracted with EtOAc (3×700 mL) and the combined organic layers were washed with H$_2$O (3×400 mL), dried over Na$_2$SO$_4$, filtered, and concentrated under reduced pressure. The residue was purified by silica gel column chromatography (9% EtOAc/pet. ether) to afford the desired product. LCMS (ESI) m/z [M+H]calcd for C$_{13}$H$_{15}$NO$_2$ 218.12; found: 218.3.

Step 3: Synthesis of benzyl (2R,3R)-3-cyclopropyl-1-(methyl-d$_3$)aziridine-2-carboxylate To a solution of benzyl (2R,3R)-3-cyclopropylaziridine-2-carboxylate (3.0 g, 13.81 mmol) in THF (50 mL) at 0° C. was added 4A MS (3 g) and Ag$_2$CO$_3$ (9.45 g, 34.54 mmol), CD3I (5.0 g, 34.54 mmol). The resulting mixture was stirred at room temperature for 16 h. The resulting mixture was then extracted with EtOAc (3×100 mL) and the combined organic layers were washed with brine (100 mL), dried over Na$_2$SO$_4$, filtered, and concentrated under reduced pressure. The residue was purified by reverse phase chromatography (20→60% MeCN/H$_2$O) to afford the desired product (1.80 g, 56% yield) as an oil. LCMS (ESI) m/z [M+H] calcd for C$_{14}$H$_{14}$D$_3$NO$_2$ 235.15; found: 235.2.

Step 4: Synthesis of lithium (2R,3R)-3-cyclopropyl-1-(methyl-d$_3$)aziridine-2-carboxylate To a solution of benzyl (2R,3R)-3-cyclopropyl-1-(methyl-d$_3$)aziridine-2-carboxylate (1.80 g, 7.69 mmol) in THF (20 mL) at 0° C. was added a solution of LiOH•H$_2$O (0.48 g, 11.54 mmol) in H$_2$O (20 mL). The resulting mixture was stirred at room temperature for 2 h and then H$_2$O (40 mL). The mixture was extracted with DCM (3×100 mL) and then the aqueous phase was concentrated under reduced pressure to afford the desired product (1.0 g, 87% yield) as solid. LCMS (ESI) m/z [M+H] calcd for C$_7$H$_8$D$_3$NO$_2$ 145.11; found: 145.2.

Intermediate B-3: Synthesis of lithium (2R,3R)-3-cyclopropyl-1-methylaziridine-2-carboxylate-3-d

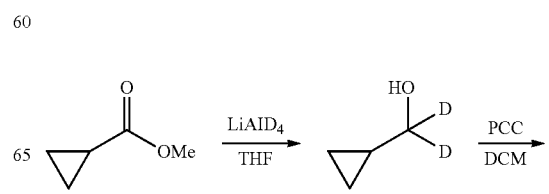

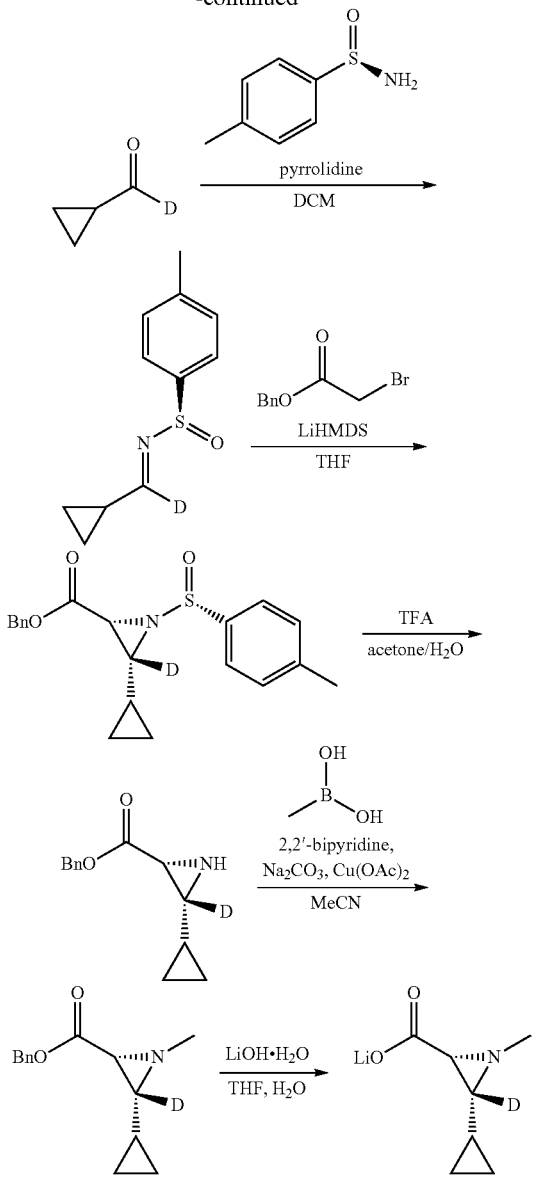

Step 1: Synthesis of cyclopropylmethan-d₂-ol

To a solution of methyl cyclopropanecarboxylate (20 g, 199.77 mmol) in THF (200 mL) at −19° C. was added LiAlD₄ (10.30 mL, 199.77 mmol) over 2.5 h. The reaction mixture was stirred at −19° C. for 1 h and then H₂O (20 mL) and a 15% NaOH solution (20 mL) were added. Additional H₂O (60 mL) was added and then the mixture was filtered. The filtrate was extracted with DCM (1000 mL) and the combined organic layers were dried over Na₂SO₄, filtered, and concentrated under reduced pressure to afford the desired product (12.3 g, 83% yield) as an oil.

Step 2: Synthesis of cyclopropanecarbaldehyde-d

To a solution of cyclopropylmethan-d₂-ol (12 g, 161.90 mmol) in DCM (120 mL) at 0° C. was added PCC (52.35 g, 242.86 mmol). The reaction mixture was stirred at 16° C. for 18 h and was then filtered, and concentrated under reduced pressure to afford the desired product (5 g, crude) as an oil.

Step 3: Synthesis of (R,E)-N-(cyclopropylmethylene-d)-4-methylbenzenesulfinamide To a suspension of 4 A MS (3.6 g) in DCM (18 mL) was added cyclopropanecarbaldehyde-d (4.95 g, 69.58 mmol) followed by pyrrolidine (96.80 μL, 1.16 mmol) and (R)-4-methylbenzenesulfinamide (3.6 g, 23.19 mmol). The mixture was stirred at room temperature for 17 h. The reaction mixture was then filtered and the combined organic phases were concentrated under reduced pressure. The residue was purified by silica gel column chromatography (0-*>17% EtOAc/pet. ether) to afford the desired product (4.42 g, 92% yield) as a solid. LCMS (ESI) m/z [M+H] calcd for $C_{11}H_{12}DNOS$: 209.09; found: 209.1.

Step 4: Synthesis of benzyl (2R,3R)-3-cyclopropyl-1-((R)-p-tolylsulfinyl)aziridine-2-carboxylate-3-d To a solution of benzyl 2-bromoacetate (879.78 mg, 3.84 mmol) in THF (16.4 mL) was added LiHMDS (1 M, 3.84 mL) at −70° C. over 20 min under N₂ and then the mixture was stirred at −70° C. for 1 h. A solution of (R,E)-N-(cyclopropylmethylene-d)-4-methylbenzenesulfinamide (0.4 g, 1.92 mmol) in THE (3.6 mL) was added to the reaction mixture at −70° C. over 20 min. The mixture was stirred at −70° C. for 1 h and was then poured into cold H₂O (10 mL) and stirred at room temperature for 5 min. The aqueous layer was extracted with EtOAc (3×10 mL) and the combined organic layers were washed with brine (10 mL), dried over Na₂SO₄, filtered and concentrated under reduced pressure to give a residue. The crude product was purified by silica gel column chromatography. (0→1 7% EtOAc/pet. ether) to afford the desired product (354.7 mg, 52% yield) as an oil. LCMS (ESI) m/z [M+H] calcd for $C_{20}H_{20}DNO_3S$: 357.14; found: 357.2.

Step 5: Synthesis of benzyl (2R,3R)-3-cyclopropylaziridine-2-carboxylate-3-d

To a solution of benzyl (2R,3R)-3-cyclopropyl-1-((R)-p-tolylsulfinyl)aziridine-2-carboxylate-3-d (350 mg, 854.24 μmol) in acetone (4 mL) and H₂O (662 μL,) at 0° C. was added TFA (316.2 μL, 4.27 mmol). The mixture was stirred at 0° C. for 1.5 h and then NH₃●H₂O (0.92 mL, 25%) Was added. The mixture was extracted with EtOAc (3×5 mL), and the combined organic layers were washed with brine (3×10 mL), filtered, dried with Na₂SO₄, filtered, and concentrated under reduced pressure. The residue was purified by silica gel column chromatography (0→1 7% EtOAc/pet. ether) to afford the desired product (133 mg, 65% yield) as an oil. LCMS (ESI) m/z [M+H] calcd for $C_{13}H_{14}DNO_2$: 219.12; found: 219.2.

Step 6: Synthesis of benzyl (2R,3R)-3-cyclopropyl-1-methylaziridine-2-carboxylate-3-d To a solution of benzyl (2R,3R)-3-cyclopropylaziridine-2-carboxylate-3-d (100 mg, 458.15 pmol) in MeCN (2 mL) was added methylboronic acid (82.27 mg, 1.37 mmol), 2,2'-bipyridine (71.56 mg, 458.15 pmol), Cu(OAc)₂ (83.22 mg, 458.15 pmol), Na₂CO₃ (145.68 mg, 1.37 mmol), and 4 A MS (400 mg). The reaction mixture was stirred at 45° C. for 10 h. The reaction mixture was poured into aq. NH₄Cl (5 mL) and extracted with DCM (3×5 mL), the combined organic layers were washed with brine (20 mL), dried with Na$_2$SO$_4$, filtered, and concentrated under reduced pressure. The residue was purified by silica gel column chromatography (1→14% EtOAc/pet. ether) to afford the desired product (72 mg, 63% yield) as an oil. LCMS (ESI) m/z [M+H] calcd for C$_{14}$H$_{16}$DNO$_2$: 233.14; found: 233.2.

Step 7: Synthesis of lithium (2R,3R)-3-cyclopropyl-1-methylaziridine-2-carboxylate-3-d To a solution of benzyl (2R,3R)-3-cyclopropyl-1-methyl-aziridine-2-carboxylate-3-d (0.77 g, 2.92 mmol) in THF (5.85 mL) and H$_2$O (1.85 mL) was added LiOH•H$_2$O (244.81 mg, 5.83 mmol). The reaction mixture was stirred at room temperature for 15 h and then H$_2$O (5 mL) was added. The mixture was lyophilized directly to give the product (570 mg, crude) as a solid.

Example A22: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-((6$^3$S,4S,Z)-1$^2$-(5-(4-cyclopropylpiperazin-1-yl)-2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)acetamide

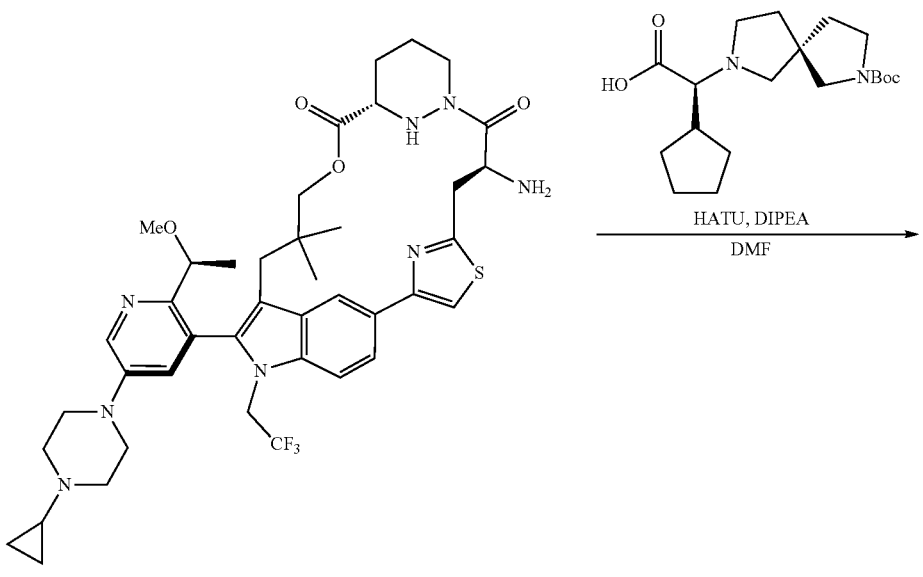

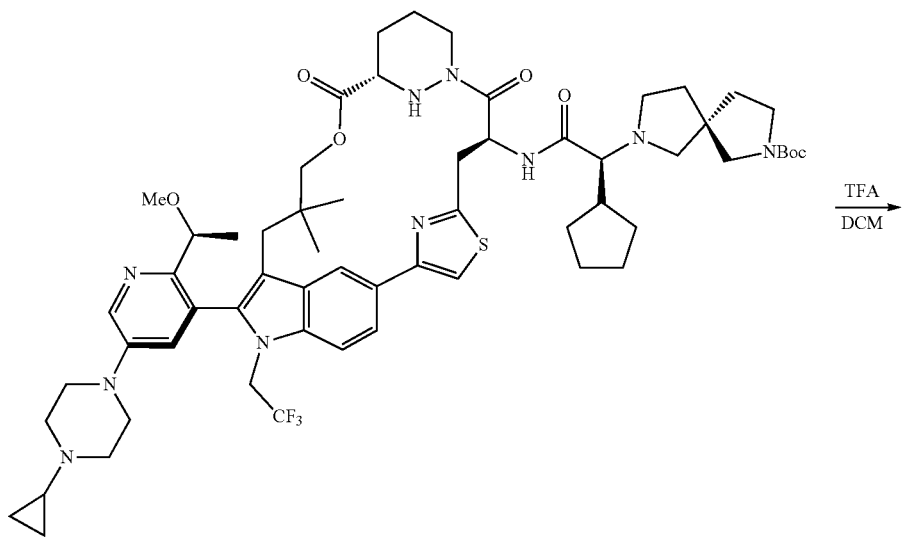

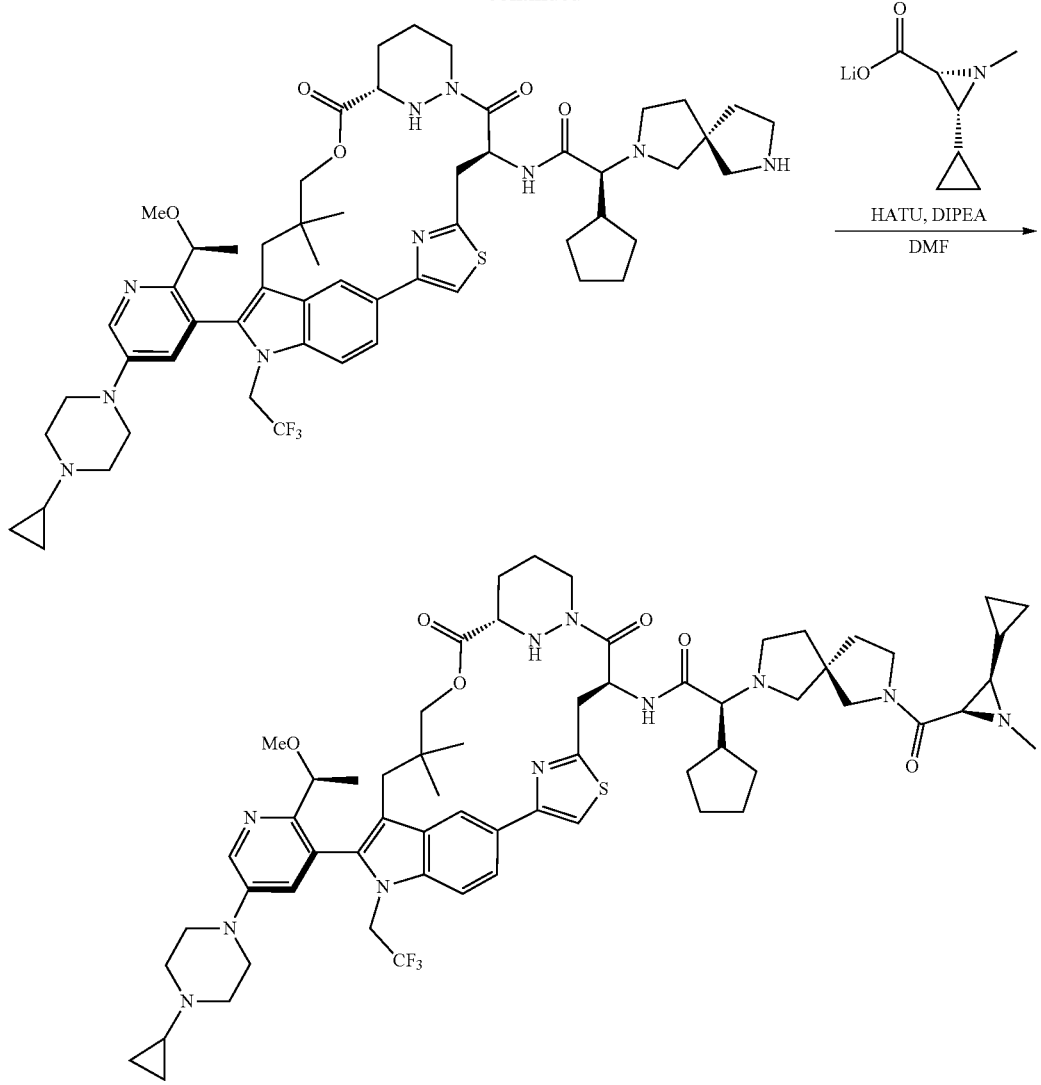

Step 1: Synthesis of tert-butyl (5S)-7-((1 S)-1-cyclopentyl-2-(((6³S,4S,Z)-12-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-61,62,63,64,65,66-hexahydro-1¹H-8-oxa-2(4,2)-thiazola-1(5,3)-indola-6(1,3)-pyridazinacycloundecaphane-4-yl)amino)-2-oxoethyl)-2,7-diazaspiro[4.4]nonane-2-carboxylate To a stirred solution of (63S,4S,Z)-4-amino-12-(5-(4-cyclopropylpiperazin-1-yl)-2-((S)-1-methoxyethyl)pyridin-3-yl)-10,10-dimethyl-1¹-(2,2,2-trifluoroethyl)-61,62,63,64,65,66-hexahydro-1¹H-8-oxa-2(4,2)-thiazola-1(5,3)-indola-6(1,3)-pyridazinacycloundecaphane-5,7-dione (1.0 g, 1.236 mmol) and DIPEA (798.84 mg, 6.18 mmol) in DMF (10 mL) at 0° C. was added (S)-2-((S)-7-(tert-butoxycarbonyl)-2,7-diazaspiro[4.4]nonan-2-yl)-2-cyclopentylacetic acid (653.5 mg, 1.854 mmol) and HATU (611 mg, 1.61 mmol). The resulting mixture was stirred at room temperature for 2 h. The mixture was extracted with EtOAc (3×30 mL), and the combined organic layers were washed with brine (40 mL), dried over Na₂SO₄, filtered, and concentrated under reduced pressure. The residue was purified by prep-TLC (6% MeOH/DCM) to afford the desired product (1.27 g, 90% yield) as a solid. LCMS (ESI) m/z [M+H] calcd for $C_{60}H_{81}F_3N_{10}O_7S$ 1143.61, found: 1143.3.

Step 2: Synthesis of (2S)-2-cyclopentyl-N-((6³S,4S,Z)-12-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)-2-((S)-2,7-diazaspiro[4.4]nonan-2-yl)acetamide To a solution of tert-butyl (5S)-7-((1 S)-1-cyclopentyl-2-(((6³S,4S,Z)-12-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-2(4,2)-thiazola-1 (5,3)-indola-6(1,3)-pyridazinacycloundecaphane-4-yl)amino)-2-oxoethyl)-2,7-diazaspiro[4.4]nonane-2-carboxylate (1.27 g, 1.11 mmol) in DCM (15 mL) at 0° C. was added TFA (7 mL, 71.4 mmol). The mixture was stirred for 2 h and was then concentrated under reduced pressure. The residue was dissolved in EtOAc (30 mL) and was adjusted to pH 8 with sat. NaHCO$_3$ (aq.). The resulting mixture was extracted with EtOAc (3×30 mL), and the combined organic layers were washed with brine (40 mL), dried over Na$_2$SO$_4$, filtered, and concentrated under reduced pressure to afford the desired product (1.1 g, 95% yield) as a solid. LCMS (ESI) m/z [M+H] calcd for C$_{55}$H$_{73}$F$_3$N$_{10}$O$_5$S 1043.55; found: 1043.7.

Step 3: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-((6$^3$S,4S,2)-1$^2$-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)acetamide To a stirred solution of (2S)-2-cyclopentyl-N-((6$^3$S,4S,Z)-1$^2$-(5-(4-cyclopropylpiperazin-1-yl)-2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)-2-((S)-2,7-diazaspiro[4.4]nonan-2-yl)acetamide (610 mg, 0.585 mmol) and lithium (2R,3R)-3-cyclopropyl-1-methylaziridine-2-carboxylate (169 mg, 1.150 mmol) in DMF (6 mL) 0° C. was added DIPEA (755 mg, 5.85 mmol) and HATU (267 mg, 0.702 mmol). The resulting mixture was stirred at room temperature for 1 h. The reaction was quenched by the addition of cold H$_2$O (30 mL) and the resulting mixture was extracted with EtOAc (3×20 mL). The combined organic layers were washed with brine (20 mL), dried over Na$_2$SO$_4$, filtered, and concentrated under reduced pressure. The residue was purified by reverse phase chromatography (MeCN/H$_2$O) to afford the desired product (350 mg, 51% yield) as a solid. LCMS (ESI) m/z [M+H] calcd for C$_{62}$H$_{82}$F$_3$N$_{11}$O$_6$S 1166.62; found: 1166.7.

Example A26: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-((2$^2$S, 6$^3$,4S)-1$^2$-(5-(4-cyclopropylpiperazin-1-yl)-2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-4-yl)acetamide

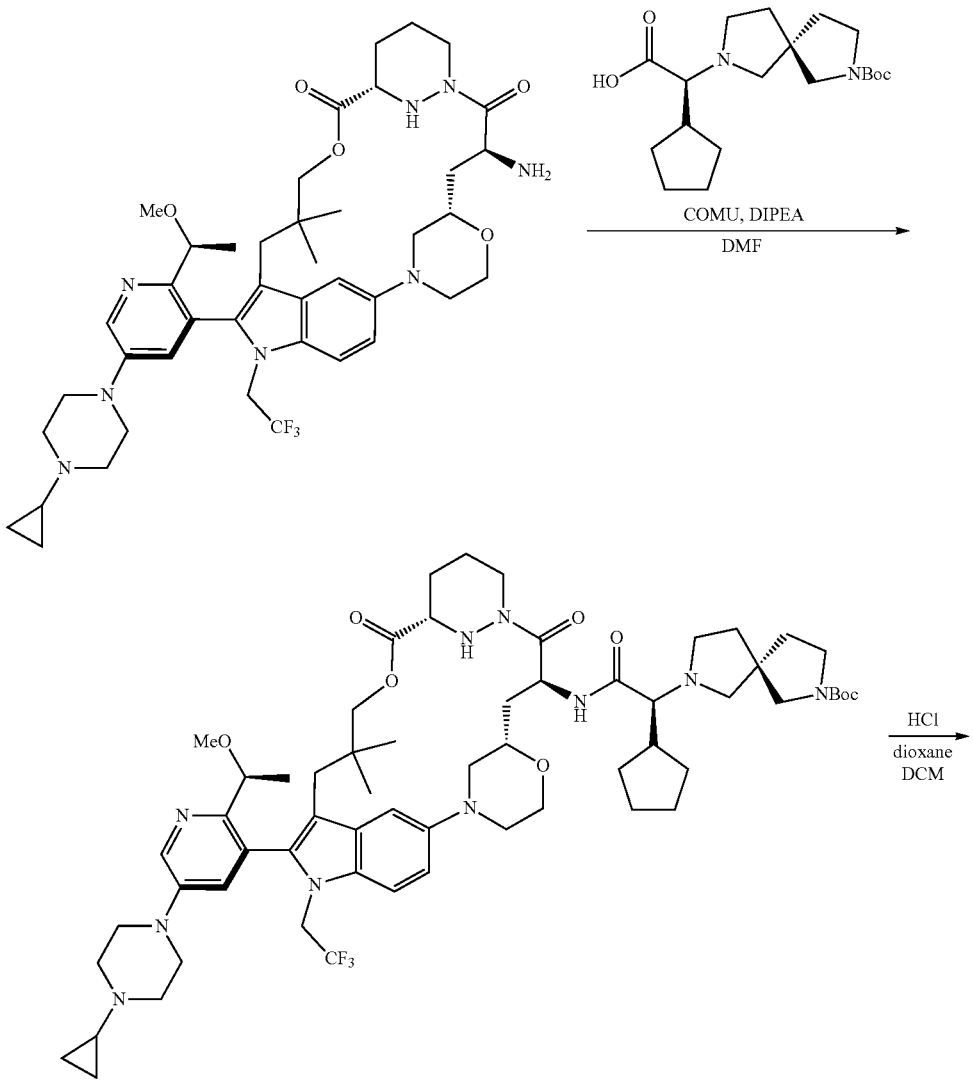

-continued

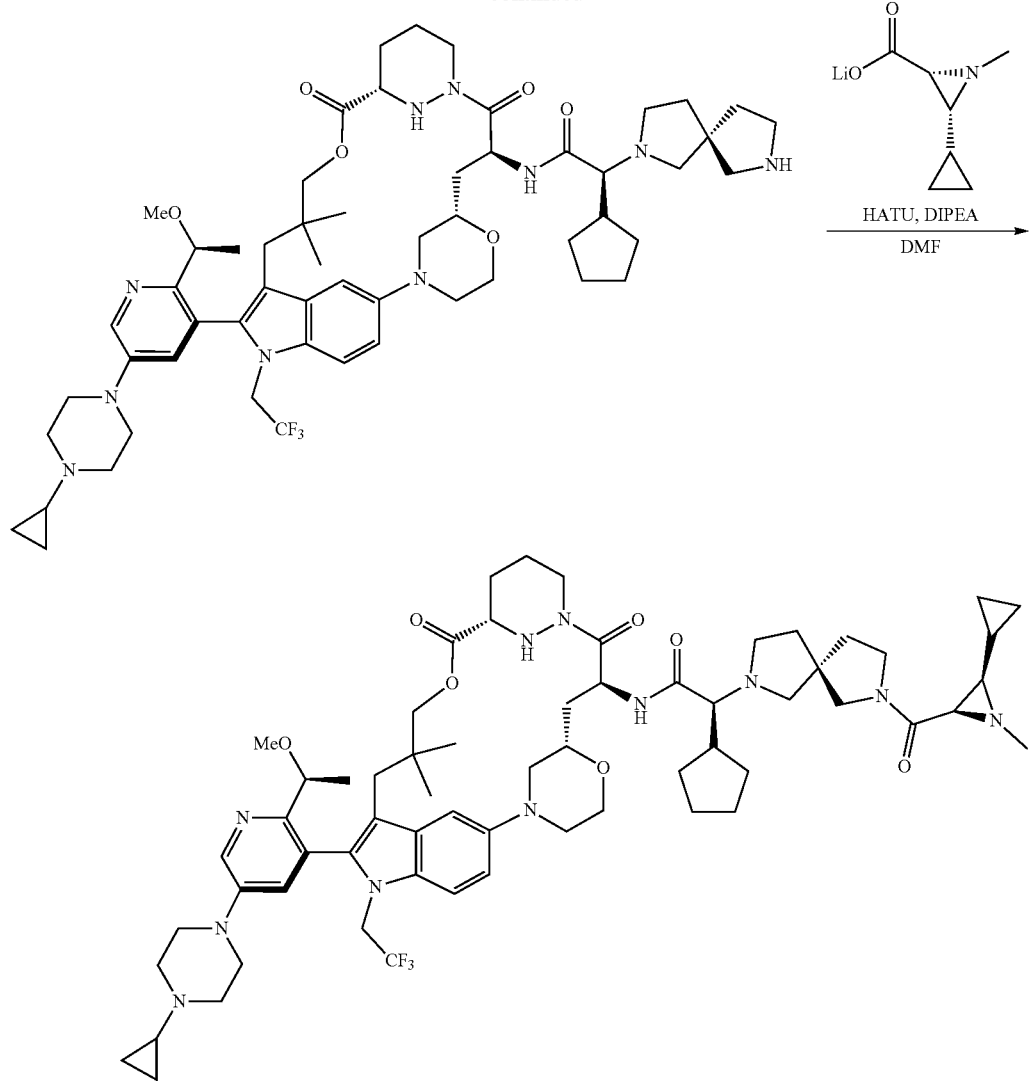

Step 1: Synthesis of tert-butyl (5S)-7-((1 S)-1-cyclopentyl-2-(((2²S,6³S,4S)-1²-(5-(4-cyclopropylpiperazin-1-yl)-2-((S)-1-methoxyethyl)pyridin-3-yl)-10, 10-dimethyl-5,7-dioxo-1¹-(2,2,2-trifluoroethyl)-6¹, 6²,6³,6⁴,6⁵,6⁶-hexahydro-1¹H-8-oxa-2(4,2)-morpholina-1(5,3)-indola-6(1,3)-pyridazinacycloundecaphane-4-yl)amino)-2-oxoethyl)-2,7-diazaspiro[4.4]nonane-2-carboxylate To a solution of (2²S,6³S,4S)-4-amino-1²-(5-(4-cyclopropylpiperazin-1-yl)-2-((S)-1-methoxyethyl)pyridin-3-yl)-10, 10-dimethyl-1¹-(2,2,2-trifluoroethyl)-6¹,6²,6³,6⁴,6⁵,6⁶-hexahydro-1¹H-8-oxa-2(4,2)-morpholina-1(5,3)-indola-6(1, 3)-pyridazinacycloundecaphane-5,7-dione (28 g, 34.43 mmol) and (S)-2-((S)-7-(tert-butoxycarbonyl)-2,7-diazaspiro[4.4]nonan-2-yl)-2-cyclopentylacetic acid (18.27 g, 51.76 mmol) in DMF (300 mL) at 0° C. was added DIPEA (240.4 mL, 1.381 mol) and COMU (19.21 g, 44.88 mmol). The resulting mixture was stirred for 1 h at room temperature. The reaction was quenched with H₂O and the mixture was extracted with EtOAc (2×500 mL). The combined organic layers were washed with brine (2150 mL), dried over Na₂SO₄, filtered, and concentrated under reduced pressure. The residue was purified by prep-TLC (10% MeOH/DCM) to afford the desired product (24.4 g, 62% yield) as a solid. LCMS (ESI) m/z [M+H] calcd for C₆₁H₈₇F₃N₁₀O₈1145.68; found: 1145.5.

Step 2: Synthesis of (2S)-2-cyclopentyl-N-((2²S, 6³S,4S)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)-2-((S)-2,7-diazaspiro[4.4]nonan-2-yl)acetamide To a solution of tert-butyl (5S)-7-((1 S)-1-cyclopentyl-2-(((2²S,6³S,4S)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)amino)-2-oxoethyl)-2,7-diazaspiro[4.4]nonane-2-carboxylate (27.2 g, 23.76 mol) in DCM (200 mL) at 0° C. was added HCl in 1,4-dioxane (240 mL). The resulting mixture was stirred for 2 h at room temperature and then the mixture was concentrated under reduced pressure to afford the desired product (28 g, crude) as a solid. LCMS (ESI) m/z [M+H] calcd for $C_{56}H_{79}F_3N_{10}O_6$ 1045.62; found: 1045.5.

Step 3: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-(($2^2$S,$6^3$S,4S)-$1^2$-(5-(4-cyclopropylpiperazin-1-yl)-2-((S)-1-methoxyethyl)pyridin-3-yl)-10,10-dimethyl-5,7-dioxo-$1'$-(2,2,2-trifluoroethyl)-$6^1$,$6^2$,$6^3$,$6^4$,$6^5$,$6^6$-hexahydro-$1^1$H-8-oxa-2(4,2)-morpholina-1(5,3)-indola-6(1,3)-pyridazinacycloundecaphane-4-yl)acetamide To a solution of (2S)-2-cyclopentyl-N-(($2^2$S,$6^3$S,4S)-$1^2$-(5-(4-cyclopropylpiperazin-1-yl)-2-((S)-1-methoxyethyl)pyridin-3-yl)-10,10-dimethyl-5,7-dioxo-$1'$-(2,2,2-trifluoroethyl)-$6^1$,$6^2$,$6^3$,$6^4$,$6^5$,$6^6$-hexahydro-$1^1$H-8-oxa-2(4,2)-morpholina-1(5,3)-indola-6(1,3)-pyridazinacycloundecaphane-4-yl)-2-((S)-2,7-diazaspiro[4.4]nonan-2-yl)acetamide (22 g, 21.05 mmol), DIPEA (13.57 g, 0.105 mol) and lithium (2R,3R)-3-cyclopropyl-1-methylaziridine-2-carboxylate (6.18 g, 42.1 mmol) in DMF (400 mL) at 0° C. was added HATU (8.79 g, 23.15 mmol). The resulting mixture was stirred for 1 h at 0° C. The mixture was then extracted with 10% MeOH/DCM (3×20 mL) and the combined organic layers were washed with brine (3×20 mL), dried over $Na_2SO_4$, filtered, and concentrated under reduced pressure. The residue was purified by reverse phase chromatography (MeCN/$H_2O$) to afford the desired product (10.1 g, 41% yield) as a solid. LCMS (ESI) m/z [M+H] calcd for $C_{63}H_{88}F_3N_{11}O_7$ 1168.69; found: 1168.8.

Example A6: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-(($6^3$,4S)-$1^2$-(5-(4-cyclopropylpiperazin-1-yl)-2-((S)-1-methoxyethyl)pyridin-3-yl)-10,10-dimethyl-5,7-dioxo-$1^1$-(2,2,2-trifluoroethyl)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)acetamide

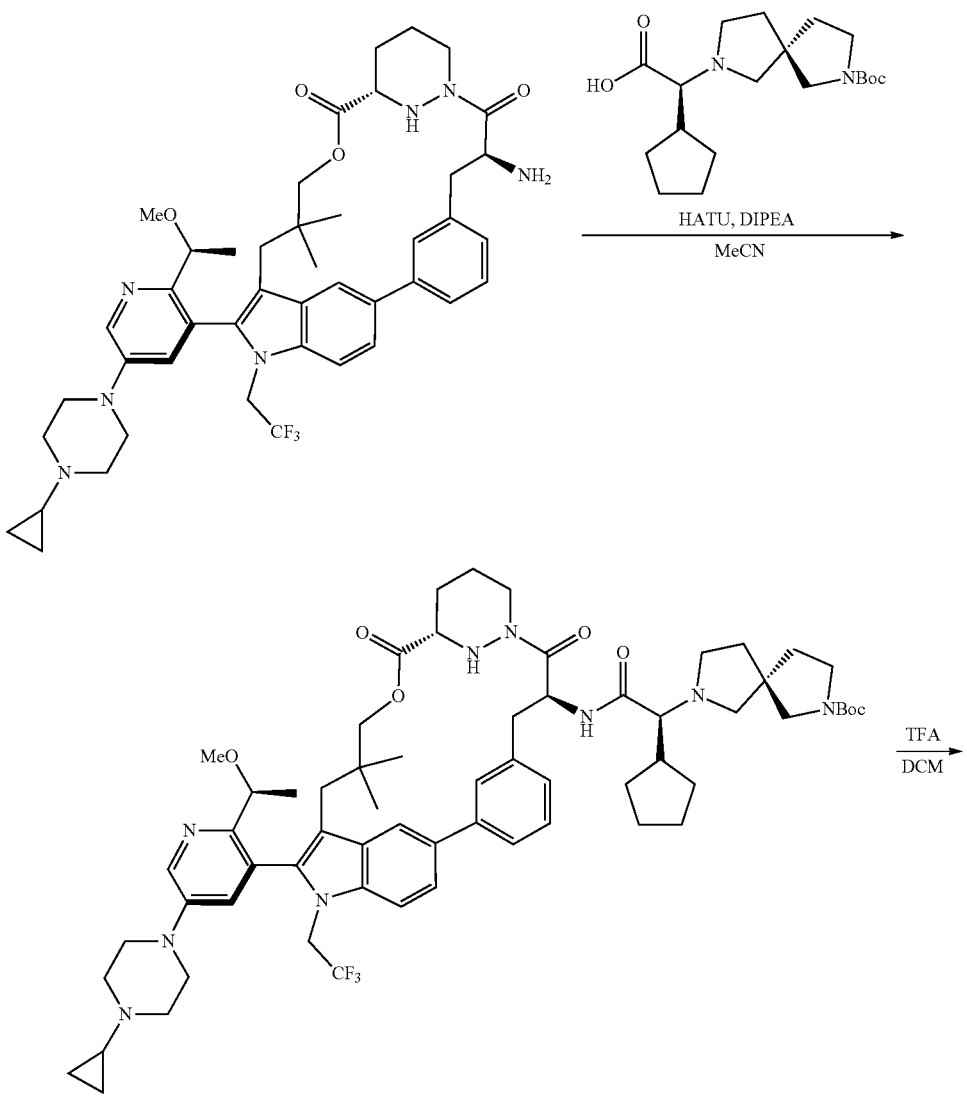

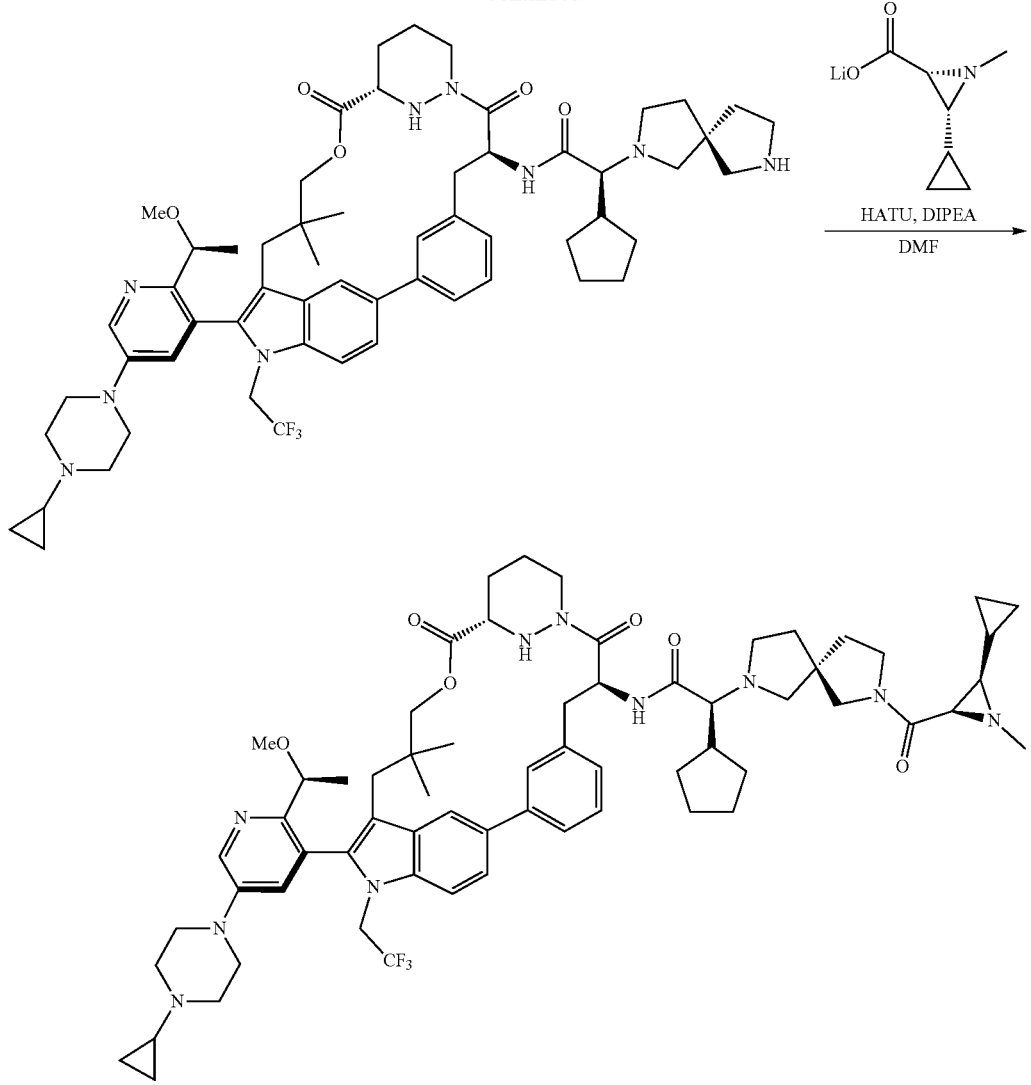

Step 1: Synthesis of tert-butyl (5S)-7-((1 S)-1-cyclopentyl-2-(((6³S,4S)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-2-oxoethyl)-2,7-diazaspiro[4.4]nonane-2-carboxylate To a solution of (S)-2-((S)-7-(tert-butoxycarbonyl)-2,7-diazaspiro[4.4]nonan-2-yl)-2-cyclopentylacetic acid (534.46 mg, 1.517 mmol) and DIPEA (734.89 mg, 5.688 mmol) in MeCN (10 mL) at 0° C. was added a solution of (6³S,4S)-4-amino-1²-(5-(4-cyclopropylpiperazin-1-yl)-2-((S)-1-methoxyethyl)pyridin-3-yl)-10,10-dimethyl-1¹-(2,2,2-trifluoroethyl)-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (760 mg, 0.948 mmol) in MeCN (5 mL). To the mixture was added a solution of HATU (468.44 mg, 1.232 mmol) in MeCN (5 mL). The resulting mixture was stirred at room temperature for 3 h. The mixture was then extracted with EtOAc (150 mL) and the combined organic layers were washed with brine (2×50 mL), dried over $Na_2SO_4$, filtered, and concentrated under reduced pressure. The residue was purified by prep-TLC (10% MeOH/DCM) to afford the desired product (1.06 g, 93% yield) as a solid. LCMS (ESI) m/z [M+H] calcd for $C_{63}H_{84}F_3N_9O_7$ 1136.65; found: 1136.4.

Step 2: Synthesis of (2S)-2-cyclopentyl-N-((6³S,4S)-1²-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-2-((S)-2,7-diazaspiro[4.4]nonan-2-yl)acetamide To a solution of tert-butyl (5S)-7-((1 S)-1-cyclopentyl-2-(((6³S,4S)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-11H-8-oxa-1(5,3)-indola-6(1,3)-pyridazina-2(1,3)-benzenacycloundecaphane-4-yl)amino)-2-oxoethyl)-2,7-diazaspiro[4.4]nonane-2-carboxylate (1.03 g, 0.906 mmol)

in DCM (16 mL) at 0° C. was added TFA (4 mL). The resulting mixture was stirred at 0° C. for 1 h and was then neutralized to pH 7 with sat. NaHCO₃ (aq). The resulting mixture was extracted with DCM (50 mL) and the combined organic layers were washed with brine (2×50 mL), dried over Na₂SO₄, filtered, and concentrated under reduced pressure to afford the desired product (890 mg, crude) as a solid. LCMS (ESI) m/z [M+H] calcd for $C_{58}H_{76}F_3N_9O_5$ 1036.60; found: 1036.6.

Step 3: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-((6³S,4S)-1²-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)acetamide To a solution of lithium (2R,3R)-3-cyclopropyl-1-methylaziridine-2-carboxylate (113.48 mg, 0.772 mmol) and DIPEA (299.32 mg, 2.316 mmol) in DMF (4 mL) at 0° C. was added a solution of HATU (190.79 mg, 0.502 mmol) in DMF (4 mL). To the mixture was added a solution of (2S)-2-cyclopentyl-N-((6³S,4S)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-2-((S)-2,7-diazaspiro[4.4]nonan-2-yl)acetamide (400 mg, 0.386 mmol) in DMF (4 mL). The resulting mixture was stirred at 0° C. for 3 h. The mixture was then extracted with EtOAc (100 mL) and the combined organic layers were washed with brine (2×50 mL), dried over Na₂SO₄, filtered, and concentrated under reduced pressure. The residue was purified by prep-TLC (6% MeOH/DCM) to afford the desired product (183 mg, 67% yield) as a solid. LCMS (ESI) m/z [M+H] calcd for $C_{65}H_{85}F_3N_{10}O_6$ 1159.67; found: 1159.8.

Example A5: Synthesis of (2S)-2-((S)-7-((2R,3R)-3-cyclopropyl-1-methylaziridine-2-carbonyl)-2,7-diazaspiro[4.4]nonan-2-yl)-N-((6³S,4S)-1²-(5-(4-cyclopropylpiperazin-1-yl)-2-((S)-1-methoxyethyl)pyridin-3-yl)-1¹-ethyl-10,10-dimethyl-5,7-dioxo-6,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide

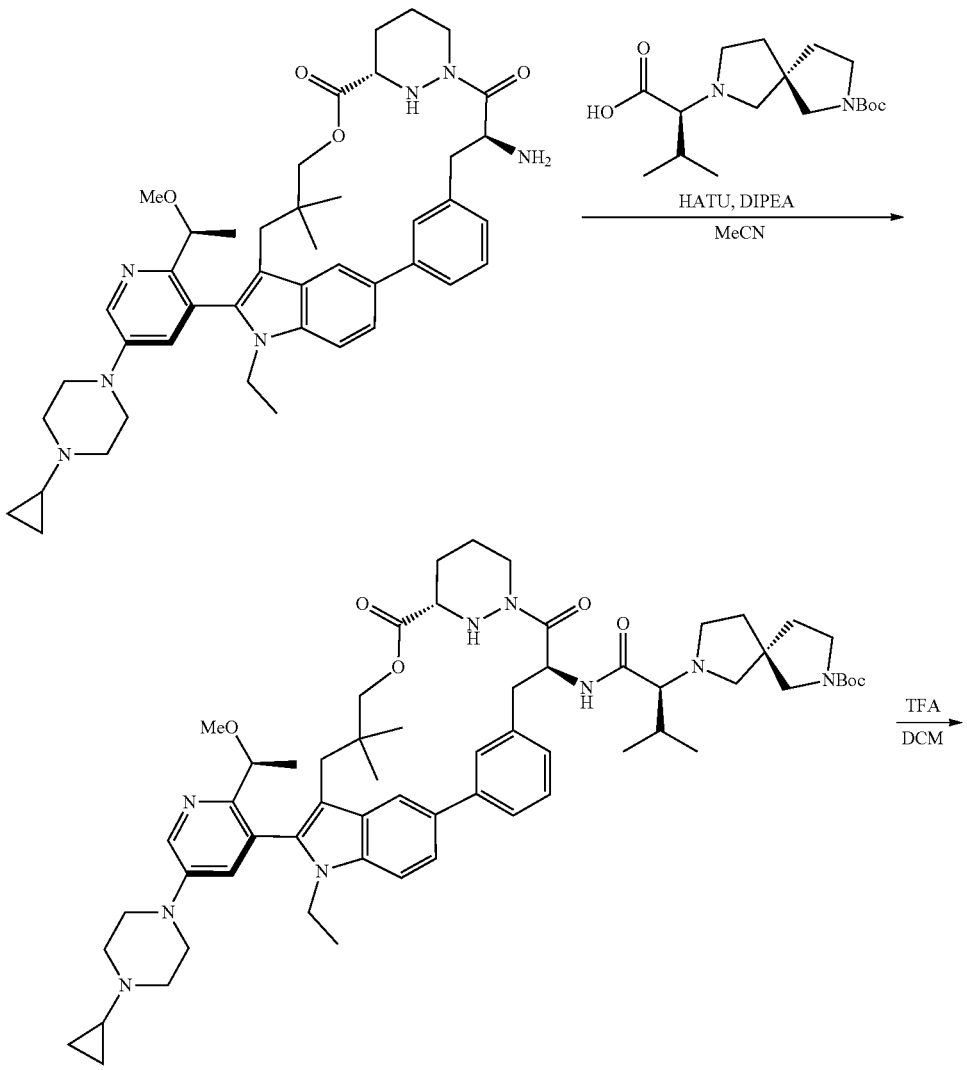

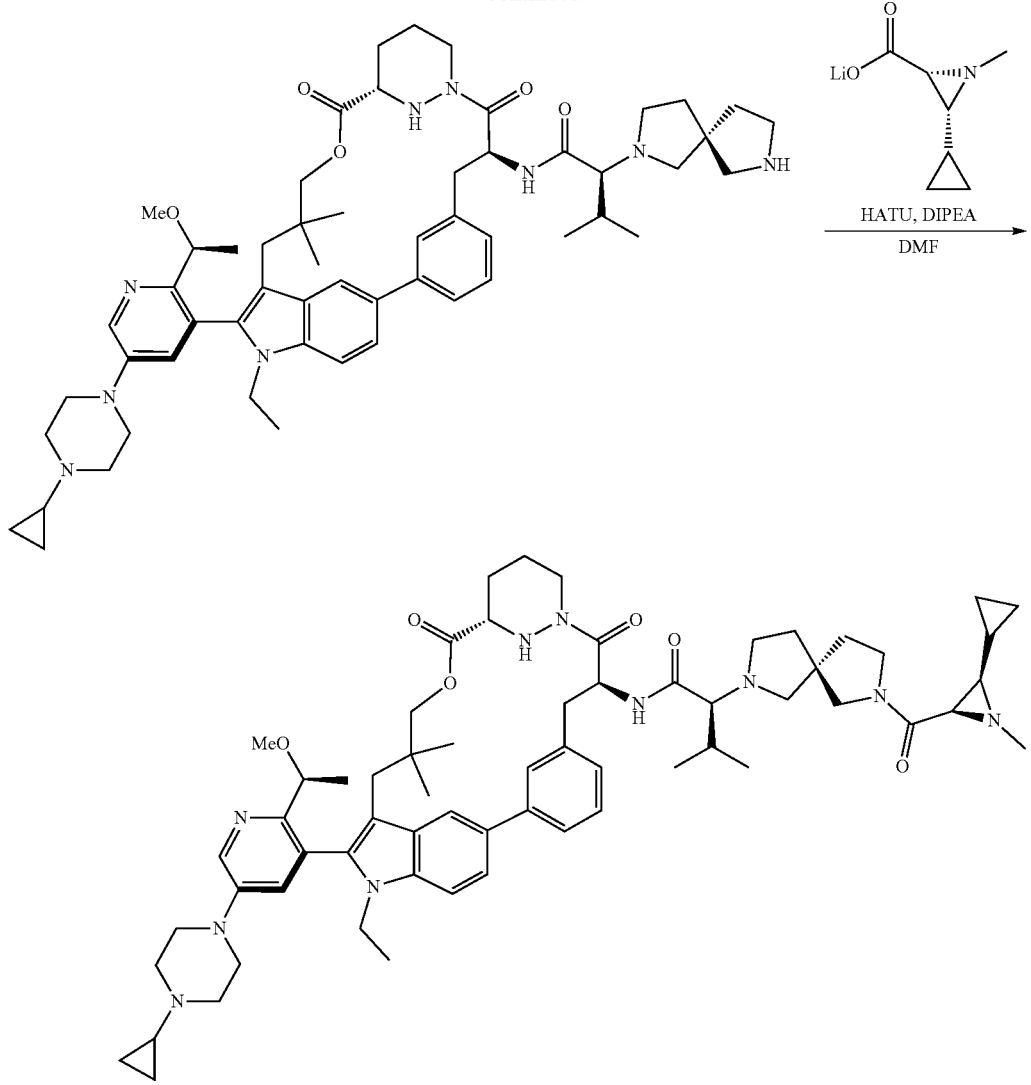

Step 1: Synthesis of tert-butyl (5S)-7-((2S)-1-(((6³S,4S)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1'H-8-oxa-1(5,3)-indola-6(1,3)-pyridazina-2(1,3)-benzenacycloundecaphane-4-yl)amino)-3-methyl-1-oxobutan-2-yl)-2,7-diazaspiro[4.4]nonane-2-carboxylate To a solution of (6³S,4S)-4-amino-1²-(5-(4-cyclopropylpiperazin-1-yl)-2-((S)-1-methoxyethyl)pyridin-3-yl)-1¹-ethyl-10,10-dimethyl-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (500 mg, 0.668 mmol) and DIPEA (863.94 mg, 6.680 mmol) in MeCN (5 mL) at 0° C. was added (S)-2-((S)-7-(tert-butoxycarbonyl)-2,7-diazaspiro[4.4]nonan-2-yl)-3-methylbutanoic acid (327.32 mg, 1.002 mmol) and HATU (330.42 mg, 0.868 mmol). The resulting mixture was stirred at room temperature for 4 h. The resulting mixture was extracted with EtOAc (2×20 mL) and the combined organic layers were washed with brine (3×10 mL), dried over Na₂SO₄, filtered, and concentrated under reduced pressure. The residue was purified by prep-TLC (10% MeOH/DCM) to afford the desired product (620 mg, 87% yield) as a solid. LCMS (ESI) m/z [M+H] calcd for C₆₁H₈₅N₉O₇ 1056.67; found: 1056.9.

Step 2: Synthesis of (2S)-N-((6³S,4S)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-((S)-2,7-diazaspiro[4.4]nonan-2-yl)butanamide A solution of tert-butyl (5S)-7-((2S)-1-(((6³S,4S)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-2,7-diazaspiro[4.4]nonane-2-carboxylate (610 mg, 0.577 mmol) and TFA (6.00 mL) in DCM (12 mL) at 0° C. was stirred for 2 h. The resulting mixture was concentrated under reduced pressure. The residue was neutralized to pH 8 with sat. NaHCO₃ (aq) and the aqueous layer was extracted with DCM (2×100 mL).

The combined organic layers were washed with brine (3×100 mL), dried over Na₂SO₄, filtered, and concentrated under reduced pressure to afford the desired product (620 mg, crude) as a solid. LCMS (ESI) m/z [M+H] calcd for $C_{56}H_{77}N_9O_5$ 956.61; found: 956.8.

Step 3: Synthesis of (2S)-2-((S)-7-((2R,3R)-3-cyclopropyl-1-methylaziridine-2-carbonyl)-2,7-diazaspiro[4.4]nonan-2-yl)-N-((6³S,4S)-1²-(5-(4-cyclopropylpiperazin-1-yl)-2-((S)-1-methoxyethyl) pyridin-3-yl)-1¹-ethyl-10,10-dimethyl-5,7-dioxo-6¹,6²,6³,6⁴,6⁵,6⁶-hexahydro-1¹H-8-oxa-1(5,3)-indola-6 (1,3)-pyridazina-2(1,3)-benzenacycloundecaphane-4-yl)-3-methylbutanamide To a solution of (2S)-N-((6³S,4S)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1¹H-8-oxa-1 (5,3)-indola-6(1,3)-pyridazina-2(1,3)-benzenacycloundecaphane-4-yl)-3-methyl-2-((S)-2,7-diazaspiro[4.4]nonan-2-yl)butanamide (400 mg, 0.418 mmol) and DIPEA (270.30 mg, 2.090 mmol) in DCM (8 mL) at 0° C. was added a solution of lithium (2R,3R)-3-cyclopropyl-1-methylaziridine-2-carboxylate (184.59 mg, 1.254 mmol) and COMU (232.88 mg, 0.543 mmol) were in DCM (4 mL). The resulting mixture was stirred at 0° C. for 2h. The mixture was extracted with EtOAc (3×20 mL) and the combined organic layers were washed with brine (3×20 mL), dried over Na₂SO₄, filtered, and concentrated under reduced pressure. The residue was purified by prep-TLC (10% MeOH/DCM) to afford the desired product (127.4 mg, 28% yield) as a solid. LCMS (ESI) m/z [M+H] calcd for $C_{63}H_{86}N_{10}O_6$ 1079.68; found: 1079.9.

Example A27: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-((2²S, 6³S,4S)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)acetamide

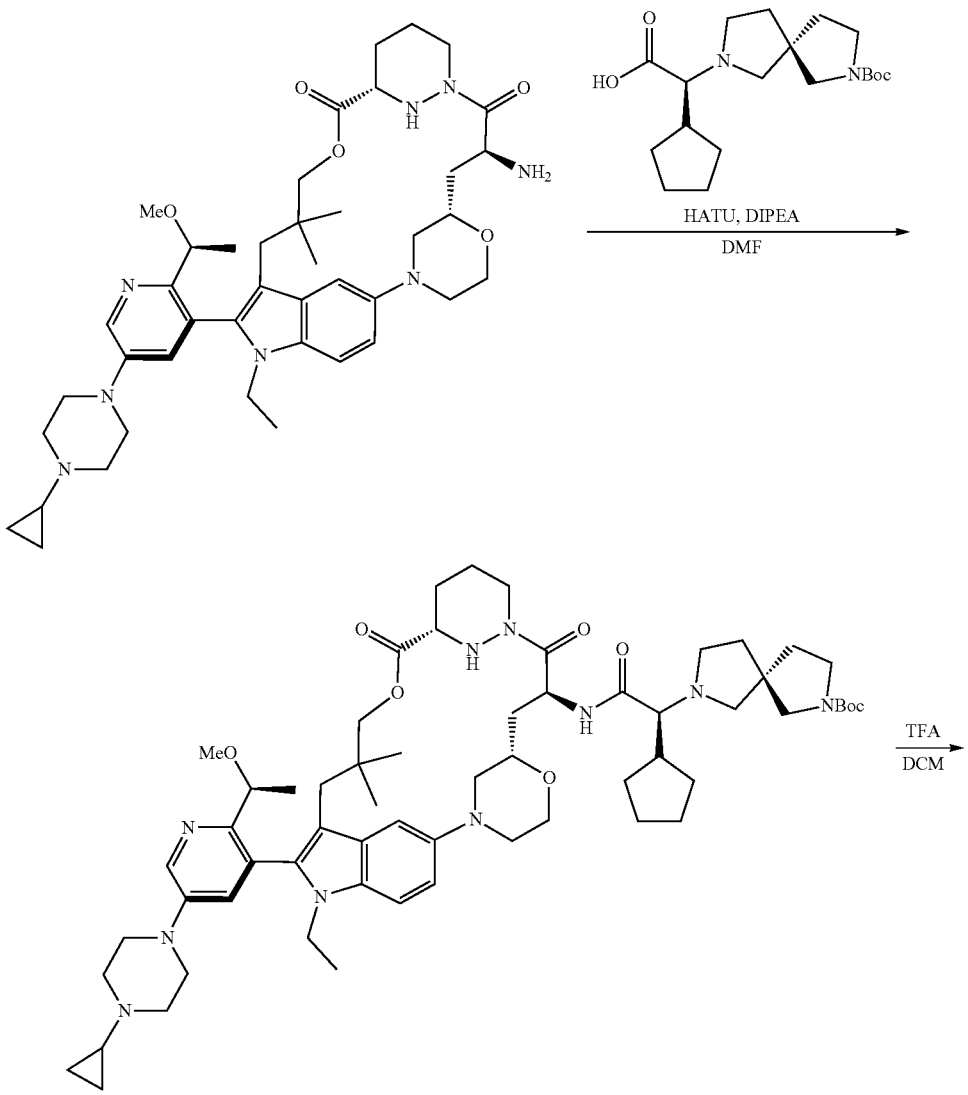

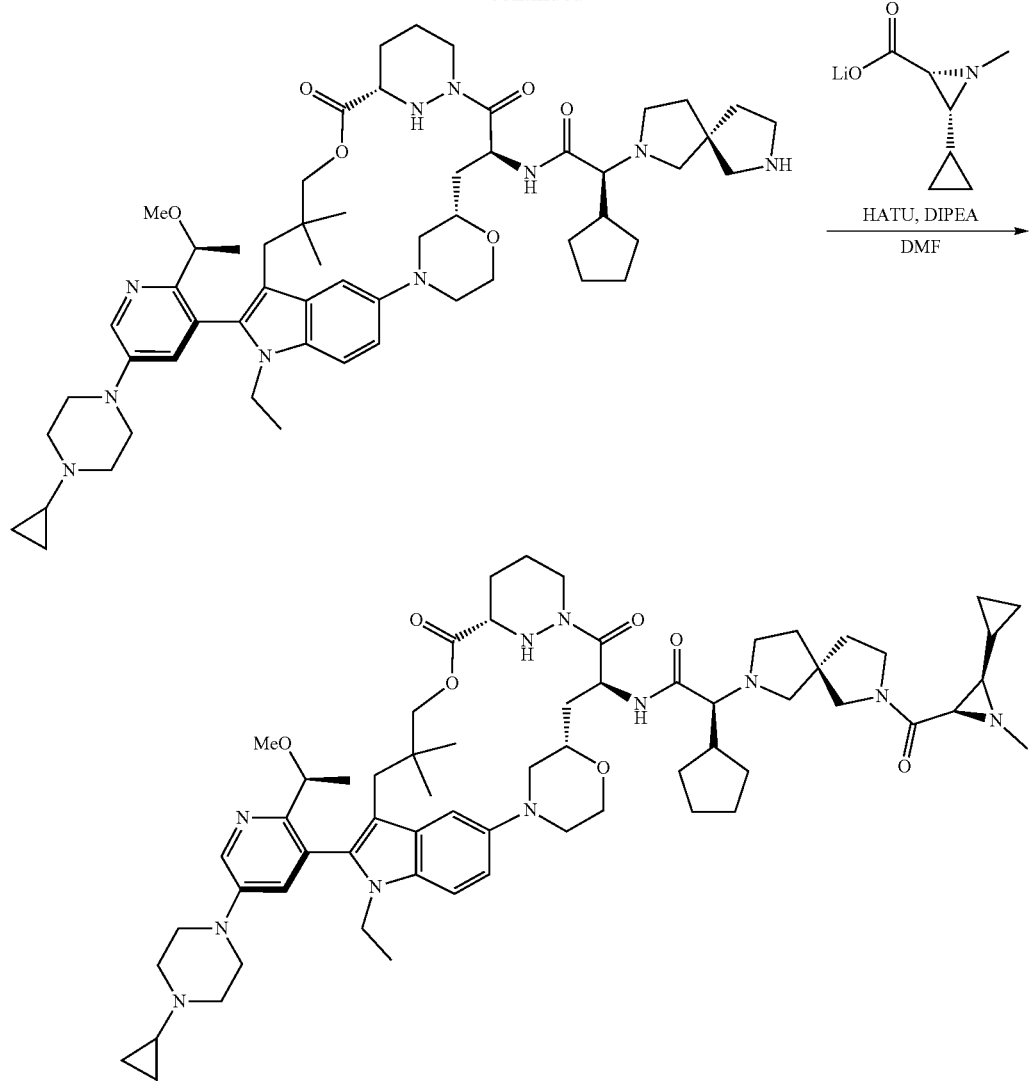

Step 1: Synthesis of tert-butyl (5S)-7-((1 S)-1-cyclopentyl-2-(((2²S,6³S,4S)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)amino)-2-oxoethyl)-2,7-diazaspiro[4.4]nonane-2-carboxylate To a solution of (S)-2-((S)-7-(tert-butoxycarbonyl)-2,7-diazaspiro[4.4]nonan-2-yl)-2-cyclopentylacetic acid (236.07 mg, 0.670 mmol) and DIPEA (332.93 mg, 2.575 mmol) in DMF (5 mL) at 0° C. was added HATU (235.07 mg, 0.618 mmol). The resulting mixture was stirred at 0° C. for 10 min. To the mixture was added (2²S,6³S,4S)-4-amino-1²-(5-(4-cyclopropylpiperazin-1-yl)-2-((S)-1-methoxyethyl)pyridin-3-yl)-1¹-ethyl-10,10-dimethyl-6¹,6²,6³,6⁴,6⁵,6⁶-hexahydro-1¹H-8-oxa-2(4,2)-morpholina-1(5,3)-indola-6(1,3)-pyridazinacycloundecaphane-5,7-dione (390 mg, 0.515 mmol). The mixture was stirred at 0° C. for 1 h and was then concentrated under reduced pressure. The residue was purified by reverse phase chromatography (0→100% MeCN/NH₄HCO₃ in H₂O) to afford the desired product (400 mg, 71% yield) as a solid. LCMS (ESI) m/z [M+H] calcd for C₆₁H₉₀N₁₀O₈ 1091.70; found: 1091.5.

Step 2: Synthesis of (2S)-2-cyclopentyl-N-((2²S, 6³S,4S)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)-2-((S)-2,7-diazaspiro[4.4]nonan-2-yl)acetamide To a solution of tert-butyl (5S)-7-((1 S)-1-cyclopentyl-2-(((2²S,6³S,4S)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1¹H-8-oxa-2(4,2)-morpholina-1(5,3)-pyridazinacycloundecaphane-4-yl)amino)-2-oxoethyl)-2,7-diazaspiro[4.4]nonane-2-carboxylate (400 mg, 0.366 mmol) in DCM (3 mL) at 0° C. was added TFA (1.5 mL). The resulting mixture was stirred at 0° C. for 1 h. The mixture was concentrated under reduced pressure then neutralized to pH 7 with sat. NaHCO$_3$(aq). The resulting mixture was extracted with 10% MeOH/DCM (3×20 mL) and the combined organic layers were washed with brine (3×10 mL), dried over Na$_2$SO$_4$, filtered, and concentrated under reduced pressure to afford the desired product (350 mg, 96% yield) as a solid. LCMS (ESI) m/z [M+H] calcd for C$_{56}$H$_{82}$N$_{10}$O$_6$ 991.65; found: 991.5.

Step 3: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-((2$^2$S,6$^3$S,4S)-1$^2$-(5-(4-cyclopropylpiperazin-1-yl)-2-((S)-1-methoxyethyl)pyridin-3-yl)-1$^1$-ethyl-10,10-dimethyl-5,7-dioxo-6$^1$,6$^2$,6$^3$,6$^4$,6$^5$,6$^6$-hexahydro-1$^1$H-8-oxa-2(4,2)-morpholina-1 (5,3)-indola-6(1,3)-pyridazinacycloundecaphane-4-yl)acetamide To a solution of (2S)-2-cyclopentyl-N-((2$^2$S,6$^3$S,4S)-1$^2$-(5-(4-cyclopropylpiperazin-1-yl)-2-((S)-1-methoxyethyl)pyridin-3-yl)-1$^1$-ethyl-10,10-dimethyl-5,7-dioxo-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-4-yl)-2-((S)-2,7-diazaspiro[4.4]nonan-2-yl)acetamide (350 mg, 0.353 mmol), DIPEA (456.30 mg, 3.530 mmol), and lithium (2R,3R)-3-cyclopropyl-1-methylaziridine-2-carboxylate (103.87 mg, 0.706 mmol) in DMF (7 mL) at 0° C. was added HATU (201.37 mg, 0.529 mmol). The resulting mixture was stirred at 0° C. for 1 h. The residue was purified by reverse phase chromatography (0→100% MeCN/NH$_4$HCO$_3$ in H$_2$O) to afford the desired product (93 mg, 21% yield) as a solid. LCMS (ESI) m/z [M+H] calcd for C$_{63}$H$_{91}$N$_{11}$O$_7$ 1114.72; found: 1114.8.

Example A25: Synthesis of (2S)-2-((S)-7-((2R,3R)-3-cyclopropyl-1-methylaziridine-2-carbonyl)-2,7-diazaspiro[4.4]nonan-2-yl)-N-((2$^2$S,6$^3$S,4S)-1$^2$-(5-(4-cyclopropylpiperazin-1-yl)-2-((S)-1-methoxyethyl)pyridin-3-yl)-10,10-dimethyl-5,7-dioxo-1$^1$-(2,2,2-trifluoroethyl)-6,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-4-yl)-3-methylbutanamide

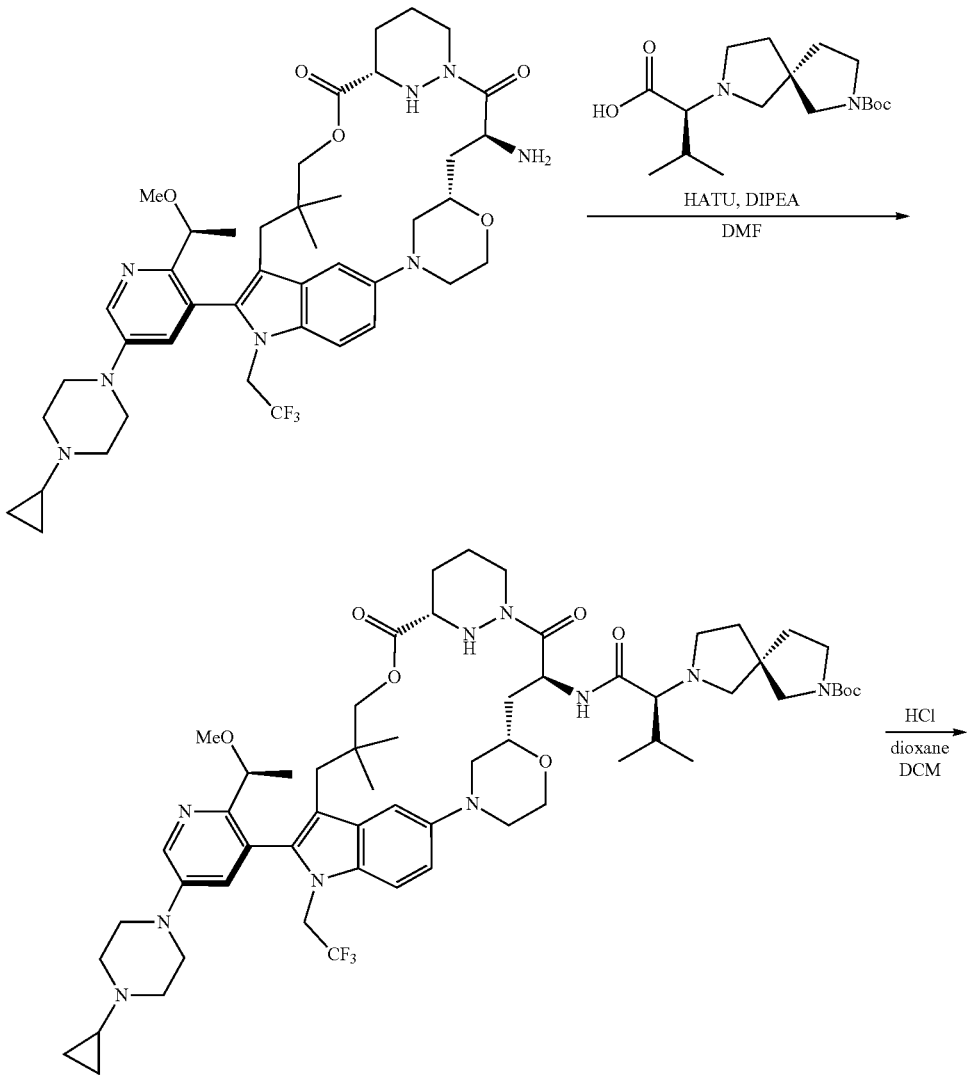

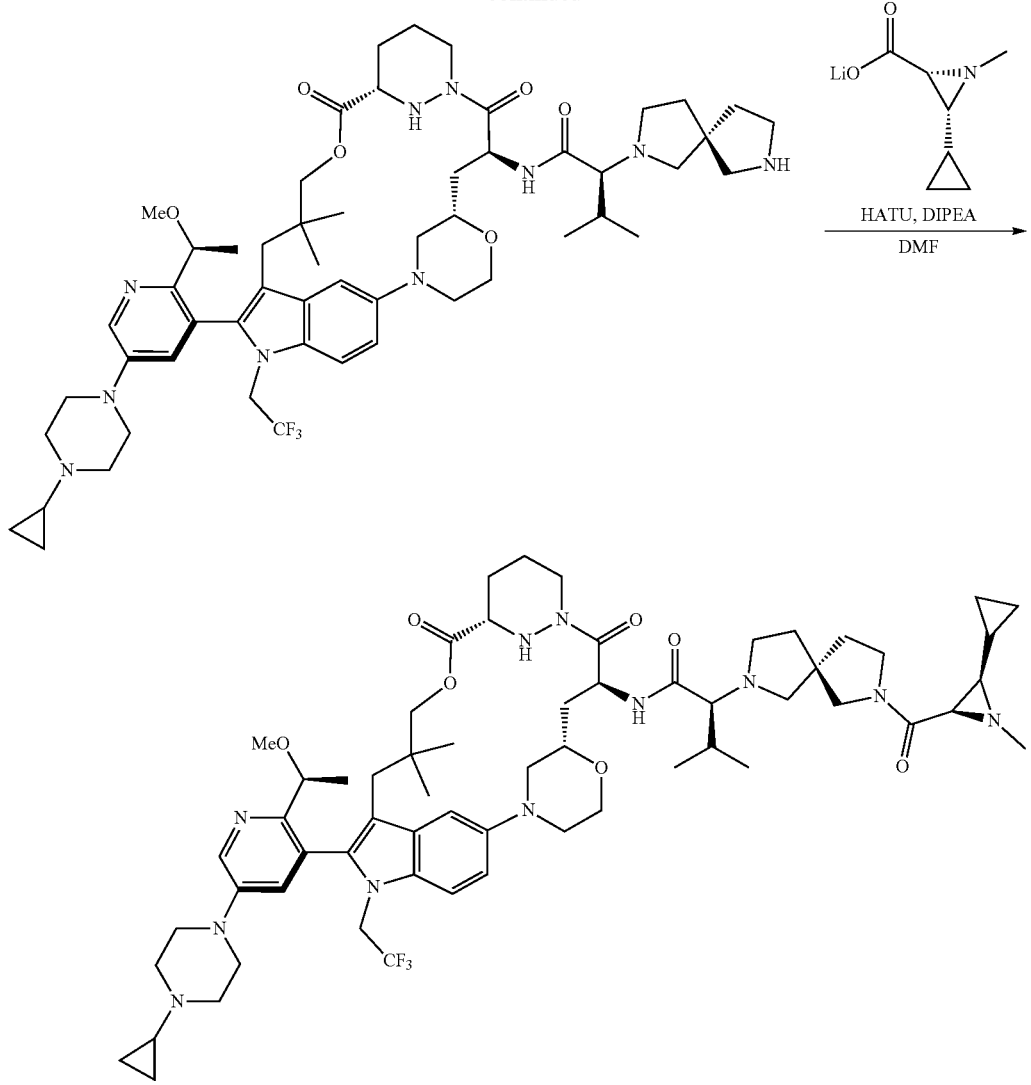

Step 1: Synthesis of tert-butyl (5S)-7-((2S)-1-(((2²S,6³S,4S)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)amino)-3-methyl-1-oxobutan-2-yl)-2,7-diazaspiro[4.4]nonane-2-carboxylate To a solution of (2²S,6³S,4S)-4-amino-1²-(5-(4-cyclopropylpiperazin-1-yl)-2-((S)-1-methoxyethyl)pyridin-3-yl)-10,10-dimethyl-1¹-(2,2,2-trifluoroethyl)-6¹,6²,6³,6⁴,6⁵,6⁶-hexahydro-1¹H-8-oxa-2(4,2)-morpholina-1(5,3)-indola-6(1,3)-pyridazinacycloundecaphane-5,7-dione (4 g, 4.932 mmol) and (S)-2-((S)-7-(tert-butoxycarbonyl)-2,7-diazaspiro[4.4]nonan-2-yl)-3-methylbutanoic acid (2.42 g, 7.398 mmol) in DMF (50 mL) at 0° C. was added DIPEA (12.89 mL, 73.980 mmol) and HATU (2.25 g, 5.918 mmol). The resulting mixture was stirred at room temperature for 1 h. The mixture was then extracted with EtOAc (3×100 mL) and the combined organic layers were washed with brine (3×100 mL), dried over Na₂SO₄, filtered, and concentrated under reduced pressure. The residue was purified by prep-TLC to afford the desired product (3.2 g, 58% yield) as a solid. LCMS (ESI) m/z [M+H] calcd for $C_{59}H_{85}F_3N_{10}O_8$ 1119.66; found: 1119.4.

Step 2: Synthesis of (2S)-N-((2²S,6³S,4S)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)-3-methyl-2-((S)-2,7-diazaspiro[4.4]nonan-2-yl)butanamide To a solution of tert-butyl (5S)-7-((2S)-1-(((2²S,6³S,4S)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)amino)-3-methyl-1-oxobutan-2-yl)-2,7-diazaspiro[4.4]nonane-2-carboxylate (500 mg, 0.447 mmol) in DCM (5 mL) at 0° C. was added a solution of HCl in 1,4-dioxane (5 mL, 164.679 mmol). The resulting mixture was stirred at room temperature for 2 h. The resulting mixture was concentrated under reduced pressure to afford the desired product. LCMS (ESI) m/z [M+H] calcd for $C_{54}H_{77}F_3N_{10}O_6$ 1019.61; found: 1019.7.

Step 3: Synthesis of (2S)-2-((S)-7-((2R,3R)-3-cyclopropyl-1-methylaziridine-2-carbonyl)-2,7-diazaspiro[4.4]nonan-2-yl)-N-((2²S,6³S,4S)-1²-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)-3-methylbutanamide To a solution of (2S)-N-((2²S,6³S,4S)-1²-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)-3-methyl-2-((S)-2,7-diazaspiro[4.4]nonan-2-yl)butanamide (700 mg, 0.687 mmol) and lithium (2R,3R)-3-cyclopropyl-1-methyl-aziridine-2-carboxylate (202.05 mg, 1.374 mmol) in DMF (7 mL) at 0° C. was added DIPEA (4.78 mL, 27.480 mmol) and HATU (391.69 mg, 1.030 mmol).The resulting mixture was stirred at room temperature for 1 h. The mixture was then diluted with EtOAc (100 mL) and the organic layer was washed with brine (2×80 mL), dried over $Na_2SO_4$, filtered, and concentrated under reduced pressure. The residue was purified by prep-TLC (6% MeOH/DCM) followed by purification by reverse phase chromatography (18→20% $MeCN/H_2O$ with 0.1% formic acid) to afford the desired product (175.6 mg, 22% yield). LCMS (ESI) m/z [M+H] calcd for $C_{61}H_{86}F_3N_{11}O_7$ 1142.68; found: 1142.7.

Example A23: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-((6³S,4S,Z)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)acetamide

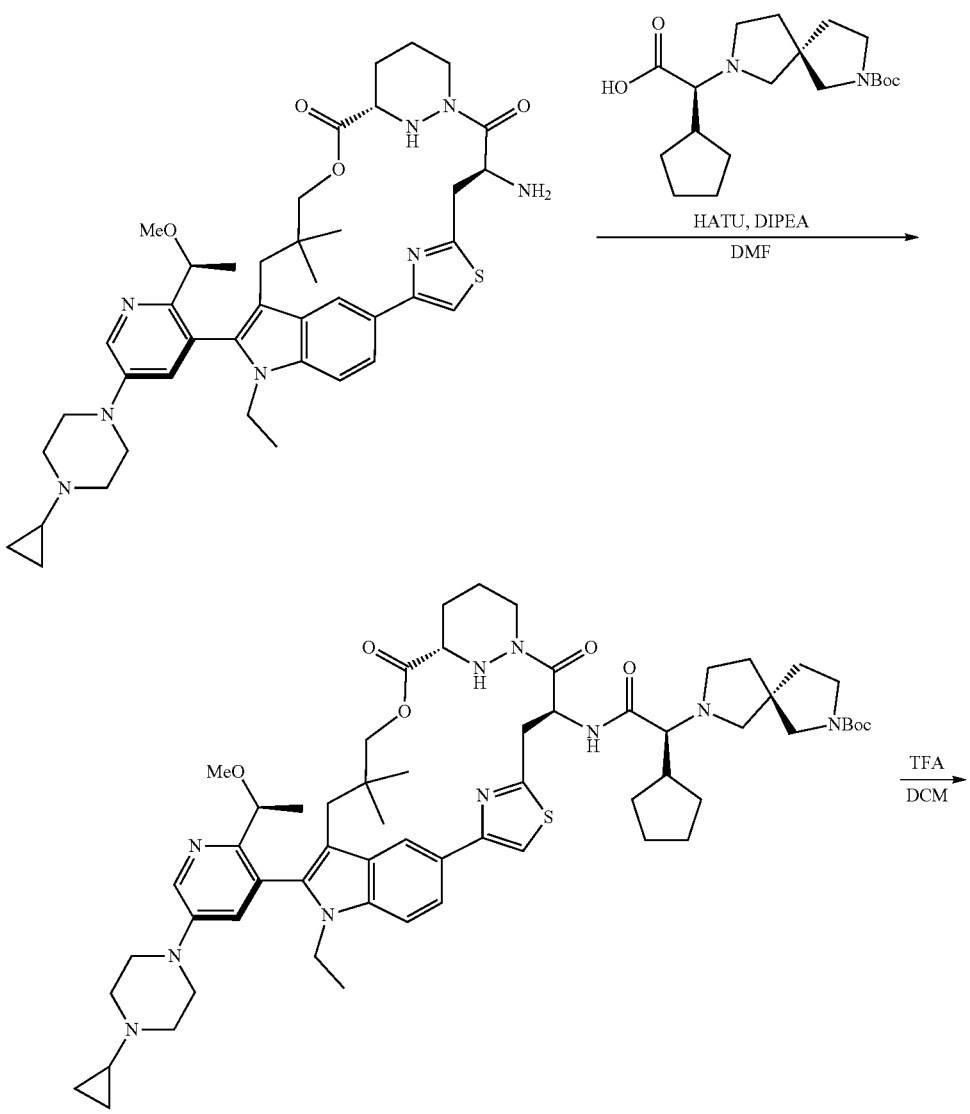

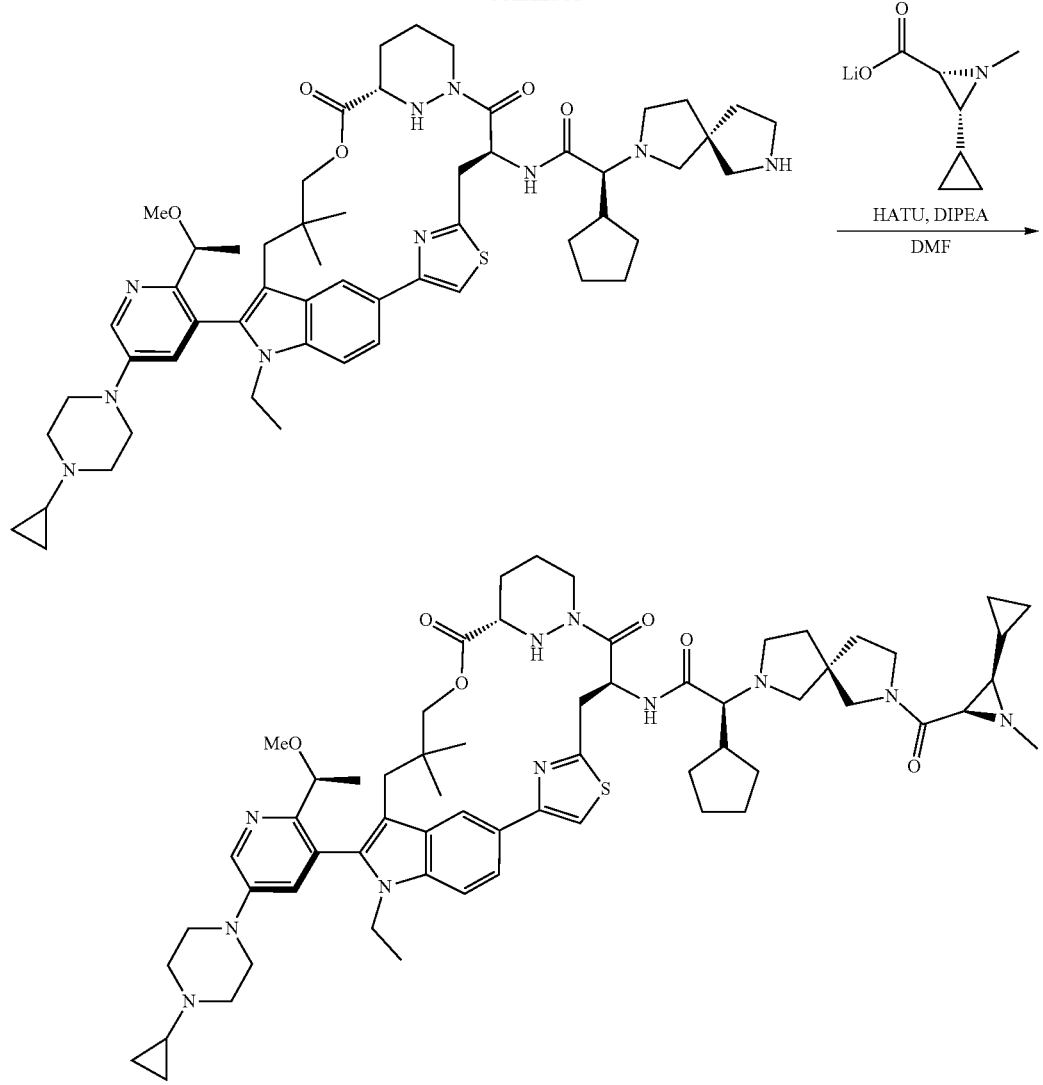

Step 1: Synthesis of tert-butyl (5S)-7-((1 S)-1-cyclopentyl-2-(((6³S,4S,Z)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)amino)-2-oxoethyl)-2,7-diazaspiro[4.4]nonane-2-carboxylate To a solution of (S)-2-((S)-7-(tert-butoxycarbonyl)-2,7-diazaspiro[4.4]nonan-2-yl)-2-cyclopentylacetic acid (245.10 mg, 0.696 mmol) and DIPEA (599.14 mg, 4.640 mmol) in DMF (3 mL) at 0° C. was added HATU (229.15 mg, 0.603 mmol) and (6³S,4S,Z)-4-amino-1²-(5-(4-cyclopropylpiperazin-1-yl)-2-((S)-1-methoxyethyl)pyridin-3-yl)-1¹-ethyl-10,10-dimethyl-6¹,6²,6³,6⁴,6⁵,6⁶-hexahydro-1¹H-8-oxa-2(4,2)-thiazola-1(5,3)-indola-6(1,3)-pyridazinacycloundecaphane-5,7-dione (350 mg, 0.464 mmol). The resulting mixture was stirred at room temperature for 2 h and then cold H₂O was added. The resulting mixture was extracted with EtOAc (3×30 mL) and the combined organic layers were washed with brine (2×10 mL), dried over Na₂SO₄, filtered, and concentrated under reduced pressure. The residue was purified by prep-TLC (6% MeOH/DCM) to afford the desired product (440 mg, 87% yield) as a solid. LCMS (ESI) m/z [M+H] calcd for C₆₀H₈₄N₁₀O₇S 1089.63; found: 1089.5.

Step 2: Synthesis of (2S)-2-cyclopentyl-N-((6³S,4S,2)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)-2-((S)-2,7-diazaspiro[4.4]nonan-2-yl)acetamide A solution of tert-butyl (5S)-7-((1 S)-1-cyclopentyl-2-(((6³S,4S,Z)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)amino)-2-oxoethyl)-2,7-diazaspiro[4.4]nonane-2-carboxylate (420 mg, 0.386 mmol) in DCM (4.5 mL) was added TFA (1.5 mL).

The reaction mixture was stirred at room temperature for 2 h. The mixture was then basified to pH 8 with sat. NaHCO₃

(aq). The mixture was extracted with EtOAc (3×40 mL) and the combined organic layers were washed with brine (2×15 mL), dried over Na$_2$SO$_4$, filtered, and concentrated under reduced pressure to afford the desired product (400 mg, crude) as a solid. LCMS (ESI) m/z [M+H] calcd for C$_{55}$H$_{76}$N$_{10}$O$_5$S 989.58; found: 990.0.

Step 3: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-((6$^3$S,4S,2)-1$^2$-(5-(4-cyclopropylpiperazin-1-yl)-2-((S)-1-methoxyethyl)pyridin-3-yl)-1$^1$-ethyl-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)acetamide To a solution of (2S)-2-cyclopentyl-N-((6$^3$S,4S,2)-1$^2$-(5-(4-cyclopropylpiperazin-1-yl)-2-((S)-1-methoxyethyl)pyridin-3-yl)-1$^1$-ethyl-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)-2-((S)-2,7-diazaspiro[4.4]nonan-2-yl)acetamide (350 mg, 0.354 mmol) and lithium (2R,3R)-3-cyclopropyl-1-methylaziridine-2-carboxylate (104.08 mg, 0.708 mmol) in DMF (4 mL) at 0° C. was added DIPEA (457.23 mg, 3.540 mmol) and COMU (227.26 mg, 0.531 mmol). The resulting mixture was stirred at room temperature for 2 h and then cold H$_2$O was added. The resulting mixture was extracted with EtOAc (3×20 mL) and the combined organic layers were washed with brine (2×20 mL), dried over Na$_2$SO$_4$, filtered, and concentrated under reduced pressure. The residue was purified by prep-TLC (8% MeOH/DCM) to afford the desired product (130 mg, 33% yield) as a solid. LCMS (ESI) m/z [M+H] calcd for C$_{62}$H$_{85}$N$_{11}$OS 1112.65; found: 1112.7.

Example A11: Synthesis of (2S)-2-((S)-7-((2R,3R)-3-cyclopropyl-1-methylaziridine-2-carbonyl)-2,7-diazaspiro[4.4]nonan-2-yl)-N-((6$^3$S,4S,Z)-1$^2$-(5-(4-cyclopropylpiperazin-1-yl)-2-((S)-1-methoxyethyl)pyridin-3-yl)-1$^1$-ethyl-10,10-dimethyl-5,7-dioxo-6, 6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)-3-methylbutanamide

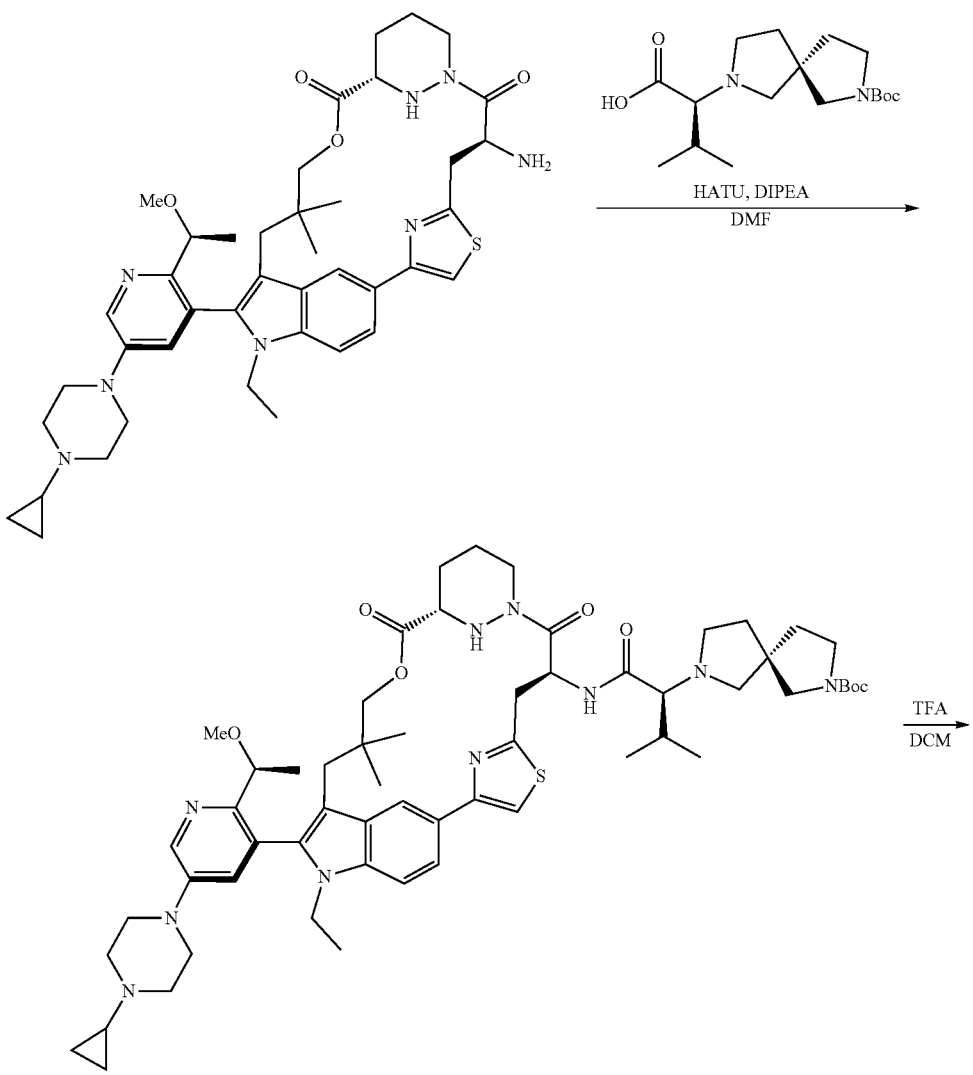

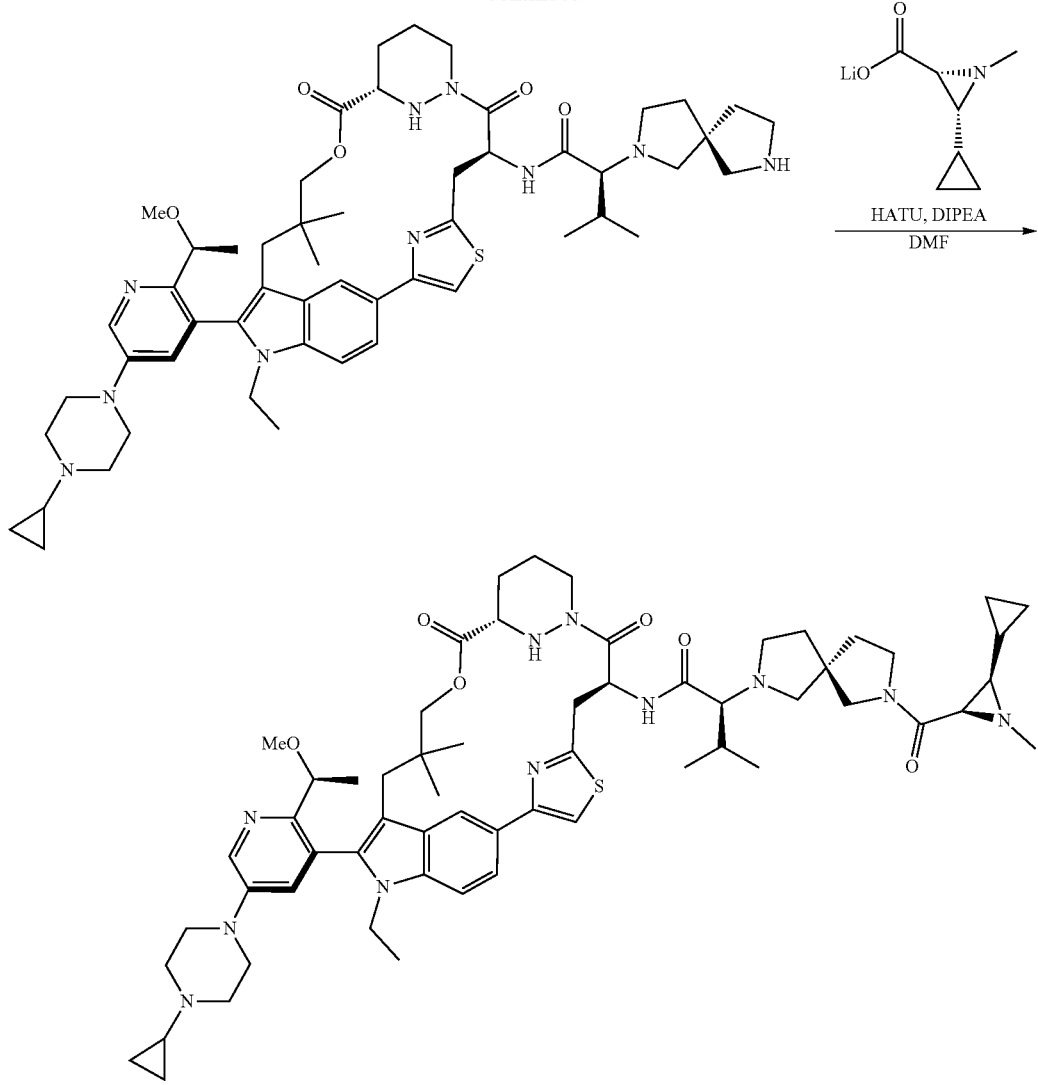

Step 1: Synthesis of tert-butyl (5S)-7-((2S)-1-(((6³S,4S,Z)-12-(5-(4-cyclopropylpiperazin-1-yl)-2-((S)-1-methoxyethyl) pyridin-3-yl)-11-ethyl-10,10-dimethyl-5,7-dioxo-6¹,6²,6³,6⁴,6⁵,6⁶-hexahydro-1¹H-8-oxa-2(4,2)-thiazola-1 (5,3)-indola-6(1,3)-pyridazinacycloundecaphane-4-yl)amino)-3-methyl-1-oxobutan-2-yl)-2,7-diazaspiro[4.4]nonane-2-carboxylate To a solution of (63S,4S,Z)-4-amino-12-(5-(4-cyclopropylpiperazin-1-yl)-2-((S)-1-methoxyethyl)pyridin-3-yl)-11-ethyl-10,10-dimethyl-6¹,6²,6³,6⁴,6⁵,6⁶-hexahydro-1¹H-8-oxa-2(4,2)-thiazola-1(5,3)-indola-6(1,3)-pyridazinacycloundecaphane-5,7-dione (400 mg, 0.530 mmol) and (S)-2-((S)-7-(tert-butoxycarbonyl)-2,7-diazaspiro[4.4]nonan-2-yl)-3-methylbutanoic acid (259.42 mg, 0.795 mmol) in DMF (4 mL) at 0° C. was added DIPEA (2.74 g, 21.200 mmol) and HATU (261.88 mg, 0.689 mmol). The resulting mixture was stirred at room temperature for 2 h and then cold H₂O was added. The resulting mixture was extracted with EtOAc (3×30 mL) and the combined organic layers were washed with brine (2×20 mL), dried over Na₂SO₄, filtered, and concentrated under reduced pressure. The residue was purified by prep-TLC (6% MeOH/DCM) to afford the desired product (520 mg, 92% yield) as a solid. LCMS (ESI) m/z [M+H] calcd for C₅₈H₈₂N₁₀O₇S 1063.62, found: 1063.5.

Step 2: Synthesis of (2S)-N-((6³S,4S,Z)-12-(5-(4-cyclopropylpiperazin-1-yl)-2-((S)-1-methoxyethyl) pyridin-3-yl)-11-ethyl-10,10-dimethyl-5,7-dioxo-61, 62,63,64,65,66-hexahydro-1¹H-8-oxa-2(4,2)-thiazola-1(5,3)-indola-6(1,3)-pyridazinacycloundecaphane-4-yl)-3-methyl-2-((S)-2,7-diazaspiro[4.4]nonan-2-yl)butanamide A solution of tert-butyl (5S)-7-((2S)-1-(((6³S,4S,Z)-12-(5-(4-cyclopropylpiperazin-1-yl)-2-((S)-1-methoxyethyl) pyridin-3-yl)-11-ethyl-10,10-dimethyl-5,7-dioxo-6¹,6²,6³,6⁴,6⁵,6⁶-hexahydro-1¹H-8-oxa-2(4,2)-thiazola-1 (5,3)-indola-6(1,3)-pyridazinacycloundecaphane-4-yl)amino)-3-methyl-1-oxobutan-2-yl)-2,7-diazaspiro[4.4]nonane-2-carboxylate (500 mg, 0.470 mmol) and TFA (2 mL) in DCM (6 mL) was stirred for 2 h at room temperature. The resulting mixture was then concentrated under reduced pressure and the reside was taken up in EtOAc (20 mL). The mixture was basified to pH 8 with sat. NaHCO$_3$ (aq). The aqueous layer was extracted with EtOAc (3×20 mL) and the combined organic layers were washed with brine (2×30 mL), dried over Na$_2$SO$_4$, filtered, and concentrated under reduced pressure to afford the desired product (483 mg, crude) as a solid. LCMS (ESI) m/z [M+H] calcd for C$_{53}$H$_{74}$N$_{10}$O$_5$S 963.57; found: 963.6.

Step 3: Synthesis of (2S)-2-((S)-7-((2R,3R)-3-cyclopropyl-1-methylaziridine-2-carbonyl)-2,7-diazaspiro[4.4]nonan-2-yl)-N-((6$^3$S,4S,Z)-1$^2$-(5-(4-cyclopropylpiperazin-1-yl)-2-((S)-1-methoxyethyl)pyridin-3-yl)-11-ethyl-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)-3-methylbutanamide To a solution of (2S)-N-((6$^3$S,4S,Z)-1$^2$-(5-(4-cyclopropylpiperazin-1-yl)-2-((S)-1-methoxyethyl)pyridin-3-yl)-1$^1$-ethyl-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)-3-methyl-2-((S)-2,7-diazaspiro[4.4]nonan-2-yl)butanamide (400 mg, 0.415 mmol) and lithium (2R,3R)-3-cyclopropyl-1-methylaziridine-2-carboxylate (122.16 mg, 0.830 mmol) in DMF (4 mL) at 0° C. was added DIPEA (536.67 mg, 4.150 mmol) and COMU (231.18 mg, 0.539 mmol). The resulting mixture was stirred at room temperature for 2 h and then cold H$_2$O was added (40 mL). The resulting mixture was extracted with EtOAc (3×20 mL) and the combined organic layers were washed with brine (2×30 mL), dried over Na$_2$SO$_4$, filtered, and concentrated under reduced pressure. The residue was purified by prep-TLC (8% MeOH/DCM) to afford the desired product (151.7 mg, 34% yield) as a solid. LCMS (ESI) m/z [M+H] calcd for C$_{60}$H$_{83}$N$_{11}$O$_6$S 1086.63; found: 1086.6.

Example A10: Synthesis of (2S)-2-((S)-7-((2R,3R)-3-cyclopropyl-1-methylaziridine-2-carbonyl)-2,7-diazaspiro[4.4]nonan-2-yl)-N-((6$^3$S,4S,Z)-1$^2$-(5-(4-cyclopropylpiperazin-1-yl)-2-((S)-1-methoxyethyl)pyridin-3-yl)-10,10-dimethyl-5,7-dioxo-1$^1$-(2,2,2-trifluoroethyl)-6,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)-3-methylbutanamide

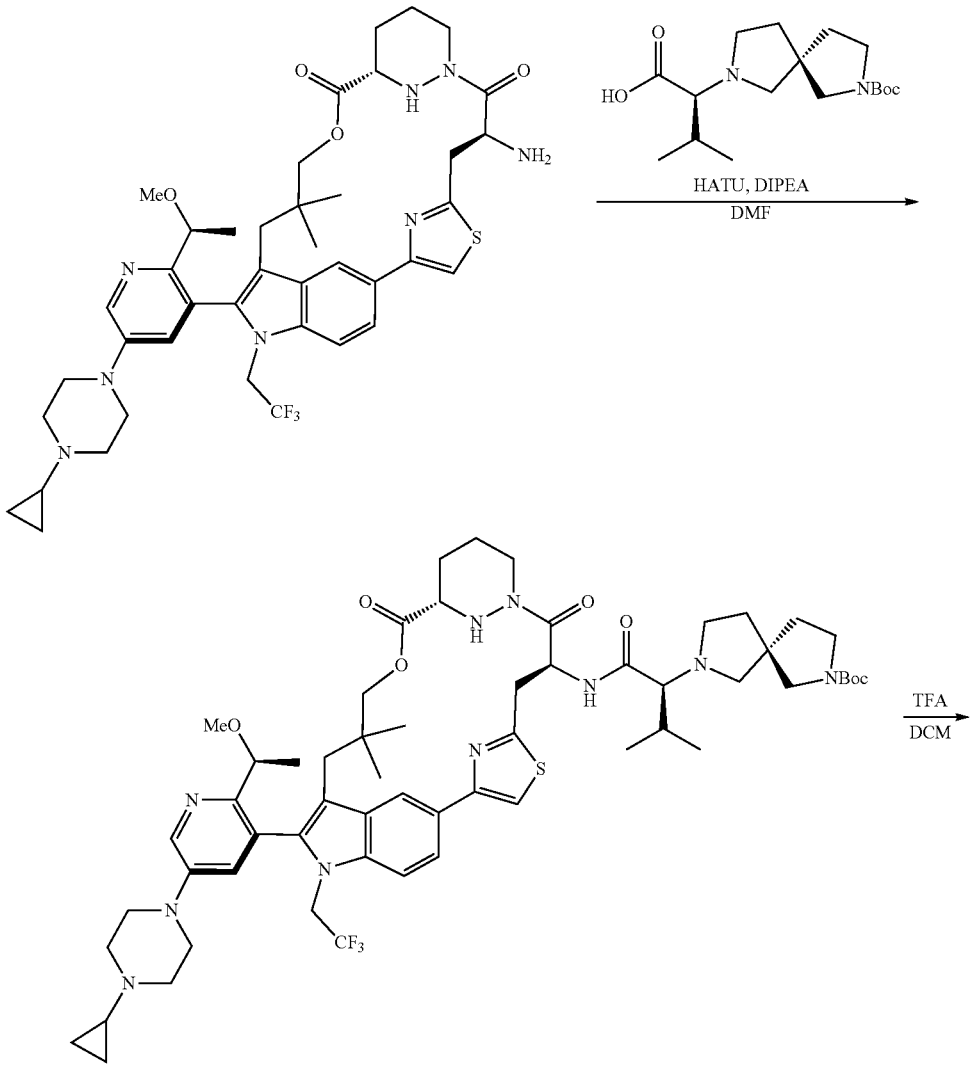

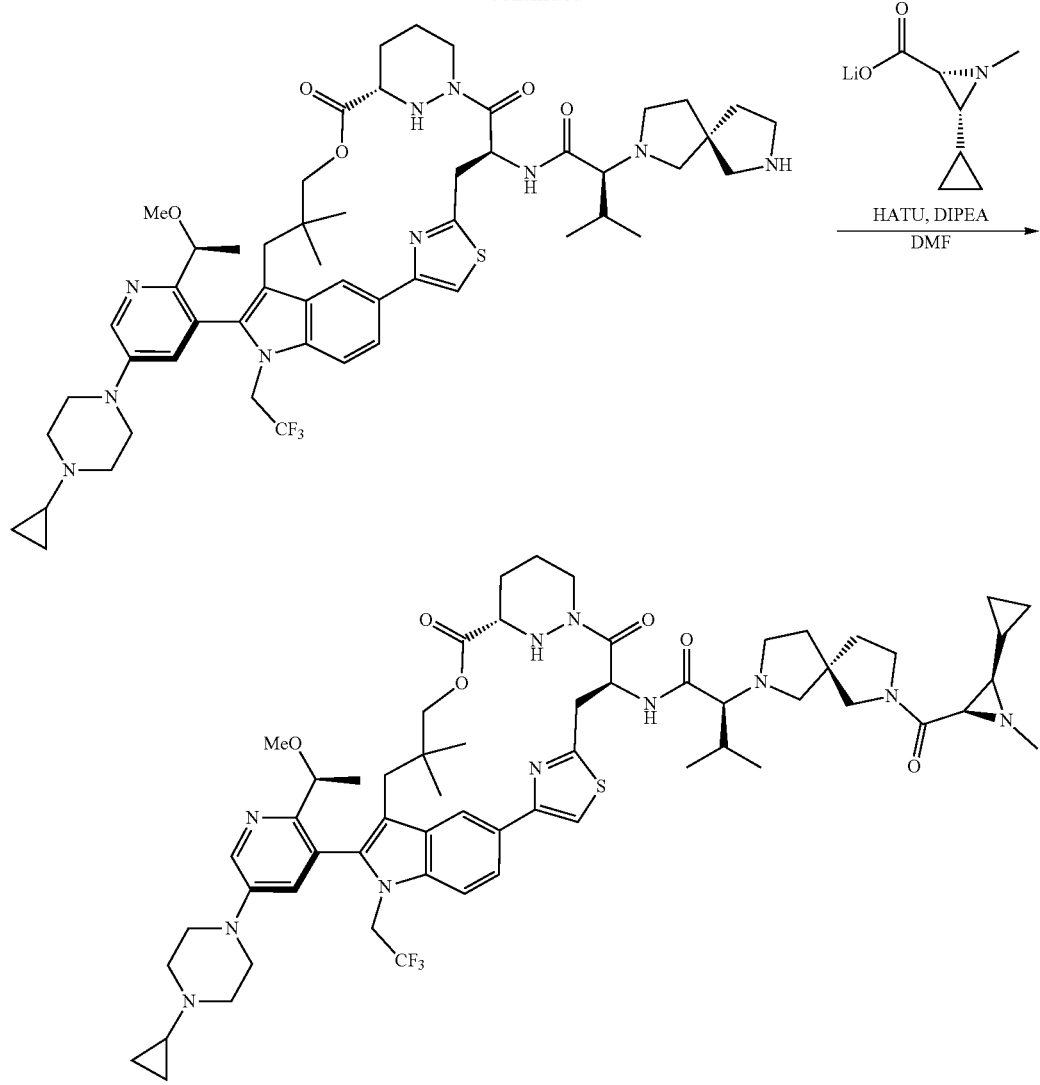

Step 1: Synthesis of tert-butyl (5S)-7-((2S)-1-(((6³S,4S,Z)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)amino)-3-methyl-1-oxobutan-2-yl)-2,7-diazaspiro[4.4]nonane-2-carboxylate To a solution of (6³S,4S,Z)-4-amino-1²-(5-(4-cyclopropylpiperazin-1-yl)-2-((S)-1-methoxyethyl)pyridin-3-yl)-10,10-dimethyl-1¹-(2,2,2-trifluoroethyl)-6¹,6²,6³,6⁴,6⁵,6⁶-hexahydro-1¹H-8-oxa-2(4,2)-thiazola-1(5,3)-indola-6(1,3)-pyridazinacycloundecaphane-5,7-dione (1 g, 1.236 mmol) and (S)-2-((S)-7-(tert-butoxycarbonyl)-2,7-diazaspiro[4.4]nonan-2-yl)-3-methylbutanoic acid (605.28 mg, 1.854 mmol) in DMF (11 mL) at 0° C. was added DIPEA (1.60 g, 12.360 mmol) and HATU (611.03 mg, 1.607 mmol). The resulting mixture was stirred at room temperature for 2 h and then cold H₂O was added (50 mL). The resulting mixture was extracted with EtOAc (3×25 mL) and the combined organic layers were washed with brine (30 mL), dried over Na₂SO₄, filtered, and concentrated under reduced pressure. The residue was purified by silica gel column chromatography, (6% MeOH/DCM) to afford the desired product (1.2 g, 87% yield) as a solid. LCMS (ESI) m/z [M+H] calcd for C₅₈H₇₉F₃N₁₀O₇S 1117.59; found: 1117.8.

Step 2: Synthesis of (2S)-N-((6³S,4S,2)-1²-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)-3-methyl-2-((S)-2,7-diazaspiro[4.4]nonan-2-yl)butanamide A solution of tert-butyl (5S)-7-((2S)-1-(((6³S,4S,Z)-1²-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)amino)-3-methyl-1-oxobutan-2-yl)-2,7-diazaspiro[4.4]nonane-2-carboxylate (1.2 g, 1.074 mmol) and TFA (6 mL) in DCM (12 mL) was stirred at 0° C. for 2 h. The resulting mixture was concentrated under reduced pressure and the residue was basified to pH 8 with sat. NaHCO$_3$ (aq). The resulting mixture was extracted with DCM (3×50 mL) and the combined organic layers were washed with brine (3×50 mL), dried over Na$_2$SO$_4$, filtered, and concentrated under reduced pressure to afford the desired product (987 mg, crude) as a solid. LCMS (ESI) m/z [M+H] calcd for C$_{53}$H$_{71}$F$_3$N$_{10}$O$_5$S 1017.54; found: 1017.3.

Step 3: Synthesis of (2S)-2-((S)-7-((2R,3R)-3-cyclopropyl-1-methylaziridine-2-carbonyl)-2,7-diazaspiro[4.4]nonan-2-yl)-N-((6$^3$S,4S,Z)-1$^2$-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)-3-methylbutanamide To a solution of (2S)-N-((6$^3$S,4S,Z)-1$^2$-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)-3-methyl-2-((S)-2,7-diazaspiro[4.4]nonan-2-yl)butanamide (977 mg, 0.960 mmol) and lithium (2R,3R)-3-cyclopropyl-1-methylaziridine-2-carboxylate (282.55 mg, 1.920 mmol) in DMF (10 mL) at 0° C. was added DIPEA (1.24 g, 9.600 mmol) and HATU (438.22 mg, 1.152 mmol). The resulting mixture was stirred at room temperature for 2 h and then cold H$_2$O (50 mL) was added. The resulting mixture was extracted with EtOAc (3×30 mL) and the combined organic layers were washed with brine (30 mL), dried over Na$_2$SO$_4$, filtered, and concentrated under reduced pressure. The residue was purified by reverse phase chromatography (5→30% MeCN/H$_2$O) to afford the desired product (413 mg, 38% yield) as a solid. LCMS (ESI) m/z [M+H] calcd for C$_{60}$H$_{80}$F$_3$N$_{10}$O$_6$S 1140.61; found: 1140.7.

Example A31: Synthesis of (2S)-2-cyclopentyl-2-((S)-7-((2R,3R)-3-cyclopropyl-1-(methyl-d$_3$)aziridine-2-carbonyl)-2,7-diazaspiro[4.4]nonan-2-yl)-N-((2$^2$S,6$^3$S,4S)-1$^2$-(5-(4-cyclopropylpiperazin-1-yl)-2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-4-yl)acetamide

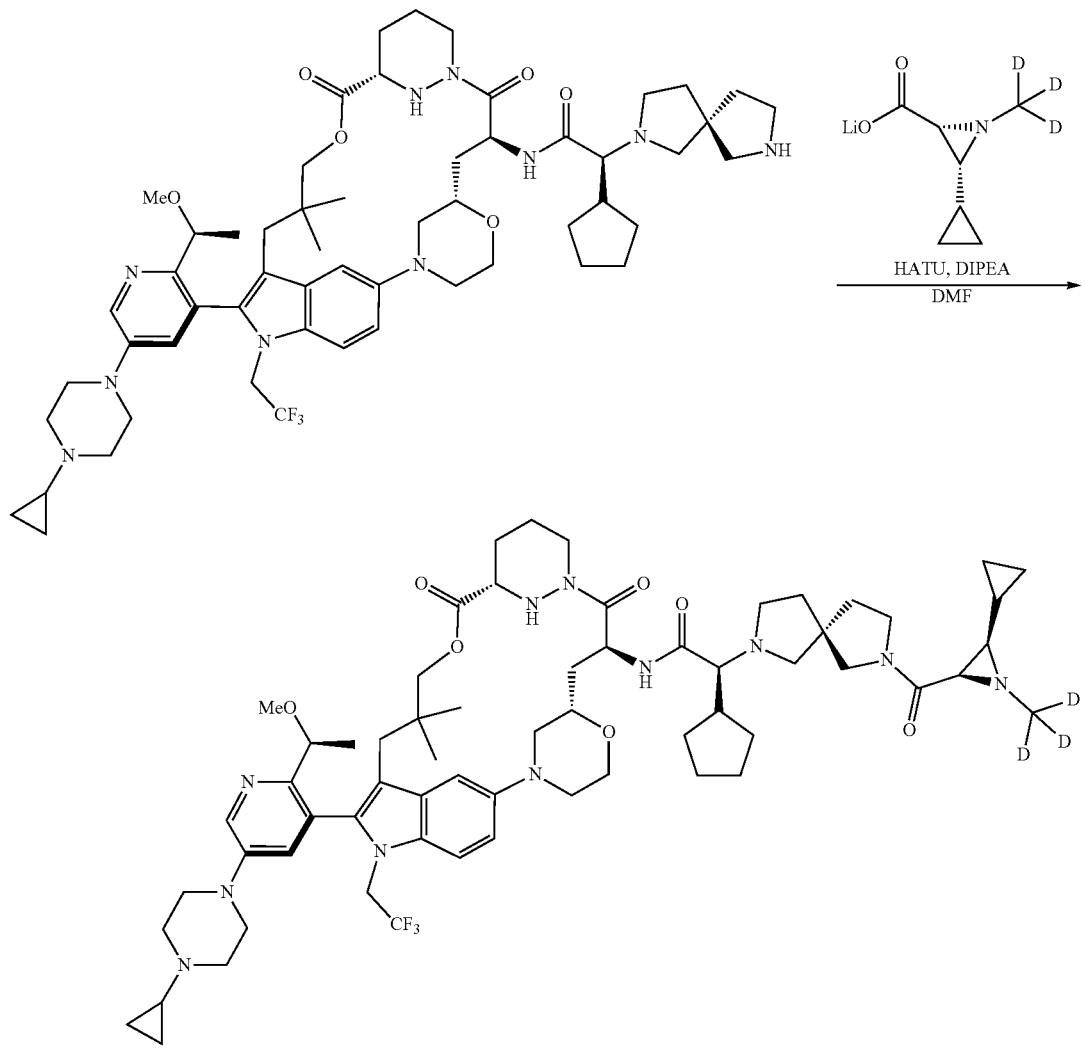

To a solution of (2S)-2-cyclopentyl-N-((2²S,6³S,4S)-1²-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)-2-((S)-2,7-diazaspiro[4.4]nonan-2-yl)acetamide (350 mg, 0.335 mmol) and lithium (2R,3R)-3-cyclopropyl-1-(methyl-d3)aziridine-2-carboxylate (57.4 mg, 0.38 mmol) in DMF (6 mL) at 0° C. was added DIPEA (216.38 mg, 1.675 mmol) and HATU (140.05 mg, 0.369 mmol). The resulting mixture was stirred at 0° C. for 1 h and was then extracted with DCM (3×20 mL). The combined organic layers were washed with brine (3×20 mL), dried over Na₂SO₄, filtered, and concentrated under reduced pressure. The residue was purified by reverse phase chromatography (11→17% MeCN/H₂O) to afford the desired product (150 mg, 37% yield) as a solid. LCMS (ESI) m/z [M+H] calcd for $C_{63}H_{85}D3F_3N_{11}O_7$ 1171.71; found: 1172.0.

Example A35: Synthesis of (2S)-2-cyclopentyl-2-((S)-7-((2R,3R)-3-cyclopropyl-1-(methyl-d₃)aziridine-2-carbonyl)-2,7-diazaspiro[4.4]nonan-2-yl)-N-((6³S,4S,Z)-1²-(5-(4-cyclopropylpiperazin-1-yl)-2-((S)-1-methoxyethyl)pyridin-3-yl)-1¹-ethyl-10,10-dimethyl-5,7-dioxo-6,6²,6³,6⁴,6⁵,6⁶-hexahydro-1¹H-8-oxa-2(4,2)-thiazola-1(5,3)-indola-6(1,3)-pyridazinacycloundecaphane-4-yl)acetamide

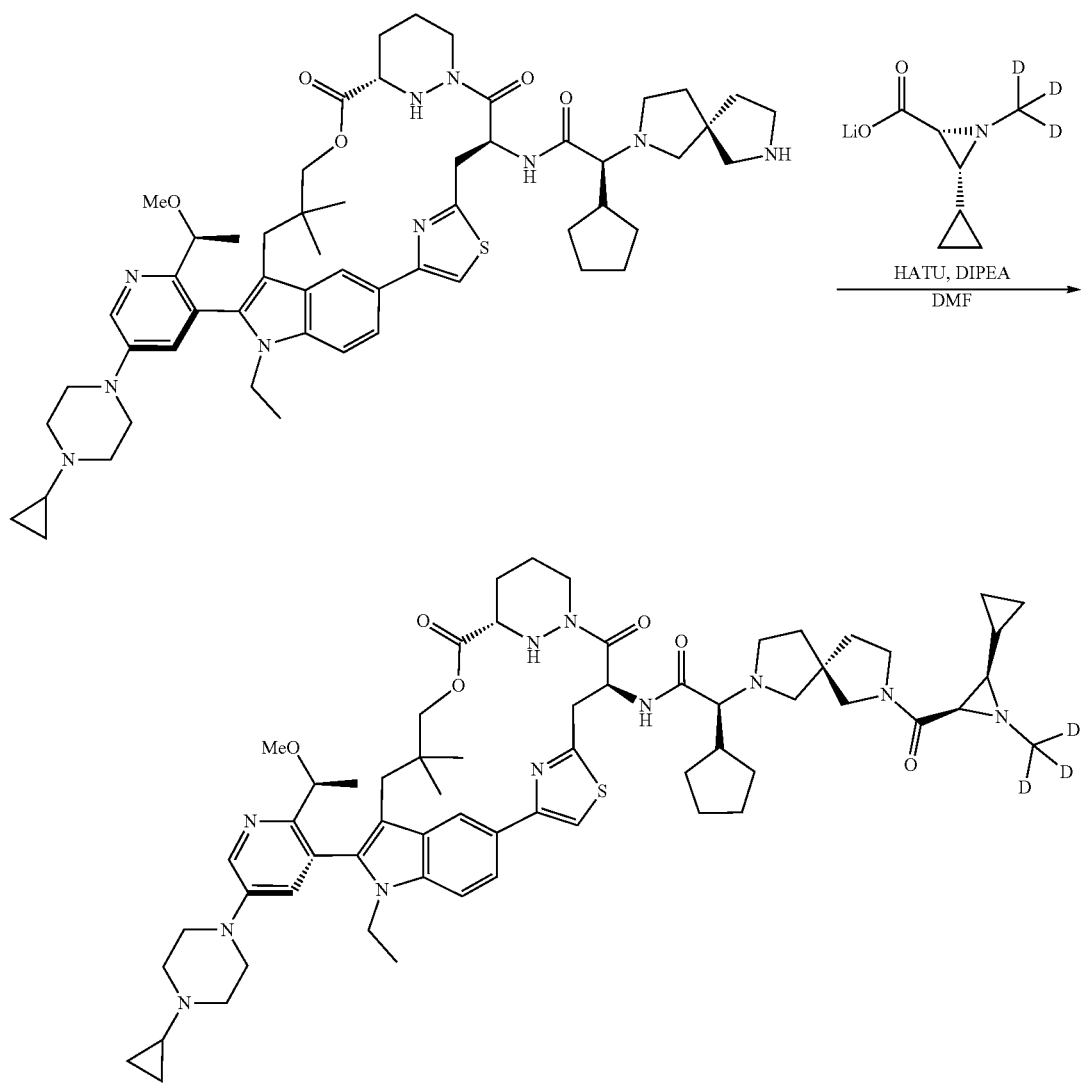

To a solution of (2S)-2-cyclopentyl-N-((6³S,4S,2)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1¹H-8-oxa-2(4,2)-thiazola-1 (5,3)-indola-6(1,3)-pyridazinacycloundecaphane-4-yl)-2-((S)-2,7-diazaspiro[4.4]nonan-2-yl)acetamide (300 mg, 0.303 mmol) and lithium (2R,3R)-3-cyclopropyl-1-(methyl-d₃)aziridine-2-carboxylate (87.44 mg, 0.606 mmol) in DMF (3 mL) at 0° C. was added DIPEA (195.96 mg, 1.515 mmol) and HATU (138.36 mg, 0.364 mmol). The resulting mixture was stirred at room temperature for 1 h and was then extracted with EtOAc (3×10 mL). The combined organic layers were washed with brine (10 mL), dried over Na₂SO₄, filtered, and concentrated under reduced pressure. The residue was purified by reverse phase chromatography (20→25% MeCN/H₂O) to afford the desired product (156.3 mg, 46% yield) as a solid. LCMS (ESI) m/z [M+H] calcd for $C_{62}H_{82}D3N_{11}O_6S$ 1115.67; found: 1115.8.

Example A34: Synthesis of (2S)-2-cyclopentyl-2-((S)-7-((2R,3R)-3-cyclopropyl-1-(methyl-d₃)aziridine-2-carbonyl)-2,7-diazaspiro[4.4]nonan-2-yl)-N-((6³S,4S,Z)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-61,6²,6³,6⁴,6⁵,6⁶-hexahydro-1¹H-8-oxa-2(4,2)-thiazola-1(5,3)-indola-6(1,3)-pyridazinacycloundecaphane-4-yl)acetamide

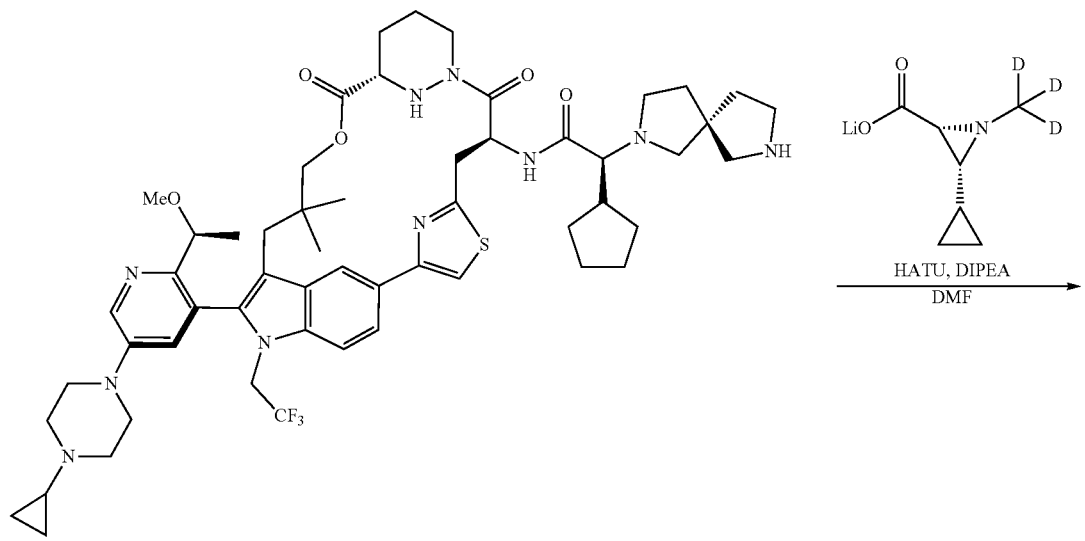

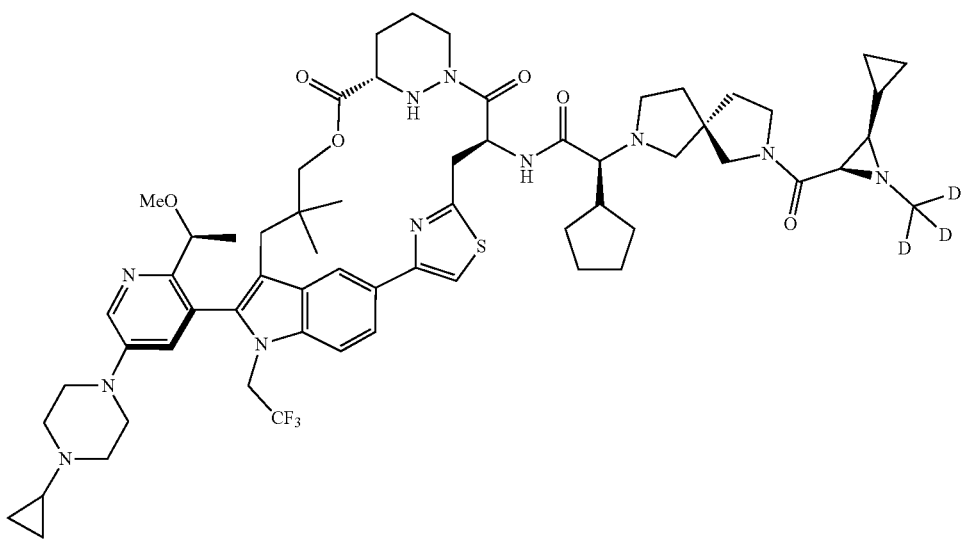

To a solution of (2S)-2-cyclopentyl-N-((6³S,4S,Z)-1²-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)-2-((S)-2,7-diazaspiro[4.4]nonan-2-yl)acetamide (300 mg, 0.288 mmol) and lithium (2R,3R)-3-cyclopropyl-1-(methyl-d3)aziridine-2-carboxylate (82.92 mg, 0.576 mmol) in DMF (3 mL) at 0° C. was added DIPEA (185.82 mg, 1.440 mmol) and HATU (131.20 mg, 0.346 mmol). The resulting mixture was stirred at room temperature for 1 h and was then extracted with EtOAc (3×10 mL). The combined organic layers were washed with brine (10 mL), dried over Na₂SO₄, filtered, and concentrated under reduced pressure. The residue was purified by reverse phase chromatography (20→25% MeCN/H₂O) to afford the desired product (147.6 mg, 44% yield) as a solid. LCMS (ESI) m/z [M+H] calcd for C₆₂H₇₉D3F₃N~O₆S 1169.64; found: 1169.7.

Example A30: Synthesis of (2S)-2-((S)-7-((2R,3R)-3-cyclopropyl-1-(methyl-d₃)aziridine-2-carbonyl)-2,7-diazaspiro[4.4]nonan-2-yl)-N-((2²S,6³S,4S)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)-3-methylbutanamide

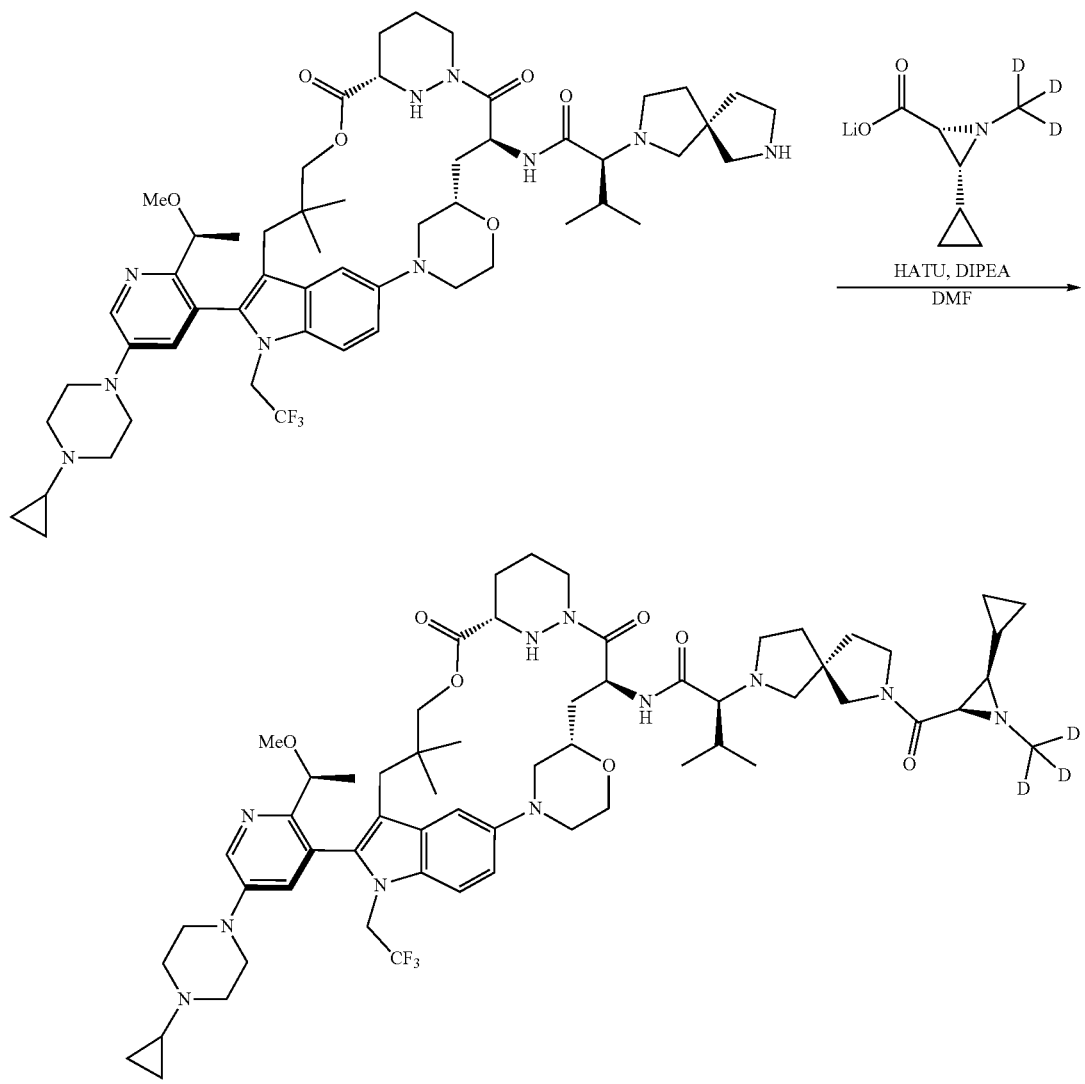

To a solution of (2S)-2-((S)-7-((2R,3R)-3-cyclopropyl-1-methylaziridine-2-carbonyl)-2,7-diazaspiro[4.4]nonan-2-yl)-N-((2²S,6³S,4S)-1²-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)-3-methylbutanamide (330 mg, 0.324 mmol) and lithium (2R,3R)-3-cyclopropyl-1-(methyl-d₃)aziridine-2-carboxylate (93.37 mg, 0.648 mmol) in DMF (3 mL) at 0° C. was added DIPEA (209.23 mg, 1.620 mmol) and HATU (147.73 mg, 0.389 mmol). The resulting mixture was stirred at 0° C. for 30 min and was then extracted with EtOAc (3×10 mL). The combined organic layers were washed with brine (10 mL), dried over Na₂SO₄, filtered, and concentrated under reduced pressure. The residue was purified by reverse phase chromatography (20→30% MeCN/H₂O) to afford the desired product (218.1 mg, 58% yield) as a solid. LCMS (ESI) m/z [M+H] calcd for $C_{61}H_{83}D3F_3N_{11}O_7$ 1145.70; found: 1145.8.

Example A33: Synthesis of (2S)-2-((S)-7-((2R,3R)-3-cyclopropyl-1-(methyl-d₃)aziridine-2-carbonyl)-2,7-diazaspiro[4.4]nonan-2-yl)-N-((6³S,4S,Z)-1²-(5-(4-cyclopropylpiperazin-1-yl)-2-((S)-1-methoxyethyl)pyridin-3-yl)-1¹-ethyl-10,10-dimethyl-5,7-dioxo-6,6²,6³,6⁴,6⁵,6⁶-hexahydro-1¹H-8-oxa-2(4,2)-thiazola-1(5,3)-indola-6(1,3)-pyridazinacycloundecaphane-4-yl)-3-methylbutanamide

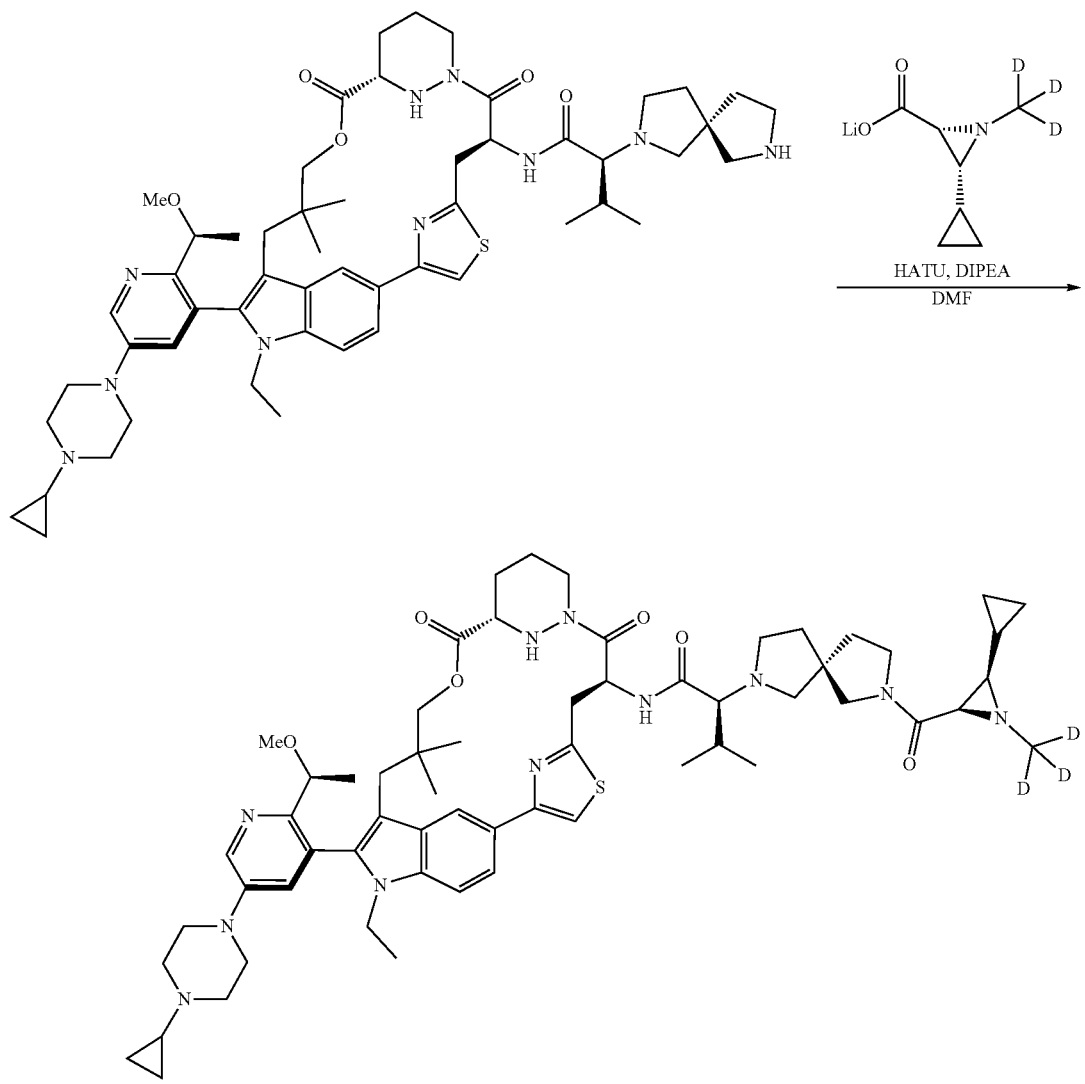

387

To a solution of (2S)-N-((6³S,4S,Z)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexa-

388

6⁵,6⁶-hexahydro-1¹H-8-oxa-2(4,2)-thiazola-1(5,3)-indola-6(1,3)-pyridazinacycloundecaphane-4-yl)-3-methylbutanamide

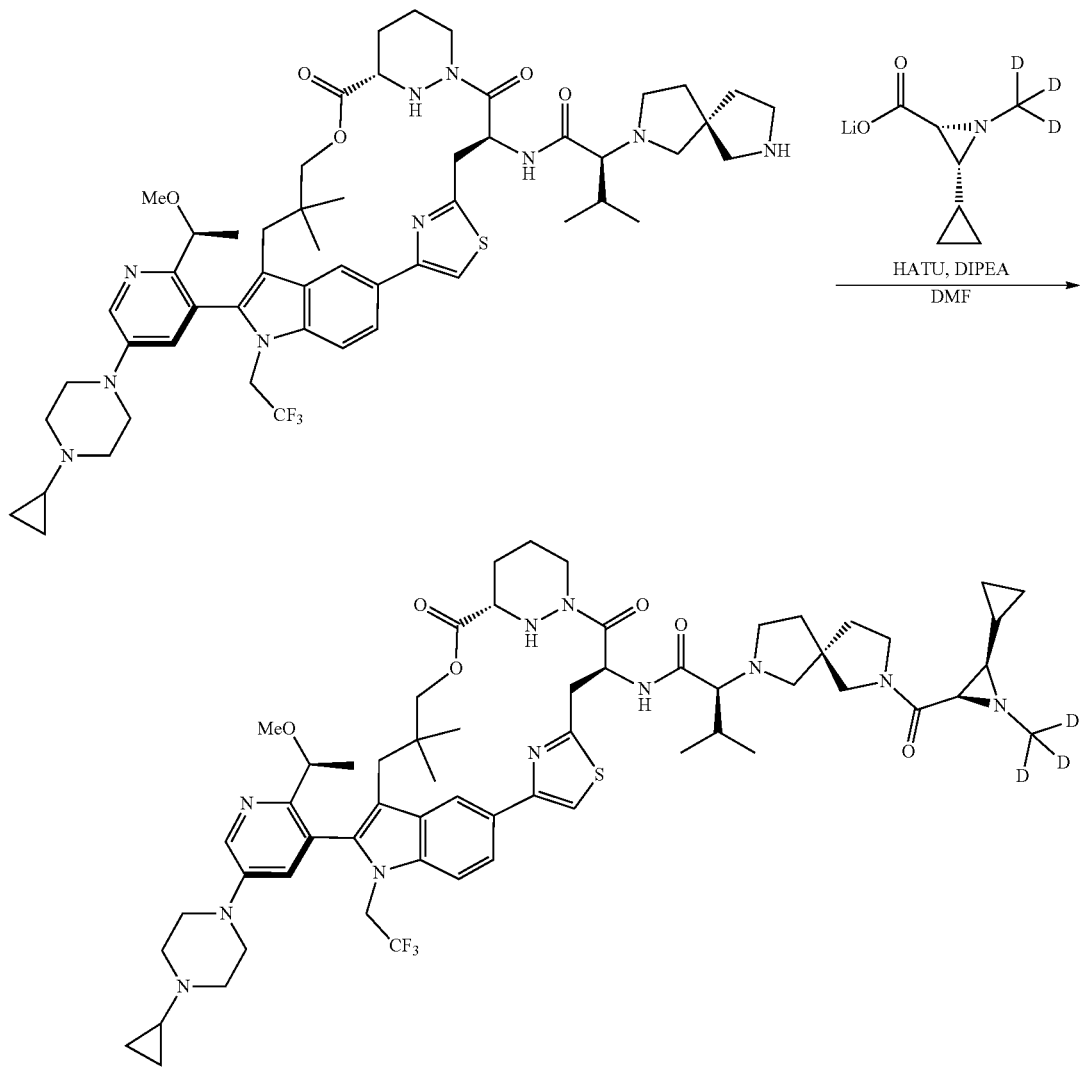

hydro-1¹H-8-oxa-2(4,2)-thiazola-1(5,3)-indola-6(1,3)-pyridazinacycloundecaphane-4-yl)-3-methyl-2-((S)-2,7-diazaspiro[4.4]nonan-2-yl)butanamide (300 mg, 0.311 mmol) and lithium (2R,3R)-3-cyclopropyl-1-(methyl-d₃) aziridine-2-carboxylate (93.50 mg, 0.622 mmol) in DMF (5 mL) at 0° C. was added DIPEA (195.9 mg, 1.515 mmol) and HATU (142.10 mg, 0.373 mmol). The resulting mixture was stirred at room temperature for 2 h and was then extracted with EtOAc (3×30 mL). The combined organic layers were washed with brine (10 mL), dried over Na₂SO₄, filtered, and concentrated under reduced pressure. The residue was purified by prep-TLC (7% MeOH/DCM) to afford the desired product (147 mg, 43% yield) as a solid. LCMS (ESI) m/z [M+H] calcd for C₆₀H₈₀D₃N₁₁O₆S 1089.65; found: 1089.8.

Example A32: Synthesis of (2S)-2-((S)-7-((2R,3R)-3-cyclopropyl-1-(methyl-d₃)aziridine-2-carbonyl)-2,7-diazaspiro[4.4]nonan-2-yl)-N-((6³S,4S,Z)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-6,6²,6³,6⁴, To a solution of (2S)-N-((6³S,4S,Z)-1²-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)-3-methyl-2-((S)-2,7-diazaspiro[4.4]nonan-2-yl)butanamide (300 mg, 0.295 mmol) and lithium (2R,3R)-3-cyclopropyl-1-(methyl-d3) aziridine-2-carboxylate (88.54 mg, 0.590 mmol) in DMF (4 mL) at 0° C. was added DIPEA (762.32 mg, 5.900 mmol) and a solution of HATU (134.56 mg, 0.354 mmol) in DMF (1 mL). The resulting mixture was stirred at room temperature for 2 h, diluted with H₂O, and was then extracted with EtOAc (3×20 mL). The combined organic layers were washed with brine (10 mL), dried over Na₂SO₄, filtered, and concentrated under reduced pressure. The residue was purified by prep-TLC (7% MeOH/DCM) to afford the desired product (139 mg, 40% yield) as a solid. LCMS (ESI) m/z [M+H] calcd for C₆₀H₇₇D3F₃N₁₁O₆S 1143.63; found: 1143.8.

Example A15: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-(($2^2$S,$6^3$S,4S)-$1^1$-ethyl-$1^2$-(5-((S)-hexahydropyrazino[2,1-c][1,4]oxazin-8(1H)-yl)-2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-2(4,2)-morpholina-1(5,3)-indola-6(1,3)-pyridazinacycloundecaphane-4-yl)acetamide
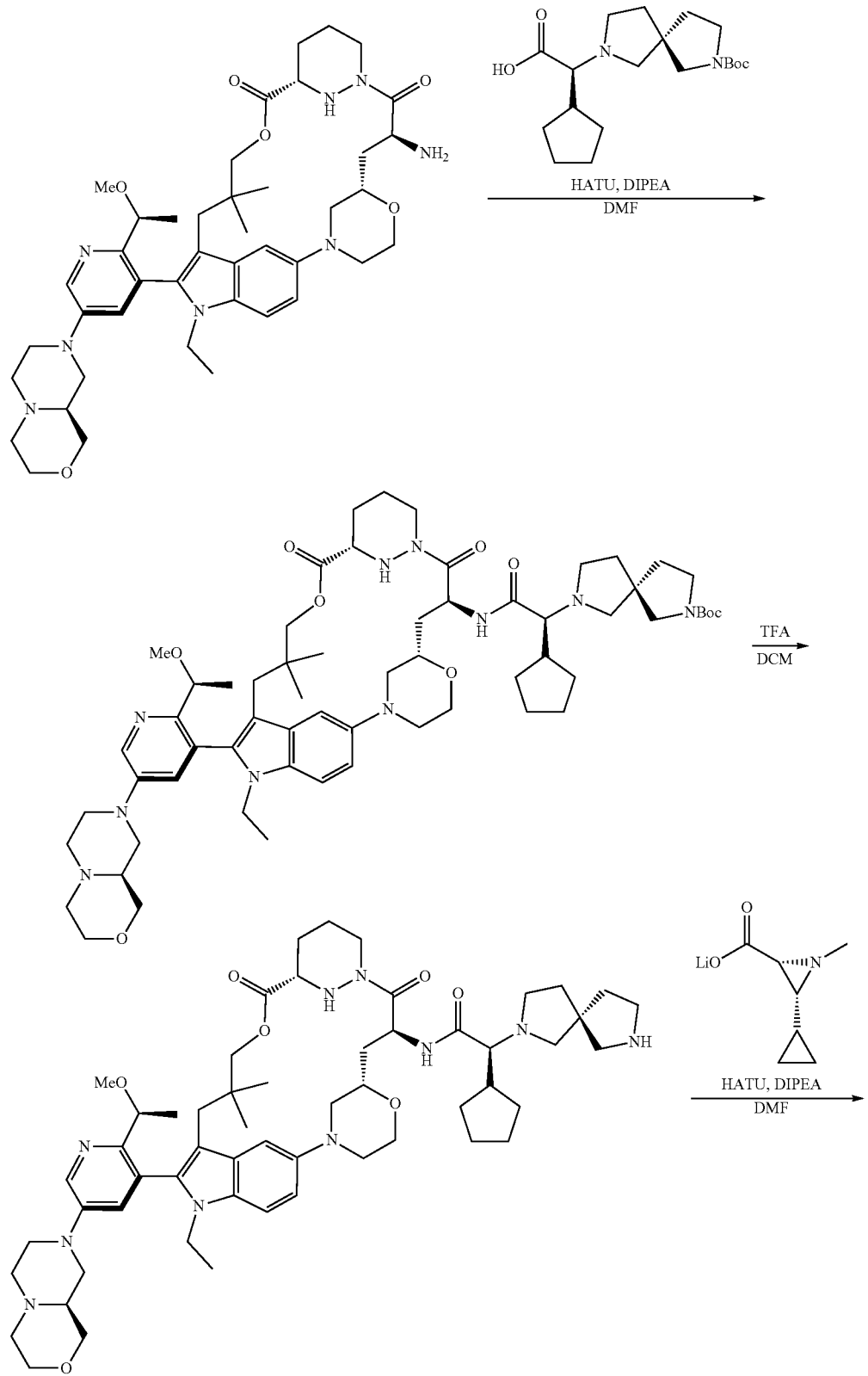

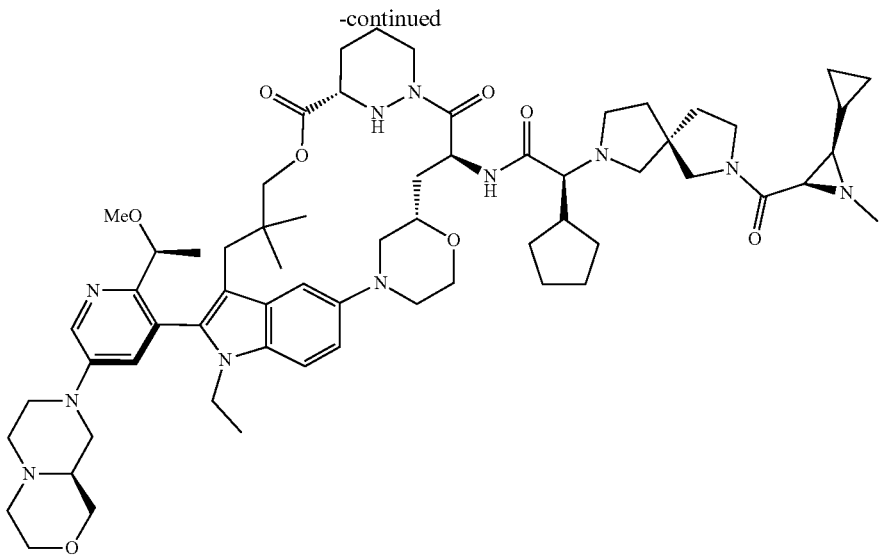

Step 1: Synthesis of tert-butyl (5S)-7-((1 S)-1-cyclopentyl-2-(((2²S,6³S,4S)-1¹-ethyl-1²-(5-((S)-hexahydropyrazino[2,1-c][1,4]oxazin-8(1 H)-yl)-2-((S)-1-methoxyethyl)pyridin-3-yl)-10,10-dimethyl-5,7-dioxo-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)amino)-2-oxoethyl)-2,7-diazaspiro[4.4]nonane-2-carboxylate To a solution of (S)-2-((S)-7-(tert-butoxycarbonyl)-2,7-diazaspiro[4.4]nonan-2-yl)-2-cyclopentylacetic acid (547.19 mg, 1.552 mmol) in DMF (6 mL) at 0° C. was added DIPEA (5.40 mL, 30.993 mmol) and HATU (442.70 mg, 1.164 mmol) followed by (2²S,6³S,4S)-4-amino-11-ethyl-1²-(5-((S)-hexahydropyrazino[2,1-c][1,4]oxazin-8(1 H)-yl)-2-((S)-1-methoxyethyl)pyridin-3-yl)-10,10-dimethyl-6¹,6²,6³,6⁴,6⁵,6⁶-hexahydro-1¹H-8-oxa-2(4,2)-morpholina-1(5,3)-indola-6(1,3)-pyridazinacycloundecaphane-5,7-dione (600 mg, 0.776 mmol). The mixture was stirred for 3 h and then H₂O was added. The resulting mixture was extracted with EtOAc (3×100 mL) and the combined organic layers were washed with brine (3×70 mL), dried over Na₂SO₄, filtered, and concentrated under reduced pressure. The residue was purified by prep-TLC (6% MeOH/DCM) to afford the desired product (700 mg, 81% yield) as a solid. LCMS (ESI) m/z [M+H] calcd for $C_{61}H_{90}N_{10}O_9$ 1107.70; found: 1107.7.

Step 2: Synthesis of (2S)-2-cyclopentyl-N-((2²S,6³S,4S)-1¹-ethyl-1²-(5-((S)-hexahydropyrazino[2,1-c][1,4]oxazin-8(1 H)-yl)-2-((S)-1-methoxyethyl)pyridin-3-yl)-10,10-dimethyl-5,7-dioxo-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)-2-((S)-2,7-diazaspiro[4.4]nonan-2-yl)acetamide A solution of tert-butyl (5S)-7-((1 S)-1-cyclopentyl-2-(((2²S,6³S,4S)-1¹-ethyl-1²-(5-((S)-hexahydropyrazino[2,1-c][1,4]oxazin-8(1 H)-yl)-2-((S)-1-methoxyethyl)pyridin-3-yl)-10,10-dimethyl-5,7-dioxo-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)amino)-2-oxoethyl)-2,7-diazaspiro[4.4]nonane-2-carboxylate (700 mg, 0.632 mmol) and TFA (3 mL) in DCM (7 mL) was stirred at 0° C. for 3 h. The resulting mixture was concentrated under reduced pressure and the residue was basified to pH 8 with sat. NaHCO₃ (aq). The resulting mixture was extracted with DCM (3×50 mL) and the combined organic layers were washed with brine (3×50 mL), dried over Na₂SO₄, filtered, and concentrated under reduced pressure to afford the desired product (700 mg, crude) as a solid. LCMS (ESI) m/z [M+H] calcd for $C_{56}H_{82}N_{10}O_7$ 1007.65; found: 1007.7.

Step 3: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-((2²S,6³S,4S)-1¹-ethyl-1²-(5-((S)-hexahydropyrazino[2,1-c][1,4]oxazin-8(1 H)-yl)-2-((S)-1-methoxyethyl)pyridin-3-yl)-10,10-dimethyl-5,7-dioxo-6,6²,6³,6⁴,6⁵,6⁶-hexahydro-11H-8-oxa-2(4,2)-morpholina-1(5,3)-indola-6(1,3)-pyridazinacycloundecaphane-4-yl)acetamide To a solution of (2S)-2-cyclopentyl-N-((2²S,6³S,4S)-1¹-ethyl-1²-(5-((S)-hexahydropyrazino[2,1-c][1,4]oxazin-8(1 H)-yl)-2-((S)-1-methoxyethyl)pyridin-3-yl)-10,10-dimethyl-5,7-dioxo-6,6²,6³,6⁴,6⁵,6⁶-hexahydro-11H-8-oxa-2(4,2)-morpholina-1(5,3)-indola-6(1,3)-pyridazinacycloundecaphane-4-yl)-2-((S)-2,7-diazaspiro[4.4]nonan-2-yl)acetamide (600 mg, 0.596 mmol) and lithium (2R,3R)-3-cyclopropyl-1-methylaziridine-2-carboxylate (175.23 mg, 1.192 mmol) in DMF (6 mL) at 0° C. was added DIPEA (769.81 mg, 5.960 mmol) and HATU (271.77 mg, 0.715 mmol). The resulting mixture was stirred at 0° C. for 3 h and then cold H₂O (50 mL) was added. The resulting mixture was extracted with EtOAc (2×50 mL) and the combined organic layers were washed with brine (2×100 mL), dried over Na₂SO₄, filtered, and concentrated under reduced pressure. The residue was purified by prep-TLC (8% MeOH/DCM) to afford the desired product (150 mg, 22% yield) as a solid. LCMS (ESI) m/z [M+H] calcd for $C_{63}H_{91}N_{11}O_8$ 1130.72; found: 1130.8.

Example A14: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-((2²S, 6³S,4S)-1²-(5-((S)-hexahydropyrazino[2,1-c][1,4]oxazin-8(1H)-yl)-2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)acetamide
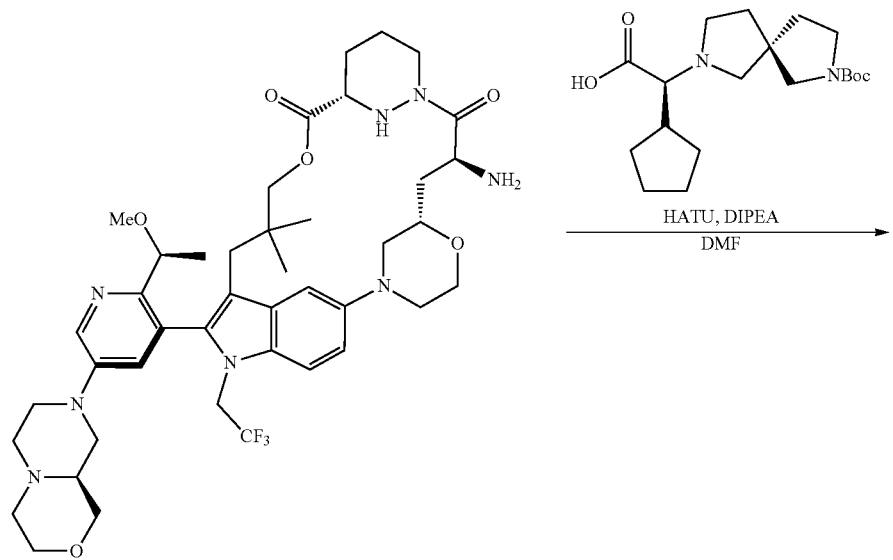
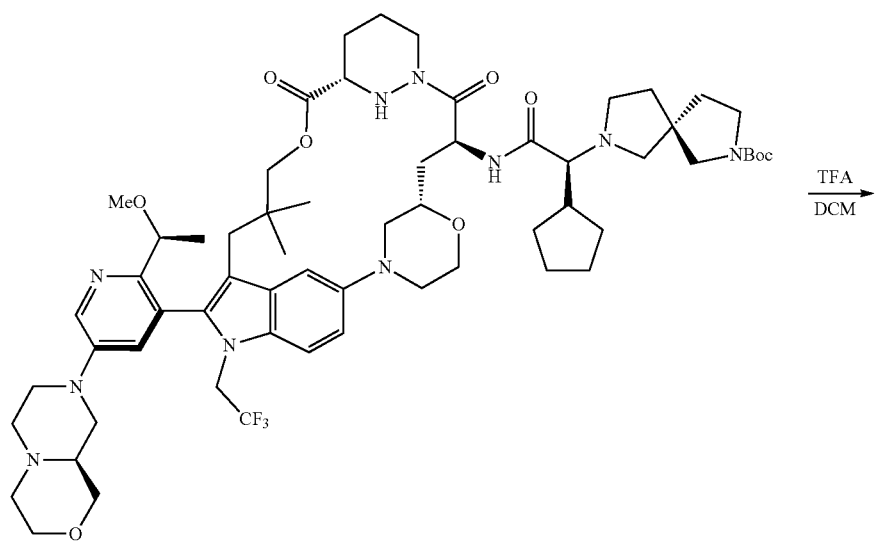

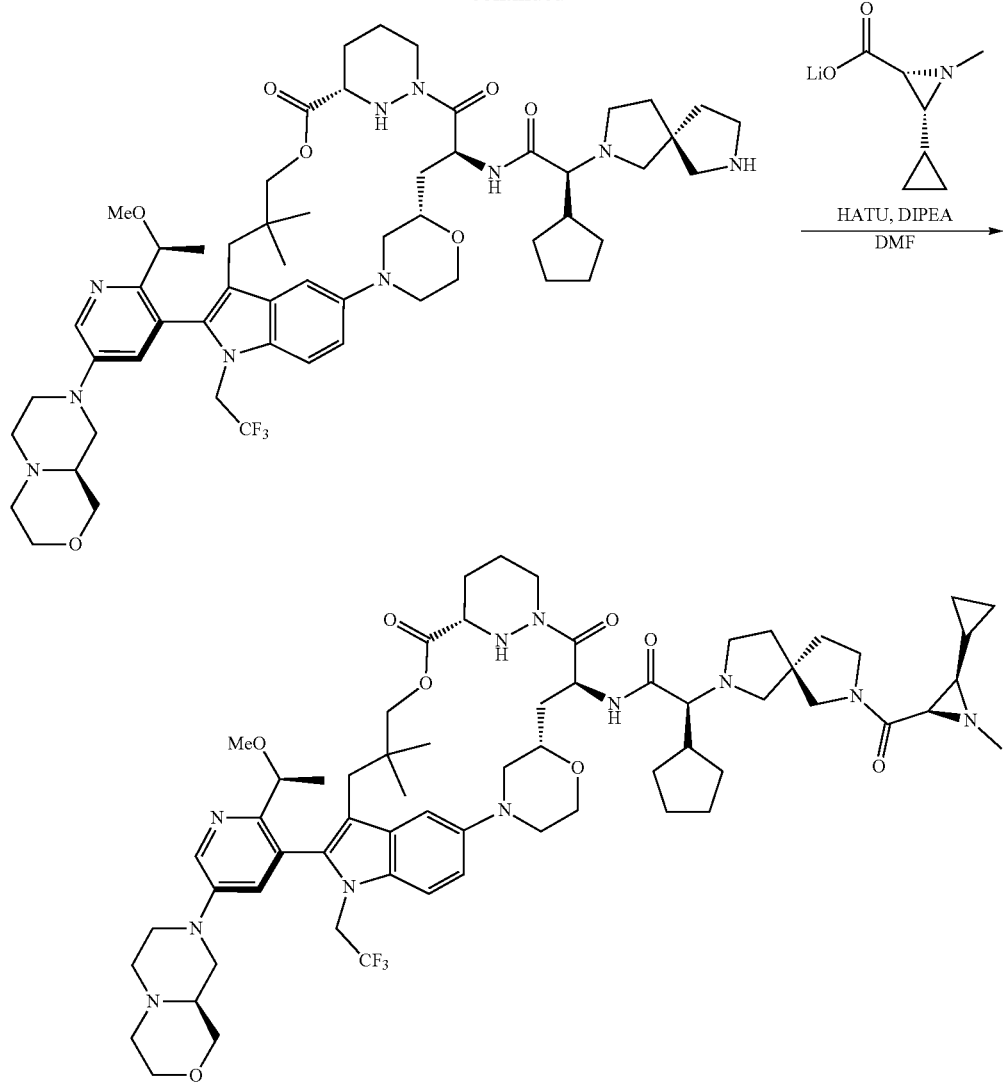

Step 1: Synthesis of tert-butyl (5S)-7-((1 S)-1-cyclopentyl-2-(((2²S,6³S,4S)-1²-(5-((S)-hexahydropyrazino[2,1-c][1,4]oxazin-8(1 H)-yl)-2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)amino)-2-oxoethyl)-2,7-diazaspiro[4.4]nonane-2-carboxylate To a solution of (S)-2-((S)-7-(tert-butoxycarbonyl)-2,7-diazaspiro[4.4]nonan-2-yl)-2-cyclopentylacetic acid (1.8 g, 5.107 mmol) in DMF (22 mL) at 0° C. was added DIPEA (3.4 g, 26.306 mmol) and HATU (1.5 g, 3.945 mmol) followed by (2²S,6³S,4S)-4-amino-1²-(5-((S)-hexahydropyrazino[2,1-c][1,4]oxazin-8(1 H)-yl)-2-((S)-1-methoxyethyl)pyridin-3-yl)-10,10-dimethyl-11-(2,2,2-trifluoroethyl)-6¹,6²,6³,6⁴,6⁵,6⁶-hexahydro-1¹H-8-oxa-2(4,2)-morpholina-1(5,3)-indola-6(1,3)- pyridazinacycloundecaphane-5,7-dione (2.2 g, 2.660 mmol). The mixture was stirred for 1 h and then H₂O was added. The resulting mixture was extracted with EtOAc (3×100 mL) and the combined organic layers were washed with brine (3×100 mL), dried over Na₂SO₄, filtered, and concentrated under reduced pressure. The residue was purified by silica gel column chromatography to afford the desired product (2 g, 61% yield) as a solid. LCMS (ESI) m/z [M+H] calcd for $C_{61}H_{87}F_3N_{10}O_9$ 1161.67; found: 1161.8.

Step 2: Synthesis of (2S)-2-cyclopentyl-N-((2²S, 6³S,4S)-1²-(5-((S)-hexahydropyrazino[2,1-c][1,4]oxazin-8(1 H)-yl)-2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-2(4,2)-morpholina-1(5,3)-indola-6(1,3)-pyridazinacycloundecaphane-4-yl)-2-((S)-2,7-diazaspiro[4.4]nonan-2-yl)acetamide A solution of tert-butyl (5S)-7-((1 S)-1-cyclopentyl-2-(((2²S,6³S,4S)-1²-(5-((S)-hexahydropyrazino[2,1-c][1,4]oxazin-8(1 H)-yl)-2-((S)-1-methoxyethyl)pyridin-3-yl)-10,10-dimethyl-5,7-dioxo-1¹-(2,2,2-trifluoroethyl)-6¹,6²,6³,6⁴, 6⁵,6⁶-hexahydro-1¹H-8-oxa-2(4,2)-morpholina-1(5,3)-indola-6(1,3)-pyridazinacycloundecaphane-4-yl)amino)-2-oxoethyl)-2,7-diazaspiro[4.4]nonane-2-carboxylate (1.8 g, 1.550 mmol) and TFA (10 mL) in DCM (20 mL) was stirred at 0° C. for 2 h and was then basified to pH 8 with sat. NaHCO$_3$ (aq.). The resulting mixture was extracted with DCM (3×300 mL). The combined organic layers were washed with brine (3×80 mL), dried over Na$_2$SO$_4$, filtered, and concentrated under reduced pressure to afford the desired product as a solid. LCMS (ESI) m/z [M+H] calcd for C$_{56}$H$_{79}$F$_3$N$_{10}$O$_7$ 1061.62; found: 1061.4.

Step 3: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-((2$^2$S,6$^3$S, 4S)-1$^2$-(5-((S)-hexahydropyrazino[2,1-c][1,4]oxazin-8(1H)-yl)-2-((S)-1-methoxyethyl)pyridin-3-yl)-10, 10-dimethyl-5,7-dioxo-1$^1$-(2,2,2-trifluoroethyl)-6$^1$, 6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-4-yl)acetamide To a solution of (2S)-2-cyclopentyl-N-((2$^2$S,6$^3$S,4S)-1$^2$-(5-((S)-hexahydropyrazino[2,1-c][1,4]oxazin-8(1 H)-yl)-2-((S)-1-methoxyethyl)pyridin-3-yl)-10,10-dimethyl-5,7-dioxo-1$^1$-(2,2,2-trifluoroethyl)-6$^1$,6$^2$,6$^3$,6$^4$,6$^5$,6$^6$-hexahydro-1$^1$H-8-oxa-2(4,2)-morpholina-1(5,3)-indola-6(1,3)-pyridazinacycloundecaphane-4-yl)-2-((S)-2,7-diazaspiro [4.4]nonan-2-yl)acetamide (600 mg, 0.565 mmol) and lithium (2R,3R)-3-cyclopropyl-1-methylaziridine-2-carboxylate (207.90 mg, 1.412 mmol) in DMF (6 mL) at 0° C. was added DIPEA (730.67 mg, 5.650 mmol) and HATU (257.95 mg, 0.678 mmol). The resulting mixture was stirred at 0° C. for 1 h and then cold H$_2$O (50 mL) was added. The resulting mixture was extracted with EtOAc (3×50 mL) and the combined organic layers were washed with brine (3×50 mL), dried over Na$_2$SO$_4$, filtered, and concentrated under reduced pressure. The residue was purified by prep-TLC (8% MeOH/DCM) to afford the desired product (150 mg, 19% yield) as a solid. LCMS (ESI) m/z [M+H] calcd for C$_{63}$H$_{88}$F$_3$N$_{11}$O$_8$ 1184.69; found: 1184.7.

Example A24: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-((6$^3$, 4S)-1$^2$-(5-(4-cyclopropylpiperazin-1-yl)-2-((S)-1-methoxyethyl)pyridin-3-yl)-10,10-dimethyl-5,7-dioxo-1$^1$-(2,2,2-trifluoroethyl)-2$^1$,2$^2$,2$^3$,2$^6$,6$^1$,6$^2$,6$^3$, 6$^4$,6$^5$,6$^6$-decahydro-1$^1$H-8-oxa-1(5,3)-indola-6(1,3)-pyridazina-2(5,1)-pyridinacycloundecaphane-4-yl) acetamide

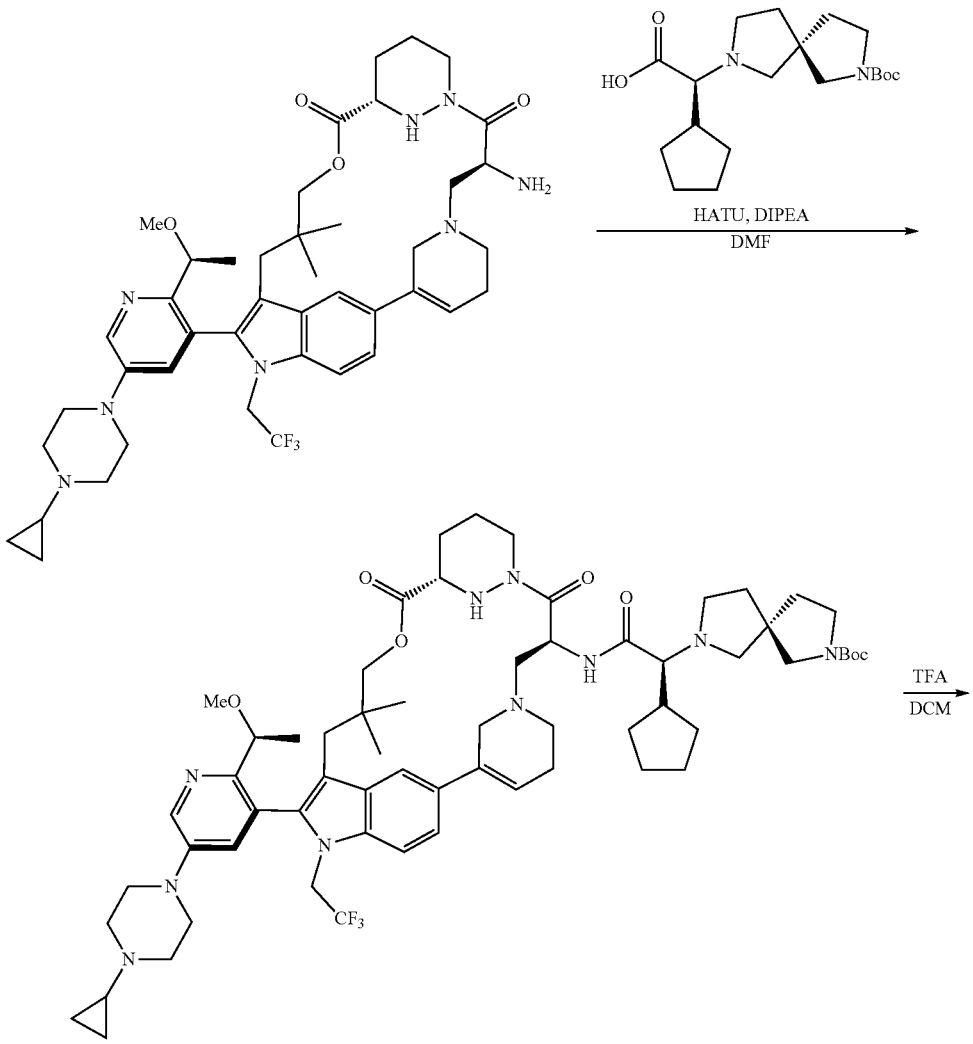

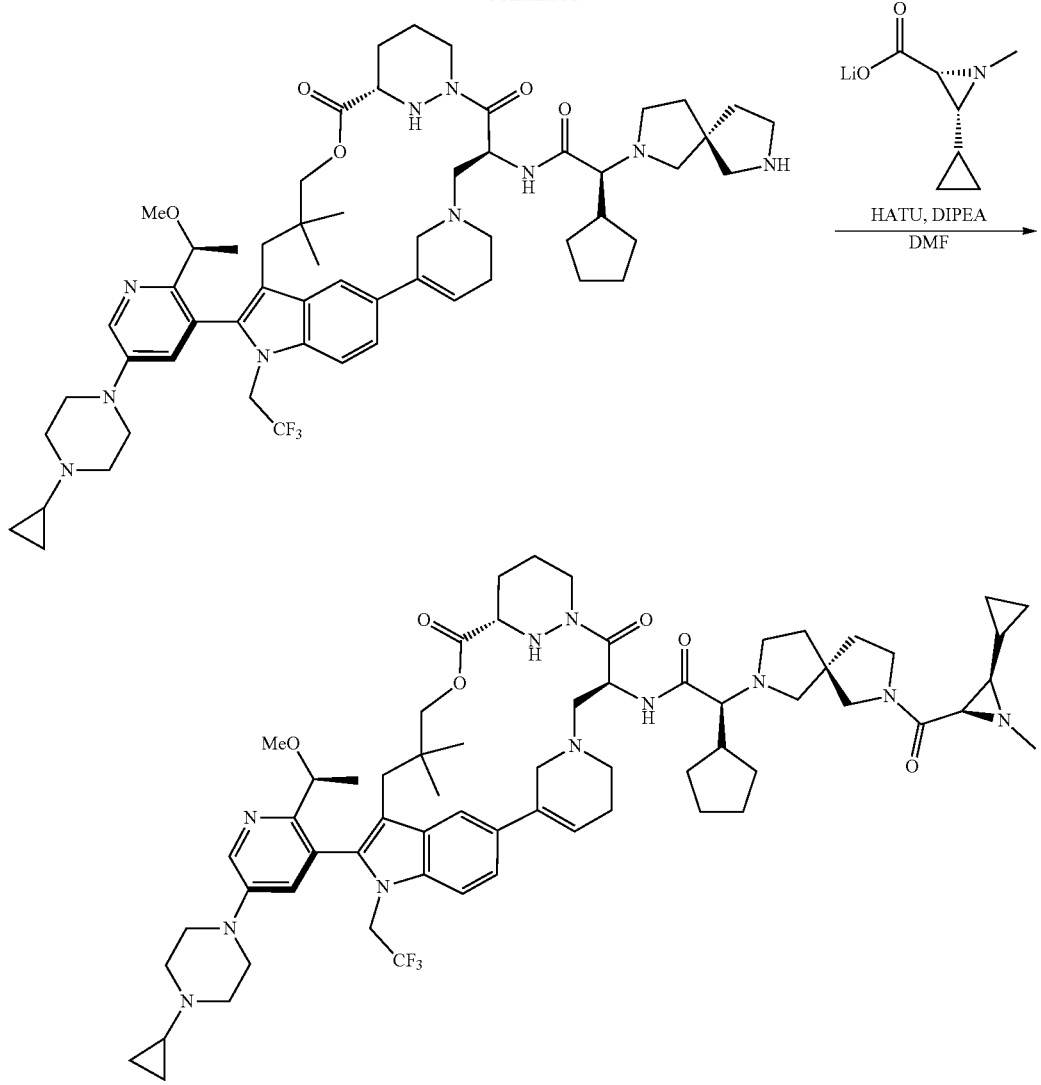

Step 1: Synthesis of tert-butyl (5S)-7-((1 S)-1-cyclopentyl-2-(((6³S,4S)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-2¹ 2²,2³,2⁶,6¹,6²,6³,6⁴,6⁵,6⁶-decahydro-1¹H-8-oxa-1(5,3)-indola-6(1,3)-pyridazina-2(5,1)-pyridinacycloundecaphane-4-yl)amino)-2-oxoethyl)-2,7-diazaspiro[4.4]nonane-2-carboxylate To a solution of (S)-2-((S)-7-(tert-butoxycarbonyl)-2,7-diazaspiro[4.4]nonan-2-yl)-2-cyclopentylacetic acid (332.54 mg, 0.944 mmol), HATU (310.89 mg, 0.818 mmol), and DIPEA (812.89 mg, 6.290 mmol) in MeCN (10 mL) at 0° C. was added (6³S,4S)-4-amino-1²-(5-(4-cyclopropylpiperazin-1-yl)-2-((S)-1-methoxyethyl)pyridin-3-yl)-10,10-dimethyl-1¹-(2,2,2-trifluoroethyl)-2¹ 2²,2³,26,61 62,6³,64,65,66-decahydro-1¹H-8-oxa-1(5,3)-indola-6(1,3)-pyridazina-2(5,1)-pyridinacycloundecaphane-5,7-dione (500 mg, 0.629 mmol). The mixture was stirred at 0° C. for 1 h and was then concentrated under reduced pressure. The residue was purified by reverse phase chromatography (0→100% MeCN/H₂O) to afford the desired product (600 mg, 78% yield) as a solid. LCMS (ESI) m/z [M+H] calcd for C₆₂H₈₇F₃N₁₀O₇ 1141.68; found: 1141.9.

Step 2: Synthesis of (2S)-2-cyclopentyl-N-((6³S, 4S)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-2¹ 2²,2³,2⁶,6¹,6²,6³,6⁴, 6⁵,6⁶-decahydro-1¹H-8-oxa-1(5,3)-indola-6(1,3)-pyridazina-2(5,1)-pyridinacycloundecaphane-4-yl)-2-((S)-2,7-diazaspiro[4.4]nonan-2-yl)acetamide To a solution of tert-butyl (5S)-7-((1 S)-1-cyclopentyl-2-(((6³S,4S)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-21,22,2³,2⁶,6¹,6²,6³,6⁴,6⁵,6⁶-decahydro-1¹H-8-oxa-1(5,3)-indola-6(1,3)-pyridazina-2(5,1)-pyridinacycloundecaphane-4-yl)amino)-2-oxoethyl)-2,7-diazaspiro[4.4]nonane-2-carboxylate (600 mg, 0.526 mmol) in DCM (6 mL) at 0° C. was added TFA (6 mL). The resulting mixture was stirred at 0° C. for 1 h. The mixture was concentrated under reduced pressure then basified to pH 8 with sat. NaHCO₃ (aq.). The resulting mixture was extracted with DCM (3×100 mL) and the combined organic layers were washed with brine (3×100 mL), dried over Na₂SO₄, filtered, and concentrated under reduced pressure to afford the desired product (503 mg, 92% yield) as a solid. LCMS (ESI) m/z [M+H] calcd for C₅₇H₇₉F₃N₁₀O₅ 1041.63; found: 1041.8.

Step 3: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-((6³S,4S)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-2¹ 2²,2³,2⁶,6¹,6²,6³,6⁴,6⁵,6⁶-decahydro-1¹H-8-oxa-1(5,3)-indola-6(1,3)-pyridazina-2(5,1)-pyridinacycloundecaphane-4-yl)acetamide To a solution of (2S)-2-cyclopentyl-N-((6³S,4S)-12-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-2¹ 2²,2³,2⁶,6¹,6²,6³,6⁴,6⁵,6⁶-decahydro-11H-8-oxa-1(5,3)-indola-6(1,3)-pyridazina-2(5,1)-pyridinacycloundecaphane-4-yl)-2-((S)-2,7-diazaspiro[4.4]nonan-2-yl)acetamide (300 mg, 0.288 mmol), DIPEA (372.34 mg, 2.880 mmol), and lithium (2R,3R)-3-cyclopropyl-1-methylaziridine-2-carboxylate (63.5 mg, 0.432 mmol) in DMF (6 mL) at 0° C. was added HATU (142.41 mg, 0.374 mmol). The mixture was stirred at 0° C. for 1 h and was then concentrated under reduced pressure. The residue was purified by reverse phase chromatography (8→23% MeCN/H₂O) to afford the desired product (100 mg, 27% yield) as a solid. LCMS (ESI) m/z [M+H] calcd for C₆₄H₈₈F₃N₁₁O₆ 1164.70; found: 1164.9.

Example A1: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-((6³S,4S)_12-(5-(4-cyclopropylpiperazin-1-yl)-2-((S)-1-methoxyethyl)pyridin-3-yl)-1¹-ethyl-10,10-dimethyl-5,7-dioxo-21²,2³,2⁶,6¹,6²,6³,6⁴,6⁵,6⁶-decahydro-1¹H-8-oxa-1(5,3)-indola-6(1,3)-pyridazina-2(5,1)-pyridinacycloundecaphane- 4-yl)acetamide

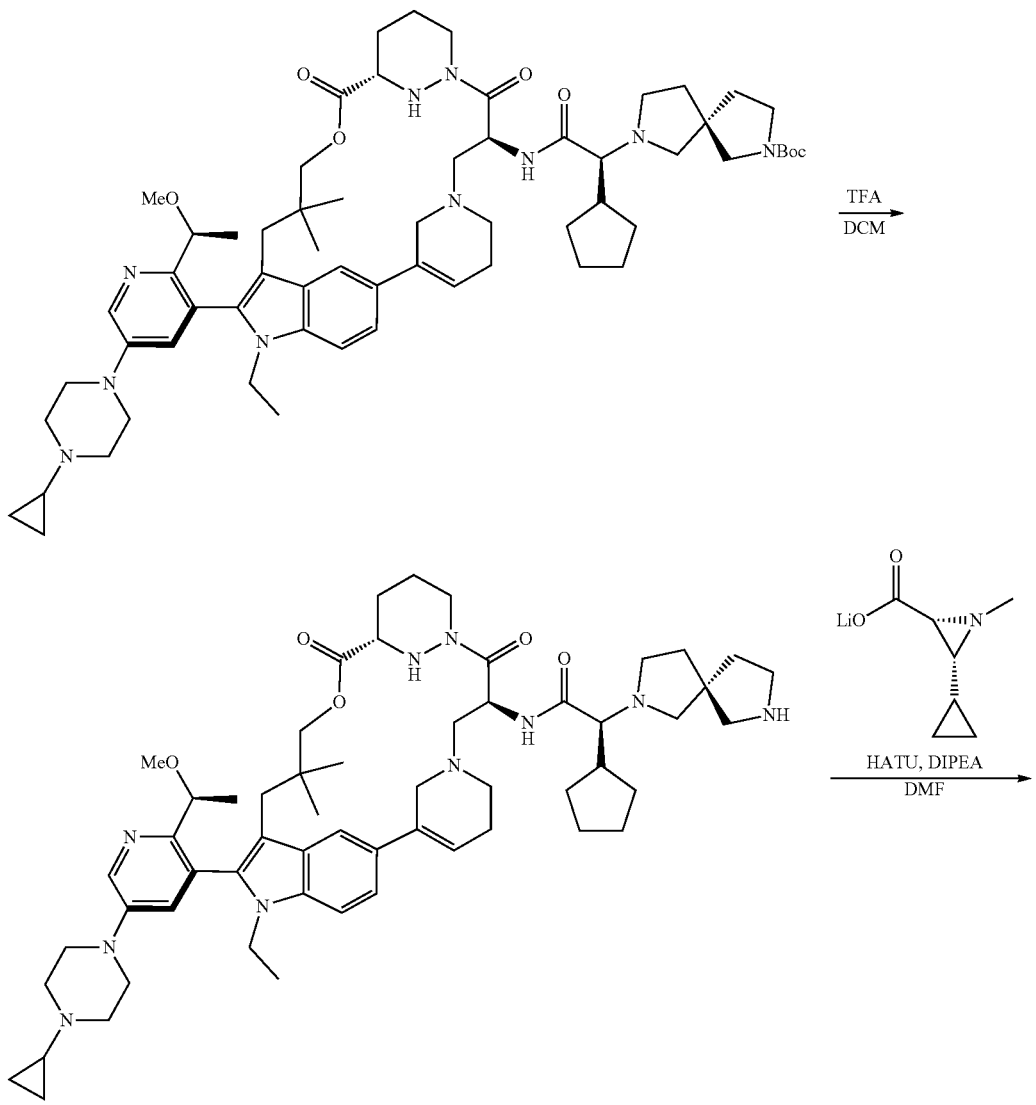

-continued

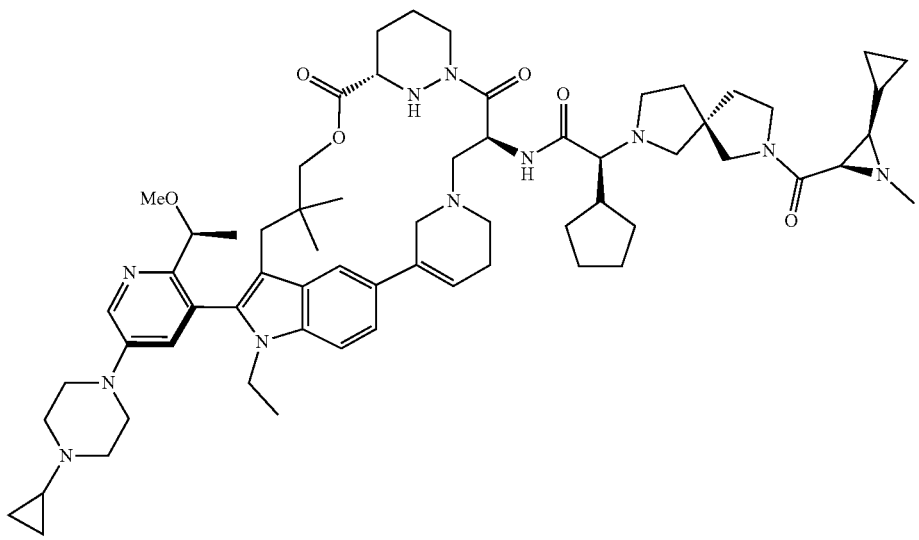

Step 1: Synthesis of (2S)-2-cyclopentyl-N-((6³S, 4S)-1²-(5-(4-cyclopropylpiperidin-1-yl)-2-((S)-1-methoxyethyl)pyridin-3-yl)-1¹-ethyl-10,10-dimethyl-5,7-dioxo-2¹ 2²,2³,2⁶,6¹,6²,6³,6⁴,6⁵,6⁶-decahydro-1¹H-8-oxa-1(5,3)-indola-6(1,3)-pyridazina-2(5,1)-pyridinacycloundecaphane-4-yl)-2-((S)-2,7-diazaspiro[4.4]nonan-2-yl)acetamide To a solution of tert-butyl (5S)-7-(((1 S)-1-cyclopentyl-2-(((6³S,4S)-1²-(5-(4-cyclopropylpiperazin-1-yl)-2-((S)-1-methoxyethyl)pyridin-3-yl)-1¹-ethyl-10,10-dimethyl-5,7-dioxo-2¹ 2²,2³,2⁶,6¹,6²,6³,6⁴,6⁵,6⁶-decahydro-1¹H-8-oxa-1(5,3)-indola-6(1,3)-pyridazina-2(5,1)-pyridinacycloundecaphane-4-yl)amino)-2-oxoethyl)-2,7-diazaspiro[4.4]nonane-2-carboxylate (900 mg, 0.828 mmol) in DCM (9 mL) at 0° C. was added TFA (4.5 mL). The resulting mixture was stirred at 0° C. for 30 min. The mixture was concentrated under reduced pressure then basified to pH 8 with sat. NaHCO₃ (aq.). The resulting mixture was extracted with DCM (3×150 mL) and the combined organic layers were washed with brine (3×120 mL), dried over Na₂SO₄, filtered, and concentrated under reduced pressure to afford the desired product (750 mg, 92% yield) as a solid. LCMS (ESI) m/z [M+H] calcd for $C_{58}H_{83}N_9O_5$ 986.66; found: 987.5.

Step 2: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-((6³S,4S)-1²-(5-(4-cyclopropylpiperazin-1-yl)-2-((S)-1-methoxyethyl)pyridin-3-yl)-1¹-ethyl-10,10-dimethyl-5,7-dioxo-2¹ 2²,2³,2⁶,6¹,6²,6³,6⁴,6⁵,6⁶-decahydro-1¹H-8-oxa-1(5,3)-indola-6(1,3)-pyridazina-2(5,1)-pyridinacycloundecaphane-4-yl) acetamide To a solution of (2S)-2-cyclopentyl-N-((6³S,4S)-1²-(5-(4-cyclopropylpiperidin-1-yl)-2-((S)-1-methoxyethyl)pyridin-3-yl)-1¹-ethyl-10,10-dimethyl-5,7-dioxo-2¹ 2²,2³,2⁶,6¹,6², 6³,6⁴,6⁵,6⁶-decahydro-1¹H-8-oxa-1(5,3)-indola-6(1,3)-pyridazina-2(5,1)-pyridinacycloundecaphane-4-yl)-2-((S)-2,7-diazaspiro[4.4]nonan-2-yl)acetamide (300 mg, 0.304 mmol), DIPEA (196.35 mg, 1.520 mmol), and lithium (2R,3R)-3-cyclopropyl-1-methylaziridine-2-carboxylate (89.39 mg, 0.608 mmol) in DMF (4 mL) at 0° C. was added HATU (150.19 mg, 0.395 mmol). The mixture was stirred at 0° C. for 1 h and was quenched with H₂O (3 mL) at 0° C. The aqueous layer was extracted with DCM/MeOH (10/1; 3×20 mL) and the combined organic layers were washed with brine (3×20 mL), dried over Na₂SO₄, filtered, and concentrated under reduced pressure. The residue was purified by prep-TLC (9% MeOH/DCM) to afford the desired product (155 mg, 43% yield) as a solid. LCMS (ESI) m/z [M+H] calcd for $C_{64}H_{91}N_{11}O_6$ 1110.73; found: 1110.8.

Example A36: Synthesis of (2S)-2-((S)-7-((2R,3R)-3-cyclopropyl-1-methylaziridine-2-carbonyl)-2,7-diazaspiro[4.4]nonan-2-yl)-N-((6³S,4S)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-21,22,2³,2⁶,6¹,6²,6³,6⁴,6⁵,6⁶-decahydro-1¹H-8-oxa-1(5,3)-indola-6(1,3)-pyridazina-2(5,1)-pyridinacycloundecaphane-4-yl)-3-methylbutanamide
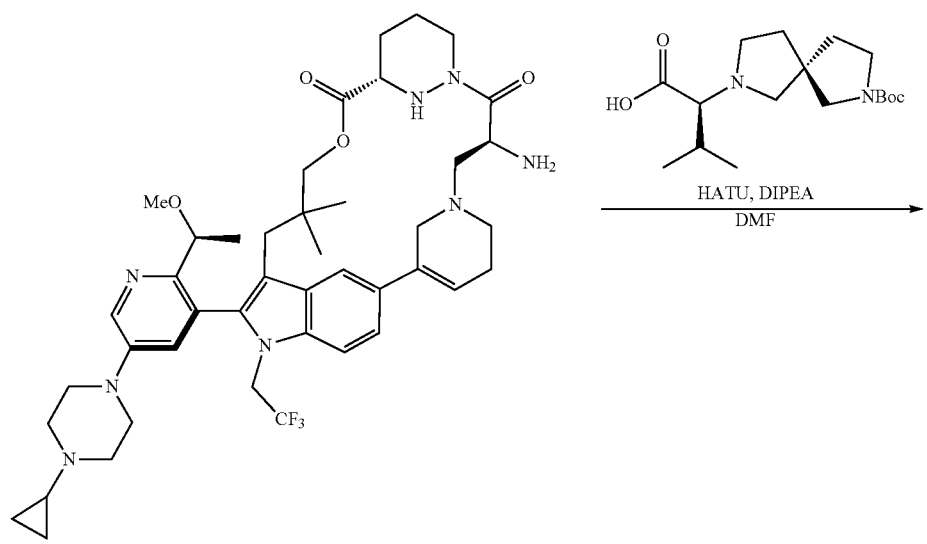
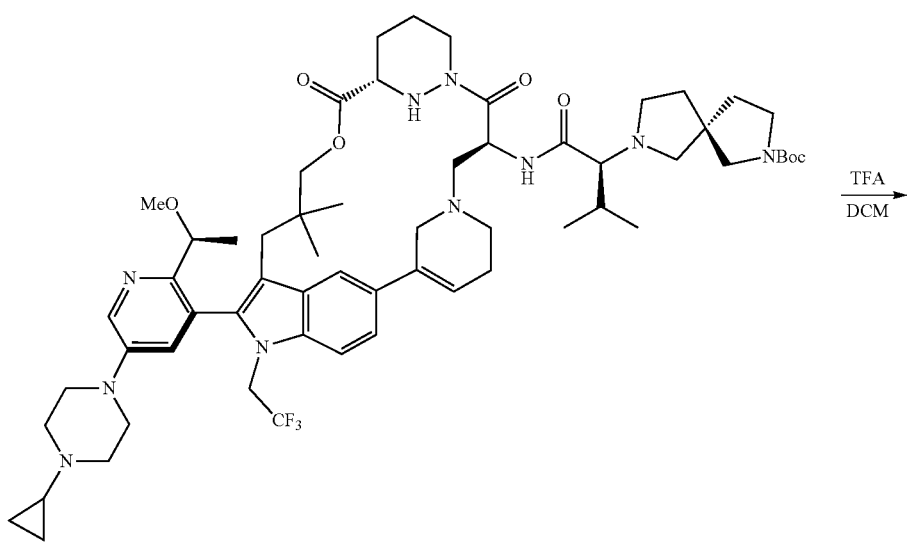

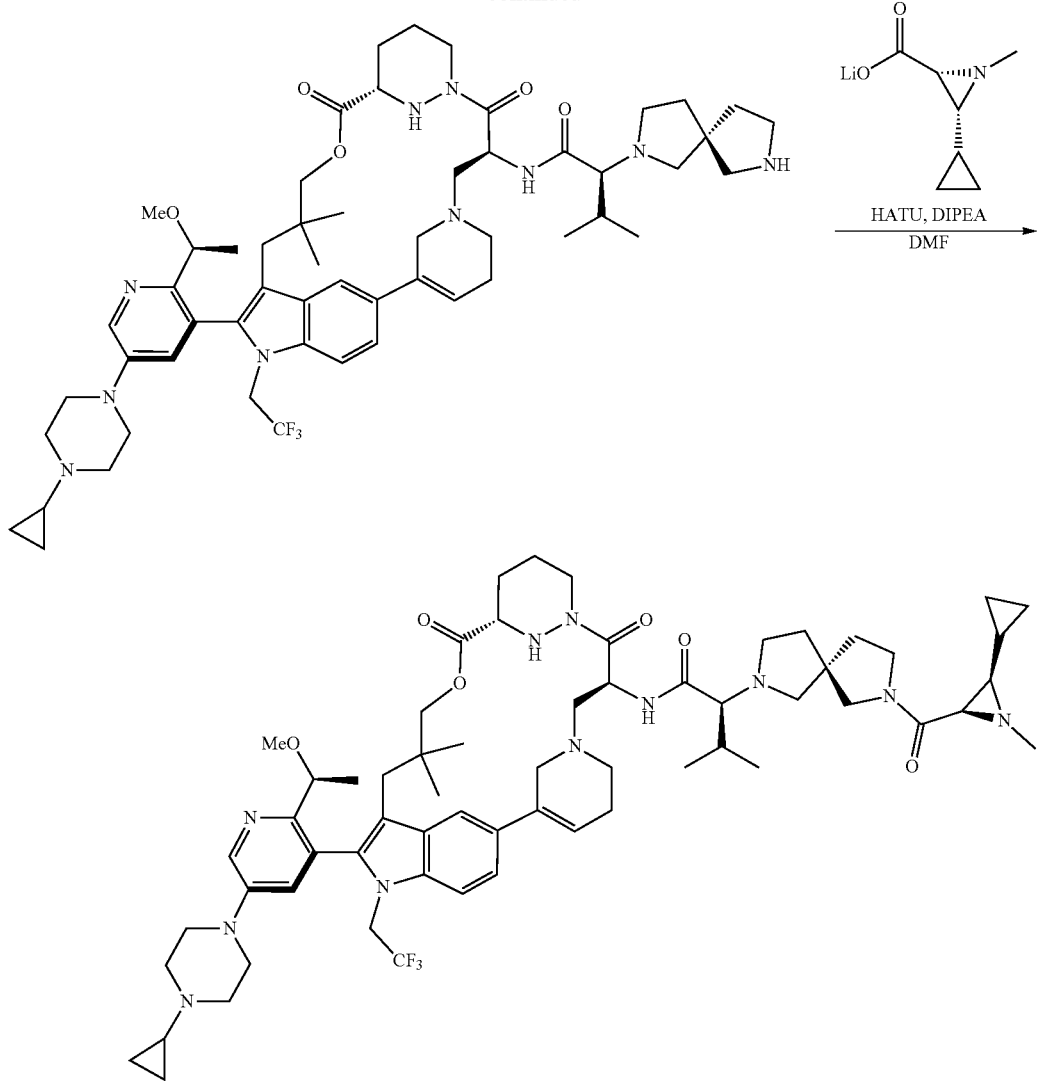

Step 1: Synthesis of tert-butyl (5S)-7-((2S)-1-(((6³S,4S)-1²-(5-(4-cyclopropylpiperazin-1-yl)-2-((S)-1-methoxyethyl)pyridin-3-yl)-10,10-dimethyl-5,7-dioxo-1-(2,2,2-trifluoroethyl)-2² 22,2³,2⁶,62, 6³,6⁴,6⁵,6⁶-decahydro-1¹H-8-oxa-1(5,3)-indola-6(1,3)-pyridazina-2(5,1)-pyridinacycloundecaphane-4-yl)amino)-3-methyl-i1-oxobutan-2-yl)-2,7-diazaspiro[4.4]nonane-2-carboxylate To a solution of (S)-2-((S)-7-(tert-butoxycarbonyl)-2,7-diazaspiro[4.4]nonan-2-yl)-3-methylbutanoic acid (318.6 mg, 1.40 mmol), HATU (451 0.0 mg, 1 0.19 mmol), and DIPEA (1393.6 mg, 10.78 mmol) in DMF (20 mL) at 0 00 was added (6³S,4S)-4-amino-1²-(5-(4-cyclopropylpiperazin-1-yl)-2-((S)-1-methoxyethyl)pyridin-3-yl)-10,10-dimethyl-1 ¹-(2,2,2-trifluoroethyl)-2¹ 2²,2³,2⁶,6¹,6²,6³,6a,6⁵,6⁶-decahydro-1 ¹H-8-oxa-1 (5,3)-indola-6(1,3)-pyridazina-2(5,1)-pyridinacycloundecaphane-5,7-dione (800.00 mg, 1.08 mmol). The mixture was stirred for 1 h at room temperature and then the reaction was quenched with H₂O (3 mL) at 0° C. The aqueous layer was extracted with DCM (3×100 mL) and the combined organic layers were washed with brine (3×100 mL), dried over Na₂SO₄, filtered, and concentrated under reduced pressure. The residue was purified by prep-TLC (9% EtOAc/pet. ether) to afford the desired product (800 mg, 78% yield) as a solid. LCMS (ESI) m/z [M+H] calcd for C₆₀H₈₅F₃N₁₀O₇ 1115.66; found: 1115.6.

Step 2: Synthesis of (2S)-N-((6³S,4S)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-2¹ 2²,2³,2⁶,6¹,6²,6³,6⁴,6⁵,6⁶-decahydro-1¹H-8-oxa-1(5,3)-indola-6(1,3)-pyridazina-2(5,1)-pyridinacycloundecaphane-4-yl)-3-methyl-2-((S)-2,7-diazaspiro[4.4]nonan-2-yl) butanamide To a solution of tert-butyl (5S)-7-((2S)-1-(((6³S,4S)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-2¹ 2²,2³,2⁶,6¹,6²,6³,6⁴,6⁵,6⁶-decahydro-1¹H-8-oxa-1 (5,3)-indola-6(1,3)-pyridazina-2(5,1)-pyridinacycloundecaphane-4-yl)amino)-3-methyl-1-oxobutan-2-yl)-2,7-diazaspiro[4.4]nonane-2-carboxylate (560 mg, 0.528 mmol) in DCM (6 mL) at 0° C. was added TFA (6 mL). The resulting mixture was stirred at room temperature for 1 h. The mixture was concentrated under reduced pressure then basified to pH 7 with sat. NaHCO$_3$ (aq.). The resulting mixture was extracted with DCM (3×100 mL) and the combined organic layers were washed with brine (3×10 mL), dried over Na$_2$SO$_4$, filtered, and concentrated under reduced pressure to afford the desired product (486 mg, 96% yield) as a solid. LCMS (ESI) m/z [M/2+H] calcd for C$_{55}$H$_{77}$F$_3$N$_{10}$O$_5$ 508.31; found: 508.5.

Step 3: Synthesis of (2S)-2-((S)-7-((2R,3R)-3-cyclopropyl-1-methylaziridine-2-carbonyl)-2,7-diazaspiro[4.4]nonan-2-yl)-N-((6$^3$S,4S)-1$^2$-(5-(4-cyclopropylpiperazin-1-yl)-2-((S)-1-methoxyethyl)pyridin-3-yl)-10,10-dimethyl-5,7-dioxo-1$^1$-(2,2,2-trifluoroethyl)-2$^1$ 2$^2$,2$^3$,2$^6$,6$^{17}$,6$^2$,6$^3$,6$^4$,6$^5$, 6$^6$-decahydro-1$^1$H-8-oxa- 1(5,3)-indola-6(1,3)-pyridazina-2(5,1)-pyridinacycloundecaphane-4-yl)-3-methylbutanamide To a solution of (2S)-N-((6$^3$S,4S)-1$^2$-(5-(4-cyclopropylpiperazin-1-yl)-2-((S)-1-methoxyethyl)pyridin-3-yl)-10,10-dimethyl-5,7-dioxo-1$^1$-(2,2,2-trifluoroethyl)-2$^1$ 2$^2$,2$^3$,2$^6$, 6$^1$,6$^2$,6$^3$,6$^4$,6$^5$,6$^6$-decahydro-11H-8-oxa-1(5,3)-indola-6(1,3)-pyridazina-2(5,1)-pyridinacycloundecaphane-4-yl)-3-methyl-2-((S)-2,7-diazaspiro[4.4]nonan-2-yl)butanamide (250 mg, 0.246 mmol), DIPEA (159.12 mg, 1.230 mmol), and lithium (2R,3R)-3-cyclopropyl-1-methylaziridine-2-carboxylate (52.14 mg, 0.369 mmol) in DMF (5 mL) at 0° C. was added HATU (121.71 mg, 0.320 mmol). The mixture was stirred at 0° C. for 1 h and was then quenched with H$_2$O (3 mL) at 0° C. The aqueous layer was extracted with DCM/MeOH (10/1; 3×50 mL) and the combined organic layers were washed with brine (3×50 mL), dried over Na$_2$SO$_4$, filtered, and concentrated under reduced pressure. The residue was purified by prep-TLC (9% MeOH/DCM) to afford the desired product (140 mg, 47% yield) as a solid. LCMS (ESI) m/z [M+H] calcd for C$_{62}$H$_{86}$F$_3$N$_{11}$O$_6$ 1138.68; found: 1138.8.

Example A12: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-((6$^3$S, 4S)-12-(5-(4-cyclopropylpiperazin-1-yl)-2-((S)-1-methoxyethyl)pyridin-3-yl)-1$^1$-ethyl-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)acetamide

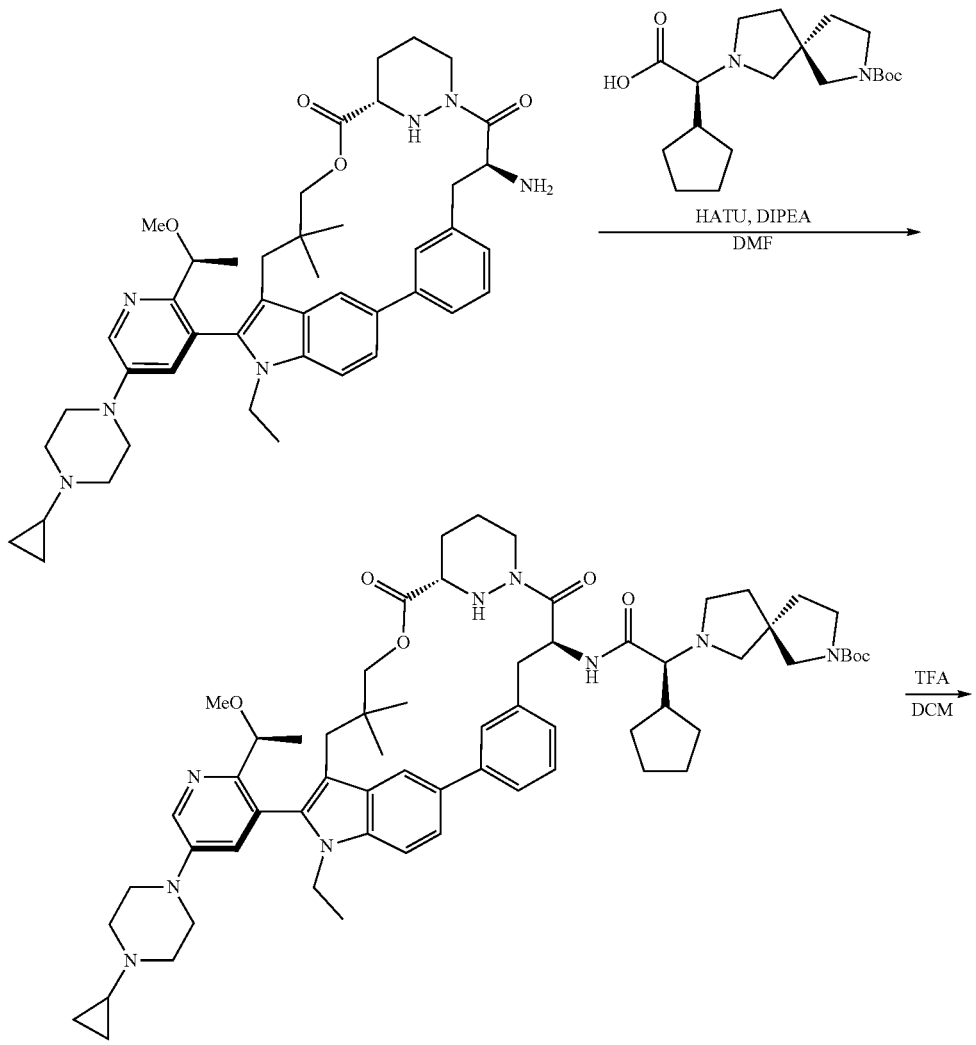

411

-continued

412

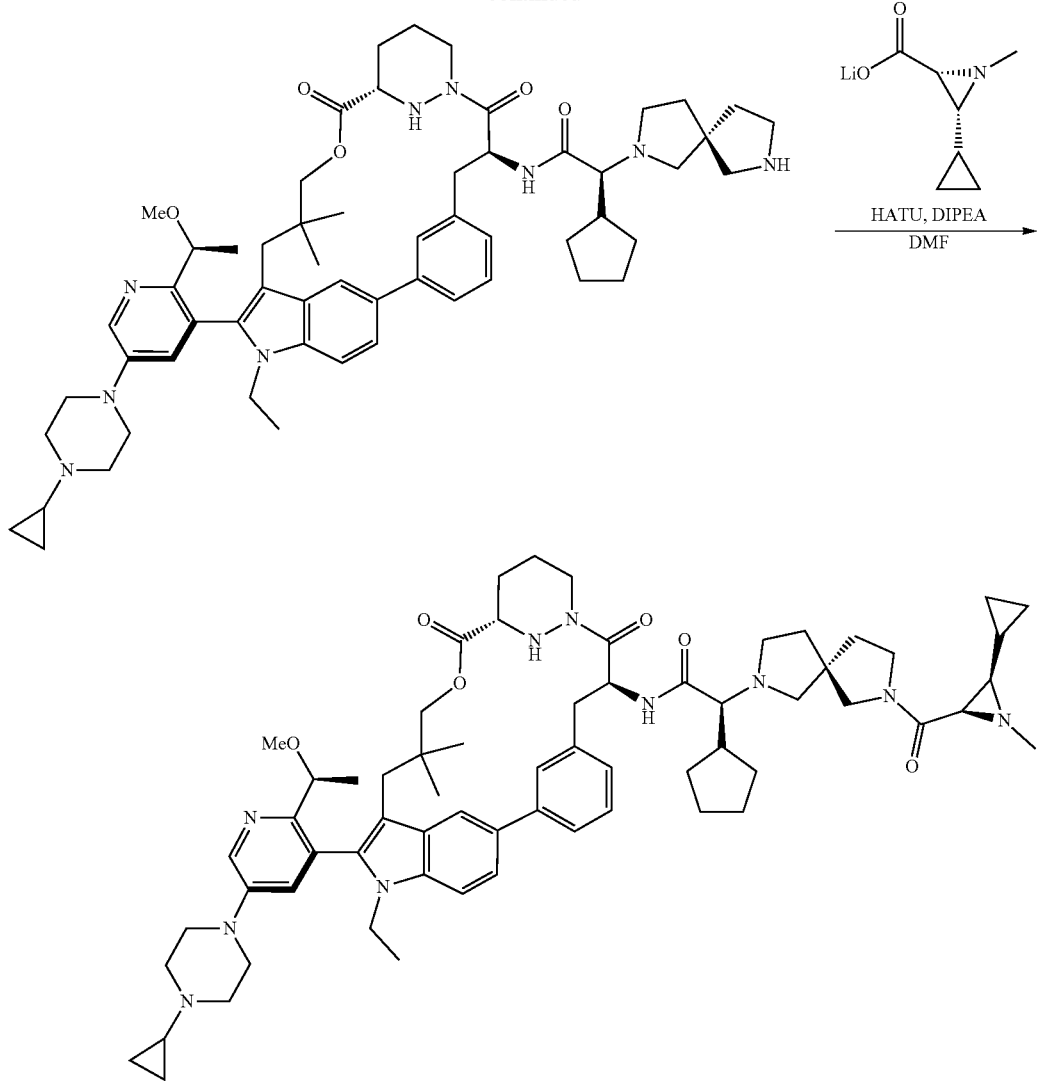

HATU, DIPEA
DMF
→

Step 1: Synthesis of tert-butyl (5S)-7-((1 S)-1-cyclopentyl-2-(((6³S,4S)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-2-oxoethyl)-2,7-diazaspiro[4.4]nonane-2-carboxylate To a solution of (6³S,4S)-4-amino-1²-(5-(4-cyclopropylpiperazin-1-yl)-2-((S)-1-methoxyethyl)pyridin-3-yl)-1¹-ethyl-10,10-dimethyl-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (420 mg, 0.562 mmol) and DIPEA (725.71 mg, 5.620 mmol) in DMF (4.5 mL) at 0° C. was added (S)-2-((S)-7-(tert-butoxycarbonyl)-2,7-diazaspiro[4.4]nonan-2-yl)-2-cyclopentylacetic acid (296.88 mg, 0.843 mmol) and HATU (312.62 mg, 0.731 mmol). The resulting mixture was stirred at room temperature for 1.5 h and was then quenched with H₂O (100 mL) at 0° C. The aqueous layer was extracted with EtOAc (3×20 mL) and the combined organic layers were washed with brine (2×10 mL), dried over Na₂SO₄, filtered, and concentrated under reduced pressure. The residue was purified by prep-TLC (6% MeOH/DCM) to afford the desired product (600 mg, 98% yield) as a solid. LCMS (ESI) m/z [M+H] calcd for C₆₃H₈₇N₉O₇ 1082.68; found: 1082.7.

Step 2: Synthesis of (2S)-2-cyclopentyl-N-((6³S,4S)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-2-((S)-2,7-diazaspiro[4.4]nonan-2-yl)acetamide To a solution of tert-butyl (5S)-7-((1 S)-1-cyclopentyl-2-(((6³S,4S)-1²-(5-(4-cyclopropylpiperazin-1-yl)-2-((S)-1-methoxyethyl)pyridin-3-yl)-1¹-ethyl-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-2-oxoethyl)-2,7-diazaspiro[4.4]nonane-2-carboxylate (680 mg, 0.628 mmol) in DCM (7 mL) at 0° C. was added TFA (2.5 mL). The reaction mixture was stirred at room temperature for 2 h and then the resulting mixture was concentrated under reduced pressure. The residue was neutralized to pH 8 with sat. NaHCO$_3$ (aq) and the aqueous layer was extracted with EtOAc (3×30 mL). The combined organic layers were washed with brine (2×15 mL), dried over Na$_2$SO$_4$, filtered, and concentrated under reduced pressure to afford the desired product (600 mg, crude) as a solid. LCMS (ESI) m/z [M+H] calcd for C$_{58}$H$_{79}$N$_9$O$_5$ 982.63; found: 982.6.

Step 3: Synthesis of (2S)-2-cyclopentyl-2-((S)-7-((2R,3R)-3-cyclopropyl-1-methylaziridine-2-carbonyl)-2,7-diazaspiro[4.4]nonan-2-yl)-N-((6$^3$S,4S)-12-(5-(4-cyclopropylpiperazin-1-yl)-2-((S)-1-methoxyethyl)pyridin-3-yl)-1$^1$-ethyl-10,10-dimethyl-5,7-dioxo-6$^1$,6$^2$,6$^3$,6$^4$,6$^5$,6$^6$-hexahydro-1$^1$H-8-oxa-1 (5,3)-indola-6(1,3)-pyridazina-2(1,3)-benzenacycloundecaphane-4-yl)acetamide To a solution of (2S)-2-cyclopentyl-N-((6$^3$S,4S)-1$^2$-(5-(4-cyclopropylpiperazin-1-yl)-2-((S)-1-methoxyethyl)pyridin-3-yl)-1$^1$-ethyl-10,10-dimethyl-5,7-dioxo-6$^1$,6$^2$,6$^3$,6$^4$,6$^5$,6$^6$-hexahydro-1$^1$H-8-oxa-1 (5,3)-indola-6(1,3)-pyridazina-2(1, 3)-benzenacycloundecaphane-4-yl)-2-((S)-2,7-diazaspiro[4.4]nonan-2-yl)acetamide (440 mg, 0.448 mmol) and DIPEA (578.90 mg, 4.480 mmol) in DMF (4 mL) at 0° C. was added a solution of lithium (2R,3R)-3-cyclopropyl-1-methylaziridine-2-carboxylate (131.78 mg, 0.896 mmol) and HATU (221.40 mg, 0.582 mmol). The resulting mixture was stirred at room temperature for 1.5 h and was then quenched with H$_2$O (40 mL) at 0° C. The aqueous layer was extracted with EtOAc (3×20 mL) and the combined organic layers were washed with brine (2×10 mL), dried over Na$_2$SO$_4$, filtered, and concentrated under reduced pressure. The residue was purified by prep-TLC (8% MeOH/DCM) to afford the desired product (200.3 mg, 40% yield) as a solid. LCMS (ESI) m/z [M/2+H] calcd for C$_{65}$H$_{88}$N$_{10}$O$_6$ 553.36; found: 553.7.

Example A4: Synthesis of (2S)-2-((S)-7-((2R,3R)-3-cyclopropyl-1-methylaziridine-2-carbonyl)-2,7-diazaspiro[4.4]nonan-2-yl)-N-((6$^3$S,4S)-1$^2$-(5-(4-cyclopropylpiperazin-1-yl)-2-((S)-1-methoxyethyl)pyridin-3-yl)-10,10-dimethyl-5,7-dioxo-1$^1$-(2,2,2-trifluoroethyl)-6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)-3-methylbutanamide

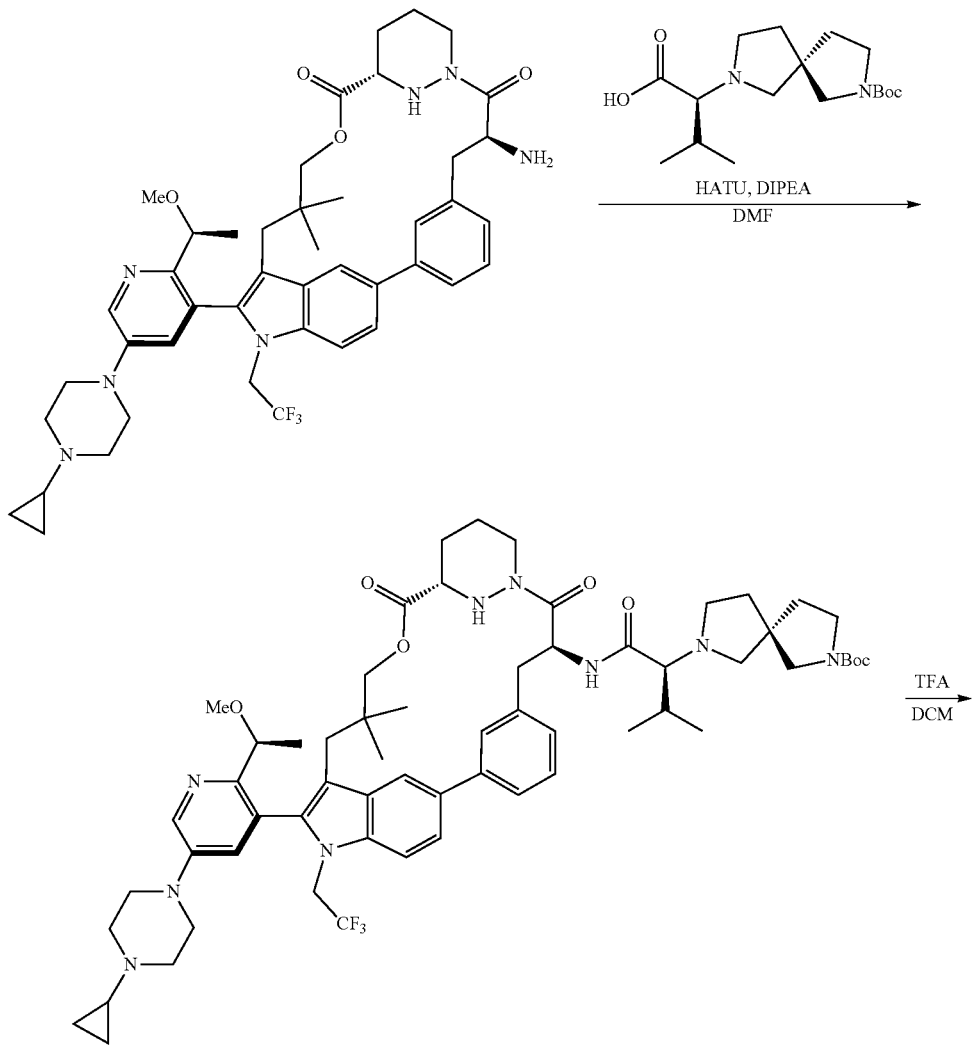

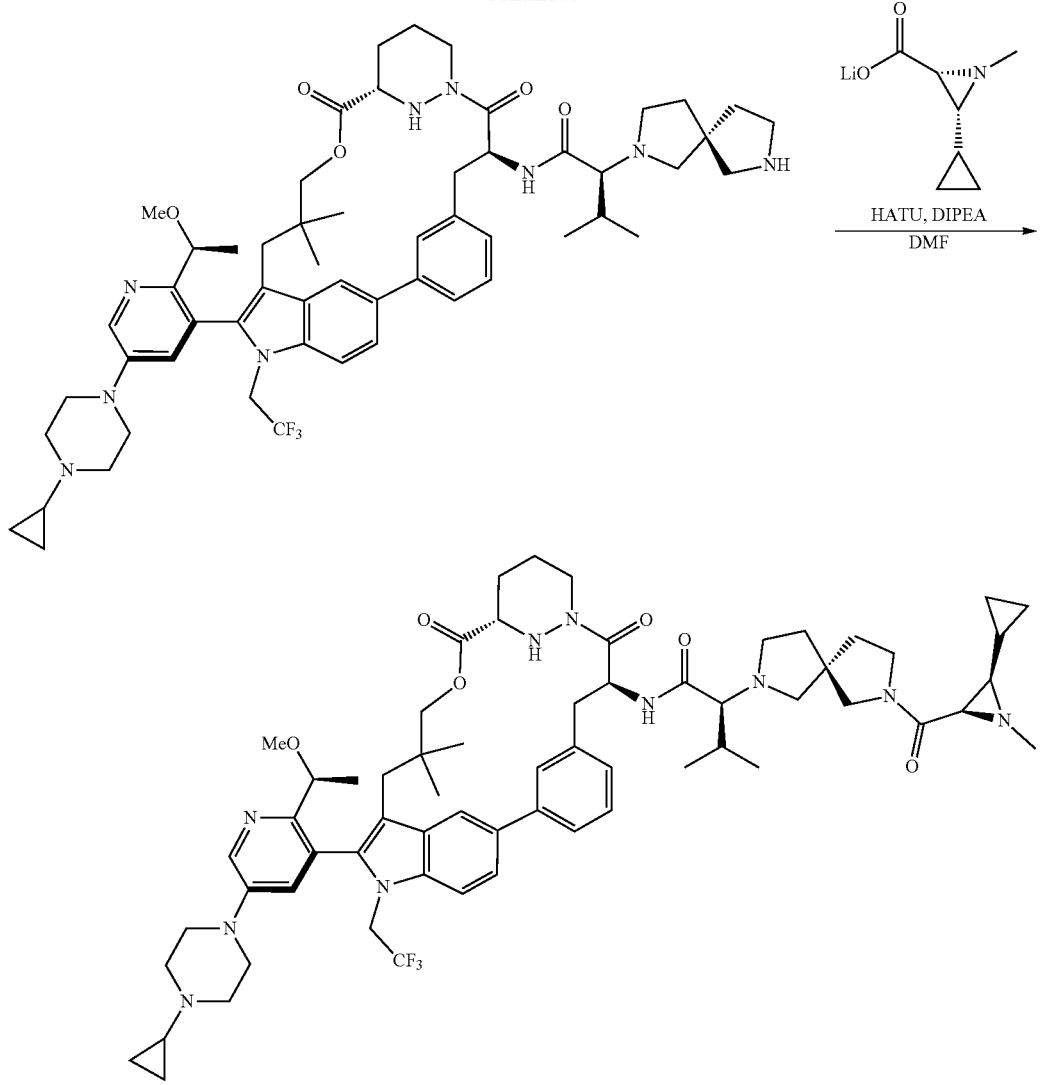

Step 1: Synthesis of tert-butyl (5S)-7-((2S)-1-(((6³S,4S)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-2,7-diazaspiro[4.4]nonane-2-carboxylate To a solution of (S)-2-((S)-7-(tert-butoxycarbonyl)-2,7-diazaspiro[4.4]nonan-2-yl)-3-methylbutanoic acid (610.58 mg, 1.871 mmol) and DIPEA (966.96 mg, 7.482 mmol) in MeCN (20 mL) at 0° C. was added a solution of (6³S,4S)-4-amino-1²-(5-(4-cyclopropylpiperazin-1-yl)-2-((S)-1-methoxyethyl)pyridin-3-yl)-10,10-dimethyl-1¹-(2,2,2-trifluoroethyl)-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (760 mg, 0.948 mmol) in MeCN (10 mL). To the mixture was added a solution of COMU (694.24 mg, 1.621 mmol) in MeCN (10 mL). The resulting mixture was stirred at 0° C. for 1 h and was then quenched with H₂O (20 mL) at 0° C. The mixture was then extracted with DCM (3×20 mL) and the combined organic layers were washed with brine (2×10 mL), dried over Na₂SO₄, filtered, and concentrated under reduced pressure. The residue was purified by silica gel column chromatography (8% MeOH/DCM) to afford the desired product (952 mg, 63%) as a solid. LCMS (ESI) m/z [M+H] calcd for $C_{61}H_{82}F_3N_9O_7$ 1110.64; found: 1110.6.

Step 2: Synthesis of (2S)-N-((6³S,4S)-1²-(5-(4-cyclopropylpiperazin-1-yl)-2-((S)-1-methoxyethyl)pyridin-3-yl)-10,10-dimethyl-5,7-dioxo-1'-(2,2,2-trifluoroethyl)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-((S)-2,7-diazaspiro[4.4]nonan-2-yl)butanamide To a solution of tert-butyl (5S)-7-((2S)-1-(((6³S,4S)-12-(5-(4-cyclopropylpiperazin-1-yl)-2-((S)-1-methoxyethyl)pyridin-3-yl)-10,10-dimethyl-5,7-dioxo-11-(2,2,2-trifluoroethyl)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-2,7-diazaspiro[4.4]

nonane-2-carboxylate (490 mg, 0.441 mmol) in DCM (9 mL) at 0° C. was added TFA (3 mL). The resulting mixture was stirred at 0° C. for 2 h and was then neutralized to pH 7 with sat. NaHCO₃ (aq). The resulting mixture was extracted with DCM (3×30 mL) and the combined organic layers were washed with brine (2×30 mL), dried over Na₂SO₄, filtered, and concentrated under reduced pressure to afford the desired product (410 mg, crude) as a solid. LCMS (ESI) m/z [M+H] calcd for $C_{56}H_{74}F_3N_9O_5$ 1010.58; found: 1010.6.

Step 3: Synthesis of (2S)-2-((S)-7-((2R,3R)-3-cyclopropyl-1-methylaziridine-2-carbonyl)-2,7-diazaspiro[4.4]nonan-2-yl)-N-((6³S,4S)-1²-(5-(4-cyclopropylpiperazin-1-yl)-2-((S)-1-methoxyethyl)pyridin-3-yl)-10,10-dimethyl-5,7-dioxo-1¹-(2,2,2-trifluoroethyl)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide To a solution of lithium (2R,3R)-3-cyclopropyl-1-methylaziridine-2-carboxylate (111.79 mg, 0.792 mmol) and DIPEA (307.03 mg, 2.376 mmol) in DMF (4 mL) at 0° C. was added a solution of HATU (195.71 mg, 0.515 mmol) in DMF (4 mL). To the mixture was added a solution of (2S)-N-((6³S,4S)-1²-(5-(4-cyclopropylpiperazin-1-yl)-2-((S)-1-methoxyethyl)pyridin-3-yl)-10,10-dimethyl-5,7-dioxo-11-(2,2,2-trifluoroethyl)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-((S)-2,7-diazaspiro[4.4]nonan-2-yl)butanamide (400 mg, 0.396 mmol) in DMF (4 mL). The resulting mixture was stirred at 0° C. for 3 h and was then quenched with H₂O (20 mL) at 0° C. The mixture was then extracted with EtOAc (2×50 mL) and the combined organic layers were washed with brine (2×20 mL), dried over Na₂SO₄, filtered, and concentrated under reduced pressure. The residue was purified by prep-TLC (6% MeOH/DCM) to afford the desired product (98.9 mg, 20% yield) as a solid. LCMS (ESI) m/z [M+H] calcd for $C_{63}H_{83}F_3N_{10}O_6$ 1133.65; found: 1133.8.

TABLE 4

Exemplary Compounds Prepared by Methods of the Present Invention

| Ex# | Molecular Formula | Calculated MW | Observed MW LCMS (ESI) m/z |
|---|---|---|---|
| A1 | $C_{64}H_{91}N_{11}O_6$ | [M + H] = 1110.73 | [M + H] = 1110.8 |
| A2 | $C_{63}H_{83}F_3N_{10}O_7$ | [M + H] = 1149.65 | [M + H] = 1149.8 |
| A3 | $C_{65}H_{85}F_3N_{10}O_7$ | [M + H] = 1175.67 | [M + H] = 1175.7 |
| A4 | $C_{63}H_{83}F_3N_{10}O_6$ | [M + H] = 1133.65 | [M + H] = 1133.8 |
| A5 | $C_{63}H_{86}N_{10}O_6$ | [M + H] = 1079.68 | [M + H] = 1079.9 |
| A6 | $C_{65}H_{85}F_3N_{10}O_6$ | [M + H] = 1159.67 | [M + H] = 1159.8 |
| A7 | $C_{65}H_{88}N_{10}O_7$ | [M/2 + H] = 561.35 | [M/2 + H] = 561.7 |
| A8 | $C_{65}H_{93}N_{11}O_6$ | [M + H] = 1124.74 | [M + H] = 1124.8 |
| A9 | $C_{63}H_{89}N_{11}O_7$ | [M + H] = 1112.70 | [M + H] = 1112.5 |
| A10 | $C_{60}H_{80}F_3N_{11}O_6S$ | [M + H] = 1140.61 | [M + H] = 1140.7 |
| A11 | $C_{60}H_{83}N_{11}O_6S$ | [M + H] = 1086.63 | [M + H] = 1086.6 |
| A12 | $C_{65}H_{88}N_{10}O_6$ | [M/2 + H] = 553.36 | [M/2 + H] = 553.7 |
| A13 | $C_{61}H_{86}F_3N_{11}O_8$ | [M + H] = 1158.67 | [M + H] = 1158.7 |
| A14 | $C_{63}H_{88}F_3N_{11}O_8$ | [M + H] = 1184.69 | [M + H] = 1184.7 |
| A15 | $C_{63}H_{91}N_{11}O_8$ | [M + H] = 1130.72 | [M + H] = 1130.8 |
| A16 | $C_{63}H_{86}N_{10}O_7$ | [M + H] = 1095.68 | [M + H] = 1095.9 |
| A17 | $C_{62}H_{81}F_3N_{10}O_7$ | [M + H] = 1135.63 | [M + H] = 1135.8 |
| A18 | $C_{64}H_{83}F_3N_{10}O_7$ | [M + H] = 1161.65 | [M + H] = 1161.9 |
| A19 | $C_{61}H_{84}F_3N_{11}O_7$ | [M + H] = 1140.66 | [M + H] = 1140.8 |
| A20 | $C_{63}H_{86}F_3N_{11}O_7$ | [M + H] = 1166.68 | [M + H] = 1166.9 |
| A21 | $C_{62}H_{86}F_3N_{11}O_8$ | [M + H] = 1170.67 | [M + H] = 1170.9 |
| A22 | $C_{62}H_{82}F_3N_{11}O_6S$ | [M + H] = 1166.62 | [M + H] = 1166.7 |

TABLE 4-continued

Exemplary Compounds Prepared by Methods of the Present Invention

| Ex# | Molecular Formula | Calculated MW | Observed MW LCMS (ESI) m/z |
|---|---|---|---|
| A23 | $C_{62}H_{85}N_{11}O_6S$ | [M + H] = 1112.65 | [M + H] = 1112.7 |
| A24 | $C_{64}H_{88}F_3N_{11}O_6$ | [M + H] = 1164.70 | [M + H] = 1164.9 |
| A25 | $C_{61}H_{86}F_3N_{11}O_7$ | [M + H] = 1142.68 | [M + H] = 1142.7 |
| A26 | $C_{63}H_{88}F_3N_{11}O_7$ | [M + H] = 1168.69 | [M + H] = 1168.8 |
| A27 | $C_{63}H_{91}N_{11}O_7$ | [M + H] = 1114.72 | [M + H] = 1114.8 |
| A28 | $C_{54}H_{71}N_9O_7S$ | [M + H] = 990.53 | [M + H] = 990.3 |
| A29 | $C_{61}H_{89}N_{11}O_8$ | [M + H] = 1104.70 | [M + H] = 1104.9 |
| A30 | $C_{61}H_{83}D_3F_3N_{11}O_7$ | [M + H] = 1145.70 | [M + H] = 1145.8 |
| A31 | $C_{63}H_{85}D_3F_3N_{11}O_7$ | [M + H] = 1171.71 | [M + H] = 1172.0 |
| A32 | $C_{60}H_{77}D_3F_3N_{11}O_6S$ | [M + H] = 1143.63 | [M + H] = 1143.8 |
| A33 | $C_{60}H_{80}D_3N_{11}O_6S$ | [M + H] = 1089.65 | [M + H] = 1089.8 |
| A34 | $C_{62}H_{79}D_3F_3N_{11}O_6S$ | [M + H] = 1169.64 | [M + H] = 1169.7 |
| A35 | $C_{62}H_{82}D_3N_{11}O_6S$ | [M + H] = 1115.67 | [M + H] = 1115.8 |
| A36 | $C_{62}H_{86}F_3N_{11}O_6$ | [M + H] = 1138.68 | [M + H] = 1138.8 |
| A37 | $C_{62}H_{82}F_3N_{11}OS$ | [M + H] = 1182.62 | [M + H] = 1182.8 |
| A38 | $C_{63}H_{83}F_3N_{10}O_7S$ | [M + H] = 1181.62 | [M + H] = 1182.1 |
| A39 | $C_{61}H_{81}F_3N_{10}O_7S$ | [M + H] = 1155.61 | [M + H] = 1155.7 |
| A40 | $C_{66}H_{86}F_3N_9O_7$ | [M/2 + H] = 587.84 | [M/2 + H] = 588.3 |
| A41 | $C_{64}H_{84}F_3N_9O_7$ | [M + H] = 1148.65 | [M + H] = 1148.9 |
| A42 | $C_{64}H_{82}F_3N_{10}O_8$ | [M + H] = 1183.69 | [M + H] = 1183.9 |
| A43 | $C_{62}H_{87}F_3N_{10}O_8$ | [M + H] = 1157.68 | [M + H] = 1157.9 |
| A44 | $C_{62}H_{85}N_{11}O_7$ | [M + H] = 1096.67 | [M + H] = 1096.9 |
| B7 | $C_{65}H_{88}N_{10}O_6$ | [M + H] = 1113.7 | [M + H] = 1113.7 |
| B8 | $C_{63}H_{88}F_3N_{11}O_7$ | [M + H] = 1176.7 | [M + H] = 1176.8 |
| B9 | $C_{60}H_{80}F_3N_{11}O_6S$ | [M + H] = 1148.7 | [M + H] = 1148.8 |
| B28 | $C_{65}H_{88}N_{10}O_6$ | [M + H] = 1106.7 | [M + H] = 1106.7 |
| B29 | $C_{63}H_{88}F_3N_{11}O_7$ | [M + H] = 1169.7 | [M + H] = 1169.7 |
| B30 | $C_{60}H_{80}F_3N_{11}O_6S$ | [M + H] = 1141.6 | [M + H] = 1141.7 |

Biological Assays

All compounds herein exhibited an IC₅₀ of 1.1 μM or less in the AsPC-1 (K-Ras G12D) pERK potency assay described below.

Potency assay: pERK

The purpose of this assay is to measure the ability of test compounds to inhibit K-Ras in cells. Activated K-Ras induces increased phosphorylation of ERK at Threonine 202 and Tyrosine 204 (pERK). This procedure measures a decrease in cellular pERK in response to test compounds. The procedure described below in AsPC-1 cells is applicable to K-Ras G12D.

Note: This protocol may be executed substituting other cell lines to characterize inhibitors of other RAS variants, including, for example, H358 (K-Ras G12C), Capan-1 (K-Ras G12V), or NCI-H1355 (K-Ras G13C).

AsPC-1 cells were grown and maintained using media and procedures recommended by the ATCC. On the day prior to compound addition, cells were plated in 384-well cell culture plates (40 μl/well) and grown overnight in a 37° C., 5% CO₂ incubator. Test compounds were prepared in 10, 3-fold dilutions in DMSO, with a high concentration of 10 mM. On the day of assay, 40 nL of test compound was added to each well of cell culture plate using an Echo550 liquid handler (LabCyte®). Concentrations of test compound were tested in duplicate. After compound addition, cells were incubated 4 hours at 37° C., 5% CO2. Following incubation, culture medium was removed and cells were washed once with phosphate buffered saline.

Cellular pERK level was determined using the AlphaLISA SureFire Ultra p-ERK1/2 Assay Kit (PerkinElmer). Cells were lysed in 25 μL lysis buffer, with shaking at 600 RPM at room temperature. Lysate (10 μL) was transferred to a 384-well Opti-plate (PerkinElmer) and 5 μL acceptor mix was added. After a 2-hour incubation in the dark, 5 μL donor mix was added, plate was sealed, and incubated 2 hours at room temperature. Signal was read on an Envision plate reader (PerkinElmer) using standard AlphaLISA settings. Analysis of raw data was carried out in Excel (Microsoft) and Prism (GraphPad). Signal was plotted vs. the decadal logarithm of compound concentration, and $IC_{50}$ was determined by fitting a 4-parameter sigmoidal concentration response model.

Compound A and Compound B, Representative KRAS G12D Inhibitors of the Present Invention, Demonstrated Strong, Durable RAS Pathway Modulation in Human Pancreatic Adenocarcinoma Xenografted Tumors in Vivo Methods: The human pancreatic adenocarcinoma HPAC $KRAS^{G12D/wt}$ xenograft mouse model was used for a single-dose PK/PD study. Compound A and Compound B were each administered by oral gavage (po) at 100 mg/kg. The treatment groups with sample collections at various time points were summarized in Table 5 below. Tumor samples were collected to assess RAS/ERK signaling pathway modulation by measuring the mRNA level of human DUSP6 in a qPCR assay. Blood samples were collected to assess unbound plasma concentration by LC-MS bioanalytical assay.

Results: In FIG. 1, both covalent $KRAS^{G12D}$ inhibitors, Compound A and Compound B, led to inhibition of DUSP6 mRNA levels in HPAC xenografted tumors by 4h post dosing, indicating strong RAS pathway modulation. The inhibitory effects of both Compound A and Compound B on DUSP6 mRNA levels were durable up to 48 hours after drug administration.

TABLE 5

Summary of treatment groups, doses, and time points for single-dose PD study using HPAC tumors.

| Compound/ group | Dose/ Regimen | PD, n = 3/time point | PK, n = 3/time point |
|---|---|---|---|
| Vehicle control | 10 ml/kg po | 1 h, 24 h | 1 h, 24 h |
| Compound A | 100 mg/kg po | 1 h, 4 h, 8 h, 24 h, 48 h | 0.5 h, 1 h, 2 h, 4 h, 8 h, 24 h, 48 h |
| Compound B | 100 mg/kg po | 1 h, 4 h, 8 h, 24 h, 48 h | 0.5 h, 1 h, 2 h, 4 h, 8 h, 24 h, 48 h |

Compound A and Compound B, Representative KRAS G12D Inhibitors of the Present Invention, Displayed Strong Tumor Cross-Linking, Consistent with Significant DUSP6 Inhibition Methods: Tumor samples collected at the designated time points from single dose PK/PD assay as described in FIG. 1 above were homogenized for protein extraction. Protein lysates were then subjected to western blotting with Ras Rabbit mAb (Abcam ab108602) and β-actin mAb (CST-4967). Appearance of higher molecular weight (MW) bands (cross-linked KRAS G12D bands) were detected from tumor samples where compounds covalently bound to KRAS G12D proteins.

Figure 2:
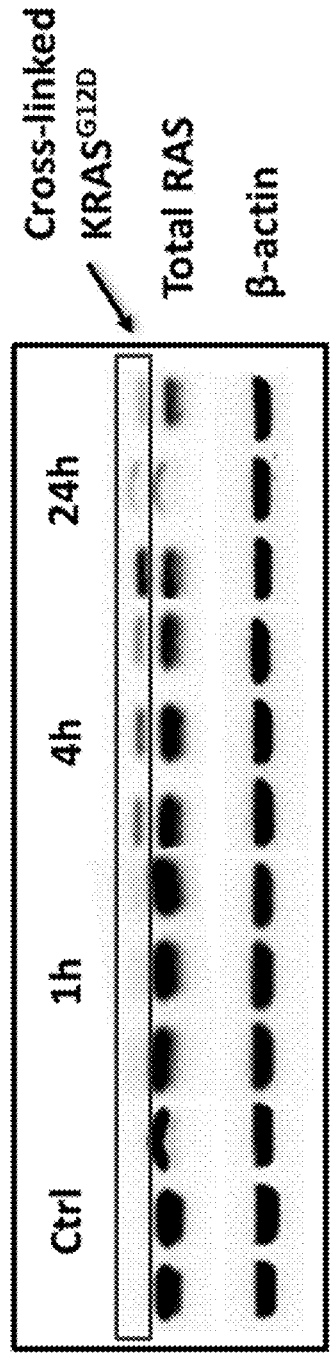
FIG. 2 shows that Compound A and Compound B displayed strong tumor cross-linking by 4 hours and up to 24 hours, consistent with significant DUSP6 inhibition. Tumor samples collected from the assay of FIG. 1 were homogenized for protein extraction. Protein lysates were subjected to western blotting with Ras Rabbit mAb (Abcam ab108602) and β-actin mAb (CST-4967). Appearance of higher molecular weight (MW) bands (cross-linked KRAS G12D bands) are detected from tumor samples where compounds covalently bound to KRAS G12D proteins.
Figure 2:
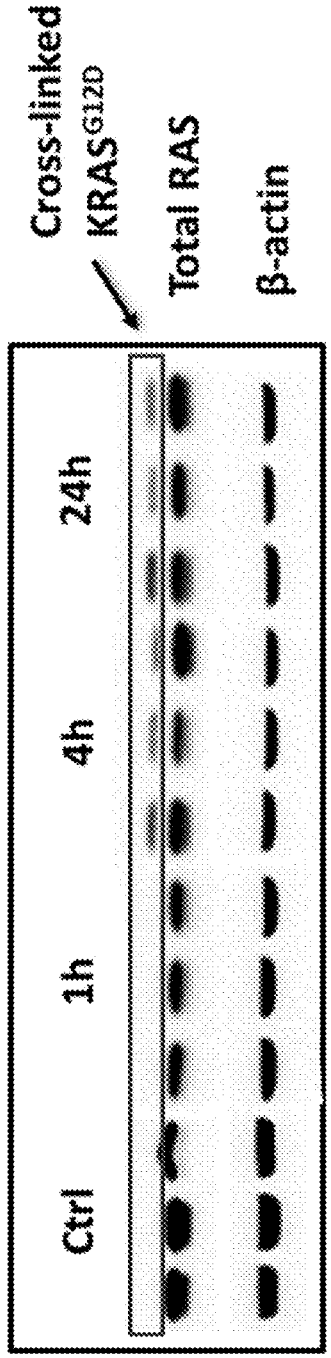

Results: As shown in FIG. 2, Compounds A and B both displayed strong tumor cross-linking by 4 hours and up to 24 hours, consistent with significant DUSP6 inhibition.

Compound A and Compound B, Representative KRAS G12D Inhibitors of the Present Invention, Drove Deep Tumor Regression and Were Tolerated in HPAC KRAS G12D CDX Model Methods: Effects of Compound A and Compound B on tumor cell growth in vivo were evaluated in the human pancreatic adenocarcinoma HPAC $KRAS^{G12D/w}$ xenograft model using female BALB/c nude mice (6-8 weeks old). Mice were implanted with HPAC tumor cells in PBS ($3\times10^6$ cells/mouse) subcutaneously in the flank. Once tumors reached an average size of ~130 mm³, mice were randomized to treatment groups to start the administration of test articles or vehicle. Each of Compound A and Compound B were administered by oral gavage (po) once daily at 100 mg/kg. Body weight and tumor volume (using calipers) was measured twice weekly until study endpoints.

Figure 3A:
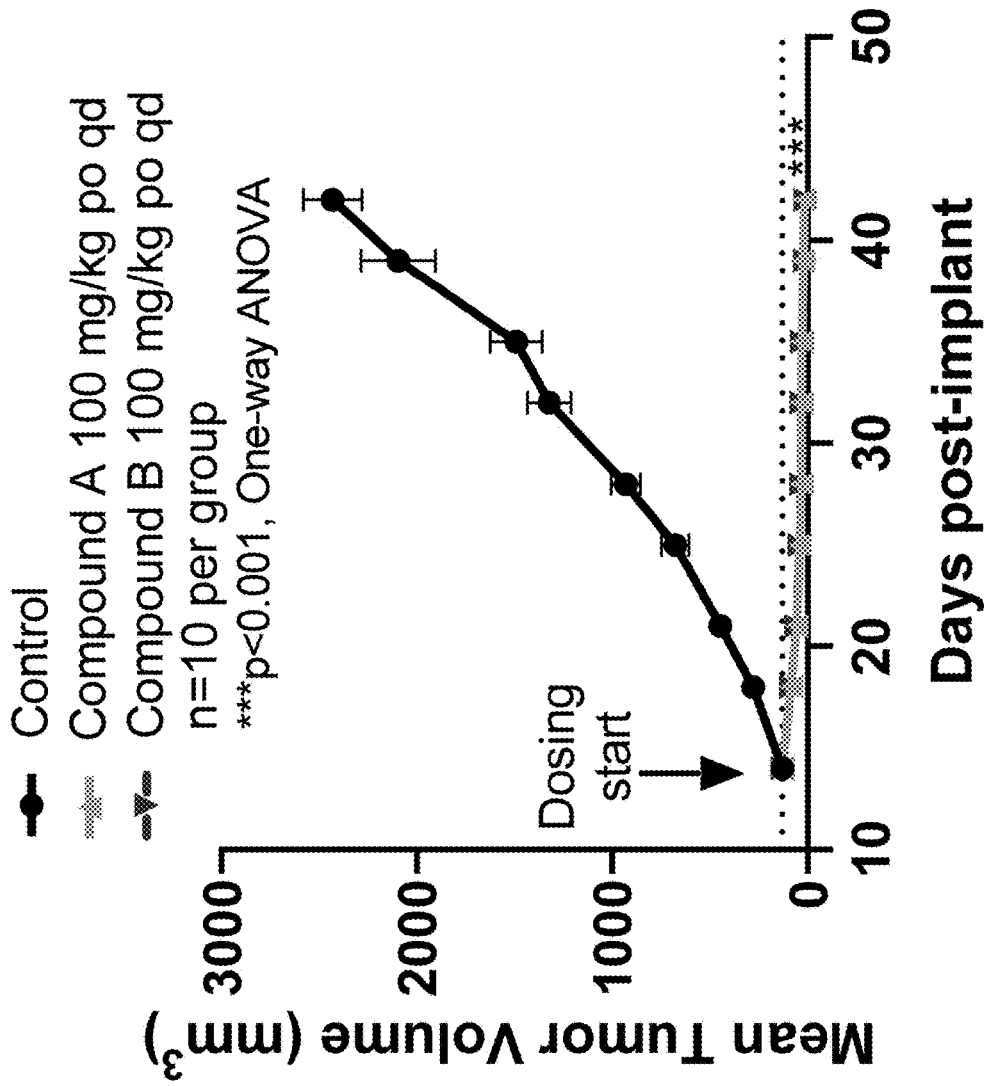
FIG. 3A shows that both Compound A and Compound B, administered as single agents at 100 mg/kg po daily, led to regression of all tumors (regression defined as >10% tumor regression from baseline) at the end of treatment (Day 28 after treatment started) in an HPAC CDX mouse xenograft model with heterozygous KRAS G12D.

Results: FIG. 3A shows that both Compound A and Compound B single agents administered at 100 mg/kg po daily led to regression of all tumors in the groups (regression defined as >10% tumor regression from baseline) at the end of treatment (Day 28 after treatment started) in HPAC CDX model with heterozygous $KRAS^{G12D}$. In fact, 8 out 10 tumors and 9 out 10 tumors reached complete regression (complete regression defined as >85% tumor regression from baseline) at Day 28 in Compound A (100 mg/kg po qd) and Compound B (100 mg/kg po qd) groups, respectively (FIG. 3C). The anti-tumor activity of both compounds was statistically significant compared with control group (***p<0.001, ordinary One-way ANOVA with multiple comparisons via a post-hoc Tukey's test).

Percentage of body weight change (% BWC) plot in FIG. 3B displays that there was no body weight loss observed from either Compound A (100 mg/kg po qd) or Compound B (100 mg/kg po qd) group, indicating both compounds at 100 mg/kg were well tolerated.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features set forth herein.

All publications, patents and patent applications are herein incorporated by reference in their entirety to the same extent as if each individual publication, patent or patent application was specifically and individually indicated to be incorporated by reference in its entirety.

The invention claimed is:

1. A compound having the structure of Formula I:

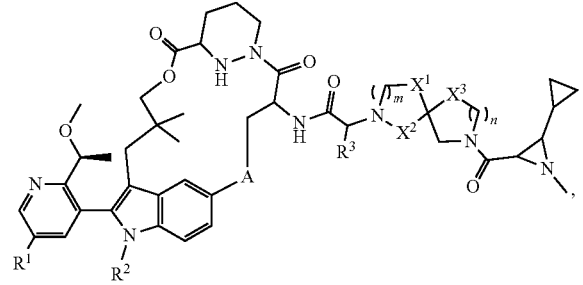

Formula I or a pharmaceutically acceptable salt thereof,
wherein A is morpholine-diyl;
$X^1$, $X^2$, and $X^3$ are each $CH_2$;
m is 1;
n is 1;
$R^1$ is hydrogen, optionally substituted $C_1$-$C_6$ heteroalkyl, or optionally substituted 3 to 10-membered heterocycloalkyl;
$R^2$ is optionally substituted $C_1$-$C_6$ alkyl; and
$R^3$ is cyclopentyl.

2. The compound of claim 1, or a pharmaceutically acceptable salt thereof, wherein A is
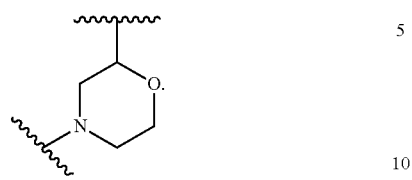
3. A compound of the following structure:
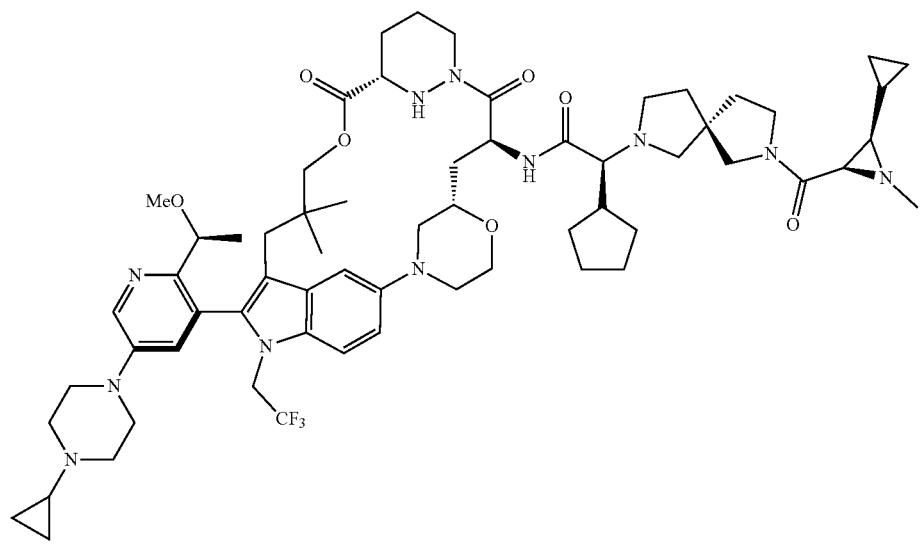
or a pharmaceutically acceptable salt thereof.
4. A compound of the following structure:
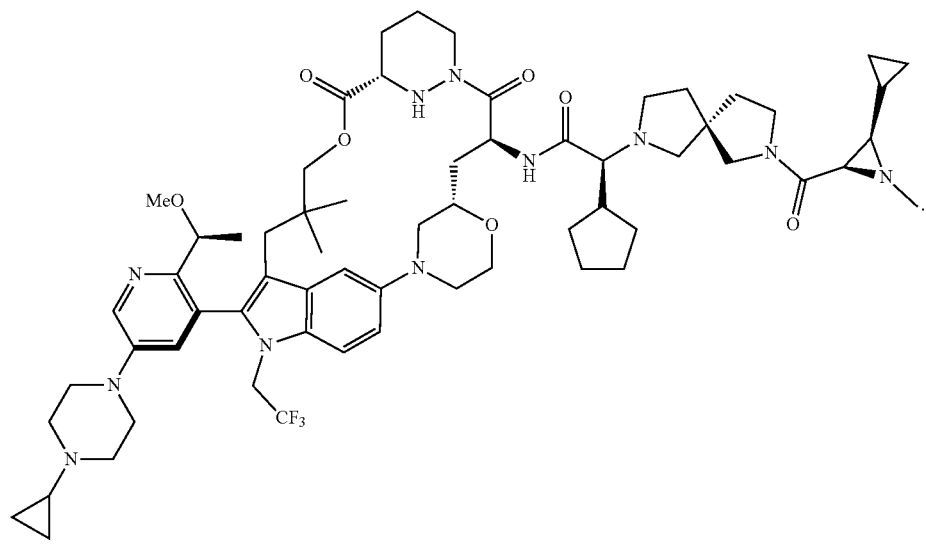

5. A pharmaceutical composition comprising a compound of the following structure:
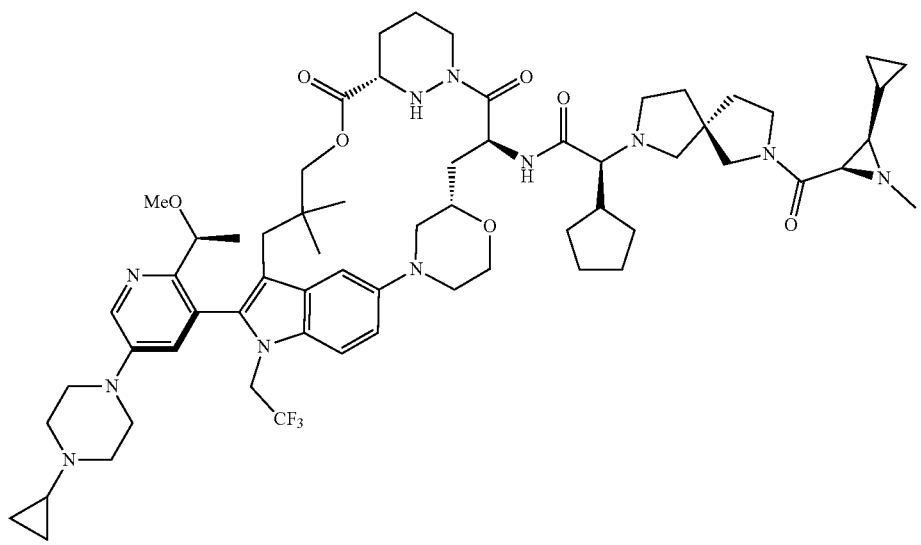
or a pharmaceutically acceptable salt thereof, and a pharmaceutically acceptable excipient.
6. A pharmaceutical composition comprising a compound of the following structure:
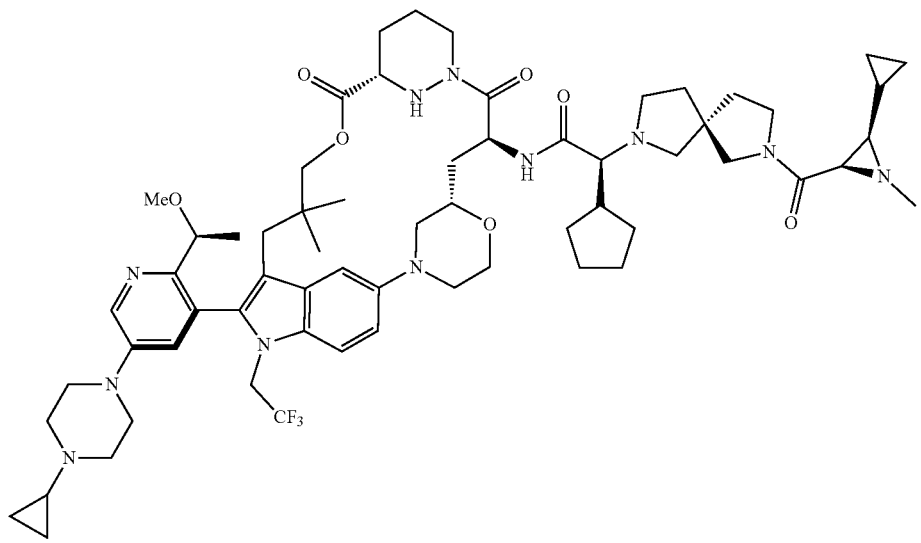
and a pharmaceutically acceptable excipient.
* * * * *